(12) United States Patent
Igawa et al.

(10) Patent No.: US 10,618,965 B2
(45) Date of Patent: Apr. 14, 2020

(54) METHOD FOR ALTERING PLASMA RETENTION AND IMMUNOGENICITY OF ANTIGEN-BINDING MOLECULE

(75) Inventors: Tomoyuki Igawa, Shizuoka (JP); Atsuhiko Maeda, Shizuoka (JP); Kenta Haraya, Shizuoka (JP); Yuki Iwayanagi, Shizuoka (JP); Tatsuhiko Tachibana, Shizuoka (JP); Futa Mimoto, Shizuoka (JP); Taichi Kuramochi, Shizuoka (JP); Hitoshi Katada, Shizuoka (JP); Shojiro Kadono, Kanagawa (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 316 days.

(21) Appl. No.: 14/007,947

(22) PCT Filed: Mar. 30, 2012

(86) PCT No.: PCT/JP2012/058603
§ 371 (c)(1),
(2), (4) Date: Dec. 30, 2013

(87) PCT Pub. No.: WO2012/133782
PCT Pub. Date: Oct. 4, 2012

(65) Prior Publication Data
US 2014/0105889 A1    Apr. 17, 2014

(30) Foreign Application Priority Data

Mar. 30, 2011 (JP) ................. 2011/001888
Sep. 30, 2011 (JP) ................. 2011/072550
Feb. 24, 2012 (JP) ................. 2012/054624

(51) Int. Cl.
C07K 16/30      (2006.01)
C07K 16/28      (2006.01)
C07K 16/08      (2006.01)
G01N 33/68      (2006.01)
C07K 16/18      (2006.01)

(52) U.S. Cl.
CPC .......... C07K 16/2866 (2013.01); C07K 16/08 (2013.01); C07K 16/18 (2013.01); C07K 16/303 (2013.01); C07K 2317/524 (2013.01); C07K 2317/72 (2013.01)

(58) Field of Classification Search
CPC ...... C07K 16/303; C07K 16/18; C07K 16/08; C07K 2317/524; C07K 2317/526; C07K 2317/72; C07K 2317/565; C07K 2317/92; C07K 2317/52; C07K 2317/94; G01N 33/6854; G01N 33/6845
See application file for complete search history.

(56) References Cited

U.S. PATENT DOCUMENTS

| 4,689,299 A | 8/1987 | Insel et al. |
| 4,801,687 A | 1/1989 | Ngo |
| 5,202,253 A | 4/1993 | Esmon et al. |
| 5,322,678 A | 6/1994 | Morgan et al. |
| 5,501,854 A | 3/1996 | Raso |
| 5,585,089 A | 12/1996 | Queen et al. |
| 5,639,641 A | 6/1997 | Pedersen et al. |
| 5,795,965 A | 8/1998 | Tsuchiya et al. |
| 5,830,478 A | 11/1998 | Raso et al. |
| 5,935,935 A | 8/1999 | Connelly et al. |
| 5,990,286 A | 11/1999 | Khawli et al. |
| 6,074,642 A | 6/2000 | Wang et al. |
| 6,329,511 B1 | 12/2001 | Vasquez et al. |
| 6,485,943 B2 | 11/2002 | Stevens et al. |
| 6,677,436 B1 | 1/2004 | Sato et al. |
| 6,737,056 B1 * | 5/2004 | Presta ................ C07K 16/4291 424/133.1 |
| 6,884,879 B1 | 4/2005 | Baca et al. |
| 6,913,747 B1 | 7/2005 | Co et al. |
| 7,052,873 B2 | 5/2006 | Tsuchiya |

(Continued)

FOREIGN PATENT DOCUMENTS

| AU | 2012/222252 | 10/2013 |
| CA | 2 647 846 | 10/2007 |

(Continued)

OTHER PUBLICATIONS

Ito et al., FEBS Lett. Aug. 31, 1992 ;309(1 ):85-8.*

(Continued)

*Primary Examiner* — Phuong Huynh

(74) *Attorney, Agent, or Firm* — Fish & Richardson P.C.

(57) ABSTRACT

The present invention demonstrated that the modification of the Fc region of an antigen-binding molecule into an Fc region that does not form in a neutral pH range a heterotetramer complex containing two molecules of FcRn and an active Fcγ receptor improved the pharmacokinetics of the antigen-binding molecule and reduced the immune response to the antigen-binding molecule. The present invention also revealed methods for producing antigen-binding molecules having the properties described above, and successfully demonstrated that pharmaceutical compositions containing as an active ingredient such an antigen-binding molecule or an antigen-binding molecule produced by a production method of the present invention have excellent features over conventional antigen-binding molecules in that when administered, they exhibit improved pharmacokinetics and reduced in vivo immune response.

33 Claims, 65 Drawing Sheets
Specification includes a Sequence Listing.

(56) References Cited

U.S. PATENT DOCUMENTS

| | | |
|---|---|---|
| 7,276,585 B2 | 10/2007 | Lazar et al. |
| 7,662,925 B2 | 2/2010 | Lazar et al. |
| 7,955,590 B2 | 6/2011 | Gillies et al. |
| 7,960,512 B2 | 6/2011 | Stavenhagen et al. |
| 8,188,231 B2 * | 5/2012 | Lazar ............... C07K 16/2893 424/130.1 |
| 8,329,867 B2 | 12/2012 | Lazar et al. |
| 8,367,805 B2 | 2/2013 | Chamberlain et al. |
| 8,388,955 B2 | 3/2013 | Lazar et al. |
| 8,551,485 B2 | 10/2013 | Bernett et al. |
| 8,562,991 B2 | 10/2013 | Igawa et al. |
| 8,568,726 B2 | 10/2013 | Beaumont et al. |
| 8,685,725 B2 | 4/2014 | Beliard et al. |
| 8,735,545 B2 | 5/2014 | Lazar et al. |
| 8,802,820 B2 | 8/2014 | Chamberlain et al. |
| 9,029,515 B2 | 5/2015 | Pons et al. |
| 9,079,949 B1 | 7/2015 | Andrien et al. |
| 9,096,651 B2 | 8/2015 | Igawa et al. |
| 9,107,861 B1 | 8/2015 | Andrien, Jr. et al. |
| 9,765,135 B2 | 9/2017 | Ruike |
| 9,828,429 B2 | 11/2017 | Igawa et al. |
| 9,868,948 B2 | 1/2018 | Igawa et al. |
| 9,890,377 B2 | 2/2018 | Igawa et al. |
| 9,969,800 B2 | 5/2018 | Igawa et al. |
| 10,000,560 B2 | 6/2018 | Ruike et al. |
| 10,024,867 B2 | 7/2018 | Igawa |
| 10,253,100 B2 | 4/2019 | Igawa et al. |
| 10,472,623 B2 | 11/2019 | Igawa et al. |
| 2002/0098193 A1 | 7/2002 | Ward |
| 2002/0142374 A1 | 10/2002 | Gallo et al. |
| 2002/0164339 A1 | 11/2002 | Do et al. |
| 2003/0059937 A1 | 3/2003 | Ruben et al. |
| 2003/0224397 A1 | 12/2003 | Lowman et al. |
| 2004/0001822 A1 | 1/2004 | Levanon et al. |
| 2004/0001839 A1 | 1/2004 | Levanon et al. |
| 2004/0002450 A1 | 1/2004 | Lazarovits et al. |
| 2004/0081651 A1 | 4/2004 | Karpusas et al. |
| 2004/0110226 A1 | 6/2004 | Lazar et al. |
| 2004/0133357 A1 | 7/2004 | Zhong et al. |
| 2004/0236080 A1 | 11/2004 | Aburatani et al. |
| 2005/0014934 A1 | 1/2005 | Hinton et al. |
| 2005/0095243 A1 | 5/2005 | Chan et al. |
| 2005/0244403 A1 | 11/2005 | Lazar et al. |
| 2005/0260213 A1 | 11/2005 | Koenig et al. |
| 2005/0260711 A1 | 11/2005 | Datta et al. |
| 2006/0014156 A1 | 1/2006 | Rabbani et al. |
| 2006/0019342 A1 | 1/2006 | Dall Acqua et al. |
| 2006/0063228 A1 | 3/2006 | Kasaian et al. |
| 2006/0134709 A1 | 6/2006 | Stavenhagen et al. |
| 2006/0141456 A1 | 6/2006 | Edwards et al. |
| 2006/0153860 A1 | 7/2006 | Cho et al. |
| 2007/0009523 A1 | 1/2007 | Presta |
| 2007/0036785 A1 | 2/2007 | Kishimoto et al. |
| 2007/0037734 A1 | 2/2007 | Rossi et al. |
| 2007/0041978 A1 | 2/2007 | Hattori et al. |
| 2007/0059312 A1 | 3/2007 | Baca et al. |
| 2007/0148164 A1 | 6/2007 | Farrington et al. |
| 2007/0160598 A1 | 7/2007 | Dennis et al. |
| 2007/0224188 A1 | 9/2007 | Allan et al. |
| 2007/0231329 A1 | 10/2007 | Lazar et al. |
| 2007/0237767 A1 * | 10/2007 | Lazar ............... C07K 16/2863 424/133.1 |
| 2007/0248602 A1 | 10/2007 | Lazar et al. |
| 2007/0253951 A1 | 11/2007 | Ng et al. |
| 2007/0269371 A1 | 11/2007 | Krummen et al. |
| 2008/0044417 A1 | 2/2008 | Johnson et al. |
| 2008/0089892 A1 | 4/2008 | Allan et al. |
| 2008/0138349 A1 | 6/2008 | Stavenhagen et al. |
| 2008/0166756 A1 | 7/2008 | Tsuchiya et al. |
| 2008/0181890 A1 | 7/2008 | Lazar et al. |
| 2008/0199471 A1 | 8/2008 | Bernett et al. |
| 2009/0035836 A1 | 2/2009 | Datta et al. |
| 2009/0041770 A1 | 2/2009 | Chamberlain et al. |
| 2009/0042291 A1 | 2/2009 | Chu et al. |
| 2009/0053240 A1 * | 2/2009 | Lazar ..................... C07K 16/00 424/172.1 |
| 2009/0076251 A1 | 3/2009 | Koenig et al. |
| 2009/0136485 A1 | 5/2009 | Chu et al. |
| 2009/0142340 A1 | 6/2009 | Lazar |
| 2009/0263392 A1 | 10/2009 | Igawa et al. |
| 2009/0324589 A1 | 12/2009 | Igawa et al. |
| 2010/0003254 A1 | 1/2010 | Hattori et al. |
| 2010/0098730 A1 | 4/2010 | Lowman et al. |
| 2010/0184959 A1 | 7/2010 | Guler-Gane et al. |
| 2010/0216187 A1 | 8/2010 | Lasters et al. |
| 2010/0239577 A1 | 9/2010 | Igawa et al. |
| 2010/0292443 A1 | 11/2010 | Sabbadini et al. |
| 2010/0298542 A1 | 11/2010 | Igawa et al. |
| 2011/0044986 A1 | 2/2011 | Biere-Citron et al. |
| 2011/0076275 A1 | 3/2011 | Igawa et al. |
| 2011/0098450 A1 | 4/2011 | Igawa et al. |
| 2011/0111406 A1 * | 5/2011 | Igawa ............... C07K 16/248 435/6.14 |
| 2011/0150888 A1 | 6/2011 | Foltz et al. |
| 2011/0223658 A1 | 9/2011 | Beliard et al. |
| 2011/0229489 A1 | 9/2011 | Pons et al. |
| 2011/0245473 A1 | 10/2011 | Igawa et al. |
| 2012/0009188 A1 | 1/2012 | Behrens et al. |
| 2012/0093818 A1 | 4/2012 | Jackson et al. |
| 2012/0321620 A1 | 12/2012 | Chu et al. |
| 2013/0011866 A1 | 1/2013 | Igawa et al. |
| 2013/0085265 A1 | 4/2013 | Jackson et al. |
| 2013/0131319 A1 | 5/2013 | Igawa et al. |
| 2013/0247234 A1 | 9/2013 | McWhirter et al. |
| 2013/0259876 A1 | 10/2013 | Murphy et al. |
| 2013/0303396 A1 | 11/2013 | Igawa et al. |
| 2013/0336963 A1 | 12/2013 | Igawa et al. |
| 2014/0044730 A1 | 2/2014 | Yancopoulos et al. |
| 2014/0082760 A1 | 3/2014 | McWhirter et al. |
| 2014/0086916 A1 | 3/2014 | Zha |
| 2014/0093496 A1 | 4/2014 | Mimoto et al. |
| 2014/0112926 A1 | 4/2014 | Liu |
| 2014/0199294 A1 | 7/2014 | Mimoto et al. |
| 2014/0234340 A1 | 8/2014 | Igawa et al. |
| 2014/0255398 A1 | 9/2014 | Igawa et al. |
| 2014/0335089 A1 | 11/2014 | Igawa |
| 2014/0356371 A1 | 12/2014 | Swergold et al. |
| 2014/0363428 A1 | 12/2014 | Igawa et al. |
| 2015/0050269 A1 | 2/2015 | Igawa et al. |
| 2015/0056182 A1 | 2/2015 | Igawa et al. |
| 2015/0166636 A1 | 6/2015 | Igawa et al. |
| 2015/0166654 A1 | 6/2015 | Igawa et al. |
| 2015/0203577 A1 | 7/2015 | Igawa et al. |
| 2015/0252107 A1 | 9/2015 | Stevis et al. |
| 2015/0284465 A1 | 10/2015 | Igawa et al. |
| 2015/0299296 A1 | 10/2015 | Katada et al. |
| 2015/0299313 A1 | 10/2015 | Igawa et al. |
| 2015/0315278 A1 | 11/2015 | Igawa et al. |
| 2015/0344570 A1 | 12/2015 | Igawa et al. |
| 2015/0353630 A1 | 12/2015 | Igawa et al. |
| 2016/0039912 A1 | 2/2016 | Mimoto et al. |
| 2016/0046693 A1 | 2/2016 | Igawa et al. |
| 2016/0229908 A1 | 8/2016 | Igawa et al. |
| 2016/0244526 A1 | 8/2016 | Igawa et al. |
| 2017/0022270 A1 | 1/2017 | Igawa et al. |
| 2017/0226206 A1 | 8/2017 | Igawa et al. |
| 2018/0142027 A1 | 5/2018 | Igawa et al. |
| 2018/0258161 A1 | 9/2018 | Igawa et al. |
| 2019/0112393 A1 | 4/2019 | Igawa et al. |
| 2019/0185557 A1 | 6/2019 | Igawa et al. |
| 2019/0218309 A1 | 7/2019 | Igawa et al. |
| 2019/0233525 A1 | 8/2019 | Igawa et al. |

FOREIGN PATENT DOCUMENTS

| | | |
|---|---|---|
| CA | 2 700 986 | 4/2009 |
| CA | 2 794 860 | 10/2011 |
| CA | 2 827 923 | 8/2012 |
| CA | 2 831 770 | 10/2012 |
| CN | 1763097 | 4/2006 |
| CN | 101001873 | 7/2007 |
| CN | 101014619 | 8/2007 |
| CN | 101098890 | 1/2008 |

(56) References Cited

FOREIGN PATENT DOCUMENTS

| | | |
|---|---|---|
| CN | 102056946 | 5/2011 |
| CN | 103492565 | 1/2014 |
| CN | 102633880 | 2/2015 |
| CN | 101874042 | 9/2018 |
| EP | 0 182 495 | 5/1986 |
| EP | 0 329 185 | 4/1994 |
| EP | 0 783 893 | 7/1997 |
| EP | 1 069 185 | 1/2001 |
| EP | 1 773 391 | 4/2007 |
| EP | 1 601 697 | 5/2007 |
| EP | 1 787 998 | 5/2007 |
| EP | 1 870 459 | 12/2007 |
| EP | 2 006 381 | 12/2008 |
| EP | 2 009 101 | 12/2008 |
| EP | 2 189 526 | 5/2010 |
| EP | 2 196 541 | 6/2010 |
| EP | 2 202 245 | 6/2010 |
| EP | 2 275 443 A1 | 1/2011 |
| EP | 2 314 618 | 4/2011 |
| EP | 2 366 713 | 9/2011 |
| EP | 2 368 911 | 9/2011 |
| EP | 2 543 730 | 1/2013 |
| EP | 2 647 706 | 10/2013 |
| EP | 2 679 681 | 1/2014 |
| EP | 2 698 431 | 2/2014 |
| EP | 2 762 166 | 8/2014 |
| EP | 2 889 377 | 7/2015 |
| JP | S61-117457 | 6/1986 |
| JP | S63-52890 | 3/1988 |
| JP | H01-144991 | 6/1989 |
| JP | H02-028200 | 1/1990 |
| JP | H02-501112 | 4/1990 |
| JP | H02-163085 | 6/1990 |
| JP | H03-500644 | 2/1991 |
| JP | 07-67688 | 3/1995 |
| JP | 2003-512019 | 4/2003 |
| JP | 2004-511426 | 4/2004 |
| JP | 2005-501514 | 1/2005 |
| JP | 2005-101105 | 3/2005 |
| JP | 2005-535341 | 11/2005 |
| JP | 2005-378266 | 12/2005 |
| JP | 2007-532139 | 11/2007 |
| JP | 2008-505174 | 2/2008 |
| JP | 2008-510466 | 4/2008 |
| JP | 2008-511292 | 4/2008 |
| JP | 2008-519860 | 6/2008 |
| JP | 2010-505436 | 2/2010 |
| JP | 2010-079667 | 3/2010 |
| JP | 2010-514460 | 5/2010 |
| JP | 2010-250830 | 11/2010 |
| JP | 4652414 | 3/2011 |
| JP | 2011-184418 | 9/2011 |
| JP | 2012-505833 | 3/2012 |
| JP | 5144499 | 2/2013 |
| JP | 2013-518131 | 5/2013 |
| JP | 2013-165716 | 8/2013 |
| JP | 5334319 | 11/2013 |
| JP | 2014-528906 | 10/2014 |
| JP | 2015-130883 | 7/2015 |
| KR | 2010/0074220 | 7/2010 |
| KR | 2011/0004435 | 1/2011 |
| RU | 2147442 | 4/2000 |
| RU | 2225721 | 3/2004 |
| RU | 2266298 | 12/2005 |
| RU | 2005/112742 | 1/2006 |
| RU | 2337107 | 10/2008 |
| RU | 2007/121679 | 12/2008 |
| RU | 2367667 | 9/2009 |
| RU | 2390527 | 5/2010 |
| RU | 2430111 | 9/2011 |
| RU | 2010/116152 | 11/2011 |
| SG | 183867 | 10/2012 |
| SG | 192945 | 9/2013 |
| TW | 2010/00127 | 1/2010 |
| TW | 2012/02419 | 1/2012 |
| WO | WO 1988/004692 | 6/1988 |
| WO | WO 89/01343 | 2/1989 |
| WO | WO 91/12023 | 8/1991 |
| WO | WO 92/19759 | 11/1992 |
| WO | WO 95/02187 | 1/1995 |
| WO | WO 95/14710 | 6/1995 |
| WO | WO 95/29697 | 11/1995 |
| WO | WO 96/11020 | 4/1996 |
| WO | WO 96/12503 | 5/1996 |
| WO | WO 97/20858 | 6/1997 |
| WO | WO 97/34631 | 9/1997 |
| WO | WO 98/03546 | 1/1998 |
| WO | WO 99/18212 | 4/1999 |
| WO | WO 99/51743 | 10/1999 |
| WO | WO 99/58572 | 11/1999 |
| WO | WO 2000/014220 | 3/2000 |
| WO | WO 00/42072 | 7/2000 |
| WO | WO 0130854 | 5/2001 |
| WO | WO 01/82899 | 11/2001 |
| WO | WO 02/060919 | 8/2002 |
| WO | WO 2003/000883 | 1/2003 |
| WO | WO 03/020949 | 3/2003 |
| WO | WO 2003/057881 | 7/2003 |
| WO | WO 2003/070760 | 8/2003 |
| WO | WO 03/105757 | 12/2003 |
| WO | WO 2003/107009 | 12/2003 |
| WO | WO 2004/007553 | 1/2004 |
| WO | WO 2004/016740 | 2/2004 |
| WO | WO 2004/029207 | 4/2004 |
| WO | WO 2004/035752 | 4/2004 |
| WO | WO 2004/039826 | 5/2004 |
| WO | WO 2004/068931 | 8/2004 |
| WO | WO 2004/092219 | 10/2004 |
| WO | WO 2004/096273 | 11/2004 |
| WO | WO 2004/099249 | 11/2004 |
| WO | WO 2005/035756 | 4/2005 |
| WO | WO 2005/037867 | 4/2005 |
| WO | WO 2005/047327 | 5/2005 |
| WO | WO 2005/059106 | 6/2005 |
| WO | WO 2005/067620 | 7/2005 |
| WO | WO 2005/070963 | 8/2005 |
| WO | WO 2005/077981 | 8/2005 |
| WO | WO 2005/112564 | 12/2005 |
| WO | WO 2005/115452 | 12/2005 |
| WO | WO 2005/123126 | 12/2005 |
| WO | WO 2005/123780 | 12/2005 |
| WO | WO 2006/004663 | 1/2006 |
| WO | WO 2006/016644 | 2/2006 |
| WO | WO 2006/019447 | 2/2006 |
| WO | WO 2006/020114 | 2/2006 |
| WO | WO 2006/023403 | 3/2006 |
| WO | WO 2006/030200 | 3/2006 |
| WO | WO 2006/030220 | 3/2006 |
| WO | WO 2006/031370 | 3/2006 |
| WO | WO 2006/050166 | 5/2006 |
| WO | WO 2006/050491 | 5/2006 |
| WO | WO 2006/053301 | 5/2006 |
| WO | WO 2006/066598 | 6/2006 |
| WO | WO 2006/067913 | 6/2006 |
| WO | WO 2009/095235 | 8/2006 |
| WO | WO 2006/105338 | 10/2006 |
| WO | WO 2006/106905 | 10/2006 |
| WO | WO 2006/109592 | 10/2006 |
| WO | WO 2006/116260 | 11/2006 |
| WO | WO 2006/121852 | 11/2006 |
| WO | WO 2006/130834 | 12/2006 |
| WO | WO 2007/021841 | 2/2007 |
| WO | WO 2007/024249 | 3/2007 |
| WO | WO 2007/024535 | 3/2007 |
| WO | WO 2007/041635 | 4/2007 |
| WO | WO 2007/060411 | 5/2007 |
| WO | WO 2007/076524 | 7/2007 |
| WO | WO 2007/084253 | 7/2007 |
| WO | WO 2007/114319 | 10/2007 |
| WO | WO 2007/114325 | 10/2007 |
| WO | WO 2007/142325 | 12/2007 |
| WO | WO 2008/002933 | 1/2008 |
| WO | WO 2008/022152 | 2/2008 |
| WO | WO 2008/043822 | 4/2008 |

(56) References Cited

FOREIGN PATENT DOCUMENTS

| | | |
|---|---|---|
| WO | WO 2008/060785 | 5/2008 |
| WO | WO 2008/091954 | 7/2008 |
| WO | WO 2008/092117 | 7/2008 |
| WO | WO 2008/143954 | 11/2008 |
| WO | WO 2009/006338 | 1/2009 |
| WO | WO 2009/008529 | 1/2009 |
| WO | WO 2009/041062 | 4/2009 |
| WO | WO 2009/041643 | 4/2009 |
| WO | WO 2009/053358 | 4/2009 |
| WO | WO 2009/058492 | 5/2009 |
| WO | WO 2009/062083 | 5/2009 |
| WO | WO 2009/086320 | 7/2009 |
| WO | WO 2009/125825 | 10/2009 |
| WO | WO 2009/139822 | 11/2009 |
| WO | WO 2009/155513 | 12/2009 |
| WO | WO 2010/015608 | 2/2010 |
| WO | WO 2010/045193 | 4/2010 |
| WO | WO 2010/058860 | 5/2010 |
| WO | WO 2010/077854 | 7/2010 |
| WO | WO 2010/081173 | 7/2010 |
| WO | WO 2010/085682 | 7/2010 |
| WO | WO 2010/106180 | 9/2010 |
| WO | WO 2010/107109 | 9/2010 |
| WO | WO 2011/043643 | 4/2011 |
| WO | WO 2011/044368 | 4/2011 |
| WO | WO 2011/091078 | 7/2011 |
| WO | WO 2011/094593 | 8/2011 |
| WO | WO 2011/108714 | 9/2011 |
| WO | WO 2011/111007 | 9/2011 |
| WO | WO 2011/122011 | 10/2011 |
| WO | WO 2012/033953 | 3/2012 |
| WO | WO 2012/044831 | 4/2012 |
| WO | WO 2012/073992 | 6/2012 |
| WO | WO 2012/115241 | 8/2012 |
| WO | WO 2012/132067 | 10/2012 |
| WO | WO 2012/133782 | 10/2012 |
| WO | WO 2013/004842 | 1/2013 |
| WO | WO 2013/046704 | 4/2013 |
| WO | WO 2013/047729 | 4/2013 |
| WO | WO 2013/047748 | 4/2013 |
| WO | WO 2013/047752 | 4/2013 |
| WO | WO 2013/081143 | 6/2013 |
| WO | WO 2013/125667 | 8/2013 |
| WO | WO 2013/138681 | 9/2013 |
| WO | WO 2013/180200 | 12/2013 |
| WO | WO 2013/180201 | 12/2013 |
| WO | WO 2014/028354 | 2/2014 |
| WO | WO 2014/030728 | 2/2014 |
| WO | WO 2014/140366 | 9/2014 |
| WO | WO 2014/144080 | 9/2014 |
| WO | WO 2014/144575 | 9/2014 |
| WO | WO 2014/144577 | 9/2014 |
| WO | WO 2014/150983 | 9/2014 |
| WO | WO 2014/163101 | 10/2014 |
| WO | WO 2014/164959 | 10/2014 |
| WO | WO 2015/042250 | 3/2015 |
| WO | WO 2015/077491 | 5/2015 |
| WO | WO 2015/134894 | 9/2015 |
| WO | WO 2016/000813 | 1/2016 |

OTHER PUBLICATIONS

Patton et al., Journal of Immunological Methods, vol. 304, Issues 1-2, Sep. 2005, pp. 189-195.*

Amigorena et al., "Fc gamma RII expression in resting and activated B lymphocytes," *Eur J Immunol.*, 19(8):1379-1385 (1989).

Amigorena et al., "Cytoplasmic domain heterogeneity and functions of IgG Fc receptors in B lymphocytes," *Science*, 256(5065):1808-1812 (1992).

Armour et al., "Differential binding to human FcgammaRIIa and FcgammaRIIb receptors by human IgG wildtype and mutant antibodies," *Mol Immunol.*, 40(9):585-593 (2003).

Blank et al., Decreased transcription of the human FCGR2B gene mediated by the −343 G/C promoter polymorphism and association with systemic lupus erythematosus. *Hum Genet.*, 117(2-3): 220-227 (2005).

Boruchov et al., "Activating and inhibitory IgG Fc receptors on human DCs mediate opposing functions," *J Clin Invest.*, 115(10):2914-2923 (2005).

Boumpas et al., "A short course of BG9588 (anti-CD40 ligand antibody) improves serologic activity and decreases hematuria in patients with proliferative lupus glomerulonephritis," *Arthritis Rheum.*, 48(3):719-727 (2003).

Bruhns et al., Specificity and affinity of human Fcgamma receptors and their polymorphic variants for human IgG subclasses, *Blood*, 113(16):3716-3725 (2009).

Cemerski et al., "Suppression of mast cell degranulation through a dual-targeting tandem IgE-IgG Fc domain biologic engineered to bind with high affinity to FcγRIIb," *Immunol Lett.*, 143(1):34-43 (2012).

Chen et al., "Association of a transmembrane polymorphism of Fcgamma receptor IIb (FCGR2B) with systemic lupus erythematosus in Taiwanese patients," *Arthritis Rheum.*, 54(12):3908-3917 (2006).

Chu et al., "Reduction of total IgE by targeted coengagement of IgE B-cell receptor and FcγRIIb with Fc-engineered antibody," *J Allergy Clin Immunol.*, 129(4):1102-1115 (2012).

Chu et al., "Inhibition of B cell receptor-mediated activation of primary human B cells by coengagement of CD19 and FcgammaRIIb with Fc-engineered antibodies," *Mol Immunol.*, 45(15):3926-3933 (2008).

Chuntharapai et al., "Isotype-dependent inhibition of tumor growth in vivo by monoclonal antibodies to death receptor 4," *J Immunol.*, 166(8):4891-4898 (2001).

Clark, "IgG effector mechanisms," *Chem Immunol.*, 65:88-110 (1997).

Dall'Acqua et al., "Properties of human IgG1s engineered for enhanced binding to the neonatal Fc receptor (FcRn)," *J Biol Chem.*, 281(33):23514-23524 (2006).

Datta-Mannan et al., "Monoclonal antibody clearance. Impact of modulating the interaction of IgG with the neonatal Fc receptor," *J Biol Chem.*, 282(3):1709-1717 (2007).

Dhodapkar et al., "Selective blockade of inhibitory Fcgamma receptor enables human dendritic cell maturation with IL-12p70 production and immunity to antibody-coated tumor cells," *Proc Natl Acad Sci USA*, 102(8):2910-2915 (2005).

Duffau et al., "Platelet CD154 potentiates interferon-alpha secretion by plasmacytoid dendritic cells in systemic lupus erythematosus," *Sci Transl Med.*, 2(47):47ra63 (2010).

Floto et al., "Loss of function of a lupus-associated FcgammaRIIb polymorphism through exclusion from lipid rafts," *Nat Med.*, 11(10):1056-1058 (2005).

Fournier et al., "Activation of human peripheral IgM+ B cells is transiently inhibited by BCR-independent aggregation of Fc gammaRIIB," *J Immunol.*, 181(8):5350-5359 (2008).

Greenwood et al., "Structural motifs involved in human IgG antibody effector functions," *Eur J Immunol.*, 23(5):1098-1104 (1993).

Heyman, "Feedback regulation by IgG antibodies," *Immunol Lett.*, 88(2):157-161 (2003).

Jefferis et al., "Interaction sites on human IgG-Fc for FcgammaR: current Models," *Immunol Lett.*, 82(1-2):57-65 (2002).

Kohrt et al., "Stimulation of natural killer cells with a CD137-specific antibody enhances trastuzumab efficacy in xenotransplant models of breast cancer," *J Clin Invest.*, 122(3):1066-1075 (2012).

Li et al., "Inhibitory Fcγ receptor engagement drives adjuvant and anti-tumor activities of agonistic CD40 antibodies," *Science*, 333(6045):1030-1034 (2011).

Li et al., "CD72 down-modulates BCR-induced signal transduction and diminishes survival in primary mature B lymphocytes," *J Immunol.*, 176(9):5321-5328 (2006).

Liang et al "Immunity against a therapeutic xenoprotein/Fc construct delivered by gene transfer is reduced through binding to the inhibitory receptor FcγRIIb," *J Gene Med.*, 13(9):470-477 (2011).

Mackay et al., "Selective dysregulation of the FcgammaIIB receptor on memory B cells in SLE," *J Exp Med.*, 203(9):2157-2164 (2006).

(56) References Cited

OTHER PUBLICATIONS

Manger et al., "Fcgamma receptor IIa polymorphism in Caucasian patients with systemic lupus erythematosus: association with clinical symptoms," *Arthritis Rheum.*, 41(7):1181-1189 (1998).
Meyer et al., "Bevacizumab immune complexes activate platelets and induce thrombosis in FCGR2A transgenic mice," *J Thromb Haemost.*, 7(1):171-181 (2009).
Mi et al., "Targeting the neonatal fc receptor for antigen delivery using engineered fc fragments," *J Immunol.*, 181(11):7550-7561 (2008).
Morgan et al., "The N-terminal end of the CH2 domain of chimeric human IgG1 anti-HLA-DR is necessary for Clq, Fc gamma RI and Fc gamma RIII binding," *Immunology.*, 86(2):319-324 (1995).
Muta et al., "A 13-amino-acid motif in the cytoplasmic domain of Fc gamma RIIb modulates B-cell receptor signaling," *Nature*,368(6466):70-73 (1994).
Nakamura et al., "Fcgamma receptor IIB-deficient mice develop Goodpasture's syndrome upon immunization with type IV collagen: a novel murine model for autoimmune glomerular basement membrane disease," *J Exp Med.*, 191(5):899-906 (2000).
Nicholas et al., "Regulation of the immune response. I. Reduction in ability of specific antibody to inhibit long-lasting IgG immunological priming after removal of the Fc fragment," *J Exp Med.*, 129(6):1183-1201 (1969).
Niebecker et al., "Safety of therapeutic monoclonal antibodies," *Curr Drug Saf.*, 5(4):275-286 (2010).
Nimmerjahn et al., "Fcgamma receptors as regulators of immune responses," *Nat Rev Immunol.*, 8(1):34-47 (2008).
Olferiev et al., "The role of activating protein 1 in the transcriptional regulation of the human FCGR2B promoter mediated by the −343 G −> C polymorphism associated with systemic lupus erythematosus," *J Biol Chem.*, 282(3):1738-1746 (2007).
Qiao et al., "Dependence of antibody-mediated presentation of antigen on FcRn," *Proc Natl Acad Sci USA*, 105(27):9337-9342 (2008).
Radaev et al., "The role of Fc glycosylation and the binding of peptide inhibitors," *J Biol Chem.*, 276(19):16478-16483 (2001).
Ravetch et al., "Immune inhibitory receptors," *Science*, 290(5489):84-89 (2000).
Richards et al., "Optimization of antibody binding to FcgammaRIIa enhances macrophage phagocytosis of tumor cells," *Mol Cancer Ther.*, 7(8):2517-2527 (2008).
Robles-Carrillo et al., "Anti-CD4OL immune complexes potently activate platelets in vitro and cause thrombosis in FCGR2A transgenic mice," *J Immunol.*, 185(3):1577-1583 (2010).
Salmon et al., "Fc gamma RIIa alleles are heritable risk factors for lupus nephritis in African Americans," *J Clin Invest.*, 97(5):1348-1354 (1996).
Scappaticci et al., "Arterial thromboembolic events in patients with metastatic carcinoma treated with chemotherapy and bevacizumab," *J Natl Cancer Inst.*, 99(16):1232-1239 (2007).
Smith et al., "FcgammaRIIB in autoimmunity and infection: evolutionary and therapeutic.implications," *Nat Rev Immunol.*, 10(5):328-343 (2010).
Su et al., "Expression profile of FcgammaRIIb on leukocytes and its dysregulation in systemic lupus erythematosus," *J Immunol.*, 178(5):3272-3280 (2007).
Veri et al., "Therapeutic control of B cell activation via recruitment of Fcgamma receptor IIb (CD32B) inhibitory function with a novel bispecific antibody scaffold," *Arthritis Rheum.*, 62(7):1933-1943 (2010).
Veri et al., "Monoclonal antibodies capable of discriminating the human inhibitory Fcgamma-receptor IIB (CD32B) from the activating Fcgamma-receptor IIA (CD32A): biochemical, biological and functional characterization," *Immunology*, 121(3):392-404 (2007).
Warmerdam et al., "Molecular basis for a polymorphism of human Fc gamma receptor II (CD32)," *J Exp Med.*, 172(1):19-25 (1990).
Wernersson et al., "IgG-mediated enhancement of antibody responses is low in Fc receptor gamma chain-deficient mice and increased in Fc gamma RII-deficient mice," *J Immunol.*, 163(2):618-622 (1999).
Wilson et al., "An Fcγ receptor-dependent mechanism drives antibody-mediated target-receptor signaling in cancer cells," *Cancer Cell*, 19(1):101-113 (2011).
Xu et al., "Fc gamma Rs modulate cytotoxicity of anti-Fas antibodies: implications for agonistic antibody-based therapeutics," *J Immunol.*,171(2):562-568 (2003).
Yuasa et al., "Deletion of fcgamma receptor IIB renders H-2(b) mice susceptible to collagen-induced arthritis," *J Exp Med.*, 189(1):187-194 (1999).
Zhang et al., "Effective therapy for a murine model of human anaplastic large-cell lymphoma with the anti-CD30 monoclonal antibody, HeFi-1,does not require activating Fc receptors," *Blood*, 108(2):705-710 (2006).
International Search Report for App. Ser. No. PCT/JP2012/058603, dated May 29, 2012, 2 pages.
Stewart et al., "Site-directed mutagenesis of a catalytic antibody: an arginine and a histidine residue play key roles," *Biochemistry*, 33(8):1994-2003 (1994).
International Search Report for App. Ser. No. PCT/JP2012/075083, dated Oct. 23, 2012, 2 pages.
International Search Report for App. Ser. No. PCT/JP2012/006218, dated Mar. 26, 2013, 11 pages.
International Preliminary Report on Patentability for App. Ser. No. PCT/JP2012/075083, dated Apr. 1, 2014, 8 pages.
Igawa et al., "Reduced elimination of IgG antibodies by engineering the variable region," *Protein Eng Des Sel.*, 23(5):385-92 (2010).
Sims et al., "HMGB1 and RAGE in inflammation and cancer," *Annu Rev Immunol.*, 28:367-88 (2010).
Wang et al., "HMG-1 as a late mediator of endotoxin lethality in mice," *Science*, 285(5425):248-51 (1999).
International Search Report for App. Ser. No. PCT/JP2012/081185, dated Feb. 26, 2013, 9 pages.
International Preliminary Report on Patentability for App. Ser. No. PCT/JP2012/081185, dated Jun. 3, 2014, 9 pages.
Drake et al., "Chapter 5: Biophysical Considerations for Development of Antibody-Based Therapeutics," *Biophysical Considerations for Development of Antibody-Based Therapeutics*, Springer Science+Business Media New York, 95-7 (2012).
Lin et al., "Preclinical pharmacokinetics, interspecies scaling, and tissue distribution of a humanized monoclonal antibody against vascular endothelial growth factor," *J Pharmacol Exp Ther.*, 288(1):371-8 (1999).
Clark, "An alignment of IgG sequences from Human, Mouse and Rat," Part II Immunoglobulin lectures (v4), pp. 5(i)-(ii) [retrieved on Jul. 25, 2014]. Retrieved from the Internet: http://www.path.cam.ac.uk/~mrc7/lecturenotes/handout1a.pdf.
Haakenstad et a., "The disappearance kinetics and glomerular deposition of small-latticed soluble immune complexes," *Immunology*, 47(3):407-14 (1982).
Hebert LA, "The clearance of immune complexes from the circulation of man and other primates," *Am J Kidney Dis.*, 17(3):352-61 (1991).
Montero-Julian et al., "Pharmacokinetic study of anti-interleukin-6 (IL-6) therapy with monoclonal antibodies: enhancement of IL-6 clearance by cocktails of anti-IL-6 antibodies," *Blood*, 85(4):917-24 (1995).
Rudge et al.,, "VEGF Trap complex formation measures production rates of VEGF, providing a biomarker for predicting efficacious angiogenic blockade," *Proc Natl Acad Sci U S A.*, 104(47):18363-70 (2007).
Alley et al., "Antibody-drug conjugates: targeted drug delivery for cancer," *Curr Opin Chem Biol.*, Aug. 2010; 14(4):529-37. doi: 10.1016/j.cbpa.2010.06.170. Epub Jul. 17, 2010.
Baeuerle et al., "BiTE: Teaching antibodies to engage T-cells for cancer therapy," *Curr Opin Mol Ther.*, 11(1):22-30 (2009).
Davda et al., "Properties of a general PK/PD model of antibody-ligand interactions for therapeutic antibodies that bind to soluble endogenous targets," *MAbs*, Sep.-Oct. 2010; 2(5):576-88. doi: 10.4161/mabs.2.5.12833. Epub Sep. 1, 2010.
De Bono et al., "ING-1, a monoclonal antibody targeting Ep-CAM in patients with advanced adenocarcinomas," *Clin Cancer Res.*, 10(22):7555-65 (2004).

(56) References Cited

OTHER PUBLICATIONS

Deng et al., "Pharmacokinetics of humanized monoclonal anti-tumor necrosis factor-{alpha} antibody and its neonatal Fc receptor variants in mice and cynomolgus monkeys," *Drug Metab Dispos.*, Apr. 2010;38(4):600-5. doi: 10.1124/dmd.109.031310. Epub Jan. 13, 2010.
Desjarlais et al., "Optimizing engagement of the immune system by anti-tumor antibodies: an engineer's perspective," *Drug Discov Today*, Nov. 2007; 12(21-22):898-910. Epub Oct. 22, 2007.
Haringman et al., "A randomized controlled trial with an anti-CCL2 (anti-monocyte chemotactic protein 1) monoclonal antibody in patients with rheumatoid arthritis," *Arthritis Rheum.*, 54(8):2387-92 (2006).
Juszczak et al., "Ipilimumab: a novel immunomodulating therapy causing autoimmune hypophysitis: a case report and review," *Eur J Endocrinol.*, Jul. 2012; 167(1):1-5. doi: 10.1530/EJE-12-0167. Epub Apr. 10, 2012.
Lewis et al., "Differential responses of human tumor cell lines to anti-p185HER2 monoclonal antibodies," *Cancer Immunol Immunother.*, 37(4):255-63 (1993).
Lutterbuese et al., "T cell-engaging BiTE antibodies specific for EGFR potently eliminate KRAS- and BRAF-mutated colorectal cancer cells," *Proc Natl Acad Sci USA*, Jul. 13, 2010; 107(28):12605-10. doi: 10.1073/pnas.1000976107. Epub Jun. 28, 2010.
Martin et al., "Preclinical safety and immune-modulatng effects of therapeutic monoclonal antibodies to interleukin-6 and tumor necrosis factor-α in cynomolgus macaques," *J Immunotoxicol.*, Jul. 1, 2004;1(3):131-9. doi:10.1080/15476910490894904.
Nam et al., "Current evidence for the management of rheumatoid arthritis with biological disease-modifying antirheumatic drugs: a systematic literature review informing the EULAR recommendations for the management of RA," *Ann Rheum Dis.*, Jun. 2010; 69(6):976-86. doi: 10.1136/ard.2009.126573. Epub May 6, 2010.
Nishimoto et al., "Mechanisms and pathologic significances in increase in serum interleukin-6 (IL-6) and soluble IL-6 receptor after administration of an anti-IL-6 receptor antibody, tocilizumab, in patients with rheumatoid arthritis and Castleman disease," *Blood*, Nov. 15, 2008;112(10):3959-64. doi: 10.1182/blood-2008-05-155846. Epub Sep. 10, 2008.
Petkova et al., "Enhanced half-life of genetically engineered human IgG1 antibodies in a humanized FcRn mouse model: potential application in humorally mediated autoimmune disease," *Int Immunol.*, 18(12):1759-69 (2006).
Reverberi et al., "Factors affecting the antigen-antibody reaction," *Blood Transfus.*, Nov. 2007; 5(4):227-40. doi: 10.2450/2007.0047-07.
Riechelmann et al., "Phase I trial with the CD44v6-targeting immunoconjugate bivatuzumab mertansine in head and neck squamous cell carcinoma," *Oral Oncol.*, Sep. 2008; 44(9):823-9. doi: 10.1016/j.oraloncology.2007.10.009. Epub Jan. 18, 2008.
Roopenian et al., "FcRn: the neonatal Fc receptor comes of age," *Nat Rev Immunol.*, 7(9):715-25 (2007).
Satoh et al., "Non-fucosylated therapeutic antibodies as next-generation therapeutic antibodies," *Expert Opin Biol Ther.*, 6(11):1161-73 (2006).
Takeuchi et al., "The Japanese experience with biologic therapies for rheumatoid arthritis," *Nat Rev Rheumatol.*, Nov. 2010; 6(11):644-52. doi: 10.1038/nrrheum.2010.154. Epub Sep. 28, 2010.
Trinh et al., "Ipilimumab in the treatment of melanoma," *Expert Opin Biol Ther.*, Jun. 2012; 12(6):773-82. doi: 10.1517/14712598.2012.675325. Epub Apr. 14, 2012.
Vaccaro et al., "Engineering the Fc region of immunoglobulin G to modulate in vivo antibody levels," *Nat Biotechnol.*, 23(10):1283-8 (2005).
Weiner et al., "Monoclonal antibodies: versatile platforms for cancer immunotherapy," *Nat Rev Immunol.*, May 2010; 10(5):317-27. doi: 10.1038/nri2744.
Xiao et al., "Pharmacokinetics of anti-hepcidin monoclonal antibody Ab 12B9m and hepcidin in cynomolgus monkeys," *AAPS J.*, Dec. 2010;12(4):646-57. doi: 10.1208/s12248-010-9222-0. Epub Aug. 25, 2010.
Zheng et al., "Translational pharmacokinetics and pharmacodynamics of an FcRn-variant anti-CD4 monoclonal antibody from preclinical model to phase I study," *Clin Pharmacol Ther.*, Feb. 2011; 89(2):283-90. doi: 10.1038/clpt.2010.311. Epub Dec. 29, 2010.
Cartron et al., "Therapeutic activity of humanized anti-CD20 monoclonal antibody and polymorphism in IgG Fc receptor FegammaRIIIa gene," *Blood*, 99(3):754-8 (2002).
Clynes et al., "Fc receptors are required in passive and active immunity to melanoma," *Proc Natl Acad Sci USA*, 95(2):652-6 (1998).
Clynes et al., "Inhibitory Fc receptors modulate in vivo cytotoxicity against tumor targets," *Nat Med.*, 6(4):443-6 (2000).
Desai et al "Fe gamma receptor IIB on dendritic cells enforces peripheral tolerance by inhibiting effector T cell responses," *J Immunol.*, 178(10):6217-26 (2007).
Horton et al., "Potent in vitro and in vivo activity of an Fc-engineered anti-CD19 monoclonal antibody against lymphoma and leukemia," *Cancer Res.*, Oct. 1, 2008;68(19):8049-57. doi: 10.1158/0008-5472.CAN-08-2268.
Lazar et al., "Engineered antibody Fc variants with enhanced effector function," *Proc Natl Acad Sci USA*, Mar. 14, 2006;103(11):4005-10. Epub Mar. 6, 2006.
Li et al., "Apoptotic and antitumor activity of death receptor antibodies require inhibitory Fcγ receptor engagement," *Proc Natl Acad Sci U S A.*, Jul. 3, 2012;109(27):10966-71. doi: 10.1073/pnas.1208698109. Epub Jun. 20, 2012.
Nimmerjahn et al., "Divergent immunoglobulin g subclass activity through selective Fc receptor binding," *Science*, 310(5753):1510-2 (2005).
Shinkawa et al., "The absence of fucose but not the presence of galactose or bisecting N-acetylglucosamine of human IgG1 complex-type oligosaccharides shows the critical role of enhancing antibody-dependent cellular cytotoxicity," *J Biol Chem.*, Jan. 31, 2003;278(5):3466-73. Epub Nov. 8, 2002.
Zalevsky et al., "Enhanced antibody half-life improves in vivo activity," *Nat Biotechnol.*Feb. 2010;28(2):157-9. doi: 10.1038/nbt.1601. Epub Jan. 17, 2010.
International Search Report for App. Ser. No. PCT/JP2013/054461, dated May 7, 2013, 7 pages.
International Preliminary Report on Patentability for App. Ser. No. PCT/JP2013/054461, dated Aug. 26, 2014, 6 pages.
International Search Report for App. Ser. No. PCT/JP2012/075092, dated Dec. 25, 2012, 4 pages.
International Preliminary Report on Patentability for App. Ser. No. PCT/JP2012/075092, dated Apr. 1, 2014, 10 pages.
Schuster et al., "Signaling of human ciliary neurotrophic factor (CNTF) revisited. The interleukin-6 receptor can serve as an alpha-receptor for CTNF," *J Biol Chem.*, Mar. 14, 2003;278(11):9528-35.
Clarkson et al., "Blockade of clearance of immune complexes by an anti-Fc gamma receptor monoclonal antibody," *J Exp Med.*, Aug. 1, 1986;164(2):474-89.
Prickett et al., "A calcium-dependent antibody for identification and purification of recombinant proteins," *Biotechniques*, Jun. 1989;7(6):580-9.
Schulke et al., "The homodimer of prostate-specific membrane antigen is a functional target for cancer therapy," *Proc Natl Acad Sci U S A.*, Oct. 28, 2003;100(22):12590-5.
Yarmush et al., "Immunoadsorption: strategies for antigen elution and production of reusable adsorbents," *Biotechnol Prog.*, May-Jun. 1992;8(3):168-78.
USPTO Non-Final Office Action in U.S. Appl. No. 13/889,484, dated Apr. 6, 2015, 12 pages.
International Search Report for App. Ser. No. PCT/JP2013/072507, dated Oct. 29, 2013, 4 pages.
International Preliminary Report on Patentability for App. Ser. No. PCT/JP2013/072507, dated Feb. 24, 2015, 6 pages.

(56) References Cited

OTHER PUBLICATIONS

Nordlund et al., "Introduction of histidine residues into avidin subunit interfaces allows pH-dependent regulation of quaternary structure and biotin binding," *FEBS Lett.*, Dec. 18, 2003;555(3):449-54.

Stearns et al., "The interaction of a Ca2+-dependent monoclonal antibody with the protein C activation peptide region. Evidence for obligatory Ca2+ binding to both antigen and antibody," *J Biol Chem.*, Jan. 15, 1988;263(2):826-32.

Ward et al., "A calcium-binding monoclonal antibody that recognizes a non-calcium-binding epitope in the short consensus repeat units (SCRs) of complement C1r," *Mol Immunol.*, Jan. 1992;29(1):83-93.

USPTO Restriction Requirement in U.S. Appl. No. 14/347,034, dated Dec. 18, 2014, 9 pages.

Fish & Richardson P.C., Reply to Restriction Requirement dated Dec. 18, 2014 in U.S. Appl. No. 14/347,034, filed Mar. 18, 2015, 2 pages.

USPTO Non-Final Office Action in U.S. Appl. No. 14/347,034, dated Apr. 16, 2015, 9 pages.

Janeway et al., Immunobiology, The Immune System in Health and Disease, 3$^{rd}$ Edition, 1997 Garland Publishing Inc., pp. 3:1-3:11.

Patton et al., "An acid dissociation bridging ELISA for detection of antibodies directed against therapeutic proteins in the presence of antigen," *J Immunol Methods*, Sep. 2005;304(1-2):189-95.

Rudikoff et al., "Single amino acid substitution altering antigen-binding specificity," *Proc Natl Acad Sci USA.*, Mar. 1982;79(6):1979-83.

USPTO Restriction Requirement in U.S. Appl. No. 13/637,415, dated Dec. 31, 2014, 8 pages.

Fish & Richardson P.C., Reply to Restriction Requirement dated Dec. 31, 2014 in U.S. Appl. No. 13/637,415, filed Feb. 25, 2015, 1 page.

USPTO Non-Final Office Action in U.S. Appl. No. 13/637,415, dated May 13, 2015, 24 pages.

Horn et al., "Analysis of the binding of pro-urokinase and urokinase-plasminogen activator inhibitor-1 complex to the low density lipoprotein receptor-related protein using a Fab fragment selected from a phage-displayed Fab library," *J Biol Chem.*, May 19, 1995;270(20):11770-5.

Malbec et al., "Antibodies against growth factor receptors can inhibit the proliferation of transformed cells via a cis-interaction with inhibitory FcR," *Immunol Lett.*, Mar. 30, 2012;143(1):28-33.

Wenink et al., "The inhibitory Fc gamma IIb receptor dampens TLR4-mediated immune responses and is selectively up-regulated on dendritic cells from rheumatoid arthritis patients with quiescent disease," *J Immunol.*, Oct. 1, 2009;183(7):4509-20. doi: 10.4049/jimmunol.0900153. Epub Sep. 4, 2009.

Zhang et al., "Immune complex/Ig negatively regulate TLR4-triggered inflammatory response in macrophages through Fc gamma RIIb-dependent PGE2 production," *J Immunol.*, Jan. 1, 2009;182(1):554-62.

Ejima et al., "Effective elution of antibodies by arginine and arginine derivatives in affinity col. chromatography," *Anal Biochem.*, Oct. 15, 2005;345(2):250-7.

Rojas et al., "Formation, distribution, and elimination of infliximab and anti-infliximab immune complexes in cynomolgus monkeys," *J Pharmacol Exp Ther.*, May 2005;313(2):578-85. Epub Jan. 12, 2005.

Singer et al., "Genes & Genomes," Moscow, "Mir," 1998;1:63-64.

USPTO Interview Summary in U.S. Appl. No. 14/347,034, dated Aug. 17, 2015, 3 pages.

Fish & Richardson P.C., Amendment and Reply to Office Action dated Apr. 6, 2015 in U.S. Appl. No. 13/889,484, filed Jul. 6, 2015, 14 pages.

USPTO Final Office Action in U.S. Appl. No. 13/889,484, dated Aug. 4, 2015, 12 pages.

Fish & Richardson P.C., Reply to Non-Final Office Action dated Apr. 16, 2015 in U.S. Appl. No. 14/347,034, filed Sep. 16, 2015, 28 pages.

Fish & Richardson P.C., Reply to Non-Final Office Action dated May 13, 2015 in U.S. Appl. No. 13/637,415, filed Aug. 13, 2015, 21 pages.

Amersham Biosciences, "Antibody Purification Handbook," Edition 18-1037-46 [online], [retrieved on Nov. 5, 2015]. Retrieved from the Internet: http://www.promix.ru/manuf/ge/chrom/lit/Antibody_Purification.pdf.

GE Healthcare. Application note 28-9277-92 AA. "High-throughput screening of elution pH for monoclonal antibodies on MabSelect SuRe using PreDictor plates" [online], [retrieved on Nov. 5, 2015]. Retrieved from the Internet: https://www.gelifesciences.com/gehcls_images/GELS/Related%20Content/Files/1314787424814/litdoc28927792AA_20110831131840.pdf.

Mimoto et al., "Engineered antibody Fc variant with selectively enhanced FcγRIIb binding over both FcγRIIa(R131) and FcγRIIa(H131)," *Protein Eng Des Sel.*, Oct. 2013;26(10):589-98. doi: 10.1093/protein/gzt022. Epub Jun. 5, 2013.

Balint et al., "Antibody engineering by parsimonious mutagenesis," *Gene.*, Dec. 27, 1993;137(1):109-18.

Batra et al., "Pharmacokinetics and biodistribution of genetically engineered antibodies," *Curr Opin Biotechnol.*, Dec. 2002;13(6):603-8.

Bruhns, "Properties of mouse and human IgG receptors and their contribution to disease models," *Blood*, Jun. 14, 2012;119(24):5640-9. doi: 10.1182/blood-2012-01-380121. Epub Apr. 25, 2012.

Burmeister et al., "Crystal structure of the complex of rat neonatal Fc receptor with Fc," *Nature*, Nov. 24, 1994;372(6504):379-83.

Hjelm et al., "Antibody-mediated regulation of the immune response," *Scand J Immunol.*, Sep. 2006;64(3):177-84.

Idusogie et al., "Mapping of the C1q binding site on rituxan, a chimeric antibody with a human IgG1 Fc," *J Immunol.*, Apr. 15, 2000;164(8):4178-84.

Kamei et al., "Quantitative methods for developing Fc mutants with extended half-lives," *Biotechnol Bioeng.*, Dec. 20, 2005;92(6):748-60.

Palladino et al., "Anti-TNF-alpha therapies: the next generation," *Nat Rev Drug Discov.*, Sep. 2003;2(9):736-46.

Radaev et al., "The structure of a human type III Fcgamma receptor in complex with Fc," *J Biol.Chem.*, May 11, 2001;276(19):16469-77. Epub Jan. 31, 2001.

Sondermann et al., "The 3.2-A crystal structure of the human IgG1 Fc fragment-Fc gammaRIII complex," *Nature*, Jul. 20, 2000;406(6793):267-73.

USPTO Final Office Action in U.S. Appl. No. 13/637,415, dated Nov. 13, 2015, 20 pages.

Fish & Richardson P.C., Reply to Final Office Action dated Oct. 16, 2015 in U.S. Appl. No. 14/347,034, filed Jan. 13, 2016, 28 pages.

Fish & Richardson P.C., Reply to Final Office Action dated Aug. 4, 2015 in U.S. Appl. No. 13/889,484, filed Dec. 2, 2015, 104 pages.

International Search Report for App. Ser. No. PCT/JP2014/059706, dated Jul. 15, 2014, 4 pages.

International Preliminary Report on Patentability for App. Ser. No. PCT/JP2014/059706, dated Oct. 6, 2015, 10 pages.

USPTO Notice of Allowance in U.S. Appl. No. 14/347,034, dated Feb. 17, 2016, 6 pages.

Tarditi et al., "Selective high-performance liquid chromatographic purification of bispecific monoclonal antibodies," J. Chromatogr., 599(1-2):13-20 (1992).

Zalevsky et al., "The impact of Fc engineering on an anti-CD19 antibody: increased Fcgamma receptor affinity enhances B-cell clearing in nonhuman primates," *Blood*, 113(16):3735-43 (2009) Epub Dec. 24, 2008.

Fish & Richardson P.C., Reply to Final Office Action dated Nov. 13, 2015 in U.S. Appl. No. 13/637,415, filed May 12, 2016, 22 pages.

USPTO Notice of Allowance in U.S. Appl. No. 14/347,034, dated Jun. 3, 2016, 5 pages.

Idusogie et al., "Engineered antibodies with increased activity to recruit complement," *J Immunol.*, Feb. 15, 2001;166(4):2571-5.

Beringhelli et al., "pH and ionic strength dependence of protein (un)folding and ligand binding to bovine beta-lactoglobulins A and B," *Biochemistry*, Dec. 24, 2002;41(51):15415-22.

Epstein, "Non-randomness of amino-acid changes in the evolution of homologous proteins," *Nature*, Jul. 22, 1967;215(5099):355-9.

(56) References Cited

OTHER PUBLICATIONS

Luttrell et al., "Reaction coupling of chelation and antigen binding in the calcium ion-dependent antibody binding of cyclic AMP," *J Biol Chem.*, Nov. 15, 1991;266(32):21626-30.
Beck et al., "Strategies and challenges for the next generation of therapeutic antibodies," *Nat Rev Immunol.*, 10(5):345-52 (2010).
Chaparro-Riggers et al., "Increasing serum half-life and extending cholesterol lowering in vivo by engineering antibody with pH-sensitive binding to PCSK9," *J Biol Chem.*, 287(14):11090-7 (2012).
Devanaboyina et al., "The effect of pH dependence of antibody-antigen interactions on subcellular trafficking dynamics," *MAbs*, 5(6):851-9 (2013).
Feinberg et al., "Mechanism of pH-dependent N-acetylgalactosamine binding by a functional mimic of the hepatocyte asialoglycoprotein receptor," *J Biol Chem.*, 275(45):35176-84 (2000).
Finkelman et al., "Anti-cytokine antibodies as carrier proteins. Prolongation of in vivo effects of exogenous cytokines by injection of cytokine-anti-cytokine antibody complexes," *J Immunol.*, 151(3):1235-44 (1993).
Igawa et al., "Engineered monoclonal antibody with novel antigen-sweeping activity in vivo," *PLoS One*, 8(5):e63236 (2013).
Igawa et al., "Antibody recycling by engineered pH-dependent antigen binding improves the duration of antigen neutralization," *Nat Biotechnol.*, 28(11):1203-7 (2010).
Lee et al., "High-affinity human antibodies from phage-displayed synthetic Fab libraries with a single framework scaffold," *J Mol Biol.*, 340(5):1073-93 (2004).
Murtaugh et al., "A combinatorial histidine scanning library approach to engineer highly pH-dependent protein switches," *Protein Sci.*, 20(9):1619-31 doi:10.1002/pro 696 (2011).
Sarkar et al., "Rational cytokine design for increased lifetime and enhanced potency using pH-activated histidine switching," *Nat Biotechnol.*, 20(9):908-13 (2002).
Tabrizi et al., "Elimination mechanisms of therapeutic monoclonal antibodies," *Drug Discov Today*, 11(1-2):81-8 (2006).
Vaughn et al., "Structural basis of pH-dependent antibody binding by the neonatal Fc receptor," *Structure*, 6(1):63-73 (1998).
Yamamoto et al., "Molecular studies of pH-dependent ligand interactions with the low-density lipoprotein receptor," *Biochemistry*, 47(44):11647-52 (2008).
Hinton et al., "Engineered human IgG antibodies with longer serum half-lives in primates," *J. Biol. Chem.*, 279(8):6213-6 (2004).
Igawa et al., "Antibody optimization technologies for developing next generation antibody therapeutics," *Bio Industry*, 28(7):15-21 (2011) (with English translation).
Ishii et al., "FcRn, a critical regulator of antibody pharmacokinetics," *Folia Pharmacol. Jpn.*, 136(5):280-284 (2010) (with English translation).
Ito et al., "The His-probe method: effects of histidine residues introduced into the complementarity-determining regions of antibodies on antigen-antibody interactions at different pH values," *FEBS Lett.*, 309:85-88 (1992).
Sigma-Aldrich, "Product Information: Monoclonal Anti-Flag ® M1, Clone M1 produced in mouse, purified immunoglobulin," Sigma-Aldrich.com, Catalog No. F3040. Retrieved from the Internet on Nov. 5, 2003 at: http://sigmaaldrich.com/content/dam/sigma-aldrich/does/Sigma/Datasheet/f3040dat.pdf.
Wojciak et al., "The crystal structure of sphingosine-1-phosphate in complex with a Fab fragment reveals metal bridging of an antibody and its antigen," *Proc Natl Acad Sci U S A.*, 106(42):17717-22 (2009).
Zhou et al., "Interfacial metal and antibody recognition," *Proc Natl Acad Sci U S A.*, 102(41):14575-80 (2005).
International Search Report for App. Ser. No. PCT/JP2011/077619, dated Feb. 28, 2012, 4 pages.
International Preliminary Report on Patentability for App. Ser. No. PCT/JP2011/077619, dated Jun. 4, 2013, 8 pages.
Adams et al., "Humanization of a recombinant monoclonal antibody to produce a therapeutic HER dimerization inhibitor, pertuzumab," *Cancer Immunol. Immunother.*, 55:717-727 (2006).
Amersham Biosciences, "Affinity Chromatography: Principles and Methods," Edition AD, pp. 16-18, 137 (2002).
Bartelds et al., "Clinical response to adalimumab: relationship to anti-adalimumab antibodies and serum adalimumab concentrations in rheumatoid arthritis," *Ann Rheum. Dis.*, 66:921-926 (2007).
Bender et al., "Immunogenicity, efficacy and adverse events of adalimumab in RA patients," *Rheumatol. Int.*, 27:269-274 (2007).
Binz et al., "Engineering novel binding proteins from nonimmunoglobulin domains," *Nat. Biotechnol.*, 23:1257-68 (2005).
Brown et al., "Tolerance of single, but not multiple, amino acid replacements in antibody $V_H$ CDR2: a means of minimizing B cell wastage from somatic hypermutation?," *J. Immunol.*, 156(9):3285-91 (1996).
Chirino et al., "Minimizing the immunogenicity of protein therapeutics," *Drug Discov. Today.*, 9:82-90 (2004).
Couto et al., "Anti-BA46 Monoclonal Antibody Mc3: Humanization Using a Novel Positional Consensus and in Vivo and in Vitro Characterization," *Cancer Res.*, 55:1717-22 (1995).
Dall'Acqua et al., "Increasing the affinity of a human IgG1 for the neonatal Fc receptor: biological consequences," *J. Immunol.*, 169(9):5171-80 (2002).
Dall'Acqua et al., "Antibody humanization by framework shuffling," *Methods*, 36(1):43-60 (2005).
Ewert et al., "Stability improvement of antibodies for extracellular and intracellular applications: CDR grafting to stable frameworks and structure-based framework engineering," *Methods*, 34:184-199 (2004).
Ghetie et al., "FcRn: the MHC class I-related receptor that is more than an IgG transporter," *Immunol. Today*, 18:592-598 (1997).
Ghetie et al., "Increasing the serum persistence of an IgG fragment by random mutagenesis," *Nat. Biotechnol.*, 15(7):637-40 (1997).
Gobburu et al., "Pharmacokinetics/dynamics of 5c8, a monoclonal antibody to CD154 (CD40 ligand) suppression of an immune response in monkeys," *J. Pharmacol. Exp. Ther.*, 286:925-930 (1998).
Graves et al., "Molecular modeling and preclinical evaluation of the humanized NR-LU-13 antibody," *Clin. Cancer Res.*, 5:899-908 (1999).
Hamilton, "Molecular engineering: applications to the clinical laboratory," *Clin. Chem.*, 39(9):1988-97 (1993).
Hanson et al., "Catalytic antibodies and their applications," *Curr. Opin. Biotechnol.*, 16:631-636 (2005).
He et al., "Humanization and pharmacokinetics of a monoclonal antibody with specificity for both E- and P-selectin," *J. Immunol.*, 160:1029-35 (1998).
Hinton et al., "An engineered human IgG1 antibody with longer serum half-life," *J. Immunol.*, 176(1):346-56 (2006).
Hwang et al., "Use of human germline genes in a CDR homology-based approach to antibody humanization," Methods, 36:35-42 (2005).
Johnson et al., "Cation exchange-HPLC and mass spectrometry reveal C-terminal amidation of an IgG1 heavy chain," *Anal. Biochem.*, 360:75-83 (2007).
Jones et al., "Identification and removal of a promiscuous CD4+ T cell epitope from the C1 domain of factor VIII," *Thromb. Haemost.*, 3:991-1000 (2005).
Kashmiri et al., "Generation, characterization, and in vivo studies of humanized anticarcinoma antibody CC49," *Hybridoma*, 14:461-473 (1995).
Kim et al., "Antibody Engineering for the Development of Therapeutic Antibodies," Mol. Cells, 20:17-29 (2005).
Lobo et al., "Antibody pharmacokinetics and pharmacodynamics," *J. Pharm. Sci.*, 93:2645-68 (2004).
MacCallum et al., "Antibody-antigen interactions: contact analysis and binding site topography," *J. Mol. Biol.*, 262:732-45 (1996).
Maini et al., "Double-blind randomized controlled clinical trial of the interleukin-6 receptor antagonist, tocilizumab, in European patients with rheumatoid arthritis who had an incomplete response to methotrexate," Arthritis Rheum., 54:2817-29 (2006).
Nishimoto et al., "Humanized anti-interleukin-6 receptor antibody treatment of multicentric Castleman disease," *Blood*, 106:2627-32 (2005).

(56) References Cited

OTHER PUBLICATIONS

Nishimoto et al., "Interleukin 6: from bench to bedside," *Nat. Clin. Pract. Rheumatol.*, 2:619-626 (2006).
Onda et al., "Lowering the Isoelectric Point of the Fv Portion of Recombinant Immunotoxins Leads to Decreased Nonspecific Animal Toxicity without Affecting Antitumor Activity," Cancer Res., 61:5070-77 (2001).
Pakula et al., "Genetic Analysis of Protein Stability and Function," Annu. Rev. Genet., 23:289-310 (1989).
Pavlou et al., "The therapeutic antibodies market to 2008," *Eur. J. Pharm. Biopharm.*, 59:389-396 (2005).
Poduslo et al., "Polyamine modification increases the permeability of proteins at the blood—nerve and blood-brain barriers," *J. Neurochem.*, 66:1599-1609 (1996).
Rajpal et al., A general method for greatly improving the affinity of antibodies by using combinatorial libraries, Proc. Natl. Acad. Sci. USA, 102:8466-71 (2005).
Rathanaswami et al., "Demonstration of an in vivo generated sub-picomolar affinity fully human monoclonal antibody to interleukin-8," Biochem. Biophys. Res. Commun., 334:1004-13 (2005).
Reichert et al., "Monoclonal antibody successes in the clinic," *Nat. Biotechnol.*, 23:1073-78 (2005).
Rich et al., "Grading the commercial optical biosensor literature—Class of 2008: 'The Mighty Binders'," *J. Mol. Recognit.*, 23(1):1-64 (2010). doi: 10.1002/jmr.1004.
Roitt et al., Immunology, M., Mir, (2000), pp. 110-111 (in Russian, with what is believed to be a published English equivalent of those pages taken from Roitt et al., "Antibody Structure and Function," Immunology, Fifth Ed., (1998), pp. 80-81).
Rothe et al., "Ribosome display for improved biotherapeutic molecules," *Expert Opin. Biol. Ther.*, 6:177-187 (2006).
Salfeld et al., "Isotype selection in antibody engineering," *Nat. Biotechnol.*, 25:1369-72 (2007).
Sato et al., "Reshaping a human antibody to inhibit the interleukin 6-dependent tumor cell growth," *Cancer Res.*, 53:851-856 (1993).
Shields et al., "High resolution mapping of the binding site on human IgG1 for Fc gamma RI, Fc gamma RII, Fc gamma RIII, and FcRn and design of IgG1 variants with improved binding to the Fc gamma R," J. Biol. Chem., 276:6591-6604 (2001) (Epub Nov. 28, 2000).
Shire et al., "Challenges in the development of high protein concentration formulations," *J. Pharm. Sci.*, 93:1390-1402 (2004).
Strand et al., "Biologic therapies in rheumatology: lessons learned, future directions," *Nat. Rev. Drug Discov.*, 6:75-92 (2007).
Suzuki et al., "Importance of neonatal FcR in regulating the serum half-life of therapeutic proteins containing the Fc domain of human IgG1: a comparative study of the affinity of monoclonal antibodies and Fc-fusion proteins to human neonatal FcR," *J. Immunol.*, 184(4):1968-76 (2010).
Tsurushita et al., "Design of humanized antibodies: From anti-Tac to Zenapax," *Methods*, 36:69-83 (2005).
Wu et al., "Development of motavizumab, an ultra-potent antibody for the prevention of respiratory syncytial virus infection in the upper and lower respiratory tract," *J Mol. Biol.*, 368:652-665 (2007).
Xiang et al., "Study of B72.3 combining sites by molecular modeling and site-directed mutagenesis," *Protein Eng.*, 13(5):339-44 (2000).
Yamasaki et al., "Pharmacokinetic analysis of in vivo disposition of succinylated proteins targeted to liver nonparenchymal cells via scavenger receptors: importance of molecular size and negative charge density for in vivo recognition by receptors," *J. Pharmacol. Exp. Ther.*, 301:467-477 (2002).
Yang et al., "CDR walking mutagenesis for the affinity maturation of a potent human anti-HIV-1 antibody into the picomolar range," *J. Mol. Biol.*, 254(3):392-403 (1995).
Yeung et al., "Engineering human IgG1 affinity to human neonatal Fc receptor: impact of affinity improvement on pharmacokinetics in primates," *J. Immunol.*, 182(12):7663-71 (2009).
Zalevsky et al., "Enhanced antibody half-life improves in vivo activity," *Nat. Biotechnol.*, 28(2):157-9 (2010).
Zhu et al., "MHC class I-related neonatal Fc receptor for IgG is functionally expressed in monocytes, intestinal macrophages, and dendritic cells," *J. Immunol.*, 166(5):3266-76 (2001).
Zuckier et al., "Chimeric human-mouse IgG antibodies with shuffled constant region exons demonstrate that multiple domains contribute to in vivo half-life," Cancer Res., 58:3905-08 (1998).
International Search Report for App. Ser. No. PCT/JP2011/001888, dated Nov. 2, 2011, 7 pages.
USPTO Restriction Requirement in U.S. Appl. No. 12/295,039, dated Oct. 12, 2010, 9 pages.
Fish & Richardson P.C., Response to Restriction Requirement dated Oct. 12, 2010 in U.S. Appl. No. 12/295,039, filed Apr. 11, 2011, 9 pages.
USPTO Non-Final Office Action in U.S. Appl. No. 12/295,039, dated Jun. 28, 2011, 9 pages.
Fish & Richardson P.C., Amendment in Reply to Action dated Jun. 28, 2011 in U.S. Appl. No. 12/295,039, filed Dec. 27, 2011, 14 pages.
USPTO Final Office Action in U.S. Appl. No. 12/295,039, dated Apr. 12, 2012, 8 pages.
Fish & Richardson P.C., Amendment in Reply to Action dated Apr. 12, 2012 in U.S. Appl. No. 12/295,039, filed Sep. 11, 2012, 12 pages.
USPTO Restriction Requirement in U.S. Appl. No. 12/679,922, dated Oct. 2, 2012, 9 pages.
Fish & Richardson P.C., Response to Restriction Requirement dated Oct. 2, 2012 in U.S. Appl. No. 12/679,922, filed Nov. 1, 2012, 2 pages.
USPTO Non-Final Office Action in U.S. Appl. No. 12/679,922, dated Jan. 3, 2013, 25 pages.
Fish & Richardson P.C., Amendment in Reply to Action dated Jan. 3, 2013 in U.S. Appl. No. 12/679,922, filed Jul. 2, 2013, 18 pages.
USPTO Final Office Action in U.S. Appl. No. 12/679,922, dated Aug. 2, 2013, 12 pages.
USPTO Restriction Requirement in U.S. Appl. No. 12/936,587, dated Dec. 6, 2011, 7 pages.
Fish & Richardson P.C., Third Preliminary Amendment and Response to Restriction Requirement dated Dec. 6, 2011 in U.S. Appl. No. 12/936,587, filed Jun. 5, 2012, 7 pages.
USPTO Restriction Requirement in U.S. Appl. No. 12/936,587, dated Jun. 25, 2012, 5 pages.
Fish & Richardson P.C., Response to Species Election Requirement dated Jun. 25, 2012 in U.S. Appl. No. 12/936,587, filed Jul. 25, 2012, 1 page.
USPTO Non-Final Office Action in U.S. Appl. No. 12/936,587, dated Nov. 7, 2012, 13 pages.
USPTO Non-Final Office Action in U.S. Appl. No. 13/595,139, dated Nov. 14, 2012, 10 pages.
Fish & Richardson P.C., Amendment in Reply to Office Action dated Nov. 14, 2012 in U.S. Appl. No. 13/595,139, filed May 14, 2013, 19 pages.
USPTO Final Office Action in U.S. Appl. No. 13/595,139, dated Aug. 1, 2013, 8 pages.
USPTO Notice of Allowance in U.S. Appl. No. 13/595,139, dated Oct. 11, 2013, 15 pages.
International Preliminary Report on Patentability for App. Ser. No. PCT/JP2012/058603, dated Oct. 8, 2013, 11 pages.
Algonomics—TripoleR applications [Online] Retrieved from the Internet on Feb. 29, 2012: http://www.algonomics.com/proteinengineering/tripole_applications.php, 2 pages (Feb. 21, 2009).
Almagro et al., "Humanization of antibodies," Front Biosci. Jan. 1, 2008;13:1619-33.
Armour et al., "Recombinant human IgG molecules lacking Fcγ receptor I binding and monocyte triggering activities," Eur J Immunol. Aug. 1999;29(8):2613-24.
Bayry et al., "Immuno affinity purification of foot and mouth disease virus type specific antibodies using recombinant protein absorbed to polystyrene wells," J Virol Methods. Aug. 1999;81(1-2):21-30.
Biasini et al., "Immunopurification of pathological prion protein aggregates," *PLoS One*, Nov. 12, 2009;4(11):e7816. doi: 10.1371/journal.pone.0007816.

(56) References Cited

OTHER PUBLICATIONS

Brown et al., "A study of the interactions between an IgG-binding domain based on the B domain of staphylococcal protein A and rabbit IgG," Mol Biotechnol., Aug. 1998;10(1):9-16.

Chau et al., "HuM291(Nuvion), a humanized Fc receptor-nonbinding antibody against CD3, anergizes peripheral blood T cells as partial agonist of the T cell receptor," Transplantation. Apr. 15, 2001;71(7):941-50.

Chen et al., "Generation and Analysis of Random Point Mutations in an Antibody CDR2 Sequence: Many Mutated Antibodies Lose Their Ability to Bind Antigen ,"J Exp Med. Sep. 1, 1992;176(3):855-66.

Chen et al., "Defective Secretion of an Immunoglobulin Caused by Mutations in the Heavy Chain Complementarity Determining Region 2," Exp Med. Aug. 1, 1994;180(2):577-86.

Chen et al., "Selection and analysis of an optimized anti-VEGF antibody: crystal structure of an affinity-matured Fab in complex with antigen," J Mol Biol., Nov. 5, 1999;293(4):865-81.

Chu et al., "Accumulation of Succinimide in a Recombinant Monoclonal Antibody in Mildly Acidic Buffers Under Elevated Temperatures," Pharm Res. Jun. 2007;24(6):1145-56. Epub Mar. 24, 2007.

Cole et al., "Human IgC2 Variants of Chimeric Anti-CD3 Are Nonmitogenic to T Cells," J Immunol. Oct. 1, 1997;159(7):3613-21.

Coloma et al., "Position effects of variable region carbohydrate on the affinity and in vivo behavior of an anti-(1—>6) dextran antibody," J Immunol., Feb. 15, 1999;162(4):2162-70.

Comper et al., "Charge selectivity in kidney ultrafiltration," Kidney Int. May 1995;47(5):1242-51.

Cordoba et al., "Non-enzymatic hinge region fragmentation of antibodies in solution," J Chromatogr B Analyt Technol Biomed Life Sci. Apr. 25, 2005;818(2):115-21.

Cuatrecasas et al "Affinity Chromatography", Methods Enzymol., 1971;12:345-78.

Damschroder et al., "Framework shuffling of antibodies to reduce immunogenicity and manipulate functional and biophysical properties," Mol Immunol. Apr. 2007; 44(11):3049-60. Epub Jan. 22, 2007.

Declaration of Nimish Gem, Ph.D., CV and Exhibits, dated Sep. 1, 2016, 24 pages.

De Groot et al., "De-immunization of Therapeutic Proteins by T-cell Epitope Modification," Dev Biol (Basel). 2005;122:171-94.

Deen et al., "Structural determinants of glomerular permeability," Am J Physiol Renal Physiol. Oct. 2001;281(4):F579-96.

Del Rio et al., "An engineered penicillin acylase with altered surface charge is more stable in alkaline pH," Ann N Y Acad Sci. Oct. 12, 1996;799:61-4.

Dufner et al., "Harnessing phage and ribosome display for antibody optimization," Trends Biotechnol., Nov. 2006;24(11):523-9. Epub Sep. 26, 2006.

Durkee et al., "Immunoaffinity Chromatographic Purification of Russell's Viper Venom Factor X Activator Using Elution in High Concentrations of Magnesium Chloride," Protein Expr Purif. Oct. 1993;4(5):405-11.

Fillipovich, Biochemical basis of human life, VLADOS, 2005:49-50 (with English translation).

Fujii, "Antibody affinity maturation by random mutagenesis," Methods Mol Biol. 2004;248:345-59.

Gerstner et al., "Sequence Plasticity in the Antigen-binding Site of a Therapeutic Anti-HER2 Antibody," J Mol Biol. Aug. 30, 2002;321(5):851-62.

Gessner et al., "The IgG Fc receptor family," Ann Hematol. Jun. 1998;76(6):231-48.

Ghetie et al., "Multiple roles for the major histocompatibility complex class I-related receptor FcRn," Annu Rev Immunol. 2000;18:739-66.

Goode et al., The glomerular basement membrane charge-selectivity barrier: an oversimplified concept? Nephrol Dial Transplant. Sep. 1996;11(9):1714-6.

Guyre et al., "Increased potency of Fc-receptor-targeted antigens," Cancer Immunol Immunother. Nov.-Dec. 1997;45(3-4):146-8.

Hird et al., "Tumour localisation with a radioactively labelled reshaped human monoclonal antibody," Br J Cancer, Nov. 1991;64(5):911-4.

Hironiwa et al., "Calcium-dependent antigen binding as a novel modality for antibody recycling by endosomal antigen dissociation," MAbs. Jan. 2016;8(1):65-73. doi: 10.1080/19420862.2015.1110660. Epub Oct. 23, 2015.

Hong et al., "Enhanced cellular uptake and transport of polyclonal immunoglobulin G and fab after their cationization," J Drug Target., 2000;8(2):67-77.

Igawa et al., "Engineering the variable region of therapeutic IgG antibodies," MAbs. May-Jun. 2011;3(3):243-52. Epub May 1, 2011.

Junghans et al., "The protection receptor for IgG catabolism is the beta2-microglobulin-containing neonatal intestinal transport receptor," Proc Natl Acad Sci U S A., May 28, 1996;93(11):5512-6.

Katayose et al., "MUC1-specific targeting immunotherapy with bispecific antibodies' inhibition of xenografted human bile duct carcinoma growth," Cancer Res. Sep. 15, 1996;56(18):4205-12.

Khawli et al., "Improved tumor localization and radioimaging with chemically modified monoclonal antibodies," Cancer Biother Radiopharm. Jun 1996;11(3):203-15.

Kim et al., "Lowering of pI by acylation improves the renal uptake of 99mTc-labeled anti-Tac dsFv: effect of different acylating reagents," Nucl Med Biol. Nov. 2002;29(8):795-801.

Kim et al., "Chemical modification to reduce renal uptake of disulfide-bonded variable region fragment of anti-Tac monoclonal antibody labeled with 99mTc," Bioconjug Chem. May-Jun. 1999;10(3):447-53.

Kobayashi et al., "A monoclonal antibody specific for a distinct region of hen egg-white lysozyme," Mol Immunol. Apr. 1982;19(4):619-30.

Kobayashi et al., "The pharmacokinetic characteristics of glycolated humanized anti-Tac Fabs are determined by their isoelectric points," Cancer Res. Jan. 15, 1999;59(2):422-30.

Komissarov et al., "Site-specific Mutagenesis of a Recombinant Anti-single-stranded DNA Fab Role of Heavy Chain Complementarity- Determining Region 3 Residues in Antigen Interaction," J Biol Chem. Oct. 24, 1997;272(43):26864-70.

Laitinen et al., "Brave new (strept)avidins in biotechnology," Trends Biotechnol., Jun. 2007;25(6):269-77. Epub Apr. 12, 2007.

Leong et al., "Adapting pharmacokinetic properties of a humanized anti-interleukin-8 antibody for therapeutic applications using site-specific pegylation," Cytokine. Nov. 7, 2001;16(3):106-19.

Li et al., "Construction and characterization of a humanized anti-human CD3 monoclonal antibody 12F6 with effective immunoregulation functions," Immunology, Dec. 2005;116(4):487-98.

Linder et al., "Design of a pH-dependent cellulose binding domain," FEBS Lett., Mar. 19, 1999;447(1):13-6.

Liu et al., "Heterogeneity of Monoclonal Antibodies," J Pharm Sci. Jul. 2008;97(7):2426-47.

Maeda et al., "pH-dependent receptor/ligand dissociation as a determining factor for intracellular sorting of ligands for epidermal growth factor receptors in rat hepatocytes," J Control Release. Jul. 18, 2002;82(1):71-82.

Maier et al., "Assessment of fully automated antibody homology modeling protocols in molecular operating environment," Proteins. Aug. 2014;82(8):1599-610. doi: 10.1002/prot.24576. Epub Apr. 23, 2014.

Marshall et al., "Rational design and engineering of therapeutic proteins," Drug Discov Today., Mar. 1, 2003;8(5):212-21.

Martin et al., "Crystal structure at 2.8 A of an FcRn/heterodimeric Fc complex: mechanism of pH-dependent binding," Mol Cell. Apr. 2001;7(4):867-77.

Matsumiya et al., "Structural comparison of fucosylated and nonfucosylated Fc fragments of human immunoglobulin G1," J Mol Biol., May 4, 2007;368(3):767-79. Epub Feb. 22, 2007.

Matsunaga et al., "A pH-dependent conformational transition of Abeta peptide and physicochemical properties of the conformers in the glial cell," Biochem J. Feb. 1, 2002;361(Pt 3):547-56.

Maxfield et al., "Endocytic recycling," Nat Rev Mol Cell Biol. Feb. 2004;5(2):121-32.

Mohan et al, CALBIOCHEM Buffers, "A guide for the preparation and use of buffers in biological systems," by Chandra Mohan,

(56) References Cited

OTHER PUBLICATIONS

Ph.D., Copyright 2003 EMD Biosciences, Inc., an Affliate of Merck K GaA, Darmastadt, Germany, 37 pages (CALBIOCHEM Buffers Booklet, 2003).
Moore et al., "Engineered Fc variant antibodies with enhanced ability to recruit complement and mediate effector functions," MAbs., Mar.-Apr. 2010;2(2):181-9.
Nesierova et al., AACR Abstract No. 656 (2007), Los Angeles, CA (Apr. 4-18, 2007), 3 pages.
Ono et al., "The humanized anti-HM1.24 antibody effectively kills multiple myeloma cells by human effector cell-mediated cytotoxicity," Mol Immunol. Apr. 1999;36(6):387-95.
Ozhegov et al., Tolkovyi Slovar Russkogo iazyka: 2004, p. 292 (with an English translation of the relevant passage defining "control").
Pardridge et al., "Enhanced Endocytosis in Cultured Human Breast Carcinoma Cells and In Vivo Biodistribution in Rats of a Humanized Monoclonal Antibody after Cationization of the Protein," J Pharmacol Exp Ther. Jul. 1998;286(1):548-54.
Pardridge et al., "Enhanced cellular uptake and in vivo biodistribution of a monoclonal antibody following cationization," J Pharm Sci., Aug. 1995;84(8):943-8.
Pavlinkova et al., "Charge-Modified Single Chain Antibody Constructs of Monoclonal Antibody CC49: Generation, Characterization, Pharmacokinetics, and Biodistribution Analysis," Nucl Med Biol. Jan. 1999;26(1):27-34.
Pons et al., "Energetic analysis of an antigen/antibody interface: Alanine scanning mutagenesis and double mutant cycles on the HyHEL-10/lysozyme interaction," Protein Sci. May 1999;8(5):958-68.
Presta, "Engineering of therapeutic antibodies to minimize immunogenicity and optimize function," Adv Drug Deliv Rev. Aug. 7, 2006; 58(5-6):640-56. Epub May 23, 2006.
Reddy et al., "Elimination of Fc Receptor-Dependent Effector Functions of a Modified IgG4 Monoclonal Antibody to Human CD4," J Immunol. Feb. 15, 2000;164(4):1925-33.
Reichert et al., "Development trends for monoclonal antibody cancer therapeutics," Nat Rev Drug Discovery May 2007;6(5):349-56.
Reimann et al., "A humanized form of a CD4-specific monoclonal antibody exhibits decreased antigenicity and prolonged plasma half-life in rhesus monkeys while retaining its unique biological and antiviral properties," AIDS Res Hum Retroviruses, Jul. 20, 1997;13(11):933-43.
Schaeffer et al., "The rat glomerular filtration barrier does not show negative charge selectivity," Microcirculation. Oct. 2002; 9(5):329-42.
Schmitz et al., "Phage display: a molecular tool for the generation of antibodies—a review," Placenta. Mar.-Apr. 2000;21 Suppl A:S106-12.
Schroeder et al., "Similarity and divergence in the development and expression of the mouse and human antibody repertoires," Dev Comp Immunol., 2006;30(1-2):119-35.
Schroter et al., "A generic approach to engineer antibody pH-switches using combinatorial histidine scanning libraries and yeast display," MAbs., 2015;7(1):138-51. doi: 10.4161/19420862.2014.985993.
Seda et al., "B-cell receptor signalling and its crosstalk with other pathways in normal and malignant cells," Eur J Haematol., Mar. 2015;94(3):193-205. doi: 10.1111/ejh.12427. Epub Sep. 13, 2014.
Sharifi et al., "Improving monoclonal antibody pharmacokinetics via chemical modification," Q J Nucl Med., Dec. 1998;42(4):242-9.
Strohl WR, Optimization of Fc-mediated effector functions of monoclonal antibodies, Curr Opin Biotechnol., Dec. 2009;20(6):685-91. doi: 10.1016/j.copbio.2009.10.011. Epub Nov. 4, 2009.
Tan et al., "Engineering the isoelectric point of a renal cell carcinoma targeting antibody greatly enhances scFv solubility," Immunotechnology. Oct. 1998;4(2):107-14.

Teeling et al., "The Biological Activity of Human CD20 Monoclonal Antibodies is Linked to Unique Epitopes on CD20," J Immunol. Jul. 1, 2006;177(1):362-71.
Ten Kate et al., "Effect of isoelectric point on biodistribution and inflammation: imaging with indium-111-labelled IgG," Eur J Nucl Med. 1990;17(6-8):305-9(abstract) [Database BIOSIS Accession No. 1991910742 20].
Tsuchiya, Credit Suisse Seminar, "Therapeutic Antibody," at Fuji-Gotemba Laboratories, p. 21 (2006) (English translation).
Vaisitti et al., "Cationization of monoclonal anti bodies: Another step towards the "Magic Bullet"?" J Biol Regul Homeost Agents. Jul.-Dec. 2005;19(3-4):105-12.
Vajdos et al., "Comprehensive Functional Maps of the Antigen-binding Site of an Anti-ErbB2 Antibody Obtained with Shotgun Scanning Mutagenesis," J Mol Biol. Jul. 5, 2002;320(2):415-28.
Van Walle et al., "Immunogenicity screening in protein drug development," Expert Opin Biol Ther. Mar. 2007;7(3):405-18.
Verhoeyen et al., "Construction of a reshaped HMFG1 antibody and comparison of its fine specificity with that of the parent mouse antibody," Immunology, Mar. 1993;78(3):364-70.
Verhoeyen et al., "Monoclonal Antibodies in Clinical Oncology," 1991, Edited by AA Epenetos, Chapter 5, pp. 37-43, Chapman and Hall.
Wang et al., "Monoclonal Antibodies with Identical Fc Sequences Can Bind to FcRn Differentially with Pharmacokinetic Consequences," *Drug Metabolism and Disposition*, Sep. 2011; 39(9):1469-77.
Wiens et al., "Somatic Mutation in VH Complementarity-Determining Region 2 and Framework Region 2," J Immunol. Aug. 1, 1997;159(3):1293-302.
Wiens et al., "Mutation of a Single Conserved Residue in VH Complementarity-Determining Region 2 Results in a Severe Ig Secretion Defect," J Immunol. Aug. 15, 2001;167(4):2179-86.
Wikipedia, "Chaotropic agent" [online], [retrieved on Nov. 2, 2015]. Retrieved from the Inernet: https://en.wikipedia.org/wiki/Chaotropic_agent, 3pages.
Yang et al., "Tailoring structure-function and pharmacokinetic properties of single-chain Fv proteins by site-specific PEGylation," Protein Eng. Oct. 2003;16(10):761-70.
Zwick et al., "The Long Third Complementarity-Determining Region of the Heavy Chain Is Important in the Activity of the Broadly Neutralizing Anti-Human Immunodeficiency Virus Type 1 Antibody 2F5," J Virol. Mar. 2004;78(6):3155-61.
USPTO Advisory Action in U.S. Appl. No. 13/889,484, dated Jan. 7, 2016, 3 pages.
USPTO Non-Final Office Action in U.S. Appl. No. 13/889,484, dated Nov. 25, 2016, 12 pages.
Non-Final Office Action for U.S. Appl. No. 14/422,207, dated Feb. 11, 2016, 11 pages.
Fish & Richardson P.C., Reply to Non-Final Office Action of Feb. 11, 2016, in U.S. Appl. No. 14/422,207, filed Aug. 10, 2016, 24 pages.
Fish & Richardson P.C., Supplemental Reply to Non-Final Office Action of Feb. 11, 2016, in U.S. Appl. No. 14/422,207, filed Oct. 13, 2016, 24 pages.
Non-Final Office Action for U.S. Appl. No. 14/422,207, dated Feb. 7, 2017, 17 pages.
U.S. Appl. No. 13/889,484, Igawa et al., filed May 8, 2013.
U.S. Appl. No. 13/889,512, Igawa et al., filed May 8, 2013.
U.S. Appl. No. 14/741,786, Igawa et al., filed Jun. 17, 2015.
U.S. Appl. No. 14/377,556, Igawa et al., filed Aug. 8, 2014.
U.S. Appl. No. 14/781,069, Igawa et al., filed Sep. 29, 2015.
Araujo et al., "Increased rheumatoid factor interference observed during immunogenicity assessment of an Fe-engineered therapeutic antibody," J Pharm Biomed Anal, Jul. 15, 2011;55(5):1041-9. doi: 10.1016/j.jpba.2011.03.008. Epub Mar. 11, 2011.
Fiedler et al., "An engineered IN-1 Fab fragment with improved affinity for the Nogo-A axonal growth inhibitor permits immunochemical detection and shows enhanced neutralizing activity," Protein Eng Nov. 2002:15(11):931-41.
Foote et al., "Antibody framework residues affecting the conformation of the hypervariable loops," J Mol Biol, Mar. 20, 1992;224(2):487-99.

(56) References Cited

OTHER PUBLICATIONS

Gera et al., "Design of pH Sensitive Binding Proteins from the Hyperthermophilic Sso7d Scaffold," PLoS One, Nov. 2012;7(11):e48928. doi: 10.1371/journal.pone.0048928. Epub Nov. 7, 2012.
Hoogenboom, "Selecting and screening recombinant antibody libraries," Nat Biotechnol, Sep. 2005;23(9):1105-16.
Janeway et al., Immunobioiogy, 5th edition. Jun. 2001:Extract from Chapter 3.
Janeway et al., Immunobioiogy, 5th edition. Jun. 2001:Extract from Chapter 4.
Knappik et al., "Fully Synthetic Human Combinatorial Antibody Libraries (HuCAL) Based on Modular Consensus Frameworks and CDRs Randomized with Trinucleotides," J Mol Biol, Feb. 11, 2000;296(1):57-86.
Maurer et al., "Antigenicity of polypeptides (poly alpha amino acids): calcium-dependent and independent antibodies," J Immunol, Sep. 1970;105(3):567-73.
Muller et al., "VEGF and the Fab fragment of a humanized neutralizing antibody: crystal structure of the complex at 2.4 Å resolution and mutational analysis of the interface," Structure, Sep. 6, 1998;(9):1153-67.
Murata et al., "Anti-Digoxin Fab Variants Generated by Phage Display," Mol Biotechnol Jun. 2013:54 (2) :269-77. doi : 10.1007/s12033-012-9564-1.
Ober et al., "Visualizing the Site and Dynamics of IgG Salvage by the MHC Class I-Related Receptor, FcRn," J Immunol Feb. 15, 2004;172(4):2021-9.
Osbourn et al., "Generation of a panel of related human scFv antibodies with high affinities for human CEA," Immunotechnology Sep. 1996:2(3):181-96.
Pancook et al., In Vitro Affinity Maturation of Human IgM Antibodies Reactive with Tumor-Associated Antigens, Hybrid Hybridomics Oct. 2001:20(5-6):383-96.
Papista et al., "Dysfunctions of the Iga system: a common link between intestinal and renal diseases," Cell Mol Immunol Mar. 2011:8(2):126-34. doi:10.1038/cmi.2010.69. Epub Jan. 31, 2011.
Pejchal et al., "A Conformational Switch in Human Immunodeficiency Virus gp41 Revealed by the Structures of Overlapping Epitopes Recognized by Neutralizing Antibodies," J Virol Sep. 2009;83(17):8451-62. doi:10.1128/JVI. 00685-09. Epub Jun. 10, 2009.
Ramos et al., "Evaluation of CA-125 and soluble CD-23 in patients with pelvic endometriosis: a case-control study," Rev Assoc Med Bras (1992). Jan.-Feb. 2012; 58(1):26-32.
Raposo et al., "Epitope-specific anitbody response is controlled by immunoglobulin Vh polymorphisms," J Exp Med Mar. 10, 2014:211(3):405-11.doi:10.1084/jem.20130968. Epub Feb. 17, 2014.
Schier et al., "Isolation of Picomolar Affinity Anti-c-erbB-2 Single-chain Fv by Molecular Evolution of the Complementarity Determining Regions in the Center of the Antibody Binding Site," J Mol Biol Nov. 8, 1996:263(4):551-67.
Singer et al., "1.3 Structure of Proteins," Genes & Genomes, 1991;67-69.
Vidarsson et al., "IgG subclasses and allotypes: from structure to effector functions," Front Immunol Oct. 20, 2014;5:520. doi: 10.3389/fimmu.2014.00520. eCollection 2014.
Wu et al., "Stepwise in vitro affinity maturation of Vitaxin, an αv⊕33-specific humanized mAb," Proc Natl Acad Sci USA May 26, 1998 ; 95(11):6037-42.
Xolair (omalizumab) Prescribing Information, https://www.gene.com/download/pdf/xolair_prescribing.pdf, Jul. 2016, 27 pages.
USPTO Restriction Requirement in U.S. Appl. No. 13/637,415, dated Dec. 1, 2016, 8 pages.
USPTO Non-Final Office Action in U.S. Appl. No. 13/637415, dated May 24, 2017, 27 pages.
USPTO Non-Final Office Action in U.S. Appl. No. 14/347,034, dated May 25, 2017, 16 pages.
USPTO Non-Final Office Action in U.S. Appl. No. 13/595,139, dated Aug. 3, 2015, 13 pages.
USPTO Reply to Non-Final Office Action in U.S. Appl. No. 13/889484, dated May 25, 2017, 16 pages.
USPTO Final Office Action in U.S. Appl. No. 13/889,484, dated Aug. 16, 2017, 14 pages.
USPTO Restriction Requirement for U.S. Appl. No. 14/422,207, dated Nov. 20, 2015, 6 pages.
Non-Final Office Action for U.S. Appl. No. 15/230,904, dated May 25, 2017, 9 pages.
U.S. Appl. No. 13/990,158, Igawa et al., filed May 29, 2013 (abandoned).
U.S. Appl. No. 16/028,140, Igawa at al., filed Jul. 5, 2018.
U.S. Appl. No. 14/347,187, Igawa et al., filed Mar. 25, 2014.
U.S. Appl. No. 61/313,102, Pons, filed Mar. 11, 2010.
Akbarzadeh-Sharbaf et al., "In silico design, construction and cloning of Trastuzumab humanized monoclonal antibody: A possible biosimilar for Herceptin," Adv Biomed Res, Jan.-Mar. 2012, 1(1):1-6. doi: 10. 4103/2277-9175. 98122. Epub Jul. 6, 2012.
Alignment of constant region sequences from WO 2009/125825 (document submitted in EP opposition and posted by EPO on Feb. 2, 2018); 1 page.
Alignment of the amino acid sequences of the Fc regions of antibodies exemplified in EP 2275443 (document submitted in EP opposition and posted by EPO on Feb. 2, 2018); 1 page.
Alignment of variable heavy and light chain amino acid sequences from WO 2009/125825 (document submitted in EP opposition and posted by EPO on Feb. 2, 2018); 2 pages.
Atherton et al., "Acid-base balance: maintenance of plasma pH," Anaesthesia & Intensive Care Medicine, Nov. 2009, 10(11):557-61 (Abstract Only).
Claims as granted for Publication No. EP 2275443, dated Jan. 19, 2011 (document submitted in EP opposition); 6 pages.
Datta-Mannan et al., "Humanized IgG1 Variants with Differential Binding Properties to the Neonatal Fc Receptor: Relationship to Pharmacokinetics in Mice and Primates," Drug Metab Dispos, Jan. 2007, 35(1):86-94. Epub Oct. 18, 2006.
Davydov, "Omalizuman (Xolair) for Treatment of Asthma," Am Fam Physician, Jan. 15, 2005 71(2):341-2.
Declaration of Nimish Gera, Ph.D., CV and Exhibits, Sep. 1, 2016 (submitted in the matter of EP 2275443, Opposition thereto by Alexion Pharmaceuticals, Inc.); 24 pages.
De Felice et al., "Formation of amyloid aggregates from human lysozyme and its disease-associated variants using hydrostatic pressure," FASEB J, Jul. 2004, 18(10):1099-101. (doi:10.1096/fj.03-1072fje; PMID 15155566).
EMA product information: Annexes to file of the tocilizumab preparation RoActemra A126(WC500054890), published Jan. 8, 2010, 109 pages.
EPO Register Extract EP 1915397 (document submitted in EP opposition and posted by EPO on Feb. 2, 2018); 4 pages.
Experimental data characterizing the binding of rituximab to its antigen CD20 and to human FcRn (document submitted in EP opposition and posted by EPO on Feb. 5, 2018); 6 pages.
Experimental information regarding off-rate of Xolair Fab for binding to human IgE at pH7.4 and pH5.5 (document submitted in EP opposition and posted by EPO on Feb. 2, 2018); 3 pages.
Expert Declaration by Dr. Madhusudan Natarajan, submitted in EP opposition regarding EP 2552955 and posted by EPO on Feb. 5, 2018; 4 pages.
Fillipovic, Biochemical basis of human life activity, VLADOS, 2005:38-43 (with English translation).
Glick et al., Molecular Biotechnology: Principles and Applications of Recombinant DNA, 3rd Edition, Chemical Industry Press, Mar. 2005, p. 168 (with English translation).
Goebl et al., "Neonatal Fc Receptor Mediates Internalization of Fc Transfected Human Endothelial Cells," Molecular Biology of the Cell, Dec. 2008, 19(12):5490-5505.
Gurbaxani et al., "Analysis of a family of antibodies with different half-lives in mice fails to find a correlation between affinity for FcRn and serum half-life," Mol Immunol, Mar. 2006, 43(9):1462-73. Epub Sep. 1, 2005.
Hamers-Casterman et al., "Naturally occurring antibodies devoid of light chains," Nature, Jun. 3, 1993, 363(6428):446-8.

(56) References Cited

OTHER PUBLICATIONS

Hotzel et al., "A strategy for risk mitigation of antibodies with fast clearance," mAbs, Nov.-Dec. 2012, 4(6):753-60. doi: 10.4161/mabs. 22189.
Irani et al., Molecular properties of human IgG subclasses and their implications for designing therapeutic monoclonal antibodies against infectious diseases, Mol Immunol, Oct. 2015, 67(2 Pt A):171-82. doi : 10. 1016/ j. molimm 2015. 03. 255. Epub Apr. 18, 2015.
Jaeger, Clinical Immunology and Allergology, M: Medicina, 2nd edition, 1990, 2:484-5 (with English translation).
King, Applications and Engineering of Monoclonal Antibodies, 1998, Chapter 2.7.1, pp. 68-71.
Kuroda et al., "Computer-aided antibody design," Protein Eng Des Sel, Oct. 2012, 25(10):507-21. Epub Jun. 2, 2012.
Maxwell et al., "Crystal structure of the human leukocyte Fc receptor, FcγRIIa," Nat Struct Biol, May 1999, 6(5):437-42.
Merchant et al., "An efficient route to human bispecific IgG," Nat Biotechnol, Jul. 1998, 16:677-681.
Molina et al., "Trastuzumab (Herceptin), a Humanized Anti-HER2 Receptor Monoclonal Antibody, Inhibits Basal and Activated HER2 Ectodomain Cleavage in Breast Cancer Cells," Cancer.Res, Jun. 15, 2001, 61(12):4744-9.
O'Donovan et al., "EGFR and HER-2 Antagonists in Breast Cancer," Anticancer Res, May-Jun. 2007, 27(3A):1285-94.
Official Action dated Oct. 13, 2016, issued for EP Application No. 11714860.1 and submitted as evidence during EP opposition; 3 pages.
Popov et al., "The Stoichiometry and Affinity of the Interaction of Murine Fc Fragments with the MHC Class I-Related Receptor, FcRn," Mol Immunol, Apr. 1996, 33(6):521-30.
Presta, "Molecular engineering and design of therapeutic antibodies," Curr Opin Immunol, Aug. 2008, 20(4):460-70. doi : 10.1016/ j.coi.2008. 06.012.
Presta at el., "Humanization of an Anti-Vascular Endothelial Growth Factor Monoclonal Antibody for the Therapy of Solid Tumors and Other Disorders," Cancer Res, Oct. 15, 1997, 57(20):4593-9.
Product labelling information for Rituxan (Rituximab), dated Nov. 1997, 2 pages.
Raghavan et al., "Analysis of the pH Dependence of the Neonatal Fc Receptor/Immunoglobulin G Interaction Using Antibody and Receptor Variants," Biochemistry, Nov. 14, 1995, 34(45):14649-57.
Roitt et al., Immunology, Moscow: Mir, 2000, 373-4 (with English translation).
Ryman et al., "Pharmacokinetics of Monoclonal Antibodies," CPT Pharmacometrics Syst Pharmacol, Sep. 2017, 6(9):576-588. doi: 10.1002/psp4.12224. Epub Jul. 29, 2017.
Sondermann et al., "Molecular Basis for Immune Complex Recognition: A Comparison of Fc-Receptor Structures," J Mol Biol, Jun. 8, 2001, 309(3):737-49.
Sondermann et al., "Crystal structure of the soluble form of the human Fcγ-receptor IIb: a new member of the immunoglobulin superfamily at 1.7 A resolution," EMBO J Journal, Mar. 1, 1999, 18(5):1095-103.
Stepanov, "Chapter 4, Primary Structure of Protein, 4.1 Primary structure as a level of protein organization," Molecular biology, Structure and functions of proteins, M.:NAUKA, 2005, pp. 61-62 (with English abstract).
Supplementary data provided by opponent for EP Application No. 11714860.1 (document submitted in EP opposition and posted by EPO on Feb. 20, 2018); 3 pages.
Summary of information about antibodies in Examples of patent (document submitted in EP opposition and posted by EPO on Apr. 13, 2018); 3 pages.
Tanabe et al., "Characterization of the Monoclonal Antibodies Against Human Protein C Specific for Calcium Ion-induced Conformers," Japanese Journal of Thrombosis and Hemostasis, Mar. 1, 1992, 3(1):29-35.
Tanzi et al., "Twenty years of the Alzheimer's disease amyloid hypothesis: a genetic perspective," Cell, Feb. 2005, 120(4):545-55. (doi:10.1016/j.cell.2005.02.008; PMID 15734686).
Vaccaro et al., "Divergent activities of an engineered antibody in murine and human systems.have implications for therapeutic antibodies," Proc Natl Acad Sci USA, Dec. 5, 2006, 103(49):18709-14. Epub Nov. 20, 2006.
Waelbroeck et al., "The pH Dependence of Insulin Binding," J Biol Chem, Jul. 25, 1982, 257(14) :8284-91.
Ward et al., "Evidence to support the cellular mechanism involved in serum IgG homeostasis in humans," Int Immunol, Feb. 2003, 15(2):187-95.
Welch et al., "Adalimumab (Humira) for the Treatment of Rheumatoid Arthritis" Am Fam Physician, Dec. 15, 2008, 78(12):1406-1408.
Written Submissions by Opponent 1 (Alexion Pharmaceuticals, Inc.) in Opposition of Ep 2006381 dated Apr. 13, 2018, 19 pages.
Written Submissions by Opponent 2 (Novo Nordisk A/S) in Opposition of EP 2006381 dated Apr. 13, 2018, 14 pages.
Written Submissions by Opponent 3 (name Unknown) in Opposition of EP 2006381 dated Apr. 13, 2018, 16 pages.
Wu et al., "Ultra-potent Antibodies Against Respiratory Syncytial Virus: Effects of Binding Kinetics and Binding Valence on Viral Neutralization," J Mol Biol, Jul. 2005, 350:126-144.
Yang et al., "Dataset of the binding kinetic rate constants of anti-PCSK9 antibodies obtained using the Biacore T100, Protean XPR36, Octet RED384, and IBIS MX96 biosensor platforms," Data Brief, Jul. 27, 2006, 8:1173-83. doi: 10. 1016/ J. dib. 2016.07.044. eCollection Sep. 2016.
Yang et al., "Maximizing in vivo target clearance by design of pH-dependent target binding.antibodies with altered affinity to FcRn," mAbs, Oct. 2017, 9(7):1105-1117. doi: 10. 1080/19420862. 2017. 1359455. Epub Aug. 8, 2017.
Yarilin, Fundamentals of Immunology. M: Medicina, 1999, pp. 169-172, 354-358 (with English translation).
Yarilin, Fundamentals of Immunology, M: Medicina, 1999, pp. 172-174 (with English translation).
Yarilin, Fundamentals of Immunology, M: Medicina, 1999, pp. 175, 182 (with English translation of Tables).
Yeung et al., "A Therapeutic Anti-VEGF Antibody with Increased Potency Independent of Pharmacokinetic Half-life," Cancer Res, Apr. 15, 2010, 70(8):3269-77. doi : 10. 1158/ 0008-5472. CAN-09-4580. Epub Mar. 30, 2010.
USPTO Final Office Action in U.S. Appl. No. 13/637,415, dated Mar. 2, 2018, 36 pages.
USPTO Non-Final Office Action in U.S. Appl. No. 14/347,034, dated Jan. 8, 2018, 15 pages.
USPTO Notice of Allowance in U.S. Appl. No. 13/889,484, dated Nov. 16, 2017, 18 pages.
USPTO Final Office Action for U.S. Appl. No. 14/422,207, dated Nov. 16, 2017, 30 pages.
USPTO Non-Final Office Action for U.S. Appl. No. 15/230,904, dated Jan. 8, 2018, 16 pages.
USPTO Restriction Requirement in U.S. Appl. No. 14/377,556, dated Dec. 15, 2016, 11 pages.
USPTO Non-Final Office Action in U.S. Appl. No. 14/377,556, dated Feb. 27, 2017, 11 pages.
USPTO Final Office Action in U.S. Appl. No. 14/377,556, dated Jul. 7, 2017, 12 pages.
USPTO Non-Final Office Action in U.S. Appl. No. 14/377,556, dated Dec. 12, 2017, 14 pages.
USPTO Final Office Action in U.S. Appl. No. 14/377,556, dated May 11, 2018, 19 pages.
U.S. Appl. No. 12/295,039, Igawa et al., filed Jan. 20, 2009.
U.S. Appl. No. 15/725,692, Igawa et al., filed Oct. 5, 2017.
U.S. Appl. No. 12/936,587, Igawa et al., filed Jan. 3, 2011.
U.S. Appl. No. 13/595,139, Igawa et al., filed Aug. 27, 2012.
U.S. Appl. No. 13/990,158, Igawa et al., filed May 29, 2013.
U.S. Appl. No. 12/936,587, Igawa et al., filed Mar. 25, 2014.
U.S. Appl. No. 10/253,100, Igawa et al., filed Apr. 9, 2019.
U.S. Appl. No. 14/423,269, Katada et al., filed Feb. 23, 2015.
U.S. Appl. No. 16/264,735, filed Feb. 1, 2019, Igawa et al.
U.S. Appl. No. 16/361,498, filed Mar. 22, 2019, Igawa et al.
Antibodies from www.bioinf.org.uk: Dr. Andrew C.R. Martin's Group, downloaded Jul. 11, 2018, 9 pages.

(56) References Cited

OTHER PUBLICATIONS

Bonvin et al., "De novo isolation of antibodies with pH-dependent binding properties," mAbs, Mar.-Apr. 2015, 7(2): 294-302.
Cruse et al., Atlas of Immunology, CRC Press LLC, 2004, excerpt from Chapter 3 "Antigens and Immunogens," p. 109.
Decision of the EPO Opposition Division for EP 2 006 381 dated Jul. 25, 2018, 17 pages.
Decision of the Opposition Division in EP 2 275 443, dated Apr. 26, 2018 (submitted on May 24, 2019 by the Patentee during EPO Opposition Procedure for EP 2 202 245), 29 pages.
Declaration of Taichi Kuramochi (submitted on May 24, 2019 by the Patentee during EPO Opposition Procedure for EP 2 202 245), 11 pages.
Declaration of Dr. Anette Henriksen, signed Apr. 17, 2019 (submitted by the Opponent during EPO opposition procedure for EP 2 006 381), 4 pages.
Ferl et al., "A Predictive Model of Therapeutic Monoclonal Antibody Dynamics and Regulation By the Neonatal Fc Receptor (FcRn)," Ann Biomed Eng, Nov. 2005, 33(11):1640-52; and Erratum, Oct. 2011, 39(10):2668.
GE Healthcare, Biacore, Sensor Surface Handbook BR-1005-71, Edition AB, Feb. 2005, pp. 1-100.
Granted claims of EP 2 275 443 (submitted on May 24, 2019 by the Patentee during EPO Opposition Procedure for EP 2 202 245), 1 page.
Hirose, "Visualization of Intracellular Calcium Signalling," Folia Pharmacol Jpn, May 2006, 127(5):362-7 (with English translation).
Kamata et al., "Comparison of pH and Ionic Strength Dependence of Interactions between Monoclonal Antibodies and Bovine β-Lactoglobulin," Biosci Biotechnol Biochem, Jan. 1996, 60(1):25-9.
King, Applications and Engineering of Monoclonal Antibodies, Taylor & Francis, ISBN 0-203-21169-3, 2005, pp. 1-236.
Mellman, "The importance of being acid: the role of acidification in intracellular membrane traffic," J. Exp. Biol., Nov. 1992, 172-39-45.
Roitt et al., Immunology, Moscow: Mir, 2000, pp. 97-113 (including what are believed to be corresponding pages from an English language edition of Immunology).
Sequence alignments and modification scheme (document filed during Oral Proceedings and mentioned in minutes of the Oral Proceedings for EP 2 006 381, posted by EPO on Jul. 25, 2018); 3 pages.
Supplemental Material to Raposo et al., "Epitope-specific antibody response is controlled by immunoglobulin VH polymorphisms," J Exp Med, Mar. 10, 2014, 211(3):405-11. doi: 10.1084/jem.20130968. Epub Feb. 17, 2014 (submitted on May 24, 2019 by the Patentee during EPO Opposition Procedure for EP 2 202 245), 4 pages.
Van Den Abbeele et al., "Antigen-Binding Site Protection During Radiolabeling Leads to a Higher Immunoreactive Fraction," J Nucl Med, Jan. 1991, 32(1):116-22.
Yarilin, Fundamentals of Immunology, M.: Medicina, 1999, pp. 181-184 (with English translation).
USPTO Final Office Action in U.S. Appl. No. 14/347,034, dated Oct. 16, 2015, 5 pages.
USPTO Non-Final Office Action in U.S. Appl. No. 13/595,139, dated Mar. 13, 2015, 12 pages.
Fish & Richardson P.C., Amendment and Reply to Office Action dated Mar. 13, 2015 in U.S. Appl. No. 13/595,139, filed Jun. 11, 2015, 19 pages.
Fish & Richardson P.C., Reply to Office Action dated Aug. 3, 2015 in U.S. Appl. No. 13/595,139, filed Dec. 2, 2015, 28 pages.
USPTO Final Office Action in U.S. Appl. No. 13/595,139, dated Feb. 12, 2016, 12 pages.
USPTO Final Office Action in U.S. Appl. No. 13/595,139, dated May 30, 2017, 23 pages.
USPTO Non-Final Office Action in U.S. Appl. No. 13/595,139, dated Sep. 26, 2018, 32 pages.
USPTO Non-Final Office Action in U.S. Appl. No. 14/377,556, dated Apr. 18, 2019, 9 pages.
USPTO Non-Final Office Action in U.S. Appl. No. 15/952,945, dated Sep. 20, 2018, 32 pages.
U.S. Appl. No. 12/936,587, Igawa et al., filed Jan. 3, 2011 (abandoned).
U.S. Appl. No. 13/595,139, Igawa et al., filed Aug. 27, 2012 (abandoned).
U.S. Appl. No. 13/637,415, Igawa et al., filed Feb. 4, 2013.
U.S. Appl. No. 15/050,145, Igawa et al. filed Feb. 22, 2016.
U.S. Appl. No. 13/990,158, Igawa et al., filed Mar. 28, 2014 (abandoned).
U.S. Appl. No. 15/988,348, Igawa et al., filed May 24, 2018.
U.S. Appl. No. 14/347,034, Igawa et al. filed Mar. 25, 2014 (abandoned).
U.S. Appl. No. 15/230,904, Igawa et al. filed Aug. 8, 2016 (abandoned).
U.S. Appl. No. 16/028,140, Igawa et al., filed Jul. 5, 2018.
U.S. Appl. No. 14/347,321, Igawa et al. filed Mar. 26, 2014 (abandoned).
U.S. Appl. No. 15/977,757, Igawa et al., filed May 11, 2018.
U.S. Appl. No. 16/264,735, Igawa et al., filed Feb. 1, 2019.
U.S. Appl. No. 14/361,013, Igawa et al. filed May 28, 2014 (abandoned).
U.S. Appl. No. 16/108,897, Igawa et al., filed Aug. 22, 2018.
U.S. Appl. No. 14/377,556, Kuramochi et al., filed Aug. 8, 2014.
U.S. Appl. No. 14/379,825, Igawa et al., filed Aug. 20, 2014.
U.S. Appl. No. 14/404,051, Igawa et al., filed Nov. 26, 2014.
U.S. Appl. No. 14/423,269, Igawa et al., filed Feb. 23, 2015.
U.S. Appl. No. 14/781,069, Mimoto et al., filed Sep. 29, 2015.
U.S. Appl. No. 15/210,360, Igawa et al., filed Jul. 14, 2016.
U.S. Appl. No. 15/210,353, Igawa et al., filed Jul. 14, 2016.
U.S. Appl. No. 15/495,026, Igawa et al., filed Apr. 24, 2017.
U.S. Appl. No. 15/952,945, Igawa et al., filed Apr. 13, 2018.
U.S. Appl. No. 15/952,951, Igawa et al., filed Apr. 13, 2018.
U.S. Appl. No. 16/361,498, Igawa et al., filed Mar. 22, 2019.
U.S. Appl. No. 13/990,158, filed Mar. 28, 2014, Igawa et al.
Aboud-Pirak et al., "Binding and Endocytosis of a Monoclonal Antibody to a High Molecular Weight Human Milk Fat Globule Membrane-associated Antigen by Cultured MCF-7 Breast Carcinoma Cells," Cancer Res, Jun. 1, 1988, 48(11):3188-96.
Anchin et al., "Recognition of Superpotent Sweetener Ligands by a Library of Monoclonal Antibodies," J Mol Recognit, Sep.-Oct. 1997, 10(5):235-42.
Barrabes et al., "Effect of sialic acid content on glycoprotein pI analyzed by two-dimensional electrophoresis," Electrophoresis, Sep. 2010, 31(17):2903-12. doi: 10.1002/elps.200900764.
Binding data for Rituximab (submitted by the Opponent during EP opposition procedure for EP 2 708 558 and posted by EPO dated Jan. 15, 2019), 6 pages.
Chang et al., "Practical Approaches to Protein Formulation Development," Pharm Biotechnol, 2002, 13:1-25.
Declaration by Madhusudan Natarajan, Ph.D. (submitted by the Opponent during EP opposition procedure for EP 2 708 558 and posted by EPO on Jan. 15, 2019), 3 pages.
Edwards et al., "The Remarkable Flexibility of the Human Antibody Repertoire; Isolation of Over One Thousand Different Antibodies to a Single Protein, BLyS," J Mol Biol, Nov. 14, 2003, 334(1):103-18.
Examination Report No. 1 for AU 2013306700 (IP Australia) dated Jun. 7, 2018, 3 pages.
Fan et al., "Self-Association of Human PCSK9 Correlates with Its LDLR-Degrading Activity," Biochemistry, Feb. 12, 2008 47(6):1631-9. doi: 10.1021/bi7016359. Epub Jan. 16, 2008.
Fisher et al., "Affinity purification of antibodies using antigens immobilized on solid supports," Biochem Soc Trans, Apr. 1988, 16(2):134-8.
Goel et al., "Plasticity within the Antigen-Combining Site May Manifest as Molecular Mimicry in the Humoral Immune Response," J Immunol, Dec. 15, 2004, 173(12):7358-67.
Gopferich et al., Chapter 15 "Drug Delivery from Bioerodible Polymers," in Formulation and Delivery of Proteins and Peptides, American Chemical Society, eds. Cleland et al., 1994, pp. 242-277.
Hughes-Jones et al., "The Effect of pH and Ionic Strength on the Reaction between Anti-D and Erythrocytes," Immunology, Jan. 1964, 7:72-81.

(56) References Cited

OTHER PUBLICATIONS

Huse et al., "Purification of antibodies by affinity chromatography," J Biochem Biophys Methods, May 31, 2002, 51(3):217-31.
Jain et al., "Engineering antibodies for clinical applications," Trends Biotechnol, Jul. 2007, 25(7):307-16. Epub May 21, 2007.
Kanyavuz et al., "Breaking the law: unconventional strategies for antibody diversification," Nat Rev Immunol, Jun. 2019, 19(6):355-368. doi: 10.1038/s41577-019-0126-7.
King, Chapter 2 "Antibody Engineering: Design for Specific Applications," in Applications and Engineering of Monoclonal Antibodies, 1998, pp. 27-75.
Kipriyanov et al., "Generation of Recombinant Antibodies," Mol Biotechnol, Sep. 1999, 12(2):173-201.
Kranz et al., "Mechanisms of Ligand Binding by Monoclonal Anti-fluorescyl Antibodies," J Biol Chem, Jun. 25, 1982, 257(12):6987-95.
Lloyd et al., "Modelling the human immune response: performance of a $10^{11}$ human antibody repertoire against a broad panel of therapeutically relevant antigens," Protein Eng Des Sel, Mar. 2009, 22(3):159-68. doi: 10.1093/protein/gzn058. Epub Oct. 29, 2008.
Male et al., Immunology, 7th edition, published by Elsevier Ltd., 2006, pp. 77-78.
Male et al., Immunology, 7th edition, published by Elsevier Ltd., 2006, pp. 59-86.
Narhi et al., "Effect of Three Elution Buffers on the Recovery and Structure of Monoclonal Antibodies," Anal Biochem, Nov. 15, 1997, 253(2):236-45.
Originally Filed Claims of EP Application No. 13195713.6 (EP Publication No. 2 708 558) (submitted by the Opponent during EP opposition procedure for EP 2 708 558 and posted by EPO on Jan. 15, 2019), 2 pages.
Originally Filed Description of EP Application No. 13195713.6 (EP Publication No. 2 708 558) (submitted by the Opponent during EP opposition procedure for EP 2 708 558 and posted by EPO on Jan. 15, 2019), 153 pages.
Patel et al., "A Forgotten Cause of Kidney Injury in Chronic Myelomonocytic Leukemia," Am J Kidney Dis, Jul. 2009, 54(1):159-64. doi: 10.1053/j.ajkd.2008.11.013. Epub Jan. 29, 2009.
Product Information Sheet from SIGMA—H-Y Medium (1998) and document establishing that it was published in 1998 (submitted by the Opponent during EP opposition procedure for EP 2 708 558 and posted by EPO on Jan. 15, 2019), 4 pages.
Promega Protocols and Applications Guide, 1991, 2nd Edition (submitted by the Opponent during EP opposition procedure for EP 2 708 558 and posted by EPO on Jan. 14, 2019), 3 pages.
Raso, "Interacellular Targeting Using Bispecific Antibodies" in Methods in Molecular Medicine, vol. 25: Drug Targeting: Strategies, Principles, and Applications, 2006, p. 37.
Raso et al., "Intracellular Targeting with Low pH-triggered Bispecific Antibodies," J Biol Chem, Oct. 31, 1997, 272(44):27623-8.
Raso et al., "Antibodies Capable of Releasing Diphtheria Toxin in Response to the Low pH Found in Endosomes," J Biol Chem, Oct. 31, 1997, 272(44):27618-22.
Rituximab (Wikipedia), accessed on Oct. 24, 2018 (submitted by the Opponent during EP opposition procedure for EP 2 708 558 and posted by EPO on Jan. 15, 2019), 7 pages (with English translation).
Rituximab biologic license application approval, dated Nov. 26, 1997 (submitted by the Opponent during EP opposition procedure for EP 2 708 558 and posted by EPO on Jan. 15, 2019), 2 pages.
Rituximab product information, IDEC, 1997 (submitted by the Opponent during EP opposition procedure for EP 2 708 558 and posted by EPO on Jan. 15, 2019), 2 pages.
Roitt et al., Immunology, Moscow: Mir, 2000, pp. 111-2 (including what are believed to be corresponding pages from an English language edition of Immunology).
Sada et al., "Effect of histidine residues in antigenic sites on pH dependence of immuno-adsorption equilibrium," Appl Microbiol Biotechnol, Feb. 1988, 27:528-32.
Sazinsky et al., "Aglycosylated immunoglobulin $G_1$ variants productively engage activating FC receptors," Proc Natl Acad Sci USA, Dec. 23, 2008, 105(51):20167-72. doi: 10.1073/pnas.0809257105. Epub Dec. 12, 2008.
Shadduck et al., "Fractionation of Antibodies to L-Cell Colony-Stimulating Factor by Affinity Chromatography," Blood, Jun. 1979, 53(6):1182-90.
Travis et al., "Isolation of Albumin from Whole Human Plasma and Fractionation of Albumin-Depleted Plasma," Biochem J, Aug. 1, 1976, 157(2):301-6.
Venturi et al., "The Monoclonal Antibody 1F6 Identifies a pH-dependent Conformational Change in the Hydrophilic NH2 Terminus of NhaA Na+/H+ Antiporter of *Escherichia coli*," J Biol Chem, Feb. 18, 2000, 275(7):4734-42.
Wang, "Instability, stabilization, and formulation of liquid protein pharmaceuticals," Int J Pharm, Aug. 20, 1999, 185(2):129-88.
Weiss et al., "Rapid mapping of protein functional epitopes by combinatorial alanine scanning," Proc Natl Acad Sci USA, Aug. 1, 2000, 97(16):8950-4.
USPTO Non-Final Office Action in U.S. Appl. No. 13/637,415, dated Jun. 10, 2019, 27 pages.
USPTO Non-Final Office Action in U.S. Appl. No. 14/422,207, dated Jun. 18, 2019, 43 pages.
USPTO Non-Final Office Action in U.S. Appl. No. 15/952,951, dated Oct. 1, 2018, 12 pages.
USPTO Applicant-Initiated Interview Summary in U.S. Appl. No. 15/952,951, dated Dec. 3, 2018, 3 pages.
USPTO Applicant-Initiated Interview Summary in U.S. Appl. No. 15/952,951, dated Feb. 8, 2019, 3 pages.
USPTO Applicant-Initiated Interview Summary in U.S. Appl. No. 15/952,951, dated Jul. 12, 2019, 3 pages.
USPTO Final Office Action in U.S. Appl. No. 15/952,951, dated Jun. 3, 2019, 67 pages.
USPTO Advisory Action in U.S. Appl. No. 15/952,951, dated Aug. 19, 2019, 5 pages.
USPTO Final Office Action in U.S. Appl. No. 14/377,556, dated Sep. 24, 2019, 17 pages.
Kakita et al., "Isolation of a Human Monoclonal Antibody with Strong Neutralizing Activity against Diphtheria Toxin," Infect Immun, Jun. 2006, 74(6):3682-3.
Medesan et al., "Comparative studies of rat IgG to further delineate the Fc:FcRn interaction site," Eur J Immunol, Jul. 1998, 28(7):2092-100.
U.S. Appl. No. 13/990,158, Igawa et al., filed Mar. 28, 2014.
U.S. Appl. No. 14/347,034, Igawa et al., filed Mar. 25, 2014.
U.S. Appl. No. 15/230,904, Igawa et al., filed Aug. 8, 2016.
U.S. Appl. No. 14/347,321, Igawa et al., filed Mar. 26, 2014.
U.S. Appl. No. 14/361,013, Igawa et al., filed May 28, 2014.
Cunningham et al., "The Covalent Structure of a Human γG-Immunoglobulin. VII. Amino Acid Sequence of Heavy-Chain Cyanogen Bromide Fragments $H_1$-$H_4$," Biochemistry, Aug. 4, 1970, 9(16):3161-70.
King, "Preparation, structure and function of monoclonal antibodies," Applications and Engineering of Monoclonal Antibodies, CRC Press, 1998, pp. 2 and 13-4.
Kurki et al., "Desmin antibodies in acute infectious myopericarditis," APMIS, Jun. 1989, 97(6):527-32.
Perng et al., "Desmin Aggregate Formation by R120G αB-Crystallin Is Caused by Altered Filament Interactions and Is Dependent upon Network Status in Cells," Mol Biol Cell, May 2004, 15(5):2335-46.
Roitt et al., "Introduction to the Immune System," Immunology, Moscow: Mir, 2000, p. 9 (with English translation).
Diamond et al., "Somatic mutation of the T15 heavy chain gives rise to an antibody with autoantibody specificity," Proc Natl Acad Sci USA, Sep. 1984, 81(18):5841-4.
Hasemann et al., Mutational Analysis of Arsonate Binding by a $CRI_{A+}$ Antibody, J Biol Chem, Apr. 25, 1991, 266(12):7626-32.
Ohno et al., "Antigen-binding specificities of antibodies are primarily determined by seven residues of $V_H$," Proc Natl Acad Sci USA, May 1985, 82(9):2945-9.

\* cited by examiner (i) CRYSTAL STRUCTURE IN THE PRESENCE OF CALCIUM ION (ii) CRYSTAL STRUCTURE IN THE ABSENCE OF CALCIUM ION

FIG. 47

(Embodiment 3)
Antigen-binding molecule in which one side of Fc has enhanced
FcRn binding under neutral conditions, and the other does not have
FcRn-binding ability under neutral conditions

```
                        SEQUENCE LISTING

<160> NUMBER OF SEQ ID NOS: 187

<210> SEQ ID NO 1
<211> LENGTH: 468
<212> TYPE: PRT
<213> ORGANISM: Homo sapiens

<400> SEQUENCE: 1

Met Leu Ala Val Gly Cys Ala Leu Leu Ala Ala Leu Leu Ala Ala Pro
1               5                   10                  15

Gly Ala Ala Leu Ala Pro Arg Arg Cys Pro Ala Gln Glu Val Ala Arg
            20                  25                  30

Gly Val Leu Thr Ser Leu Pro Gly Asp Ser Val Thr Leu Thr Cys Pro
        35                  40                  45

Gly Val Glu Pro Glu Asp Asn Ala Thr Val His Trp Val Leu Arg Lys
    50                  55                  60

Pro Ala Ala Gly Ser His Pro Ser Arg Trp Ala Gly Met Gly Arg Arg
65                  70                  75                  80

Leu Leu Leu Arg Ser Val Gln Leu His Asp Ser Gly Asn Tyr Ser Cys
                85                  90                  95

Tyr Arg Ala Gly Arg Pro Ala Gly Thr Val His Leu Leu Val Asp Val
            100                 105                 110

Pro Pro Glu Glu Pro Gln Leu Ser Cys Phe Arg Lys Ser Pro Leu Ser
        115                 120                 125

Asn Val Val Cys Glu Trp Gly Pro Arg Ser Thr Pro Ser Leu Thr Thr
    130                 135                 140

Lys Ala Val Leu Leu Val Arg Lys Phe Gln Asn Ser Pro Ala Glu Asp
145                 150                 155                 160

Phe Gln Glu Pro Cys Gln Tyr Ser Gln Glu Ser Gln Lys Phe Ser Cys
                165                 170                 175

Gln Leu Ala Val Pro Glu Gly Asp Ser Ser Phe Tyr Ile Val Ser Met
            180                 185                 190

Cys Val Ala Ser Ser Val Gly Ser Lys Phe Ser Lys Thr Gln Thr Phe
        195                 200                 205

Gln Gly Cys Gly Ile Leu Gln Pro Asp Pro Pro Ala Asn Ile Thr Val
    210                 215                 220

Thr Ala Val Ala Arg Asn Pro Arg Trp Leu Ser Val Thr Trp Gln Asp
225                 230                 235                 240

Pro His Ser Trp Asn Ser Ser Phe Tyr Arg Leu Arg Phe Glu Leu Arg
                245                 250                 255

Tyr Arg Ala Glu Arg Ser Lys Thr Phe Thr Thr Trp Met Val Lys Asp
            260                 265                 270

Leu Gln His His Cys Val Ile His Asp Ala Trp Ser Gly Leu Arg His
        275                 280                 285

Val Val Gln Leu Arg Ala Gln Glu Glu Phe Gly Gln Gly Glu Trp Ser
    290                 295                 300

Glu Trp Ser Pro Glu Ala Met Gly Thr Pro Trp Thr Glu Ser Arg Ser
305                 310                 315                 320

Pro Pro Ala Glu Asn Glu Val Ser Thr Pro Met Gln Ala Leu Thr Thr
                325                 330                 335
```

```
Asn Lys Asp Asp Asp Asn Ile Leu Phe Arg Asp Ser Ala Asn Ala Thr
            340                 345                 350

Ser Leu Pro Val Gln Asp Ser Ser Val Pro Leu Pro Thr Phe Leu
        355                 360                 365

Val Ala Gly Gly Ser Leu Ala Phe Gly Thr Leu Leu Cys Ile Ala Ile
370                 375                 380

Val Leu Arg Phe Lys Lys Thr Trp Lys Leu Arg Ala Leu Lys Glu Gly
385                 390                 395                 400

Lys Thr Ser Met His Pro Pro Tyr Ser Leu Gly Gln Leu Val Pro Glu
                405                 410                 415

Arg Pro Arg Pro Thr Pro Val Leu Val Pro Leu Ile Ser Pro Pro Val
            420                 425                 430

Ser Pro Ser Ser Leu Gly Ser Asp Asn Thr Ser Ser His Asn Arg Pro
            435                 440                 445

Asp Ala Arg Asp Pro Arg Ser Pro Tyr Asp Ile Ser Asn Thr Asp Tyr
            450                 455                 460

Phe Phe Pro Arg
465

<210> SEQ ID NO 2
<211> LENGTH: 1407
<212> TYPE: DNA
<213> ORGANISM: Homo sapiens

<400> SEQUENCE: 2
atgctggccg tcggctgcgc gctgctggct gccctgctgg ccgcgccggg agcggcgctg      60
gccccaaggc gctgccctgc gcaggaggtg gcgagaggcg tgctgaccag tctgccagga     120
gacagcgtga ctctgacctg cccgggggta gagccggaag acaatgccac tgttcactgg     180
gtgctcagga agccggctgc aggctcccac cccagcagat gggctggcat gggaaggagg     240
ctgctgctga ggtcggtgca gctccacgac tctggaaact attcatgcta ccgggccggc     300
cgcccagctg ggactgtgca cttgctggtg gatgttcccc ccgaggagcc ccagctctcc     360
tgcttccgga gagccccct cagcaatgtt gtttgtgagt ggggtcctcg gagcacccca     420
tccctgacga caaaggctgt gctcttggtg aggaagtttc agaacagtcc ggccgaagac     480
ttccaggagc cgtgccagta ttcccaggag tcccagaagt ctcctgccag ttagcagtc     540 ccggagggag acagctcttt ctacatagtg tccatgtgcg tcgccagtag tgtcgggagc     600
aagttcagca aaactcaaac ctttcagggt tgtggaatct gcagcctga tccgcctgcc     660 aacatcacag tcactgccgt ggccagaaac ccccgctggc tcagtgtcac ctggcaagac     720
ccccactcct ggaactcatc tttctacaga ctacggtttg agctcagata tcgggctgaa     780
cggtcaaaga cattcacaac atggatggtc aaggacctcc agcatcactg tgtcatccac     840
gacgcctgga gcggcctgag gcacgtggtg cagcttcgtg cccaggagga gttcgggcaa     900
ggcgagtgga gcgagtggag cccggaggcc atgggcacgc cttggacaga atccaggagt     960
cctccagctg agaacgaggt gtccaccccc atgcaggcac ttactactaa taagacgat    1020 gataatattc tcttcagaga ttctgcaaat gcgacaagcc tcccagtgca agattcttct    1080
tcagtaccac tgcccacatt cctggttgct ggagggagcc tggccttcgg aacgctcctc    1140
tgcattgcca ttgttctgag gttcaagaag acgtggaagc tgcgggctct gaaggaaggc    1200
aagacaagca tgcatccgcc gtactctttg gggcagctgg tccgagagag gcctcgaccc    1260
accccagtgc ttgttcctct catctcccca ccggtgtccc ccagcagcct ggggtctgac    1320
```

```
aatacctcga gccacaaccg accagatgcc agggacccac ggagcccta tgacatcagc    1380 aatacagact acttcttccc cagatag                                       1407
```

<210> SEQ ID NO 3
<211> LENGTH: 19
<212> TYPE: PRT
<213> ORGANISM: Artificial Sequence
<220> FEATURE:
<223> OTHER INFORMATION: an artificially synthesized sequence

<400> SEQUENCE: 3

```
Met Gly Trp Ser Cys Ile Ile Leu Phe Leu Val Ala Thr Ala Thr Gly
1               5                   10                  15

Val His Ser
```

<210> SEQ ID NO 4
<211> LENGTH: 107
<212> TYPE: PRT
<213> ORGANISM: Homo sapiens

<400> SEQUENCE: 4

```
Glu Thr Thr Leu Thr Gln Ser Pro Ala Phe Met Ser Ala Thr Pro Gly
1               5                   10                  15

Asp Lys Val Asn Ile Ser Cys Lys Ala Ser Gln Asp Ile Asp Asp Asp
                20                  25                  30

Met Asn Trp Tyr Gln Gln Lys Pro Gly Glu Ala Ala Ile Phe Ile Ile
            35                  40                  45

Gln Glu Ala Thr Thr Leu Val Pro Gly Ile Ser Pro Arg Phe Ser Gly
    50                  55                  60

Ser Gly Tyr Gly Thr Asp Phe Thr Leu Thr Ile Asn Asn Ile Glu Ser
65                  70                  75                  80

Glu Asp Ala Ala Tyr Tyr Phe Cys Leu Gln His Asp Asn Phe Pro Tyr
                85                  90                  95

Thr Phe Gly Gln Gly Thr Lys Leu Glu Ile Lys
            100                 105
```

<210> SEQ ID NO 5
<211> LENGTH: 107
<212> TYPE: PRT
<213> ORGANISM: Homo sapiens

<400> SEQUENCE: 5

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
                20                  25                  30

Leu Asn Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Phe
                85                  90                  95

Thr Phe Gly Pro Gly Thr Lys Val Asp Ile Lys
            100                 105
```

<210> SEQ ID NO 6

```
<211> LENGTH: 112
<212> TYPE: PRT
<213> ORGANISM: Homo sapiens

<400> SEQUENCE: 6

Asp Ile Val Met Thr Gln Ser Pro Leu Ser Leu Pro Val Thr Pro Gly
1               5                   10                  15

Glu Pro Ala Ser Ile Ser Cys Arg Ser Gln Ser Leu Leu His Ser
            20                  25                  30

Asn Gly Asp Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Val
                85                  90                  95

Leu Arg Asn Pro Leu Thr Phe Gly Gly Gly Thr Lys Val Glu Ile Gln
            100                 105                 110

<210> SEQ ID NO 7
<211> LENGTH: 107
<212> TYPE: PRT
<213> ORGANISM: Homo sapiens

<400> SEQUENCE: 7

Glu Ile Val Met Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
                85                  90                  95

Thr Phe Gly Gln Gly Thr Lys Val Glu Ile Lys
            100                 105

<210> SEQ ID NO 8
<211> LENGTH: 112
<212> TYPE: PRT
<213> ORGANISM: Homo sapiens

<400> SEQUENCE: 8

Asp Ile Val Met Thr Gln Ser Pro Glu Ser Leu Val Leu Ser Leu Gly
1               5                   10                  15

Gly Thr Ala Thr Ile Asn Cys Arg Ser Ser Gln Ser Val Leu Tyr Ser
            20                  25                  30

Ser Asn Asn Lys Asn Tyr Leu Thr Trp Tyr Gln Gln Lys Pro Gly Gln
        35                  40                  45

Pro Pro Thr Leu Leu Phe Ser Trp Ala Ser Ile Arg Asp Ser Gly Val
    50                  55                  60

Pro Asp Arg Phe Ser Ala Ser Gly Ser Gly Thr Glu Phe Thr Leu Thr
65                  70                  75                  80
```

Ile Ser Asp Leu Gln Ala Glu Asp Ala Ala Val Tyr Tyr Cys Gln Gln
                85                  90                  95

Tyr Tyr Arg Ala Pro Ser Phe Gly Gln Gly Thr Lys Leu Gln Ile Lys
            100                 105                 110

<210> SEQ ID NO 9
<211> LENGTH: 121
<212> TYPE: PRT
<213> ORGANISM: Homo sapiens

<400> SEQUENCE: 9

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Tyr Met His Trp Val Arg Gln Ala Pro Gly Gln Gly Leu Glu Trp Met
            35                  40                  45

Gly Ile Ile Asn Pro Ser Gly Gly Ser Thr Ser Tyr Ala Gln Lys Phe
        50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Asp Pro Gly Gly Gly Glu Tyr Tyr Phe Asp Tyr Trp Gly
            100                 105                 110

Gln Gly Thr Leu Val Thr Val Ser Ser
        115                 120

<210> SEQ ID NO 10
<211> LENGTH: 126
<212> TYPE: PRT
<213> ORGANISM: Homo sapiens

<400> SEQUENCE: 10

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
                20                  25                  30

Glu Met Asn Trp Val Arg Gln Ala Pro Gly Lys Gly Leu Glu Trp Val
            35                  40                  45

Ser Tyr Ile Ser Ser Ser Gly Ser Thr Ile Tyr Tyr Ala Asp Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Ala Pro Tyr Tyr Tyr Asp Ser Ser Gly Tyr Thr Asp Ala
            100                 105                 110

Phe Asp Ile Trp Gly Gln Gly Thr Met Val Thr Val Ser Ser
        115                 120                 125

<210> SEQ ID NO 11
<211> LENGTH: 330
<212> TYPE: PRT
<213> ORGANISM: Artificial Sequence
<220> FEATURE:
<223> OTHER INFORMATION: an artificially synthesized sequence

<400> SEQUENCE: 11

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 12
<211> LENGTH: 326
<212> TYPE: PRT
<213> ORGANISM: Artificial Sequence
<220> FEATURE:
<223> OTHER INFORMATION: an artificially synthesized sequence

<400> SEQUENCE: 12

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30
```

```
Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
 50                  55                  60

Leu Ser Ser Val Val Thr Val Pro Ser Ser Asn Phe Gly Thr Gln Thr
 65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
            115                 120                 125

Thr Leu Met Ile Ser Arg Thr Pro Glu Val Thr Cys Val Val Val Asp
        130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
210                 215                 220

Pro Gln Val Tyr Thr Leu Pro Pro Ser Arg Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 13
<211> LENGTH: 377
<212> TYPE: PRT
<213> ORGANISM: Homo sapiens

<400> SEQUENCE: 13

Ala Ser Thr Lys Gly Pro Ser Val Phe Pro Leu Ala Pro Cys Ser Arg
 1               5                  10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
 50                  55                  60

Leu Ser Ser Val Val Thr Val Pro Ser Ser Ser Leu Gly Thr Gln Thr
```

```
                65                  70                  75                  80
Tyr Thr Cys Asn Val Asn His Lys Pro Ser Asn Thr Lys Val Asp Lys
                    85                  90                  95
Arg Val Glu Leu Lys Thr Pro Leu Gly Asp Thr Thr His Thr Cys Pro
                100                 105                 110
Arg Cys Pro Glu Pro Lys Ser Cys Asp Thr Pro Pro Cys Pro Arg
            115                 120                 125
Cys Pro Glu Pro Lys Ser Cys Asp Thr Pro Pro Cys Pro Arg Cys
130                 135                 140
Pro Glu Pro Lys Ser Cys Asp Thr Pro Pro Cys Pro Arg Cys Pro
145                 150                 155                 160
Ala Pro Glu Leu Leu Gly Gly Pro Ser Val Phe Leu Phe Pro Pro Lys
                165                 170                 175
Pro Lys Asp Thr Leu Met Ile Ser Arg Thr Pro Glu Val Thr Cys Val
                180                 185                 190
Val Val Asp Val Ser His Glu Asp Pro Glu Val Gln Phe Lys Trp Tyr
            195                 200                 205
Val Asp Gly Val Glu Val His Asn Ala Lys Thr Lys Pro Arg Glu Glu
210                 215                 220
Gln Tyr Asn Ser Thr Phe Arg Val Val Ser Val Leu Thr Val Leu His
225                 230                 235                 240
Gln Asp Trp Leu Asn Gly Lys Glu Tyr Lys Cys Lys Val Ser Asn Lys
                245                 250                 255
Ala Leu Pro Ala Pro Ile Glu Lys Thr Ile Ser Lys Thr Lys Gly Gln
                260                 265                 270
Pro Arg Glu Pro Gln Val Tyr Thr Leu Pro Pro Ser Arg Glu Glu Met
            275                 280                 285
Thr Lys Asn Gln Val Ser Leu Thr Cys Leu Val Lys Gly Phe Tyr Pro
            290                 295                 300
Ser Asp Ile Ala Val Glu Trp Glu Ser Ser Gly Gln Pro Glu Asn Asn
305                 310                 315                 320
Tyr Asn Thr Thr Pro Pro Met Leu Asp Ser Asp Gly Ser Phe Phe Leu
                325                 330                 335
Tyr Ser Lys Leu Thr Val Asp Lys Ser Arg Trp Gln Gln Gly Asn Ile
            340                 345                 350
Phe Ser Cys Ser Val Met His Glu Ala Leu His Asn Arg Phe Thr Gln
            355                 360                 365
Lys Ser Leu Ser Leu Ser Pro Gly Lys
        370                 375

<210> SEQ ID NO 14
<211> LENGTH: 327
<212> TYPE: PRT
<213> ORGANISM: Artificial Sequence
<220> FEATURE:
<223> OTHER INFORMATION: an artificially synthesized sequence

<400> SEQUENCE: 14

Ala Ser Thr Lys Gly Pro Ser Val Phe Pro Leu Ala Pro Cys Ser Arg
1               5                   10                  15
Ser Thr Ser Glu Ser Thr Ala Ala Leu Gly Cys Leu Val Lys Asp Tyr
                20                  25                  30
Phe Pro Glu Pro Val Thr Val Ser Trp Asn Ser Gly Ala Leu Thr Ser
            35                  40                  45
Gly Val His Thr Phe Pro Ala Val Leu Gln Ser Ser Gly Leu Tyr Ser
```

```
            50                  55                  60
Leu Ser Ser Val Val Thr Val Pro Ser Ser Leu Gly Thr Lys Thr
 65                  70                  75                  80

Tyr Thr Cys Asn Val Asp His Lys Pro Ser Asn Thr Lys Val Asp Lys
                 85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
            115                 120                 125

Asp Thr Leu Met Ile Ser Arg Thr Pro Glu Val Thr Cys Val Val Val
            130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
            195                 200                 205

Pro Ser Ser Ile Glu Lys Thr Ile Ser Lys Ala Lys Gly Gln Pro Arg
            210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
            275                 280                 285

Arg Leu Thr Val Asp Lys Ser Arg Trp Gln Glu Gly Asn Val Phe Ser
            290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 15
<211> LENGTH: 365
<212> TYPE: PRT
<213> ORGANISM: Homo sapiens

<400> SEQUENCE: 15

Met Gly Val Pro Arg Pro Gln Pro Trp Ala Leu Gly Leu Leu Leu Phe
 1               5                  10                  15

Leu Leu Pro Gly Ser Leu Gly Ala Glu Ser His Leu Ser Leu Leu Tyr
            20                  25                  30

His Leu Thr Ala Val Ser Ser Pro Ala Pro Gly Thr Pro Ala Phe Trp
            35                  40                  45

Val Ser Gly Trp Leu Gly Pro Gln Gln Tyr Leu Ser Tyr Asn Ser Leu
 50                  55                  60

Arg Gly Glu Ala Glu Pro Cys Gly Ala Trp Val Trp Glu Asn Gln Val
 65                  70                  75                  80

Ser Trp Tyr Trp Glu Lys Glu Thr Thr Asp Leu Arg Ile Lys Glu Lys
                 85                  90                  95
```

Leu Phe Leu Glu Ala Phe Lys Ala Leu Gly Lys Gly Pro Tyr Thr
                100                 105                 110

Leu Gln Gly Leu Leu Gly Cys Glu Leu Gly Pro Asp Asn Thr Ser Val
            115                 120                 125

Pro Thr Ala Lys Phe Ala Leu Asn Gly Glu Glu Phe Met Asn Phe Asp
        130                 135                 140

Leu Lys Gln Gly Thr Trp Gly Gly Asp Trp Pro Glu Ala Leu Ala Ile
145                 150                 155                 160

Ser Gln Arg Trp Gln Gln Gln Asp Lys Ala Ala Asn Lys Glu Leu Thr
                165                 170                 175

Phe Leu Leu Phe Ser Cys Pro His Arg Leu Arg Glu His Leu Glu Arg
            180                 185                 190

Gly Arg Gly Asn Leu Glu Trp Lys Glu Pro Pro Ser Met Arg Leu Lys
        195                 200                 205

Ala Arg Pro Ser Ser Pro Gly Phe Ser Val Leu Thr Cys Ser Ala Phe
    210                 215                 220

Ser Phe Tyr Pro Pro Glu Leu Gln Leu Arg Phe Leu Arg Asn Gly Leu
225                 230                 235                 240

Ala Ala Gly Thr Gly Gln Gly Asp Phe Gly Pro Asn Ser Asp Gly Ser
                245                 250                 255

Phe His Ala Ser Ser Ser Leu Thr Val Lys Ser Gly Asp Glu His His
            260                 265                 270

Tyr Cys Cys Ile Val Gln His Ala Gly Leu Ala Gln Pro Leu Arg Val
        275                 280                 285

Glu Leu Glu Ser Pro Ala Lys Ser Ser Val Leu Val Val Gly Ile Val
    290                 295                 300

Ile Gly Val Leu Leu Leu Thr Ala Ala Ala Val Gly Gly Ala Leu Leu
305                 310                 315                 320

Trp Arg Arg Met Arg Ser Gly Leu Pro Ala Pro Trp Ile Ser Leu Arg
                325                 330                 335

Gly Asp Asp Thr Gly Val Leu Leu Pro Thr Pro Gly Glu Ala Gln Asp
            340                 345                 350

Ala Asp Leu Lys Asp Val Asn Val Ile Pro Ala Thr Ala
        355                 360                 365

<210> SEQ ID NO 16
<211> LENGTH: 119
<212> TYPE: PRT
<213> ORGANISM: Homo sapiens

<400> SEQUENCE: 16

Met Ser Arg Ser Val Ala Leu Ala Val Leu Ala Leu Leu Ser Leu Ser
1               5                   10                  15

Gly Leu Glu Ala Ile Gln Arg Thr Pro Lys Ile Gln Val Tyr Ser Arg
                20                  25                  30

His Pro Ala Glu Asn Gly Lys Ser Asn Phe Leu Asn Cys Tyr Val Ser
            35                  40                  45

Gly Phe His Pro Ser Asp Ile Glu Val Asp Leu Leu Lys Asn Gly Glu
        50                  55                  60

Arg Ile Glu Lys Val Glu His Ser Asp Leu Ser Phe Ser Lys Asp Trp
65                  70                  75                  80

Ser Phe Tyr Leu Leu Tyr Tyr Thr Glu Phe Thr Pro Thr Glu Lys Asp
                85                  90                  95

Glu Tyr Ala Cys Arg Val Asn His Val Thr Leu Ser Gln Pro Lys Ile
            100                 105                 110

```
Val Lys Trp Asp Arg Asp Met
        115

<210> SEQ ID NO 17
<211> LENGTH: 4
<212> TYPE: PRT
<213> ORGANISM: Artificial Sequence
<220> FEATURE:
<223> OTHER INFORMATION: an artificially synthesized sequence

<400> SEQUENCE: 17

Gly Gly Gly Ser
1

<210> SEQ ID NO 18
<211> LENGTH: 4
<212> TYPE: PRT
<213> ORGANISM: Artificial Sequence
<220> FEATURE:
<223> OTHER INFORMATION: an artificially synthesized sequence

<400> SEQUENCE: 18

Ser Gly Gly Gly
1

<210> SEQ ID NO 19
<211> LENGTH: 5
<212> TYPE: PRT
<213> ORGANISM: Artificial Sequence
<220> FEATURE:
<223> OTHER INFORMATION: an artificially synthesized sequence

<400> SEQUENCE: 19

Gly Gly Gly Gly Ser
1               5

<210> SEQ ID NO 20
<211> LENGTH: 5
<212> TYPE: PRT
<213> ORGANISM: Artificial Sequence
<220> FEATURE:
<223> OTHER INFORMATION: an artificially synthesized sequence

<400> SEQUENCE: 20

Ser Gly Gly Gly Gly
1               5

<210> SEQ ID NO 21
<211> LENGTH: 6
<212> TYPE: PRT
<213> ORGANISM: Artificial Sequence
<220> FEATURE:
<223> OTHER INFORMATION: an artificially synthesized sequence

<400> SEQUENCE: 21

Gly Gly Gly Gly Gly Ser
1               5

<210> SEQ ID NO 22
<211> LENGTH: 6
<212> TYPE: PRT
<213> ORGANISM: Artificial Sequence
<220> FEATURE:
<223> OTHER INFORMATION: an artificially synthesized sequence

<400> SEQUENCE: 22
```

Ser Gly Gly Gly Gly Gly
1               5

<210> SEQ ID NO 23
<211> LENGTH: 7
<212> TYPE: PRT
<213> ORGANISM: Artificial Sequence
<220> FEATURE:
<223> OTHER INFORMATION: an artificially synthesized sequence

<400> SEQUENCE: 23

Gly Gly Gly Gly Gly Gly Ser
1               5

<210> SEQ ID NO 24
<211> LENGTH: 7
<212> TYPE: PRT
<213> ORGANISM: Artificial Sequence
<220> FEATURE:
<223> OTHER INFORMATION: an artificially synthesized sequence

<400> SEQUENCE: 24

Ser Gly Gly Gly Gly Gly Gly
1               5

<210> SEQ ID NO 25
<211> LENGTH: 1125
<212> TYPE: DNA
<213> ORGANISM: Homo sapiens

<400> SEQUENCE: 25

```
atgtggttct tgacaactct gctcctttgg gttccagttg atgggcaagt ggacaccaca        60
aaggcagtga tcactttgca gcctccatgg gtcagcgtgt tccaagagga aaccgtaacc       120
ttgcactgtg aggtgctcca tctgcctggg agcagctcta cacagtggtt tctcaatggc       180
acagccactc agacctcgac ccccagctac agaatcacct ctgccagtgt caatgacagt       240
ggtgaataca ggtgccagag aggtctctca gggcgaagtg accccataca gctggaaatc       300
cacagaggct ggctactact gcaggtctcc agcagagtct tcacggaagg agaacctctg       360
gccttgaggt gtcatgcgtg aaggataag ctggtgtaca atgtgcttta ctatcgaaat       420
ggcaaagcct ttaagttttt ccactggaat tctaacctca ccattctgaa accaacata        480
agtcacaatg caacctacca ttgctcaggc atgggaaagc atcgctacac atcagcagga       540
atatctgtca ctgtgaaaga gctatttcca gctccagtgc tgaatgcatc tgtgacatcc       600
ccactcctgg aggggaatct ggtcaccctg agctgtgaaa caaagttgct cttgcagaga       660
cctggtttgc agctttactt ctccttctac atgggcagca agaccctgcg aggcaggaac       720
acatcctctg aataccaaat actaactgct agaagagaag actctgggtt atactggtgc       780
gaggctgcca cagaggatgg aaatgtcctt aagcgcagcc ctgagttgga gcttcaagtg       840
cttggcctcc agttaccaac tcctgtctgg tttcatgtcc tttctatct ggcagtggga       900
ataatgtttt tagtgaacac tgttctctgg gtgacaatac gtaaagaact gaaaagaaag       960
aaaaagtggg atttagaaat ctctttggat tctggtcatg agaagaaggt aatttccagc      1020
cttcaagaag acagacattt agaagaagag ctgaaatgtc aggaacaaaa agaagaacag      1080
ctgcaggaag gggtgcaccg gaaggagccc caggggggcca cgtag                     1125
```

<210> SEQ ID NO 26
<211> LENGTH: 374
<212> TYPE: PRT

<213> ORGANISM: Homo sapiens

<400> SEQUENCE: 26

Met Trp Phe Leu Thr Thr Leu Leu Leu Trp Val Pro Val Asp Gly Gln
1               5                   10                  15

Val Asp Thr Thr Lys Ala Val Ile Thr Leu Gln Pro Pro Trp Val Ser
            20                  25                  30

Val Phe Gln Glu Glu Thr Val Thr Leu His Cys Glu Val Leu His Leu
        35                  40                  45

Pro Gly Ser Ser Ser Thr Gln Trp Phe Leu Asn Gly Thr Ala Thr Gln
    50                  55                  60

Thr Ser Thr Pro Ser Tyr Arg Ile Thr Ser Ala Ser Val Asn Asp Ser
65                  70                  75                  80

Gly Glu Tyr Arg Cys Gln Arg Gly Leu Ser Gly Arg Ser Asp Pro Ile
                85                  90                  95

Gln Leu Glu Ile His Arg Gly Trp Leu Leu Leu Gln Val Ser Ser Arg
            100                 105                 110

Val Phe Thr Glu Gly Glu Pro Leu Ala Leu Arg Cys His Ala Trp Lys
        115                 120                 125

Asp Lys Leu Val Tyr Asn Val Leu Tyr Tyr Arg Asn Gly Lys Ala Phe
    130                 135                 140

Lys Phe Phe His Trp Asn Ser Asn Leu Thr Ile Leu Lys Thr Asn Ile
145                 150                 155                 160

Ser His Asn Gly Thr Tyr His Cys Ser Gly Met Gly Lys His Arg Tyr
                165                 170                 175

Thr Ser Ala Gly Ile Ser Val Thr Val Lys Glu Leu Phe Pro Ala Pro
            180                 185                 190

Val Leu Asn Ala Ser Val Thr Ser Pro Leu Leu Glu Gly Asn Leu Val
        195                 200                 205

Thr Leu Ser Cys Glu Thr Lys Leu Leu Leu Gln Arg Pro Gly Leu Gln
    210                 215                 220

Leu Tyr Phe Ser Phe Tyr Met Gly Ser Lys Thr Leu Arg Gly Arg Asn
225                 230                 235                 240

Thr Ser Ser Glu Tyr Gln Ile Leu Thr Ala Arg Arg Glu Asp Ser Gly
                245                 250                 255

Leu Tyr Trp Cys Glu Ala Ala Thr Glu Asp Gly Asn Val Leu Lys Arg
            260                 265                 270

Ser Pro Glu Leu Glu Leu Gln Val Leu Gly Leu Gln Leu Pro Thr Pro
        275                 280                 285

Val Trp Phe His Val Leu Phe Tyr Leu Ala Val Gly Ile Met Phe Leu
    290                 295                 300

Val Asn Thr Val Leu Trp Val Thr Ile Arg Lys Glu Leu Lys Arg Lys
305                 310                 315                 320

Lys Lys Trp Asp Leu Glu Ile Ser Leu Asp Ser Gly His Glu Lys Lys
                325                 330                 335

Val Ile Ser Ser Leu Gln Glu Asp Arg His Leu Glu Glu Glu Leu Lys
            340                 345                 350

Cys Gln Glu Gln Lys Glu Glu Gln Leu Gln Glu Gly Val His Arg Lys
        355                 360                 365

Glu Pro Gln Gly Ala Thr
    370

<210> SEQ ID NO 27
<211> LENGTH: 951

<212> TYPE: DNA
<213> ORGANISM: Homo sapiens

<400> SEQUENCE: 27

```
atgactatgg agacccaaat gtctcagaat gtatgtccca gaaacctgtg gctgcttcaa      60
ccattgacag ttttgctgct gctggcttct gcagacagtc aagctgctcc cccaaaggct     120
gtgctgaaac ttgagccccc gtggatcaac gtgctccagg aggactctgt gactctgaca     180
tgccagggggg ctcgcagccc tgagagcgac tccattcagt ggttccacaa tgggaatctc    240
attcccaccc acacgcagcc cagctacagg ttcaaggcca acaacaatga cagcggggag     300
tacacgtgcc agactggcca gaccagcctc agcgaccctg tgcatctgac tgtgctttcc     360
gaatggctgg tgctccagac ccctcacctg gagttccagg agggagaaac catcatgctg     420
aggtgccaca gctggaagga caagcctctg gtcaaggtca cattcttcca gaatggaaaa     480
tcccagaaat tctcccattt ggatcccacc ttctccatcc cacaagcaaa ccacagtcac     540
agtggtgatt accactgcac aggaaacata ggctacacgc tgttctcatc caagcctgtg     600
accatcactg tccaagtgcc agcatgggc agctcttcac caatgggggt cattgtggct      660
gtggtcattg cgactgctgt agcagccatt gttgctgctg tagtggcctt gatctactgc     720
aggaaaaagc ggatttcagc caattccact gatcctgtga aggctgccca atttgagcca     780
cctggacgtc aaatgattgc catcagaaag agacaacttg aagaaccaa caatgactat      840
gaaacagctg acggcggcta catgactctg aaccccaggg cacctactga cgatgataaa     900
aacatctacc tgactcttcc tcccaacgac catgtcaaca gtaataacta a              951
```

<210> SEQ ID NO 28
<211> LENGTH: 316
<212> TYPE: PRT
<213> ORGANISM: Homo sapiens

<400> SEQUENCE: 28

```
Met Thr Met Glu Thr Gln Met Ser Gln Asn Val Cys Pro Arg Asn Leu
1               5                   10                  15

Trp Leu Gln Pro Leu Thr Val Leu Leu Leu Leu Ala Ser Ala Asp
            20                  25                  30

Ser Gln Ala Ala Pro Pro Lys Ala Val Leu Lys Leu Glu Pro Pro Trp
        35                  40                  45

Ile Asn Val Leu Gln Glu Asp Ser Val Thr Leu Thr Cys Gln Gly Ala
    50                  55                  60

Arg Ser Pro Glu Ser Asp Ser Ile Gln Trp Phe His Asn Gly Asn Leu
65                  70                  75                  80

Ile Pro Thr His Thr Gln Pro Ser Tyr Arg Phe Lys Ala Asn Asn Asn
                85                  90                  95

Asp Ser Gly Glu Tyr Thr Cys Gln Thr Gly Gln Thr Ser Leu Ser Asp
            100                 105                 110

Pro Val His Leu Thr Val Leu Ser Glu Trp Leu Val Leu Gln Thr Pro
        115                 120                 125

His Leu Glu Phe Gln Glu Gly Glu Thr Ile Met Leu Arg Cys His Ser
    130                 135                 140

Trp Lys Asp Lys Pro Leu Val Lys Val Thr Phe Phe Gln Asn Gly Lys
145                 150                 155                 160

Ser Gln Lys Phe Ser His Leu Asp Pro Thr Phe Ser Ile Pro Gln Ala
                165                 170                 175

Asn His Ser His Ser Gly Asp Tyr His Cys Thr Gly Asn Ile Gly Tyr
```

```
                180             185             190
Thr Leu Phe Ser Ser Lys Pro Val Thr Ile Thr Val Gln Val Pro Ser
            195             200             205

Met Gly Ser Ser Ser Pro Met Gly Val Ile Val Ala Val Ile Ala
    210             215             220

Thr Ala Val Ala Ala Ile Val Ala Ala Val Val Ala Leu Ile Tyr Cys
225             230             235             240

Arg Lys Lys Arg Ile Ser Ala Asn Ser Thr Asp Pro Val Lys Ala Ala
            245             250             255

Gln Phe Glu Pro Pro Gly Arg Gln Met Ile Ala Ile Arg Lys Arg Gln
            260             265             270

Leu Glu Glu Thr Asn Asn Asp Tyr Glu Thr Ala Asp Gly Gly Tyr Met
            275             280             285

Thr Leu Asn Pro Arg Ala Pro Thr Asp Asp Lys Asn Ile Tyr Leu
            290             295             300

Thr Leu Pro Pro Asn Asp His Val Asn Ser Asn Asn
305             310             315
```

```
<210> SEQ ID NO 29
<211> LENGTH: 876
<212> TYPE: DNA
<213> ORGANISM: Homo sapiens

<400> SEQUENCE: 29
atgggaatcc tgtcattctt acctgtcctt gccactgaga gtgactgggc tgactgcaag      60
tcccccagc cttggggtca tatgcttctg tggacagctg tgctattcct ggctcctgtt     120
gctgggacac ctgcagctcc cccaaaggct gtgctgaaac tcgagcccca gtggatcaac     180
gtgctccagg aggactctgt gactctgaca tgccggggga ctcacagccc tgagagcgac     240
tccattcagt ggttccacaa tgggaatctc attccaccc acacgcagcc cagctacagg     300
ttcaaggcca acaacaatga cagcggggag tacacgtgcc agactggcca gaccagcctc     360
agcgaccctg tgcatctgac tgtgctttct gagtggctgg tgctccagac ccctcacctg     420
gagttccagg agggagaaac catcgtgctg aggtgccaca ctggaaggg caagcctctg     480
gtcaaggtca cattcttcca gaatggaaaa tccaagaaat ttcccgttc ggatcccaac     540
ttctccatcc acaagcaaa ccacagtcac agtggtgatt accactgcac aggaaacata     600
ggctacacgc tgtactcatc aagcctgtg accatcactg tccagctcc cagctcttca     660
ccgatgggga tcattgtggc tgtggtcact gggattgctg tagcggccat gttgctgct     720
gtagtggcct tgatctactg caggaaaaag cggatttcag ccaatcccac taatcctgat     780
gaggctgaca agttggggc tgagaacaca atcacctatt cacttctcat gcacccggat     840
gctctggaag agcctgatga ccagaaccgt atttag                               876
```

```
<210> SEQ ID NO 30
<211> LENGTH: 291
<212> TYPE: PRT
<213> ORGANISM: Homo sapiens

<400> SEQUENCE: 30

Met Gly Ile Leu Ser Phe Leu Pro Val Leu Ala Thr Glu Ser Asp Trp
1               5                   10                  15

Ala Asp Cys Lys Ser Pro Gln Pro Trp Gly His Met Leu Leu Trp Thr
            20                  25                  30

Ala Val Leu Phe Leu Ala Pro Val Ala Gly Thr Pro Ala Ala Pro Pro
```

```
            35                  40                  45
Lys Ala Val Leu Lys Leu Glu Pro Gln Trp Ile Asn Val Leu Gln Glu
 50                  55                  60

Asp Ser Val Thr Leu Thr Cys Arg Gly Thr His Ser Pro Glu Ser Asp
 65                  70                  75                  80

Ser Ile Gln Trp Phe His Asn Gly Asn Leu Ile Pro Thr His Thr Gln
                 85                  90                  95

Pro Ser Tyr Arg Phe Lys Ala Asn Asn Asn Asp Ser Gly Glu Tyr Thr
            100                 105                 110

Cys Gln Thr Gly Gln Thr Ser Leu Ser Asp Pro Val His Leu Thr Val
        115                 120                 125

Leu Ser Glu Trp Leu Val Leu Gln Thr Pro His Leu Glu Phe Gln Glu
    130                 135                 140

Gly Glu Thr Ile Val Leu Arg Cys His Ser Trp Lys Asp Lys Pro Leu
145                 150                 155                 160

Val Lys Val Thr Phe Phe Gln Asn Gly Lys Ser Lys Lys Phe Ser Arg
                165                 170                 175

Ser Asp Pro Asn Phe Ser Ile Pro Gln Ala Asn His Ser His Ser Gly
            180                 185                 190

Asp Tyr His Cys Thr Gly Asn Ile Gly Tyr Thr Leu Tyr Ser Ser Lys
        195                 200                 205

Pro Val Thr Ile Thr Val Gln Ala Pro Ser Ser Ser Pro Met Gly Ile
    210                 215                 220

Ile Val Ala Val Val Thr Gly Ile Ala Val Ala Ala Ile Val Ala Ala
225                 230                 235                 240

Val Val Ala Leu Ile Tyr Cys Arg Lys Lys Arg Ile Ser Ala Asn Pro
                245                 250                 255

Thr Asn Pro Asp Glu Ala Asp Lys Val Gly Ala Glu Asn Thr Ile Thr
            260                 265                 270

Tyr Ser Leu Leu Met His Pro Asp Ala Leu Glu Glu Pro Asp Asp Gln
        275                 280                 285

Asn Arg Ile
    290

<210> SEQ ID NO 31
<211> LENGTH: 765
<212> TYPE: DNA
<213> ORGANISM: Homo sapiens

<400> SEQUENCE: 31
atgtggcagc tgctcctccc aactgctctg ctacttctag tttcagctgg catgcggact    60
gaagatctcc caaggctgt ggtgttcctg gagcctcaat ggtacagggt gctcgagaag    120
gacagtgtga ctctgaagtg ccagggagcc tactcccctg aggacaattc acacagtgg    180 tttcacaatg agagcctcat ctcaagccag gcctcgagct acttcattga cgctgccaca    240
gttgacgaca gtggagagta caggtgccag acaaacctct ccaccctcag tgacccggtg    300
cagctagaag tccatatcgg ctggctgttg ctccaggccc tcggtgggt gttcaaggag    360 gaagacccta ttcacctgag gtgtcacagc tggaagaaca ctgctctgca taaggtcaca    420
tatttacaga atggcaaagg caggaagtat tttcatcata attctgactt ctacattcca    480
aaagccacac tcaaagacag cggctcctac ttctgcaggg ggcttgttgg gagtaaaaat    540
gtgtcttcag agactgtgaa catcaccatc actcaaggtt tgtcagtgtc aaccatctca    600
tcattctttc cacctgggta ccaagtctct ttctgcttgg tgatggtact cctttttgca    660
```

```
gtggacacag gactatattt ctctgtgaag acaaacattc gaagctcaac aagagactgg    720
aaggaccata aatttaaatg gagaaaggac cctcaagaca aatga                   765
```

<210> SEQ ID NO 32
<211> LENGTH: 254
<212> TYPE: PRT
<213> ORGANISM: Homo sapiens

<400> SEQUENCE: 32

```
Met Trp Gln Leu Leu Leu Pro Thr Ala Leu Leu Leu Val Ser Ala
1               5                   10                  15

Gly Met Arg Thr Glu Asp Leu Pro Lys Ala Val Val Phe Leu Glu Pro
            20                  25                  30

Gln Trp Tyr Arg Val Leu Glu Lys Asp Ser Val Thr Leu Lys Cys Gln
        35                  40                  45

Gly Ala Tyr Ser Pro Glu Asp Asn Ser Thr Gln Trp Phe His Asn Glu
    50                  55                  60

Ser Leu Ile Ser Ser Gln Ala Ser Ser Tyr Phe Ile Asp Ala Ala Thr
65                  70                  75                  80

Val Asp Asp Ser Gly Glu Tyr Arg Cys Gln Thr Asn Leu Ser Thr Leu
                85                  90                  95

Ser Asp Pro Val Gln Leu Glu Val His Ile Gly Trp Leu Leu Leu Gln
            100                 105                 110

Ala Pro Arg Trp Val Phe Lys Glu Glu Asp Pro Ile His Leu Arg Cys
        115                 120                 125

His Ser Trp Lys Asn Thr Ala Leu His Lys Val Thr Tyr Leu Gln Asn
    130                 135                 140

Gly Lys Gly Arg Lys Tyr Phe His His Asn Ser Asp Phe Tyr Ile Pro
145                 150                 155                 160

Lys Ala Thr Leu Lys Asp Ser Gly Ser Tyr Phe Cys Arg Gly Leu Val
                165                 170                 175

Gly Ser Lys Asn Val Ser Ser Glu Thr Val Asn Ile Thr Ile Thr Gln
            180                 185                 190

Gly Leu Ser Val Ser Thr Ile Ser Ser Phe Phe Pro Pro Gly Tyr Gln
        195                 200                 205

Val Ser Phe Cys Leu Val Met Val Leu Leu Phe Ala Val Asp Thr Gly
    210                 215                 220

Leu Tyr Phe Ser Val Lys Thr Asn Ile Arg Ser Ser Thr Arg Asp Trp
225                 230                 235                 240

Lys Asp His Lys Phe Lys Trp Arg Lys Asp Pro Gln Asp Lys
                245                 250
```

<210> SEQ ID NO 33
<211> LENGTH: 702
<212> TYPE: DNA
<213> ORGANISM: Homo sapiens

<400> SEQUENCE: 33

```
atgtggcagc tgctcctccc aactgctctg ctacttctag tttcagctgg catgcggact    60
gaagatctcc caaggctgt ggtgttcctg agcctcaat ggtacagcgt gcttgagaag    120
gacagtgtga ctctgaagtg ccagggagcc tactcccctg aggacaattc cacacagtgg    180
tttcacaatg agagcctcat ctcaagccag gcctcgagct acttcattga cgctgccaca    240
gtcaacgaca gtggagagta caggtgccag acaaacctct ccaccctcag tgacccggtg    300
```

```
cagctagaag tccatatcgg ctggctgttg ctccaggccc ctcggtgggt gttcaaggag    360
gaagacccta ttcacctgag gtgtcacagc tggaagaaca ctgctctgca taaggtcaca    420
tatttacaga atgcaaaga caggaagtat tttcatcata attctgactt ccacattcca    480
aaagccacac tcaaagatag cggctcctac ttctgcaggg ggcttgttgg gagtaaaaat    540
gtgtcttcag agactgtgaa catcaccatc actcaaggtt tggcagtgtc aaccatctca    600
tcattctctc cacctgggta ccaagtctct ttctgcttgg tgatggtact ccttttttgca   660 gtggacacag gactatattt ctctgtgaag acaaacattt ga                       702
```

```
<210> SEQ ID NO 34
<211> LENGTH: 233
<212> TYPE: PRT
<213> ORGANISM: Homo sapiens

<400> SEQUENCE: 34
```

Met Trp Gln Leu Leu Pro Thr Ala Leu Leu Leu Val Ser Ala
1               5                   10                  15

Gly Met Arg Thr Glu Asp Leu Pro Lys Ala Val Val Phe Leu Glu Pro
            20                  25                  30

Gln Trp Tyr Ser Val Leu Glu Lys Asp Ser Val Thr Leu Lys Cys Gln
        35                  40                  45

Gly Ala Tyr Ser Pro Glu Asp Asn Ser Thr Gln Trp Phe His Asn Glu
    50                  55                  60

Ser Leu Ile Ser Ser Gln Ala Ser Ser Tyr Phe Ile Asp Ala Ala Thr
65                  70                  75                  80

Val Asn Asp Ser Gly Glu Tyr Arg Cys Gln Thr Asn Leu Ser Thr Leu
                85                  90                  95

Ser Asp Pro Val Gln Leu Glu Val His Ile Gly Trp Leu Leu Leu Gln
            100                 105                 110

Ala Pro Arg Trp Val Phe Lys Glu Glu Asp Pro Ile His Leu Arg Cys
        115                 120                 125

His Ser Trp Lys Asn Thr Ala Leu His Lys Val Thr Tyr Leu Gln Asn
    130                 135                 140

Gly Lys Asp Arg Lys Tyr Phe His His Asn Ser Asp Phe His Ile Pro
145                 150                 155                 160

Lys Ala Thr Leu Lys Asp Ser Gly Ser Tyr Phe Cys Arg Gly Leu Val
                165                 170                 175

Gly Ser Lys Asn Val Ser Ser Glu Thr Val Asn Ile Thr Ile Thr Gln
            180                 185                 190

Gly Leu Ala Val Ser Thr Ile Ser Ser Phe Ser Pro Pro Gly Tyr Gln
        195                 200                 205

Val Ser Phe Cys Leu Val Met Val Leu Leu Phe Ala Val Asp Thr Gly
    210                 215                 220

Leu Tyr Phe Ser Val Lys Thr Asn Ile
225                 230

```
<210> SEQ ID NO 35
<211> LENGTH: 447
<212> TYPE: PRT
<213> ORGANISM: Homo sapiens

<400> SEQUENCE: 35
```

Gln Val Gln Leu Gln Glu Ser Gly Pro Gly Leu Val Lys Pro Ser Glu
1               5                   10                  15

Thr Leu Ser Leu Thr Cys Ala Val Ser Gly His Ser Ile Ser His Asp

```
                20                  25                  30
His Ala Trp Ser Trp Val Arg Gln Pro Gly Glu Gly Leu Glu Trp
            35                  40                  45
Ile Gly Phe Ile Ser Tyr Ser Gly Ile Thr Asn Tyr Asn Pro Ser Leu
 50                  55                  60
Gln Gly Arg Val Thr Ile Ser Arg Asp Asn Ser Lys Asn Thr Leu Tyr
 65                  70                  75                  80
Leu Gln Met Asn Ser Leu Arg Ala Glu Asp Thr Ala Val Tyr Tyr Cys
                85                  90                  95
Ala Arg Ser Leu Ala Arg Thr Thr Ala Met Asp Tyr Trp Gly Glu Gly
            100                 105                 110
Thr Leu Val Thr Val Ser Ser Ala Ser Thr Lys Gly Pro Ser Val Phe
            115                 120                 125
Pro Leu Ala Pro Ser Ser Lys Ser Thr Ser Gly Gly Thr Ala Ala Leu
            130                 135                 140
Gly Cys Leu Val Lys Asp Tyr Phe Pro Glu Pro Val Thr Val Ser Trp
145                 150                 155                 160
Asn Ser Gly Ala Leu Thr Ser Gly Val His Thr Phe Pro Ala Val Leu
                165                 170                 175
Gln Ser Ser Gly Leu Tyr Ser Leu Ser Ser Val Val Thr Val Pro Ser
            180                 185                 190
Ser Ser Leu Gly Thr Gln Thr Tyr Ile Cys Asn Val Asn His Lys Pro
            195                 200                 205
Ser Asn Thr Lys Val Asp Lys Lys Val Glu Pro Lys Ser Cys Asp Lys
            210                 215                 220
Thr His Thr Cys Pro Pro Cys Pro Ala Pro Glu Leu Leu Gly Gly Pro
225                 230                 235                 240
Ser Val Phe Leu Phe Pro Pro Lys Pro Lys Asp Thr Leu Met Ile Ser
                245                 250                 255
Arg Thr Pro Glu Val Thr Cys Val Val Val Asp Val Ser His Glu Asp
            260                 265                 270
Pro Glu Val Lys Phe Asn Trp Tyr Val Asp Gly Val Glu Val His Asn
            275                 280                 285
Ala Lys Thr Lys Pro Arg Glu Glu Gln Tyr Asn Ser Thr Tyr Arg Val
            290                 295                 300
Val Ser Val Leu Thr Val Leu His Gln Asp Trp Leu Asn Gly Lys Glu
305                 310                 315                 320
Tyr Lys Cys Lys Val Ser Asn Lys Ala Leu Pro Ala Pro Ile Glu Lys
                325                 330                 335
Thr Ile Ser Lys Ala Lys Gly Gln Pro Arg Glu Pro Gln Val Tyr Thr
            340                 345                 350
Leu Pro Pro Ser Arg Asp Glu Leu Thr Lys Asn Gln Val Ser Leu Thr
            355                 360                 365
Cys Leu Val Lys Gly Phe Tyr Pro Ser Asp Ile Ala Val Glu Trp Glu
            370                 375                 380
Ser Asn Gly Gln Pro Glu Asn Asn Tyr Lys Thr Thr Pro Pro Val Leu
385                 390                 395                 400
Asp Ser Asp Gly Ser Phe Phe Leu Tyr Ser Lys Leu Thr Val Asp Lys
                405                 410                 415
Ser Arg Trp Gln Gln Gly Asn Val Phe Ser Cys Ser Val Met His Glu
            420                 425                 430
Ala Leu His Asn His Tyr Thr Gln Lys Ser Leu Ser Leu Ser Pro
            435                 440                 445
```

<210> SEQ ID NO 36
<211> LENGTH: 214
<212> TYPE: PRT
<213> ORGANISM: Homo sapiens

<400> SEQUENCE: 36

Asp Ile Gln Met Thr Gln Ser Pro Ser Ser Leu Ser Ala Ser Val Gly
1               5                   10                  15

Asp Ser Val Thr Ile Thr Cys Gln Ala Ser Thr Asp Ile Ser Ser His
            20                  25                  30

Leu Asn Trp Tyr Gln Gln Lys Pro Gly Lys Ala Pro Glu Leu Leu Ile
        35                  40                  45

Tyr Tyr Gly Ser His Leu Leu Ser Gly Val Pro Ser Arg Phe Ser Gly
    50                  55                  60

Ser Gly Ser Gly Thr Asp Phe Thr Phe Thr Ile Ser Ser Leu Glu Ala
65                  70                  75                  80

Glu Asp Ala Ala Thr Tyr Tyr Cys Gly Gln Gly Asn Arg Leu Pro Tyr
                85                  90                  95

Thr Phe Gly Gln Gly Thr Lys Val Glu Ile Glu Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 37
<211> LENGTH: 447
<212> TYPE: PRT
<213> ORGANISM: Artificial Sequence
<220> FEATURE:
<223> OTHER INFORMATION: an artificially synthesized sequence

<400> SEQUENCE: 37

Gln Val Gln Leu Gln Glu Ser Gly Pro Gly Leu Val Lys Pro Ser Glu
1               5                   10                  15

Thr Leu Ser Leu Thr Cys Ala Val Ser Gly His Ser Ile Ser His Asp
            20                  25                  30

His Ala Trp Ser Trp Val Arg Gln Pro Pro Gly Glu Gly Leu Glu Trp
        35                  40                  45

Ile Gly Phe Ile Ser Tyr Ser Gly Ile Thr Asn Tyr Asn Pro Ser Leu
    50                  55                  60

Gln Gly Arg Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

```
Ala Arg Ser Leu Ala Arg Thr Thr Ala Met Asp Tyr Trp Gly Glu Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
        130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
        210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
        290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Trp His Tyr Thr Gln Lys Ser Leu Ser Leu Ser Pro
        435                 440                 445

<210> SEQ ID NO 38
<211> LENGTH: 447
<212> TYPE: PRT
<213> ORGANISM: Artificial Sequence
<220> FEATURE:
<223> OTHER INFORMATION: an artificially synthesized sequence

<400> SEQUENCE: 38

Gln Val Gln Leu Gln Glu Ser Gly Pro Gly Leu Val Lys Pro Ser Glu
1               5                   10                  15
```

```
Thr Leu Ser Leu Thr Cys Ala Val Ser Gly His Ser Ile Ser His Asp
            20                  25                  30

His Ala Trp Ser Trp Val Arg Gln Pro Pro Gly Glu Gly Leu Glu Trp
            35                  40                  45

Ile Gly Phe Ile Ser Tyr Ser Gly Ile Thr Asn Tyr Asn Pro Ser Leu
        50                  55                  60

Gln Gly Arg Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Leu Ala Arg Thr Thr Ala Met Asp Tyr Trp Gly Glu Gly
            100                 105                 110

Thr Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
        130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys Asp Lys
210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
            245                 250                 255

Arg Thr Ala Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
        290                 295                 300

Val Ser Val Leu Thr Pro Leu His Gln Asp Trp Leu Asn Gly Lys Glu
305                 310                 315                 320

Tyr Lys Cys Lys Val Ser Asn Lys Ala Leu Pro Ala Pro Ile Glu Lys
            325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Leu His Glu
            420                 425                 430

Ala Leu His Tyr His Tyr Thr Gln Lys Ser Leu Ser Leu Ser Pro
```

<210> SEQ ID NO 39
<211> LENGTH: 447
<212> TYPE: PRT
<213> ORGANISM: Artificial Sequence
<220> FEATURE:
<223> OTHER INFORMATION: an artificially synthesized sequence

<400> SEQUENCE: 39

Gln Val Gln Leu Gln Glu Ser Gly Pro Gly Leu Val Lys Pro Ser Glu
1               5                   10                  15

Thr Leu Ser Leu Thr Cys Ala Val Ser Gly His Ser Ile Ser His Asp
            20                  25                  30

His Ala Trp Ser Trp Val Arg Gln Pro Pro Gly Glu Gly Leu Glu Trp
        35                  40                  45

Ile Gly Phe Ile Ser Tyr Ser Gly Ile Thr Asn Tyr Asn Pro Ser Leu
    50                  55                  60

Gln Gly Arg Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Leu Ala Arg Thr Thr Ala Met Asp Tyr Trp Gly Glu Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Phe Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr

```
                355                 360                 365
Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
                420                 425                 430

Ala Leu His Tyr His Tyr Thr Gln Lys Ser Leu Ser Leu Ser Pro
                435                 440                 445

<210> SEQ ID NO 40
<211> LENGTH: 447
<212> TYPE: PRT
<213> ORGANISM: Artificial Sequence
<220> FEATURE:
<223> OTHER INFORMATION: an artificially synthesized sequence

<400> SEQUENCE: 40

Gln Val Gln Leu Gln Glu Ser Gly Pro Gly Leu Val Lys Pro Ser Glu
1               5                   10                  15

Thr Leu Ser Leu Thr Cys Ala Val Ser Gly His Ser Ile Ser His Asp
                20                  25                  30

His Ala Trp Ser Trp Val Arg Gln Pro Pro Gly Glu Gly Leu Glu Trp
            35                  40                  45

Ile Gly Phe Ile Ser Tyr Ser Gly Ile Thr Asn Tyr Asn Pro Ser Leu
    50                  55                  60

Gln Gly Arg Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Leu Ala Arg Thr Thr Ala Met Asp Tyr Trp Gly Glu Gly
                100                 105                 110

Thr Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
    195                 200                 205

Ser Asn Thr Lys Val Asp Lys Lys Val Glu Pro Lys Ser Cys Asp Lys
210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Tyr Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
```

```
                275                 280                 285
Ala Lys Thr Lys Pro Arg Glu Glu Gln Tyr Asn Ser Thr Tyr Arg Val
            290                 295                 300

Val Ser Val Leu Thr Pro Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
                355                 360                 365

Cys Leu Val Lys Gly Phe Tyr Pro Ser Asp Ile Ala Val Glu Trp Glu
            370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Tyr His Tyr Thr Gln Lys Ser Leu Ser Leu Ser Pro
            435                 440                 445

<210> SEQ ID NO 41
<211> LENGTH: 214
<212> TYPE: PRT
<213> ORGANISM: Artificial Sequence
<220> FEATURE:
<223> OTHER INFORMATION: an artificially synthesized sequence

<400> SEQUENCE: 41

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Ser Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Gly Asn Thr Leu Pro Tyr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
```

```
                195                 200                 205

Phe Asn Arg Gly Glu Cys
    210

<210> SEQ ID NO 42
<211> LENGTH: 119
<212> TYPE: PRT
<213> ORGANISM: Mus musculus

<400> SEQUENCE: 42

Asp Val Gln Leu Gln Glu Ser Gly Pro Val Leu Val Lys Pro Ser Gln
1               5                   10                  15

Ser Leu Ser Leu Thr Cys Thr Val Thr Gly Tyr Ser Ile Thr Ser Asp
            20                  25                  30

His Ala Trp Ser Trp Ile Arg Gln Phe Pro Gly Asn Lys Leu Glu Trp
        35                  40                  45

Met Gly Tyr Ile Ser Tyr Ser Gly Ile Thr Thr Tyr Asn Pro Ser Leu
    50                  55                  60

Lys Ser Arg Ile Ser Ile Thr Arg Asp Thr Ser Lys Asn Gln Phe Phe
65                  70                  75                  80

Leu Gln Leu Asn Ser Val Thr Thr Gly Asp Thr Ser Thr Tyr Tyr Cys
                85                  90                  95

Ala Arg Ser Leu Ala Arg Thr Thr Ala Met Asp Tyr Trp Gly Gln Gly
            100                 105                 110

Thr Ser Val Thr Val Ser Ser
        115

<210> SEQ ID NO 43
<211> LENGTH: 107
<212> TYPE: PRT
<213> ORGANISM: Mus musculus

<400> SEQUENCE: 43

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Ser Tyr
            20                  25                  30

Leu Asn Trp Tyr Gln Gln Lys Pro Asp Gly Thr Ile Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Tyr Ser Leu Thr Ile Asn Asn Leu Glu Gln
65                  70                  75                  80

Glu Asp Ile Ala Thr Tyr Phe Cys Gln Gln Gly Asn Thr Leu Pro Tyr
                85                  90                  95

Thr Phe Gly Gly Gly Thr Lys Leu Glu Ile Lys
            100                 105

<210> SEQ ID NO 44
<211> LENGTH: 324
<212> TYPE: PRT
<213> ORGANISM: Mus musculus

<400> SEQUENCE: 44

Ala Lys Thr Thr Pro Pro Ser Val Tyr Pro Leu Ala Pro Gly Ser Ala
1               5                   10                  15

Ala Gln Thr Asn Ser Met Val Thr Leu Gly Cys Leu Val Lys Gly Tyr
            20                  25                  30
```

```
Phe Pro Glu Pro Val Thr Val Thr Trp Asn Ser Gly Ser Leu Ser Ser
             35                  40                  45

Gly Val His Thr Phe Pro Ala Val Leu Gln Ser Asp Leu Tyr Thr Leu
 50                  55                  60

Ser Ser Ser Val Thr Val Pro Ser Ser Thr Trp Pro Ser Glu Thr Val
 65                  70                  75                  80

Thr Cys Asn Val Ala His Pro Ala Ser Ser Thr Lys Val Asp Lys Lys
                 85                  90                  95

Ile Val Pro Arg Asp Cys Gly Cys Lys Pro Cys Ile Cys Thr Val Pro
                100                 105                 110

Glu Val Ser Ser Val Phe Ile Phe Pro Pro Lys Pro Lys Asp Val Leu
            115                 120                 125

Thr Ile Thr Leu Thr Pro Lys Val Thr Cys Val Val Val Asp Ile Ser
        130                 135                 140

Lys Asp Asp Pro Glu Val Gln Phe Ser Trp Phe Val Asp Asp Val Glu
145                 150                 155                 160

Val His Thr Ala Gln Thr Gln Pro Arg Glu Glu Gln Phe Asn Ser Thr
                165                 170                 175

Phe Arg Ser Val Ser Glu Leu Pro Ile Met His Gln Asp Trp Leu Asn
            180                 185                 190

Gly Lys Glu Phe Lys Cys Arg Val Asn Ser Ala Ala Phe Pro Ala Pro
        195                 200                 205

Ile Glu Lys Thr Ile Ser Lys Thr Lys Gly Arg Pro Lys Ala Pro Gln
    210                 215                 220

Val Tyr Thr Ile Pro Pro Pro Lys Glu Gln Met Ala Lys Asp Lys Val
225                 230                 235                 240

Ser Leu Thr Cys Met Ile Thr Asp Phe Phe Pro Glu Asp Ile Thr Val
                245                 250                 255

Glu Trp Gln Trp Asn Gly Gln Pro Ala Glu Asn Tyr Lys Asn Thr Gln
            260                 265                 270

Pro Ile Met Asp Thr Asp Gly Ser Tyr Phe Val Tyr Ser Lys Leu Asn
        275                 280                 285

Val Gln Lys Ser Asn Trp Glu Ala Gly Asn Thr Phe Thr Cys Ser Val
    290                 295                 300

Leu His Glu Gly Leu His Asn His His Thr Glu Lys Ser Leu Ser His
305                 310                 315                 320

Ser Pro Gly Lys

<210> SEQ ID NO 45
<211> LENGTH: 107
<212> TYPE: PRT
<213> ORGANISM: Mus musculus

<400> SEQUENCE: 45

Arg Ala Asp Ala Ala Pro Thr Val Ser Ile Phe Pro Pro Ser Ser Glu
 1               5                  10                  15

Gln Leu Thr Ser Gly Gly Ala Ser Val Val Cys Phe Leu Asn Asn Phe
             20                  25                  30

Tyr Pro Lys Asp Ile Asn Val Lys Trp Lys Ile Asp Gly Ser Glu Arg
         35                  40                  45

Gln Asn Gly Val Leu Asn Ser Trp Thr Asp Gln Asp Ser Lys Asp Ser
     50                  55                  60

Thr Tyr Ser Met Ser Ser Thr Leu Thr Leu Thr Lys Asp Glu Tyr Glu
 65                  70                  75                  80
```

Arg His Asn Ser Tyr Thr Cys Glu Ala Thr His Lys Thr Ser Thr Ser
            85                  90                  95

Pro Ile Val Lys Ser Phe Asn Arg Asn Glu Cys
            100                 105

<210> SEQ ID NO 46
<211> LENGTH: 443
<212> TYPE: PRT
<213> ORGANISM: Mus musculus

<400> SEQUENCE: 46

Asp Val Gln Leu Gln Glu Ser Gly Pro Val Leu Val Lys Pro Ser Gln
1               5                   10                  15

Ser Leu Ser Leu Thr Cys Thr Val Thr Gly Tyr Ser Ile Thr Ser Asp
            20                  25                  30

His Ala Trp Ser Trp Ile Arg Gln Phe Pro Gly Asn Lys Leu Glu Trp
        35                  40                  45

Met Gly Tyr Ile Ser Tyr Ser Gly Ile Thr Thr Tyr Asn Pro Ser Leu
    50                  55                  60

Lys Ser Arg Ile Ser Ile Thr Arg Asp Thr Ser Lys Asn Gln Phe Phe
65                  70                  75                  80

Leu Gln Leu Asn Ser Val Thr Thr Gly Asp Thr Ser Thr Tyr Tyr Cys
                85                  90                  95

Ala Arg Ser Leu Ala Arg Thr Thr Ala Met Asp Tyr Trp Gly Gln Gly
            100                 105                 110

Thr Ser Val Thr Val Ser Ser Ala Lys Thr Thr Pro Pro Ser Val Tyr
        115                 120                 125

Pro Leu Ala Pro Gly Ser Ala Ala Gln Thr Asn Ser Met Val Thr Leu
    130                 135                 140

Gly Cys Leu Val Lys Gly Tyr Phe Pro Glu Pro Val Thr Val Thr Trp
145                 150                 155                 160

Asn Ser Gly Ser Leu Ser Ser Gly Val His Thr Phe Pro Ala Val Leu
                165                 170                 175

Gln Ser Asp Leu Tyr Thr Leu Ser Ser Ser Val Thr Val Pro Ser Ser
            180                 185                 190

Thr Trp Pro Ser Glu Thr Val Thr Cys Asn Val Ala His Pro Ala Ser
        195                 200                 205

Ser Thr Lys Val Asp Lys Lys Ile Val Pro Arg Asp Cys Gly Cys Lys
    210                 215                 220

Pro Cys Ile Cys Thr Val Pro Glu Val Ser Ser Val Phe Ile Phe Pro
225                 230                 235                 240

Pro Lys Pro Lys Asp Val Leu Thr Ile Thr Leu Thr Pro Lys Val Thr
                245                 250                 255

Cys Val Val Val Asp Ile Ser Lys Asp Asp Pro Glu Val Gln Phe Ser
            260                 265                 270

Trp Phe Val Asp Asp Val Glu Val His Thr Ala Gln Thr Gln Pro Arg
        275                 280                 285

Glu Glu Gln Phe Asn Ser Thr Phe Arg Ser Val Ser Glu Leu Pro Ile
    290                 295                 300

Met His Gln Asp Trp Leu Asn Gly Lys Glu Phe Lys Cys Arg Val Asn
305                 310                 315                 320

Ser Ala Ala Phe Pro Ala Pro Ile Glu Lys Thr Ile Ser Lys Thr Lys
                325                 330                 335

Gly Arg Pro Lys Ala Pro Gln Val Tyr Thr Ile Pro Pro Pro Lys Glu

```
                    340                 345                 350
Gln Met Ala Lys Asp Lys Val Ser Leu Thr Cys Met Ile Thr Asp Phe
            355                 360                 365

Phe Pro Glu Asp Ile Thr Val Glu Trp Gln Trp Asn Gly Gln Pro Ala
370                 375                 380

Glu Asn Tyr Lys Asn Thr Gln Pro Ile Met Asp Thr Asp Gly Ser Tyr
385                 390                 395                 400

Phe Val Tyr Ser Lys Leu Asn Val Gln Lys Ser Asn Trp Glu Ala Gly
            405                 410                 415

Asn Thr Phe Thr Cys Ser Val Leu His Glu Gly Leu His Asn His His
            420                 425                 430

Thr Glu Lys Ser Leu Ser His Ser Pro Gly Lys
            435                 440

<210> SEQ ID NO 47
<211> LENGTH: 214
<212> TYPE: PRT
<213> ORGANISM: Mus musculus

<400> SEQUENCE: 47

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Ser Tyr
            20                  25                  30

Leu Asn Trp Tyr Gln Gln Lys Pro Asp Gly Thr Ile Lys Leu Leu Ile
        35                  40                  45

Tyr Tyr Thr Ser Arg Leu His Ser Gly Val Pro Ser Arg Phe Ser Gly
50                  55                  60

Ser Gly Ser Gly Thr Asp Tyr Ser Leu Thr Ile Asn Asn Leu Glu Gln
65                  70                  75                  80

Glu Asp Ile Ala Thr Tyr Phe Cys Gln Gln Gly Asn Thr Leu Pro Tyr
            85                  90                  95

Thr Phe Gly Gly Gly Thr Lys Leu Glu Ile Lys Arg Ala Asp Ala Ala
            100                 105                 110

Pro Thr Val Ser Ile Phe Pro Pro Ser Ser Glu Gln Leu Thr Ser Gly
        115                 120                 125

Gly Ala Ser Val Val Cys Phe Leu Asn Asn Phe Tyr Pro Lys Asp Ile
130                 135                 140

Asn Val Lys Trp Lys Ile Asp Gly Ser Glu Arg Gln Asn Gly Val Leu
145                 150                 155                 160

Asn Ser Trp Thr Asp Gln Asp Ser Lys Asp Ser Thr Tyr Ser Met Ser
            165                 170                 175

Ser Thr Leu Thr Leu Thr Lys Asp Glu Tyr Glu Arg His Asn Ser Tyr
            180                 185                 190

Thr Cys Glu Ala Thr His Lys Thr Ser Thr Ser Pro Ile Val Lys Ser
            195                 200                 205

Phe Asn Arg Asn Glu Cys
        210

<210> SEQ ID NO 48
<211> LENGTH: 443
<212> TYPE: PRT
<213> ORGANISM: Artificial Sequence
<220> FEATURE:
<223> OTHER INFORMATION: an artificially synthesized sequence

<400> SEQUENCE: 48
```

-continued

```
Asp Val Gln Leu Gln Glu Ser Gly Pro Val Leu Val Lys Pro Ser Gln
1               5                   10                  15

Ser Leu Ser Leu Thr Cys Thr Val Thr Gly Tyr Ser Ile Thr Ser Asp
            20                  25                  30

His Ala Trp Ser Trp Ile Arg Gln Phe Pro Gly Asn Lys Leu Glu Trp
        35                  40                  45

Met Gly Tyr Ile Ser Tyr Ser Gly Ile Thr Thr Tyr Asn Pro Ser Leu
    50                  55                  60

Lys Ser Arg Ile Ser Ile Thr Arg Asp Thr Ser Lys Asn Gln Phe Phe
65                  70                  75                  80

Leu Gln Leu Asn Ser Val Thr Thr Gly Asp Thr Ser Tyr Tyr Cys
                85                  90                  95

Ala Arg Ser Leu Ala Arg Thr Thr Ala Met Asp Tyr Trp Gly Gln Gly
            100                 105                 110

Thr Ser Val Thr Val Ser Ser Ala Lys Thr Thr Pro Pro Ser Val Tyr
        115                 120                 125

Pro Leu Ala Pro Gly Ser Ala Ala Gln Thr Asn Ser Met Val Thr Leu
        130                 135                 140

Gly Cys Leu Val Lys Gly Tyr Phe Pro Glu Pro Val Thr Val Thr Trp
145                 150                 155                 160

Asn Ser Gly Ser Leu Ser Ser Gly Val His Thr Phe Pro Ala Val Leu
                165                 170                 175

Gln Ser Asp Leu Tyr Thr Leu Ser Ser Ser Val Thr Val Pro Ser Ser
            180                 185                 190

Thr Trp Pro Ser Glu Thr Val Thr Cys Asn Val Ala His Pro Ala Ser
        195                 200                 205

Ser Thr Lys Val Asp Lys Lys Ile Val Pro Arg Asp Cys Gly Cys Lys
    210                 215                 220

Pro Cys Ile Cys Thr Val Pro Glu Val Ser Ser Val Phe Ile Phe Pro
225                 230                 235                 240

Pro Lys Pro Lys Asp Val Leu Tyr Ile Thr Leu Glu Pro Lys Val Thr
            245                 250                 255

Cys Val Val Asp Ile Ser Lys Asp Asp Pro Glu Val Gln Phe Ser
        260                 265                 270

Trp Phe Val Asp Asp Val Glu Val His Thr Ala Gln Thr Gln Pro Arg
    275                 280                 285

Glu Glu Gln Phe Asn Ser Thr Phe Arg Ser Val Ser Glu Leu Pro Ile
290                 295                 300

Met His Gln Asp Trp Leu Asn Gly Lys Glu Phe Lys Cys Arg Val Asn
305                 310                 315                 320

Ser Ala Ala Phe Pro Ala Pro Ile Glu Lys Thr Ile Ser Lys Thr Lys
            325                 330                 335

Gly Arg Pro Lys Ala Pro Gln Val Tyr Thr Ile Pro Pro Lys Glu
        340                 345                 350

Gln Met Ala Lys Asp Lys Val Ser Leu Thr Cys Met Ile Thr Asp Phe
    355                 360                 365

Phe Pro Glu Asp Ile Thr Val Glu Trp Gln Trp Asn Gly Gln Pro Ala
370                 375                 380

Glu Asn Tyr Lys Asn Thr Gln Pro Ile Met Asp Thr Asp Gly Ser Tyr
385                 390                 395                 400

Phe Val Tyr Ser Lys Leu Asn Val Gln Lys Ser Asn Trp Glu Ala Gly
            405                 410                 415
```

Asn Thr Phe Thr Cys Ser Val Leu His Glu Gly Leu Lys Phe His His
            420                 425                 430

Thr Glu Lys Ser Leu Ser His Ser Pro Gly Lys
            435                 440

<210> SEQ ID NO 49
<211> LENGTH: 443
<212> TYPE: PRT
<213> ORGANISM: Artificial Sequence
<220> FEATURE:
<223> OTHER INFORMATION: an artificially synthesized sequence

<400> SEQUENCE: 49

Asp Val Gln Leu Gln Glu Ser Gly Pro Val Leu Val Lys Pro Ser Gln
1               5                   10                  15

Ser Leu Ser Leu Thr Cys Thr Val Thr Gly Tyr Ser Ile Thr Ser Asp
            20                  25                  30

His Ala Trp Ser Trp Ile Arg Gln Phe Pro Gly Asn Lys Leu Glu Trp
        35                  40                  45

Met Gly Tyr Ile Ser Tyr Ser Gly Ile Thr Thr Tyr Asn Pro Ser Leu
    50                  55                  60

Lys Ser Arg Ile Ser Ile Thr Arg Asp Thr Ser Lys Asn Gln Phe Phe
65                  70                  75                  80

Leu Gln Leu Asn Ser Val Thr Thr Gly Asp Thr Ser Thr Tyr Tyr Cys
                85                  90                  95

Ala Arg Ser Leu Ala Arg Thr Thr Ala Met Asp Tyr Trp Gly Gln Gly
            100                 105                 110

Thr Ser Val Thr Val Ser Ser Ala Lys Thr Thr Pro Pro Ser Val Tyr
        115                 120                 125

Pro Leu Ala Pro Gly Ser Ala Ala Gln Thr Asn Ser Met Val Thr Leu
    130                 135                 140

Gly Cys Leu Val Lys Gly Tyr Phe Pro Glu Pro Val Thr Val Thr Trp
145                 150                 155                 160

Asn Ser Gly Ser Leu Ser Ser Gly Val His Thr Phe Pro Ala Val Leu
                165                 170                 175

Gln Ser Asp Leu Tyr Thr Leu Ser Ser Val Thr Val Pro Ser Ser
            180                 185                 190

Thr Trp Pro Ser Glu Thr Val Thr Cys Asn Val Ala His Pro Ala Ser
        195                 200                 205

Ser Thr Lys Val Asp Lys Lys Ile Val Pro Arg Asp Cys Gly Cys Lys
    210                 215                 220

Pro Cys Ile Cys Thr Val Pro Glu Val Ser Ser Val Phe Ile Phe Pro
225                 230                 235                 240

Pro Lys Pro Lys Asp Val Leu Tyr Ile Thr Leu Glu Pro Lys Val Thr
                245                 250                 255

Cys Val Val Val Asp Ile Ser Lys Asp Asp Pro Glu Val Gln Phe Ser
            260                 265                 270

Trp Phe Val Asp Asp Val Glu Val His Thr Ala Gln Thr Gln Pro Arg
        275                 280                 285

Glu Glu Gln Phe Asn Ser Thr Phe Arg Ser Val Ser Glu Leu Pro Ile
    290                 295                 300

Met His Gln Asp Trp Leu Asn Gly Lys Glu Phe Lys Cys Arg Val Asn
305                 310                 315                 320

Ser Ala Ala Phe Pro Ala Pro Ile Glu Lys Thr Ile Ser Lys Thr Lys
                325                 330                 335

```
Gly Arg Pro Lys Ala Pro Gln Val Tyr Thr Ile Pro Pro Lys Glu
                340                 345                 350

Gln Met Ala Lys Asp Lys Val Ser Leu Thr Cys Met Ile Thr Asp Phe
            355                 360                 365

Phe Pro Glu Asp Ile Thr Val Glu Trp Gln Trp Asn Gly Gln Pro Ala
    370                 375                 380

Glu Asn Tyr Lys Asn Thr Gln Pro Ile Met Asp Thr Asp Gly Ser Tyr
385                 390                 395                 400

Phe Val Tyr Ser Lys Leu Asn Val Gln Lys Ser Asn Trp Glu Ala Gly
                405                 410                 415

Asn Thr Phe Thr Cys Ser Val Leu His Glu Gly Leu Lys Asn His His
            420                 425                 430

Thr Glu Lys Ser Leu Ser His Ser Pro Gly Lys
            435                 440

<210> SEQ ID NO 50
<211> LENGTH: 443
<212> TYPE: PRT
<213> ORGANISM: Artificial Sequence
<220> FEATURE:
<223> OTHER INFORMATION: an artificially synthesized sequence

<400> SEQUENCE: 50

Asp Val Gln Leu Gln Glu Ser Gly Pro Val Leu Val Lys Pro Ser Gln
1               5                   10                  15

Ser Leu Ser Leu Thr Cys Thr Val Thr Gly Tyr Ser Ile Thr Ser Asp
                20                  25                  30

His Ala Trp Ser Trp Ile Arg Gln Phe Pro Gly Asn Lys Leu Glu Trp
            35                  40                  45

Met Gly Tyr Ile Ser Tyr Ser Gly Ile Thr Thr Tyr Asn Pro Ser Leu
        50                  55                  60

Lys Ser Arg Ile Ser Ile Thr Arg Asp Thr Ser Lys Asn Gln Phe Phe
65                  70                  75                  80

Leu Gln Leu Asn Ser Val Thr Thr Gly Asp Thr Ser Thr Tyr Tyr Cys
                85                  90                  95

Ala Arg Ser Leu Ala Arg Thr Thr Ala Met Asp Tyr Trp Gly Gln Gly
            100                 105                 110

Thr Ser Val Thr Val Ser Ser Ala Lys Thr Thr Pro Pro Ser Val Tyr
        115                 120                 125

Pro Leu Ala Pro Gly Ser Ala Ala Gln Thr Asn Ser Met Val Thr Leu
    130                 135                 140

Gly Cys Leu Val Lys Gly Tyr Phe Pro Glu Pro Val Thr Val Thr Trp
145                 150                 155                 160

Asn Ser Gly Ser Leu Ser Ser Gly Val His Thr Phe Pro Ala Val Leu
                165                 170                 175

Gln Ser Asp Leu Tyr Thr Leu Ser Ser Ser Val Thr Val Pro Ser Ser
            180                 185                 190

Thr Trp Pro Ser Glu Thr Val Thr Cys Asn Val Ala His Pro Ala Ser
        195                 200                 205

Ser Thr Lys Val Asp Lys Lys Ile Val Pro Arg Asp Cys Gly Cys Lys
    210                 215                 220

Pro Cys Ile Cys Thr Val Pro Glu Val Ser Ser Val Phe Ile Phe Pro
225                 230                 235                 240

Pro Lys Pro Lys Asp Val Leu Tyr Ile Thr Leu Glu Pro Lys Val Thr
                245                 250                 255
```

Cys Val Val Val Asp Ile Ser Lys Asp Asp Pro Glu Val Gln Phe Ser
            260                 265                 270

Trp Phe Val Asp Asp Val Glu Val His Thr Ala Gln Thr Gln Pro Arg
        275                 280                 285

Glu Glu Gln Phe Asn Ser Thr Phe Arg Ser Val Ser Glu Leu Pro Ile
        290                 295                 300

Met His Gln Asp Trp Leu Asn Gly Lys Glu Phe Lys Cys Arg Val Asn
305                 310                 315                 320

Ser Ala Ala Phe Pro Ala Pro Ile Glu Lys Thr Ile Ser Lys Thr Lys
                325                 330                 335

Gly Arg Pro Lys Ala Pro Gln Val Tyr Thr Ile Pro Pro Lys Glu
            340                 345                 350

Gln Met Ala Lys Asp Lys Val Ser Leu Thr Cys Met Ile Thr Asp Phe
            355                 360                 365

Phe Pro Glu Asp Ile Thr Val Glu Trp Gln Trp Asn Gly Gln Pro Ala
        370                 375                 380

Glu Asn Tyr Lys Asn Thr Gln Pro Ile Met Asp Thr Asp Gly Ser Tyr
385                 390                 395                 400

Phe Val Tyr Ser Lys Leu Asn Val Gln Lys Ser Asn Trp Glu Ala Gly
            405                 410                 415

Asn Thr Phe Thr Cys Ser Val Leu His Glu Gly Leu His Trp His His
            420                 425                 430

Thr Glu Lys Ser Leu Ser His Ser Pro Gly Lys
            435                 440

<210> SEQ ID NO 51
<211> LENGTH: 447
<212> TYPE: PRT
<213> ORGANISM: Artificial Sequence
<220> FEATURE:
<223> OTHER INFORMATION: an artificially synthesized sequence

<400> SEQUENCE: 51

Gln Val Gln Leu Gln Glu Ser Gly Pro Gly Leu Val Lys Pro Ser Glu
1               5                   10                  15

Thr Leu Ser Leu Thr Cys Ala Val Ser Gly His Ser Ile Ser His Asp
            20                  25                  30

His Ala Trp Ser Trp Val Arg Gln Pro Pro Gly Glu Gly Leu Glu Trp
        35                  40                  45

Ile Gly Phe Ile Ser Tyr Ser Gly Ile Thr Asn Tyr Asn Pro Ser Leu
    50                  55                  60

Gln Gly Arg Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Leu Ala Arg Thr Thr Ala Met Asp Tyr Trp Gly Glu Gly
            100                 105                 110

Thr Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
        130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
            165                 170                 175

```
Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
210                 215                 220

Thr His Thr Cys Pro Pro Cys Pro Ala Pro Glu Leu Leu Gly Gly Pro
225                 230                 235                 240

Lys Val Phe Leu Phe Pro Pro Lys Pro Lys Asp Thr Leu Tyr Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Tyr His Tyr Thr Gln Lys Ser Leu Ser Leu Ser Pro
        435                 440                 445

<210> SEQ ID NO 52
<211> LENGTH: 447
<212> TYPE: PRT
<213> ORGANISM: Artificial Sequence
<220> FEATURE:
<223> OTHER INFORMATION: an artificially synthesized sequence

<400> SEQUENCE: 52

Gln Val Gln Leu Gln Glu Ser Gly Pro Gly Leu Val Lys Pro Ser Glu
1               5                   10                  15

Thr Leu Ser Leu Thr Cys Ala Val Ser Gly His Ser Ile Ser His Asp
            20                  25                  30

His Ala Trp Ser Trp Val Arg Gln Pro Pro Gly Glu Gly Leu Glu Trp
        35                  40                  45

Ile Gly Phe Ile Ser Tyr Ser Gly Ile Thr Asn Tyr Asn Pro Ser Leu
    50                  55                  60

Gln Gly Arg Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95
```

```
Ala Arg Ser Leu Ala Arg Thr Thr Ala Met Asp Tyr Trp Gly Glu Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Lys Val Phe Leu Phe Pro Pro Lys Pro Lys Asp Thr Leu Met Ile Ser
                245                 250                 255

Arg Thr Ala Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Pro Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Leu His Glu
            420                 425                 430

Ala Leu His Tyr His Tyr Thr Gln Lys Ser Leu Ser Leu Ser Pro
        435                 440                 445

<210> SEQ ID NO 53
<211> LENGTH: 447
<212> TYPE: PRT
<213> ORGANISM: Artificial Sequence
<220> FEATURE:
<223> OTHER INFORMATION: an artificially synthesized sequence

<400> SEQUENCE: 53

Gln Val Gln Leu Gln Glu Ser Gly Pro Gly Leu Val Lys Pro Ser Glu
1               5                   10                  15
```

-continued

```
Thr Leu Ser Leu Thr Cys Ala Val Ser Gly His Ser Ile Ser His Asp
         20                  25                  30

His Ala Trp Ser Trp Val Arg Gln Pro Pro Gly Glu Gly Leu Glu Trp
         35                  40                  45

Ile Gly Phe Ile Ser Tyr Ser Gly Ile Thr Asn Tyr Asn Pro Ser Leu
         50                  55                  60

Gln Gly Arg Val Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Ser Leu Ala Arg Thr Thr Ala Met Asp Tyr Trp Gly Glu Gly
                100                 105                 110

Thr Leu Val Thr Val Ser Ser Ala Ser Thr Lys Gly Pro Ser Val Phe
                115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
                180                 185                 190

Ser Ser Leu Gly Thr Gln Thr Tyr Ile Cys Asn Val Asn His Lys Pro
                195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Arg Gly Gly Pro
225                 230                 235                 240

Lys Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
                260                 265                 270

Pro Glu Val Lys Phe Asn Trp Tyr Val Asp Gly Val Glu Val His Asn
                275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
                340                 345                 350

Leu Pro Pro Ser Arg Asp Glu Leu Thr Lys Asn Gln Val Ser Leu Thr
                355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro
```

<210> SEQ ID NO 54
<211> LENGTH: 447
<212> TYPE: PRT
<213> ORGANISM: Artificial Sequence
<220> FEATURE:
<223> OTHER INFORMATION: an artificially synthesized sequence

<400> SEQUENCE: 54

Gln Val Gln Leu Gln Glu Ser Gly Pro Gly Leu Val Lys Pro Ser Glu
1               5                   10                  15

Thr Leu Ser Leu Thr Cys Ala Val Ser Gly His Ser Ile Ser His Asp
            20                  25                  30

His Ala Trp Ser Trp Val Arg Gln Pro Pro Gly Glu Gly Leu Glu Trp
        35                  40                  45

Ile Gly Phe Ile Ser Tyr Ser Gly Ile Thr Asn Tyr Asn Pro Ser Leu
    50                  55                  60

Gln Gly Arg Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Leu Ala Arg Thr Thr Ala Met Asp Tyr Trp Gly Glu Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Tyr Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr

```
                355                 360                 365
Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Tyr His Tyr Thr Gln Lys Ser Leu Ser Leu Ser Pro
            435                 440                 445

<210> SEQ ID NO 55
<211> LENGTH: 447
<212> TYPE: PRT
<213> ORGANISM: Artificial Sequence
<220> FEATURE:
<223> OTHER INFORMATION: an artificially synthesized sequence

<400> SEQUENCE: 55

Gln Val Gln Leu Gln Glu Ser Gly Pro Gly Leu Val Lys Pro Ser Glu
1               5                   10                  15

Thr Leu Ser Leu Thr Cys Ala Val Ser Gly His Ser Ile Ser His Asp
            20                  25                  30

His Ala Trp Ser Trp Val Arg Gln Pro Pro Gly Glu Gly Leu Glu Trp
        35                  40                  45

Ile Gly Phe Ile Ser Tyr Ser Gly Ile Thr Asn Tyr Asn Pro Ser Leu
50                  55                  60

Gln Gly Arg Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Leu Ala Arg Thr Thr Ala Met Asp Tyr Trp Gly Glu Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Tyr Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
```

```
                    275                 280                 285
Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
                340                 345                 350

Leu Pro Pro Ser Arg Asp Glu Leu Thr Lys Asn Gln Val Ser Leu Thr
                355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
                420                 425                 430

Ala Leu His Tyr His Val Thr Gln Lys Ser Leu Ser Leu Ser Pro
                435                 440                 445

<210> SEQ ID NO 56
<211> LENGTH: 447
<212> TYPE: PRT
<213> ORGANISM: Artificial Sequence
<220> FEATURE:
<223> OTHER INFORMATION: an artificially synthesized sequence

<400> SEQUENCE: 56

Gln Val Gln Leu Gln Glu Ser Gly Pro Gly Leu Val Lys Pro Ser Glu
1               5                   10                  15

Thr Leu Ser Leu Thr Cys Ala Val Ser Gly His Ser Ile Ser His Asp
                20                  25                  30

His Ala Trp Ser Trp Val Arg Gln Pro Pro Gly Glu Gly Leu Glu Trp
            35                  40                  45

Ile Gly Phe Ile Ser Tyr Ser Gly Ile Thr Asn Tyr Asn Pro Ser Leu
50                  55                  60

Gln Gly Arg Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Leu Ala Arg Thr Thr Ala Met Asp Tyr Trp Gly Glu Gly
                100                 105                 110

Thr Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
        130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
```

```
                195                 200                 205
Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Val Leu Tyr Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Tyr His Val Thr Gln Lys Ser Leu Ser Leu Ser Pro
        435                 440                 445

<210> SEQ ID NO 57
<211> LENGTH: 447
<212> TYPE: PRT
<213> ORGANISM: Artificial Sequence
<220> FEATURE:
<223> OTHER INFORMATION: an artificially synthesized sequence

<400> SEQUENCE: 57

Gln Val Gln Leu Gln Glu Ser Gly Pro Gly Leu Val Lys Pro Ser Glu
1               5                   10                  15

Thr Leu Ser Leu Thr Cys Ala Val Ser Gly His Ser Ile Ser His Asp
            20                  25                  30

His Ala Trp Ser Trp Val Arg Gln Pro Pro Gly Glu Gly Leu Glu Trp
        35                  40                  45

Ile Gly Phe Ile Ser Tyr Ser Gly Ile Thr Asn Tyr Asn Pro Ser Leu
    50                  55                  60

Gln Gly Arg Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Leu Ala Arg Thr Thr Ala Met Asp Tyr Trp Gly Glu Gly
            100                 105                 110

Thr Leu Val Thr Val Ser Ser Ala Ser Thr Lys Gly Pro Ser Val Phe
```

```
            115                 120                 125
Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Arg Gly Gly Pro
225                 230                 235                 240

Lys Val Phe Leu Phe Pro Pro Lys Pro Lys Asp Thr Leu Tyr Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Tyr His Tyr Thr Gln Lys Ser Leu Ser Leu Ser Pro
        435                 440                 445

<210> SEQ ID NO 58
<211> LENGTH: 447
<212> TYPE: PRT
<213> ORGANISM: Artificial Sequence
<220> FEATURE:
<223> OTHER INFORMATION: an artificially synthesized sequence

<400> SEQUENCE: 58

Gln Val Gln Leu Gln Glu Ser Gly Pro Gly Leu Val Lys Pro Ser Glu
1               5                   10                  15

Thr Leu Ser Leu Thr Cys Ala Val Ser Gly His Ser Ile Ser His Asp
            20                  25                  30

His Ala Trp Ser Trp Val Arg Gln Pro Pro Gly Glu Gly Leu Glu Trp
```

```
              35                  40                  45
Ile Gly Phe Ile Ser Tyr Ser Gly Ile Thr Asn Tyr Asn Pro Ser Leu
 50                  55                  60

Gln Gly Arg Val Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Ser Leu Ala Arg Thr Thr Ala Met Asp Tyr Trp Gly Glu Gly
            100                 105                 110

Thr Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
            130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys Asp Lys
210                 215                 220

Thr His Thr Cys Pro Pro Cys Pro Ala Pro Glu Leu Arg Gly Gly Pro
225                 230                 235                 240

Lys Val Phe Leu Phe Pro Pro Lys Pro Lys Asp Thr Leu Tyr Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
            290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
            355                 360                 365

Cys Leu Val Lys Gly Phe Tyr Pro Ser Asp Ile Ala Val Glu Trp Glu
            370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Tyr His Val Thr Gln Lys Ser Leu Ser Leu Ser Pro
            435                 440                 445

<210> SEQ ID NO 59
```

<211> LENGTH: 447
<212> TYPE: PRT
<213> ORGANISM: Artificial Sequence
<220> FEATURE:
<223> OTHER INFORMATION: an artificially synthesized sequence

<400> SEQUENCE: 59

```
Gln Val Gln Leu Gln Glu Ser Gly Pro Gly Leu Val Lys Pro Ser Glu
1               5                   10                  15

Thr Leu Ser Leu Thr Cys Ala Val Ser Gly His Ser Ile Ser His Asp
            20                  25                  30

His Ala Trp Ser Trp Val Arg Gln Pro Pro Gly Glu Gly Leu Glu Trp
        35                  40                  45

Ile Gly Phe Ile Ser Tyr Ser Gly Ile Thr Asn Tyr Asn Pro Ser Leu
50                  55                  60

Gln Gly Arg Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Leu Ala Arg Thr Thr Ala Met Asp Tyr Trp Gly Glu Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
210                 215                 220

Thr His Thr Cys Pro Pro Cys Pro Ala Pro Glu Leu Arg Gly Gly Pro
225                 230                 235                 240

Lys Val Phe Leu Phe Pro Pro Lys Pro Lys Asp Val Leu Tyr Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
290                 295                 300

Val Ser Val Leu Gln Pro Leu His Ala Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
370                 375                 380
```

```
Ser Asn Gly Gln Pro Glu Asn Tyr Lys Thr Thr Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Tyr His Val Thr Gln Lys Ser Leu Ser Leu Ser Pro
            435                 440                 445

<210> SEQ ID NO 60
<211> LENGTH: 443
<212> TYPE: PRT
<213> ORGANISM: Artificial Sequence
<220> FEATURE:
<223> OTHER INFORMATION: an artificially synthesized sequence

<400> SEQUENCE: 60

Asp Val Gln Leu Gln Glu Ser Gly Pro Val Leu Val Lys Pro Ser Gln
1               5                   10                  15

Ser Leu Ser Leu Thr Cys Thr Val Thr Gly Tyr Ser Ile Thr Ser Asp
                20                  25                  30

His Ala Trp Ser Trp Ile Arg Gln Phe Pro Gly Asn Lys Leu Glu Trp
            35                  40                  45

Met Gly Tyr Ile Ser Tyr Ser Gly Ile Thr Thr Tyr Asn Pro Ser Leu
    50                  55                  60

Lys Ser Arg Ile Ser Ile Thr Arg Asp Thr Ser Lys Asn Gln Phe Phe
65                  70                  75                  80

Leu Gln Leu Asn Ser Val Thr Thr Gly Asp Thr Ser Thr Tyr Tyr Cys
                85                  90                  95

Ala Arg Ser Leu Ala Arg Thr Thr Ala Met Asp Tyr Trp Gly Gln Gly
            100                 105                 110

Thr Ser Val Thr Val Ser Ser Ala Lys Thr Thr Pro Pro Ser Val Tyr
            115                 120                 125

Pro Leu Ala Pro Gly Ser Ala Ala Gln Thr Asn Ser Met Val Thr Leu
    130                 135                 140

Gly Cys Leu Val Lys Gly Tyr Phe Pro Glu Pro Val Thr Val Thr Trp
145                 150                 155                 160

Asn Ser Gly Ser Leu Ser Ser Gly Val His Thr Phe Pro Ala Val Leu
                165                 170                 175

Gln Ser Asp Leu Tyr Thr Leu Ser Ser Ser Val Thr Val Pro Ser Ser
            180                 185                 190

Thr Trp Pro Ser Glu Thr Val Thr Cys Asn Val Ala His Pro Ala Ser
    195                 200                 205

Ser Thr Lys Val Asp Lys Lys Ile Val Pro Arg Asp Cys Gly Cys Lys
            210                 215                 220

Pro Cys Ile Cys Thr Val Lys Glu Val Ser Lys Val Phe Ile Phe Pro
225                 230                 235                 240

Pro Lys Pro Lys Asp Val Leu Tyr Ile Thr Leu Glu Pro Lys Val Thr
                245                 250                 255

Cys Val Val Val Asp Ile Ser Lys Asp Asp Pro Glu Val Gln Phe Ser
            260                 265                 270

Trp Phe Val Asp Asp Val Glu Val His Thr Ala Gln Thr Gln Pro Arg
    275                 280                 285

Glu Glu Gln Phe Asn Ser Thr Phe Arg Ser Val Ser Glu Leu Pro Ile
            290                 295                 300
```

```
Met His Gln Asp Trp Leu Asn Gly Lys Glu Phe Lys Cys Arg Val Asn
305                 310                 315                 320

Ser Ala Ala Phe Pro Ala Pro Ile Glu Lys Thr Ile Ser Lys Thr Lys
            325                 330                 335

Gly Arg Pro Lys Ala Pro Gln Val Tyr Thr Ile Pro Pro Lys Glu
        340                 345                 350

Gln Met Ala Lys Asp Lys Val Ser Leu Thr Cys Met Ile Thr Asp Phe
            355                 360                 365

Phe Pro Glu Asp Ile Thr Val Glu Trp Gln Trp Asn Gly Gln Pro Ala
    370                 375                 380

Glu Asn Tyr Lys Asn Thr Gln Pro Ile Met Asp Thr Asp Gly Ser Tyr
385                 390                 395                 400

Phe Val Tyr Ser Lys Leu Asn Val Gln Lys Ser Asn Trp Glu Ala Gly
            405                 410                 415

Asn Thr Phe Thr Cys Ser Val Leu His Glu Gly Leu His Trp His His
            420                 425                 430

Thr Glu Lys Ser Leu Ser His Ser Pro Gly Lys
            435                 440

<210> SEQ ID NO 61
<211> LENGTH: 443
<212> TYPE: PRT
<213> ORGANISM: Artificial Sequence
<220> FEATURE:
<223> OTHER INFORMATION: an artificially synthesized sequence

<400> SEQUENCE: 61

Asp Val Gln Leu Gln Glu Ser Gly Pro Val Leu Val Lys Pro Ser Gln
1               5                   10                  15

Ser Leu Ser Leu Thr Cys Thr Val Thr Gly Tyr Ser Ile Thr Ser Asp
            20                  25                  30

His Ala Trp Ser Trp Ile Arg Gln Phe Pro Gly Asn Lys Leu Glu Trp
        35                  40                  45

Met Gly Tyr Ile Ser Tyr Ser Gly Ile Thr Thr Tyr Asn Pro Ser Leu
    50                  55                  60

Lys Ser Arg Ile Ser Ile Thr Arg Asp Thr Ser Lys Asn Gln Phe Phe
65                  70                  75                  80

Leu Gln Leu Asn Ser Val Thr Thr Gly Asp Thr Ser Thr Tyr Tyr Cys
            85                  90                  95

Ala Arg Ser Leu Ala Arg Thr Thr Ala Met Asp Tyr Trp Gly Gln Gly
        100                 105                 110

Thr Ser Val Thr Val Ser Ser Ala Lys Thr Thr Pro Pro Ser Val Tyr
    115                 120                 125

Pro Leu Ala Pro Gly Ser Ala Ala Gln Thr Asn Ser Met Val Thr Leu
    130                 135                 140

Gly Cys Leu Val Lys Gly Tyr Phe Pro Glu Pro Val Thr Val Thr Trp
145                 150                 155                 160

Asn Ser Gly Ser Leu Ser Ser Gly Val His Thr Phe Pro Ala Val Leu
            165                 170                 175

Gln Ser Asp Leu Tyr Thr Leu Ser Ser Val Thr Val Pro Ser Ser
        180                 185                 190

Thr Trp Pro Ser Glu Thr Val Thr Cys Asn Val Ala His Pro Ala Ser
    195                 200                 205

Ser Thr Lys Val Asp Lys Lys Ile Val Pro Arg Asp Cys Gly Cys Lys
    210                 215                 220
```

```
Pro Cys Ile Cys Thr Val Lys Glu Val Ser Lys Val Phe Ile Phe Pro
225                 230                 235                 240

Pro Lys Pro Lys Asp Val Leu Tyr Ile Thr Leu Glu Pro Lys Val Thr
            245                 250                 255

Cys Val Val Asp Ile Ser Lys Asp Asp Pro Glu Val Gln Phe Ser
        260                 265                 270

Trp Phe Val Asp Asp Val Glu Val His Thr Ala Gln Thr Gln Pro Arg
        275                 280                 285

Glu Glu Gln Phe Asn Ser Thr Phe Arg Ser Val Ser Glu Leu Pro Ile
290                 295                 300

Met His Gln Asp Trp Leu Asn Gly Lys Glu Phe Lys Cys Arg Val Asn
305                 310                 315                 320

Ser Ala Ala Phe Pro Ala Pro Ile Glu Lys Thr Ile Ser Lys Thr Lys
                325                 330                 335

Gly Arg Pro Lys Ala Pro Gln Val Tyr Thr Ile Pro Pro Lys Glu
            340                 345                 350

Gln Met Ala Lys Asp Lys Val Ser Leu Thr Cys Met Ile Thr Asp Phe
        355                 360                 365

Phe Pro Glu Asp Ile Thr Val Glu Trp Gln Trp Asn Gly Gln Pro Ala
370                 375                 380

Glu Asn Tyr Lys Asn Thr Gln Pro Ile Met Asp Thr Asp Gly Ser Tyr
385                 390                 395                 400

Phe Val Tyr Ser Lys Leu Asn Val Gln Lys Ser Asn Trp Glu Ala Gly
            405                 410                 415

Asn Thr Phe Thr Cys Ser Val Leu His Glu Gly Leu Lys Asn His His
                420                 425                 430

Thr Glu Lys Ser Leu Ser His Ser Pro Gly Lys
            435                 440

<210> SEQ ID NO 62
<211> LENGTH: 117
<212> TYPE: PRT
<213> ORGANISM: Homo sapiens

<400> SEQUENCE: 62

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Ala Phe Ser Thr Tyr
            20                  25                  30

Asp Met Ser Trp Val Arg Gln Ala Pro Gly Lys Gly Leu Glu Trp Val
        35                  40                  45

Ala Thr Ile Ser Ser Gly Gly Ser Tyr Thr Tyr Tyr Leu Asp Ser Val
    50                  55                  60

Lys Gly Arg Phe Thr Ile Ser Arg Asp Ser Ser Lys Asn Thr Leu Tyr
65                  70                  75                  80

Leu Gln Met Asn Ser Leu Gln Ala Glu Asp Ser Ala Ile Tyr Tyr Cys
                85                  90                  95

Ala Pro Thr Thr Val Val Pro Phe Ala Tyr Trp Gly Gln Gly Thr Leu
            100                 105                 110

Val Thr Val Ser Ser
            115

<210> SEQ ID NO 63
<211> LENGTH: 107
<212> TYPE: PRT
```

<213> ORGANISM: Homo sapiens

<400> SEQUENCE: 63

Asp Ile Gln Met Thr Gln Ser Pro Ser Ser Leu Ser Val Ser Val Gly
1               5                   10                  15

Asp Arg Val Thr Ile Thr Cys Lys Ala Ser Gln Asn Val Arg Thr Val
            20                  25                  30

Val Ala Trp Tyr Gln Gln Lys Pro Gly Leu Ala Pro Lys Thr Leu Ile
        35                  40                  45

Tyr Leu Ala Ser Asn Arg His Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Phe Cys Gln Gln His Trp Ser Tyr Pro Leu
                85                  90                  95

Thr Phe Gly Gln Gly Thr Lys Val Glu Val Lys
            100                 105

<210> SEQ ID NO 64
<211> LENGTH: 107
<212> TYPE: PRT
<213> ORGANISM: Homo sapiens

<400> SEQUENCE: 64

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 65
<211> LENGTH: 445
<212> TYPE: PRT
<213> ORGANISM: Artificial Sequence
<220> FEATURE:
<223> OTHER INFORMATION: an artificially synthesized sequence

<400> SEQUENCE: 65

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Ala Phe Ser Thr Tyr
            20                  25                  30

Asp Met Ser Trp Val Arg Gln Ala Pro Gly Lys Gly Leu Glu Trp Val
        35                  40                  45

Ala Thr Ile Ser Ser Gly Gly Ser Tyr Thr Tyr Tyr Leu Asp Ser Val
    50                  55                  60

Lys Gly Arg Phe Thr Ile Ser Arg Asp Ser Ser Lys Asn Thr Leu Tyr
65                  70                  75                  80

Leu Gln Met Asn Ser Leu Gln Ala Glu Asp Ser Ala Ile Tyr Tyr Cys
                85                  90                  95

Ala Pro Thr Thr Val Val Pro Phe Ala Tyr Trp Gly Gln Gly Thr Leu
            100                 105                 110

Val Thr Val Ser Ser Ala Ser Thr Lys Gly Pro Ser Val Phe Pro Leu
            115                 120                 125

Ala Pro Ser Ser Lys Ser Thr Ser Gly Gly Thr Ala Ala Leu Gly Cys
130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
            195                 200                 205

Thr Lys Val Asp Lys Lys Val Glu Pro Lys Ser Cys Asp Lys Thr His
        210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Tyr Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Pro Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
        355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Tyr His Tyr Thr Gln Lys Ser Leu Ser Leu Ser Pro
            435                 440                 445

<210> SEQ ID NO 66
<211> LENGTH: 445
<212> TYPE: PRT
<213> ORGANISM: Artificial Sequence
<220> FEATURE:
<223> OTHER INFORMATION: an artificially synthesized sequence

<400> SEQUENCE: 66

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Ala Phe Ser Thr Tyr
            20                  25                  30

Asp Met Ser Trp Val Arg Gln Ala Pro Gly Lys Gly Leu Glu Trp Val
        35                  40                  45

Ala Thr Ile Ser Ser Gly Gly Ser Tyr Thr Tyr Tyr Leu Asp Ser Val
    50                  55                  60

Lys Gly Arg Phe Thr Ile Ser Arg Asp Ser Lys Asn Thr Leu Tyr
65                  70                  75                  80

Leu Gln Met Asn Ser Leu Gln Ala Glu Asp Ser Ala Ile Tyr Tyr Cys
                85                  90                  95

Ala Pro Thr Thr Val Val Pro Phe Ala Tyr Trp Gly Gln Gly Thr Leu
            100                 105                 110

Val Thr Val Ser Ser Ala Ser Thr Lys Gly Pro Ser Val Phe Pro Leu
            115                 120                 125

Ala Pro Ser Ser Lys Ser Thr Ser Gly Gly Thr Ala Ala Leu Gly Cys
            130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
            165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
            195                 200                 205

Thr Lys Val Asp Lys Lys Val Glu Pro Lys Ser Cys Asp Lys Thr His
            210                 215                 220

Thr Cys Pro Pro Cys Pro Ala Pro Glu Leu Leu Gly Gly Pro Lys Val
225                 230                 235                 240

Phe Leu Phe Pro Pro Lys Pro Lys Asp Thr Leu Tyr Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
            275                 280                 285

Thr Lys Pro Arg Glu Glu Gln Tyr Asn Ser Thr Tyr Arg Val Val Ser
            290                 295                 300

Val Leu Thr Pro Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
            355                 360                 365

Val Lys Gly Phe Tyr Pro Ser Asp Ile Ala Val Glu Trp Glu Ser Asn
            370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
```

His Tyr His Tyr Thr Gln Lys Ser Leu Ser Leu Ser Pro
            435                 440                 445

<210> SEQ ID NO 67
<211> LENGTH: 445
<212> TYPE: PRT
<213> ORGANISM: Artificial Sequence
<220> FEATURE:
<223> OTHER INFORMATION: an artificially synthesized sequence

<400> SEQUENCE: 67

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Ala Phe Ser Thr Tyr
            20                  25                  30

Asp Met Ser Trp Val Arg Gln Ala Pro Gly Lys Gly Leu Glu Trp Val
        35                  40                  45

Ala Thr Ile Ser Ser Gly Gly Ser Tyr Thr Tyr Tyr Leu Asp Ser Val
    50                  55                  60

Lys Gly Arg Phe Thr Ile Ser Arg Asp Ser Ser Lys Asn Thr Leu Tyr
65                  70                  75                  80

Leu Gln Met Asn Ser Leu Gln Ala Glu Asp Ser Ala Ile Tyr Tyr Cys
                85                  90                  95

Ala Pro Thr Thr Val Val Pro Phe Ala Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Tyr Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Glu Ala Lys
        275                 280                 285

Thr Lys Pro Arg Glu Glu Gln Tyr Asn Ser Thr Tyr Arg Val Val Ser
    290                 295                 300

Val Leu Gln Val Leu His Ala Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro

-continued

```
                340                 345                 350
Pro Ser Arg Asp Glu Leu Thr Lys Asn Gln Val Ser Leu Thr Cys Leu
            355                 360                 365

Val Lys Gly Phe Tyr Pro Ser Asp Ile Ala Val Glu Trp Glu Ser Asn
        370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Tyr His Tyr Thr Gln Lys Ser Leu Ser Leu Ser Pro
        435                 440                 445

<210> SEQ ID NO 68
<211> LENGTH: 445
<212> TYPE: PRT
<213> ORGANISM: Artificial Sequence
<220> FEATURE:
<223> OTHER INFORMATION: an artificially synthesized sequence

<400> SEQUENCE: 68

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Ala Phe Ser Thr Tyr
            20                  25                  30

Asp Met Ser Trp Val Arg Gln Ala Pro Gly Lys Gly Leu Glu Trp Val
        35                  40                  45

Ala Thr Ile Ser Ser Gly Gly Ser Tyr Thr Tyr Tyr Leu Asp Ser Val
    50                  55                  60

Lys Gly Arg Phe Thr Ile Ser Arg Asp Ser Ser Lys Asn Thr Leu Tyr
65                  70                  75                  80

Leu Gln Met Asn Ser Leu Gln Ala Glu Asp Ser Ala Ile Tyr Tyr Cys
                85                  90                  95

Ala Pro Thr Thr Val Val Pro Phe Ala Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Leu Leu Gly Gly Pro Lys Val
225                 230                 235                 240

Phe Leu Phe Pro Pro Lys Pro Lys Asp Thr Leu Tyr Ile Ser Arg Thr
                245                 250                 255

Pro Glu Val Thr Cys Val Val Val Asp Val Ser His Glu Asp Pro Glu
```

260                 265                 270
Val Lys Phe Asn Trp Tyr Val Asp Gly Val Glu Val His Glu Ala Lys
            275                 280                 285

Thr Lys Pro Arg Glu Glu Gln Tyr Asn Ser Thr Tyr Arg Val Val Ser
        290                 295                 300

Val Leu Gln Val Leu His Ala Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
        355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Tyr His Tyr Thr Gln Lys Ser Leu Ser Leu Ser Pro
        435                 440                 445

<210> SEQ ID NO 69
<211> LENGTH: 445
<212> TYPE: PRT
<213> ORGANISM: Artificial Sequence
<220> FEATURE:
<223> OTHER INFORMATION: an artificially synthesized sequence

<400> SEQUENCE: 69

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Ala Phe Ser Thr Tyr
            20                  25                  30

Asp Met Ser Trp Val Arg Gln Ala Pro Gly Lys Gly Leu Glu Trp Val
        35                  40                  45

Ala Thr Ile Ser Ser Gly Gly Ser Tyr Thr Tyr Tyr Leu Asp Ser Val
    50                  55                  60

Lys Gly Arg Phe Thr Ile Ser Arg Asp Ser Ser Lys Asn Thr Leu Tyr
65                  70                  75                  80

Leu Gln Met Asn Ser Leu Gln Ala Glu Asp Ser Ala Ile Tyr Tyr Cys
                85                  90                  95

Ala Pro Thr Thr Val Val Pro Phe Ala Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser

```
                180             185             190
Leu Gly Thr Gln Thr Tyr Ile Cys Asn Val Asn His Lys Pro Ser Asn
            195             200             205
Thr Lys Val Asp Lys Lys Val Glu Pro Lys Ser Cys Asp Lys Thr His
        210             215             220
Thr Cys Pro Pro Cys Pro Ala Pro Glu Leu Arg Gly Gly Pro Lys Val
225             230             235             240
Phe Leu Phe Pro Pro Lys Pro Lys Asp Thr Leu Tyr Ile Ser Arg Thr
            245             250             255
Pro Glu Val Thr Cys Val Val Val Asp Val Ser His Glu Asp Pro Glu
        260             265             270
Val Lys Phe Asn Trp Tyr Val Asp Gly Val Glu Val His Glu Ala Lys
    275             280             285
Thr Lys Pro Arg Glu Glu Gln Tyr Asn Ser Thr Tyr Arg Val Val Ser
        290             295             300
Val Leu Gln Val Leu His Ala Asp Trp Leu Asn Gly Lys Glu Tyr Lys
305             310             315             320
Cys Lys Val Ser Asn Lys Ala Leu Pro Ala Pro Ile Glu Lys Thr Ile
            325             330             335
Ser Lys Ala Lys Gly Gln Pro Arg Glu Pro Gln Val Tyr Thr Leu Pro
        340             345             350
Pro Ser Arg Asp Glu Leu Thr Lys Asn Gln Val Ser Leu Thr Cys Leu
        355             360             365
Val Lys Gly Phe Tyr Pro Ser Asp Ile Ala Val Glu Trp Glu Ser Asn
    370             375             380
Gly Gln Pro Glu Asn Asn Tyr Lys Thr Thr Pro Pro Val Leu Asp Ser
385             390             395             400
Asp Gly Ser Phe Phe Leu Tyr Ser Lys Leu Thr Val Asp Lys Ser Arg
            405             410             415
Trp Gln Gln Gly Asn Val Phe Ser Cys Ser Val Met His Glu Ala Leu
        420             425             430
His Tyr His Tyr Thr Gln Lys Ser Leu Ser Leu Ser Pro
        435             440             445

<210> SEQ ID NO 70
<211> LENGTH: 447
<212> TYPE: PRT
<213> ORGANISM: Artificial Sequence
<220> FEATURE:
<223> OTHER INFORMATION: an artificially synthesized sequence

<400> SEQUENCE: 70

Gln Val Gln Leu Gln Glu Ser Gly Pro Gly Leu Val Lys Pro Ser Glu
1               5                   10                  15
Thr Leu Ser Leu Thr Cys Ala Val Ser Gly His Ser Ile Ser His Asp
            20                  25                  30
His Ala Trp Ser Trp Val Arg Gln Pro Pro Gly Glu Gly Leu Glu Trp
        35                  40                  45
Ile Gly Phe Ile Ser Tyr Ser Gly Ile Thr Asn Tyr Asn Pro Ser Leu
    50                  55                  60
Gln Gly Arg Val Thr Ile Ser Arg Asp Asn Ser Lys Asn Thr Leu Tyr
65                  70                  75                  80
Leu Gln Met Asn Ser Leu Arg Ala Glu Asp Thr Ala Val Tyr Tyr Cys
                85                  90                  95
Ala Arg Ser Leu Ala Arg Thr Thr Ala Met Asp Tyr Trp Gly Glu Gly
```

```
                100             105              110
Thr Leu Val Thr Val Ser Ser Ala Ser Thr Lys Gly Pro Ser Val Phe
            115                 120             125

Pro Leu Ala Pro Ser Ser Lys Ser Thr Ser Gly Gly Thr Ala Ala Leu
130             135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
                180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys Asp Lys
        210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Val Leu Tyr Ile Ser
                245                 250                 255

Arg Thr Pro Glu Val Thr Cys Val Val Val Asp Val Ser His Glu Asp
                260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
290                 295                 300

Val Ser Val Leu Gln Pro Leu His Ala Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
                340                 345                 350

Leu Pro Pro Ser Arg Asp Glu Leu Thr Lys Asn Gln Val Ser Leu Thr
            355                 360                 365

Cys Leu Val Lys Gly Phe Tyr Pro Ser Asp Ile Ala Val Glu Trp Glu
        370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Tyr His Val Thr Gln Lys Ser Leu Ser Leu Ser Pro
        435                 440                 445

<210> SEQ ID NO 71
<211> LENGTH: 447
<212> TYPE: PRT
<213> ORGANISM: Artificial Sequence
<220> FEATURE:
<223> OTHER INFORMATION: an artificially synthesized sequence

<400> SEQUENCE: 71

Gln Val Gln Leu Gln Glu Ser Gly Pro Gly Leu Val Lys Pro Ser Glu
1               5                   10                  15

Thr Leu Ser Leu Thr Cys Ala Val Ser Gly His Ser Ile Ser His Asp
```

-continued

```
                20                  25                  30
His Ala Trp Ser Trp Val Arg Gln Pro Gly Glu Gly Leu Glu Trp
            35                  40                  45
Ile Gly Phe Ile Ser Tyr Ser Gly Ile Thr Asn Tyr Asn Pro Ser Leu
        50                  55                  60
Gln Gly Arg Val Thr Ile Ser Arg Asp Asn Ser Lys Asn Thr Leu Tyr
65                  70                  75                  80
Leu Gln Met Asn Ser Leu Arg Ala Glu Asp Thr Ala Val Tyr Tyr Cys
                85                  90                  95
Ala Arg Ser Leu Ala Arg Thr Thr Ala Met Asp Tyr Trp Gly Glu Gly
            100                 105                 110
Thr Leu Val Thr Val Ser Ser Ala Ser Thr Lys Gly Pro Ser Val Phe
        115                 120                 125
Pro Leu Ala Pro Ser Ser Lys Ser Thr Ser Gly Gly Thr Ala Ala Leu
        130                 135                 140
Gly Cys Leu Val Lys Asp Tyr Phe Pro Glu Pro Val Thr Val Ser Trp
145                 150                 155                 160
Asn Ser Gly Ala Leu Thr Ser Gly Val His Thr Phe Pro Ala Val Leu
                165                 170                 175
Gln Ser Ser Gly Leu Tyr Ser Leu Ser Ser Val Val Thr Val Pro Ser
            180                 185                 190
Ser Ser Leu Gly Thr Gln Thr Tyr Ile Cys Asn Val Asn His Lys Pro
        195                 200                 205
Ser Asn Thr Lys Val Asp Lys Lys Val Glu Pro Lys Ser Cys Asp Lys
        210                 215                 220
Thr His Thr Cys Pro Pro Cys Pro Ala Pro Glu Leu Leu Gly Gly Pro
225                 230                 235                 240
Ser Val Phe Leu Phe Pro Pro Lys Pro Lys Asp Thr Leu Met Ala Ser
                245                 250                 255
Arg Thr Pro Glu Val Thr Cys Val Val Val Asp Val Ser His Glu Asp
            260                 265                 270
Pro Glu Val Lys Phe Asn Trp Tyr Val Asp Gly Val Glu Val His Asn
        275                 280                 285
Ala Lys Thr Lys Pro Arg Glu Glu Gln Tyr Asn Ser Thr Tyr Arg Val
        290                 295                 300
Val Ser Val Leu Thr Val Leu His Gln Asp Trp Leu Asn Gly Lys Glu
305                 310                 315                 320
Tyr Lys Cys Lys Val Ser Asn Lys Ala Leu Pro Ala Pro Ile Glu Lys
                325                 330                 335
Thr Ile Ser Lys Ala Lys Gly Gln Pro Arg Glu Pro Gln Val Tyr Thr
            340                 345                 350
Leu Pro Pro Ser Arg Asp Glu Leu Thr Lys Asn Gln Val Ser Leu Thr
        355                 360                 365
Cys Leu Val Lys Gly Phe Tyr Pro Ser Asp Ile Ala Val Glu Trp Glu
        370                 375                 380
Ser Asn Gly Gln Pro Glu Asn Asn Tyr Lys Thr Thr Pro Pro Val Leu
385                 390                 395                 400
Asp Ser Asp Gly Ser Phe Phe Leu Tyr Ser Lys Leu Thr Val Asp Lys
                405                 410                 415
Ser Arg Trp Gln Gln Gly Asn Val Phe Ser Cys Ser Val Met His Glu
            420                 425                 430
Ala Leu His Asn His Tyr Thr Gln Lys Ser Leu Ser Leu Ser Pro
        435                 440                 445
```

<210> SEQ ID NO 72
<211> LENGTH: 447
<212> TYPE: PRT
<213> ORGANISM: Artificial Sequence
<220> FEATURE:
<223> OTHER INFORMATION: an artificially synthesized sequence

<400> SEQUENCE: 72

```
Gln Val Gln Leu Gln Glu Ser Gly Pro Gly Leu Val Lys Pro Ser Glu
1               5                   10                  15

Thr Leu Ser Leu Thr Cys Ala Val Ser Gly His Ser Ile Ser His Asp
            20                  25                  30

His Ala Trp Ser Trp Val Arg Gln Pro Pro Gly Glu Gly Leu Glu Trp
        35                  40                  45

Ile Gly Phe Ile Ser Tyr Ser Gly Ile Thr Asn Tyr Asn Pro Ser Leu
    50                  55                  60

Gln Gly Arg Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Leu Ala Arg Thr Thr Ala Met Asp Tyr Trp Gly Glu Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Val Leu Tyr Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Gln Pro Leu His Ala Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Lys Lys Leu Thr Lys Asn Gln Val Ser Leu Thr
        355                 360                 365
```

```
Cys Leu Val Lys Gly Phe Tyr Pro Ser Asp Ile Ala Val Glu Trp Glu
        370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
                420                 425                 430

Ala Leu His Tyr His Val Thr Gln Lys Ser Leu Ser Leu Ser Pro
            435                 440                 445

<210> SEQ ID NO 73
<211> LENGTH: 447
<212> TYPE: PRT
<213> ORGANISM: Artificial Sequence
<220> FEATURE:
<223> OTHER INFORMATION: an artificially synthesized sequence

<400> SEQUENCE: 73

Gln Val Gln Leu Gln Glu Ser Gly Pro Gly Leu Val Lys Pro Ser Glu
1               5                   10                  15

Thr Leu Ser Leu Thr Cys Ala Val Ser Gly His Ser Ile Ser His Asp
                20                  25                  30

His Ala Trp Ser Trp Val Arg Gln Pro Pro Gly Glu Gly Leu Glu Trp
            35                  40                  45

Ile Gly Phe Ile Ser Tyr Ser Gly Ile Thr Asn Tyr Asn Pro Ser Leu
        50                  55                  60

Gln Gly Arg Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Leu Ala Arg Thr Thr Ala Met Asp Tyr Trp Gly Glu Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ala Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285
```

Ala Lys Thr Lys Pro Arg Glu Glu Gln Tyr Asn Ser Thr Tyr Arg Val
            290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
            355                 360                 365

Cys Leu Val Glu Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn Arg Tyr Thr Gln Glu Ser Leu Ser Leu Ser Pro
            435                 440                 445

<210> SEQ ID NO 74
<211> LENGTH: 115
<212> TYPE: PRT
<213> ORGANISM: Artificial Sequence
<220> FEATURE:
<223> OTHER INFORMATION: an artificially synthesized sequence

<400> SEQUENCE: 74

Gln Val Gln Leu Val Gln Ser Gly Ala Glu Val Lys Lys Pro Gly Ala
1               5                   10                  15

Ser Val Thr Val Ser Cys Lys Ala Ser Gly Tyr Thr Phe Thr Asp Tyr
            20                  25                  30

Glu Met His Trp Ile Arg Gln Pro Pro Gly Glu Gly Leu Glu Trp Ile
        35                  40                  45

Gly Ala Ile Asp Pro Lys Thr Gly Asp Thr Ala Tyr Ser Glu Ser Phe
    50                  55                  60

Gln Asp Arg Val Thr Leu Thr Ala Asp Lys Ser Thr Ser Thr Ala Tyr
65                  70                  75                  80

Met Glu Leu Ser Ser Leu Thr Ser Glu Asp Thr Ala Val Tyr Tyr Cys
                85                  90                  95

Thr Arg Phe Tyr Ser Tyr Thr Tyr Trp Gly Gln Gly Thr Leu Val Thr
            100                 105                 110

Val Ser Ser
        115

<210> SEQ ID NO 75
<211> LENGTH: 112
<212> TYPE: PRT
<213> ORGANISM: Artificial Sequence
<220> FEATURE:
<223> OTHER INFORMATION: an artificially synthesized sequence

<400> SEQUENCE: 75

Asp Ile Val Met Thr Gln Ser Pro Leu Ser Leu Pro Val Thr Pro Gly
1               5                   10                  15

Glu Pro Ala Ser Ile Ser Cys Gln Ala Ser Glu Ser Leu Val His Ser

```
                    20                  25                  30
Asn Arg Asn Thr Tyr Leu His Trp Tyr Leu Gln Lys Pro Gly Gln Ser
            35                  40                  45

Pro Gln Leu Leu Ile Tyr Lys Val Ser Asn Arg Phe Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Asn
                85                  90                  95

Thr His Val Pro Pro Thr Phe Gly Gln Gly Thr Lys Val Glu Ile Glu
            100                 105                 110

<210> SEQ ID NO 76
<211> LENGTH: 328
<212> TYPE: PRT
<213> ORGANISM: Artificial Sequence
<220> FEATURE:
<223> OTHER INFORMATION: an artificially synthesized sequence

<400> SEQUENCE: 76

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
```

```
                275                 280                 285
Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Glu Ser Leu Ser Leu Ser Pro
                325

<210> SEQ ID NO 77
<211> LENGTH: 443
<212> TYPE: PRT
<213> ORGANISM: Artificial Sequence
<220> FEATURE:
<223> OTHER INFORMATION: an artificially synthesized sequence

<400> SEQUENCE: 77

Gln Val Gln Leu Val Gln Ser Gly Ala Glu Val Lys Lys Pro Gly Ala
1               5                   10                  15

Ser Val Thr Val Ser Cys Lys Ala Ser Gly Tyr Thr Phe Thr Asp Tyr
            20                  25                  30

Glu Met His Trp Ile Arg Gln Pro Pro Gly Glu Gly Leu Glu Trp Ile
        35                  40                  45

Gly Ala Ile Asp Pro Lys Thr Gly Asp Thr Ala Tyr Ser Glu Ser Phe
    50                  55                  60

Gln Asp Arg Val Thr Leu Thr Ala Asp Lys Ser Thr Ser Thr Ala Tyr
65                  70                  75                  80

Met Glu Leu Ser Ser Leu Thr Ser Glu Asp Thr Ala Val Tyr Tyr Cys
                85                  90                  95

Thr Arg Phe Tyr Ser Tyr Thr Tyr Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
    210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
    290                 295                 300

Thr Val Leu His Gln Asp Trp Leu Asn Gly Lys Glu Tyr Lys Cys Lys
```

```
305                 310                 315                 320
Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
                340                 345                 350

Arg Asp Glu Leu Thr Lys Asn Gln Val Ser Leu Thr Cys Leu Val Lys
                355                 360                 365

Gly Phe Tyr Pro Ser Asp Ile Ala Val Glu Trp Glu Ser Asn Gly Gln
                370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
                420                 425                 430

His Tyr Thr Gln Glu Ser Leu Ser Leu Ser Pro
                435                 440

<210> SEQ ID NO 78
<211> LENGTH: 119
<212> TYPE: PRT
<213> ORGANISM: Homo sapiens

<400> SEQUENCE: 78

Gln Val Gln Leu Gln Glu Ser Gly Pro Gly Leu Val Lys Pro Ser Glu
1               5                   10                  15

Thr Leu Ser Leu Thr Cys Ala Val Ser Gly His Ser Ile Ser His Asp
                20                  25                  30

His Ala Trp Ser Trp Val Arg Gln Pro Pro Gly Glu Gly Leu Glu Trp
                35                  40                  45

Ile Gly Phe Ile Ser Tyr Ser Gly Ile Thr Asn Tyr Asn Pro Ser Leu
            50                  55                  60

Gln Gly Arg Val Thr Ile Ser Arg Asp Asn Ser Lys Asn Thr Leu Tyr
65              70                  75                  80

Leu Gln Met Asn Ser Leu Arg Ala Glu Asp Thr Ala Val Tyr Tyr Cys
                85                  90                  95

Ala Arg Ser Leu Ala Arg Thr Thr Ala Met Asp Tyr Trp Gly Glu Gly
                100                 105                 110

Thr Leu Val Thr Val Ser Ser
            115

<210> SEQ ID NO 79
<211> LENGTH: 447
<212> TYPE: PRT
<213> ORGANISM: Artificial Sequence
<220> FEATURE:
<223> OTHER INFORMATION: an artificially synthesized sequence

<400> SEQUENCE: 79

Gln Val Gln Leu Gln Glu Ser Gly Pro Gly Leu Val Lys Pro Ser Glu
1               5                   10                  15

Thr Leu Ser Leu Thr Cys Ala Val Ser Gly His Ser Ile Ser His Asp
                20                  25                  30

His Ala Trp Ser Trp Val Arg Gln Pro Pro Gly Glu Gly Leu Glu Trp
                35                  40                  45

Ile Gly Phe Ile Ser Tyr Ser Gly Ile Thr Asn Tyr Asn Pro Ser Leu
            50                  55                  60
```

Gln Gly Arg Val Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
             85                  90                  95

Ala Arg Ser Leu Ala Arg Thr Thr Ala Met Asp Tyr Trp Gly Glu Gly
            100                 105                 110

Thr Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys Asp Lys
210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
            355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro
            435                 440                 445

<210> SEQ ID NO 80
<211> LENGTH: 447
<212> TYPE: PRT
<213> ORGANISM: Artificial Sequence
<220> FEATURE:

<223> OTHER INFORMATION: an artificially synthesized sequence

<400> SEQUENCE: 80

```
Gln Val Gln Leu Gln Glu Ser Gly Pro Gly Leu Val Lys Pro Ser Glu
1               5                   10                  15

Thr Leu Ser Leu Thr Cys Ala Val Ser Gly His Ser Ile Ser His Asp
            20                  25                  30

His Ala Trp Ser Trp Val Arg Gln Pro Pro Gly Glu Gly Leu Glu Trp
        35                  40                  45

Ile Gly Phe Ile Ser Tyr Ser Gly Ile Thr Asn Tyr Asn Pro Ser Leu
    50                  55                  60

Gln Gly Arg Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Leu Ala Arg Thr Thr Ala Met Asp Tyr Trp Gly Glu Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Asp
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400
```

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro
        435                 440                 445

<210> SEQ ID NO 81
<211> LENGTH: 447
<212> TYPE: PRT
<213> ORGANISM: Artificial Sequence
<220> FEATURE:
<223> OTHER INFORMATION: an artificially synthesized sequence

<400> SEQUENCE: 81

Gln Val Gln Leu Gln Glu Ser Gly Pro Gly Leu Val Lys Pro Ser Glu
1               5                   10                  15

Thr Leu Ser Leu Thr Cys Ala Val Ser Gly His Ser Ile Ser His Asp
            20                  25                  30

His Ala Trp Ser Trp Val Arg Gln Pro Pro Gly Glu Gly Leu Glu Trp
        35                  40                  45

Ile Gly Phe Ile Ser Tyr Ser Gly Ile Thr Asn Tyr Asn Pro Ser Leu
    50                  55                  60

Gln Gly Arg Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Leu Ala Arg Thr Thr Ala Met Asp Tyr Trp Gly Glu Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

```
Tyr Lys Cys Lys Val Ser Asn Lys Ala Glu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro
        435                 440                 445

<210> SEQ ID NO 82
<211> LENGTH: 447
<212> TYPE: PRT
<213> ORGANISM: Artificial Sequence
<220> FEATURE:
<223> OTHER INFORMATION: an artificially synthesized sequence

<400> SEQUENCE: 82

Gln Val Gln Leu Gln Glu Ser Gly Pro Gly Leu Val Lys Pro Ser Glu
1               5                   10                  15

Thr Leu Ser Leu Thr Cys Ala Val Ser Gly His Ser Ile Ser His Asp
            20                  25                  30

His Ala Trp Ser Trp Val Arg Gln Pro Pro Gly Glu Gly Leu Glu Trp
        35                  40                  45

Ile Gly Phe Ile Ser Tyr Ser Gly Ile Thr Asn Tyr Asn Pro Ser Leu
    50                  55                  60

Gln Gly Arg Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Leu Ala Arg Thr Thr Ala Met Asp Tyr Trp Gly Glu Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240
```

Ser Val Phe Leu Phe Pro Pro Lys Pro Lys Asp Thr Leu Met Ile Ser
                245                 250                 255

Arg Thr Pro Glu Val Thr Cys Val Val Val Asp Val Glu His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Phe Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro
        435                 440                 445

<210> SEQ ID NO 83
<211> LENGTH: 107
<212> TYPE: PRT
<213> ORGANISM: Homo sapiens

<400> SEQUENCE: 83

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Ser Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Gly Asn Thr Leu Pro Tyr
                85                  90                  95

Thr Phe Gly Gln Gly Thr Lys Val Glu Ile Lys
            100                 105

<210> SEQ ID NO 84
<211> LENGTH: 447
<212> TYPE: PRT
<213> ORGANISM: Artificial Sequence
<220> FEATURE:
<223> OTHER INFORMATION: an artificially synthesized sequence

<400> SEQUENCE: 84

Gln Val Gln Leu Gln Glu Ser Gly Pro Gly Leu Val Lys Pro Ser Glu

-continued

```
1               5                   10                  15
Thr Leu Ser Leu Thr Cys Ala Val Ser Gly His Ser Ile Ser His Asp
                20                  25                  30
His Ala Trp Ser Trp Val Arg Gln Pro Pro Gly Glu Gly Leu Glu Trp
                35                  40                  45
Ile Gly Phe Ile Ser Tyr Ser Gly Ile Thr Asn Tyr Asn Pro Ser Leu
 50                  55                  60
Gln Gly Arg Val Thr Ile Ser Arg Asp Asn Ser Lys Asn Thr Leu Tyr
 65                  70                  75                  80
Leu Gln Met Asn Ser Leu Arg Ala Glu Asp Thr Ala Val Tyr Tyr Cys
                85                  90                  95
Ala Arg Ser Leu Ala Arg Thr Thr Ala Met Asp Tyr Trp Gly Gln Gly
                100                 105                 110
Thr Leu Val Thr Val Ser Ser Ala Ser Thr Lys Gly Pro Ser Val Phe
                115                 120                 125
Pro Leu Ala Pro Ser Ser Lys Ser Thr Ser Gly Gly Thr Ala Ala Leu
 130                 135                 140
Gly Cys Leu Val Lys Asp Tyr Phe Pro Glu Pro Val Thr Val Ser Trp
 145                 150                 155                 160
Asn Ser Gly Ala Leu Thr Ser Gly Val His Thr Phe Pro Ala Val Leu
                165                 170                 175
Gln Ser Ser Gly Leu Tyr Ser Leu Ser Ser Val Val Thr Val Pro Ser
                180                 185                 190
Ser Ser Leu Gly Thr Gln Thr Tyr Ile Cys Asn Val Asn His Lys Pro
                195                 200                 205
Ser Asn Thr Lys Val Asp Lys Lys Val Glu Pro Lys Ser Cys Asp Lys
 210                 215                 220
Thr His Thr Cys Pro Pro Cys Pro Ala Pro Glu Leu Leu Gly Gly Asp
 225                 230                 235                 240
Ser Val Phe Leu Phe Pro Pro Lys Pro Lys Asp Thr Leu Met Ile Ser
                245                 250                 255
Arg Thr Pro Glu Val Thr Cys Val Val Val Asp Val Ser His Glu Asp
                260                 265                 270
Pro Glu Val Lys Phe Asn Trp Tyr Val Asp Gly Val Glu Val His Asn
                275                 280                 285
Ala Lys Thr Lys Pro Arg Glu Glu Gln Tyr Asn Ser Thr Tyr Arg Val
 290                 295                 300
Val Ser Val Leu Thr Val Leu His Gln Asp Trp Leu Asn Gly Lys Glu
 305                 310                 315                 320
Tyr Lys Cys Lys Val Ser Asn Lys Ala Leu Pro Ala Pro Ile Glu Lys
                325                 330                 335
Thr Ile Ser Lys Ala Lys Gly Gln Pro Arg Glu Pro Gln Val Tyr Thr
                340                 345                 350
Leu Pro Pro Ser Arg Asp Glu Leu Thr Lys Asn Gln Val Ser Leu Thr
                355                 360                 365
Cys Leu Val Lys Gly Phe Tyr Pro Ser Asp Ile Ala Val Glu Trp Glu
 370                 375                 380
Ser Asn Gly Gln Pro Glu Asn Asn Tyr Lys Thr Thr Pro Pro Val Leu
 385                 390                 395                 400
Asp Ser Asp Gly Ser Phe Phe Leu Tyr Ser Lys Leu Thr Val Asp Lys
                405                 410                 415
Ser Arg Trp Gln Gln Gly Asn Val Phe Ser Cys Ser Val Met His Glu
                420                 425                 430
```

```
Ala Leu His Asn His Tyr Thr Gln Lys Ser Leu Ser Leu Ser Pro
            435                 440                 445

<210> SEQ ID NO 85
<211> LENGTH: 447
<212> TYPE: PRT
<213> ORGANISM: Artificial Sequence
<220> FEATURE:
<223> OTHER INFORMATION: an artificially synthesized sequence

<400> SEQUENCE: 85

Gln Val Gln Leu Gln Glu Ser Gly Pro Gly Leu Val Lys Pro Ser Glu
1               5                  10                  15

Thr Leu Ser Leu Thr Cys Ala Val Ser Gly His Ser Ile Ser His Asp
            20                  25                  30

His Ala Trp Ser Trp Val Arg Gln Pro Pro Gly Glu Gly Leu Glu Trp
        35                  40                  45

Ile Gly Phe Ile Ser Tyr Ser Gly Ile Thr Asn Tyr Asn Pro Ser Leu
    50                  55                  60

Gln Gly Arg Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Leu Ala Arg Thr Thr Ala Met Asp Tyr Trp Gly Glu Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Asp
225                 230                 235                 240

Ser Val Phe Leu Phe Pro Pro Lys Pro Lys Asp Thr Leu Tyr Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350
```

```
Leu Pro Pro Ser Arg Asp Glu Leu Thr Lys Asn Gln Val Ser Leu Thr
            355                 360                 365

Cys Leu Val Lys Gly Phe Tyr Pro Ser Asp Ile Ala Val Glu Trp Glu
        370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Tyr His Tyr Thr Gln Lys Ser Leu Ser Leu Ser Pro
            435                 440                 445

<210> SEQ ID NO 86
<211> LENGTH: 447
<212> TYPE: PRT
<213> ORGANISM: Artificial Sequence
<220> FEATURE:
<223> OTHER INFORMATION: an artificially synthesized sequence

<400> SEQUENCE: 86

Gln Val Gln Leu Gln Glu Ser Gly Pro Gly Leu Val Lys Pro Ser Glu
1               5                   10                  15

Thr Leu Ser Leu Thr Cys Ala Val Ser Gly His Ser Ile Ser His Asp
            20                  25                  30

His Ala Trp Ser Trp Val Arg Gln Pro Pro Gly Glu Gly Leu Glu Trp
        35                  40                  45

Ile Gly Phe Ile Ser Tyr Ser Gly Ile Thr Asn Tyr Asn Pro Ser Leu
    50                  55                  60

Gln Gly Arg Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Arg Ser Leu Ala Arg Thr Thr Ala Met Asp Tyr Trp Gly Glu Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
            165                 170                 175

Gln Ser Ser Gly Leu Tyr Ser Leu Ser Ser Val Val Thr Val Pro Ser
        180                 185                 190

Ser Ser Leu Gly Thr Gln Thr Tyr Ile Cys Asn Val Asn His Lys Pro
    195                 200                 205

Ser Asn Thr Lys Val Asp Lys Lys Val Glu Pro Lys Ser Cys Asp Lys
210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Trp Ile Ser
            245                 250                 255

Arg Thr Pro Glu Val Thr Cys Val Val Val Asp Val Ser His Glu Asp
        260                 265                 270
```

```
Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
        290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Trp His Tyr Thr Gln Lys Ser Leu Ser Leu Ser Pro
        435                 440                 445

<210> SEQ ID NO 87
<211> LENGTH: 447
<212> TYPE: PRT
<213> ORGANISM: Artificial Sequence
<220> FEATURE:
<223> OTHER INFORMATION: an artificially synthesized sequence

<400> SEQUENCE: 87

Gln Val Gln Leu Gln Glu Ser Gly Pro Gly Leu Val Lys Pro Ser Glu
1               5                   10                  15

Thr Leu Ser Leu Thr Cys Ala Val Ser Gly His Ser Ile Ser His Asp
            20                  25                  30

His Ala Trp Ser Trp Val Arg Gln Pro Pro Gly Glu Gly Leu Glu Trp
        35                  40                  45

Ile Gly Phe Ile Ser Tyr Ser Gly Ile Thr Asn Tyr Asn Pro Ser Leu
    50                  55                  60

Gln Gly Arg Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Leu Ala Arg Thr Thr Ala Met Asp Tyr Trp Gly Glu Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190
```

```
Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Tyr Ile Thr
                245                 250                 255

Arg Glu Pro Glu Val Thr Cys Val Val Val Asp Val Ser His Glu Asp
                260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
        290                 295                 300

Val Ser Val Leu Thr Pro Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Trp His Tyr Thr Gln Lys Ser Leu Ser Leu Ser Pro
        435                 440                 445

<210> SEQ ID NO 88
<211> LENGTH: 447
<212> TYPE: PRT
<213> ORGANISM: Artificial Sequence
<220> FEATURE:
<223> OTHER INFORMATION: an artificially synthesized sequence

<400> SEQUENCE: 88

Gln Val Gln Leu Gln Glu Ser Gly Pro Gly Leu Val Lys Pro Ser Glu
1               5                   10                  15

Thr Leu Ser Leu Thr Cys Ala Val Ser Gly His Ser Ile Ser His Asp
            20                  25                  30

His Ala Trp Ser Trp Val Arg Gln Pro Pro Gly Glu Gly Leu Glu Trp
        35                  40                  45

Ile Gly Phe Ile Ser Tyr Ser Gly Ile Thr Asn Tyr Asn Pro Ser Leu
    50                  55                  60

Gln Gly Arg Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Leu Ala Arg Thr Thr Ala Met Asp Tyr Trp Gly Glu Gly
            100                 105                 110
```

Thr Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
        130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Val Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Tyr His Tyr Thr Gln Lys Ser Leu Ser Leu Ser Pro
        435                 440                 445

<210> SEQ ID NO 89
<211> LENGTH: 447
<212> TYPE: PRT
<213> ORGANISM: Artificial Sequence
<220> FEATURE:
<223> OTHER INFORMATION: an artificially synthesized sequence

<400> SEQUENCE: 89

Gln Val Gln Leu Gln Glu Ser Gly Pro Gly Leu Val Lys Pro Ser Glu
1               5                   10                  15

Thr Leu Ser Leu Thr Cys Ala Val Ser Gly His Ser Ile Ser His Asp
            20                  25                  30

```
His Ala Trp Ser Trp Val Arg Gln Pro Pro Gly Glu Gly Leu Glu Trp
         35                  40                  45

Ile Gly Phe Ile Ser Tyr Ser Gly Ile Thr Asn Tyr Asn Pro Ser Leu
 50                  55                  60

Gln Gly Arg Val Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Ser Leu Ala Arg Thr Thr Ala Met Asp Tyr Trp Gly Glu Gly
            100                 105                 110

Thr Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
            130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys Asp Lys
            210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Glu Pro Glu Val Thr Cys Val Val Val Asp Val Ser His Glu Asp
            260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
            290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
            355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Tyr His Tyr Thr Gln Lys Ser Leu Ser Leu Ser Pro
            435                 440                 445
```

<210> SEQ ID NO 90
<211> LENGTH: 447
<212> TYPE: PRT
<213> ORGANISM: Artificial Sequence
<220> FEATURE:
<223> OTHER INFORMATION: an artificially synthesized sequence

<400> SEQUENCE: 90

```
Gln Val Gln Leu Gln Glu Ser Gly Pro Gly Leu Val Lys Pro Ser Glu
1               5                   10                  15

Thr Leu Ser Leu Thr Cys Ala Val Ser Gly His Ser Ile Ser His Asp
            20                  25                  30

His Ala Trp Ser Trp Val Arg Gln Pro Pro Gly Glu Gly Leu Glu Trp
        35                  40                  45

Ile Gly Phe Ile Ser Tyr Ser Gly Ile Thr Asn Tyr Asn Pro Ser Leu
    50                  55                  60

Gln Gly Arg Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Leu Ala Arg Thr Thr Ala Met Asp Tyr Trp Gly Glu Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Tyr Ile Ser
                245                 250                 255

Arg Gln Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365
```

-continued

```
Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
                420                 425                 430

Ala Leu His Tyr His Tyr Thr Gln Lys Ser Leu Ser Leu Ser Pro
                435                 440                 445

<210> SEQ ID NO 91
<211> LENGTH: 447
<212> TYPE: PRT
<213> ORGANISM: Artificial Sequence
<220> FEATURE:
<223> OTHER INFORMATION: an artificially synthesized sequence

<400> SEQUENCE: 91

Gln Val Gln Leu Gln Glu Ser Gly Pro Gly Leu Val Lys Pro Ser Glu
1               5                   10                  15

Thr Leu Ser Leu Thr Cys Ala Val Ser Gly His Ser Ile Ser His Asp
                20                  25                  30

His Ala Trp Ser Trp Val Arg Gln Pro Pro Gly Glu Gly Leu Glu Trp
            35                  40                  45

Ile Gly Phe Ile Ser Tyr Ser Gly Ile Thr Asn Tyr Asn Pro Ser Leu
        50                  55                  60

Gln Gly Arg Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Leu Ala Arg Thr Thr Ala Met Asp Tyr Trp Gly Glu Gly
                100                 105                 110

Thr Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
        130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
                180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys Asp Lys
        210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Trp Ile Ser
                245                 250                 255

Arg Thr Pro Glu Val Thr Cys Val Val Val Asp Val Ser His Glu Asp
                260                 265                 270

Pro Glu Val Lys Phe Asn Trp Tyr Val Asp Gly Val Glu Val His Asn
            275                 280                 285
```

```
Ala Lys Thr Lys Pro Arg Glu Glu Gln Tyr Asn Ser Thr Tyr Arg Val
    290                 295                 300
Val Ser Val Leu Thr Val Leu His Gln Asp Trp Leu Asn Gly Lys Glu
305                 310                 315                 320
Tyr Lys Cys Lys Val Ser Asn Lys Ala Leu Pro Ala Pro Ile Glu Lys
                325                 330                 335
Thr Ile Ser Lys Ala Lys Gly Gln Pro Arg Glu Pro Gln Val Tyr Thr
            340                 345                 350
Leu Pro Pro Ser Arg Asp Glu Leu Thr Lys Asn Gln Val Ser Leu Thr
            355                 360                 365
Cys Leu Val Lys Gly Phe Tyr Pro Ser Asp Ile Ala Val Glu Trp Glu
370                 375                 380
Ser Asn Gly Gln Pro Glu Asn Asn Tyr Lys Thr Thr Pro Pro Val Leu
385                 390                 395                 400
Asp Ser Asp Gly Ser Phe Phe Leu Tyr Ser Lys Leu Thr Val Asp Lys
                405                 410                 415
Ser Arg Trp Gln Gln Gly Asn Val Phe Ser Cys Ser Val Leu His Glu
                420                 425                 430
Ala Leu His Trp His Tyr Thr Gln Lys Ser Leu Ser Leu Ser Pro
            435                 440                 445

<210> SEQ ID NO 92
<211> LENGTH: 447
<212> TYPE: PRT
<213> ORGANISM: Artificial Sequence
<220> FEATURE:
<223> OTHER INFORMATION: an artificially synthesized sequence

<400> SEQUENCE: 92

Gln Val Gln Leu Gln Glu Ser Gly Pro Gly Leu Val Lys Pro Ser Glu
1               5                   10                  15
Thr Leu Ser Leu Thr Cys Ala Val Ser Gly His Ser Ile Ser His Asp
            20                  25                  30
His Ala Trp Ser Trp Val Arg Gln Pro Pro Gly Glu Gly Leu Glu Trp
        35                  40                  45
Ile Gly Phe Ile Ser Tyr Ser Gly Ile Thr Asn Tyr Asn Pro Ser Leu
    50                  55                  60
Gln Gly Arg Val Thr Ile Ser Arg Asp Asn Ser Lys Asn Thr Leu Tyr
65                  70                  75                  80
Leu Gln Met Asn Ser Leu Arg Ala Glu Asp Thr Ala Val Tyr Tyr Cys
                85                  90                  95
Ala Arg Ser Leu Ala Arg Thr Thr Ala Met Asp Tyr Trp Gly Glu Gly
            100                 105                 110
Thr Leu Val Thr Val Ser Ser Ala Ser Thr Lys Gly Pro Ser Val Phe
        115                 120                 125
Pro Leu Ala Pro Ser Ser Lys Ser Thr Ser Gly Gly Thr Ala Ala Leu
    130                 135                 140
Gly Cys Leu Val Lys Asp Tyr Phe Pro Glu Pro Val Thr Val Ser Trp
145                 150                 155                 160
Asn Ser Gly Ala Leu Thr Ser Gly Val His Thr Phe Pro Ala Val Leu
                165                 170                 175
Gln Ser Ser Gly Leu Tyr Ser Leu Ser Ser Val Val Thr Val Pro Ser
            180                 185                 190
Ser Ser Leu Gly Thr Gln Thr Tyr Ile Cys Asn Val Asn His Lys Pro
        195                 200                 205
```

```
Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
            245                 250                 255

Arg Thr Leu Glu Val Thr Cys Val Val Val Asp Val Ser His Glu Asp
        260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Leu His Glu
            420                 425                 430

Ala Leu His Tyr His Tyr Thr Gln Lys Ser Leu Ser Leu Ser Pro
        435                 440                 445

<210> SEQ ID NO 93
<211> LENGTH: 216
<212> TYPE: PRT
<213> ORGANISM: Homo sapiens

<400> SEQUENCE: 93

Gln Ser Val Leu Thr Gln Pro Pro Ser Val Ser Gly Ala Pro Gly Gln
1               5                   10                  15

Arg Val Thr Ile Ser Cys Thr Gly Ser Arg Ser Asn Met Gly Ala Gly
            20                  25                  30

Tyr Asp Val His Trp Tyr Gln Leu Leu Pro Gly Ala Ala Pro Lys Leu
        35                  40                  45

Leu Ile Ser His Asn Thr His Arg Pro Ser Gly Val Pro Asp Arg Phe
    50                  55                  60

Ser Gly Ser Lys Ser Gly Ala Ser Ala Ser Leu Ala Ile Thr Gly Leu
65                  70                  75                  80

Gln Ala Glu Asp Glu Ala Asp Tyr Tyr Cys Gln Ser His Asp Ser Ser
                85                  90                  95

Leu Ser Ala Val Val Phe Gly Gly Gly Thr Lys Leu Thr Val Leu Ser
            100                 105                 110

Gln Pro Lys Ala Ala Pro Ser Val Thr Leu Phe Pro Pro Ser Ser Glu
        115                 120                 125

Glu Leu Gln Ala Asn Lys Ala Thr Leu Val Cys Leu Ile Ser Asp Phe
    130                 135                 140
```

Tyr Pro Gly Ala Val Thr Val Ala Trp Lys Ala Asp Ser Ser Pro Val
145                 150                 155                 160

Lys Ala Gly Val Glu Thr Thr Thr Pro Ser Lys Gln Ser Asn Asn Lys
                165                 170                 175

Tyr Ala Ala Ser Ser Tyr Leu Ser Leu Thr Pro Glu Gln Trp Lys Ser
            180                 185                 190

His Arg Ser Tyr Ser Cys Gln Val Thr His Glu Gly Ser Thr Val Glu
        195                 200                 205

Lys Thr Val Ala Pro Thr Glu Cys
    210                 215

<210> SEQ ID NO 94
<211> LENGTH: 453
<212> TYPE: PRT
<213> ORGANISM: Homo sapiens

<400> SEQUENCE: 94

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Arg Asp Tyr Tyr Asp Ser Ser Gly Tyr Tyr Asp Ala Phe
            100                 105                 110

Asp Ile Trp Gly Gln Gly Thr Met Val Thr Val Ser Ser Ala Ser Thr
        115                 120                 125

Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
        195                 200                 205

Asn Val Asn His Lys Pro Ser Asn Thr Lys Val Asp Lys Lys Val Glu
    210                 215                 220

Pro Lys Ser Cys Asp Lys Thr His Thr Cys Pro Pro Cys Pro Ala Pro
225                 230                 235                 240

Glu Leu Leu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
        275                 280                 285

Gly Val Glu Val His Asn Ala Lys Thr Lys Pro Arg Glu Glu Gln Tyr

```
              290                 295                 300
Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly Gln Pro Arg
            340                 345                 350

Glu Pro Gln Val Tyr Thr Leu Pro Pro Ser Arg Asp Glu Leu Thr Lys
        355                 360                 365

Asn Gln Val Ser Leu Thr Cys Leu Val Lys Gly Phe Tyr Pro Ser Asp
    370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Lys Leu Thr Val Asp Lys Ser Arg Trp Gln Gln Gly Asn Val Phe Ser
            420                 425                 430

Cys Ser Val Met His Glu Ala Leu His Asn His Tyr Thr Gln Lys Ser
        435                 440                 445

Leu Ser Leu Ser Pro
    450

<210> SEQ ID NO 95
<211> LENGTH: 214
<212> TYPE: PRT
<213> ORGANISM: Homo sapiens

<400> SEQUENCE: 95

Glu Thr Thr Val Thr Gln Ser Pro Ser Phe Leu Ser Ala Ser Val Gly
1               5                   10                  15

Asp Arg Val Thr Ile Thr Cys Ile Thr Thr Asp Ile Asp Asp Asp
            20                  25                  30

Met Asn Trp Phe Gln Gln Glu Pro Gly Lys Ala Pro Lys Leu Leu Ile
        35                  40                  45

Ser Glu Gly Asn Ile Leu Arg Pro Gly Val Pro Ser Arg Phe Ser Ser
    50                  55                  60

Ser Gly Tyr Gly Thr Asp Phe Thr Leu Thr Ile Ser Lys Leu Gln Pro
65                  70                  75                  80

Glu Asp Phe Ala Thr Tyr Tyr Cys Leu Gln Ser Asp Asn Leu Pro Phe
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205
```

```
Phe Asn Arg Gly Glu Cys
    210

<210> SEQ ID NO 96
<211> LENGTH: 447
<212> TYPE: PRT
<213> ORGANISM: Homo sapiens

<400> SEQUENCE: 96

Gln Val Gln Leu Gln Glu Ser Gly Pro Gly Leu Val Lys Pro Ser Glu
1               5                   10                  15

Thr Leu Ser Leu Thr Cys Ala Val Ser Gly Tyr Ser Ile Ser Asp Asp
            20                  25                  30

Gln Ala Trp Ser Trp Val Arg Gln Pro Pro Gly Glu Gly Leu Glu Trp
        35                  40                  45

Ile Gly Tyr Ile Ser Tyr Ser Gly Ile Thr Asn Tyr Asn Pro Ser Leu
    50                  55                  60

Lys Gly Arg Val Thr Ile Ser Arg Asp Thr Ser Lys Asn Gln Phe Ser
65                  70                  75                  80

Leu Lys Leu Ser Ser Val Thr Ala Ala Asp Thr Ala Ala Tyr Tyr Cys
                85                  90                  95

Ala Arg Ser Leu Ala Arg Thr Thr Ala Met Asp Tyr Trp Gly Glu Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365
```

```
Cys Leu Val Lys Gly Phe Tyr Pro Ser Asp Ile Ala Val Glu Trp Glu
        370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro
        435                 440                 445
```

<210> SEQ ID NO 97
<211> LENGTH: 214
<212> TYPE: PRT
<213> ORGANISM: Homo sapiens

<400> SEQUENCE: 97

```
Asp Ile Gln Met Thr Gln Ser Pro Ser Ser Leu Ser Ala Ser Val Gly
1               5                   10                  15

Asp Ser Val Thr Ile Thr Cys Gln Ala Ser Gln Asp Ile Ser Ser Tyr
            20                  25                  30

Leu Asn Trp Tyr Gln Gln Lys Pro Gly Lys Ala Pro Glu Leu Leu Ile
        35                  40                  45

Tyr Tyr Gly Ser Glu Leu His Ser Gly Val Pro Ser Arg Phe Ser Gly
    50                  55                  60

Ser Gly Ser Gly Thr Asp Phe Thr Phe Thr Ile Ser Ser Leu Glu Ala
65                  70                  75                  80

Glu Asp Ala Ala Thr Tyr Tyr Cys Gln Gln Gly Asn Ser Leu Pro Tyr
                85                  90                  95

Thr Phe Gly Gln Gly Thr Lys Val Glu Ile Glu Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 98
<211> LENGTH: 106
<212> TYPE: PRT
<213> ORGANISM: Homo sapiens

<400> SEQUENCE: 98

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30
```

```
Leu Ala Trp Tyr Gln Gln Lys Pro Gly Gln Ala Pro Arg Leu Leu Ile
            35                  40                  45

Phe Asp Ala Ser Asn Arg Ala Ala Gly Ile Pro Ala Arg Phe Ser Gly
     50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Phe Asp Lys Trp Val Thr
                 85                  90                  95

Phe Gly Gly Gly Thr Thr Val Glu Ile Arg
            100                 105

<210> SEQ ID NO 99
<211> LENGTH: 454
<212> TYPE: PRT
<213> ORGANISM: Artificial Sequence
<220> FEATURE:
<223> OTHER INFORMATION: an artificially synthesized sequence

<400> SEQUENCE: 99

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
            20                  25                  30

Glu Met Asn Trp Val Arg Gln Ala Pro Gly Lys Gly Leu Glu Trp Val
        35                  40                  45

Ser Tyr Ile Ser Ser Ser Gly Ser Thr Ile Tyr Tyr Ala Asp Ser Val
     50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Asp Ala Pro Tyr Tyr Tyr Asp Ser Ser Gly Tyr Thr Asp Ala
            100                 105                 110

Phe Asp Ile Trp Gly Gln Gly Thr Met Val Thr Val Ser Ser Ala Ser
        115                 120                 125

Thr Lys Gly Pro Ser Val Phe Pro Leu Ala Pro Ser Ser Lys Ser Thr
    130                 135                 140

Ser Gly Gly Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

Ser Val Val Thr Val Pro Ser Ser Ser Leu Gly Thr Gln Thr Tyr Ile
        195                 200                 205

Cys Asn Val Asn His Lys Pro Ser Asn Thr Lys Val Asp Lys Lys Val
    210                 215                 220

Glu Pro Lys Ser Cys Asp Lys Thr His Thr Cys Pro Pro Cys Pro Ala
225                 230                 235                 240

Pro Glu Leu Leu Gly Gly Pro Ser Val Phe Leu Phe Pro Pro Lys Pro
                245                 250                 255

Lys Asp Thr Leu Met Ile Ser Arg Thr Pro Glu Val Thr Cys Val Val
            260                 265                 270

Val Asp Val Ser His Glu Asp Pro Glu Val Lys Phe Asn Trp Tyr Val
        275                 280                 285
```

-continued

Asp Gly Val Glu Val His Asn Ala Lys Thr Lys Pro Arg Glu Glu Gln
            290                 295                 300

Tyr Asn Ser Thr Tyr Arg Val Val Ser Val Leu Thr Val Leu His Gln
305                 310                 315                 320

Asp Trp Leu Asn Gly Lys Glu Tyr Lys Cys Lys Val Ser Asn Lys Ala
                325                 330                 335

Leu Pro Ala Pro Ile Glu Lys Thr Ile Ser Lys Ala Lys Gly Gln Pro
            340                 345                 350

Arg Glu Pro Gln Val Tyr Thr Leu Pro Pro Ser Arg Asp Glu Leu Thr
        355                 360                 365

Lys Asn Gln Val Ser Leu Thr Cys Leu Val Lys Gly Phe Tyr Pro Ser
370                 375                 380

Asp Ile Ala Val Glu Trp Glu Ser Asn Gly Gln Pro Glu Asn Asn Tyr
385                 390                 395                 400

Lys Thr Thr Pro Pro Val Leu Asp Ser Asp Gly Ser Phe Phe Leu Tyr
            405                 410                 415

Ser Lys Leu Thr Val Asp Lys Ser Arg Trp Gln Gln Gly Asn Val Phe
            420                 425                 430

Ser Cys Ser Val Met His Glu Ala Leu His Asn His Tyr Thr Gln Lys
        435                 440                 445

Ser Leu Ser Leu Ser Pro
    450

<210> SEQ ID NO 100
<211> LENGTH: 107
<212> TYPE: PRT
<213> ORGANISM: Homo sapiens

<400> SEQUENCE: 100

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 101
<211> LENGTH: 213
<212> TYPE: PRT
<213> ORGANISM: Artificial Sequence
<220> FEATURE:
<223> OTHER INFORMATION: an artificially synthesized sequence

<400> SEQUENCE: 101

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
            35                  40                  45

Phe Asp Ala Ser Asn Arg Ala Ala Gly Ile Pro Ala Arg Phe Ser Gly
 50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Phe Asp Lys Trp Val Thr
                85                  90                  95

Phe Gly Gly Gly Thr Thr Val Glu Ile Arg Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 102
<211> LENGTH: 454
<212> TYPE: PRT
<213> ORGANISM: Artificial Sequence
<220> FEATURE:
<223> OTHER INFORMATION: an artificially synthesized sequence

<400> SEQUENCE: 102

Glu Val Gln Leu Val Glu Ser Gly Gly Gly Leu Val Gln Pro Gly Gly
 1               5                   10                  15

Ser Leu Arg Leu Ser Cys Ala Ala Ser Gly Phe Thr Phe Ser Ser Tyr
            20                  25                  30

Glu Met Asn Trp Val Arg Gln Ala Pro Gly Lys Gly Leu Glu Trp Val
        35                  40                  45

Ser Tyr Ile Ser Ser Ser Gly Ser Thr Ile Tyr Tyr Ala Ala Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Ala Pro Tyr Tyr Tyr Asp Ser Ser Gly Tyr Thr Asp Ala
            100                 105                 110

Phe Asp Ile Trp Gly Gln Gly Thr Met Val Thr Val Ser Ser Ala Ser
        115                 120                 125

Thr Lys Gly Pro Ser Val Phe Pro Leu Ala Pro Ser Ser Lys Ser Thr
130                 135                 140

Ser Gly Gly Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

Ser Val Val Thr Val Pro Ser Ser Leu Gly Thr Gln Thr Tyr Ile
            195                 200                 205

Cys Asn Val Asn His Lys Pro Ser Asn Thr Lys Val Asp Lys Lys Val
210                 215                 220

Glu Pro Lys Ser Cys Asp Lys Thr His Thr Cys Pro Pro Cys Pro Ala
225                 230                 235                 240

Pro Glu Leu Leu Gly Gly Pro Ser Val Phe Leu Phe Pro Pro Lys Pro
            245                 250                 255

Lys Asp Thr Leu Met Ile Ser Arg Thr Pro Glu Val Thr Cys Val Val
            260                 265                 270

Val Asp Val Ser His Glu Asp Pro Glu Val Lys Phe Asn Trp Tyr Val
            275                 280                 285

Asp Gly Val Glu Val His Asn Ala Lys Thr Lys Pro Arg Glu Glu Gln
            290                 295                 300

Tyr Asn Ser Thr Tyr Arg Val Val Ser Val Leu Thr Val Leu His Gln
305                 310                 315                 320

Asp Trp Leu Asn Gly Lys Glu Tyr Lys Cys Lys Val Ser Asn Lys Ala
            325                 330                 335

Leu Pro Ala Pro Ile Glu Lys Thr Ile Ser Lys Ala Lys Gly Gln Pro
            340                 345                 350

Arg Glu Pro Gln Val Tyr Thr Leu Pro Pro Ser Arg Asp Glu Leu Thr
            355                 360                 365

Lys Asn Gln Val Ser Leu Thr Cys Leu Val Lys Gly Phe Tyr Pro Ser
            370                 375                 380

Asp Ile Ala Val Glu Trp Glu Ser Asn Gly Gln Pro Glu Asn Asn Tyr
385                 390                 395                 400

Lys Thr Thr Pro Pro Val Leu Asp Ser Asp Gly Ser Phe Phe Leu Tyr
            405                 410                 415

Ser Lys Leu Thr Val Asp Lys Ser Arg Trp Gln Gln Gly Asn Val Phe
            420                 425                 430

Ser Cys Ser Val Met His Glu Ala Leu His Asn His Tyr Thr Gln Lys
            435                 440                 445

Ser Leu Ser Leu Ser Pro
    450

<210> SEQ ID NO 103
<211> LENGTH: 454
<212> TYPE: PRT
<213> ORGANISM: Artificial Sequence
<220> FEATURE:
<223> OTHER INFORMATION: an artificially synthesized sequence

<400> SEQUENCE: 103

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Glu Met Asn Trp Val Arg Gln Ala Pro Gly Lys Gly Leu Glu Trp Val
            35                  40                  45

Ser Tyr Ile Ser Ser Ser Gly Ser Thr Ile Tyr Tyr Ala Asp Ser Val
            50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                 85                  90                  95

Ala Arg Ala Ala Pro Tyr Tyr Tyr Asp Ser Ser Gly Tyr Thr Asp Ala
            100                 105                 110

Phe Asp Ile Trp Gly Gln Gly Thr Met Val Thr Val Ser Ser Ala Ser
            115                 120                 125

Thr Lys Gly Pro Ser Val Phe Pro Leu Ala Pro Ser Ser Lys Ser Thr
130                 135                 140

Ser Gly Gly Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

Ser Val Val Thr Val Pro Ser Ser Ser Leu Gly Thr Gln Thr Tyr Ile
        195                 200                 205

Cys Asn Val Asn His Lys Pro Ser Asn Thr Lys Val Asp Lys Lys Val
210                 215                 220

Glu Pro Lys Ser Cys Asp Lys Thr His Thr Cys Pro Pro Cys Pro Ala
225                 230                 235                 240

Pro Glu Leu Leu Gly Gly Pro Ser Val Phe Leu Phe Pro Pro Lys Pro
                245                 250                 255

Lys Asp Thr Leu Met Ile Ser Arg Thr Pro Glu Val Thr Cys Val Val
            260                 265                 270

Val Asp Val Ser His Glu Asp Pro Glu Val Lys Phe Asn Trp Tyr Val
        275                 280                 285

Asp Gly Val Glu Val His Asn Ala Lys Thr Lys Pro Arg Glu Glu Gln
290                 295                 300

Tyr Asn Ser Thr Tyr Arg Val Val Ser Val Leu Thr Val Leu His Gln
305                 310                 315                 320

Asp Trp Leu Asn Gly Lys Glu Tyr Lys Cys Lys Val Ser Asn Lys Ala
                325                 330                 335

Leu Pro Ala Pro Ile Glu Lys Thr Ile Ser Lys Ala Lys Gly Gln Pro
            340                 345                 350

Arg Glu Pro Gln Val Tyr Thr Leu Pro Pro Ser Arg Asp Glu Leu Thr
        355                 360                 365

Lys Asn Gln Val Ser Leu Thr Cys Leu Val Lys Gly Phe Tyr Pro Ser
370                 375                 380

Asp Ile Ala Val Glu Trp Glu Ser Asn Gly Gln Pro Glu Asn Asn Tyr
385                 390                 395                 400

Lys Thr Thr Pro Pro Val Leu Asp Ser Asp Gly Ser Phe Phe Leu Tyr
                405                 410                 415

Ser Lys Leu Thr Val Asp Lys Ser Arg Trp Gln Gln Gly Asn Val Phe
            420                 425                 430

Ser Cys Ser Val Met His Glu Ala Leu His Asn His Tyr Thr Gln Lys
        435                 440                 445

Ser Leu Ser Leu Ser Pro
    450

<210> SEQ ID NO 104
<211> LENGTH: 454
<212> TYPE: PRT
<213> ORGANISM: Artificial Sequence
<220> FEATURE:
<223> OTHER INFORMATION: an artificially synthesized sequence

<400> SEQUENCE: 104

| | | | | | | | | | | | | | |
|---|---|---|---|---|---|---|---|---|---|---|---|---|---|
|Glu|Val|Gln|Leu|Val|Glu|Ser|Gly|Gly|Gly|Leu|Val|Gln|Pro|Gly|Gly
1| | | |5| | | | |10| | | | |15|

Ser Leu Arg Leu Ser Cys Ala Ala Ser Gly Phe Thr Phe Ser Ser Tyr
           20                  25                  30

Glu Met Asn Trp Val Arg Gln Ala Pro Gly Lys Gly Leu Glu Trp Val
           35                  40                  45

Ser Tyr Ile Ser Ser Gly Ser Thr Ile Tyr Tyr Ala Asp Ser Val
50                   55                  60

Lys Gly Arg Phe Thr Ile Ser Arg Asp Asn Ala Lys Asn Ser Leu Tyr
65                   70                  75                  80

Leu Gln Met Asn Ser Leu Arg Ala Glu Asp Thr Ala Val Tyr Tyr Cys
           85                  90                  95

Ala Arg Asp Ala Pro Tyr Tyr Ala Ser Ser Gly Tyr Thr Asp Ala
            100                 105              110

Phe Asp Ile Trp Gly Gln Gly Thr Met Val Thr Val Ser Ser Ala Ser
           115                 120              125

Thr Lys Gly Pro Ser Val Phe Pro Leu Ala Pro Ser Ser Lys Ser Thr
130                   135                  140

Ser Gly Gly Thr Ala Ala Leu Gly Cys Leu Val Lys Asp Tyr Phe Pro
145                   150                  155                  160

Glu Pro Val Thr Val Ser Trp Asn Ser Gly Ala Leu Thr Ser Gly Val
           165                 170              175

His Thr Phe Pro Ala Val Leu Gln Ser Ser Gly Leu Tyr Ser Leu Ser
           180                 185              190

Ser Val Val Thr Val Pro Ser Ser Ser Leu Gly Thr Gln Thr Tyr Ile
195                   200                  205

Cys Asn Val Asn His Lys Pro Ser Asn Thr Lys Val Asp Lys Lys Val
210                   215                  220

Glu Pro Lys Ser Cys Asp Lys Thr His Thr Cys Pro Pro Cys Pro Ala
225                   230                  235                  240

Pro Glu Leu Leu Gly Gly Pro Ser Val Phe Leu Phe Pro Pro Lys Pro
           245                 250              255

Lys Asp Thr Leu Met Ile Ser Arg Thr Pro Glu Val Thr Cys Val Val
           260                 265              270

Val Asp Val Ser His Glu Asp Pro Glu Val Lys Phe Asn Trp Tyr Val
           275                 280              285

Asp Gly Val Glu Val His Asn Ala Lys Thr Lys Pro Arg Glu Glu Gln
290                   295                  300

Tyr Asn Ser Thr Tyr Arg Val Val Ser Val Leu Thr Val Leu His Gln
305                   310                  315                  320

Asp Trp Leu Asn Gly Lys Glu Tyr Lys Cys Lys Val Ser Asn Lys Ala
           325                 330              335

Leu Pro Ala Pro Ile Glu Lys Thr Ile Ser Lys Ala Lys Gly Gln Pro
           340                 345              350

Arg Glu Pro Gln Val Tyr Thr Leu Pro Pro Ser Arg Asp Glu Leu Thr
           355                 360              365

Lys Asn Gln Val Ser Leu Thr Cys Leu Val Lys Gly Phe Tyr Pro Ser
           370                 375              380

Asp Ile Ala Val Glu Trp Glu Ser Asn Gly Gln Pro Glu Asn Asn Tyr
385                   390                  395                  400

Lys Thr Thr Pro Pro Val Leu Asp Ser Asp Gly Ser Phe Phe Leu Tyr

```
                         405                 410                 415
Ser Lys Leu Thr Val Asp Lys Ser Arg Trp Gln Gln Gly Asn Val Phe
        420                 425                 430

Ser Cys Ser Val Met His Glu Ala Leu His Asn His Tyr Thr Gln Lys
        435                 440                 445

Ser Leu Ser Leu Ser Pro
    450

<210> SEQ ID NO 105
<211> LENGTH: 454
<212> TYPE: PRT
<213> ORGANISM: Artificial Sequence
<220> FEATURE:
<223> OTHER INFORMATION: an artificially synthesized sequence

<400> SEQUENCE: 105

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Glu Met Asn Trp Val Arg Gln Ala Pro Gly Lys Gly Leu Glu Trp Val
        35                  40                  45

Ser Tyr Ile Ser Ser Ser Gly Ser Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Ala Pro Tyr Tyr Tyr Asp Ser Ser Gly Tyr Thr Ala Ala
            100                 105                 110

Phe Asp Ile Trp Gly Gln Gly Thr Met Val Thr Val Ser Ser Ala Ser
        115                 120                 125

Thr Lys Gly Pro Ser Val Phe Pro Leu Ala Pro Ser Ser Lys Ser Thr
    130                 135                 140

Ser Gly Gly Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

Ser Val Val Thr Val Pro Ser Ser Ser Leu Gly Thr Gln Thr Tyr Ile
        195                 200                 205

Cys Asn Val Asn His Lys Pro Ser Asn Thr Lys Val Asp Lys Lys Val
    210                 215                 220

Glu Pro Lys Ser Cys Asp Lys Thr His Thr Cys Pro Pro Cys Pro Ala
225                 230                 235                 240

Pro Glu Leu Leu Gly Gly Pro Ser Val Phe Leu Phe Pro Pro Lys Pro
                245                 250                 255

Lys Asp Thr Leu Met Ile Ser Arg Thr Pro Glu Val Thr Cys Val Val
            260                 265                 270

Val Asp Val Ser His Glu Asp Pro Glu Val Lys Phe Asn Trp Tyr Val
        275                 280                 285

Asp Gly Val Glu Val His Asn Ala Lys Thr Lys Pro Arg Glu Glu Gln
    290                 295                 300

Tyr Asn Ser Thr Tyr Arg Val Val Ser Val Leu Thr Val Leu His Gln
```

```
                305                 310                 315                 320
Asp Trp Leu Asn Gly Lys Glu Tyr Lys Cys Lys Val Ser Asn Lys Ala
                    325                 330                 335

Leu Pro Ala Pro Ile Glu Lys Thr Ile Ser Lys Ala Lys Gly Gln Pro
                340                 345                 350

Arg Glu Pro Gln Val Tyr Thr Leu Pro Pro Ser Arg Asp Glu Leu Thr
            355                 360                 365

Lys Asn Gln Val Ser Leu Thr Cys Leu Val Lys Gly Phe Tyr Pro Ser
        370                 375                 380

Asp Ile Ala Val Glu Trp Glu Ser Asn Gly Gln Pro Glu Asn Asn Tyr
385                 390                 395                 400

Lys Thr Thr Pro Pro Val Leu Asp Ser Asp Gly Ser Phe Phe Leu Tyr
                405                 410                 415

Ser Lys Leu Thr Val Asp Lys Ser Arg Trp Gln Gln Gly Asn Val Phe
                    420                 425                 430

Ser Cys Ser Val Met His Glu Ala Leu His Asn His Tyr Thr Gln Lys
                        435                 440                 445

Ser Leu Ser Leu Ser Pro
        450

<210> SEQ ID NO 106
<211> LENGTH: 454
<212> TYPE: PRT
<213> ORGANISM: Artificial Sequence
<220> FEATURE:
<223> OTHER INFORMATION: an artificially synthesized sequence

<400> SEQUENCE: 106

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Glu Met Asn Trp Val Arg Gln Ala Pro Gly Lys Gly Leu Glu Trp Val
        35                  40                  45

Ser Tyr Ile Ser Ser Ser Gly Ser Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Ala Pro Tyr Tyr Tyr Asp Ser Ser Gly Tyr Thr Asp Ala
            100                 105                 110

Phe Ala Ile Trp Gly Gln Gly Thr Met Val Thr Val Ser Ser Ala Ser
        115                 120                 125

Thr Lys Gly Pro Ser Val Phe Pro Leu Ala Pro Ser Ser Lys Ser Thr
    130                 135                 140

Ser Gly Gly Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

Ser Val Val Thr Val Pro Ser Ser Ser Leu Gly Thr Gln Thr Tyr Ile
        195                 200                 205

Cys Asn Val Asn His Lys Pro Ser Asn Thr Lys Val Asp Lys Lys Val
```

-continued

```
            210                 215                 220
Glu Pro Lys Ser Cys Asp Lys Thr His Thr Cys Pro Cys Pro Ala
225                 230                 235                 240

Pro Glu Leu Leu Gly Gly Pro Ser Val Phe Leu Phe Pro Pro Lys Pro
                245                 250                 255

Lys Asp Thr Leu Met Ile Ser Arg Thr Pro Glu Val Thr Cys Val Val
                260                 265                 270

Val Asp Val Ser His Glu Asp Pro Glu Val Lys Phe Asn Trp Tyr Val
            275                 280                 285

Asp Gly Val Glu Val His Asn Ala Lys Thr Lys Pro Arg Glu Glu Gln
        290                 295                 300

Tyr Asn Ser Thr Tyr Arg Val Val Ser Val Leu Thr Val Leu His Gln
305                 310                 315                 320

Asp Trp Leu Asn Gly Lys Glu Tyr Lys Cys Lys Val Ser Asn Lys Ala
                325                 330                 335

Leu Pro Ala Pro Ile Glu Lys Thr Ile Ser Lys Ala Lys Gly Gln Pro
                340                 345                 350

Arg Glu Pro Gln Val Tyr Thr Leu Pro Pro Ser Arg Asp Glu Leu Thr
            355                 360                 365

Lys Asn Gln Val Ser Leu Thr Cys Leu Val Lys Gly Phe Tyr Pro Ser
370                 375                 380

Asp Ile Ala Val Glu Trp Glu Ser Asn Gly Gln Pro Glu Asn Asn Tyr
385                 390                 395                 400

Lys Thr Thr Pro Pro Val Leu Asp Ser Asp Gly Ser Phe Phe Leu Tyr
                405                 410                 415

Ser Lys Leu Thr Val Asp Lys Ser Arg Trp Gln Gln Gly Asn Val Phe
                420                 425                 430

Ser Cys Ser Val Met His Glu Ala Leu His Asn His Tyr Thr Gln Lys
            435                 440                 445

Ser Leu Ser Leu Ser Pro
            450
```

<210> SEQ ID NO 107
<211> LENGTH: 213
<212> TYPE: PRT
<213> ORGANISM: Artificial Sequence
<220> FEATURE:
<223> OTHER INFORMATION: an artificially synthesized sequence

<400> SEQUENCE: 107

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
                20                  25                  30

Leu Ala Trp Tyr Gln Gln Lys Pro Gly Gln Ala Pro Arg Leu Leu Ile
            35                  40                  45

Phe Ala Ala Ser Asn Arg Ala Ala Gly Ile Pro Ala Arg Phe Ser Gly
        50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Phe Asp Lys Trp Val Thr
                85                  90                  95

Phe Gly Gly Gly Thr Thr Val Glu Ile Arg Arg Thr Val Ala Ala Pro
            100                 105                 110

Ser Val Phe Ile Phe Pro Pro Ser Asp Glu Gln Leu Lys Ser Gly Thr
```

115                 120                 125
Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 108
<211> LENGTH: 213
<212> TYPE: PRT
<213> ORGANISM: Artificial Sequence
<220> FEATURE:
<223> OTHER INFORMATION: an artificially synthesized sequence

<400> SEQUENCE: 108

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Phe Asp Ala Ser Asn Arg Ala Ala Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Phe Ala Lys Trp Val Thr
                85                  90                  95

Phe Gly Gly Gly Thr Thr Val Glu Ile Arg Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 109
<211> LENGTH: 449
<212> TYPE: PRT
<213> ORGANISM: Homo sapiens

<400> SEQUENCE: 109

```
Gln Val Gln Leu Gln Glu Ser Gly Pro Gly Leu Val Arg Pro Ser Gln
1               5                   10                  15

Thr Leu Ser Leu Thr Cys Thr Val Ser Gly Tyr Ser Ile Thr Ser Asp
            20                  25                  30

His Ala Trp Ser Trp Val Arg Gln Pro Pro Gly Arg Gly Leu Glu Trp
        35                  40                  45

Ile Gly Tyr Ile Ser Tyr Ser Gly Ile Thr Thr Tyr Asn Pro Ser Leu
    50                  55                  60

Lys Ser Arg Val Thr Met Leu Arg Asp Thr Ser Lys Asn Gln Phe Ser
65                  70                  75                  80

Leu Arg Leu Ser Ser Val Thr Ala Ala Asp Thr Ala Val Tyr Tyr Cys
                85                  90                  95

Ala Arg Ser Leu Ala Arg Thr Thr Ala Met Asp Tyr Trp Gly Gln Gly
            100                 105                 110

Ser Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
    355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415
```

```
Ser Arg Trp Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445

Lys

<210> SEQ ID NO 110
<211> LENGTH: 453
<212> TYPE: PRT
<213> ORGANISM: Artificial Sequence
<220> FEATURE:
<223> OTHER INFORMATION: an artificially synthesized sequence

<400> SEQUENCE: 110

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Arg Asp Tyr Tyr Asp Ser Ser Gly Tyr Tyr Asp Ala Phe
            100                 105                 110

Asp Ile Trp Gly Gln Gly Thr Met Val Thr Val Ser Ser Ala Ser Thr
        115                 120                 125

Lys Gly Pro Ser Val Phe Pro Leu Ala Pro Ser Ser Lys Ser Thr Ser
130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
        195                 200                 205

Asn Val Asn His Lys Pro Ser Asn Thr Lys Val Asp Lys Lys Val Glu
    210                 215                 220

Pro Lys Ser Cys Asp Lys Thr His Thr Cys Pro Pro Cys Pro Ala Pro
225                 230                 235                 240

Glu Leu Leu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
        275                 280                 285

Gly Val Glu Val His Asn Ala Lys Thr Lys Pro Arg Glu Glu Gln Tyr
    290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
```

```
                     325                 330                 335
Pro Ala Pro Ile Glu Lys Thr Ile Ser Lys Ala Lys Gly Gln Pro Arg
            340                 345                 350
Glu Pro Gln Val Tyr Thr Leu Pro Pro Ser Arg Asp Glu Leu Thr Lys
            355                 360                 365
Asn Gln Val Ser Leu Thr Cys Leu Val Lys Gly Phe Tyr Pro Ser Asp
            370                 375                 380
Ile Ala Val Glu Trp Glu Ser Asn Gly Gln Pro Glu Asn Asn Tyr Lys
385                 390                 395                 400
Thr Thr Pro Pro Val Leu Asp Ser Asp Gly Ser Phe Phe Leu Tyr Ser
            405                 410                 415
Lys Leu Thr Val Asp Lys Ser Arg Trp Gln Gln Gly Asn Val Phe Ser
            420                 425                 430
Cys Ser Val Met His Glu Ala Leu His Trp His Tyr Thr Gln Lys Ser
            435                 440                 445
Leu Ser Leu Ser Pro
            450

<210> SEQ ID NO 111
<211> LENGTH: 449
<212> TYPE: PRT
<213> ORGANISM: Artificial Sequence
<220> FEATURE:
<223> OTHER INFORMATION: an artificially synthesized sequence

<400> SEQUENCE: 111

Gln Val Gln Leu Val Gln Ser Gly Ala Glu Val Lys Lys Pro Gly Ala
1               5                   10                  15
Ser Val Lys Val Ser Cys Lys Ala Ser Gly Tyr Thr Phe Thr Ser Tyr
            20                  25                  30
Tyr Met His Trp Val Arg Gln Ala Pro Gly Gln Gly Leu Glu Trp Met
        35                  40                  45
Gly Ile Ile Asn Pro Ser Gly Gly Ser Thr Ser Tyr Ala Gln Lys Phe
    50                  55                  60
Gln Gly Arg Val Thr Met Thr Arg Asp Thr Ser Thr Ser Thr Val Tyr
65                  70                  75                  80
Met Glu Leu Ser Ser Leu Arg Ser Glu Asp Thr Ala Val Tyr Tyr Cys
            85                  90                  95
Ala Arg Asp Asp Pro Gly Gly Gly Glu Tyr Tyr Phe Asp Tyr Trp Gly
            100                 105                 110
Gln Gly Thr Leu Val Thr Val Ser Ser Ala Ser Thr Lys Gly Pro Ser
            115                 120                 125
Val Phe Pro Leu Ala Pro Ser Ser Lys Ser Thr Ser Gly Gly Thr Ala
            130                 135                 140
Ala Leu Gly Cys Leu Val Lys Asp Tyr Phe Pro Glu Pro Val Thr Val
145                 150                 155                 160
Ser Trp Asn Ser Gly Ala Leu Thr Ser Gly Val His Thr Phe Pro Ala
            165                 170                 175
Val Leu Gln Ser Ser Gly Leu Tyr Ser Leu Ser Ser Val Val Thr Val
            180                 185                 190
Pro Ser Ser Ser Leu Gly Thr Gln Thr Tyr Ile Cys Asn Val Asn His
            195                 200                 205
Lys Pro Ser Asn Thr Lys Val Asp Lys Val Glu Pro Lys Ser Cys
            210                 215                 220
Asp Lys Thr His Thr Cys Pro Pro Cys Pro Ala Pro Glu Leu Leu Gly
```

```
                225                 230                 235                 240
Gly Pro Ser Val Phe Leu Phe Pro Pro Lys Pro Lys Asp Thr Leu Met
                    245                 250                 255

Ile Ser Arg Thr Pro Glu Val Thr Cys Val Val Val Asp Val Ser His
                260                 265                 270

Glu Asp Pro Glu Val Lys Phe Asn Trp Tyr Val Asp Gly Val Glu Val
                275                 280                 285

His Asn Ala Lys Thr Lys Pro Arg Glu Glu Gln Tyr Asn Ser Thr Tyr
            290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                    325                 330                 335

Glu Lys Thr Ile Ser Lys Ala Lys Gly Gln Pro Arg Glu Pro Gln Val
                340                 345                 350

Tyr Thr Leu Pro Pro Ser Arg Asp Glu Leu Thr Lys Asn Gln Val Ser
                355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                    405                 410                 415

Asp Lys Ser Arg Trp Gln Gln Gly Asn Val Phe Ser Cys Ser Val Met
                420                 425                 430

His Glu Ala Leu His Trp His Tyr Thr Gln Lys Ser Leu Ser Leu Ser
                435                 440                 445

Pro

<210> SEQ ID NO 112
<211> LENGTH: 447
<212> TYPE: PRT
<213> ORGANISM: Artificial Sequence
<220> FEATURE:
<223> OTHER INFORMATION: an artificially synthesized sequence

<400> SEQUENCE: 112

Gln Val Gln Leu Gln Glu Ser Gly Pro Gly Leu Val Lys Pro Ser Glu
1               5                   10                  15

Thr Leu Ser Leu Thr Cys Ala Val Ser Gly Tyr Ser Ile Ser Asp Asp
                20                  25                  30

Gln Ala Trp Ser Trp Val Arg Gln Pro Pro Gly Glu Gly Leu Glu Trp
            35                  40                  45

Ile Gly Tyr Ile Ser Tyr Ser Gly Ile Thr Asn Tyr Asn Pro Ser Leu
        50                  55                  60

Lys Gly Arg Val Thr Ile Ser Arg Asp Thr Ser Lys Asn Gln Phe Ser
65                  70                  75                  80

Leu Lys Leu Ser Ser Val Thr Ala Ala Asp Thr Ala Ala Tyr Tyr Cys
                    85                  90                  95

Ala Arg Ser Leu Ala Arg Thr Thr Ala Met Asp Tyr Trp Gly Glu Gly
                100                 105                 110

Thr Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
        130                 135                 140
```

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
            165                 170                 175

Gln Ser Ser Gly Leu Tyr Ser Leu Ser Ser Val Val Thr Val Pro Ser
        180                 185                 190

Ser Ser Leu Gly Thr Gln Thr Tyr Ile Cys Asn Val Asn His Lys Pro
    195                 200                 205

Ser Asn Thr Lys Val Asp Lys Lys Val Glu Pro Lys Ser Cys Asp Lys
210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
                260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Trp His Tyr Thr Gln Lys Ser Leu Ser Leu Ser Pro
        435                 440                 445

<210> SEQ ID NO 113
<211> LENGTH: 128
<212> TYPE: PRT
<213> ORGANISM: Homo sapiens

<400> SEQUENCE: 113

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr

```
            65                  70                  75                  80
Met Glu Leu Ser Ser Leu Arg Ser Glu Asp Thr Ala Val Tyr Tyr Cys
                85                  90                  95

Ala Arg Asp Gly Thr Leu Tyr Asp Phe Trp Ser Gly Tyr Tyr Ser Tyr
            100                 105                 110

Asp Ala Phe Asp Ile Trp Gly Gln Gly Thr Met Val Thr Val Ser Ser
            115                 120                 125

<210> SEQ ID NO 114
<211> LENGTH: 122
<212> TYPE: PRT
<213> ORGANISM: Homo sapiens

<400> SEQUENCE: 114

Gln Met Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
                20                  25                  30

Ala Ile Ser Trp Val Arg Gln Ala Pro Gly Gln Gly Leu Glu Trp Met
            35                  40                  45

Gly Gly Ile Ile Pro Ile Phe Gly Thr Ala Asn Tyr Ala Gln Lys Phe
        50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Leu Asp Thr Gly Pro Tyr Tyr Gly Met Asp Val Trp
            100                 105                 110

Gly Gln Gly Thr Met Val Thr Val Ser Ser
            115                 120

<210> SEQ ID NO 115
<211> LENGTH: 124
<212> TYPE: PRT
<213> ORGANISM: Homo sapiens

<400> SEQUENCE: 115

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
                20                  25                  30

Ala Ile Ser Trp Val Arg Gln Ala Pro Gly Gln Gly Leu Glu Trp Met
            35                  40                  45

Gly Gly Ile Ile Pro Ile Phe Gly Thr Ala Asn Tyr Ala Gln Lys Phe
        50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Ser Pro Val Pro Gly Val Tyr Tyr Tyr Gly Met Asp
            100                 105                 110

Val Trp Gly Gln Gly Thr Met Val Thr Val Ser Ser
            115                 120

<210> SEQ ID NO 116
<211> LENGTH: 119
<212> TYPE: PRT
```

<213> ORGANISM: Homo sapiens

<400> SEQUENCE: 116

Gln Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg His Arg Ala Gly Asp Leu Gly Gly Asp Tyr Trp Gly Gln Gly
            100                 105                 110

Thr Leu Val Thr Val Ser Ser
        115

<210> SEQ ID NO 117
<211> LENGTH: 445
<212> TYPE: PRT
<213> ORGANISM: Artificial Sequence
<220> FEATURE:
<223> OTHER INFORMATION: an artificially synthesized sequence

<400> SEQUENCE: 117

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Ile Met Asn Trp Val Arg Gln Ala Pro Gly Gln Gly Leu Glu Trp Met
        35                  40                  45

Gly Leu Ile Asn Pro Tyr Asn Gly Gly Thr Asp Tyr Asn Pro Gln Phe
    50                  55                  60

Gln Asp Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Gly Tyr Asp Asp Gly Pro Tyr Thr Leu Glu Thr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Asn Phe Gly Thr Gln Thr Tyr Thr Cys Asn Val Asp His
        195                 200                 205

Lys Pro Ser Asn Thr Lys Val Asp Lys Thr Val Glu Arg Lys Ser Cys
    210                 215                 220

Val Glu Cys Pro Pro Cys Pro Ala Pro Val Ala Gly Pro Ser Val
225                 230                 235                 240

Phe Leu Phe Pro Pro Lys Pro Lys Asp Thr Leu Met Ile Ser Arg Thr
            245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Phe Arg Val Val Ser
    290                 295                 300

Val Leu Thr Val Val His Gln Asp Trp Leu Asn Gly Lys Glu Tyr Lys
305                 310                 315                 320

Cys Lys Val Ser Asn Lys Gly Leu Pro Ala Pro Ile Glu Lys Thr Ile
            325                 330                 335

Ser Lys Thr Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Met Leu Asp Ser
385                 390                 395                 400

Asp Gly Ser Phe Phe Leu Tyr Ser Lys Leu Thr Val Asp Lys Ser Arg
            405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Pro
            435                 440                 445

<210> SEQ ID NO 118
<211> LENGTH: 214
<212> TYPE: PRT
<213> ORGANISM: Artificial Sequence
<220> FEATURE:
<223> OTHER INFORMATION: an artificially synthesized sequence

<400> SEQUENCE: 118

Glu Thr Thr Leu Thr Gln Ser Pro Ala Phe Met Ser Ala Thr Pro Gly
1               5                   10                  15

Asp Lys Val Thr Ile Ser Cys Lys Ala Ser Gln Asp Ile Asp Asp Asp
            20                  25                  30

Met Asn Trp Tyr Gln Gln Lys Pro Gly Glu Ala Ala Ile Phe Ile Ile
        35                  40                  45

Gln Glu Ala Thr Thr Leu Val Pro Gly Ile Ser Pro Arg Phe Ser Gly
    50                  55                  60

Ser Gly Tyr Gly Thr Asp Phe Thr Leu Thr Ile Asn Asn Ile Glu Ser
65                  70                  75                  80

Glu Asp Ala Ala Tyr Tyr Phe Cys Leu Gln His Asp Asn Phe Pro Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

```
Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 119
<211> LENGTH: 107
<212> TYPE: PRT
<213> ORGANISM: Artificial Sequence
<220> FEATURE:
<223> OTHER INFORMATION: an artificially synthesized sequence

<400> SEQUENCE: 119

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Ile Asp Asp Asp
            20                  25                  30

Met Asn Trp Tyr Gln Gln Lys Pro Gly Lys Ala Pro Lys Leu Leu Ile
        35                  40                  45

Tyr Glu Ala Thr Thr Leu Val Pro Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln His Asp Asn Phe Pro Tyr
                85                  90                  95

Thr Phe Gly Gln Gly Thr Lys Val Glu Ile Lys
            100                 105
```

<210> SEQ ID NO 120
<211> LENGTH: 107
<212> TYPE: PRT
<213> ORGANISM: Artificial Sequence
<220> FEATURE:
<223> OTHER INFORMATION: an artificially synthesized sequence

<400> SEQUENCE: 120

```
Asp Ile Val Met Thr Gln Ser Pro Leu Ser Leu Pro Val Thr Pro Gly
1               5                   10                  15

Glu Pro Ala Ser Ile Ser Cys Lys Ala Ser Gln Asp Ile Asp Asp Asp
            20                  25                  30

Met Asn Trp Tyr Leu Gln Lys Pro Gly Gln Ser Pro Gln Leu Leu Ile
        35                  40                  45

Tyr Glu Ala Thr Thr Leu Val Pro Gly Val Pro Asp Arg Phe Ser Gly
    50                  55                  60

Ser Gly Ser Gly Thr Asp Phe Thr Leu Lys Ile Ser Arg Val Glu Ala
65                  70                  75                  80

Glu Asp Val Gly Val Tyr Tyr Cys Leu Gln His Asp Asn Phe Pro Tyr
                85                  90                  95

Thr Phe Gly Gln Gly Thr Lys Leu Glu Ile Lys
            100                 105
```

```
<210> SEQ ID NO 121
<211> LENGTH: 107
<212> TYPE: PRT
<213> ORGANISM: Artificial Sequence
<220> FEATURE:
<223> OTHER INFORMATION: an artificially synthesized sequence

<400> SEQUENCE: 121
```

Glu Ile Val Leu Thr Gln Ser Pro Gly Thr Leu Ser Leu Ser Pro Gly
1               5                   10                  15

Glu Arg Ala Thr Leu Ser Cys Lys Ala Ser Gln Asp Ile Asp Asp Asp
            20                  25                  30

Met Asn Trp Tyr Gln Gln Lys Pro Gly Gln Ala Pro Arg Leu Leu Ile
        35                  40                  45

Tyr Glu Ala Thr Thr Leu Val Pro Gly Ile Pro Asp Arg Phe Ser Gly
50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Leu Gln His Asp Asn Phe Pro Tyr
                85                  90                  95

Thr Phe Gly Gln Gly Thr Lys Val Glu Ile Lys
            100                 105

```
<210> SEQ ID NO 122
<211> LENGTH: 107
<212> TYPE: PRT
<213> ORGANISM: Artificial Sequence
<220> FEATURE:
<223> OTHER INFORMATION: an artificially synthesized sequence

<400> SEQUENCE: 122
```

Asp Ile Val Met Thr Gln Ser Pro Asp Ser Leu Ala Val Ser Leu Gly
1               5                   10                  15

Glu Arg Ala Thr Ile Asn Cys Lys Ala Ser Gln Asp Ile Asp Asp Asp
            20                  25                  30

Met Asn Trp Tyr Gln Gln Lys Pro Gly Gln Pro Pro Lys Leu Leu Ile
        35                  40                  45

Tyr Glu Ala Thr Thr Leu Val Pro Gly Val Pro Asp Arg Phe Ser Gly
50                  55                  60

Ser Gly Ser Gly Thr Asp Phe Thr Leu Thr Ile Ser Ser Leu Gln Ala
65                  70                  75                  80

Glu Asp Val Ala Val Tyr Tyr Cys Leu Gln His Asp Asn Phe Pro Tyr
                85                  90                  95

Thr Phe Gly Gln Gly Thr Lys Leu Glu Ile Lys
            100                 105

```
<210> SEQ ID NO 123
<211> LENGTH: 214
<212> TYPE: PRT
<213> ORGANISM: Artificial Sequence
<220> FEATURE:
<223> OTHER INFORMATION: an artificially synthesized sequence

<400> SEQUENCE: 123
```

Glu Thr Thr Leu Thr Gln Ser Pro Ala Phe Met Ser Ala Thr Pro Gly
1               5                   10                  15

Asp Lys Val Thr Ile Ser Cys Lys Ala Ser Gln Asp Ile Ala Asp Asp
            20                  25                  30

Met Asn Trp Tyr Gln Gln Lys Pro Gly Glu Ala Ala Ile Phe Ile Ile
        35                  40                  45

```
Gln Glu Ala Thr Thr Leu Val Pro Gly Ile Ser Pro Arg Phe Ser Gly
    50                  55                  60

Ser Gly Tyr Gly Thr Asp Phe Thr Leu Thr Ile Asn Asn Ile Glu Ser
65                  70                  75                  80

Glu Asp Ala Ala Tyr Tyr Phe Cys Leu Gln His Asp Asn Phe Pro Tyr
                85                  90                  95

Thr Phe Gly Gln Gly Thr Lys Leu Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
                195                 200                 205

Phe Asn Arg Gly Glu Cys
    210

<210> SEQ ID NO 124
<211> LENGTH: 214
<212> TYPE: PRT
<213> ORGANISM: Artificial Sequence
<220> FEATURE:
<223> OTHER INFORMATION: an artificially synthesized sequence

<400> SEQUENCE: 124

Glu Thr Thr Leu Thr Gln Ser Pro Ala Phe Met Ser Ala Thr Pro Gly
1               5                   10                  15

Asp Lys Val Thr Ile Ser Cys Lys Ala Ser Gln Asp Ile Asp Ala Asp
                20                  25                  30

Met Asn Trp Tyr Gln Gln Lys Pro Gly Glu Ala Ala Ile Phe Ile Ile
            35                  40                  45

Gln Glu Ala Thr Thr Leu Val Pro Gly Ile Ser Pro Arg Phe Ser Gly
    50                  55                  60

Ser Gly Tyr Gly Thr Asp Phe Thr Leu Thr Ile Asn Asn Ile Glu Ser
65                  70                  75                  80

Glu Asp Ala Ala Tyr Tyr Phe Cys Leu Gln His Asp Asn Phe Pro Tyr
                85                  90                  95

Thr Phe Gly Gln Gly Thr Lys Leu Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190
```

Ala Cys Glu Val Thr His Gln Gly Leu Ser Ser Pro Val Thr Lys Ser
        195                 200                 205

Phe Asn Arg Gly Glu Cys
    210

<210> SEQ ID NO 125
<211> LENGTH: 214
<212> TYPE: PRT
<213> ORGANISM: Artificial Sequence
<220> FEATURE:
<223> OTHER INFORMATION: an artificially synthesized sequence

<400> SEQUENCE: 125

Glu Thr Thr Leu Thr Gln Ser Pro Ala Phe Met Ser Ala Thr Pro Gly
1               5                   10                  15

Asp Lys Val Thr Ile Ser Cys Lys Ala Ser Gln Asp Ile Asp Asp Ala
            20                  25                  30

Met Asn Trp Tyr Gln Gln Lys Pro Gly Glu Ala Ala Ile Phe Ile Ile
        35                  40                  45

Gln Glu Ala Thr Thr Leu Val Pro Gly Ile Ser Pro Arg Phe Ser Gly
    50                  55                  60

Ser Gly Tyr Gly Thr Asp Phe Thr Leu Thr Ile Asn Asn Ile Glu Ser
65                  70                  75                  80

Glu Asp Ala Ala Tyr Tyr Phe Cys Leu Gln His Asp Asn Phe Pro Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 126
<211> LENGTH: 214
<212> TYPE: PRT
<213> ORGANISM: Artificial Sequence
<220> FEATURE:
<223> OTHER INFORMATION: an artificially synthesized sequence

<400> SEQUENCE: 126

Glu Thr Thr Leu Thr Gln Ser Pro Ala Phe Met Ser Ala Thr Pro Gly
1               5                   10                  15

Asp Lys Val Thr Ile Ser Cys Lys Ala Ser Gln Asp Ile Asp Asp Asp
            20                  25                  30

Met Asn Trp Tyr Gln Gln Lys Pro Gly Glu Ala Ala Ile Phe Ile Ile
        35                  40                  45

Gln Ala Ala Thr Thr Leu Val Pro Gly Ile Ser Pro Arg Phe Ser Gly

```
                50                  55                  60
Ser Gly Tyr Gly Thr Asp Phe Thr Leu Thr Ile Asn Asn Ile Glu Ser
 65                  70                  75                  80

Glu Asp Ala Ala Tyr Tyr Phe Cys Leu Gln His Asp Asn Phe Pro Tyr
                 85                  90                  95

Thr Phe Gly Gln Gly Thr Lys Leu Glu Ile Lys Arg Thr Val Ala Ala
                100                 105                 110

Pro Ser Val Phe Ile Phe Pro Pro Ser Asp Glu Gln Leu Lys Ser Gly
                115                 120                 125

Thr Ala Ser Val Val Cys Leu Leu Asn Asn Phe Tyr Pro Arg Glu Ala
            130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
           210
```

<210> SEQ ID NO 127
<211> LENGTH: 214
<212> TYPE: PRT
<213> ORGANISM: Artificial Sequence
<220> FEATURE:
<223> OTHER INFORMATION: an artificially synthesized sequence

<400> SEQUENCE: 127

```
Glu Thr Thr Leu Thr Gln Ser Pro Ala Phe Met Ser Ala Thr Pro Gly
  1               5                  10                  15

Asp Lys Val Thr Ile Ser Cys Lys Ala Ser Gln Asp Ile Ala Asp Ala
                 20                  25                  30

Met Asn Trp Tyr Gln Gln Lys Pro Gly Glu Ala Ala Ile Phe Ile Ile
             35                  40                  45

Gln Glu Ala Thr Thr Leu Val Pro Gly Ile Ser Pro Arg Phe Ser Gly
 50                  55                  60

Ser Gly Tyr Gly Thr Asp Phe Thr Leu Thr Ile Asn Asn Ile Glu Ser
 65                  70                  75                  80

Glu Asp Ala Ala Tyr Tyr Phe Cys Leu Gln His Asp Asn Phe Pro Tyr
                 85                  90                  95

Thr Phe Gly Gln Gly Thr Lys Leu Glu Ile Lys Arg Thr Val Ala Ala
                100                 105                 110

Pro Ser Val Phe Ile Phe Pro Pro Ser Asp Glu Gln Leu Lys Ser Gly
                115                 120                 125

Thr Ala Ser Val Val Cys Leu Leu Asn Asn Phe Tyr Pro Arg Glu Ala
            130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
```

-continued

```
                195                 200                 205
Phe Asn Arg Gly Glu Cys
    210

<210> SEQ ID NO 128
<211> LENGTH: 214
<212> TYPE: PRT
<213> ORGANISM: Artificial Sequence
<220> FEATURE:
<223> OTHER INFORMATION: an artificially synthesized sequence

<400> SEQUENCE: 128

Glu Thr Thr Leu Thr Gln Ser Pro Ala Phe Met Ser Ala Thr Pro Gly
1               5                   10                  15

Asp Lys Val Thr Ile Ser Cys Lys Ala Ser Gln Asp Ile Ala Asp Asp
            20                  25                  30

Met Asn Trp Tyr Gln Gln Lys Pro Gly Glu Ala Ala Ile Phe Ile Ile
        35                  40                  45

Gln Ala Ala Thr Thr Leu Val Pro Gly Ile Ser Pro Arg Phe Ser Gly
    50                  55                  60

Ser Gly Tyr Gly Thr Asp Phe Thr Leu Thr Ile Asn Asn Ile Glu Ser
65                  70                  75                  80

Glu Asp Ala Ala Tyr Tyr Phe Cys Leu Gln His Asp Asn Phe Pro Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 129
<211> LENGTH: 214
<212> TYPE: PRT
<213> ORGANISM: Artificial Sequence
<220> FEATURE:
<223> OTHER INFORMATION: an artificially synthesized sequence

<400> SEQUENCE: 129

Glu Thr Thr Leu Thr Gln Ser Pro Ala Phe Met Ser Ala Thr Pro Gly
1               5                   10                  15

Asp Lys Val Thr Ile Ser Cys Lys Ala Ser Gln Asp Ile Ala Asp Ala
            20                  25                  30

Met Asn Trp Tyr Gln Gln Lys Pro Gly Glu Ala Ala Ile Phe Ile Ile
        35                  40                  45

Gln Ala Ala Thr Thr Leu Val Pro Gly Ile Ser Pro Arg Phe Ser Gly
    50                  55                  60
```

```
Ser Gly Tyr Gly Thr Asp Phe Thr Leu Thr Ile Asn Asn Ile Glu Ser
 65                  70                  75                  80

Glu Asp Ala Ala Tyr Tyr Phe Cys Leu Gln His Asp Asn Phe Pro Tyr
                 85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
            165                 170                 175

Ser Thr Leu Thr Leu Ser Lys Ala Asp Tyr Glu Lys His Lys Val Tyr
        180                 185                 190

Ala Cys Glu Val Thr His Gln Gly Leu Ser Ser Pro Val Thr Lys Ser
    195                 200                 205

Phe Asn Arg Gly Glu Cys
210

<210> SEQ ID NO 130
<211> LENGTH: 214
<212> TYPE: PRT
<213> ORGANISM: Artificial Sequence
<220> FEATURE:
<223> OTHER INFORMATION: an artificially synthesized sequence

<400> SEQUENCE: 130

Glu Thr Thr Leu Thr Gln Ser Pro Ala Phe Met Ser Ala Thr Pro Gly
  1               5                  10                  15

Asp Lys Val Thr Ile Ser Cys Lys Ala Ser Gln Asp Ile Asp Asp Asp
             20                  25                  30

Met Asn Trp Tyr Gln Gln Lys Pro Gly Glu Ala Ala Ile Phe Ile Ile
         35                  40                  45

Gln Glu Ala Thr Thr Leu Val Pro Gly Ile Ser Pro Arg Phe Ser Gly
 50                  55                  60

Ser Gly Tyr Gly Thr Asp Phe Thr Leu Thr Ile Asn Asn Ile Glu Ser
 65                  70                  75                  80

Glu Asp Ala Ala Tyr Tyr Phe Cys Leu Gln His Ala Asn Phe Pro Tyr
                 85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
            165                 170                 175

Ser Thr Leu Thr Leu Ser Lys Ala Asp Tyr Glu Lys His Lys Val Tyr
        180                 185                 190

Ala Cys Glu Val Thr His Gln Gly Leu Ser Ser Pro Val Thr Lys Ser
    195                 200                 205
```

Phe Asn Arg Gly Glu Cys
    210

<210> SEQ ID NO 131
<211> LENGTH: 214
<212> TYPE: PRT
<213> ORGANISM: Artificial Sequence
<220> FEATURE:
<223> OTHER INFORMATION: an artificially synthesized sequence

<400> SEQUENCE: 131

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Asp Asp Asp
            20                  25                  30

Leu Asn Trp Tyr Gln Gln Lys Pro Gly Lys Ala Pro Lys Leu Leu Ile
        35                  40                  45

Tyr Glu Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Asp Ser Thr Pro Tyr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 132
<211> LENGTH: 214
<212> TYPE: PRT
<213> ORGANISM: Artificial Sequence
<220> FEATURE:
<223> OTHER INFORMATION: an artificially synthesized sequence

<400> SEQUENCE: 132

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Tyr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
            165                 170                 175

Ser Thr Leu Thr Leu Ser Lys Ala Asp Tyr Glu Lys His Lys Val Tyr
        180                 185                 190

Ala Cys Glu Val Thr His Gln Gly Leu Ser Ser Pro Val Thr Lys Ser
    195                 200                 205

Phe Asn Arg Gly Glu Cys
    210

<210> SEQ ID NO 133
<211> LENGTH: 456
<212> TYPE: PRT
<213> ORGANISM: Artificial Sequence
<220> FEATURE:
<223> OTHER INFORMATION: an artificially synthesized sequence

<400> SEQUENCE: 133

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Tyr Tyr Trp Gly Trp Ile Arg Gln Pro Pro Gly Lys Gly Leu Glu
        35                  40                  45

Trp Ile Gly Ser Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
            85                  90                  95

Cys Ala Arg Val Pro Pro Tyr Ser Ser Ser Ser Tyr Tyr Tyr Tyr Tyr
        100                 105                 110

Tyr Tyr Met Asp Val Trp Gly Lys Gly Thr Thr Val Thr Val Ser Ser
    115                 120                 125

Ala Ser Thr Lys Gly Pro Ser Val Phe Pro Leu Ala Pro Ser Ser Lys
    130                 135                 140

Ser Thr Ser Gly Gly Thr Ala Ala Leu Gly Cys Leu Val Lys Asp Tyr
145                 150                 155                 160

Phe Pro Glu Pro Val Thr Val Ser Trp Asn Ser Gly Ala Leu Thr Ser
            165                 170                 175

Gly Val His Thr Phe Pro Ala Val Leu Gln Ser Ser Gly Leu Tyr Ser
        180                 185                 190

Leu Ser Ser Val Val Thr Val Pro Ser Ser Ser Leu Gly Thr Gln Thr
    195                 200                 205

Tyr Ile Cys Asn Val Asn His Lys Pro Ser Asn Thr Lys Val Asp Lys
    210                 215                 220

```
Lys Val Glu Pro Lys Ser Cys Asp Lys Thr His Thr Cys Pro Pro Cys
225                 230                 235                 240

Pro Ala Pro Glu Leu Leu Gly Gly Pro Ser Val Phe Leu Phe Pro Pro
            245                 250                 255

Lys Pro Lys Asp Thr Leu Met Ile Ser Arg Thr Pro Glu Val Thr Cys
        260                 265                 270

Val Val Val Asp Val Ser His Glu Asp Pro Glu Val Lys Phe Asn Trp
            275                 280                 285

Tyr Val Asp Gly Val Glu Val His Asn Ala Lys Thr Lys Pro Arg Glu
        290                 295                 300

Glu Gln Tyr Asn Ser Thr Tyr Arg Val Val Ser Val Leu Thr Val Leu
305                 310                 315                 320

His Gln Asp Trp Leu Asn Gly Lys Glu Tyr Lys Cys Lys Val Ser Asn
            325                 330                 335

Lys Ala Leu Pro Ala Pro Ile Glu Lys Thr Ile Ser Lys Ala Lys Gly
        340                 345                 350

Gln Pro Arg Glu Pro Gln Val Tyr Thr Leu Pro Pro Ser Arg Asp Glu
            355                 360                 365

Leu Thr Lys Asn Gln Val Ser Leu Thr Cys Leu Val Lys Gly Phe Tyr
370                 375                 380

Pro Ser Asp Ile Ala Val Glu Trp Glu Ser Asn Gly Gln Pro Glu Asn
385                 390                 395                 400

Asn Tyr Lys Thr Thr Pro Pro Val Leu Asp Ser Asp Gly Ser Phe Phe
            405                 410                 415

Leu Tyr Ser Lys Leu Thr Val Asp Lys Ser Arg Trp Gln Gln Gly Asn
            420                 425                 430

Val Phe Ser Cys Ser Val Met His Glu Ala Leu His Asn His Tyr Thr
            435                 440                 445

Gln Lys Ser Leu Ser Leu Ser Pro
    450                 455

<210> SEQ ID NO 134
<211> LENGTH: 452
<212> TYPE: PRT
<213> ORGANISM: Artificial Sequence
<220> FEATURE:
<223> OTHER INFORMATION: an artificially synthesized sequence

<400> SEQUENCE: 134

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ala Pro Gly Ile Gln Leu Trp Leu Arg Pro Ser Tyr Phe Asp
            100                 105                 110

Tyr Trp Gly Gln Gly Thr Leu Val Thr Val Ser Ser Ala Ser Thr Lys
        115                 120                 125
```

Gly Pro Ser Val Phe Pro Leu Ala Pro Ser Ser Lys Ser Thr Ser Gly
            130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205

Val Asn His Lys Pro Ser Asn Thr Lys Val Asp Lys Val Glu Pro
    210                 215                 220

Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp Gly
        275                 280                 285

Val Glu Val His Asn Ala Lys Thr Lys Pro Arg Glu Glu Gln Tyr Asn
    290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Ala Pro Ile Glu Lys Thr Ile Ser Lys Ala Lys Gly Gln Pro Arg Glu
            340                 345                 350

Pro Gln Val Tyr Thr Leu Pro Pro Ser Arg Asp Glu Leu Thr Lys Asn
        355                 360                 365

Gln Val Ser Leu Thr Cys Leu Val Lys Gly Phe Tyr Pro Ser Asp Ile
    370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
            420                 425                 430

Ser Val Met His Glu Ala Leu His Asn His Tyr Thr Gln Lys Ser Leu
        435                 440                 445

Ser Leu Ser Pro
    450

<210> SEQ ID NO 135
<211> LENGTH: 447
<212> TYPE: PRT
<213> ORGANISM: Artificial Sequence
<220> FEATURE:
<223> OTHER INFORMATION: an artificially synthesized sequence

<400> SEQUENCE: 135

Gln Val Gln Leu Gln Glu Ser Gly Pro Gly Leu Val Lys Pro Trp Glu
1               5                   10                  15

Thr Leu Ser Leu Thr Cys Thr Val Ala Gly Asp Ser Ile Lys Tyr Ser
            20                  25                  30

Ser Asp Tyr Trp Gly Trp Val Arg Gln Ser Pro Gly Lys Gly Leu Glu
        35                  40                  45

Trp Ile Gly Ser Ser Tyr Leu Ser Gly Thr Thr Gln Tyr Asn Pro Ser
    50                  55                  60

Leu Lys Ser Arg Val Thr Met Ser Val Asp Thr Ser Lys Asn Gln Phe
65                  70                  75                  80

Ser Leu Arg Leu Ser Ser Val Thr Ala Ala Asp Thr Ala Val Tyr Tyr
            85                  90                  95

Cys Ala Arg His Arg Gly Pro Thr Gly Val Asp Gln Trp Gly Gln Gly
            100                 105                 110

Thr Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
            130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
            165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys Asp Lys
            210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
            245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
            290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
            325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
            355                 360                 365

Cys Leu Val Lys Gly Phe Tyr Pro Ser Asp Ile Ala Val Glu Trp Glu
            370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
            405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro
            435                 440                 445

<210> SEQ ID NO 136
<211> LENGTH: 449
<212> TYPE: PRT
<213> ORGANISM: Artificial Sequence
<220> FEATURE:
<223> OTHER INFORMATION: an artificially synthesized sequence

<400> SEQUENCE: 136

```
Glu Val Gln Leu Val Gln Ser Gly Gly Gly Leu Val Gln Pro Gly Arg
1               5                   10                  15

Ser Leu Thr Leu Ser Cys Val Gly Tyr Gly Phe Thr Phe His Glu Asn
            20                  25                  30

Asp Met His Trp Leu Arg Gln Pro Leu Gly Lys Gly Leu Glu Trp Val
        35                  40                  45

Ser His Ile Gly Trp Asn Asn Asn Arg Val Ala Tyr Ala Asp Ser Val
    50                  55                  60

Lys Gly Arg Phe Ala Val Ser Arg Asp Asn Ala Lys Asn Ser Leu Phe
65                  70                  75                  80

Leu His Met Asn Ser Leu Arg Pro Asp Asp Thr Ala Leu Tyr Tyr Cys
                85                  90                  95

Ala Lys Asp Leu Gly Asn Pro Ile Tyr Asp Val Phe Asp Val Trp Gly
            100                 105                 110

Gln Gly Thr Met Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365
```

```
Leu Thr Cys Leu Val Lys Gly Phe Tyr Pro Ser Asp Ile Ala Val Glu
    370                 375                 380

Trp Glu Ser Asn Gly Gln Pro Glu Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
                420                 425                 430

His Glu Ala Leu His Asn His Tyr Thr Gln Lys Ser Leu Ser Leu Ser
                435                 440                 445

Pro

<210> SEQ ID NO 137
<211> LENGTH: 452
<212> TYPE: PRT
<213> ORGANISM: Artificial Sequence
<220> FEATURE:
<223> OTHER INFORMATION: an artificially synthesized sequence

<400> SEQUENCE: 137

Gln Pro Ala Leu Ala Gln Met Gln Leu Val Glu Ser Gly Gly Gly Leu
1               5                   10                  15

Val Gln Pro Gly Arg Ser Leu Arg Leu Ser Cys Ala Ala Ser Gly Phe
            20                  25                  30

Thr Phe Asp Asp Tyr Ala Met His Trp Val Arg Gln Ala Pro Gly Lys
        35                  40                  45

Gly Leu Glu Trp Val Ser Gly Ile Ser Trp Asn Ser Gly Ser Ile Gly
50                  55                  60

Tyr Ala Asp Ser Val Lys Gly Arg Phe Thr Ile Ser Arg Asp Asn Ala
65                  70                  75                  80

Lys Asn Ser Leu Tyr Leu Gln Met Asn Ser Leu Arg Ala Glu Asp Thr
                85                  90                  95

Ala Leu Tyr Tyr Cys Ala Arg Glu Gly Val Leu Gly Asp Ala Phe Asp
            100                 105                 110

Ile Trp Gly Gln Gly Thr Met Val Thr Val Ser Ser Ala Ser Thr Lys
        115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205

Val Asn His Lys Pro Ser Asn Thr Lys Val Asp Lys Lys Val Glu Pro
    210                 215                 220

Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp Gly
```

```
                     275                 280                 285
Val Glu Val His Asn Ala Lys Thr Lys Pro Arg Glu Gln Tyr Asn
290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Ala Pro Ile Glu Lys Thr Ile Ser Lys Ala Lys Gly Gln Pro Arg Glu
            340                 345                 350

Pro Gln Val Tyr Thr Leu Pro Pro Ser Arg Asp Glu Leu Thr Lys Asn
        355                 360                 365

Gln Val Ser Leu Thr Cys Leu Val Lys Gly Phe Tyr Pro Ser Asp Ile
370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
            420                 425                 430

Ser Val Met His Glu Ala Leu His Asn His Tyr Thr Gln Lys Ser Leu
        435                 440                 445

Ser Leu Ser Pro
    450

<210> SEQ ID NO 138
<211> LENGTH: 454
<212> TYPE: PRT
<213> ORGANISM: Artificial Sequence
<220> FEATURE:
<223> OTHER INFORMATION: an artificially synthesized sequence

<400> SEQUENCE: 138

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
            20                  25                  30

Ser Ala Ala Trp Asn Trp Ile Arg Gln Ser Pro Ser Arg Gly Leu Glu
        35                  40                  45

Trp Leu Gly Arg Thr Tyr Tyr Arg Ser Lys Trp Tyr Asn Asp Tyr Ala
    50                  55                  60

Val Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Arg Val Arg Ser Gly Ser Tyr Tyr Tyr Tyr Gly
            100                 105                 110

Met Asp Val Trp Gly Gln Gly Thr Thr Val Thr Val Ser Ser Ala Ser
        115                 120                 125

Thr Lys Gly Pro Ser Val Phe Pro Leu Ala Pro Ser Ser Lys Ser Thr
    130                 135                 140

Ser Gly Gly Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
```

```
                180             185             190
        Ser Val Val Thr Val Pro Ser Ser Leu Gly Thr Gln Thr Tyr Ile
                    195             200             205

Cys Asn Val Asn His Lys Pro Ser Asn Thr Lys Val Asp Lys Val
                210             215             220

Glu Pro Lys Ser Cys Asp Lys Thr His Thr Cys Pro Pro Cys Pro Ala
        225             230             235             240

Pro Glu Leu Leu Gly Gly Pro Ser Val Phe Leu Phe Pro Pro Lys Pro
                        245             250             255

Lys Asp Thr Leu Met Ile Ser Arg Thr Pro Glu Val Thr Cys Val Val
                    260             265             270

Val Asp Val Ser His Glu Asp Pro Glu Val Lys Phe Asn Trp Tyr Val
                    275             280             285

Asp Gly Val Glu Val His Asn Ala Lys Thr Lys Pro Arg Glu Glu Gln
                    290             295             300

Tyr Asn Ser Thr Tyr Arg Val Val Ser Val Leu Thr Val Leu His Gln
        305             310             315             320

Asp Trp Leu Asn Gly Lys Glu Tyr Lys Cys Lys Val Ser Asn Lys Ala
                        325             330             335

Leu Pro Ala Pro Ile Glu Lys Thr Ile Ser Lys Ala Lys Gly Gln Pro
                        340             345             350

Arg Glu Pro Gln Val Tyr Thr Leu Pro Pro Ser Arg Asp Glu Leu Thr
                    355             360             365

Lys Asn Gln Val Ser Leu Thr Cys Leu Val Lys Gly Phe Tyr Pro Ser
                370             375             380

Asp Ile Ala Val Glu Trp Glu Ser Asn Gly Gln Pro Glu Asn Asn Tyr
        385             390             395             400

Lys Thr Thr Pro Pro Val Leu Asp Ser Asp Gly Ser Phe Phe Leu Tyr
                        405             410             415

Ser Lys Leu Thr Val Asp Lys Ser Arg Trp Gln Gln Gly Asn Val Phe
                    420             425             430

Ser Cys Ser Val Met His Glu Ala Leu His Asn His Tyr Thr Gln Lys
                435             440             445

Ser Leu Ser Leu Ser Pro
                450

<210> SEQ ID NO 139
<211> LENGTH: 450
<212> TYPE: PRT
<213> ORGANISM: Artificial Sequence
<220> FEATURE:
<223> OTHER INFORMATION: an artificially synthesized sequence

<400> SEQUENCE: 139

Gln Val Gln Leu Gln Glu Ser Gly Pro Gly Leu Val Lys Pro Ser Gln
1               5                   10                  15

Thr Leu Ser Leu Thr Cys Ala Ile Ser Gly Asp Ser Val Ser Ser Asn
            20                  25                  30

Ser Ala Ala Trp Asn Trp Ile Arg Gln Ser Pro Ser Arg Gly Leu Glu
        35                  40                  45

Trp Leu Gly Arg Thr Tyr Tyr Arg Ser Lys Trp Tyr Asn Asp Tyr Ala
        50                  55                  60

Val Ser Val Lys Ser Arg Ile Thr Ile Ile Pro Asp Thr Ser Lys Asn
65                  70                  75                  80

Gln Phe Ser Leu Gln Leu Asn Ser Val Thr Pro Glu Asp Thr Ala Val
```

```
                        85                  90                  95
Tyr Tyr Cys Ala Arg Lys Asp Pro Arg Val Trp Ala Phe Asp Ile Trp
            100                 105                 110
Gly Gln Gly Thr Met Val Thr Val Ser Ser Ala Ser Thr Lys Gly Pro
            115                 120                 125
Ser Val Phe Pro Leu Ala Pro Ser Ser Lys Ser Thr Ser Gly Gly Thr
            130                 135                 140
Ala Ala Leu Gly Cys Leu Val Lys Asp Tyr Phe Pro Glu Pro Val Thr
145                 150                 155                 160
Val Ser Trp Asn Ser Gly Ala Leu Thr Ser Gly Val His Thr Phe Pro
            165                 170                 175
Ala Val Leu Gln Ser Ser Gly Leu Tyr Ser Leu Ser Ser Val Val Thr
            180                 185                 190
Val Pro Ser Ser Ser Leu Gly Thr Gln Thr Tyr Ile Cys Asn Val Asn
            195                 200                 205
His Lys Pro Ser Asn Thr Lys Val Asp Lys Lys Val Glu Pro Lys Ser
            210                 215                 220
Cys Asp Lys Thr His Thr Cys Pro Pro Cys Pro Ala Pro Glu Leu Leu
225                 230                 235                 240
Gly Gly Pro Ser Val Phe Leu Phe Pro Pro Lys Pro Lys Asp Thr Leu
            245                 250                 255
Met Ile Ser Arg Thr Pro Glu Val Thr Cys Val Val Val Asp Val Ser
            260                 265                 270
His Glu Asp Pro Glu Val Lys Phe Asn Trp Tyr Val Asp Gly Val Glu
            275                 280                 285
Val His Asn Ala Lys Thr Lys Pro Arg Glu Glu Gln Tyr Asn Ser Thr
            290                 295                 300
Tyr Arg Val Val Ser Val Leu Thr Val Leu His Gln Asp Trp Leu Asn
305                 310                 315                 320
Gly Lys Glu Tyr Lys Cys Lys Val Ser Asn Lys Ala Leu Pro Ala Pro
            325                 330                 335
Ile Glu Lys Thr Ile Ser Lys Ala Lys Gly Gln Pro Arg Glu Pro Gln
            340                 345                 350
Val Tyr Thr Leu Pro Pro Ser Arg Asp Glu Leu Thr Lys Asn Gln Val
            355                 360                 365
Ser Leu Thr Cys Leu Val Lys Gly Phe Tyr Pro Ser Asp Ile Ala Val
            370                 375                 380
Glu Trp Glu Ser Asn Gly Gln Pro Glu Asn Asn Tyr Lys Thr Thr Pro
385                 390                 395                 400
Pro Val Leu Asp Ser Asp Gly Ser Phe Phe Leu Tyr Ser Lys Leu Thr
            405                 410                 415
Val Asp Lys Ser Arg Trp Gln Gln Gly Asn Val Phe Ser Cys Ser Val
            420                 425                 430
Met His Glu Ala Leu His Asn His Tyr Thr Gln Lys Ser Leu Ser Leu
            435                 440                 445
Ser Pro
450

<210> SEQ ID NO 140
<211> LENGTH: 449
<212> TYPE: PRT
<213> ORGANISM: Artificial Sequence
<220> FEATURE:
<223> OTHER INFORMATION: an artificially synthesized sequence
```

<400> SEQUENCE: 140

```
Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Arg Ile Ile Pro Val Leu Ala Ile Ala Asn Tyr Ala Gln Lys Phe
    50                  55                  60

Gln Gly Arg Val Thr Ile Thr Ala Asp Lys Ser Thr His Thr Ala Tyr
65                  70                  75                  80

Met Glu Leu Ser Ser Leu Arg Ser Gly Asp Thr Ala Val Tyr Tyr Cys
                85                  90                  95

Ala Arg Asp Ser Gly Tyr Ser Ala Gly Tyr Gly Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415
```

-continued

Asp Lys Ser Arg Trp Gln Gly Asn Val Phe Ser Cys Ser Val Met
              420             425             430

His Glu Ala Leu His Asn His Tyr Thr Gln Lys Ser Leu Ser Leu Ser
              435             440             445

Pro

<210> SEQ ID NO 141
<211> LENGTH: 447
<212> TYPE: PRT
<213> ORGANISM: Artificial Sequence
<220> FEATURE:
<223> OTHER INFORMATION: an artificially synthesized sequence

<400> SEQUENCE: 141

Glu Val Gln Leu Val Glu Ser Gly Gly Asp Leu Val Gln Pro Gly Gly
1               5                   10                  15

Ser Leu Arg Leu Ser Cys Ala Ala Ser Gly Phe Thr Phe Lys Thr Tyr
            20                  25                  30

Trp Met Asn Trp Val Arg Gln Ala Pro Gly Lys Gly Leu Glu Trp Val
        35                  40                  45

Ala Asn Ile Arg Ala Asp Gly Gly Gln Met Tyr Tyr Ala Asp Ser Val
    50                  55                  60

Lys Gly Arg Phe Thr Ile Ser Arg Asp Asn Ala Lys Asp Ser Leu Tyr
65                  70                  75                  80

Leu Gln Met Ile Ser Leu Arg Pro Glu Asp Thr Ala Leu Tyr Tyr Cys
                85                  90                  95

Ala Arg Asp Pro Phe Ala Ser Gly Gly Leu Asp Gln Trp Gly Gln Gly
            100                 105                 110

Thr Met Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

```
Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
        340                 345                 350

Leu Pro Pro Ser Arg Asp Glu Leu Thr Lys Asn Gln Val Ser Leu Thr
            355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro
                435                 440                 445

<210> SEQ ID NO 142
<211> LENGTH: 450
<212> TYPE: PRT
<213> ORGANISM: Artificial Sequence
<220> FEATURE:
<223> OTHER INFORMATION: an artificially synthesized sequence

<400> SEQUENCE: 142

Glu Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met Glu Trp Val Arg Gln Ala Pro Gly Lys Gly Leu Glu Trp Val
        35                  40                  45

Ala Leu Ile Ser His Asp Gly Asn Asn Lys Tyr Tyr Ala Asp Ser Val
50                  55                  60

Glu Gly Arg Phe Thr Ile Ser Arg Asp Asn Ser Arg Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Arg Val Arg Tyr Phe Asp Ser Tyr Gly Met Asp Val Trp
            100                 105                 110

Gly His Gly Thr Thr Val Thr Val Ser Ser Ala Ser Thr Lys Gly Pro
        115                 120                 125

Ser Val Phe Pro Leu Ala Pro Ser Ser Lys Ser Thr Ser Gly Gly Thr
130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Lys Val Glu Pro Lys Ser
210                 215                 220

Cys Asp Lys Thr His Thr Cys Pro Pro Cys Pro Ala Pro Glu Leu Leu
225                 230                 235                 240
```

```
Gly Gly Pro Ser Val Phe Leu Phe Pro Pro Lys Pro Lys Asp Thr Leu
            245                 250                 255

Met Ile Ser Arg Thr Pro Glu Val Thr Cys Val Val Val Asp Val Ser
        260                 265                 270

His Glu Asp Pro Glu Val Lys Phe Asn Trp Tyr Val Asp Gly Val Glu
    275                 280                 285

Val His Asn Ala Lys Thr Lys Pro Arg Glu Glu Gln Tyr Asn Ser Thr
290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
            325                 330                 335

Ile Glu Lys Thr Ile Ser Lys Ala Lys Gly Gln Pro Arg Glu Pro Gln
        340                 345                 350

Val Tyr Thr Leu Pro Pro Ser Arg Asp Glu Leu Thr Lys Asn Gln Val
    355                 360                 365

Ser Leu Thr Cys Leu Val Lys Gly Phe Tyr Pro Ser Asp Ile Ala Val
370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
            405                 410                 415

Val Asp Lys Ser Arg Trp Gln Gln Gly Asn Val Phe Ser Cys Ser Val
        420                 425                 430

Met His Glu Ala Leu His Asn His Tyr Thr Gln Lys Ser Leu Ser Leu
    435                 440                 445

Ser Pro
    450

<210> SEQ ID NO 143
<211> LENGTH: 449
<212> TYPE: PRT
<213> ORGANISM: Artificial Sequence
<220> FEATURE:
<223> OTHER INFORMATION: an artificially synthesized sequence

<400> SEQUENCE: 143

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Ser Phe Thr Ser Phe
            20                  25                  30

Trp Ile Asn Trp Val Arg Gln Met Pro Gly Lys Gly Leu Glu Trp Met
        35                  40                  45

Gly Asn Ile Asp Pro Ser Asp Ser Tyr Thr Asn Tyr Ser Pro Ser Phe
    50                  55                  60

Gln Gly His Val Ala Ile Ser Ala Asp Lys Ser Ile Ser Thr Ala Tyr
65                  70                  75                  80

Leu His Trp Asn Ser Leu Lys Ala Ser Asp Thr Ala Met Tyr Tyr Cys
                85                  90                  95

Ala Arg His Arg Tyr Leu Gly Gln Leu Ala Pro Phe Asp Pro Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140
```

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
            165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
            195                 200                 205

Lys Pro Ser Asn Thr Lys Val Asp Lys Val Glu Pro Lys Ser Cys
210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
            245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
            275                 280                 285

His Asn Ala Lys Thr Lys Pro Arg Glu Glu Gln Tyr Asn Ser Thr Tyr
290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
            325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
            355                 360                 365

Leu Thr Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
            405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
            435                 440                 445

Pro

<210> SEQ ID NO 144
<211> LENGTH: 214
<212> TYPE: PRT
<213> ORGANISM: Artificial Sequence
<220> FEATURE:
<223> OTHER INFORMATION: an artificially synthesized sequence

<400> SEQUENCE: 144

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Glu Asp Asp
            20                  25                  30

Leu Ala Trp Tyr Gln Gln Lys Pro Gly Lys Ala Pro Lys Leu Leu Ile
            35                  40                  45

Tyr Glu Ala Ser Ser Leu Gln Ser Gly Val Pro Ser Arg Phe Ser Gly

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Arg Asp Asn Tyr Pro Leu
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
            195                 200                 205

Phe Asn Arg Gly Glu Cys
        210

<210> SEQ ID NO 145
<211> LENGTH: 214
<212> TYPE: PRT
<213> ORGANISM: Artificial Sequence
<220> FEATURE:
<223> OTHER INFORMATION: an artificially synthesized sequence

<400> SEQUENCE: 145

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Glu Asp Asp
            20                  25                  30

Leu Ala Trp Tyr Gln Gln Lys Pro Gly Lys Ala Pro Lys Leu Leu Ile
        35                  40                  45

Tyr His Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Asp Ser Ser Pro Leu
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser

```
                    195                 200                 205

Phe Asn Arg Gly Glu Cys
    210

<210> SEQ ID NO 146
<211> LENGTH: 214
<212> TYPE: PRT
<213> ORGANISM: Artificial Sequence
<220> FEATURE:
<223> OTHER INFORMATION: an artificially synthesized sequence

<400> SEQUENCE: 146

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Glu Asp Asp
            20                  25                  30

Leu Ala Trp Tyr Gln Gln Lys Pro Gly Lys Ala Pro Lys Leu Leu Ile
        35                  40                  45

Tyr Glu Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Ser Asn Tyr Pro Leu
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 147
<211> LENGTH: 214
<212> TYPE: PRT
<213> ORGANISM: Artificial Sequence
<220> FEATURE:
<223> OTHER INFORMATION: an artificially synthesized sequence

<400> SEQUENCE: 147

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Glu Asp Asp
            20                  25                  30

Leu Ala Trp Tyr Gln Gln Lys Pro Gly Lys Ala Pro Lys Leu Leu Ile
        35                  40                  45

Tyr Glu Ala Ser Ser Leu Gln Ser Gly Val Pro Ser Arg Phe Ser Gly
    50                  55                  60
```

```
Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Asp Gly Tyr Pro Tyr
                 85                  90                  95

Thr Phe Gly Gln Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
                115                 120                 125

Thr Ala Ser Val Val Cys Leu Leu Asn Asn Phe Tyr Pro Arg Glu Ala
                130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
                195                 200                 205

Phe Asn Arg Gly Glu Cys
                210

<210> SEQ ID NO 148
<211> LENGTH: 214
<212> TYPE: PRT
<213> ORGANISM: Artificial Sequence
<220> FEATURE:
<223> OTHER INFORMATION: an artificially synthesized sequence

<400> SEQUENCE: 148

Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Ser Ile Glu Asp Asp
                 20                  25                  30

Leu Asn Trp Tyr Gln Gln Lys Pro Gly Lys Ala Pro Lys Leu Leu Ile
                 35                  40                  45

Tyr Glu Ala Ser Asn Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln His Ser Ser Pro Pro Tyr
                 85                  90                  95

Thr Phe Gly Gln Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
                115                 120                 125

Thr Ala Ser Val Val Cys Leu Leu Asn Asn Phe Tyr Pro Arg Glu Ala
                130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
                195                 200                 205
```

```
Phe Asn Arg Gly Glu Cys
    210
```

<210> SEQ ID NO 149
<211> LENGTH: 214
<212> TYPE: PRT
<213> ORGANISM: Artificial Sequence
<220> FEATURE:
<223> OTHER INFORMATION: an artificially synthesized sequence

<400> SEQUENCE: 149

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Glu Asp Asp
            20                  25                  30

Leu Ala Trp Tyr Gln Gln Lys Pro Gly Lys Ala Pro Lys Leu Leu Ile
        35                  40                  45

Tyr Glu Ala Ser Asn Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asp Ser Tyr Pro Tyr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 150
<211> LENGTH: 214
<212> TYPE: PRT
<213> ORGANISM: Artificial Sequence
<220> FEATURE:
<223> OTHER INFORMATION: an artificially synthesized sequence

<400> SEQUENCE: 150

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Asp Asp
            20                  25                  30

Leu Ala Trp Tyr Gln Gln Lys Pro Gly Lys Ala Pro Lys Leu Leu Ile
        35                  40                  45

Tyr His Ala Ser His Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
65                  70                  75                  80
```

```
Glu Asp Phe Ala Thr Tyr Tyr Cys Gln Gln Tyr Asp Asn Ser Pro Leu
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
            130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
    210
```

<210> SEQ ID NO 151
<211> LENGTH: 214
<212> TYPE: PRT
<213> ORGANISM: Artificial Sequence
<220> FEATURE:
<223> OTHER INFORMATION: an artificially synthesized sequence

<400> SEQUENCE: 151

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Asp Asp
                20                  25                  30

Leu Ala Trp Tyr Gln Gln Lys Pro Gly Lys Ala Pro Lys Leu Leu Ile
            35                  40                  45

Tyr His Ala Ser Asn Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asp Asn Tyr Pro Tyr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
            130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
    210
```

<210> SEQ ID NO 152
<211> LENGTH: 214
<212> TYPE: PRT
<213> ORGANISM: Artificial Sequence
<220> FEATURE:
<223> OTHER INFORMATION: an artificially synthesized sequence

<400> SEQUENCE: 152

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Glu Asp Asp
            20                  25                  30

Leu Asn Trp Tyr Gln Gln Lys Pro Gly Lys Ala Pro Lys Leu Leu Ile
        35                  40                  45

Tyr Glu Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Arg Asp Ser Ser Pro Tyr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 153
<211> LENGTH: 214
<212> TYPE: PRT
<213> ORGANISM: Artificial Sequence
<220> FEATURE:
<223> OTHER INFORMATION: an artificially synthesized sequence

<400> SEQUENCE: 153

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Glu Asp Asp
            20                  25                  30

Leu Asn Trp Tyr Gln Gln Lys Pro Gly Lys Ala Pro Lys Leu Leu Ile
        35                  40                  45

Tyr Glu Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Asn Asp Tyr Pro Tyr
```

```
                    85                  90                  95
Thr Phe Gly Gln Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 154
<211> LENGTH: 214
<212> TYPE: PRT
<213> ORGANISM: Artificial Sequence
<220> FEATURE:
<223> OTHER INFORMATION: an artificially synthesized sequence

<400> SEQUENCE: 154

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Glu Asp Asp
            20                  25                  30

Leu Ala Trp Tyr Gln Gln Lys Pro Gly Lys Ala Pro Lys Leu Leu Ile
        35                  40                  45

Tyr Glu Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln His Asp Asn Tyr Pro Tyr
                85                  90                  95

Thr Phe Gly Gln Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

```
<210> SEQ ID NO 155
<211> LENGTH: 447
<212> TYPE: PRT
<213> ORGANISM: Artificial Sequence
<220> FEATURE:
<223> OTHER INFORMATION: an artificially synthesized sequence

<400> SEQUENCE: 155

Gln Val Gln Leu Gln Glu Ser Gly Pro Gly Leu Val Lys Pro Ser Glu
1               5                   10                  15

Thr Leu Ser Leu Thr Cys Ala Val Ser Gly His Ser Ile Ser His Asp
            20                  25                  30

His Ala Trp Ser Trp Val Arg Gln Pro Pro Gly Glu Gly Leu Glu Trp
        35                  40                  45

Ile Gly Phe Ile Ser Tyr Ser Gly Ile Thr Asn Tyr Asn Pro Ser Leu
    50                  55                  60

Gln Gly Arg Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Leu Ala Arg Thr Thr Ala Met Asp Tyr Trp Gly Glu Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Ala Ala Gly Gly Pro
225                 230                 235                 240

Ser Val Phe Leu Phe Pro Pro Lys Pro Lys Asp Val Leu Tyr Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Gln Pro Leu His Ala Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
```

```
              370                 375                 380
Ser Asn Gly Gln Pro Glu Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
                420                 425                 430

Ala Leu His Tyr His Val Thr Gln Lys Ser Leu Ser Leu Ser Pro
                435                 440                 445

<210> SEQ ID NO 156
<211> LENGTH: 447
<212> TYPE: PRT
<213> ORGANISM: Artificial Sequence
<220> FEATURE:
<223> OTHER INFORMATION: an artificially synthesized sequence

<400> SEQUENCE: 156

Gln Val Gln Leu Gln Glu Ser Gly Pro Gly Leu Val Lys Pro Ser Glu
1               5                   10                  15

Thr Leu Ser Leu Thr Cys Ala Val Ser Gly His Ser Ile Ser His Asp
                20                  25                  30

His Ala Trp Ser Trp Val Arg Gln Pro Pro Gly Glu Gly Leu Glu Trp
            35                  40                  45

Ile Gly Phe Ile Ser Tyr Ser Gly Ile Thr Asn Tyr Asn Pro Ser Leu
        50                  55                  60

Gln Gly Arg Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Leu Ala Arg Thr Thr Ala Met Asp Tyr Trp Gly Glu Gly
                100                 105                 110

Thr Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
        130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Lys Gly Gly Pro
225                 230                 235                 240

Lys Val Phe Leu Phe Pro Pro Lys Pro Lys Asp Thr Leu Tyr Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
```

```
            290                 295                 300
Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
                340                 345                 350

Leu Pro Pro Ser Arg Asp Glu Leu Thr Lys Asn Gln Val Ser Leu Thr
                355                 360                 365

Cys Leu Val Lys Gly Phe Tyr Pro Ser Asp Ile Ala Val Glu Trp Glu
            370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
                420                 425                 430

Ala Leu His Tyr His Val Thr Gln Lys Ser Leu Ser Leu Ser Pro
            435                 440                 445

<210> SEQ ID NO 157
<211> LENGTH: 447
<212> TYPE: PRT
<213> ORGANISM: Artificial Sequence
<220> FEATURE:
<223> OTHER INFORMATION: an artificially synthesized sequence

<400> SEQUENCE: 157

Gln Val Gln Leu Gln Glu Ser Gly Pro Gly Leu Val Lys Pro Ser Glu
1               5                   10                  15

Thr Leu Ser Leu Thr Cys Ala Val Ser Gly His Ser Ile Ser His Asp
                20                  25                  30

His Ala Trp Ser Trp Val Arg Gln Pro Pro Gly Glu Gly Leu Glu Trp
            35                  40                  45

Ile Gly Phe Ile Ser Tyr Ser Gly Ile Thr Asn Tyr Asn Pro Ser Leu
50                  55                  60

Gln Gly Arg Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Leu Ala Arg Thr Thr Ala Met Asp Tyr Trp Gly Glu Gly
                100                 105                 110

Thr Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys Asp Lys
```

```
                210                 215                 220
Thr His Thr Cys Pro Pro Cys Pro Ala Pro Glu Leu Gly Lys Pro
225                 230                 235                 240

Lys Val Phe Leu Phe Pro Pro Lys Pro Lys Asp Thr Leu Tyr Ile Ser
                245                 250                 255

Arg Thr Pro Glu Val Thr Cys Val Val Val Asp Val Ser His Glu Asp
                260                 265                 270

Pro Glu Val Lys Phe Asn Trp Tyr Val Asp Gly Val Glu Val His Asn
                275                 280                 285

Ala Lys Thr Lys Pro Arg Glu Glu Gln Tyr Asn Ser Thr Tyr Arg Val
                290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
                340                 345                 350

Leu Pro Pro Ser Arg Asp Glu Leu Thr Lys Asn Gln Val Ser Leu Thr
                355                 360                 365

Cys Leu Val Lys Gly Phe Tyr Pro Ser Asp Ile Ala Val Glu Trp Glu
                370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
                420                 425                 430

Ala Leu His Tyr His Val Thr Gln Lys Ser Leu Ser Leu Ser Pro
                435                 440                 445

<210> SEQ ID NO 158
<211> LENGTH: 447
<212> TYPE: PRT
<213> ORGANISM: Artificial Sequence
<220> FEATURE:
<223> OTHER INFORMATION: an artificially synthesized sequence

<400> SEQUENCE: 158

Gln Val Gln Leu Gln Glu Ser Gly Pro Gly Leu Val Lys Pro Ser Glu
1               5                   10                  15

Thr Leu Ser Leu Thr Cys Ala Val Ser Gly His Ser Ile Ser His Asp
                20                  25                  30

His Ala Trp Ser Trp Val Arg Gln Pro Pro Gly Glu Gly Leu Glu Trp
            35                  40                  45

Ile Gly Phe Ile Ser Tyr Ser Gly Ile Thr Asn Tyr Asn Pro Ser Leu
        50                  55                  60

Gln Gly Arg Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Leu Ala Arg Thr Thr Ala Met Asp Tyr Trp Gly Glu Gly
                100                 105                 110

Thr Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
```

```
                130                 135                 140
Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
                180                 185                 190

Ser Ser Leu Gly Thr Gln Thr Tyr Ile Cys Asn Val Asn His Lys Pro
                195                 200                 205

Ser Asn Thr Lys Val Asp Lys Lys Val Glu Pro Lys Ser Cys Asp Lys
                210                 215                 220

Thr His Thr Cys Pro Pro Cys Pro Ala Pro Glu Leu Leu Gly Arg Pro
225                 230                 235                 240

Lys Val Phe Leu Phe Pro Pro Lys Pro Lys Asp Thr Leu Tyr Ile Ser
                245                 250                 255

Arg Thr Pro Glu Val Thr Cys Val Val Val Asp Val Ser His Glu Asp
                260                 265                 270

Pro Glu Val Lys Phe Asn Trp Tyr Val Asp Gly Val Glu Val His Asn
                275                 280                 285

Ala Lys Thr Lys Pro Arg Glu Glu Gln Tyr Asn Ser Thr Tyr Arg Val
                290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
                340                 345                 350

Leu Pro Pro Ser Arg Asp Glu Leu Thr Lys Asn Gln Val Ser Leu Thr
                355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
                420                 425                 430

Ala Leu His Tyr His Val Thr Gln Lys Ser Leu Ser Leu Ser Pro
                435                 440                 445

<210> SEQ ID NO 159
<211> LENGTH: 447
<212> TYPE: PRT
<213> ORGANISM: Artificial Sequence
<220> FEATURE:
<223> OTHER INFORMATION: an artificially synthesized sequence

<400> SEQUENCE: 159

Gln Val Gln Leu Gln Glu Ser Gly Pro Gly Leu Val Lys Pro Ser Glu
1               5                   10                  15

Thr Leu Ser Leu Thr Cys Ala Val Ser Gly His Ser Ile Ser His Asp
                20                  25                  30

His Ala Trp Ser Trp Val Arg Gln Pro Pro Gly Glu Gly Leu Glu Trp
                35                  40                  45

Ile Gly Phe Ile Ser Tyr Ser Gly Ile Thr Asn Tyr Asn Pro Ser Leu
```

```
            50                  55                  60
Gln Gly Arg Val Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                     85                  90                  95

Ala Arg Ser Leu Ala Arg Thr Thr Ala Met Asp Tyr Trp Gly Glu Gly
                    100                 105                 110

Thr Leu Val Thr Val Ser Ser Ala Ser Thr Lys Gly Pro Ser Val Phe
                    115                 120                 125

Pro Leu Ala Pro Ser Ser Lys Ser Thr Ser Gly Gly Thr Ala Ala Leu
                    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                    165                 170                 175

Gln Ser Ser Gly Leu Tyr Ser Leu Ser Ser Val Val Thr Val Pro Ser
                    180                 185                 190

Ser Ser Leu Gly Thr Gln Thr Tyr Ile Cys Asn Val Asn His Lys Pro
                    195                 200                 205

Ser Asn Thr Lys Val Asp Lys Lys Val Glu Pro Lys Ser Cys Asp Lys
210                 215                 220

Thr His Thr Cys Pro Pro Cys Pro Ala Pro Glu Leu Leu Gly Gly Pro
225                 230                 235                 240

Lys Val Phe Leu Phe Pro Pro Lys Pro Lys Asp Thr Leu Tyr Ile Ser
                    245                 250                 255

Arg Thr Pro Glu Val Thr Cys Val Val Val Asp Val Ser His Glu Asp
                    260                 265                 270

Pro Glu Val Lys Phe Asn Trp Tyr Val Asp Gly Val Glu Val His Asn
                    275                 280                 285

Ala Lys Thr Lys Pro Arg Glu Glu Gln Tyr Asn Ser Thr Tyr Arg Val
                    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Lys Ala Pro Ile Glu Lys
                    325                 330                 335

Thr Ile Ser Lys Ala Lys Gly Gln Pro Arg Glu Pro Gln Val Tyr Thr
                    340                 345                 350

Leu Pro Pro Ser Arg Asp Glu Leu Thr Lys Asn Gln Val Ser Leu Thr
                    355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                    405                 410                 415

Ser Arg Trp Gln Gln Gly Asn Val Phe Ser Cys Ser Val Met His Glu
                    420                 425                 430

Ala Leu His Tyr His Val Thr Gln Lys Ser Leu Ser Leu Ser Pro
                    435                 440                 445

<210> SEQ ID NO 160
<211> LENGTH: 447
<212> TYPE: PRT
<213> ORGANISM: Artificial Sequence
```

<220> FEATURE:
<223> OTHER INFORMATION: an artificially synthesized sequence

<400> SEQUENCE: 160

```
Gln Val Gln Leu Gln Glu Ser Gly Pro Gly Leu Val Lys Pro Ser Glu
1               5                   10                  15

Thr Leu Ser Leu Thr Cys Ala Val Ser Gly His Ser Ile Ser His Asp
            20                  25                  30

His Ala Trp Ser Trp Val Arg Gln Pro Pro Gly Glu Gly Leu Glu Trp
        35                  40                  45

Ile Gly Phe Ile Ser Tyr Ser Gly Ile Thr Asn Tyr Asn Pro Ser Leu
    50                  55                  60

Gln Gly Arg Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Leu Ala Arg Thr Thr Ala Met Asp Tyr Trp Gly Glu Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Lys Val Phe Leu Phe Pro Pro Lys Pro Lys Asp Thr Leu Tyr Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Arg Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400
```

```
Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Tyr His Val Thr Gln Lys Ser Leu Ser Leu Ser Pro
            435                 440                 445

<210> SEQ ID NO 161
<211> LENGTH: 447
<212> TYPE: PRT
<213> ORGANISM: Artificial Sequence
<220> FEATURE:
<223> OTHER INFORMATION: an artificially synthesized sequence

<400> SEQUENCE: 161

Gln Val Gln Leu Gln Glu Ser Gly Pro Gly Leu Val Lys Pro Ser Glu
1               5                   10                  15

Thr Leu Ser Leu Thr Cys Ala Val Ser Gly His Ser Ile Ser His Asp
            20                  25                  30

His Ala Trp Ser Trp Val Arg Gln Pro Pro Gly Glu Gly Leu Glu Trp
        35                  40                  45

Ile Gly Phe Ile Ser Tyr Ser Gly Ile Thr Asn Tyr Asn Pro Ser Leu
50                  55                  60

Gln Gly Arg Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Leu Ala Arg Thr Thr Ala Met Asp Tyr Trp Gly Glu Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
210                 215                 220

Thr His Thr Cys Pro Pro Cys Pro Ala Pro Glu Ala Ala Gly Gly Pro
225                 230                 235                 240

Ser Val Phe Leu Phe Pro Pro Lys Pro Lys Asp Thr Leu Tyr Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320
```

```
Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Tyr His Val Thr Gln Lys Ser Leu Ser Leu Ser Pro
        435                 440                 445

<210> SEQ ID NO 162
<211> LENGTH: 447
<212> TYPE: PRT
<213> ORGANISM: Artificial Sequence
<220> FEATURE:
<223> OTHER INFORMATION: an artificially synthesized sequence

<400> SEQUENCE: 162

Gln Val Gln Leu Gln Glu Ser Gly Pro Gly Leu Val Lys Pro Ser Glu
1               5                   10                  15

Thr Leu Ser Leu Thr Cys Ala Val Ser Gly His Ser Ile Ser His Asp
            20                  25                  30

His Ala Trp Ser Trp Val Arg Gln Pro Pro Gly Glu Gly Leu Glu Trp
        35                  40                  45

Ile Gly Phe Ile Ser Tyr Ser Gly Ile Thr Asn Tyr Asn Pro Ser Leu
    50                  55                  60

Gln Gly Arg Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Leu Ala Arg Thr Thr Ala Met Asp Tyr Trp Gly Glu Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Ala Ala Gly Gly Pro
225                 230                 235                 240
```

```
Ser Val Phe Leu Phe Pro Lys Pro Lys Asp Thr Leu Tyr Ile Ser
            245             250                 255

Arg Thr Pro Glu Val Thr Cys Val Val Val Asp Val Ser His Glu Asp
        260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Ala Ser Thr Tyr Arg Val
        290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Tyr His Val Thr Gln Lys Ser Leu Ser Leu Ser Pro
        435                 440                 445

<210> SEQ ID NO 163
<211> LENGTH: 447
<212> TYPE: PRT
<213> ORGANISM: Artificial Sequence
<220> FEATURE:
<223> OTHER INFORMATION: an artificially synthesized sequence

<400> SEQUENCE: 163

Gln Val Gln Leu Gln Glu Ser Gly Pro Gly Leu Val Lys Pro Ser Glu
1               5                   10                  15

Thr Leu Ser Leu Thr Cys Ala Val Ser Gly His Ser Ile Ser His Asp
            20                  25                  30

His Ala Trp Ser Trp Val Arg Gln Pro Pro Gly Glu Gly Leu Glu Trp
        35                  40                  45

Ile Gly Phe Ile Ser Tyr Ser Gly Ile Thr Asn Tyr Asn Pro Ser Leu
    50                  55                  60

Gln Gly Arg Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Leu Ala Arg Thr Thr Ala Met Asp Tyr Trp Gly Glu Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160
```

-continued

Asn Ser Gly Ala Leu Thr Ser Gly Val His Thr Phe Pro Ala Val Leu
            165                 170                 175

Gln Ser Ser Gly Leu Tyr Ser Leu Ser Ser Val Val Thr Val Pro Ser
        180                 185                 190

Ser Ser Leu Gly Thr Gln Thr Tyr Ile Cys Asn Val Asn His Lys Pro
    195                 200                 205

Ser Asn Thr Lys Val Asp Lys Lys Val Glu Pro Lys Ser Cys Asp Lys
210                 215                 220

Thr His Thr Cys Pro Pro Cys Pro Ala Pro Glu Leu Arg Arg Gly Pro
225                 230                 235                 240

Lys Val Phe Leu Phe Pro Pro Lys Pro Lys Asp Thr Leu Tyr Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Tyr His Val Thr Gln Lys Ser Leu Ser Leu Ser Pro
        435                 440                 445

<210> SEQ ID NO 164
<211> LENGTH: 447
<212> TYPE: PRT
<213> ORGANISM: Artificial Sequence
<220> FEATURE:
<223> OTHER INFORMATION: an artificially synthesized sequence

<400> SEQUENCE: 164

Gln Val Gln Leu Gln Glu Ser Gly Pro Gly Leu Val Lys Pro Ser Glu
1               5                   10                  15

Thr Leu Ser Leu Thr Cys Ala Val Ser Gly His Ser Ile Ser His Asp
            20                  25                  30

His Ala Trp Ser Trp Val Arg Gln Pro Pro Gly Glu Gly Leu Glu Trp
        35                  40                  45

Ile Gly Phe Ile Ser Tyr Ser Gly Ile Thr Asn Tyr Asn Pro Ser Leu
    50                  55                  60

Gln Gly Arg Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Leu Ala Arg Thr Thr Ala Met Asp Tyr Trp Gly Glu Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Arg Gly Pro
225                 230                 235                 240

Ser Val Phe Leu Phe Pro Pro Lys Pro Lys Asp Thr Leu Tyr Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Arg Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Tyr His Val Thr Gln Lys Ser Leu Ser Leu Ser Pro
        435                 440                 445

<210> SEQ ID NO 165
<211> LENGTH: 447
<212> TYPE: PRT
<213> ORGANISM: Artificial Sequence
<220> FEATURE:
<223> OTHER INFORMATION: an artificially synthesized sequence

<400> SEQUENCE: 165

```
Gln Val Gln Leu Gln Glu Ser Gly Pro Gly Leu Val Lys Pro Ser Glu
  1               5                  10                  15

Thr Leu Ser Leu Thr Cys Ala Val Ser Gly His Ser Ile Ser His Asp
             20                  25                  30

His Ala Trp Ser Trp Val Arg Gln Pro Pro Gly Glu Gly Leu Glu Trp
         35                  40                  45

Ile Gly Phe Ile Ser Tyr Ser Gly Ile Thr Asn Tyr Asn Pro Ser Leu
     50                  55                  60

Gln Gly Arg Val Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Ser Leu Ala Arg Thr Thr Ala Met Asp Tyr Trp Gly Glu Gly
             100                 105                 110

Thr Leu Val Thr Val Ser Ser Ala Ser Thr Lys Gly Pro Ser Val Phe
         115                 120                 125

Pro Leu Ala Pro Ser Ser Lys Ser Thr Ser Gly Gly Thr Ala Ala Leu
     130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                 165                 170                 175

Gln Ser Ser Gly Leu Tyr Ser Leu Ser Ser Val Val Thr Val Pro Ser
             180                 185                 190

Ser Ser Leu Gly Thr Gln Thr Tyr Ile Cys Asn Val Asn His Lys Pro
         195                 200                 205

Ser Asn Thr Lys Val Asp Lys Lys Val Glu Pro Lys Ser Cys Asp Lys
210                 215                 220

Thr His Thr Cys Pro Pro Cys Pro Ala Pro Glu Ala Ala Gly Gly Pro
225                 230                 235                 240

Ser Val Phe Leu Phe Pro Pro Lys Pro Lys Asp Val Leu Tyr Ile Ser
             245                 250                 255

Arg Thr Pro Glu Val Thr Cys Val Val Val Asp Val Ser His Glu Asp
         260                 265                 270

Pro Glu Val Lys Phe Asn Trp Tyr Val Asp Gly Val Glu Val His Asn
     275                 280                 285

Ala Lys Thr Lys Pro Arg Glu Glu Gln Tyr Ala Ser Thr Tyr Arg Val
 290                 295                 300

Val Ser Val Leu Gln Pro Leu His Ala Asp Trp Leu Asn Gly Lys Glu
305                 310                 315                 320

Tyr Lys Cys Lys Val Ser Asn Lys Ala Leu Pro Ala Pro Ile Glu Lys
                 325                 330                 335

Thr Ile Ser Lys Ala Lys Gly Gln Pro Arg Glu Pro Gln Val Tyr Thr
             340                 345                 350

Leu Pro Pro Ser Arg Asp Glu Leu Thr Lys Asn Gln Val Ser Leu Thr
         355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                 405                 410                 415
```

-continued

Ser Arg Trp Gln Gln Gly Asn Val Phe Ser Cys Ser Val Met His Glu
                420                 425                 430

Ala Leu His Tyr His Val Thr Gln Lys Ser Leu Ser Leu Ser Pro
            435                 440                 445

<210> SEQ ID NO 166
<211> LENGTH: 443
<212> TYPE: PRT
<213> ORGANISM: Homo sapiens

<400> SEQUENCE: 166

Gln Val Gln Leu Gln Glu Ser Gly Pro Gly Leu Val Lys Pro Ser Glu
1               5                   10                  15

Thr Leu Ser Leu Thr Cys Ala Val Ser Gly His Ser Ile Ser His Asp
            20                  25                  30

His Ala Trp Ser Trp Val Arg Gln Pro Pro Gly Glu Gly Leu Glu Trp
        35                  40                  45

Ile Gly Phe Ile Ser Tyr Ser Gly Ile Thr Asn Tyr Asn Pro Ser Leu
    50                  55                  60

Gln Gly Arg Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Leu Ala Arg Thr Thr Ala Met Asp Tyr Trp Gly Glu Gly
            100                 105                 110

Thr Leu Val Thr Val Ser Ser Ala Ser Thr Lys Gly Pro Ser Val Phe
        115                 120                 125

Pro Leu Ala Pro Cys Ser Arg Ser Thr Ser Glu Ser Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Asn Phe Gly Thr Gln Thr Tyr Thr Cys Asn Val Asp His Lys Pro
        195                 200                 205

Ser Asn Thr Lys Val Asp Lys Thr Val Glu Arg Lys Cys Cys Val Glu
    210                 215                 220

Cys Pro Pro Cys Pro Ala Pro Pro Val Ala Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Asp Val Ser His Glu Asp Pro Glu Val Gln
            260                 265                 270

Phe Asn Trp Tyr Val Asp Gly Val Glu Val His Asn Ala Lys Thr Lys
        275                 280                 285

Pro Arg Glu Glu Gln Phe Asn Ser Thr Phe Arg Val Val Ser Val Leu
    290                 295                 300

Thr Val Val His Gln Asp Trp Leu Asn Gly Lys Glu Tyr Lys Cys Lys
305                 310                 315                 320

Val Ser Asn Lys Gly Leu Pro Ala Pro Ile Glu Lys Thr Ile Ser Lys
                325                 330                 335

Thr Lys Gly Gln Pro Arg Glu Pro Gln Val Tyr Thr Leu Pro Pro Ser
            340                 345                 350

```
Arg Glu Glu Met Thr Lys Asn Gln Val Ser Leu Thr Cys Leu Val Lys
        355                 360                 365
Gly Phe Tyr Pro Ser Asp Ile Ala Val Glu Trp Glu Ser Asn Gly Gln
    370                 375                 380
Pro Glu Asn Asn Tyr Lys Thr Thr Pro Pro Met Leu Asp Ser Asp Gly
385                 390                 395                 400
Ser Phe Phe Leu Tyr Ser Lys Leu Thr Val Asp Lys Ser Arg Trp Gln
                405                 410                 415
Gln Gly Asn Val Phe Ser Cys Ser Val Met His Glu Ala Leu His Asn
            420                 425                 430
His Tyr Thr Gln Lys Ser Leu Ser Leu Ser Pro
        435                 440

<210> SEQ ID NO 167
<211> LENGTH: 444
<212> TYPE: PRT
<213> ORGANISM: Homo sapiens

<400> SEQUENCE: 167

Gln Val Gln Leu Gln Glu Ser Gly Pro Gly Leu Val Lys Pro Ser Glu
1               5                   10                  15
Thr Leu Ser Leu Thr Cys Ala Val Ser Gly His Ser Ile Ser His Asp
            20                  25                  30
His Ala Trp Ser Trp Val Arg Gln Pro Pro Gly Glu Gly Leu Glu Trp
        35                  40                  45
Ile Gly Phe Ile Ser Tyr Ser Gly Ile Thr Asn Tyr Asn Pro Ser Leu
    50                  55                  60
Gln Gly Arg Val Thr Ile Ser Arg Asp Asn Ser Lys Asn Thr Leu Tyr
65                  70                  75                  80
Leu Gln Met Asn Ser Leu Arg Ala Glu Asp Thr Ala Val Tyr Tyr Cys
                85                  90                  95
Ala Arg Ser Leu Ala Arg Thr Thr Ala Met Asp Tyr Trp Gly Glu Gly
            100                 105                 110
Thr Leu Val Thr Val Ser Ser Ala Ser Thr Lys Gly Pro Ser Val Phe
        115                 120                 125
Pro Leu Ala Pro Cys Ser Arg Ser Thr Ser Glu Ser Thr Ala Ala Leu
    130                 135                 140
Gly Cys Leu Val Lys Asp Tyr Phe Pro Glu Pro Val Thr Val Ser Trp
145                 150                 155                 160
Asn Ser Gly Ala Leu Thr Ser Gly Val His Thr Phe Pro Ala Val Leu
                165                 170                 175
Gln Ser Ser Gly Leu Tyr Ser Leu Ser Ser Val Val Thr Val Pro Ser
            180                 185                 190
Ser Ser Leu Gly Thr Lys Thr Tyr Thr Cys Asn Val Asp His Lys Pro
        195                 200                 205
Ser Asn Thr Lys Val Asp Lys Arg Val Glu Ser Lys Tyr Gly Pro Pro
    210                 215                 220
Cys Pro Pro Cys Pro Ala Pro Glu Phe Leu Gly Gly Pro Ser Val Phe
225                 230                 235                 240
Leu Phe Pro Pro Lys Pro Lys Asp Thr Leu Met Ile Ser Arg Thr Pro
                245                 250                 255
Glu Val Thr Cys Val Val Val Asp Val Ser Gln Glu Asp Pro Glu Val
            260                 265                 270
Gln Phe Asn Trp Tyr Val Asp Gly Val Glu Val His Asn Ala Lys Thr
```

```
                275                 280                 285
Lys Pro Arg Glu Glu Gln Phe Asn Ser Thr Tyr Arg Val Ser Val
            290                 295                 300
Leu Thr Val Leu His Gln Asp Trp Leu Asn Gly Lys Glu Tyr Lys Cys
305                 310                 315                 320
Lys Val Ser Asn Lys Gly Leu Pro Ser Ser Ile Glu Lys Thr Ile Ser
                325                 330                 335
Lys Ala Lys Gly Gln Pro Arg Glu Pro Gln Val Tyr Thr Leu Pro Pro
            340                 345                 350
Ser Gln Glu Glu Met Thr Lys Asn Gln Val Ser Leu Thr Cys Leu Val
                355                 360                 365
Lys Gly Phe Tyr Pro Ser Asp Ile Ala Val Glu Trp Glu Ser Asn Gly
            370                 375                 380
Gln Pro Glu Asn Asn Tyr Lys Thr Thr Pro Pro Val Leu Asp Ser Asp
385                 390                 395                 400
Gly Ser Phe Phe Leu Tyr Ser Arg Leu Thr Val Asp Lys Ser Arg Trp
                405                 410                 415
Gln Glu Gly Asn Val Phe Ser Cys Ser Val Met His Glu Ala Leu His
            420                 425                 430
Asn His Tyr Thr Gln Lys Ser Leu Ser Leu Ser Leu
                435                 440

<210> SEQ ID NO 168
<211> LENGTH: 443
<212> TYPE: PRT
<213> ORGANISM: Artificial Sequence
<220> FEATURE:
<223> OTHER INFORMATION: an artificially synthesized sequence

<400> SEQUENCE: 168

Gln Val Gln Leu Gln Glu Ser Gly Pro Gly Leu Val Lys Pro Ser Glu
1               5                   10                  15
Thr Leu Ser Leu Thr Cys Ala Val Ser Gly His Ser Ile Ser His Asp
            20                  25                  30
His Ala Trp Ser Trp Val Arg Gln Pro Pro Gly Glu Gly Leu Glu Trp
        35                  40                  45
Ile Gly Phe Ile Ser Tyr Ser Gly Ile Thr Asn Tyr Asn Pro Ser Leu
    50                  55                  60
Gln Gly Arg Val Thr Ile Ser Arg Asp Asn Ser Lys Asn Thr Leu Tyr
65                  70                  75                  80
Leu Gln Met Asn Ser Leu Arg Ala Glu Asp Thr Ala Val Tyr Tyr Cys
                85                  90                  95
Ala Arg Ser Leu Ala Arg Thr Thr Ala Met Asp Tyr Trp Gly Glu Gly
            100                 105                 110
Thr Leu Val Thr Val Ser Ser Ala Ser Thr Lys Gly Pro Ser Val Phe
        115                 120                 125
Pro Leu Ala Pro Cys Ser Arg Ser Thr Ser Glu Ser Thr Ala Ala Leu
    130                 135                 140
Gly Cys Leu Val Lys Asp Tyr Phe Pro Glu Pro Val Thr Val Ser Trp
145                 150                 155                 160
Asn Ser Gly Ala Leu Thr Ser Gly Val His Thr Phe Pro Ala Val Leu
                165                 170                 175
Gln Ser Ser Gly Leu Tyr Ser Leu Ser Ser Val Val Thr Val Pro Ser
            180                 185                 190
Ser Asn Phe Gly Thr Gln Thr Tyr Thr Cys Asn Val Asp His Lys Pro
```

```
            195                 200                 205
Ser Asn Thr Lys Val Asp Lys Thr Val Glu Arg Lys Cys Cys Val Glu
    210                 215                 220

Cys Pro Cys Pro Ala Pro Pro Val Ala Gly Pro Ser Val Phe Leu
225                 230                 235                 240

Phe Pro Pro Lys Pro Lys Asp Thr Leu Tyr Ile Ser Arg Thr Pro Glu
                245                 250                 255

Val Thr Cys Val Val Val Asp Val Ser His Glu Asp Pro Glu Val Gln
            260                 265                 270

Phe Asn Trp Tyr Val Asp Gly Val Glu Val His Asn Ala Lys Thr Lys
        275                 280                 285

Pro Arg Glu Glu Gln Phe Asn Ser Thr Phe Arg Val Val Ser Val Leu
    290                 295                 300

Thr Val Val His Gln Asp Trp Leu Asn Gly Lys Glu Tyr Lys Cys Lys
305                 310                 315                 320

Val Ser Asn Lys Gly Leu Pro Ala Pro Ile Glu Lys Thr Ile Ser Lys
                325                 330                 335

Thr Lys Gly Gln Pro Arg Glu Pro Gln Val Tyr Thr Leu Pro Pro Ser
            340                 345                 350

Arg Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Met Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Tyr
            420                 425                 430

His Val Thr Gln Lys Ser Leu Ser Leu Ser Pro
        435                 440

<210> SEQ ID NO 169
<211> LENGTH: 444
<212> TYPE: PRT
<213> ORGANISM: Artificial Sequence
<220> FEATURE:
<223> OTHER INFORMATION: an artificially synthesized sequence

<400> SEQUENCE: 169

Gln Val Gln Leu Gln Glu Ser Gly Pro Gly Leu Val Lys Pro Ser Glu
1               5                   10                  15

Thr Leu Ser Leu Thr Cys Ala Val Ser Gly His Ser Ile Ser His Asp
            20                  25                  30

His Ala Trp Ser Trp Val Arg Gln Pro Pro Gly Glu Gly Leu Glu Trp
        35                  40                  45

Ile Gly Phe Ile Ser Tyr Ser Gly Ile Thr Asn Tyr Asn Pro Ser Leu
    50                  55                  60

Gln Gly Arg Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Leu Ala Arg Thr Thr Ala Met Asp Tyr Trp Gly Glu Gly
            100                 105                 110

Thr Leu Val Thr Val Ser Ser Ala Ser Thr Lys Gly Pro Ser Val Phe
```

```
                 115                 120                 125
Pro Leu Ala Pro Cys Ser Arg Ser Thr Ser Glu Ser Thr Ala Ala Leu
            130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Lys Thr Tyr Thr Cys Asn Val Asp His Lys Pro
        195                 200                 205

Ser Asn Thr Lys Val Asp Lys Arg Val Glu Ser Lys Tyr Gly Pro Pro
    210                 215                 220

Cys Pro Pro Cys Pro Ala Pro Glu Phe Leu Gly Gly Pro Ser Val Phe
225                 230                 235                 240

Leu Phe Pro Pro Lys Pro Lys Asp Thr Leu Tyr Ile Ser Arg Thr Pro
                245                 250                 255

Glu Val Thr Cys Val Val Val Asp Val Ser Gln Glu Asp Pro Glu Val
            260                 265                 270

Gln Phe Asn Trp Tyr Val Asp Gly Val Glu Val His Asn Ala Lys Thr
        275                 280                 285

Lys Pro Arg Glu Glu Gln Phe Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Gln Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Arg Leu Thr Val Asp Lys Ser Arg Trp
                405                 410                 415

Gln Glu Gly Asn Val Phe Ser Cys Ser Val Met His Glu Ala Leu His
            420                 425                 430

Tyr His Val Thr Gln Lys Ser Leu Ser Leu Ser Leu
        435                 440

<210> SEQ ID NO 170
<211> LENGTH: 443
<212> TYPE: PRT
<213> ORGANISM: Artificial Sequence
<220> FEATURE:
<223> OTHER INFORMATION: an artificially synthesized sequence

<400> SEQUENCE: 170

Gln Val Gln Leu Gln Glu Ser Gly Pro Gly Leu Val Lys Pro Ser Glu
1               5                   10                  15

Thr Leu Ser Leu Thr Cys Ala Val Ser Gly His Ser Ile Ser His Asp
            20                  25                  30

His Ala Trp Ser Trp Val Arg Gln Pro Pro Gly Glu Gly Leu Glu Trp
```

-continued

Ile Gly Phe Ile Ser Tyr Ser Gly Ile Thr Asn Tyr Asn Pro Ser Leu
 50                  55                  60

Gln Gly Arg Val Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
             85                  90                  95

Ala Arg Ser Leu Ala Arg Thr Thr Ala Met Asp Tyr Trp Gly Glu Gly
            100                 105                 110

Thr Leu Val Thr Val Ser Ser Ala Ser Thr Lys Gly Pro Ser Val Phe
        115                 120                 125

Pro Leu Ala Pro Cys Ser Arg Ser Thr Ser Glu Ser Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Asn Phe Gly Thr Gln Thr Tyr Thr Cys Asn Val Asp His Lys Pro
        195                 200                 205

Ser Asn Thr Lys Val Asp Lys Thr Val Glu Arg Lys Cys Cys Val Glu
    210                 215                 220

Cys Pro Pro Cys Pro Ala Pro Pro Val Arg Gly Pro Lys Val Phe Leu
225                 230                 235                 240

Phe Pro Pro Lys Pro Lys Asp Thr Leu Tyr Ile Ser Arg Thr Pro Glu
                245                 250                 255

Val Thr Cys Val Val Val Asp Val Ser His Glu Asp Pro Glu Val Gln
            260                 265                 270

Phe Asn Trp Tyr Val Asp Gly Val Glu Val His Asn Ala Lys Thr Lys
        275                 280                 285

Pro Arg Glu Glu Gln Phe Asn Ser Thr Phe Arg Val Val Ser Val Leu
    290                 295                 300

Thr Val Val His Gln Asp Trp Leu Asn Gly Lys Glu Tyr Lys Cys Lys
305                 310                 315                 320

Val Ser Asn Lys Gly Leu Pro Ala Pro Ile Glu Lys Thr Ile Ser Lys
                325                 330                 335

Thr Lys Gly Gln Pro Arg Glu Pro Gln Val Tyr Thr Leu Pro Pro Ser
            340                 345                 350

Arg Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Met Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Tyr
            420                 425                 430

His Val Thr Gln Lys Ser Leu Ser Leu Ser Pro
        435                 440

<210> SEQ ID NO 171

<211> LENGTH: 444
<212> TYPE: PRT
<213> ORGANISM: Artificial Sequence
<220> FEATURE:
<223> OTHER INFORMATION: an artificially synthesized sequence

<400> SEQUENCE: 171

```
Gln Val Gln Leu Gln Glu Ser Gly Pro Gly Leu Val Lys Pro Ser Glu
1               5                   10                  15

Thr Leu Ser Leu Thr Cys Ala Val Ser Gly His Ser Ile Ser His Asp
            20                  25                  30

His Ala Trp Ser Trp Val Arg Gln Pro Pro Gly Glu Gly Leu Glu Trp
        35                  40                  45

Ile Gly Phe Ile Ser Tyr Ser Gly Ile Thr Asn Tyr Asn Pro Ser Leu
    50                  55                  60

Gln Gly Arg Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Leu Ala Arg Thr Thr Ala Met Asp Tyr Trp Gly Glu Gly
            100                 105                 110

Thr Leu Val Thr Val Ser Ser Ala Ser Thr Lys Gly Pro Ser Val Phe
        115                 120                 125

Pro Leu Ala Pro Cys Ser Arg Ser Thr Ser Glu Ser Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Lys Thr Tyr Thr Cys Asn Val Asp His Lys Pro
        195                 200                 205

Ser Asn Thr Lys Val Asp Lys Arg Val Glu Ser Lys Tyr Gly Pro Pro
    210                 215                 220

Cys Pro Pro Cys Pro Ala Pro Glu Phe Arg Gly Gly Pro Lys Val Phe
225                 230                 235                 240

Leu Phe Pro Pro Lys Pro Lys Asp Thr Leu Tyr Ile Ser Arg Thr Pro
                245                 250                 255

Glu Val Thr Cys Val Val Val Asp Val Ser Gln Glu Asp Pro Glu Val
            260                 265                 270

Gln Phe Asn Trp Tyr Val Asp Gly Val Glu Val His Asn Ala Lys Thr
        275                 280                 285

Lys Pro Arg Glu Glu Gln Phe Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Gln Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380
```

Gln Pro Glu Asn Asn Tyr Lys Thr Thr Pro Pro Val Leu Asp Ser Asp
385                 390                 395                 400

Gly Ser Phe Phe Leu Tyr Ser Arg Leu Thr Val Asp Lys Ser Arg Trp
            405                 410                 415

Gln Glu Gly Asn Val Phe Ser Cys Ser Val Met His Glu Ala Leu His
        420                 425                 430

Tyr His Val Thr Gln Lys Ser Leu Ser Leu Ser Leu
    435                 440

<210> SEQ ID NO 172
<211> LENGTH: 447
<212> TYPE: PRT
<213> ORGANISM: Artificial Sequence
<220> FEATURE:
<223> OTHER INFORMATION: an artificially synthesized sequence

<400> SEQUENCE: 172

Gln Val Gln Leu Gln Glu Ser Gly Pro Gly Leu Val Lys Pro Ser Glu
1               5                   10                  15

Thr Leu Ser Leu Thr Cys Ala Val Ser Gly His Ser Ile Ser His Asp
            20                  25                  30

His Ala Trp Ser Trp Val Arg Gln Pro Pro Gly Glu Gly Leu Glu Trp
        35                  40                  45

Ile Gly Phe Ile Ser Tyr Ser Gly Ile Thr Asn Tyr Asn Pro Ser Leu
    50                  55                  60

Gln Gly Arg Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Leu Ala Arg Thr Thr Ala Met Asp Tyr Trp Gly Glu Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Asp
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

```
Val Ser Val Leu Thr Val Leu His Gln Asp Trp Leu Asn Gly Lys Glu
305                 310                 315                 320

Tyr Lys Cys Lys Val Ser Asn Lys Ala Glu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
                355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro
                435                 440                 445

<210> SEQ ID NO 173
<211> LENGTH: 447
<212> TYPE: PRT
<213> ORGANISM: Artificial Sequence
<220> FEATURE:
<223> OTHER INFORMATION: an artificially synthesized sequence

<400> SEQUENCE: 173

Gln Val Gln Leu Gln Glu Ser Gly Pro Gly Leu Val Lys Pro Ser Glu
1               5                   10                  15

Thr Leu Ser Leu Thr Cys Ala Val Ser Gly His Ser Ile Ser His Asp
                20                  25                  30

His Ala Trp Ser Trp Val Arg Gln Pro Pro Gly Glu Gly Leu Glu Trp
            35                  40                  45

Ile Gly Phe Ile Ser Tyr Ser Gly Ile Thr Asn Tyr Asn Pro Ser Leu
50                  55                  60

Gln Gly Arg Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Leu Ala Arg Thr Thr Ala Met Asp Tyr Trp Gly Glu Gly
                100                 105                 110

Thr Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
210                 215                 220
```

Thr His Thr Cys Pro Pro Cys Pro Ala Pro Glu Leu Leu Gly Gly Asp
225                 230                 235                 240

Ser Val Phe Leu Phe Pro Pro Lys Pro Lys Asp Thr Leu Met Ile Ser
            245                 250                 255

Arg Thr Pro Glu Val Thr Cys Val Val Val Asp Val Glu His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Phe Pro Ala Pro Ile Glu Lys
            325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
            405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro
        435                 440                 445

<210> SEQ ID NO 174
<211> LENGTH: 447
<212> TYPE: PRT
<213> ORGANISM: Artificial Sequence
<220> FEATURE:
<223> OTHER INFORMATION: an artificially synthesized sequence

<400> SEQUENCE: 174

Gln Val Gln Leu Gln Glu Ser Gly Pro Gly Leu Val Lys Pro Ser Glu
1               5                   10                  15

Thr Leu Ser Leu Thr Cys Ala Val Ser Gly His Ser Ile Ser His Asp
            20                  25                  30

His Ala Trp Ser Trp Val Arg Gln Pro Pro Gly Glu Gly Leu Glu Trp
        35                  40                  45

Ile Gly Phe Ile Ser Tyr Ser Gly Ile Thr Asn Tyr Asn Pro Ser Leu
    50                  55                  60

Gln Gly Arg Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Leu Ala Arg Thr Thr Ala Met Asp Tyr Trp Gly Glu Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
            165                 170                 175

Gln Ser Ser Gly Leu Tyr Ser Leu Ser Ser Val Val Thr Val Pro Ser
        180                 185                 190

Ser Ser Leu Gly Thr Gln Thr Tyr Ile Cys Asn Val Asn His Lys Pro
    195                 200                 205

Ser Asn Thr Lys Val Asp Lys Lys Val Glu Pro Lys Ser Cys Asp Lys
210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Tyr Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Tyr His Tyr Thr Gln Lys Ser Leu Ser Leu Ser Pro
        435                 440                 445

<210> SEQ ID NO 175
<211> LENGTH: 447
<212> TYPE: PRT
<213> ORGANISM: Artificial Sequence
<220> FEATURE:
<223> OTHER INFORMATION: an artificially synthesized sequence

<400> SEQUENCE: 175

Gln Val Gln Leu Gln Glu Ser Gly Pro Gly Leu Val Lys Pro Ser Glu
1               5                   10                  15

Thr Leu Ser Leu Thr Cys Ala Val Ser Gly His Ser Ile Ser His Asp
            20                  25                  30

His Ala Trp Ser Trp Val Arg Gln Pro Pro Gly Glu Gly Leu Glu Trp
        35                  40                  45

Ile Gly Phe Ile Ser Tyr Ser Gly Ile Thr Asn Tyr Asn Pro Ser Leu
    50                  55                  60

Gln Gly Arg Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Arg Ser Leu Ala Arg Thr Thr Ala Met Asp Tyr Trp Gly Glu Gly
        100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
            165                 170                 175

Gln Ser Ser Gly Leu Tyr Ser Leu Ser Ser Val Val Thr Val Pro Ser
        180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
210                 215                 220

Thr His Thr Cys Pro Pro Cys Pro Ala Pro Glu Leu Leu Gly Gly Asp
225                 230                 235                 240

Ser Val Phe Leu Phe Pro Pro Lys Pro Lys Asp Thr Leu Tyr Ile Ser
            245                 250                 255

Arg Thr Pro Glu Val Thr Cys Val Val Val Asp Val Ser His Glu Asp
        260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
            325                 330                 335

Thr Ile Ser Lys Ala Lys Gly Gln Pro Arg Glu Pro Gln Val Tyr Thr
        340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
            405                 410                 415

Ser Arg Trp Gln Gln Gly Asn Val Phe Ser Cys Ser Val Met His Glu
        420                 425                 430

Ala Leu His Tyr His Tyr Thr Gln Lys Ser Leu Ser Leu Ser Pro
        435                 440                 445

<210> SEQ ID NO 176
<211> LENGTH: 447
<212> TYPE: PRT
<213> ORGANISM: Artificial Sequence
<220> FEATURE:

<223> OTHER INFORMATION: an artificially synthesized sequence

<400> SEQUENCE: 176

```
Gln Val Gln Leu Gln Glu Ser Gly Pro Gly Leu Val Lys Pro Ser Glu
1               5                   10                  15

Thr Leu Ser Leu Thr Cys Ala Val Ser Gly His Ser Ile Ser His Asp
            20                  25                  30

His Ala Trp Ser Trp Val Arg Gln Pro Pro Gly Glu Gly Leu Glu Trp
        35                  40                  45

Ile Gly Phe Ile Ser Tyr Ser Gly Ile Thr Asn Tyr Asn Pro Ser Leu
    50                  55                  60

Gln Gly Arg Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Leu Ala Arg Thr Thr Ala Met Asp Tyr Trp Gly Gln Gly
            100                 105                 110

Thr Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
            165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys Asp Lys
210                 215                 220

Thr His Thr Cys Pro Pro Cys Pro Ala Pro Glu Trp Leu Gly Gly Asp
225                 230                 235                 240

Ser Val Phe Leu Phe Pro Pro Lys Pro Lys Asp Thr Leu Tyr Ile Ser
            245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
            290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
            325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
            355                 360                 365

Cys Leu Val Lys Gly Phe Tyr Pro Ser Asp Ile Ala Val Glu Trp Glu
            370                 375                 380

Ser Asn Gly Gln Pro Glu Asn Asn Tyr Lys Thr Thr Pro Pro Val Leu
385                 390                 395                 400
```

```
Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
        420                 425                 430

Ala Leu His Tyr His Tyr Thr Gln Lys Ser Leu Ser Leu Ser Pro
        435                 440                 445

<210> SEQ ID NO 177
<211> LENGTH: 447
<212> TYPE: PRT
<213> ORGANISM: Artificial Sequence
<220> FEATURE:
<223> OTHER INFORMATION: an artificially synthesized sequence

<400> SEQUENCE: 177

Gln Val Gln Leu Gln Glu Ser Gly Pro Gly Leu Val Lys Pro Ser Glu
1               5                   10                  15

Thr Leu Ser Leu Thr Cys Ala Val Ser Gly His Ser Ile Ser His Asp
            20                  25                  30

His Ala Trp Ser Trp Val Arg Gln Pro Pro Gly Glu Gly Leu Glu Trp
        35                  40                  45

Ile Gly Phe Ile Ser Tyr Ser Gly Ile Thr Asn Tyr Asn Pro Ser Leu
    50                  55                  60

Gln Gly Arg Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Leu Ala Arg Thr Thr Ala Met Asp Tyr Trp Gly Glu Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Tyr Leu Gly Gly Asp
225                 230                 235                 240

Ser Val Phe Leu Phe Pro Pro Lys Pro Lys Asp Thr Leu Tyr Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320
```

-continued

```
Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Tyr His Tyr Thr Gln Lys Ser Leu Ser Leu Ser Pro
        435                 440                 445

<210> SEQ ID NO 178
<211> LENGTH: 447
<212> TYPE: PRT
<213> ORGANISM: Artificial Sequence
<220> FEATURE:
<223> OTHER INFORMATION: an artificially synthesized sequence

<400> SEQUENCE: 178

Gln Val Gln Leu Gln Glu Ser Gly Pro Gly Leu Val Lys Pro Ser Glu
1               5                   10                  15

Thr Leu Ser Leu Thr Cys Ala Val Ser Gly His Ser Ile Ser His Asp
            20                  25                  30

His Ala Trp Ser Trp Val Arg Gln Pro Pro Gly Glu Gly Leu Glu Trp
        35                  40                  45

Ile Gly Phe Ile Ser Tyr Ser Gly Ile Thr Asn Tyr Asn Pro Ser Leu
    50                  55                  60

Gln Gly Arg Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Leu Ala Arg Thr Thr Ala Met Asp Tyr Trp Gly Glu Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Ala Asp
225                 230                 235                 240
```

Ser Val Phe Leu Phe Pro Pro Lys Pro Lys Asp Thr Leu Tyr Ile Ser
            245                 250                 255

Arg Thr Pro Glu Val Thr Cys Val Val Val Asp Val Ser His Glu Asp
        260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
        290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Tyr His Tyr Thr Gln Lys Ser Leu Ser Leu Ser Pro
        435                 440                 445

<210> SEQ ID NO 179
<211> LENGTH: 447
<212> TYPE: PRT
<213> ORGANISM: Artificial Sequence
<220> FEATURE:
<223> OTHER INFORMATION: an artificially synthesized sequence

<400> SEQUENCE: 179

Gln Val Gln Leu Gln Glu Ser Gly Pro Gly Leu Val Lys Pro Ser Glu
1               5                   10                  15

Thr Leu Ser Leu Thr Cys Ala Val Ser Gly His Ser Ile Ser His Asp
            20                  25                  30

His Ala Trp Ser Trp Val Arg Gln Pro Pro Gly Glu Gly Leu Glu Trp
        35                  40                  45

Ile Gly Phe Ile Ser Tyr Ser Gly Ile Thr Asn Tyr Asn Pro Ser Leu
    50                  55                  60

Gln Gly Arg Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Leu Ala Arg Thr Thr Ala Met Asp Tyr Trp Gly Glu Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Ala Asp
225                 230                 235                 240

Ser Val Phe Leu Phe Pro Pro Lys Pro Lys Asp Thr Leu Tyr Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Tyr His Tyr Thr Gln Lys Ser Leu Ser Leu Ser Pro
        435                 440                 445

<210> SEQ ID NO 180
<211> LENGTH: 447
<212> TYPE: PRT
<213> ORGANISM: Artificial Sequence
<220> FEATURE:
<223> OTHER INFORMATION: an artificially synthesized sequence

<400> SEQUENCE: 180

Gln Val Gln Leu Gln Glu Ser Gly Pro Gly Leu Val Lys Pro Ser Glu
1               5                   10                  15

Thr Leu Ser Leu Thr Cys Ala Val Ser Gly His Ser Ile Ser His Asp
            20                  25                  30

His Ala Trp Ser Trp Val Arg Gln Pro Pro Gly Glu Gly Leu Glu Trp
        35                  40                  45

Ile Gly Phe Ile Ser Tyr Ser Gly Ile Thr Asn Tyr Asn Pro Ser Leu
    50                  55                  60

Gln Gly Arg Val Thr Ile Ser Arg Asp Asn Ser Lys Asn Thr Leu Tyr
65                  70                  75                  80

-continued

Leu Gln Met Asn Ser Leu Arg Ala Glu Asp Thr Ala Val Tyr Tyr Cys
                85                  90                  95

Ala Arg Ser Leu Ala Arg Thr Thr Ala Met Asp Tyr Trp Gly Glu Gly
            100                 105                 110

Thr Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
                180                 185                 190

Ser Ser Leu Gly Thr Gln Thr Tyr Ile Cys Asn Val Asn His Lys Pro
                195                 200                 205

Ser Asn Thr Lys Val Asp Lys Lys Val Glu Pro Lys Ser Cys Asp Lys
                210                 215                 220

Thr His Thr Cys Pro Pro Cys Pro Ala Pro Glu Leu Leu Gly Glu Asp
225                 230                 235                 240

Ser Val Phe Leu Phe Pro Pro Lys Pro Lys Asp Thr Leu Tyr Ile Ser
                245                 250                 255

Arg Thr Pro Glu Val Thr Cys Val Val Val Asp Val Ser His Glu Asp
                260                 265                 270

Pro Glu Val Lys Phe Asn Trp Tyr Val Asp Gly Val Glu Val His Asn
                275                 280                 285

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
                340                 345                 350

Leu Pro Pro Ser Arg Asp Glu Leu Thr Lys Asn Gln Val Ser Leu Thr
                355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
                420                 425                 430

Ala Leu His Tyr His Tyr Thr Gln Lys Ser Leu Ser Leu Ser Pro
                435                 440                 445

<210> SEQ ID NO 181
<211> LENGTH: 447
<212> TYPE: PRT
<213> ORGANISM: Artificial Sequence
<220> FEATURE:
<223> OTHER INFORMATION: an artificially synthesized sequence

<400> SEQUENCE: 181

-continued

```
Gln Val Gln Leu Gln Glu Ser Gly Pro Gly Leu Val Lys Pro Ser Glu
1               5                   10                  15

Thr Leu Ser Leu Thr Cys Ala Val Ser Gly His Ser Ile Ser His Asp
            20                  25                  30

His Ala Trp Ser Trp Val Arg Gln Pro Pro Gly Glu Gly Leu Glu Trp
        35                  40                  45

Ile Gly Phe Ile Ser Tyr Ser Gly Ile Thr Asn Tyr Asn Pro Ser Leu
50                  55                  60

Gln Gly Arg Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Leu Ala Arg Thr Thr Ala Met Asp Tyr Trp Gly Glu Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Phe Asp
225                 230                 235                 240

Ser Val Phe Leu Phe Pro Pro Lys Pro Lys Asp Thr Leu Tyr Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
```

```
                        420                 425                 430
Ala Leu His Tyr His Tyr Thr Gln Lys Ser Leu Ser Leu Ser Pro
                435                 440                 445

<210> SEQ ID NO 182
<211> LENGTH: 447
<212> TYPE: PRT
<213> ORGANISM: Artificial Sequence
<220> FEATURE:
<223> OTHER INFORMATION: an artificially synthesized sequence

<400> SEQUENCE: 182

Gln Val Gln Leu Gln Glu Ser Gly Pro Gly Leu Val Lys Pro Ser Glu
1               5                   10                  15

Thr Leu Ser Leu Thr Cys Ala Val Ser Gly His Ser Ile Ser His Asp
            20                  25                  30

His Ala Trp Ser Trp Val Arg Gln Pro Pro Gly Glu Gly Leu Glu Trp
        35                  40                  45

Ile Gly Phe Ile Ser Tyr Ser Gly Ile Thr Asn Tyr Asn Pro Ser Leu
    50                  55                  60

Gln Gly Arg Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Leu Ala Arg Thr Thr Ala Met Asp Tyr Trp Gly Glu Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Leu Asp
225                 230                 235                 240

Ser Val Phe Leu Phe Pro Pro Lys Pro Lys Asp Thr Leu Tyr Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
```

```
                340                 345                 350
Leu Pro Pro Ser Arg Asp Glu Leu Thr Lys Asn Gln Val Ser Leu Thr
            355                 360                 365

Cys Leu Val Lys Gly Phe Tyr Pro Ser Asp Ile Ala Val Glu Trp Glu
        370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Tyr His Tyr Thr Gln Lys Ser Leu Ser Leu Ser Pro
        435                 440                 445

<210> SEQ ID NO 183
<211> LENGTH: 447
<212> TYPE: PRT
<213> ORGANISM: Artificial Sequence
<220> FEATURE:
<223> OTHER INFORMATION: an artificially synthesized sequence

<400> SEQUENCE: 183

Gln Val Gln Leu Gln Glu Ser Gly Pro Gly Leu Val Lys Pro Ser Glu
1               5                   10                  15

Thr Leu Ser Leu Thr Cys Ala Val Ser Gly His Ser Ile Ser His Asp
            20                  25                  30

His Ala Trp Ser Trp Val Arg Gln Pro Pro Gly Glu Gly Leu Glu Trp
        35                  40                  45

Ile Gly Phe Ile Ser Tyr Ser Gly Ile Thr Asn Tyr Asn Pro Ser Leu
    50                  55                  60

Gln Gly Arg Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Leu Ala Arg Thr Thr Ala Met Asp Tyr Trp Gly Glu Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Met Asp
225                 230                 235                 240

Ser Val Phe Leu Phe Pro Pro Lys Pro Lys Asp Thr Leu Tyr Ile Ser
                245                 250                 255

Arg Thr Pro Glu Val Thr Cys Val Val Val Asp Val Ser His Glu Asp
```

```
                260                 265                 270
Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
        290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Tyr His Tyr Thr Gln Lys Ser Leu Ser Leu Ser Pro
        435                 440                 445

<210> SEQ ID NO 184
<211> LENGTH: 447
<212> TYPE: PRT
<213> ORGANISM: Artificial Sequence
<220> FEATURE:
<223> OTHER INFORMATION: an artificially synthesized sequence

<400> SEQUENCE: 184

Gln Val Gln Leu Gln Glu Ser Gly Pro Gly Leu Val Lys Pro Ser Glu
1               5                   10                  15

Thr Leu Ser Leu Thr Cys Ala Val Ser Gly His Ser Ile Ser His Asp
            20                  25                  30

His Ala Trp Ser Trp Val Arg Gln Pro Pro Gly Glu Gly Leu Glu Trp
        35                  40                  45

Ile Gly Phe Ile Ser Tyr Ser Gly Ile Thr Asn Tyr Asn Pro Ser Leu
    50                  55                  60

Gln Gly Arg Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Leu Ala Arg Thr Thr Ala Met Asp Tyr Trp Gly Glu Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
```

```
            180                 185                 190
Ser Ser Leu Gly Thr Gln Thr Tyr Ile Cys Asn Val Asn His Lys Pro
        195                 200                 205
Ser Asn Thr Lys Val Asp Lys Lys Val Glu Pro Lys Ser Cys Asp Lys
    210                 215                 220
Thr His Thr Cys Pro Pro Cys Pro Ala Pro Glu Leu Leu Gly Trp Asp
225                 230                 235                 240
Ser Val Phe Leu Phe Pro Pro Lys Pro Lys Asp Thr Leu Tyr Ile Ser
                245                 250                 255
Arg Thr Pro Glu Val Thr Cys Val Val Val Asp Val Ser His Glu Asp
            260                 265                 270
Pro Glu Val Lys Phe Asn Trp Tyr Val Asp Gly Val Glu Val His Asn
        275                 280                 285
Ala Lys Thr Lys Pro Arg Glu Glu Gln Tyr Asn Ser Thr Tyr Arg Val
    290                 295                 300
Val Ser Val Leu Thr Val Leu His Gln Asp Trp Leu Asn Gly Lys Glu
305                 310                 315                 320
Tyr Lys Cys Lys Val Ser Asn Lys Ala Leu Pro Ala Pro Ile Glu Lys
                325                 330                 335
Thr Ile Ser Lys Ala Lys Gly Gln Pro Arg Glu Pro Gln Val Tyr Thr
            340                 345                 350
Leu Pro Pro Ser Arg Asp Glu Leu Thr Lys Asn Gln Val Ser Leu Thr
        355                 360                 365
Cys Leu Val Lys Gly Phe Tyr Pro Ser Asp Ile Ala Val Glu Trp Glu
    370                 375                 380
Ser Asn Gly Gln Pro Glu Asn Asn Tyr Lys Thr Thr Pro Pro Val Leu
385                 390                 395                 400
Asp Ser Asp Gly Ser Phe Phe Leu Tyr Ser Lys Leu Thr Val Asp Lys
                405                 410                 415
Ser Arg Trp Gln Gln Gly Asn Val Phe Ser Cys Ser Val Met His Glu
            420                 425                 430
Ala Leu His Tyr His Tyr Thr Gln Lys Ser Leu Ser Leu Ser Pro
        435                 440                 445

<210> SEQ ID NO 185
<211> LENGTH: 447
<212> TYPE: PRT
<213> ORGANISM: Artificial Sequence
<220> FEATURE:
<223> OTHER INFORMATION: an artificially synthesized sequence

<400> SEQUENCE: 185

Gln Val Gln Leu Gln Glu Ser Gly Pro Gly Leu Val Lys Pro Ser Glu
1               5                   10                  15

Thr Leu Ser Leu Thr Cys Ala Val Ser Gly His Ser Ile Ser His Asp
            20                  25                  30

His Ala Trp Ser Trp Val Arg Gln Pro Pro Gly Glu Gly Leu Glu Trp
        35                  40                  45

Ile Gly Phe Ile Ser Tyr Ser Gly Ile Thr Asn Tyr Asn Pro Ser Leu
    50                  55                  60

Gln Gly Arg Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Leu Ala Arg Thr Thr Ala Met Asp Tyr Trp Gly Glu Gly
```

```
            100             105             110
Thr Leu Val Thr Val Ser Ser Ala Ser Thr Lys Gly Pro Ser Val Phe
        115             120             125

Pro Leu Ala Pro Ser Ser Lys Ser Thr Ser Gly Gly Thr Ala Ala Leu
    130             135             140

Gly Cys Leu Val Lys Asp Tyr Phe Pro Glu Pro Val Thr Val Ser Trp
145             150             155             160

Asn Ser Gly Ala Leu Thr Ser Gly Val His Thr Phe Pro Ala Val Leu
            165             170             175

Gln Ser Ser Gly Leu Tyr Ser Leu Ser Ser Val Val Thr Val Pro Ser
        180             185             190

Ser Ser Leu Gly Thr Gln Thr Tyr Ile Cys Asn Val Asn His Lys Pro
    195             200             205

Ser Asn Thr Lys Val Asp Lys Lys Val Glu Pro Lys Ser Cys Asp Lys
210             215             220

Thr His Thr Cys Pro Pro Cys Pro Ala Pro Glu Leu Leu Gly Tyr Asp
225             230             235             240

Ser Val Phe Leu Phe Pro Pro Lys Pro Lys Asp Thr Leu Tyr Ile Ser
            245             250             255

Arg Thr Pro Glu Val Thr Cys Val Val Val Asp Val Ser His Glu Asp
        260             265             270

Pro Glu Val Lys Phe Asn Trp Tyr Val Asp Gly Val Glu Val His Asn
    275             280             285

Ala Lys Thr Lys Pro Arg Glu Glu Gln Tyr Asn Ser Thr Tyr Arg Val
290             295             300

Val Ser Val Leu Thr Val Leu His Gln Asp Trp Leu Asn Gly Lys Glu
305             310             315             320

Tyr Lys Cys Lys Val Ser Asn Lys Ala Leu Pro Ala Pro Ile Glu Lys
            325             330             335

Thr Ile Ser Lys Ala Lys Gly Gln Pro Arg Glu Pro Gln Val Tyr Thr
        340             345             350

Leu Pro Pro Ser Arg Asp Glu Leu Thr Lys Asn Gln Val Ser Leu Thr
    355             360             365

Cys Leu Val Lys Gly Phe Tyr Pro Ser Asp Ile Ala Val Glu Trp Glu
370             375             380

Ser Asn Gly Gln Pro Glu Asn Asn Tyr Lys Thr Thr Pro Pro Val Leu
385             390             395             400

Asp Ser Asp Gly Ser Phe Phe Leu Tyr Ser Lys Leu Thr Val Asp Lys
            405             410             415

Ser Arg Trp Gln Gln Gly Asn Val Phe Ser Cys Ser Val Met His Glu
        420             425             430

Ala Leu His Tyr His Tyr Thr Gln Lys Ser Leu Ser Leu Ser Pro
    435             440             445

<210> SEQ ID NO 186
<211> LENGTH: 447
<212> TYPE: PRT
<213> ORGANISM: Artificial Sequence
<220> FEATURE:
<223> OTHER INFORMATION: an artificially synthesized sequence

<400> SEQUENCE: 186

Gln Val Gln Leu Gln Glu Ser Gly Pro Gly Leu Val Lys Pro Ser Glu
1               5               10              15

Thr Leu Ser Leu Thr Cys Ala Val Ser Gly His Ser Ile Ser His Asp
```

-continued

```
            20                  25                  30
His Ala Trp Ser Trp Val Arg Gln Pro Gly Glu Gly Leu Glu Trp
        35                  40                  45
Ile Gly Phe Ile Ser Tyr Ser Gly Ile Thr Asn Tyr Asn Pro Ser Leu
    50                  55                  60
Gln Gly Arg Val Thr Ile Ser Arg Asp Asn Ser Lys Asn Thr Leu Tyr
65                  70                  75                  80
Leu Gln Met Asn Ser Leu Arg Ala Glu Asp Thr Ala Val Tyr Tyr Cys
                85                  90                  95
Ala Arg Ser Leu Ala Arg Thr Thr Ala Met Asp Tyr Trp Gly Glu Gly
            100                 105                 110
Thr Leu Val Thr Val Ser Ser Ala Ser Thr Lys Gly Pro Ser Val Phe
        115                 120                 125
Pro Leu Ala Pro Ser Ser Lys Ser Thr Ser Gly Gly Thr Ala Ala Leu
        130                 135                 140
Gly Cys Leu Val Lys Asp Tyr Phe Pro Glu Pro Val Thr Val Ser Trp
145                 150                 155                 160
Asn Ser Gly Ala Leu Thr Ser Gly Val His Thr Phe Pro Ala Val Leu
                165                 170                 175
Gln Ser Ser Gly Leu Tyr Ser Leu Ser Ser Val Val Thr Val Pro Ser
            180                 185                 190
Ser Ser Leu Gly Thr Gln Thr Tyr Ile Cys Asn Val Asn His Lys Pro
        195                 200                 205
Ser Asn Thr Lys Val Asp Lys Lys Val Glu Pro Lys Ser Cys Asp Lys
    210                 215                 220
Thr His Thr Cys Pro Pro Cys Pro Ala Pro Glu Leu Leu Gly Gly Asp
225                 230                 235                 240
Asp Val Phe Leu Phe Pro Pro Lys Pro Lys Asp Thr Leu Tyr Ile Ser
                245                 250                 255
Arg Thr Pro Glu Val Thr Cys Val Val Val Asp Val Ser His Glu Asp
            260                 265                 270
Pro Glu Val Lys Phe Asn Trp Tyr Val Asp Gly Val Glu Val His Asn
        275                 280                 285
Ala Lys Thr Lys Pro Arg Glu Glu Gln Tyr Asn Ser Thr Tyr Arg Val
        290                 295                 300
Val Ser Val Leu Thr Val Leu His Gln Asp Trp Leu Asn Gly Lys Glu
305                 310                 315                 320
Tyr Lys Cys Lys Val Ser Asn Lys Ala Leu Pro Ala Pro Ile Glu Lys
                325                 330                 335
Thr Ile Ser Lys Ala Lys Gly Gln Pro Arg Glu Pro Gln Val Tyr Thr
            340                 345                 350
Leu Pro Pro Ser Arg Asp Glu Leu Thr Lys Asn Gln Val Ser Leu Thr
        355                 360                 365
Cys Leu Val Lys Gly Phe Tyr Pro Ser Asp Ile Ala Val Glu Trp Glu
        370                 375                 380
Ser Asn Gly Gln Pro Glu Asn Asn Tyr Lys Thr Thr Pro Pro Val Leu
385                 390                 395                 400
Asp Ser Asp Gly Ser Phe Phe Leu Tyr Ser Lys Leu Thr Val Asp Lys
                405                 410                 415
Ser Arg Trp Gln Gln Gly Asn Val Phe Ser Cys Ser Val Met His Glu
            420                 425                 430
Ala Leu His Tyr His Tyr Thr Gln Lys Ser Leu Ser Leu Ser Pro
        435                 440                 445
```

```
<210> SEQ ID NO 187
<211> LENGTH: 447
<212> TYPE: PRT
<213> ORGANISM: Artificial Sequence
<220> FEATURE:
<223> OTHER INFORMATION: an artificially synthesized sequence

<400> SEQUENCE: 187
```

| | | | | | | | | | | | | | | | |
|---|---|---|---|---|---|---|---|---|---|---|---|---|---|---|---|
|Gln|Val|Gln|Leu|Gln|Glu|Ser|Gly|Pro|Gly|Leu|Val|Lys|Pro|Ser|Glu|
|1| | | |5| | | | |10| | | | |15| |
|Thr|Leu|Ser|Leu|Thr|Cys|Ala|Val|Ser|Gly|His|Ser|Ile|Ser|His|Asp|
| | | |20| | | | |25| | | | |30| | |
|His|Ala|Trp|Ser|Trp|Val|Arg|Gln|Pro|Pro|Gly|Glu|Gly|Leu|Glu|Trp|
| | |35| | | | |40| | | | |45| | | |
|Ile|Gly|Phe|Ile|Ser|Tyr|Ser|Gly|Ile|Thr|Asn|Tyr|Asn|Pro|Ser|Leu|
| |50| | | | |55| | | | |60| | | | |
|Gln|Gly|Arg|Val|Thr|Ile|Ser|Arg|Asp|Asn|Ser|Lys|Asn|Thr|Leu|Tyr|
|65| | | | |70| | | | |75| | | | |80|
|Leu|Gln|Met|Asn|Ser|Leu|Arg|Ala|Glu|Asp|Thr|Ala|Val|Tyr|Tyr|Cys|
| | | | |85| | | | |90| | | | |95| |
|Ala|Arg|Ser|Leu|Ala|Arg|Thr|Thr|Ala|Met|Asp|Tyr|Trp|Gly|Glu|Gly|
| | | |100| | | | |105| | | | |110| | |
|Thr|Leu|Val|Thr|Val|Ser|Ser|Ala|Ser|Thr|Lys|Gly|Pro|Ser|Val|Phe|
| | |115| | | | |120| | | | |125| | | |
|Pro|Leu|Ala|Pro|Ser|Ser|Lys|Ser|Thr|Ser|Gly|Gly|Thr|Ala|Ala|Leu|
| |130| | | | |135| | | | |140| | | | |
|Gly|Cys|Leu|Val|Lys|Asp|Tyr|Phe|Pro|Glu|Pro|Val|Thr|Val|Ser|Trp|
|145| | | | |150| | | | |155| | | | |160|
|Asn|Ser|Gly|Ala|Leu|Thr|Ser|Gly|Val|His|Thr|Phe|Pro|Ala|Val|Leu|
| | | | |165| | | | |170| | | | |175| |
|Gln|Ser|Ser|Gly|Leu|Tyr|Ser|Leu|Ser|Ser|Val|Val|Thr|Val|Pro|Ser|
| | | |180| | | | |185| | | | |190| | |
|Ser|Ser|Leu|Gly|Thr|Gln|Thr|Tyr|Ile|Cys|Asn|Val|Asn|His|Lys|Pro|
| | |195| | | | |200| | | | |205| | | |
|Ser|Asn|Thr|Lys|Val|Asp|Lys|Lys|Val|Glu|Pro|Lys|Ser|Cys|Asp|Lys|
| |210| | | | |215| | | | |220| | | | |
|Thr|His|Thr|Cys|Pro|Pro|Cys|Pro|Ala|Pro|Glu|Leu|Leu|Gly|Gly|Pro|
|225| | | | |230| | | | |235| | | | |240|
|Ser|Val|Phe|Leu|Phe|Pro|Pro|Lys|Pro|Lys|Asp|Thr|Leu|Met|Ile|Ser|
| | | | |245| | | | |250| | | | |255| |
|Arg|Thr|Pro|Glu|Val|Thr|Cys|Val|Val|Val|Asp|Val|Ser|His|Glu|Asp|
| | | |260| | | | |265| | | | |270| | |
|Pro|Glu|Val|Lys|Phe|Asn|Trp|Tyr|Val|Asp|Gly|Val|Glu|Val|His|Asn|
| | |275| | | | |280| | | | |285| | | |
|Ala|Lys|Thr|Lys|Pro|Arg|Glu|Glu|Gln|Tyr|Asn|Ser|Thr|Tyr|Arg|Val|
| |290| | | | |295| | | | |300| | | | |
|Val|Ser|Val|Leu|Thr|Val|Leu|His|Gln|Asp|Trp|Leu|Asn|Gly|Lys|Glu|
|305| | | | |310| | | | |315| | | | |320|
|Tyr|Lys|Cys|Lys|Val|Ser|Asn|Lys|Ala|Leu|Pro|Ala|Pro|Ile|Glu|Lys|
| | | | |325| | | | |330| | | | |335| |
|Thr|Ile|Ser|Lys|Ala|Lys|Gly|Gln|Pro|Arg|Glu|Pro|Gln|Val|Tyr|Thr|
| | | |340| | | | |345| | | | |350| | |
|Leu|Pro|Pro|Ser|Arg|Asp|Glu|Leu|Thr|Lys|Asn|Gln|Val|Ser|Leu|Thr|
| | |355| | | | |360| | | | |365| | | |

```
Cys Leu Val Lys Gly Phe Tyr Pro Ser Asp Ile Ala Val Glu Trp Glu
    370             375             380
Ser Asn Gly Gln Pro Glu Asn Asn Tyr Lys Thr Thr Pro Pro Val Leu
385             390             395             400
Asp Ser Asp Gly Ser Phe Phe Leu Tyr Ser Lys Leu Thr Val Asp Lys
            405             410             415
Ser Arg Trp Gln Gln Gly Asn Val Phe Ser Cys Ser Val Met His Glu
        420             425             430
Ala Leu His Asn His Tyr Thr Gln Glu Ser Leu Ser Leu Ser Pro
        435             440             445
```

METHOD FOR ALTERING PLASMA RETENTION AND IMMUNOGENICITY OF ANTIGEN-BINDING MOLECULE

CROSS-REFERENCE TO RELATED APPLICATIONS

This application is the National Stage of International Application Serial No. PCT/JP2012/058603, filed on Mar. 30, 2012, which claims the benefit of Application Ser. Nos. PCT/JP2011/001888, filed on Mar. 30, 2011, PCT/JP2011/072550, filed on Sep. 30, 2011, and PCT/JP2012/054624, filed on Feb. 24, 2012.

TECHNICAL FIELD

The present invention relates to methods for improving pharmacokinetics of an antigen-binding molecule in animals administered with the molecule and methods for reducing immune response to an antigen-binding molecule, by modifying the Fc region of the antigen-binding molecule which has an antigen-binding domain whose antigen-binding activity varies depending on ion concentration and an Fc region that has FcRn-binding activity in a neutral pH range. The present invention also relates to antigen-binding molecules that exhibit improved pharmacokinetics or reduced immune response in animals administered with the molecules. Furthermore, the present invention relates to methods for producing the antigen-binding molecules and to pharmaceutical compositions comprising as an active ingredient such an antigen-binding molecule.

BACKGROUND ART

Antibodies are drawing attention as pharmaceuticals as they are highly stable in plasma and have few side effects. At present, a number of IgG-type antibody pharmaceuticals are available on the market and many antibody pharmaceuticals are currently under development (Non-patent Documents 1 and 2). Meanwhile, various technologies applicable to second-generation antibody pharmaceuticals have been reported, including those that enhance effector function, antigen-binding ability, pharmacokinetics, and stability, and those that reduce the risk of immunogenicity (Non-patent Document 3). In general, the requisite dose of an antibody pharmaceutical is very high. This, in turn, has led to problems, such as high production cost, as well as the difficulty in producing subcutaneous formulations. In theory, the dose of an antibody pharmaceutical may be reduced by improving antibody pharmacokinetics or improving the affinity between antibodies and antigens.

The literature has reported methods for improving antibody pharmacokinetics using artificial substitution of amino acids in constant regions (Non-patent Documents 4 and 5). Similarly, affinity maturation has been reported as a technology for enhancing antigen-binding ability or antigen-neutralizing activity (Non-patent Document 6). This technology enables enhancement of antigen-binding activity by introduction of amino acid mutations into the CDR region of a variable region or such. The enhancement of antigen-binding ability enables improvement of in vitro biological activity or reduction of dosage, and further enables improvement of in vivo efficacy (Non-patent Document 7).

The antigen-neutralizing capacity of a single antibody molecule depends on its affinity. By increasing the affinity, an antigen can be neutralized by smaller amount of an antibody. Various methods can be used to enhance the antibody affinity (Non-patent Document 6). Furthermore, if the affinity could be made infinite by covalently binding the antibody to the antigen, a single antibody molecule could neutralize one antigen molecule (a divalent antibody can neutralize two antigen molecules). However, the stoichiometric neutralization of one antibody against one antigen (one divalent antibody against two antigens) is the limit of pre-existing methods, and thus it is impossible to completely neutralize antigen with the smaller amount of antibody than the amount of antigen. In other words, the affinity enhancing effect has a limit (Non-patent Document 9). To prolong the neutralization effect of a neutralizing antibody for a certain period, the antibody must be administered at a dose higher than the amount of antigen produced in the body during the same period. With the improvement of antibody pharmacokinetics or affinity maturation technology alone described above, there is thus a limitation in the reduction of the required antibody dose. Accordingly, in order to sustain antibody's antigen-neutralizing effect for a target period with smaller amount of the antibody than the amount of antigen, a single antibody must neutralize multiple antigens. An antibody that binds to an antigen in a pH-dependent manner has recently been reported as a novel method for achieving the above objective (Patent Document 1). The pH-dependent antigen-binding antibodies, which strongly bind to an antigen under the neutral conditions in plasma and dissociate from the antigen under acidic conditions in the endosome, can dissociate from the antigen in the endosome. When a pH-dependent antigen-binding antibody dissociates from the antigen is recycled to the plasma by FcRn, it can bind to another antigen again. Thus, a single pH-dependent antigen-binding antibody can bind to a number of antigens repeatedly.

In addition, plasma retention of an antigen is very short as compared to antibodies recycled via FcRn binding. When an antibody with such long plasma retention binds to the antigen, the plasma retention time of the antigen-antibody complex is prolonged to the same as that of the antibody. Thus, the plasma retention of the antigen is prolonged by binding to the antibody, and thus the plasma antigen concentration is increased.

IgG antibody has longer plasma retention time as a result of FcRn binding. The binding between IgG and FcRn is only observed under an acidic condition (pH 6.0). By contrast, the binding is almost undetectable under a neutral condition (pH 7.4). IgG antibody is taken up into cells in a nonspecific manner. The antibody returns to the cell surface by binding to endosomal FcRn under the endosomal acidic condition, and then is dissociated from FcRn under the plasma neutral condition. When the FcRn binding under the acidic condition is lost by introducing mutations into the IgG Fc region, absence of antibody recycling to the plasma from the endosome markedly impairs the antibody retention time in plasma. A reported method for improving the plasma retention of IgG antibody is to enhance the FcRn binding under acidic conditions. Amino acid mutations are introduced into the Fc region of IgG antibody to improve the FcRn binding under acidic conditions. This increases the efficiency of recycling to the plasma from the endosome, resulting in improvement of the plasma retention. An important requirement in the amino acid substitution is not to augment the FcRn binding under neutral conditions. If an IgG antibody binds to FcRn under neutral conditions, the antibody returns to the cell surface by binding to FcRn under the endosomal acidic condition is not dissociated from FcRn under the plasma neutral condition. In this case, the plasma retention is rather lost because the IgG antibody is not recycled to the plasma. For example, an IgG1 antibody modified by introducing amino acid substations so that the resulting antibody is capable of binding to mouse FcRn under a neutral condition (pH 7.4) was reported to exhibit very poor plasma retention when administered to mice (Non-patent Document 10). Furthermore, an IgG1 antibody has been modified by introducing amino acid substitutions so that the resulting antibody exhibits improved human FcRn binding under an acidic condition (pH 6.0) and at the same time becomes capable of binding to human FcRn under a neutral condition (pH 7.4) (Non-patent Documents 10, 11, and 12). The resulting antibody was reported to show neither improvement nor alteration in the plasma retention when administered to cynomolgus monkeys. Thus, the antibody engineering technology for improving antibody functions has only focused on the improvement of antibody plasma retention by enhancing the human FcRn binding under acidic conditions without enhancing it under a neutral condition (pH 7.4). To date, there is no report describing the advantage of improving the human FcRn binding under a neutral condition (pH 7.4) by introducing amino acid substitutions into the Fc region of an IgG antibody. Even if the antigen affinity of the antibody is improved, antigen elimination from the plasma cannot be enhanced. The above-described pH-dependent antigen-binding antibodies have been reported to be more effective as a method for enhancing antigen elimination from the plasma as compared to typical antibodies (Patent Document 1).

Thus, a single pH-dependent antigen-binding antibody binds to a number of antigens and is capable of facilitating antigen elimination from the plasma as compared to typical antibodies. Accordingly, the pH-dependent antigen-binding antibodies have effects not achieved by typical antibodies. However, to date, there is no report on antibody engineering methods for further improving the ability of pH-dependent antigen-binding antibodies to repeatedly bind to antigens and the effect of enhancing antigen elimination from the plasma.

Meanwhile, the immunogenicity of antibody pharmaceuticals is very important from the viewpoint of plasma retention, effectiveness, and safety when they are administered to humans.

It has been reported that if antibodies are produced against administered antibody pharmaceuticals in the human body, they cause undesirable effects such as accelerating elimination of the antibody pharmaceuticals from plasma, reducing effectiveness, and eliciting hypersensitivity reaction and affecting safety (Non-patent Document 13).

First of all, when taking into consideration the immunogenicity of antibody pharmaceuticals, one has to understand the in vivo functions of natural antibodies. First, most antibody pharmaceuticals are antibodies that belong to the IgG class, and the presence of Fcγ receptors (hereinafter also referred to as FcγR) as Fc receptors that function by binding to the Fc region of IgG antibodies is known. FcγRs are expressed on the cell membrane of dendritic cells, NK cells, macrophages, neutrophils, adipocytes, and others; and they are known to transduce activating or inhibitory intracellular signals into immune cells upon binding of an IgG Fc region. For the human FcγR protein family, isoforms FcγRIa, FcγRIIa, FcγRIIb, FcγRIIIa, and FcγRIIIb are known, and their allotypes have also been reported (Non-patent Document 14). Two allotypes have been reported for human FcγRIIa: Arg (hFcγRIIa(R)) and His (hFcγRIIa(H)) at position 131. Furthermore, two allotypes have been reported for human FcγRIIIa: Val (hFcγRIIIa(V)) and Phe (hFcγRIIIa(F)) at position 158. Meanwhile, for the mouse FcγR protein family, FcγRI, FcγRIIb, FcγRIII, and FcγRIV have been reported (Non-patent Document 15).

Human FcγRs include activating receptors FcγRIa, FcγRIIa, FcγRIIIa, and FcγRIIIb, and inhibitory receptor FcγRIIb. Likewise, mouse FcγRs include activating receptors FcγRI, FcγRIII, and FcγRIV, and inhibitory receptor FcγRIIb.

When activating FcγR is cross-linked with an immune complex, it phosphorylates immunoreceptor tyrosine-based activating motifs (ITAMs) contained in the intracellular domain or FcR common γ-chain (an interaction partner), activates a signal transducer SYK, and triggers inflammatory immune response by initiating an activation signal cascade (Non-patent Document 15).

It has been demonstrated that for the binding between an Fc region and FcγR, certain amino acid residues in the antibody hinge region and CH2 domain, and the sugar chain attached to the CH2 domain at Asn of position 297 in the EU numbering system are important (Non-patent Documents 15 to 17). With a focus on antibodies introduced with mutations at the sites described above, mutants with varying FcγR-binding properties have been investigated, and Fc region mutants that have higher affinity for activating FcγRs were obtained (Patent Documents 2 to 5).

Meanwhile, FcγRIIb, which is an inhibitory FcγR, is the only FcγR expressed on B cells (Non-patent Document 18). Interaction of the antibody Fc region with FcγRIIb has been reported to suppress the primary immune response of B cells (Non-patent Document 19). Furthermore, it is reported that when FcγRIIb on B cells and a B cell receptor (BCR) are cross-linked via an immune complex in blood, B cell activation is suppressed, and antibody production by B cells is suppressed (Non-patent Document 20). In this immunosuppressive signal transduction mediated by BCR and FcγRIIb, the immunoreceptor tyrosine-based inhibitory motif (ITIM) contained in the intracellular domain of FcγRIIb is necessary (Non-patent Documents 21 and 22). This immunosuppressive action is caused by ITIM phosphorylation. As a result of phosphorylation, SH2-containing inositol polyphosphate 5-phosphatase (SHIP) is recruited, transduction of other activating FcγR signal cascades is inhibited, and inflammatory immune response is suppressed (Non-patent Document 23).

Because of this property, FcγRIIb is promising as a means for directly reducing the immunogenicity of antibody pharmaceuticals. Exendin-4 (Ex4) is a foreign protein for mice, but antibodies are not produced even when a fused molecule with IgG1 (Ex4/Fc) is administered to mice. Meanwhile, antibodies are produced against Ex4 upon administration of the (Ex4/Fc mut) molecule which is obtained by modifying Ex4/Fc to not bind FcγRIIb on B cells (Non-patent Document 24). This result suggests that Ex4/Fc binds to FcγRIIb on B cells and inhibits the production of mouse antibodies against Ex4 in B cells.

Furthermore, FcγRIIb is also expressed on dendritic cells, macrophages, activated neutrophils, mast cells, and basophils. FcγRIIb inhibits the functions of activating FcγR such as phagocytosis and release of inflammatory cytokines in these cells, and suppresses inflammatory immune responses (Non-patent Document 25).

The importance of immunosuppressive functions of FcγRIIb has been elucidated so far through studies using FcγRIIb knockout mice. There are reports that in FcγRIIb knockout mice, humoral immunity is not appropriately regulated (Non-Patent Document 26), sensitivity towards collagen-induced arthritis (CIA) is increased (Non-patent Document 27), lupus-like symptoms are presented, and Goodpasture's syndrome-like symptoms are presented (Non-patent Document 28).

Furthermore, regulatory inadequacy of FcγRIIb has been reported to be related to human autoimmnue diseases. For example, the relationship between genetic polymorphism in the transmembrane region and promoter region of FcγRIIb, and the frequency of development of systemic lupus erythematosus (SLE) (Non-patent Documents 29, 30, 31, 32, and 33), and decrease of FcγRIIb expression on the surface of B cells in SLE patients (Non-patent Document 34 and 35) have been reported.

From mouse models and clinical findings as such, FcγRIIb is considered to play the role of controlling autoimmune diseases and inflammatory diseases mainly through involvement with B cells, and it is a promising target molecule for controlling autoimmune diseases and inflammatory diseases.

IgG1, mainly used as a commercially available antibody pharmaceutical, is known to bind not only to FcγRIIb, but also strongly to activating FcγR (Non-patent Document 36). It may be possible to develop antibody pharmaceuticals having greater immunosuppressive properties compared with those of IgG1, by utilizing an Fc region with enhanced FcγRIIb binding, or improved FcγRIIb-binding selectivity compared with activating FcγR. For example, it has been suggested that the use of an antibody having a variable region that binds to BCR and an Fc with enhanced FcγRIIb binding may inhibit B cell activation (Non-patent Document 37).

However, FcγRIIb shares 93% sequence identity in the extracellular region with that of FcγRIIa which is one of the activating FcγRs, and they are very similar structurally. There are allotypes of FcγRIIa, H type and R type, in which the amino acid at position 131 is His (type H) or Arg (type R), and yet each of them reacts differently with the antibodies (Non-patent Document 38). Therefore, to produce an Fc region that specifically binds to FcγRIIb, the most difficult problem may be conferring to the antibody Fc region with the property of selectively improved FcγRIIb-binding activity, which involves decreasing or not increasing the binding activity towards each allotype of FcγRIIa, while increasing the binding activity towards FcγRIIb.

There is a reported case on enhancement of the specificity of FcγRIIb binding by introducing amino acid mutations into the Fc region (Non-patent Document 39). According to this document, mutants were constructed so that when compared to IgG1, they retain their binding to FcγRIIb more than to FcγRIIa which has two polymorphic forms. However, in comparison to natural IgG1, all mutants reported to have improved specificity to FcγRIIb in this document were found to have impaired FcγRIIb binding. Thus, it is considered difficult for the mutants to induce an FcγRIIb-mediated immunosuppressive reaction more strongly than IgG1.

There is also a report on augmentation of the FcγRIIb binding (Non-patent Document 37). In this document, the FcγRIIb binding was augmented by introducing mutations such as S267E/L328F, G236D/S267E, and S239D/S267E into the antibody Fc region. Among them, an antibody introduced with the S267E/L328F mutation bound most strongly to FcγRIIb. This mutant was shown to retain the binding to FcγRIa and to FcγRIIa type H at levels comparable to those of natural IgG1. Even if FcγRIIb binding was augmented relative to IgG1, only the augmentation of FcγRIIa binding but not the augmentation of FcγRIIb binding is expected to have an effect on cells such as platelets which express FcγRIIa but not FcγRIIb (Non-patent Document 25). For example, it has been reported that platelets are activated via an FcγRIIa-dependent mechanism in systemic erythematosus and platelet activation is correlated with the severity (Non-patent Document 40). According to another report, the above-described mutation enhanced the binding to FcγRIIa type R several hundred-fold to the same degree as the FcγRIIb binding, and did not improve the binding specificity for FcγRIIb when compared to FcγRIIa type R (Patent Document 17). Furthermore, in cell types that express both FcγRIIa and FcγRIIb such as dendritic cells and macrophages, the binding selectivity for FcγRIIb relative to FcγRIIa is essential for the transduction of inhibitory signals; however, such selectivity could not be achieved for type R.

FcγRIIa type H and type R are found at almost the same rate among Caucasian and African-American people (Non-patent Documents 41 and 42). Hence, there are certain restrictions on the use of antibodies with augmented binding to FcγRIIa type R to treat autoimmune diseases. Even if the FcγRIIb binding was augmented as compared to activating FcγRs, the fact that the binding to any polymorphic form of FcγRIIa is augmented cannot be overlooked from the standpoint of its use as a therapeutic agent for autoimmune diseases.

When antibody pharmaceuticals targeting FcγRIIb are produced to treat autoimmune diseases, it is important that the activity of Fc-mediated binding to any polymorphic forms of FcγRIIa is not increased or is preferably reduced, and that the binding activity to FcγRIIb is augmented as compared to natural IgG. However, there have been no reports of mutants having the above-described properties, and thus there is a demand to develop such mutants.

Prior art documents of the present invention are shown below.

PRIOR ART DOCUMENTS

Patent Documents

[Patent Document 1] WO 2009/125825
[Patent Document 2] WO 2000/042072
[Patent Document 3] WO 2006/019447
[Patent Document 4] WO 2004/099249
[Patent Document 5] WO 2004/029207
[Non-patent Documents]
[Non-patent Document 1] Janice M Reichert, Clark J Rosensweig, Laura B Faden & Matthew C Dewitz, Monoclonal antibody successes in the clinic., Nat. Biotechnol. (2005) 23, 1073-1078
[Non-patent Document 2] Pavlou A K, Belsey M J., The therapeutic antibodies market to 2008., Eur J Pharm Biopharm. (2005) 59 (3), 389-396
[Non-patent Document 3] Kim S J, Park Y, Hong H J., Antibody engineering for the development of therapeutic antibodies., Mol Cells. (2005) 20 (1), 17-29
[Non-patent Document 4] Hinton P R, Xiong J M, Johlfs M G, Tang M T, Keller S, Tsurushita N., An engineered human IgG1 antibody with longer serum half-life., J. Immunol. (2006) 176 (1), 346-356
[Non-patent Document 5] Ghetie V, Popov S, Borvak J, Radu C, Matesoi D, Medesan C, Ober R J, Ward E S., Increasing the serum persistence of an IgG fragment by random mutagenesis., Nat. Biotechnol. (1997) 15 (7), 637-640
[Non-patent Document 6] Rajpal A, Beyaz N, Haber L, Cappuccilli G, Yee H, Bhatt R R, Takeuchi T, Lerner R A, Crea R., A general method for greatly improving the affinity of antibodies by using combinatorial libraries., Proc. Natl. Acad. Sci. U.S.A. (2005) 102 (24), 8466-8471

[Non-patent Document 7] Wu H, Pfarr D S, Johnson S, Brewah Y A, Woods R M, Patel N K, White W I, Young J F, Kiener P A., Development of Motavizumab, an Ultra-potent Antibody for the Prevention of Respiratory Syncytial Virus Infection in the Upper and Lower Respiratory Tract., J. Mol. Biol. (2007) 368, 652-665

[Non-patent Document 8] Hanson C V, Nishiyama Y, Paul S., Catalytic antibodies and their applications., Curr Opin Biotechnol. (2005) 16 (6), 631-636

[Non-patent Document 9] Rathanaswami P, Roalstad S, Roskos L, Su Q J, Lackie S, Babcook J., Demonstration of an in vivo generated sub-picomolar affinity fully human monoclonal antibody to interleukin-8., Biochem. Biophys. Res. Commun. (2005) 334 (4), 1004-1013

[Non-patent Document 10] Dall'Acqua W F, Woods R M, Ward E S, Palaszynski S R, Patel N K, Brewah Y A, Wu H, Kiener P A, Langermann S., Increasing the affinity of a human IgG1 for the neonatal Fc receptor: biological consequences., J. Immunol. (2002) 169 (9), 5171-5180

[Non-patent Document 11] Yeung Y A, Leabman M K, Marvin J S, Qiu J, Adams C W, Lien S, Starovasnik M A, Lowman H B., Engineering human IgG1 affinity to human neonatal Fc receptor: impact of affinity improvement on pharmacokinetics in primates., J. Immunol. (2009) 182 (12), 7663-7671

[Non-patent Document 12] Datta-Mannan A, Witcher D R, Tang Y, Watkins J, Wroblewski V J., Monoclonal antibody clearance. Impact of modulating the interaction of IgG with the neonatal Fc receptor., J. Biol. Chem. (2007) 282 (3), 1709-1717

[Non-patent Document 13] Niebecker R, Kloft C., Safety of therapeutic monoclonal antibodies., Curr. Drug Saf. (2010) 5 (4), 275-286

[Non-patent Document 14] Jefferis R, Lund J., Interaction sites on human IgG-Fc for FcgammaR: current models., Immunol. Lett. (2002) 82, 57-65

[Non-patent Document 15] Nimmerjahn F, Ravetch J V., Fcgamma receptors as regulators of immune responses., Nat. Rev. Immunol. (2008) 8 (1), 34-47

[Non-patent Document 16] M. Clark, Antibody Engineering IgG Effector Mechanisms., Chemical Immunology (1997), 65, 88-110

[Non-patent Document 17] Greenwood J, Clark M, Waldmann H., Structural motifs involved in human IgG antibody effector functions., Eur. J. Immunol. (1993) 23, 1098-1104

[Non-patent Document 18] Amigorena S, Bonnerot C, Choquet D, Fridman W H, Teillaud J L., Fc gamma RII expression in resting and activated B lymphocytes., Eur. J. Immunol. (1989) 19, 1379-1385

[Non-patent Document 19] Nicholas R, Sinclair S C, Regulation of the immune response. I. Reduction in ability of specific antibody to inhibit long-lasting IgG immunological priming after removal of the Fc fragment., J. Exp. Med. (1969) 129, 1183-1201

[Non-patent Document 20] Heyman B., Feedback regulation by IgG antibodies., Immunol. Lett. (2003) 88, 157-161

[Non-patent Document 21] S Amigorena, C Bonnerot, Drake, J R, D Choquet, W Hunziker, J G Guillet, P Webster, C Sautes, I Mellman, and W H Fridman, Cytoplasmic domain heterogeneity and functions of IgG Fc receptors in B lymphocytes., Science (1992) 256, 1808-1812

[Non-patent Document 22] Muta, T., Kurosaki, T., Misulovin, Z., Sanchez, M., Nussenzweig, M. C., and Ravetch, J. V., A 13-amino-acid motif in the cytoplasmic domain of FcγRIIB modulates B-cell receptor signaling., Nature (1994) 368, 70-73

[Non-patent Document 23] Ravetch J V, Lanier L L., Immune inhibitory receptors., Science (2000) 290, 84-89

[Non-patent Document 24] Liang Y, Qiu H, Glinka Y, Lazarus A H, Ni H, Prud'homme G J, Wang Q., Immunity against a therapeutic xenoprotein/Fc construct delivered by gene transfer is reduced through binding to the inhibitory receptor FcγRIIb., J. Gene Med. (2011) doi: 10.1002/jgm.1598

[Non-patent Document 25] Smith K G, Clatworthy M R., FcgammaRIIB in autoimmunity and infection: evolutionary and therapeutic implications., Nat. Rev. Immunol. (2010) 10, 328-343

[Non-patent Document 26] Wernersson S, Karlsson M C, Dahlström J, Mattsson R, Verbeek J S, Heyman B., IgG-mediated enhancement of antibody responses is low in Fc receptor gamma chain-deficient mice and increased in Fc gamma Rh-deficient mice., J. Immunol. (1999) 163, 618-622

[Non-patent Document 27] Joachim L. Schultze, Sabine Michalak, Joel Lowne, Adam Wong, Maria H. Gilleece, John G. Gribben, and Lee M. Nadler, Human Non-Germinal Center B Cell Interleukin (IL)-12 Production Is Primarily Regulated by T Cell Signals CD40 Ligand, Interferon γ, and IL-10: Role of B Cells in the Maintenance of T Cell Responses., J. Exp. Med. (1999) 189, 187-194

[Non-patent Document 28] Nakamura, A., Yuasa, T., Ujike, A., Ono, M., Nukiwa, T., Ravetch, J. V., Takai, T., Fcγ receptor HB-deficient mice develop Goodpasture's syndrome upon immunization with type IV collagen: A novel murine model for autoimmune glomerular basement membrane disease., J. Exp. Med. (2000) 191, 899-906

[Non-patent Document 29] Blank M C, Stefanescu R N, Masuda E, Marti F, King P D, Redecha P B, Wurzburger R J, Peterson M G, Tanaka S, Pricop L., Decreased transcription of the human FCGR2B gene mediated by the −343 G/C promoter polymorphism and association with systemic lupus erythematosus., Hum. Genet. (2005) 117, 220-227

[Non-patent Document 30] Olferiev M, Masuda E, Tanaka S, Blank M C, Pricop L., The Role of Activating Protein 1 in the Transcriptional Regulation of the Human FCGR2B Promoter Mediated by the −343 G->C Polymorphism Associated with Systemic Lupus Erythematosus., J. Biol. Chem. (2007) 282, 1738-1746

[Non-patent Document 31] Lv J, Yang Y, Zhou X, Yu L, Li R, Hou P, Zhang H., FCGR3B copy number variation is not associated with lupus nephritis in a Chinese population., Arthritis Rheum. (2006) 54, 3908-3917

[Non-patent Document 32] Floto R A, Clatworthy M R, Heilbronn K R, Rosner D R, MacAry P A, Rankin A, Lehner P J, Ouwehand W H, Allen J M, Watkins N A, Smith K G., Loss of function of a lupus-associated FcgammaRIIb polymorphism through exclusion from lipid rafts., Nat. Med. (2005) 11, 1056-1058

[Non-patent Document 33] Li D H, Tung J W, Tamer I H, Snow A L, Yukinari T, Ngernmaneepothong R, Martinez O M, Parnes J R., CD72 Down-Modulates BCR-Induced Signal Transduction and Diminishes Survival in Primary Mature B Lymphocytes., J. Immunol. (2006) 176, 5321-5328

[Non-patent Document 34] Mackay M, Stanevsky A, Wang T, Aranow C, Li M, Koenig S, Ravetch J V, Diamond B., Selective dysregulation of the FcgammaIIB receptor on memory B cells in SLE., J. Exp. Med. (2006) 203, 2157-2164

[Non-patent Document 35] Su K, Yang H, Li X, Li X, Gibson A W, Cafardi J M, Zhou T, Edberg J C, Kimberly R P., Expression profile of FcgammaRIIb on leukocytes and its dysregulation in systemic lupus erythematosus., J. Immunol. (2007) 178, 3272-3280

[Non-patent Document 36] Bruhns P, Iannascoli B, England P, Mancardi D A, Fernandez N, Jorieux S, Daëron M., Specificity and affinity of human Fcgamma receptors and their polymorphic variants for human IgG subclasses., Blood (2009) 113, 3716

[Non-patent Document 37] Chu S Y, Vostiar I, Karki S, Moore G L, Lazar G A, Pong E, Joyce P F, Szymkowski D E, Desjarlais J R, Inhibition of B cell receptor-mediated activation of primary human B cells by coengagement of CD19 and FcgammaRIIb with Fc-engineered antibodies., Mol. Immunol. (2008) 45, 3926-3933

[Non-patent Document 38] Warmerdam P A, van de Winkel J G, Gosselin E J, Capel P J., Molecular basis for a polymorphism of human Fc gamma receptor II (CD32)., J. Exp. Med. (1990) 172, 19-25

[Non-patent Document 39] Armour, K L, van de Winkel, J G, Williamson, L M, Clark, M R., Differential binding to human FcgammaRIIa and FcgammaRIIb receptors by human IgG wildtype and mutant antibodies., Mol. Immunol. (2003) 40, 585-593

[Non-patent Document 40] Science Translational Medicine (2010) Vol. 2, Issue 47, p. 47ra63

[Non-patent Document 41] Salmon J E, Millard S, Schachter L A, Arnett F C, Ginzler E M, Gourley M F, Ramsey-Goldman R, Peterson M G, Kimberly R P., Fc gamma RIIA alleles are heritable risk factors for lupus nephritis in African Americans., J. Clin. Invest. (1996) 97, 1348-1354

[Non-patent Document 42] Manger K, Repp R, Spriewald B M, Rascu A, Geiger A, Wassmuth R, Westerdaal N A, Wentz B, Manger B, Kalden J R, van de Winkel J G., Fcgamma receptor IIa polymorphism in Caucasian patients with systemic lupus erythematosus: association with clinical symptoms., Arthritis Rheum. (1998) 41, 1181-1189

[Non-patent Document 43] Qiao S W, Kobayashi K, Johansen F E, Sollid L M, Andersen J T, Milford E, Roopenian D C, Lencer W I, Blumberg R S., Dependence of antibody-mediated presentation of antigen on FcRn., Proc. Natl. Acad. Sci. (2008) 105 (27) 9337-9342

[Non-patent Document 44] Mi W, Wanjie S, Lo S T, Gan Z, Pickl-Herk B, Ober R J, Ward E S., Targeting the neonatal fc receptor for antigen delivery using engineered fc fragments., J. Immunol. (2008) 181 (11), 7550-7561

SUMMARY OF THE INVENTION

Problems to be Solved by the Invention

In addition to the involvement of activating FcγR described above, the so-called antigen presentation mechanism is very important as a factor in the induction of immune response to administered antibody pharmaceuticals. Antigen presentation refers to an immunological mechanism in which after intracellular internalization and degradation of foreign antigens such as bacteria, and endogenous antigens, antigen presenting cells such as macrophages and dendritic cells present portions of the antigens on cell surface. The presented antigens are recognized by T cells and others, and activate both cellular and humoral immunity.

The pathway of antigen presentation by dendritic cells involves internalization of an antigen as an immune complex (a complex formed between a multivalent antibody and an antigen) into cells, degradation in the lysosome, and presentation of the resulting peptides derived from the antigen by MHC class II molecules. FcRn plays an important role in this pathway; and it has been reported that when using FcRn-deficient dendritic cells or immune complexes that are incapable of binding to FcRn, antigen presentation and resultant T cell activation do not occur (Non-patent Document 43).

When normal animals are administered with an antigen protein as a foreign substance, they often produce antibodies against the administered antigen protein. For example, when mice are administered with a soluble human IL-6 receptor as a foreign protein, they produce mouse antibodies against the soluble human IL-6 receptor. On the other hand, even when mice are administered with a human IgG1 antibody as a foreign protein, they hardly produce mouse antibodies against the human IgG1 antibody. This difference suggests that the rate of elimination of the administered foreign protein from plasma might be an influence.

As described in Reference Example 4, a human IgG1 antibody has the ability to bind mouse FcRn under acidic conditions, and thus, like mouse antibodies, a human IgG1 antibody is recycled via mouse FcRn when incorporated into endosomes. For this reason, when a human IgG1 antibody is administered to normal mice, elimination of the antibody from plasma is very slow. Meanwhile, a soluble human IL-6 receptor is not recycled via mouse FcRn and is thus eliminated rapidly after administration. On the other hand, as described in Reference Example 4, the production of mouse antibodies against a soluble human IL-6R antibody is observed in normal mice administered with a soluble human IL-6 receptor, while the production of mouse antibodies against a human IgG1 antibody is not found in normal mice administered with a human IgG1 antibody. In other words, a soluble human IL-6 receptor that is eliminated rapidly is more immunogenic in mice than a human IgG1 antibody that is eliminated slowly.

Part of the pathway for elimination of these foreign proteins (soluble human IL-6 receptor and human IgG1 antibody) from plasma is assumed to be uptake by antigen-presenting cells. The foreign proteins incorporated into antigen-presenting cells associate with MHC class II molecules after intracellular processing, and are transported onto the cell membrane. Then, the presentation of an antigen to antigen-specific T cells (for example, T cells that are specifically responsive to a soluble human IL-6 receptor or human IgG1 antibody) induces activation of antigen-specific T cells. In this context, it is presumably difficult for a foreign protein that is eliminated slowly from plasma be processed in antigen-presenting cells, and as a result antigen presentation to antigen-specific T cells is unlikely to occur.

The binding to FcRn under neutral conditions is known to adversely affect antibody retention in plasma. Once an IgG antibody is bound to FcRn under neutral conditions, even if it is returned to the cell surface under endosomal acidic conditions as a result of binding to FcRn, the IgG antibody cannot be recycled to plasma without dissociation from FcRn under the neutral condition in plasma; and this adversely impairs plasma retention. For example, according to a report (Non-patent Document 10), when an antibody which becomes capable of binding to mouse FcRn under a neutral condition (pH 7.4) as a result of amino acid substitutions introduced into IgG1 was administered to mice, the retention of the antibody in plasma worsened. Meanwhile, it has been reported that when an antibody that has been confirmed to bind human FcRn under a neutral condition (pH 7.4) was administered to Cynomolgus monkeys, the antibody retention in plasma was not prolonged but rather remained unaltered (Non-patent Documents 10 to 12). When the retention time of an antigen-binding molecule in plasma is shortened due to augmentation of its binding to FcRn under a neutral condition (pH 7.4), immunogenicity may become higher due to accelerated elimination of the antigen-binding molecule.

Furthermore, FcRn has been reported to be expressed in antigen-presenting cells and involved in antigen presentation. According to a report published on the immunogenicity assessment of a protein resulting from fusion of myelin basic protein (MBP), although not an antigen-binding molecule, to the Fc region of mouse IgG1 (hereinafter abbreviated as MBP-Fc), T cells that are responsive in an MBP-Fc-specific manner are activated and proliferated when cultured in the presence of MBP-Fc. In this aspect, it is known that T cell activation is intensified in vitro by adding to the Fc region of MBP-Fc a modification that enhances the FcRn binding to increase incorporation into antigen-presenting cells via FcRn expressed on the antigen-presenting cells. It has been reported that regardless of the accelerated elimination from plasma as a result of adding a modification that enhances the binding to FcRn, in vivo T cell activation has been reported to be rather impaired (Non-patent Document 44). Thus, immunogenicity is not necessarily enhanced when the elimination is accelerated by augmenting the binding to FcRn.

As described above, there has not been sufficient research to understand how augmentation of the FcRn binding of an antigen-binding molecule that has an FcRn-binding domain under a neutral condition (pH 7.4) influences the plasma retention and immunogenicity of the antigen-binding molecule. Thus, there is no reported method for improving the plasma retention and immunogenicity of antigen-binding molecules having FcRn-binding activity under a neutral condition (pH 7.4).

It has been revealed that antigen elimination from plasma can be accelerated by the use of an antigen-binding molecule that comprises the antigen-binding domain of an antigen-binding molecule whose antigen-binding activity varies depending on ion concentration and an Fc region that has FcRn-binding activity in a neutral pH range. However, sufficient studies have not been conducted to understand how augmentation of the FcRn-binding activity of an Fc region in a neutral pH range influences the retention of antigen-binding molecules in plasma and immunogenicity. During studies, the present inventors found a problem that as a result of augmentation of the FcRn-binding activity of the Fc region in a neutral pH range, the retention time of the antigen-binding molecule in plasma is reduced (the pharmacokinetics is worsened) and the immunogenicity of the antigen-binding molecule is elevated (the immune response to the antigen-binding molecule is aggravated).

The present invention was achieved in view of the circumstances described above. An objective of the present invention is to provide methods for improving the pharmacokinetics in animals administered with an antigen-binding molecule by modifying the Fc region of the antigen-binding molecule which comprises the antigen-binding domain of an antigen-binding molecule whose antigen-binding activity varies depending on ion concentration and an Fc region that has FcRn-binding activity in a neutral pH range. Another objective of the present invention is to provide methods for reducing the immune response to an antigen-binding molecule by modifying the Fc region of the antigen-binding molecule which comprises the antigen-binding domain of an antigen-binding molecule whose antigen-binding activity varies depending on ion concentration and an Fc region that has FcRn-binding activity in a neutral pH range. Still another objective of the present invention is to provide antigen-binding molecules that exhibit improved pharmacokinetics or impaired in vivo immune response when administered to animals. Yet another objective of the present invention is to provide methods for producing such antigen-binding molecules as well as pharmaceutical compositions comprising as an active ingredient the antigen-binding molecules.

Means for Solving the Problems

The present inventors conducted dedicated studies to achieve the above-described objectives. As a result, the present inventors revealed that an antigen-binding molecule that comprises the antigen-binding domain of an antigen-binding molecule whose antigen-binding activity varies depending on ion concentration and an Fc region that has FcRn-binding activity in a neutral pH range formed a hetero complex consisting of four molecules: antigen-binding molecule/two molecules of FcRn/activating Fcγ receptor (FIG. 48). The present inventors also demonstrated that the tetramer formation adversely affected the pharmacokinetics and immune response. The present inventors demonstrated that the pharmacokinetics of an antigen-binding molecule was improved by modifying the Fc region of such antigen-binding molecule into an Fc region that in a neutral pH range does not form a hetero tetramer complex comprising two molecules of FcRn and an activating Fcγ receptor. The present inventors also demonstrated that the immune response in animals administered with an antigen-binding molecule could be altered by modifying the Fc region of such an antigen-binding molecule into an Fc region that in a neutral pH range does not form a tetramer complex comprising two molecules of FcRn and an activating Fcγ receptor. The present inventors also demonstrated that immune response to the antigen-binding molecule was reduced by modification into an Fc region that in a neutral pH range does not form a hetero tetramer complex comprising two molecules of FcRn and an activating Fcγ receptor. Furthermore, the present inventors discovered antigen-binding molecules and methods for producing them, and in addition found that when administered, pharmaceutical compositions comprising as an active ingredient such an antigen-binding molecule or an antigen-binding molecule produced by a production method of the present invention had superior properties such as improved pharmacokinetics and reduction of immune response in the administered living organism as compared to conventional antigen-binding molecules; and thereby completed the present invention.

More specifically, the present invention provides the following.

[1] A method of either (a) or (b) below, wherein the method comprises modifying the Fc region of an antigen-binding molecule comprising an antigen-binding domain whose antigen-binding activity varies depending on ion concentration and an Fc region that has FcRn-binding activity in a neutral pH range into an Fc region that does not form a hetero complex comprising two molecules of FcRn and one molecule of activating Fcγ receptor in a neutral pH range:

(a) a method for improving pharmacokinetics of an antigen-binding molecule; and (b) a method for reducing immunogenicity of an antigen-binding molecule.

[2] The method of [1], wherein the modification into an Fc region that does not form said hetero complex comprises modifying the Fc region into an Fc region whose binding activity to an activating Fcγ receptor is lower than the binding activity of an Fc region of native human IgG to the activating Fcγ receptor.
[3] The method of [1] or [2], wherein the activating Fcγ receptor is human FcγRIa, human FcγRIIa(R), human FcγRIIa(H), human FcγRIIIa(V), or human FcγRIIIa(F).
[4] The method of any one of [1] to [3], which comprises substituting an amino acid of said Fc region at any one or more amino acids of positions 235, 237, 238, 239, 270, 298, 325, and 329 as indicated by EU numbering.
[5] The method of [4], which comprises substituting an amino acid of said Fc region as indicated by EU numbering at any one or more of:
the amino acid of position 234 with any one of Ala, Arg, Asn, Asp, Gln, Glu, Gly, His, Lys, Met, Phe, Pro, Ser, Thr, and Trp;
the amino acid of position 235 with any one of Ala, Asn, Asp, Gln, Glu, Gly, His, Ile, Lys, Met, Pro, Ser, Thr, Val, and Arg;
the amino acid of position 236 with any one of Arg, Asn, Gln, His, Leu, Lys, Met, Phe, Pro, and Tyr;
the amino acid of position 237 with any one of Ala, Asn, Asp, Gln, Glu, His, Ile, Leu, Lys, Met, Pro, Ser, Thr, Val, Tyr, and Arg;
the amino acid of position 238 with any one of Ala, Asn, Gln, Glu, Gly, His, Ile, Lys, Thr, Trp, and Arg;
the amino acid of position 239 with any one of Gln, His, Lys, Phe, Pro, Trp, Tyr, and Arg;
the amino acid of position 265 with any one of Ala, Arg, Asn, Gln, Gly, His, Ile, Leu, Lys, Met, Phe, Ser, Thr, Trp, Tyr, and Val;
the amino acid of position 266 with any one of Ala, Arg, Asn, Asp, Gln, Glu, Gly, His, Lys, Phe, Pro, Ser, Thr, Trp, and Tyr;
the amino acid of position 267 with any one of Arg, His, Lys, Phe, Pro, Trp, and Tyr;
the amino acid of position 269 with any one of Ala, Arg, Asn, Gln, Gly, His, Ile, Leu, Lys, Met, Phe, Pro, Ser, Thr, Trp, Tyr, and Val;
the amino acid of position 270 with any one of Ala, Arg, Asn, Gln, Gly, His, Ile, Leu, Lys, Met, Phe, Pro, Ser, Thr, Trp, Tyr, and Val;
the amino acid of position 271 with any one of Arg, His, Phe, Ser, Thr, Trp, and Tyr;
the amino acid of position 295 with any one of Arg, Asn, Asp, Gly, His, Phe, Ser, Trp, and Tyr;
the amino acid of position 296 with any one of Arg, Gly, Lys, and Pro;
the amino acid of position 297 with Ala;
the amino acid of position 298 with any one of Arg, Gly, Lys, Pro, Trp, and Tyr;
the amino acid of position 300 with any one of Arg, Lys, and Pro;
the amino acid of position 324 with Lys or Pro;
the amino acid of position 325 with any one of Ala, Arg, Gly, His, Ile, Lys, Phe, Pro, Thr, Trp, Tyr, and Val;
the amino acid of position 327 with any one of Arg, Gln, His, Ile, Leu, Lys, Met, Phe, Pro, Ser, Thr, Trp, Tyr, and Val;
the amino acid of position 328 with any one of Arg, Asn, Gly, His, Lys, and Pro;
the amino acid of position 329 with any one of Asn, Asp, Gln, Glu, Gly, His, Ile, Leu, Lys, Met, Phe, Ser, Thr, Trp, Tyr, Val, and Arg;
the amino acid of position 330 with Pro or Ser;

the amino acid of position 331 with any one of Arg, Gly, and Lys; or
the amino acid of position 332 with any one of Arg, Lys, and Pro.
[6] The method of [1], wherein the modification into an Fc region that does not form said hetero complex comprises modifying the Fc region into an Fc region that has a higher binding activity to an inhibitory Fcγ receptor than to an activating Fcγ receptor.
[7] The method of [6], wherein the inhibitory Fcγ receptor is human FcγRIIb.
[8] The method of [6] or [7], wherein the activating Fcγ receptor is human FcγRIa, human FcγRIIa(R), human FcγRIIa(H), human FcγRIIIa(V), or human FcγRIIIa(F).
[9] The method of any one of [6] to [8], which comprises substituting the amino acid of position 238 or 328 indicated by EU numbering.
[10] The method of [9], which comprises substituting Asp for the amino acid of position 238 or Glu for the amino acid of position 328 indicated by EU numbering.
[11] The method of [9] or [10], which comprises substituting any one or more amino acids of:
the amino acid of position 233 with Asp;
the amino acid of position 234 with Trp or Tyr;
the amino acid of position 237 with any one of Ala, Asp, Glu, Leu, Met, Phe, Trp, and Tyr;
the amino acid of position 239 with Asp;
the amino acid of position 267 with any one of Ala, Gln, and Val;
the amino acid of position 268 with any one of Asn, Asp, and Glu;
the amino acid of position 271 with Gly;
the amino acid of position 326 with any one of Ala, Asn, Asp, Gln, Glu, Leu, Met, Ser, and Thr;
the amino acid of position 330 with any one of Arg, Lys, and Met;
the amino acid of position 323 with any one of Ile, Leu, and Met; and
the amino acid of position 296 with Asp; wherein the amino acids are indicated by EU numbering.
[12] The method of any one of [1] to [11], wherein the Fc region comprises one or more amino acids that are different from amino acids of the native Fc region at any of amino acid positions 237, 248, 250, 252, 254, 255, 256, 257, 258, 265, 286, 289, 297, 298, 303, 305, 307, 308, 309, 311, 312, 314, 315, 317, 332, 334, 360, 376, 380, 382, 384, 385, 386, 387, 389, 424, 428, 433, 434, and 436 of said Fc region as indicated by EU numbering.
[13] The method of [12], wherein the amino acids of said Fc region indicated by EU numbering are a combination of one or more of:
Met at amino acid position 237;
Ile at amino acid position 248;
any one of Ala, Phe, Ile, Met, Gln, Ser, Val, Trp, and Tyr at amino acid position 250;
any one of Phe, Trp, and Tyr at amino acid position 252;
Thr at amino acid position 254;
Glu at amino acid position 255;
any one of Asp, Asn, Glu, and Gln at amino acid position 256;
any one of Ala, Gly, Ile, Leu, Met, Asn, Ser, Thr, and Val at amino acid position 257;
His at amino acid position 258;
Ala at amino acid position 265;
Ala or Glu at amino acid position 286;
His at amino acid position 289;
Ala at amino acid position 297;

Gly at amino acid position 298;
Ala at amino acid position 303;
Ala at amino acid position 305;
any one of Ala, Asp, Phe, Gly, His, Ile, Lys, Leu, Met, Asn, Pro, Gln, Arg, Ser, Val, Trp, and Tyr at amino acid position 307;
any one of Ala, Phe, Ile, Leu, Met, Pro, Gln, and Thr at amino acid position 308;
any one of Ala, Asp, Glu, Pro, and Arg at amino acid position 309;
any one of Ala, His, and Ile at amino acid position 311;
Ala or His at amino acid position 312;
Lys or Arg at amino acid position 314;
any one of Ala, Asp, and His at amino acid position 315;
Ala at amino acid position 317;
Val at amino acid position 332;
Leu at amino acid position 334;
His at amino acid position 360;
Ala at amino acid position 376;
Ala at amino acid position 380;
Ala at amino acid position 382;
Ala at amino acid position 384;
Asp or His at amino acid position 385;
Pro at amino acid position 386;
Glu at amino acid position 387;
Ala or Ser at amino acid position 389;
Ala at amino acid position 424;
any one of Ala, Asp, Phe, Gly, His, Ile, Lys, Leu, Asn, Pro, Gln, Ser, Thr, Val, Trp, and Tyr at amino acid position 428;
Lys at amino acid position 433;
any one of Ala, Phe, His, Ser, Trp, and Tyr at amino acid position 434; and any one of His, Ile, Leu, Phe, Thr, and Val at amino acid position 436.

[14] The method of any one of [1] to [13], wherein said antigen-binding domain is an antigen-binding domain whose antigen-binding activity varies depending on calcium ion concentration.

[15] The method of [14], wherein said antigen-binding domain is an antigen-binding domain whose antigen-binding activity varies in a way that the antigen-binding activity at a low calcium ion concentration is lower than the antigen-binding activity at a high calcium ion concentration.

[16] The method of any one of [1] to [13], wherein said antigen-binding domain is an antigen-binding domain whose antigen-binding activity varies depending on pH.

[17] The method of [16], wherein said antigen-binding domain is an antigen-binding domain whose antigen-binding activity varies in a way that the antigen-binding activity in an acidic pH range is lower than the antigen-binding activity in a neutral pH range.

[18] The method of any one of [1] to [17], wherein the antigen-binding domain is an antibody variable region.

[19] The method of any one of [1] to [18], wherein the antigen-binding molecule is an antibody.

[20] The method of [1], wherein the modification into an Fc region that does not form said hetero complex comprises modification into an Fc region in which one of the two polypeptides constituting the Fc region has FcRn-binding activity in a neutral pH range and the other does not have FcRn-binding activity in a neutral pH range.

[21] The method of [20], which comprises substituting an amino acid at any one or more of positions 237, 248, 250, 252, 254, 255, 256, 257, 258, 265, 286, 289, 297, 298, 303, 305, 307, 308, 309, 311, 312, 314, 315, 317, 332, 334, 360, 376, 380, 382, 384, 385, 386, 387, 389, 424, 428, 433, 434, and 436 as indicated by EU numbering in the amino acid sequence of one of the two polypeptides constituting said Fc region.

[22] The method of [21], which comprises substituting an amino acid of said Fc region at any one or more of:
the amino acid of position 237 with Met;
the amino acid of position 248 with Ile;
the amino acid of position 250 with Ala, Phe, Ile, Met, Gln, Ser, Val, Trp, or Tyr;
the amino acid of position 252 with Phe, Trp, or Tyr;
the amino acid of position 254 with Thr;
the amino acid of position 255 with Glu;
the amino acid of position 256 with Asp, Asn, Glu, or Gln;
the amino acid of position 257 with Ala, Gly, Ile, Leu, Met, Asn, Ser, Thr, or Val;
the amino acid of position 258 with His;
the amino acid of position 265 with Ala;
the amino acid of position 286 with Ala or Glu;
the amino acid of position 289 with His;
the amino acid of position 297 with Ala;
the amino acid of position 298 with Gly;
the amino acid of position 303 with Ala;
the amino acid of position 305 with Ala;
the amino acid of position 307 with Ala, Asp, Phe, Gly, His, Ile, Lys, Leu, Met, Asn, Pro, Gln, Arg, Ser, Val, Trp, or Tyr;
the amino acid of position 308 with Ala, Phe, Ile, Leu, Met, Pro, Gln, or Thr;
the amino acid of position 309 with Ala, Asp, Glu, Pro, or Arg;
the amino acid of position 311 with Ala, His, or Ile;
the amino acid of position 312 with Ala or His;
the amino acid of position 314 with Lys or Arg;
the amino acid of position 315 with Ala, Asp, or His;
the amino acid of position 317 with Ala;
the amino acid of position 332 with Val;
the amino acid of position 334 with Leu;
the amino acid of position 360 with His;
the amino acid of position 376 with Ala;
the amino acid of position 380 with Ala;
the amino acid of position 382 with Ala;
the amino acid of position 384 with Ala;
the amino acid of position 385 with Asp or His;
the amino acid of position 386 with Pro;
the amino acid of position 387 with Glu;
the amino acid of position 389 with Ala or Ser;
the amino acid of position 424 with Ala;
the amino acid of position 428 with Ala, Asp, Phe, Gly, His, Ile, Lys, Leu, Asn, Pro, Gln, Ser, Thr, Val, Trp, or Tyr;
the amino acid of position 433 with Lys;
the amino acid of position 434 with Ala, Phe, His, Ser, Trp, or Tyr; and
the amino acid of position 436 with His, Ile, Leu, Phe, Thr, or Val; wherein the amino acids are indicated by EU numbering.

[23] The method of any one of [20] to [22], wherein the antigen-binding domain is an antigen-binding domain whose antigen-binding activity varies depending on calcium concentration.

[24] The method of [23], wherein the antigen-binding domain is an antigen-binding domain whose antigen-binding activity varies in a way that the antigen-binding activity at a low calcium concentration is lower than the antigen-binding activity at a high calcium concentration.

[25] The method of any one of [20] to [22], wherein the antigen-binding domain is an antigen-binding domain whose antigen-binding activity varies depending on pH.

[26] The method of [25], wherein the antigen-binding domain is an antigen-binding domain whose antigen-binding activity varies in a way that the antigen-binding activity in an acidic pH range is lower than the antigen-binding activity in a neutral pH range.

[27] The method of any one of [20] to [26], wherein the antigen-binding domain is an antibody variable region.

[28] The method of any one of [20] to [27], wherein the antigen-binding molecule is an antibody.

[29] An antigen-binding molecule comprising an antigen-binding domain whose antigen-binding activity varies depending on ion concentration and an Fc region that has FcRn-binding activity in a neutral pH range, wherein the Fc region comprises one or more amino acids selected from:
Ala at amino acid position 234;
Ala, Lys, or Arg at amino acid position 235;
Arg at amino acid position 236;
Arg at amino acid position 238;
Lys at amino acid position 239;
Phe at amino acid position 270;
Ala at amino acid position 297;
Gly at amino acid position 298;
Gly at amino acid position 325;
Arg at amino acid position 328; and
Lys or Arg at amino acid position 329; wherein the amino acids are indicated by EU numbering.

[30] The antigen-binding molecule of [29], which comprises one or more amino acids selected from:
Lys or Arg at amino acid position 237;
Lys at amino acid position 238;
Arg at amino acid position 239; and
Lys or Arg at amino acid position 329; wherein the amino acids are indicated by EU numbering.

[31] An antigen-binding molecule comprising an antigen-binding domain whose antigen-binding activity varies depending on ion concentration and an Fc region in which one of the two polypeptides constituting the Fc region has FcRn-binding activity in a neutral pH range and the other does not have FcRn-binding activity in a neutral pH range.

[32] The antigen-binding molecule of any one of [29] to [31], wherein the Fc region comprises one or more amino acids that are different from amino acids of a native Fc region at any of amino acid positions 237, 248, 250, 252, 254, 255, 256, 257, 258, 265, 286, 289, 297, 303, 305, 307, 308, 309, 311, 312, 314, 315, 317, 332, 334, 360, 376, 380, 382, 384, 385, 386, 387, 389, 424, 428, 433, 434, and 436 indicated by EU numbering in the amino acid sequence of one of the two polypeptides constituting the Fc region.

[33] The antigen-binding molecule of [32], which comprises a combination of one or more amino acids of said Fc region of:
Met at amino acid position 237;
Ile at amino acid position 248;
Ala, Phe, Ile, Met, Gln, Ser, Val, Trp, or Tyr at amino acid position 250;
Phe, Trp, or Tyr at amino acid position 252;
Thr at amino acid position 254;
Glu at amino acid position 255;
Asp, Asn, Glu, or Gln at amino acid position 256;
Ala, Gly, Ile, Leu, Met, Asn, Ser, Thr, or Val at amino acid position 257;
His at amino acid position 258;
Ala at amino acid position 265;
Ala or Glu at amino acid position 286;
His at amino acid position 289;
Ala at amino acid position 297;
Ala at amino acid position 303;
Ala at amino acid position 305;
Ala, Asp, Phe, Gly, His, Ile, Lys, Leu, Met, Asn, Pro, Gln, Arg, Ser, Val, Trp, or Tyr at amino acid position 307;
Ala, Phe, Ile, Leu, Met, Pro, Gln, or Thr at amino acid position 308;
Ala, Asp, Glu, Pro, or Arg at amino acid position 309;
Ala, His, or Ile at amino acid position 311;
Ala or His at amino acid position 312;
Lys or Arg at amino acid position 314;
Ala, Asp, or His at amino acid position 315;
Ala at amino acid position 317;
Val at amino acid position 332;
Leu at amino acid position 334;
His at amino acid position 360;
Ala at amino acid position 376;
Ala at amino acid position 380;
Ala at amino acid position 382;
Ala at amino acid position 384;
Asp or His at amino acid position 385;
Pro at amino acid position 386;
Glu at amino acid position 387;
Ala or Ser at amino acid position 389;
Ala at amino acid position 424;
Ala, Asp, Phe, Gly, His, Ile, Lys, Leu, Asn, Pro, Gln, Ser, Thr, Val, Trp, or Tyr at amino acid position 428;
Lys at amino acid position 433;
Ala, Phe, His, Ser, Trp, or Tyr at amino acid position 434; and
His, Ile, Leu, Phe, Thr, or Val at amino acid position 436;
wherein the amino acids are indicated by EU numbering.

[34] The antigen-binding molecule of any one of [29] to [33], wherein the antigen-binding domain is an antigen-binding domain whose antigen-binding activity varies depending on calcium ion concentration.

[35] The antigen-binding molecule of [34], wherein the antigen-binding domain is an antigen-binding domain whose antigen-binding activity varies in a way that the antigen-binding activity at a low calcium concentration is lower than the antigen-binding activity at a high calcium concentration.

[36] The antigen-binding molecule of any one of [29] to [33], wherein the antigen-binding domain is an antigen-binding domain whose antigen-binding activity varies depending on pH.

[37] The antigen-binding molecule of [36], wherein the antigen-binding domain is an antigen-binding domain whose antigen-binding activity varies in a way that the antigen-binding activity in an acidic pH range is lower than the antigen-binding activity in a neutral pH range.

[38] The antigen-binding molecule of any one of [29] to [37], wherein the antigen-binding domain is an antibody variable region.

[39] The antigen-binding molecule of any one of [29] to [38], wherein the antigen-binding molecule is an antibody.

[40] A polynucleotide encoding the antigen-binding molecule of any one of [29] to [39].

[41] A vector which is operably linked to the polynucleotide of [40].

[42] A cell introduced with the vector of [41].

[43] A method for producing the antigen-binding molecule of any one of [29] to [39], which comprises the step of collecting the antigen-binding molecule from a culture of the cell of [42].

[44] A pharmaceutical composition which comprises as an active ingredient the antigen-binding molecule of any one of [29] to [39] or an antigen-binding molecule obtained by the production method of [43].

Furthermore, the present invention relates to kits for use in the methods of the present invention, which comprise an antigen-binding molecule of the present invention or an antigen-binding molecule produced by a production method of the present invention. The present invention also relates to agents for improving the pharmacokinetics of an antigen-binding molecule and agents for impairing the immunogenicity of an antigen-binding molecule, which comprise as an active ingredient an antigen-binding molecule of the present invention or an antigen-binding molecule produced by a production method of the present invention. The present invention also relates to methods for treating immune/inflammatory diseases, which comprise the step of administering to a subject an antigen-binding molecule of the present invention or an antigen-binding molecule produced by a production method of the present invention. In addition, the present invention relates to the use of antigen-binding molecules of the present invention or antigen-binding molecules produced by a production method of the present invention in producing agents for improving the pharmacokinetics of antigen-binding molecules and agents for impairing the immunogenicity of antigen-binding molecules. The present invention also relates to antigen-binding molecules of the present invention or antigen-binding molecules produced by a production method of the present invention for use in the methods of the present invention.

Effects of the Invention

The present invention provides methods for improving pharmacokinetics of antigen-binding molecules and methods for impairing the immunogenicity of antigen-binding molecules. The present invention enables antibody therapy without causing unfavorable in vivo effects as compared to general antibodies.

BRIEF DESCRIPTION OF THE DRAWINGS

Figure 47:
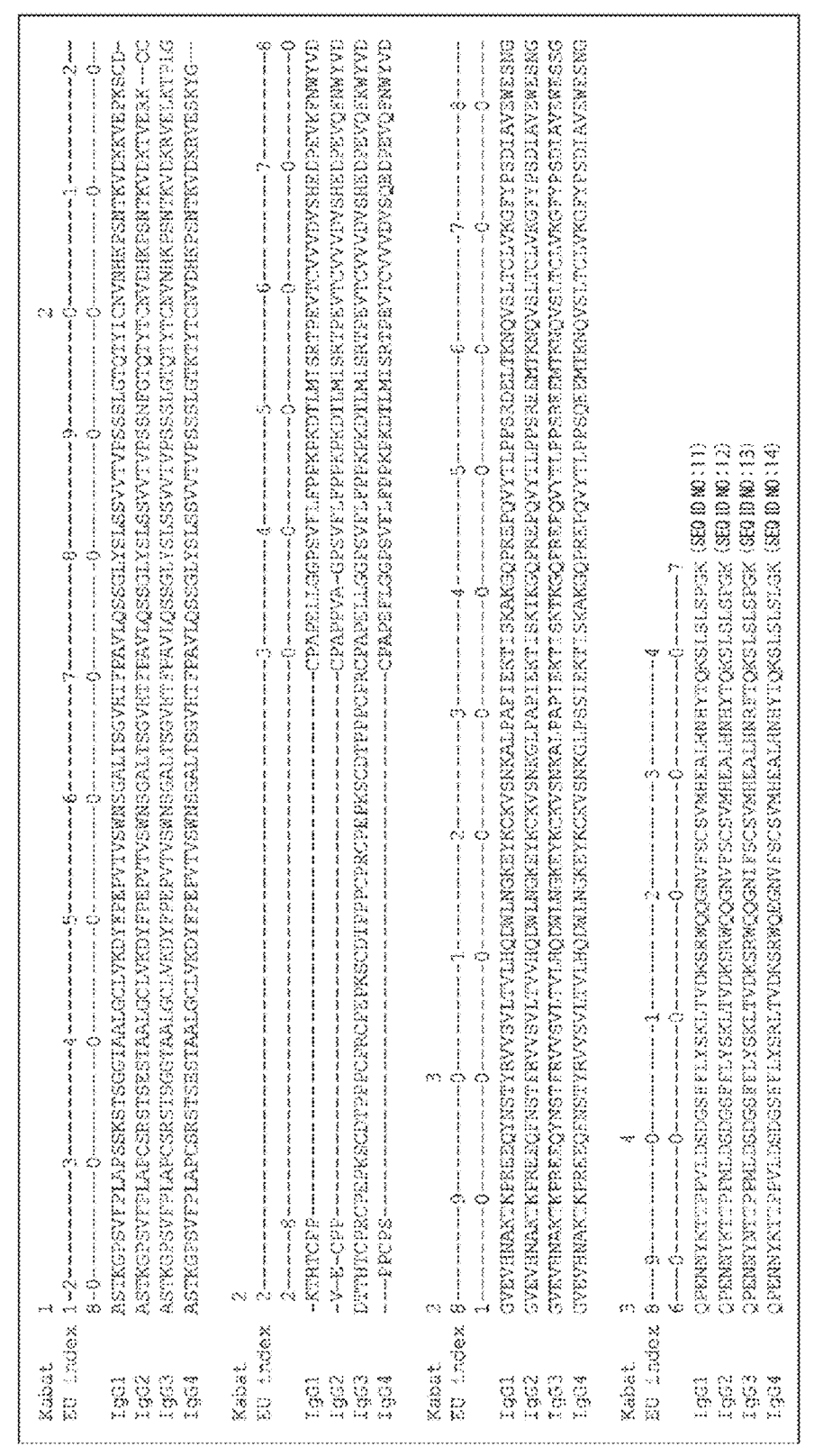

FIG. 47 is a diagram showing an alignment of the constant region sequences of IgG1, IgG2, IgG3, and IgG4, which are numbered according to the EU numbering system.

MODE FOR CARRYING OUT THE INVENTION

Figure 1:
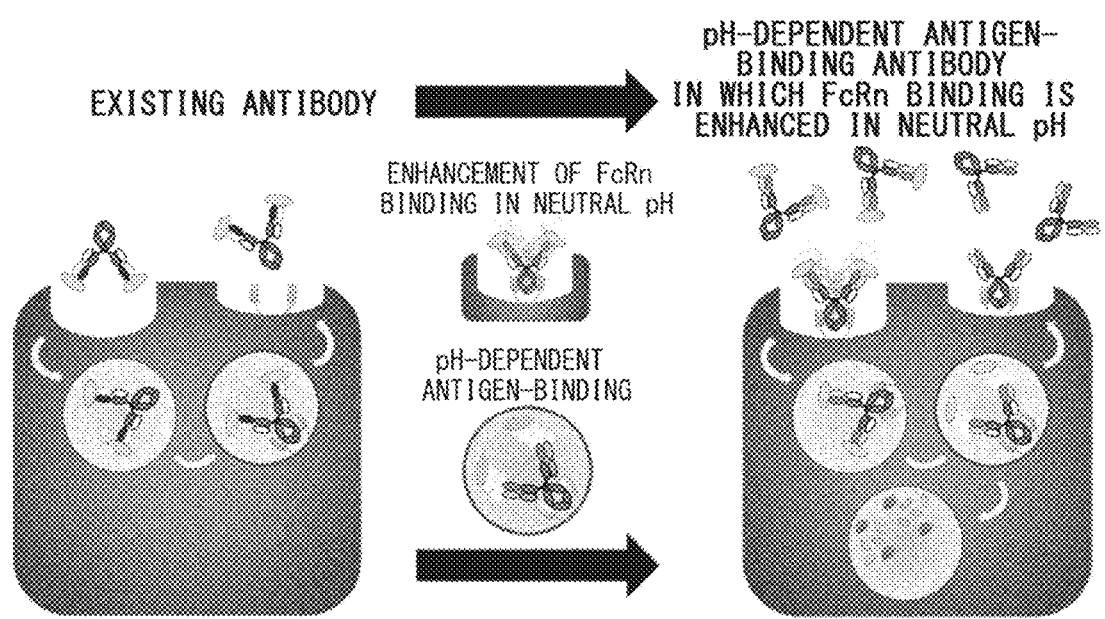
FIG. 1 is a diagram showing effects on a soluble antigen of an existing neutralizing antibody and an antibody that binds to an antigen in a pH-dependent manner and exhibits augmented FcRn binding under a neutral condition.

The definitions and detailed description below are provided to help the understanding of the present invention illustrated herein.

Amino Acids

Herein, amino acids are described in one- or three-letter codes or both, for example, Ala/A, Leu/L, Arg/R, Lys/K, Asn/N, Met/M, Asp/D, Phe/F, Cys/C, Pro/P, Gln/Q, Ser/S, Glu/E, Thr/T, Gly/G, Trp/W, His/H, Tyr/Y, Ile/I, or Val/V.

Antigens

Herein, "antigens" are not particularly limited in their structure, as long as they comprise epitopes to which antigen-binding domains bind. In other words, antigens can be inorganic or organic substances.

Other antigens include, for example, the molecules below: 17-IA, 4-1BB, 4Dc, 6-keto-PGF1a, 8-iso-PGF2a, 8-oxo-dG, A1 adenosine receptor, A33, ACE, ACE-2, activin, activin A, activin AB, activin B, activin C, activin RIA, activin RIA ALK-2, activin RIB ALK-4, activin RIIA, activin RIIB, ADAM, ADAM10, ADAM12, ADAM15, ADAM17/TACE, ADAMS, ADAM9, ADAMTS, ADAMTS4, ADAMTS5, addressin, aFGF, ALCAM, ALK, ALK-1, ALK-7,alpha-1-antitrypsin, alpha-V/beta-1 antagonist, ANG, Ang, APAF-1, APE, APJ, APP, APRIL, AR, ARC, ART, artemin, anti-Id, ASPARTIC, atrial natriuretic peptide, av/b3 integrin, Axl, b2M, B7-1, B7-2, B7-H, B-lymphocyte stimulating factor (BlyS), BACE, BACE-1, Bad, BAFF, BAFF-R, Bag-1, BAK, Bax, BCA-1, BCAM, Bcl, BCMA, BDNF, b-ECGF, bFGF, BID, Bik, BIM, BLC, BL-CAM, BLK, BMP, BMP-2 BMP-2a, BMP-3 Osteogenin, BMP-4 BMP-2b, BMP-5, BMP-6 Vgr-1, BMP-7 (OP-1), BMP-8 (BMP-8a, OP-2), BMPR, BMPR-IA (ALK-3), BMPR-IB (ALK-6), BRK-2, RPK-1, BMPR-II (BRK-3), BMP, b-NGF, BOK, bombesin, bone-derived neurotrophic factor, BPDE, BPDE-DNA, BTC, complement factor 3 (C3), C3a, C4, C5, C5a, C10, CA125, CAD-8, calcitonin, cAMP, carcinoembryonic antigen (CEA), cancer associated antigen, cathepsin A, cathepsin B, cathepsin C/DPPI, cathepsin D, cathepsin E, cathepsin H, cathepsin L, cathepsin O, cathepsin S, cathepsin V, cathepsin X/Z/P, CBL, CCI, CCK2, CCL, CCL1, CCL11, CCL12, CCL13, CCL14, CCL15, CCL16, CCL17, CCL18, CCL19, CCL2, CCL20, CCL21, CCL22, CCL23, CCL24, CCL25, CCL26, CCL27, CCL28, CCL3, CCL4, CCL5, CCL6, CCL7, CCL8, CCL9/10, CCR, CCR1, CCR10, CCR10, CCR2, CCR3, CCR4, CCR5, CCR6, CCR7, CCR8, CCR9, CD1, CD2, CD3, CD3E, CD4, CD5, CD6, CD7, CD8, CD10, CD11a, CD11b, CD11c, CD13, CD14, CD15, CD16, CD18, CD19, CD20, CD21, CD22, CD23, CD25, CD27L, CD28, CD29, CD30, CD30L, CD32, CD33 (p67 protein), CD34, CD38, CD40, CD40L, CD44, CD45, CD46, CD49a, CD52, CD54, CD55, CD56, CD61, CD64, CD66e, CD74, CD80 (B7-1), CD89, CD95, CD123, CD137, CD138, CD140a, CD146, CD147, CD148, CD152, CD164, CEACAM5, CFTR, cGMP, CINC, Botulinum toxin, *Clostridium perfringens* toxin, CKb8-1, CLC, CMV, CMV UL, CNTF, CNTN-1, COX, C-Ret, CRG-2, CT-1, CTACK, CTGF, CTLA-4, CX3CL1, CX3CR1, CXCL, CXCL1, CXCL2, CXCL3, CXCL4, CXCL5, CXCL6, CXCL7, CXCL8, CXCL9, CXCL10, CXCL11, CXCL12, CXCL13, CXCL14, CXCL15, CXCL16, CXCR, CXCR1, CXCR2, CXCR3, CXCR4, CXCR5, CXCR6, cytokeratin tumor associated antigen, DAN, DCC, DcR3, DC-SIGN, complement regulatory factor (Decay accelerating factor), des (1-3)-IGF-I (brain IGF-1), Dhh, digoxin, DNAM-1, Dnase, Dpp, DPPIV/CD26, Dtk, EGAD, EDA, EDA-A1, EDA-A2, EDAR, EGF, EGFR (ErbB-1), EMA, EMMPRIN, ENA, endothelin receptor, enkephalinase, eNOS, Eot, eotaxin 1, EpCAM, ephrin B2/EphB4, EPO, ERCC, E-selectin, ET-1, factor IIa, factor VII, factor VIIIc, factor IX, fibroblast activation protein (FAP), Fas, FcR1, FEN-1, ferritin, FGF, FGF-19, FGF-2, FGF3, FGF-8, FGFR, FGFR-3, fibrin, FL, FLIP, Flt-3, Flt-4, follicle stimulating hormone, fractalkine, FZD1, FZD2, FZD3, FZD4, FZD5, FZD6, FZD7, FZD8, FZD9, FZD10, G250, Gas6, GCP-2, GCSF, GD2, GD3, GDF, GDF-1, GDF-3 (Vgr-2), GDF-5 (BMP-14, CDMP-1), GDF-6 (BMP-13, CDMP-2), GDF-7 (BMP-12, CDMP-3), GDF-8 (myostatin), GDF-9, GDF-15 (MIC-1), GDNF, GDNF, GFAP, GFRa-1, GFR-alpha1, GFR-alpha2, GFR-alpha3, GITR, glucagon, Glut4, glycoprotein IIb/IIIa (GPIIb/IIIa), GM-CSF, gp130, gp72, GRO, growth hormone releasing hormone, hapten (NP-cap or NIP-cap), HB-EGF, HCC, HCMV gB envelope glycoprotein, HCMV gH envelope glycoprotein, HCMV UL, hematopoietic growth factor (HGF), Hep B gp120, heparanase, Her2, Her2/neu (ErbB-2), Her3 (ErbB-3), Her4 (ErbB-4), herpes simplex virus (HSV) gB glycoprotein, HSV gD glycoprotein, HGFA, high molecular weight melanoma-associated antigen (HMW-MAA), HIV gp120, HIV IIIB gp120 V3 loop, HLA, HLA-DR, HM1.24, HMFG PEM, HRG, Hrk, human cardiac myosin, human cytomegalovirus (HCMV), human growth hormone (HGH), HVEM, 1-309, IAP, ICAM, ICAM-1, ICAM-3, ICE, ICOS, IFNg, Ig, IgA receptor, IgE, IGF, IGF binding protein, IGF-1R, IGFBP, IGF-I, IGF-II, IL, IL-1, IL-1R, IL-2, IL-2R, IL-4, IL-4R, IL-5, IL-5R, IL-6, IL-6R, IL-8, IL-9, IL-10, IL-12, IL-13, IL-15, IL-18, IL-18R, IL-23, interferon (INF)-alpha, INF-beta, INF-gamma, inhibin, iNOS, insulin A chain, insulin B chain, insulin-like growth factor1, integrin alpha2, integrin alpha3, integrin alpha4, integrin alpha4/beta1, integrin alpha4/beta7, integrin alpha5 (alpha V), integrin alpha5/beta1, integrin alpha5/beta3, integrin alpha6, integrin beta1, integrin beta2, interferon gamma, IP-10, I-TAC, JE, kallikrein 2, kallikrein 5, kallikrein 6, kallikrein 11, kallikrein 12, kallikrein 14, kallikrein 15, kallikrein L1, kallikrein L2, kallikrein L3, kallikrein L4, KC, KDR, keratinocyte growth factor (KGF), laminin 5, LAMP, LAP, LAP (TGF-1), latent TGF-1, latent TGF-1 bp1, LBP, LDGF, LECT2, lefty, Lewis-Y antigen, Lewis-Y associated antigen, LFA-1, LFA-3, Lfo, LIF, LIGHT, lipoprotein, LIX, LKN, Lptn, L-selectin, LT-a, LT-b, LTB4, LTBP-1, lung surface, luteinizing hormone, lymphotoxin beta receptor, Mac-1, MAdCAM, MAG, MAP2, MARC, MCAM, MCAM, MCK-2, MCP, M-CSF, MDC, Mer, METALLOPROTEASES, MGDF receptor, MGMT, MHC (HLA-DR), MIF, MIG, MIP, MIP-1-alpha, MK, MMAC1, MMP, MMP-1, MMP-10, MMP-11, MMP-12, MMP-13, MMP-14, MMP-15, MMP-2, MMP-24, MMP-3, MMP-7, MMP-8, MMP-9, MPIF, Mpo, MSK, MSP, mucin (Muc1), MUC18, Mullerian-inhibiting substance, Mug, MuSK, NAIP, NAP, NCAD, N-C adherin, NCA 90, NCAM, NCAM, neprilysin, neurotrophin-3, -4, or -6, neurturin, nerve growth factor (NGF), NGFR, NGF-beta, nNOS, NO, NOS, Npn, NRG-3, NT, NTN, OB, OGG1, OPG, OPN, OSM, OX40L, OX40R, p150, p95, PADPr, parathyroid hormone, PARC, PARP, PBR, PBSF, PCAD, P-cadherin, PCNA, PDGF, PDGF, PDK-1, PECAM, PEM, PF4, PGE, PGF, PGI2, PGD2, PIN, PLA2, placental alkaline phosphatase (PLAP), P1GF, PLP, PP14, proinsulin, prorelaxin, protein C, PS, PSA, PSCA, prostate-specific membrane antigen (PSMA), PTEN, PTHrp, Ptk, PTN, R51, RANK, RANKL, RANTES, RANTES, relaxin A chain, relaxin B chain, renin, respiratory syncytial virus (RSV) F, RSV Fgp, Ret, Rheumatoid factor, RLIP76, RPA2, RSK, S100, SCF/KL, SDF-1, SERINE, serum albumin, sFRP-3, Shh, SIGIRR, SK-1, SLAM, SLPI, SMAC, SMDF, SMOH, SOD, SPARC, Stat, STEAP, STEAP-II, TACE, TACI, TAG-72 (tumor-associated glycoprotein-72), TARC, TCA-3, T-cell receptor (for example, T-cell receptor alpha/beta), TdT, TECK, TEM1, TEM5, TEM7, TEM8, TERT, testis PLAP-like alkaline phosphatase, TfR, TGF, TGF-alpha, TGF-beta, TGF-beta Pan Specific, TGF-betaRI (ALK-5), TGF-betaRII, TGF-betaRIIb, TGF-betaRIII, TGF-beta1, TGF-beta2, TGF-beta3, TGF-beta4, TGF-beta5, thrombin, thymus Ck-1, thyroid-stimulating hormone, Tie, TIMP, TIQ, tissue factor, TMEFF2, Tmpo, TMPRSS2, TNF, TNF-alpha, TNF-alpha-beta, TNF-beta2, TNFc , TNF-RI, TNF-RII, TNFRSF10A (TRAIL R1 Apo-2, DR4), TNFRSF10B (TRAIL R2 DR5, KILLER, TRICK-2A, TRICK-B), TNFRSF10C (TRAIL R3 DcR1, LIT, TRID), TNFRSF10D (TRAIL R4 DcR2, TRUNDD), TNFRSF11A (RANK ODF R, TRANCE R), TNFRSF11B (OPG OCIF, TR1), TNFRSF12 (TWEAK R FN14), TNFRSF13B (TACI), TNFRSF13C (BAFF R), TNFRSF14 (HVEM ATAR, HveA, LIGHT R, TR2), TNFRSF16 (NGFR p75NTR), TNFRSF17 (BCMA), TNFRSF18 (GITR AITR), TNFRSF19 (TROY TAJ, TRADE), TNFRSF19L (RELT), TNFRSF1A (TNF RI CD120a, p55-60), TNFRSF1B (TNF RII CD120b, p75-80), TNFRSF26 (TNFRH3), TNFRSF3 (LTbR TNF RIII, TNFC R), TNFRSF4 (OX40 ACT35, TXGP1 R), TNFRSF5 (CD40 p50), TNFRSF6 (Fas Apo-1, APT1, CD95), TNFRSF6B (DcR3 M68, TR6), TNFRSF7 (CD27), TNFRSF8 (CD30), TNFRSF9 (4-1BB CD137, ILA), TNFRSF21 (DR6), TNFRSF22 (DcTRAIL R2 TNFRH2), TNFRST23 (DcTRAIL R1TNFRH1), TNFRSF25 (DR3 Apo-3, LARD, TR-3, TRAMP, WSL-1), TNFSF10 (TRAIL Apo-2 ligand, TL2), TNFSF11 (TRANCE/RANK ligand ODF, OPG ligand), TNFSF12 (TWEAK Apo-3 ligand, DR3 ligand), TNFSF13 (APRIL TALL2), TNFSF13B (BAFF BLYS, TALL1, THANK, TNFSF20), TNFSF14 (LIGHT HVEM ligand, LTg), TNFSF15 (TL1A/VEGI), TNFSF18 (GITR ligand AITR ligand, TL6), TNFSF1A (TNF-a Conectin, DIF, TNFSF2), TNFSF1B (TNF-b LTa, TNFSF1), TNFSF3 (LTb TNFC, p33), TNFSF4 (OX40 ligand gp34, TXGP1), TNFSF5 (CD40 ligand CD154, gp39, HIGM1, IMD3, TRAP), TNFSF6 (Fas ligand Apo-1 ligand, APT1 ligand), TNFSF7 (CD27 ligand CD70), TNFSF8 (CD30 ligand CD153), TNFSF9 (4-1BB ligand CD137 ligand), TP-1, t-PA, Tpo, TRAIL, TRAIL R, TRAIL-R1, TRAIL-R2, TRANCE, transferrin receptor, TRF, Trk, TROP-2, TSG, TSLP, tumor associated antigen CA125, tumor associated antigen expressing Lewis-Y associated carbohydrates, TWEAK, TXB2, Ung, uPAR, uPAR-1, urokinase, VCAM, VCAM-1, VECAD, VE-Cadherin, VE-cadherin-2, VEFGR-1 (flt-1), VEGF, VEGFR, VEGFR-3 (flt-4), VEGI, VIM, virus antigen, VLA, VLA-1, VLA-4, VNR integrin, von Willebrand factor, WIF-1, WNT1, WNT2, WNT2B/13, WNT3, WNT3A, WNT4, WNT5A, WNT5B, WNT6, WNT7A, WNT7B, WNT8A, WNT8B, WNT9A, WNT9A, WNT9B, WNT10A, WNT10B, WNT11, WNT16, XCL1, XCL2, XCR1, XCR1, XEDAR, XIAP, XPD, HMGB1, IgA, Aβ, CD81, CD97, CD98, DDR1, DKK1, EREG, Hsp90, IL-17/IL-17R, IL-20/IL-20R, oxidized LDL, PCSK9, prekallikrein, RON, TMEM16F, SOD1, Chromogranin A, Chromogranin B, tau, VAP1, high molecular weight kininogen, IL-31, IL-31R, Nav1.1, Nav1.2, Nav1.3, Nav1.4, Nav1.5, Nav1.6, Nav1.7, Nav1.8, Nav1.9, EPCR, C1, C1q, C1r, C1s, C2, C2a, C2b, C3, C3a, C3b, C4, C4a, C4b, C5, CSa, CSb, C6, C7, C8, C9, factor B, factor D, factor H, properdin, sclerostin, fibrinogen, fibrin, prothrombin, thrombin, tissue factor, factor V, factor Va, factor VII, factor VIIa, factor VIII, factor VIIIa, factor IX, factor IXa, factor X, factor Xa, factor XI, factor XIa, factor XII, factor XIIa, factor XIII, factor XIIIa, TFPI, antithrombin III, EPCR, thrombomodulin, TAPI, tPA, plasminogen, plasmin, PAI-1, PAI-2, GPC3, Syndecan-1, Syndecan-2, Syndecan-3, Syndecan-4, LPA, and SIP; and receptors for hormone and growth factors.

"Epitope" means an antigenic determinant in an antigen, and refers to an antigen site to which the antigen-binding domain of an antigen-binding molecule disclosed herein binds. Thus, for example, the epitope can be defined according to its structure. Alternatively, the epitope may be defined according to the antigen-binding activity of an antigen-binding molecule that recognizes the epitope. When the antigen is a peptide or polypeptide, the epitope can be specified by the amino acid residues forming the epitope. Alternatively, when the epitope is a sugar chain, the epitope can be specified by its specific sugar chain structure.

A linear epitope is an epitope that contains an epitope whose primary amino acid sequence is recognized. Such a linear epitope typically contains at least three and most commonly at least five, for example, about 8 to 10 or 6 to 20 amino acids in its specific sequence.

In contrast to the linear epitope, "conformational epitope" is an epitope in which the primary amino acid sequence containing the epitope is not the only determinant of the recognized epitope (for example, the primary amino acid sequence of a conformational epitope is not necessarily recognized by an epitope-defining antibody). Conformational epitopes may contain a greater number of amino acids compared to linear epitopes. A conformational epitope-recognizing antibody recognizes the three-dimensional structure of a peptide or protein. For example, when a protein molecule folds and forms a three-dimensional structure, amino acids and/or polypeptide main chains that form a conformational epitope become aligned, and the epitope is made recognizable by the antibody. Methods for determining epitope conformations include, for example, X ray crystallography, two-dimensional nuclear magnetic resonance, site-specific spin labeling, and electron paramagnetic resonance, but are not limited thereto. See, for example, Epitope Mapping Protocols in Methods in Molecular Biology (1996), Vol. 66, Morris (ed.).

Binding Activity

Examples of a method for assessing the epitope binding by a test antigen-binding molecule containing an IL-6R antigen-binding domain are described below. According to the examples below, methods for assessing the epitope binding by a test antigen-binding molecule containing an antigen-binding domain for an antigen other than IL-6R, can also be appropriately conducted.

For example, whether a test antigen-binding molecule containing an IL-6R antigen-binding domain recognizes a linear epitope in the IL-6R molecule can be confirmed for example as mentioned below. A linear peptide comprising an amino acid sequence forming the extracellular domain of IL-6R is synthesized for the above purpose. The peptide can be synthesized chemically, or obtained by genetic engineering techniques using a region encoding the amino acid sequence corresponding to the extracellular domain in an IL-6R cDNA. Then, a test antigen-binding molecule containing an IL-6R antigen-binding domain is assessed for its binding activity towards a linear peptide comprising the amino acid sequence forming the extracellular domain. For example, an immobilized linear peptide can be used as an antigen by ELISA to evaluate the binding activity of the antigen-binding molecule towards the peptide. Alternatively, the binding activity towards a linear peptide can be assessed based on the level that the linear peptide inhibits the binding of the antigen-binding molecule to IL-6R-expressing cells. These tests can demonstrate the binding activity of the antigen-binding molecule towards the linear peptide.

Whether a test antigen-binding molecule containing an IL-6R antigen-binding domain recognizes a conformational epitope can be assessed as follows. IL-6R-expressing cells are prepared for the above purpose. A test antigen-binding molecule containing an IL-6R antigen-binding domain can be determined to recognize a conformational epitope when it strongly binds to IL-6R-expressing cells upon contact, but does not substantially bind to an immobilized linear peptide comprising an amino acid sequence forming the extracellular domain of IL-6R. Herein, "not substantially bind" means that the binding activity is 80% or less, generally 50% or less, preferably 30% or less, and particularly preferably 15% or less compared to the binding activity towards cells expressing human IL-6R.

Methods for assaying the binding activity of a test antigen-binding molecule containing an IL-6R antigen-binding domain towards IL-6R-expressing cells include, for example, the methods described in Antibodies: A Laboratory Manual (Ed Harlow, David Lane, Cold Spring Harbor Laboratory (1988) 359-420). Specifically, the assessment can be performed based on the principle of ELISA or fluorescence activated cell sorting (FACS) using IL-6R-expressing cells as antigen.

In the ELISA format, the binding activity of a test antigen-binding molecule containing an IL-6R antigen-binding domain towards IL-6R-expressing cells can be assessed quantitatively by comparing the levels of signal generated by enzymatic reaction. Specifically, a test polypeptide complex is added to an ELISA plate onto which IL-6R-expressing cells are immobilized. Then, the test antigen-binding molecule bound to the cells is detected using an enzyme-labeled antibody that recognizes the test antigen-binding molecule. Alternatively, when FACS is used, a dilution series of a test antigen-binding molecule is prepared, and the antibody binding titer for IL-6R-expressing cells can be determined to compare the binding activity of the test antigen-binding molecule towards IL-6R-expressing cells.

The binding of a test antigen-binding molecule towards an antigen expressed on the surface of cells suspended in buffer or the like can be detected using a flow cytometer. Known flow cytometers include, for example, the following devices:

FACSCanto™ II
FACSAria™
FACSArray™
FACSVantage™ SE
FACSCalibur™ (all are trade names of BD Biosciences)
EPICS ALTRA HyPerSort
Cytomics FC 500
EPICS XL-MCL ADC EPICS XL ADC
Cell Lab Quanta/Cell Lab Quanta SC (all are trade names of Beckman Coulter).

Preferable methods for assaying the binding activity of a test antigen-binding molecule containing an IL-6R antigen-binding domain towards an antigen include, for example, the following method. First, IL-6R-expressing cells are reacted with a test antigen-binding molecule, and then this is stained with an FITC-labeled secondary antibody that recognizes the antigen-binding molecule. The test antigen-binding molecule is appropriately diluted with a suitable buffer to prepare the molecule at a desired concentration. For example, the molecule can be used at a concentration within the range of 10 µg/ml to 10 ng/ml. Then, the fluorescence intensity and cell count are determined using FACSCalibur (BD). The fluorescence intensity obtained by analysis using the CELL QUEST Software (BD), i.e., the Geometric Mean value, reflects the quantity of antibody bound to cells. That is, the binding activity of a test antigen-binding molecule, which is represented by the quantity of the test antigen-binding molecule bound, can be determined by measuring the Geometric Mean value.

Whether a test antigen-binding molecule containing an IL-6R antigen-binding domain shares a common epitope with another antigen-binding molecule can be assessed based on the competition between the two molecules for the same epitope. The competition between antigen-binding molecules can be detected by cross-blocking assay or the like. For example, the competitive ELISA assay is a preferred cross-blocking assay.

Specifically, in cross-blocking assay, the IL-6R protein immobilized to the wells of a microtiter plate is pre-incubated in the presence or absence of a candidate competitor antigen-binding molecule, and then a test antigen-binding molecule is added thereto. The quantity of test antigen-binding molecule bound to the IL-6R protein in the wells is indirectly correlated with the binding ability of a candidate competitor antigen-binding molecule that competes for the binding to the same epitope. That is, the greater the affinity of the competitor antigen-binding molecule for the same epitope, the lower the binding activity of the test antigen-binding molecule towards the IL-6R protein-coated wells.

The quantity of the test antigen-binding molecule bound to the wells via the IL-6R protein can be readily determined by labeling the antigen-binding molecule in advance. For example, a biotin-labeled antigen-binding molecule is measured using an avidin/peroxidase conjugate and appropriate substrate. In particular, cross-blocking assay that uses enzyme labels such as peroxidase is called "competitive ELISA assay". The antigen-binding molecule can also be labeled with other labeling substances that enable detection or measurement. Specifically, radiolabels, fluorescent labels, and such are known.

When the candidate competitor antigen-binding molecule can block the binding by a test antigen-binding molecule containing an IL-6R antigen-binding domain by at least 20%, preferably at least 20 to 50%, and more preferably at least 50% compared to the binding activity in a control experiment conducted in the absence of the competitor antigen-binding molecule, the test antigen-binding molecule is determined to substantially bind to the same epitope bound by the competitor antigen-binding molecule, or compete for the binding to the same epitope.

When the structure of an epitope bound by a test antigen-binding molecule containing an IL-6R antigen-binding domain has already been identified, whether the test and control antigen-binding molecules share a common epitope can be assessed by comparing the binding activities of the two antigen-binding molecules towards a peptide prepared by introducing amino acid mutations into the peptide forming the epitope.

To measure the above binding activities, for example, the binding activities of test and control antigen-binding molecules towards a linear peptide into which a mutation is introduced are compared in the above ELISA format. Besides the ELISA methods, the binding activity towards the mutant peptide bound to a column can be determined by flowing test and control antigen-binding molecules in the column, and then quantifying the antigen-binding molecule eluted in the elution solution. Methods for adsorbing a mutant peptide to a column, for example, in the form of a GST fusion peptide, are known.

Alternatively, when the identified epitope is a conformational epitope, whether test and control antigen-binding molecules share a common epitope can be assessed by the following method. First, IL-6R-expressing cells and cells expressing IL-6R with a mutation introduced into the epitope are prepared. The test and control antigen-binding molecules are added to a cell suspension prepared by suspending these cells in an appropriate buffer such as PBS. Then, the cell suspensions are appropriately washed with a buffer, and an FITC-labeled antibody that recognizes the test and control antigen-binding molecules is added thereto. The fluorescence intensity and number of cells stained with the labeled antibody are determined using FACSCalibur (BD). The test and control antigen-binding molecules are appropriately diluted using a suitable buffer, and used at desired concentrations. For example, they may be used at a concentration within the range of 10 µg/ml to 10 ng/ml. The fluorescence intensity determined by analysis using the CELL QUEST Software (BD), i.e., the Geometric Mean value, reflects the quantity of labeled antibody bound to cells. That is, the binding activities of the test and control antigen-binding molecules, which are represented by the quantity of labeled antibody bound, can be determined by measuring the Geometric Mean value.

In the above method, whether an antigen-binding molecule does "not substantially bind to cells expressing mutant IL-6R" can be assessed, for example, by the following method. First, the test and control antigen-binding molecules bound to cells expressing mutant IL-6R are stained with a labeled antibody. Then, the fluorescence intensity of the cells is determined. When FACSCalibur is used for fluorescence detection by flow cytometry, the determined fluorescence intensity can be analyzed using the CELL QUEST Software. From the Geometric Mean values in the presence and absence of the polypeptide complex, the comparison value (ΔGeo-Mean) can be calculated according to the following formula to determine the ratio of increase in fluorescence intensity as a result of the binding by the antigen-binding molecule.

$$\Delta\text{Geo-Mean} = \text{Geo-Mean (in the presence of the polypeptide complex)}/\text{Geo-Mean (in the absence of the polypeptide complex)}$$

The Geometric Mean comparison value (ΔGeo-Mean value for the mutant IL-6R molecule) determined by the above analysis, which reflects the quantity of a test antigen-binding molecule bound to cells expressing mutant IL-6R, is compared to the ΔGeo-Mean comparison value that reflects the quantity of the test antigen-binding molecule bound to IL-6R-expressing cells. In this case, the concentrations of the test antigen-binding molecule used to determine the ΔGeo-Mean comparison values for IL-6R-expressing cells and cells expressing mutant IL-6R are particularly preferably adjusted to be equal or substantially equal. An antigen-binding molecule that has been confirmed to recognize an epitope in IL-6R is used as a control antigen-binding molecule.

If the ΔGeo-Mean comparison value of a test antigen-binding molecule for cells expressing mutant IL-6R is smaller than the ΔGeo-Mean comparison value of the test antigen-binding molecule for IL-6R-expressing cells by at least 80%, preferably 50%, more preferably 30%, and particularly preferably 15%, then the test antigen-binding molecule "does not substantially bind to cells expressing mutant IL-6R". The formula for determining the Geo-Mean (Geometric Mean) value is described in the CELL QUEST Software User's Guide (BD biosciences). When the comparison shows that the comparison values are substantially equivalent, the epitope for the test and control antigen-binding molecules can be determined to be the same.

Antigen-binding Domain

Herein, an "antigen-binding domain" may be of any structure as long as it binds to an antigen of interest. Such domains preferably include, for example:
antibody heavy-chain and light-chain variable regions;
a module of about 35 amino acids called A domain which is contained in the in vivo cell membrane protein Avimer (WO 2004/044011, WO 2005/040229);
Adnectin containing the 10Fn3 domain which binds to the protein moiety of fibronectin, a glycoprotein expressed on cell membrane (WO 2002/032925);
Affibody which is composed of a 58-amino acid three-helix bundle based on the scaffold of the IgG-binding domain of Protein A (WO 1995/001937);
Designed Ankyrin Repeat proteins (DARPins) which are a region exposed on the molecular surface of ankyrin repeats (AR) having a structure in which a subunit consisting of a turn comprising 33 amino acid residues, two antiparallel helices, and a loop is repeatedly stacked (WO 2002/020565);
Anticalins and such, which are domains consisting of four loops that support one side of a barrel structure composed of eight circularly arranged antiparallel strands that are highly conserved among lipocalin molecules such as neutrophil gelatinase-associated lipocalin (NGAL) (WO 2003/029462); and the concave region formed by the parallel-sheet structure inside the horseshoe-shaped structure constituted by stacked repeats of the leucine-rich-repeat (LRR) module of the variable lymphocyte receptor (VLR) which does not have the immunoglobulin structure and is used in the system of acquired immunity in jawless vertebrate such as lampery and hagfish (WO 2008/016854). Preferred antigen-binding domains of the present invention include, for example, those having antibody heavy-chain and light-chain variable regions. Preferred examples of antigen-binding domains include "single chain Fv (scFv)", "single chain antibody", "Fv", "single chain Fv 2 (scFv2)", "Fab", and "F(ab')2".

The antigen-binding domains of antigen-binding molecules of the present invention can bind to an identical epitope. Such epitope can be present, for example, in a protein comprising the amino acid sequence of SEQ ID NO: 1. Alternatively, the epitope can be present in the protein comprising the amino acids at positions 20 to 365 in the amino acid sequence of SEQ ID NO: 1. Alternatively, each of the antigen-binding domains of antigen-binding molecules of the present invention can bind to a different epitope. Herein, the different epitope can be present in, for example, a protein comprising the amino acid sequence of SEQ ID NO: 1. Alternatively, the epitope can be present in the protein comprising the amino acids at positions 20 to 365 in the amino acid sequence of SEQ ID NO: 1.

Specificity

"Specific" means that one of molecules that specifically binds to does not show any significant binding to molecules other than a single or a number of binding partner molecules. Furthermore, "specific" is also used when an antigen-binding domain is specific to a particular epitope among multiple epitopes in an antigen. When an epitope bound by an antigen-binding domain is contained in multiple different antigens, antigen-binding molecules containing the antigen-binding domain can bind to various antigens that have the epitope.

Antibody

Herein, "antibody" refers to a natural immunoglobulin or an immunoglobulin produced by partial or complete synthesis. Antibodies can be isolated from natural sources such as naturally-occurring plasma and serum, or culture supernatants of antibody-producing hybridomas. Alternatively, antibodies can be partially or completely synthesized using techniques such as genetic recombination. Preferred antibodies include, for example, antibodies of an immunoglobulin isotype or subclass belonging thereto. Known human immunoglobulins include antibodies of the following nine classes (isotypes): IgG1, IgG2, IgG3, IgG4, IgA1, IgA2, IgD, IgE, and IgM. Of these isotypes, antibodies of the present invention include IgG1, IgG2, IgG3, and IgG4.

Methods for producing an antibody with desired binding activity are known to those skilled in the art. Below is an example that describes a method for producing an antibody that binds to IL-6R (anti-IL-6R antibody). Antibodies that bind to an antigen other than IL-6R can also be produced according to the example described below.

Anti-IL-6R antibodies can be obtained as polyclonal or monoclonal antibodies using known methods. The anti-IL-6R antibodies preferably produced are monoclonal antibodies derived from mammals. Such mammal-derived monoclonal antibodies include antibodies produced by hybridomas or host cells transformed with an expression vector carrying an antibody gene by genetic engineering techniques. "Humanized antibodies" or "chimeric antibodies" are included in the monoclonal antibodies of the present invention.

Monoclonal antibody-producing hybridomas can be produced using known techniques, for example, as described below. Specifically, mammals are immunized by conventional immunization methods using an IL-6R protein as a sensitizing antigen. Resulting immune cells are fused with known parental cells by conventional cell fusion methods. Then, hybridomas producing an anti-IL-6R antibody can be selected by screening for monoclonal antibody-producing cells using conventional screening methods.

Specifically, monoclonal antibodies are prepared as mentioned below. First, the IL-6R gene whose nucleotide sequence is disclosed in SEQ ID NO: 2 can be expressed to produce an IL-6R protein shown in SEQ ID NO: 1, which will be used as a sensitizing antigen for antibody preparation. That is, a gene sequence encoding IL-6R is inserted into a known expression vector, and appropriate host cells are transformed with this vector. The desired human IL-6R protein is purified from the host cells or their culture supernatants by known methods. In order to obtain soluble IL-6R from culture supernatants, for example, a protein consisting of the amino acids at positions 1 to 357 in the IL-6R polypeptide sequence of SEQ ID NO: 1, such as described in Mullberg et al. (J. Immunol. (1994) 152 (10), 4958-4968), is expressed as a soluble IL-6R, instead of the IL-6R protein of SEQ ID NO: 1. Purified natural IL-6R protein can also be used as a sensitizing antigen.

The purified IL-6R protein can be used as a sensitizing antigen for immunization of mammals. A partial IL-6R peptide may also be used as a sensitizing antigen. In this case, a partial peptide can be prepared by chemical synthesis based on the amino acid sequence of human IL-6R, or by inserting a partial IL-6R gene into an expression vector for expression. Alternatively, a partial peptide can be produced by degrading an IL-6R protein with a protease. The length and region of the partial IL-6R peptide are not limited to particular embodiments. A preferred region can be arbitrarily selected from the amino acid sequence at amino acid positions 20 to 357 in the amino acid sequence of SEQ ID NO: 1. The number of amino acids forming a peptide to be used as a sensitizing antigen is preferably at least five or more, six or more, or seven or more. More specifically, a peptide of 8 to 50 residues, more preferably 10 to 30 residues can be used as a sensitizing antigen.

For sensitizing antigen, alternatively it is possible to use a fusion protein prepared by fusing a desired partial polypeptide or peptide of the IL-6R protein with a different polypeptide. For example, antibody Fc fragments and peptide tags are preferably used to produce fusion proteins to be used as sensitizing antigens. Vectors for expression of such fusion proteins can be constructed by fusing in frame genes encoding two or more desired polypeptide fragments and inserting the fusion gene into an expression vector as described above. Methods for producing fusion proteins are described in Molecular Cloning 2nd ed. (Sambrook, J et al., Molecular Cloning 2nd ed., 9.47-9.58 (1989) Cold Spring Harbor Lab. Press). Methods for preparing IL-6R to be used as a sensitizing antigen, and immunization methods using IL-6R are specifically described in WO 2003/000883, WO 2004/022754, WO 2006/006693, and such.

There is no particular limitation on the mammals to be immunized with the sensitizing antigen. However, it is preferable to select the mammals by considering their compatibility with the parent cells to be used for cell fusion. In general, rodents such as mice, rats, and hamsters, rabbits, and monkeys are preferably used.

The above animals are immunized with a sensitizing antigen by known methods. Generally performed immunization methods include, for example, intraperitoneal or subcutaneous injection of a sensitizing antigen into mammals. Specifically, a sensitizing antigen is appropriately diluted with PBS (Phosphate-Buffered Saline), physiological saline, or the like. If desired, a conventional adjuvant such as Freund's complete adjuvant is mixed with the antigen, and the mixture is emulsified. Then, the sensitizing antigen is administered to a mammal several times at 4- to 21-day intervals. Appropriate carriers may be used in immunization with the sensitizing antigen. In particular, when a low-molecular-weight partial peptide is used as the sensitizing antigen, it is sometimes desirable to couple the sensitizing antigen peptide to a carrier protein such as albumin or keyhole limpet hemocyanin for immunization.

Alternatively, hybridomas producing a desired antibody can be prepared using DNA immunization as mentioned below. DNA immunization is an immunization method that confers immunostimulation by expressing a sensitizing antigen in an animal immunized as a result of administering a vector DNA constructed to allow expression of an antigen protein-encoding gene in the animal. As compared to conventional immunization methods in which a protein antigen is administered to animals to be immunized, DNA immunization is expected to be superior in that:

immunostimulation can be provided while retaining the structure of a membrane protein such as IL-6R; and
there is no need to purify the antigen for immunization.

In order to prepare a monoclonal antibody of the present invention using DNA immunization, first, a DNA expressing an IL-6R protein is administered to an animal to be immunized. The IL-6R-encoding DNA can be synthesized by known methods such as PCR. The obtained DNA is inserted into an appropriate expression vector, and then this is administered to an animal to be immunized. Preferably used expression vectors include, for example, commercially-available expression vectors such as pcDNA3.1. Vectors can be administered to an organism using conventional methods. For example, DNA immunization is performed by using a gene gun to introduce expression vector-coated gold particles into cells in the body of an animal to be immunized. Antibodies that recognized IL-6R can also be produced by the methods described in WO 2003/104453.

After immunizing a mammal as described above, an increase in the titer of an IL-6R-binding antibody is confirmed in the serum. Then, immune cells are collected from the mammal, and then subjected to cell fusion. In particular, splenocytes are preferably used as immune cells.

A mammalian myeloma cell is used as a cell to be fused with the above-mentioned immune cells. The myeloma cells preferably comprise a suitable selection marker for screening. A selection marker confers characteristics to cells for their survival (or death) under a specific culture condition. Hypoxanthine-guanine phosphoribosyltransferase deficiency (hereinafter abbreviated as HGPRT deficiency) and thymidine kinase deficiency (hereinafter abbreviated as TK deficiency) are known as selection markers. Cells with HGPRT or TK deficiency have hypoxanthine-aminopterin-thymidine sensitivity (hereinafter abbreviated as HAT sensitivity). HAT-sensitive cells cannot synthesize DNA in a HAT selection medium, and are thus killed. However, when the cells are fused with normal cells, they can continue DNA synthesis using the salvage pathway of the normal cells, and therefore they can grow even in the HAT selection medium.

HGPRT-deficient and TK-deficient cells can be selected in a medium containing 6-thioguanine, 8-azaguanine (hereinafter abbreviated as 8AG), or 5'-bromodeoxyuridine, respectively. Normal cells are killed because they incorporate these pyrimidine analogs into their DNA. Meanwhile, cells that are deficient in these enzymes can survive in the selection medium, since they cannot incorporate these pyrimidine analogs. In addition, a selection marker referred to as G418 resistance provided by the neomycin-resistant gene confers resistance to 2-deoxystreptamine antibiotics (gentamycin analogs). Various types of myeloma cells that are suitable for cell fusion are known.

For example, myeloma cells including the following cells can be preferably used:
P3(P3x63Ag8.653) (J. Immunol. (1979) 123 (4), 1548-1550);
P3x63Ag8U.1 (Current Topics in Microbiology and Immunology (1978)81, 1-7);
NS-1 (C. Eur. J. Immunol. (1976)6 (7), 511-519);
MPC-11 (Cell (1976) 8 (3), 405-415);
SP2/0 (Nature (1978) 276 (5685), 269-270);
FO (J. Immunol. Methods (1980) 35 (1-2), 1-21);
S194/5.XX0.BU.1 (J. Exp. Med. (1978) 148 (1), 313-323);
R210 (Nature (1979) 277 (5692), 131-133), etc.

Cell fusions between the immunocytes and myeloma cells are essentially carried out using known methods, for example, a method by Kohler and Milstein et al. (Methods Enzymol. (1981) 73: 3-46).

More specifically, cell fusion can be carried out, for example, in a conventional culture medium in the presence of a cell fusion-promoting agent. The fusion-promoting agents include, for example, polyethylene glycol (PEG) and Sendai virus (HVJ). If required, an auxiliary substance such as dimethyl sulfoxide is also added to improve fusion efficiency.

The ratio of immune cells to myeloma cells may be determined at one's own discretion, preferably, for example, one myeloma cell for every one to ten immunocytes. Culture media to be used for cell fusions include, for example, media that are suitable for the growth of myeloma cell lines, such as RPMI1640 medium and MEM medium, and other conventional culture medium used for this type of cell culture. In addition, serum supplements such as fetal calf serum (FCS) may be preferably added to the culture medium.

For cell fusion, predetermined amounts of the above immune cells and myeloma cells are mixed well in the above culture medium. Then, a PEG solution (for example, the average molecular weight is about 1,000 to 6,000) prewarmed to about 37° C. is added thereto at a concentration of generally 30% to 60% (w/v). This is gently mixed to produce desired fusion cells (hybridomas). Then, an appropriate culture medium mentioned above is gradually added to the cells, and this is repeatedly centrifuged to remove the supernatant. Thus, cell fusion agents and such which are unfavorable to hybridoma growth can be removed.

The hybridomas thus obtained can be selected by culture using a conventional selective medium, for example, HAT medium (a culture medium containing hypoxanthine, aminopterin, and thymidine). Cells other than the desired hybridomas (non-fused cells) can be killed by continuing culture in the above HAT medium for a sufficient period of time. Typically, the period is several days to several weeks. Then, hybridomas producing the desired antibody are screened and singly cloned by conventional limiting dilution methods.

The hybridomas thus obtained can be selected using a selection medium based on the selection marker possessed by the myeloma used for cell fusion. For example, HGPRT- or TK-deficient cells can be selected by culture using the HAT medium (a culture medium containing hypoxanthine, aminopterin, and thymidine). Specifically, when HAT-sensitive myeloma cells are used for cell fusion, cells successfully fused with normal cells can selectively proliferate in the HAT medium. Cells other than the desired hybridomas (non-fused cells) can be killed by continuing culture in the above HAT medium for a sufficient period of time. Specifically, desired hybridomas can be selected by culture for generally several days to several weeks. Then, hybridomas producing the desired antibody are screened and singly cloned by conventional limiting dilution methods.

Desired antibodies can be preferably selected and singly cloned by screening methods based on known antigen/antibody reaction. For example, an IL-6R-binding monoclonal antibody can bind to IL-6R expressed on the cell surface. Such a monoclonal antibody can be screened by fluorescence activated cell sorting (FACS). FACS is a system that assesses the binding of an antibody to cell surface by analyzing cells contacted with a fluorescent antibody using laser beam, and measuring the fluorescence emitted from individual cells.

To screen for hybridomas that produce a monoclonal antibody of the present invention by FACS, IL-6R-expressing cells are first prepared. Cells preferably used for screening are mammalian cells in which IL-6R is forcedly expressed. As control, the activity of an antibody to bind to cell-surface IL-6R can be selectively detected using non-transformed mammalian cells as host cells. Specifically, hybridomas producing an anti-IL-6R monoclonal antibody can be isolated by selecting hybridomas that produce an antibody which binds to cells forced to express IL-6R, but not to host cells.

Alternatively, the activity of an antibody to bind to immobilized IL-6R-expressing cells can be assessed based on the principle of ELISA. For example, IL-6R-expressing cells are immobilized to the wells of an ELISA plate. Culture supernatants of hybridomas are contacted with the immobilized cells in the wells, and antibodies that bind to the immobilized cells are detected. When the monoclonal antibodies are derived from mouse, antibodies bound to the cells can be detected using an anti-mouse immunoglobulin antibody. Hybridomas producing a desired antibody having the antigen-binding ability are selected by the above screening, and they can be cloned by a limiting dilution method or the like.

Monoclonal antibody-producing hybridomas thus prepared can be passaged in a conventional culture medium, and stored in liquid nitrogen for a long period.

The above hybridomas are cultured by a conventional method, and desired monoclonal antibodies can be prepared from the culture supernatants. Alternatively, the hybridomas are administered to and grown in compatible mammals, and monoclonal antibodies are prepared from the ascites. The former method is suitable for preparing antibodies with high purity.

Antibodies encoded by antibody genes that are cloned from antibody-producing cells such as the above hybridomas can also be preferably used. A cloned antibody gene is inserted into an appropriate vector, and this is introduced into a host to express the antibody encoded by the gene. Methods for isolating antibody genes, inserting the genes into vectors, and transforming host cells have already been established, for example, by Vandamme et al. (Eur. J. Biochem. (1990) 192(3), 767-775). Methods for producing recombinant antibodies are also known as described below.

For example, a cDNA encoding the variable region (V region) of an anti-IL-6R antibody is prepared from hybridoma cells expressing the anti-IL-6R antibody. For this purpose, total RNA is first extracted from hybridomas. Methods used for extracting mRNAs from cells include, for example:

the guanidine ultracentrifugation method (Biochemistry (1979) 18(24), 5294-5299), and the AGPC method (Anal. Biochem. (1987) 162(1), 156-159)

Extracted mRNAs can be purified using the mRNA Purification Kit (GE Healthcare Bioscience) or such. Alternatively, kits for extracting total mRNA directly from cells, such as the QuickPrep mRNA Purification Kit (GE Healthcare Bioscience), are also commercially available. mRNAs can be prepared from hybridomas using such kits. cDNAs encoding the antibody V region can be synthesized from the prepared mRNAs using a reverse transcriptase. cDNAs can be synthesized using the AMV Reverse Transcriptase First-strand cDNA Synthesis Kit (Seikagaku Co.) or such. Furthermore, the SMART RACE cDNA amplification kit (Clontech) and the PCR-based 5'-RACE method (Proc. Natl. Acad. Sci. USA (1988) 85(23), 8998-9002; Nucleic Acids Res. (1989) 17(8), 2919-2932) can be appropriately used to synthesize and amplify cDNAs. In such a cDNA synthesis process, appropriate restriction enzyme sites described below may be introduced into both ends of a cDNA.

The cDNA fragment of interest is purified from the resulting PCR product, and then this is ligated to a vector DNA. A recombinant vector is thus constructed, and introduced into *E. coli* or such. After colony selection, the desired recombinant vector can be prepared from the colony-forming *E. coli*. Then, whether the recombinant vector has the cDNA nucleotide sequence of interest is tested by a known method such as the dideoxy nucleotide chain termination method.

The 5'-RACE method which uses primers to amplify the variable region gene is conveniently used for isolating the gene encoding the variable region. First, a 5'-RACE cDNA library is constructed by cDNA synthesis using RNAs extracted from hybridoma cells as a template. A commercially available kit such as the SMART RACE cDNA amplification kit is appropriately used to synthesize the 5'-RACE cDNA library.

The antibody gene is amplified by PCR using the prepared 5'-RACE cDNA library as a template. Primers for amplifying the mouse antibody gene can be designed based on known antibody gene sequences. The nucleotide sequences of the primers vary depending on the immunoglobulin subclass. Therefore, it is preferable that the subclass is determined in advance using a commercially available kit such as the Iso Strip mouse monoclonal antibody isotyping kit (Roche Diagnostics).

Specifically, for example, primers that allow amplification of genes encoding γ1, γ2a, γ72b, and γ3 heavy chains and κ and λ light chains are used to isolate mouse IgG-encoding genes. In general, a primer that anneals to a constant region site close to the variable region is used as a 3'-side primer to amplify an IgG variable region gene. Meanwhile, a primer attached to a 5'RACE cDNA library construction kit is used as a 5'-side primer.

PCR products thus amplified are used to reshape immunoglobulins composed of a combination of heavy and light chains. A desired antibody can be selected using the IL-6R-binding activity of a reshaped immunoglobulin as an indicator. For example, when the objective is to isolate an antibody against IL-6R, it is more preferred that the binding of the antibody to IL-6R is specific. An IL-6R-binding antibody can be screened, for example, by the following steps:

(1) contacting an IL-6R-expressing cell with an antibody comprising the V region encoded by a cDNA isolated from a hybridoma;
(2) detecting the binding of the antibody to the IL-6R-expressing cell; and
(3) selecting an antibody that binds to the IL-6R-expressing cell.

Methods for detecting the binding of an antibody to IL-6R-expressing cells are known. Specifically, the binding of an antibody to IL-6R-expressing cells can be detected by the above-described techniques such as FACS. Immobilized samples of IL-6R-expressing cells are appropriately used to assess the binding activity of an antibody.

Preferred antibody screening methods that use the binding activity as an indicator also include panning methods using phage vectors. Screening methods using phage vectors are advantageous when the antibody genes are isolated from heavy-chain and light-chain subclass libraries from a polyclonal antibody-expressing cell population. Genes encoding the heavy-chain and light-chain variable regions can be linked by an appropriate linker sequence to form a single-chain Fv (scFv). Phages presenting scFv on their surface can be produced by inserting a gene encoding scFv into a phage vector. The phages are contacted with an antigen of interest. Then, a DNA encoding scFv having the binding activity of interest can be isolated by collecting phages bound to the antigen. This process can be repeated as necessary to enrich scFv having the binding activity of interest.

After isolation of the cDNA encoding the V region of the anti-IL-6R antibody of interest, the cDNA is digested with restriction enzymes that recognize the restriction sites introduced into both ends of the cDNA. Preferred restriction enzymes recognize and cleave a nucleotide sequence that occurs in the nucleotide sequence of the antibody gene at a low frequency. Furthermore, a restriction site for an enzyme that produces a sticky end is preferably introduced into a vector to insert a single-copy digested fragment in the correct orientation. The cDNA encoding the V region of the anti-IL-6R antibody is digested as described above, and this is inserted into an appropriate expression vector to construct an antibody expression vector. In this case, if a gene encoding the antibody constant region (C region) and a gene encoding the above V region are fused in-frame, a chimeric antibody is obtained. Herein, "chimeric antibody" means that the origin of the constant region is different from that of the variable region. Thus, in addition to mouse/human heterochimeric antibodies, human/human allochimeric antibodies are included in the chimeric antibodies of the present invention. A chimeric antibody expression vector can be constructed by inserting the above V region gene into an expression vector that already has the constant region. Specifically, for example, a recognition sequence for a restriction enzyme that excises the above V region gene can be appropriately placed on the 5' side of an expression vector carrying a DNA encoding a desired antibody constant region (C region). A chimeric antibody expression vector is constructed by fusing in frame the two genes digested with the same combination of restriction enzymes.

To produce an anti-IL-6R monoclonal antibody, antibody genes are inserted into an expression vector so that the genes are expressed under the control of an expression regulatory region. The expression regulatory region for antibody expression includes, for example, enhancers and promoters. Furthermore, an appropriate signal sequence may be attached to the amino terminus so that the expressed antibody is secreted to the outside of cells. In the Examples described later, a peptide having the amino acid sequence MGWSCIILFLVATATGVHS (SEQ ID NO: 3) are used as a signal sequence. Meanwhile, other appropriate signal sequences may be attached. The expressed polypeptide is cleaved at the carboxyl terminus of the above sequence, and the resulting polypeptide is secreted to the outside of cells as a mature polypeptide. Then, appropriate host cells are transformed with the expression vector, and recombinant cells expressing the anti-IL-6R antibody-encoding DNA are obtained.

DNAs encoding the antibody heavy chain (H chain) and light chain (L chain) are separately inserted into different expression vectors to express the antibody gene. An antibody molecule having the H and L chains can be expressed by co-transfecting the same host cell with vectors into which the H-chain and L-chain genes are respectively inserted. Alternatively, host cells can be transformed with a single expression vector into which DNAs encoding the H and L chains are inserted (see WO 1994/011523).

There are various known host cell/expression vector combinations for antibody preparation by introducing isolated antibody genes into appropriate hosts. All of these expression systems are applicable to isolation of the antigen-binding domains of the present invention. Appropriate eukaryotic cells used as host cells include animal cells, plant cells, and fungal cells. Specifically, the animal cells include, for example, the following cells.

(1) mammalian cells: CHO, COS, myeloma, baby hamster kidney (BHK), HeLa, Vero, human embryonic kidney (HEK) 293, or such;
(2) amphibian cells: *Xenopus* oocytes, or such; and
(3) insect cells: sf9, sf21, Tn5, or such.

In addition, as a plant cell, an antibody gene expression system using cells derived from the *Nicotiana* genus such as *Nicotiana tabacum* is known. Callus cultured cells can be appropriately used to transform plant cells.

Furthermore, the following cells can be used as fungal cells:

yeasts: the *Saccharomyces* genus such as *Saccharomyces serevisiae*, and the *Pichia* genus such as *Pichia pastoris*; and filamentous fungi: the *Aspergillus* genus such as *Aspergillus niger*.

Furthermore, antibody gene expression systems that utilize prokaryotic cells are also known. For example, when using bacterial cells, *E. coli* cells, *Bacillus subtilis* cells, and such can suitably be utilized in the present invention. Expression vectors carrying the antibody genes of interest are introduced into these cells by transfection. The transfected cells are cultured in vitro, and the desired antibody can be prepared from the culture of transformed cells.

In addition to the above-described host cells, transgenic animals can also be used to produce a recombinant antibody. That is, the antibody can be obtained from an animal into which the gene encoding the antibody of interest is introduced. For example, the antibody gene can be constructed as a fusion gene by inserting in frame into a gene that encodes a protein produced specifically in milk. Goat β-casein or such can be used, for example, as the protein secreted in milk. DNA fragments containing the fused gene inserted with the antibody gene is injected into a goat embryo, and then this embryo is introduced into a female goat. Desired antibodies can be obtained as a protein fused with the milk protein from milk produced by the transgenic goat born from the embryo-recipient goat (or progeny thereof). In addition, to increase the volume of milk containing the desired antibody produced by the transgenic goat, hormones can be administered to the transgenic goat as necessary (Ebert, K. M. et al., Bio/Technology (1994) 12 (7), 699-702).

When a polypeptide complex described herein is administered to human, an antigen-binding domain derived from a genetically recombinant antibody that has been artificially modified to reduce the heterologous antigenicity against human and such, can be appropriately used as the antigen-binding domain of the complex. Such genetically recombinant antibodies include, for example, humanized antibodies. These modified antibodies are appropriately produced by known methods.

An antibody variable region used to produce the antigen-binding domain of a polypeptide complex described herein is generally formed by three complementarity-determining regions (CDRs) that are separated by four framework regions (FRs). CDR is a region that substantially determines the binding specificity of an antibody. The amino acid sequences of CDRs are highly diverse. On the other hand, the FR-forming amino acid sequences often have high identity even among antibodies with different binding specificities. Therefore, generally, the binding specificity of a certain antibody can be introduced to another antibody by CDR grafting.

A humanized antibody is also called a reshaped human antibody. Specifically, humanized antibodies prepared by grafting the CDR of a non-human animal antibody such as a mouse antibody to a human antibody and such are known. Common genetic engineering techniques for obtaining humanized antibodies are also known. Specifically, for example, overlap extension PCR is known as a method for grafting a mouse antibody CDR to a human FR. In overlap extension PCR, a nucleotide sequence encoding a mouse antibody CDR to be grafted is added to primers for synthesizing a human antibody FR. Primers are prepared for each of the four FRs. It is generally considered that when grafting a mouse CDR to a human FR, selecting a human FR that has high identity to a mouse FR is advantageous for maintaining the CDR function. That is, it is generally preferable to use a human FR comprising an amino acid sequence which has high identity to the amino acid sequence of the FR adjacent to the mouse CDR to be grafted.

Nucleotide sequences to be ligated are designed so that they will be connected to each other in frame. Human FRs are individually synthesized using the respective primers. As a result, products in which the mouse CDR-encoding DNA is attached to the individual FR-encoding DNAs are obtained. Nucleotide sequences encoding the mouse CDR of each product are designed so that they overlap with each other. Then, complementary strand synthesis reaction is conducted to anneal the overlapping CDR regions of the products synthesized using a human antibody gene as template. Human FRs are ligated via the mouse CDR sequences by this reaction.

The full length V region gene, in which three CDRs and four FRs are ultimately ligated, is amplified using primers that anneal to its 5'- or 3'-end, which are added with suitable restriction enzyme recognition sequences. An expression vector for humanized antibody can be produced by inserting the DNA obtained as described above and a DNA that encodes a human antibody C region into an expression vector so that they will ligate in frame. After the recombinant vector is transfected into a host to establish recombinant cells, the recombinant cells are cultured, and the DNA encoding the humanized antibody is expressed to produce the humanized antibody in the cell culture (see, European Patent Publication No. EP 239400 and International Patent Publication No. WO 1996/002576).

By qualitatively or quantitatively measuring and evaluating the antigen-binding activity of the humanized antibody produced as described above, one can suitably select human antibody FRs that allow CDRs to form a favorable antigen-binding site when ligated through the CDRs. Amino acid residues in FRs may be substituted as necessary, so that the CDRs of a reshaped human antibody form an appropriate antigen-binding site. For example, amino acid sequence mutations can be introduced into FRs by applying the PCR method used for grafting a mouse CDR into a human FR. More specifically, partial nucleotide sequence mutations can be introduced into primers that anneal to the FR. Nucleotide sequence mutations are introduced into the FRs synthesized by using such primers. Mutant FR sequences having the desired characteristics can be selected by measuring and evaluating the activity of the amino acid-substituted mutant antibody to bind to the antigen by the above-mentioned method (Cancer Res. (1993) 53: 851-856).

Alternatively, desired human antibodies can be obtained by immunizing transgenic animals having the entire repertoire of human antibody genes (see WO 1993/012227; WO 1992/003918; WO 1994/002602; WO 1994/025585; WO 1996/034096; WO 1996/033735) by DNA immunization.

Furthermore, techniques for preparing human antibodies by panning using human antibody libraries are also known. For example, the V region of a human antibody is expressed as a single-chain antibody (scFv) on phage surface by the phage display method. Phages expressing an scFv that binds to the antigen can be selected. The DNA sequence encoding the human antibody V region that binds to the antigen can be determined by analyzing the genes of selected phages. The DNA sequence of the scFv that binds to the antigen is determined. An expression vector is prepared by fusing the V region sequence in frame with the C region sequence of a desired human antibody, and inserting this into an appropriate expression vector. The expression vector is introduced into cells appropriate for expression such as those described above. The human antibody can be produced by expressing the human antibody-encoding gene in the cells. These methods are already known (see WO 1992/001047; WO 1992/020791; WO 1993/006213; WO 1993/011236; WO 1993/019172; WO 1995/001438; WO 1995/015388).

In addition to the techniques described above, techniques of B cell cloning (identification of each antibody-encoding sequence, cloning and its isolation; use in constructing expression vector in order to prepare each antibody (IgG1, IgG2, IgG3, or IgG4 in particular); and such) such as described in Bernasconi et al. (Science (2002) 298: 2199-2202) or in WO 2008/081008 can be appropriately used to isolate antibody genes.

EU Numbering System and Kabat's Numbering System

According to the methods used in the present invention, amino acid positions assigned to antibody CDR and FR are specified according to Kabat's numbering (Sequences of Proteins of Immunological Interest (National Institute of Health, Bethesda, Md., 1987 and 1991)). Herein, when an antigen-binding molecule is an antibody or antigen-binding fragment, variable region amino acids are indicated according to Kabat's numbering system, while constant region amino acids are indicated according to EU numbering system based on Kabat's amino acid positions.

Conditions of Ion Concentration

Conditions of Metal Ion Concentration

In one embodiment of the present invention, the ion concentration refers to a metal ion concentration. "Metal ions" refer to ions of group I elements except hydrogen such as alkaline metals and copper group elements, group II elements such as alkaline earth metals and zinc group elements, group III elements except boron, group IV elements except carbon and silicon, group VIII elements such as iron group and platinum group elements, elements belonging to subgroup A of groups V, VI, and VII, and metal elements such as antimony, bismuth, and polonium. Metal atoms have the property of releasing valence electrons to become cations. This is referred to as ionization tendency. Metals with strong ionization tendency are deemed to be chemically active.

In the present invention, preferred metal ions include, for example, calcium ion. Calcium ion is involved in modulation of many biological phenomena, including contraction of muscles such as skeletal, smooth, and cardiac muscles; activation of movement, phagocytosis, and the like of leukocytes; activation of shape change, secretion, and the like of platelets; activation of lymphocytes; activation of mast cells including secretion of histamine; cell responses mediated by catecholamine α receptor or acetylcholine receptor; exocytosis; release of transmitter substances from neuron terminals; and axoplasmic flow in neurons. Known intracellular calcium ion receptors include troponin C, calmodulin, parvalbumin, and myosin light chain, which have several calcium ion-binding sites and are believed to be derived from a common origin in terms of molecular evolution. There are also many known calcium-binding motifs. Such well-known motifs include, for example, cadherin domains, EF-hand of calmodulin, C2 domain of Protein kinase C, Gla domain of blood coagulation protein Factor IX, C-type lectins of acyaroglycoprotein receptor and mannose-binding receptor, A domains of LDL receptors, annexin, thrombospondin type 3 domain, and EGF-like domains.

In the present invention, when the metal ion is calcium ion, the conditions of calcium ion concentration include low calcium ion concentrations and high calcium ion concentrations. "The binding activity varies depending on calcium ion concentrations" means that the antigen-binding activity of an antigen-binding molecule varies due to the difference in the conditions between low and high calcium ion concentrations. For example, the antigen-binding activity of an antigen-binding molecule may be higher at a high calcium ion concentration than at a low calcium ion concentration. Alternatively, the antigen-binding activity of an antigen-binding molecule may be higher at a low calcium ion concentration than at a high calcium ion concentration.

Herein, the high calcium ion concentration is not particularly limited to a specific value; however, the concentration may preferably be selected between 100 μM and 10 mM. In another embodiment, the concentration may be selected between 200 μM and 5 mM. In an alternative embodiment, the concentration may be selected between 400 μM and 3 mM. In still another embodiment, the concentration may be selected between 200 μM and 2 mM. Furthermore, the concentration may be selected between 400 μM and 1 mM. In particular, a concentration selected between 500 μM and 2.5 mM, which is close to the plasma (blood) concentration of calcium ion in vivo, is preferred.

Herein, the low calcium ion concentration is not particularly limited to a specific value; however, the concentration may preferably be selected between 0.1 μM and 30 μM. In another embodiment, the concentration may be selected between 0.2 μM and 20 μM. In still another embodiment, the concentration may be selected between 0.5 μM and 10 μM. In an alternative embodiment, the concentration may be selected between 1 μM and 5 μM. Furthermore, the concentration may be selected between 2 μM and 4 μM. In particular, a concentration selected between 1 μM and 5 μM, which is close to the concentration of ionized calcium in early endosomes in vivo, is preferred.

Herein, "the antigen-binding activity is lower at a low calcium ion concentration than at a high calcium ion concentration" means that the antigen-binding activity of an antigen-binding molecule is weaker at a calcium ion concentration selected between 0.1 μM and 30 μM than at a calcium ion concentration selected between 100 μM and 10 mM. Preferably, it means that the antigen-binding activity of an antigen-binding molecule is weaker at a calcium ion concentration selected between 0.5 μM and 10 μM than at a calcium ion concentration selected between 200 μM and 5 mM. It particularly preferably means that the antigen-binding activity at the calcium ion concentration in the early endosome in vivo is weaker than that at the in vivo plasma calcium ion concentration; and specifically, it means that the antigen-binding activity of an antigen-binding molecule is weaker at a calcium ion concentration selected between 1 μM and 5 μM than at a calcium ion concentration selected between 500 μM and 2.5 mM.

Whether the antigen-binding activity of an antigen-binding molecule is changed depending on metal ion concentrations can be determined, for example, by the use of known measurement methods such as those described in the section "Binding Activity" above. For example, in order to confirm that the antigen-binding activity of an antigen-binding molecule becomes higher at a high calcium ion concentration than at a low calcium ion concentration, the antigen-binding activity of the antigen-binding molecule at low and high calcium ion concentrations is compared.

In the present invention, the expression "the antigen-binding activity is lower at a low calcium ion concentration than at a high calcium ion concentration" can also be expressed as "the antigen-binding activity of an antigen-binding molecule is higher at a high calcium ion concentration than at a low calcium ion concentration". In the present invention, "the antigen-binding activity is lower at a low calcium ion concentration than at a high calcium ion concentration" is sometimes written as "the antigen-binding ability is weaker at a low calcium ion concentration than at a high calcium ion concentration". Also, "the antigen-binding activity at a low calcium ion concentration is reduced to be lower than that at a high calcium ion concentration" may be written as "the antigen-binding ability at a low calcium ion concentration is made weaker than that at a high calcium ion concentration".

When determining the antigen-binding activity, the conditions other than calcium ion concentration can be appropriately selected by those skilled in the art, and are not particularly limited. For example, the activity can be determined at 37° C. in HEPES buffer. For example, a BIACORE™ system (GE Healthcare) or such can be used for the determination. When the antigen is a soluble antigen, the antigen-binding activity of an antigen-binding molecule can be assessed by flowing the antigen as an analyte over a chip onto which the antigen-binding molecule is immobilized. When the antigen is a membrane antigen, the binding activity of an antigen-binding molecule to the membrane antigen can be assessed by flowing the antigen-binding molecule as an analyte over a chip onto which the antigen is immobilized.

As long as the antigen-binding activity of an antigen-binding molecule of the present invention is weaker at a low calcium ion concentration than at a high calcium ion concentration, the ratio of the antigen-binding activity between low and high calcium ion concentrations is not particularly limited. However, the ratio of the KD (dissociation constant) of the antigen-binding molecule for an antigen at a low calcium ion concentration with respect to the KD at a high calcium ion concentration, i.e. the value of KD (3 µM Ca)/KD (2 mM Ca), is preferably 2 or more, more preferably 10 or more, and still more preferably 40 or more. The upper limit of the KD (3 µM Ca)/KD (2 mM Ca) value is not particularly limited, and may be any value such as 400, 1000, or 10000 as long as the molecule can be produced by techniques known to those skilled in the art.

When the antigen is a soluble antigen, KD (dissociation constant) can be used to represent the antigen-binding activity. Meanwhile, when the antigen is a membrane antigen, apparent KD (apparent dissociation constant) can be used to represent the activity. KD (dissociation constant) and apparent KD (apparent dissociation constant) can be determined by methods known to those skilled in the art, for example, using BIACORE™ system (GE healthcare), Scatchard plot, or flow cytometer.

Alternatively, for example, the dissociation rate constant (kd) can also be preferably used as an index to represent the ratio of the antigen-binding activity of an antigen-binding molecule of the present invention between low and high calcium concentrations. When the dissociation rate constant (kd) is used instead of the dissociation constant (KD) as an index to represent the binding activity ratio, the ratio of the dissociation rate constant (kd) between low and high calcium concentrations, i.e. the value of kd (low calcium concentration)/kd (high calcium concentration), is preferably 2 or more, more preferably 5 or more, still more preferably 10 or more, and yet more preferably 30 or more. The upper limit of the Kd (low calcium concentration)/kd (high calcium concentration) value is not particularly limited, and can be any value such as 50, 100, or 200 as long as the molecule can be produced by techniques known to those skilled in the art.

When the antigen is a soluble antigen, kd (dissociation rate constant) can be used to represent the antigen-binding activity. Meanwhile, when the antigen is a membrane antigen, apparent kd (apparent dissociation rate constant) can be used to represent the antigen-binding activity. The kd (dissociation rate constant) and apparent kd (apparent dissociation rate constant) can be determined by methods known to those skilled in the art, for example, using a BIACORE™ system (GE healthcare) or flow cytometer. In the present invention, when the antigen-binding activity of an antigen-binding molecule is determined at different calcium ion concentrations, it is preferable to use the same conditions except for the calcium concentrations.

For example, an antigen-binding domain or antibody whose antigen-binding activity is lower at a low calcium ion concentration than at a high calcium ion concentration, which is one embodiment of the present invention, can be obtained via screening of antigen-binding domains or antibodies including the steps of:
(a) determining the antigen-binding activity of an antigen-binding domain or antibody at a low calcium concentration;
(b) determining the antigen-binding activity of an antigen-binding domain or antibody at a high calcium concentration; and
(c) selecting an antigen-binding domain or antibody whose antigen-binding activity is lower at a low calcium concentration than at a high calcium concentration.

Moreover, an antigen-binding domain or antibody whose antigen-binding activity is lower at a low calcium ion concentration than at a high calcium ion concentration, which is one embodiment of the present invention, can be obtained via screening of antigen-binding domains or antibodies, or a library thereof, including the steps of:
(a) contacting an antigen with an antigen-binding domain or antibody, or a library thereof at a high calcium concentration;
(b) incubating at a low calcium concentration an antigen-binding domain or antibody that has bound to the antigen in step (a); and
(c) isolating an antigen-binding domain or antibody dissociated in step (b).

Furthermore, an antigen-binding domain or antibody whose antigen-binding activity is lower at a low calcium ion concentration than at a high calcium ion concentration, which is one embodiment of the present invention, can be obtained via screening of antigen-binding domains or antibodies, or a library thereof, including the steps of:
(a) contacting an antigen with a library of antigen-binding domains or antibodies at a low calcium concentration;
(b) selecting an antigen-binding domain or antibody which does not bind to the antigen in step (a);
(c) allowing the antigen-binding domain or antibody selected in step (c) to bind to the antigen at a high calcium concentration; and
(d) isolating an antigen-binding domain or antibody that has bound to the antigen in step (c).

In addition, an antigen-binding domain or antibody whose antigen-binding activity is lower at a low calcium ion concentration than at a high calcium ion concentration, which is one embodiment of the present invention, can be obtained by a screening method comprising the steps of:
(a) contacting at a high calcium concentration a library of antigen-binding domains or antibodies with a column onto which an antigen is immobilized;
(b) eluting an antigen-binding domain or antibody that has bound to the column in step (a) from the column at a low calcium concentration; and
(c) isolating the antigen-binding domain or antibody eluted in step (b).

Furthermore, an antigen-binding domain or antibody whose antigen-binding activity is lower at a low calcium ion concentration than at a high calcium ion concentration, which is one embodiment of the present invention, can be obtained by a screening method comprising the steps of:
(a) allowing at a low calcium concentration a library of antigen-binding domains or antibodies to pass through a column onto which an antigen is immobilized;
(b) collecting an antigen-binding domain or antibody that has been eluted without binding to the column in step (a);
(c) allowing the antigen-binding domain or antibody collected in step (b) to bind to the antigen at a high calcium concentration; and
(d) isolating an antigen-binding domain or antibody that has bound to the antigen in step (c).

Moreover, an antigen-binding domain or antibody whose antigen-binding activity is lower at a low calcium ion concentration than at a high calcium ion concentration, which is one embodiment of the present invention, can be obtained by a screening method comprising the steps of:
(a) contacting an antigen with a library of antigen-binding domains or antibodies at a high calcium concentration;
(b) obtaining an antigen-binding domain or antibody that has bound to the antigen in step (a);
(c) incubating at a low calcium concentration the antigen-binding domain or antibody obtained in step (b); and (d) isolating an antigen-binding domain or antibody whose antigen-binding activity in step (c) is weaker than the criterion for the selection of step (b).

The above-described steps may be repeated twice or more times. Thus, the present invention provides antigen-binding domains or antibodies whose antigen-binding activity is lower at a low calcium ion concentration than at a high calcium ion concentration, which are obtained by screening methods that further comprises the step of repeating twice or more times steps (a) to (c) or (a) to (d) in the above-described screening methods. The number of cycles of steps (a) to (c) or (a) to (d) is not particularly limited, but generally is 10 or less.

In the screening methods of the present invention, the antigen-binding activity of an antigen-binding domain or antibody at a low calcium concentration is not particularly limited as long as it is antigen-binding activity at an ionized calcium concentration of between 0.1 µM and 30 µM, but preferably is antigen-binding activity at an ionized calcium concentration of between 0.5 µM and 10 µM. More preferably, it is antigen-binding activity at the ionized calcium concentration in the early endosome in vivo, specifically, between 1 µM and 5 Meanwhile, the antigen-binding activity of an antigen-binding domain or antibody at a high calcium concentration is not particularly limited, as long as it is antigen-binding activity at an ionized calcium concentration of between 100 µM and 10 mM, but preferably is antigen-binding activity at an ionized calcium concentration of between 200 µM and 5 mM. More preferably, it is antigen-binding activity at the ionized calcium concentration in plasma in vivo, specifically, between 0.5 mM and 2.5 mM.

The antigen-binding activity of an antigen-binding domain or antibody can be measured by methods known to those skilled in the art. Conditions other than the ionized calcium concentration can be determined by those skilled in the art. The antigen-binding activity of an antigen-binding domain or antibody can be evaluated as a dissociation constant (KD), apparent dissociation constant (apparent KD), dissociation rate constant (kd), apparent dissociation constant (apparent kd), and such. These can be determined by methods known to those skilled in the art, for example, using a BIACORE™ system (GE healthcare), Scatchard plot, or FACS.

In the present invention, the step of selecting an antigen-binding domain or antibody whose antigen-binding activity is higher at a high calcium concentration than at a low calcium concentration is synonymous with the step of selecting an antigen-binding domain or antibody whose antigen-binding activity is lower at a low calcium concentration than at a high calcium concentration.

As long as the antigen-binding activity is higher at a high calcium concentration than at a low calcium concentration, the difference in the antigen-binding activity between high and low calcium concentrations is not particularly limited; however, the antigen-binding activity at a high calcium concentration is preferably twice or more, more preferably 10 times or more, and still more preferably 40 times or more than that at a low calcium concentration.

Antigen-binding domains or antibodies of the present invention to be screened by the screening methods described above may be any antigen-binding domains and antibodies. For example, it is possible to screen the above-described antigen-binding domains or antibodies. For example, antigen-binding domains or antibodies having natural sequences or substituted amino acid sequences may be screened.

Libraries

In an embodiment, an antigen-binding domain or antibody of the present invention can be obtained from a library that is mainly composed of a plurality of antigen-binding molecules whose sequences are different from one another and whose antigen-binding domains have at least one amino acid residue that alters the antigen-binding activity of the antigen-binding molecules depending on ion concentrations. The ion concentrations preferably include, for example, metal ion concentration and hydrogen ion concentration.

Herein, a "library" refers to a plurality of antigen-binding molecules or a plurality of fusion polypeptides containing antigen-binding molecules, or nucleic acids or polynucleotides encoding their sequences. The sequences of a plurality of antigen-binding molecules or a plurality of fusion polypeptides containing antigen-binding molecules in a library are not identical, but are different from one another.

Herein, the phrase "sequences are different from one another" in the expression "a plurality of antigen-binding molecules whose sequences are different from one another" means that the sequences of antigen-binding molecules in a library are different from one another. Specifically, in a library, the number of sequences different from one another reflects the number of independent clones with different sequences, and may also be referred to as "library size". The library size of a conventional phage display library ranges from $10^6$ to $10^{12}$. The library size can be increased up to $10^{14}$ by the use of known techniques such as ribosome display. However, the actual number of phage particles used in panning selection of a phage library is in general 10-10000 times greater than the library size. This excess multiplicity is also referred to as "the number of library equivalents", and means that there are 10 to 10,000 individual clones that have the same amino acid sequence. Thus, in the present invention, the phrase "sequences are different from one another" means that the sequences of independent antigen-binding molecules in a library, excluding library equivalents, are different from one another. More specifically, the above means that there are $10^6$ to $10^{14}$ antigen-binding molecules whose sequences are different from one another, preferably $10^7$ to $10^{12}$ molecules, more preferably $10^8$ to $10^{11}$ molecules, and particularly preferably $10^8$ to $10^{10}$ molecules whose sequences are different from one another.

Herein, the phrase "a plurality of" in the expression "a library mainly composed of a plurality of antigen-binding molecules" generally refers to, in the case of, for example, antigen-binding molecules, fusion polypeptides, polynucleotide molecules, vectors, or viruses of the present invention, a group of two or more types of the substance. For example, when two or more substances are different from one another in a particular characteristic, this means that there are two or more types of the substance. Such examples may include, for example, mutant amino acids observed at specific amino acid positions in an amino acid sequence. For example, when there are two or more antigen-binding molecules of the present invention whose sequences are substantially the same or preferably the same except for flexible residues or except for particular mutant amino acids at hypervariable positions exposed on the surface, there are a plurality of antigen-binding molecules of the present invention. In another example, when there are two or more polynucleotide molecules whose sequences are substantially the same or preferably the same except for nucleotides encoding flexible residues or nucleotides encoding mutant amino acids of hypervariable positions exposed on the surface, there are a plurality of polynucleotide molecules of the present invention.

In addition, herein, the phrase "mainly composed of" in the expression "a library mainly composed of a plurality of antigen-binding molecules" reflects the number of antigen-binding molecules whose antigen-binding activity varies depending on ion concentrations, among independent clones with different sequences in a library. Specifically, it is preferable that there are at least $10^4$ antigen-binding molecules having such binding activity in a library. More preferably, antigen-binding domains of the present invention can be obtained from a library containing at least $10^5$ antigen-binding molecules having such binding activity. Still more preferably, antigen-binding domains of the present invention can be obtained from a library containing at least $10^6$ antigen-binding molecules having such binding activity. Particularly preferably, antigen-binding domains of the present invention can be obtained from a library containing at least $10^7$ antigen-binding molecules having such binding activity. Yet more preferably, antigen-binding domains of the present invention can be obtained from a library containing at least $10^8$ antigen-binding molecules having such binding activity. Alternatively, this may also be preferably expressed as the ratio of the number of antigen-binding molecules whose antigen-binding activity varies depending on ion concentrations with respect to the number of independent clones having different sequences in a library. Specifically, antigen-binding domains of the present invention can be obtained from a library in which antigen-binding molecules having such binding activity account for 0.1% to 80%, preferably 0.5% to 60%, more preferably 1% to 40%, still more preferably 2% to 20%, and particularly preferably 4% to 10% of independent clones with different sequences in the library. In the case of fusion polypeptides, polynucleotide molecules, or vectors, similar expressions may be possible using the number of molecules or the ratio to the total number of molecules. In the case of viruses, similar expressions may also be possible using the number of virions or the ratio to total number of virions.

Amino Acids that Alter the Antigen-binding Activity of Antigen-binding Domains Depending on Calcium Ion Concentrations Antigen-binding domains or antibodies of the present invention to be screened by the above-described screening methods may be prepared in any manner. For example, when the metal ion is calcium ion, it is possible to use preexisting antibodies, preexisting libraries (phage library, etc.), antibodies or libraries prepared from hybridomas obtained by immunizing animals or from B cells of immunized animals, antibodies or libraries obtained by introducing amino acids capable of chelating calcium (for example, aspartic acid and glutamic acid) or unnatural amino acid mutations into the above-described antibodies or libraries (calcium-cheletable amino acids (such as aspartic acid and glutamic acid), libraries with increased content of unnatural amino acids, libraries prepared by introducing calcium-chelatable amino acids (such as aspartic acid and glutamic acid) or unnatural amino acid mutations at particular positions, or the like.

Examples of the amino acids that alter the antigen-binding activity of antigen-binding molecules depending on ion concentrations as described above may be any types of amino acids as long as the amino acids form a calcium-binding motif. Calcium-binding motifs are well known to those skilled in the art and have been described in details (for example, Springer et al. (Cell (2000) 102, 275-277); Kawasaki and Kretsinger (Protein Prof. (1995) 2, 305-490); Moncrief et al. (J. Mol. Evol. (1990) 30, 522-562); Chauvaux et al. (Biochem. J. (1990) 265, 261-265); Bairoch and Cox (FEBS Lett. (1990) 269, 454-456); Davis (New Biol. (1990) 2, 410-419); Schaefer et al. (Genomics (1995) 25, 638-643); Economou et al. (EMBO J. (1990) 9, 349-354); Wurzburg et al. (Structure. (2006) 14, 6, 1049-1058)). Specifically, any known calcium-binding motifs, including type C lectins such as ASGPR, CD23, MBR, and DC-SIGN, can be included in antigen-binding molecules of the present invention. Preferred examples of such preferred calcium-binding motifs also include, in addition to those described above, for example, the calcium-binding motif in the antigen-binding domain of SEQ ID NO: 4.

Furthermore, as amino acids that alter the antigen-binding activity of antigen-binding molecules depending on calcium ion concentrations, for example, amino acids having metal-chelating activity may also be preferably used. Examples of such metal-chelating amino acids include, for example, serine (Ser(S)), threonine (Thr(T)), asparagine (Asn(N)), glutamine (Gln(Q)), aspartic acid (Asp(D)), and glutamic acid (Glu(E)).

Positions in the antigen-binding domains at which the above-described amino acids are contained are not particularly limited to particular positions, and may be any positions within the heavy chain variable region or light chain variable region that forms an antigen-binding domain, as long as they alter the antigen-binding activity of antigen-binding molecules depending on calcium ion concentrations. Specifically, antigen-binding domains of the present invention can be obtained from a library mainly composed of antigen-binding molecules whose sequences are different from one another and whose heavy chain antigen-binding domains contain amino acids that alter the antigen-binding activity of the antigen-binding molecules depending on calcium ion concentrations. In another embodiment, antigen-binding domains of the present invention can be obtained from a library mainly composed of antigen-binding molecules whose sequences are different from one another and whose heavy chain CDR3 domains contain the above-mentioned amino acids. In still another embodiment, antigen-binding domains of the present invention can be obtained from a library mainly composed of antigen-binding molecules whose sequences are different from one another and whose heavy chain CDR3 domains contain the above-mentioned amino acids at positions 95, 96, 100a, and/or 101 as indicated according to the Kabat numbering system.

Meanwhile, in an embodiment of the present invention, antigen-binding domains of the present invention can be obtained from a library mainly composed of antigen-binding molecules whose sequences are different from one another and whose light chain antigen-binding domains contain amino acids that alter the antigen-binding activity of anti-gen-binding molecules depending on calcium ion concentrations. In another embodiment, antigen-binding domains of the present invention can be obtained from a library mainly composed of antigen-binding molecules whose sequences are different from one another and whose light chain CDR1 domains contain the above-mentioned amino acids. In still another embodiment, antigen-binding domains of the present invention can be obtained from a library mainly composed of antigen-binding molecules whose sequences are different from one another and whose light chain CDR1 domains contain the above-mentioned amino acids at positions 30, 31, and/or 32 as indicated according to the Kabat numbering system.

In another embodiment, antigen-binding domains of the present invention can be obtained from a library mainly composed of antigen-binding molecules whose sequences are different from one another and whose light chain CDR2 domains contain the above-mentioned amino acid residues.

In yet another embodiment, the present invention provides libraries mainly composed of antigen-binding molecules whose sequences are different from one another and whose light chain CDR2 domains contain the above-mentioned amino acid residues at position 50 as indicated according to the Kabat numbering system.

In still another embodiment of the present invention, antigen-binding domains of the present invention can be obtained from a library mainly composed of antigen-binding molecules whose sequences are different from one another and whose light chain CDR3 domains contain the above-mentioned amino acid residues. In an alternative embodiment, antigen-binding domains of the present invention can be obtained from a library mainly composed of antigen-binding molecules whose sequences are different from one another and whose light chain CDR3 domains contain the above-mentioned amino acid residues at position 92 as indicated according to the Kabat numbering system.

Furthermore, in a different embodiment of the present invention, antigen-binding domains of the present invention can be obtained from a library mainly composed of antigen-binding molecules whose sequences are different from one another and in which two or three CDRs selected from the above-described light chain CDR1, CDR2, and CDR3 contain the aforementioned amino acid residues. Moreover, antigen-binding domains of the present invention can be obtained from a library mainly composed of antigen-binding molecules whose sequences are different from one another and whose light chains contain the aforementioned amino acid residues at any one or more of positions 30, 31, 32, 50, and/or 92 as indicated according to the Kabat numbering system.

In a particularly preferred embodiment, the framework sequences of the light chain and/or heavy chain variable region of an antigen-binding molecule preferably contain human germ line framework sequences. Thus, in an embodiment of the present invention, when the framework sequences are completely human sequences, it is expected that when such an antigen-binding molecule of the present invention is administered to humans (for example, to treat diseases), it induces little or no immunogenic response. In the above sense, the phrase "containing a germ line sequence" in the present invention means that a part of the framework sequences of the present invention is identical to a part of any human germ line framework sequences. For example, when the heavy chain FR2 sequence of an antigen-binding molecule of the present invention is a combination of heavy chain FR2 sequences of different human germ line framework sequences, such a molecule is also an antigen-binding molecule of the present invention "containing a germ line sequence".

Preferred examples of the frameworks include, for example, fully human framework region sequences currently known, which are included in the website of V-Base (http://vbase.mrc-cpe.cam.ac.uk/) or others. Those framework region sequences can be appropriately used as a germ line sequence contained in an antigen-binding molecule of the present invention. The germ line sequences may be categorized according to their similarity (Tomlinson et al. (J. Mol. Biol. (1992) 227, 776-798); Williams and Winter (Eur. J. Immunol. (1993) 23, 1456-1461); Cox et al. (Nat. Genetics (1994) 7, 162-168)). Appropriate germ line sequences can be selected from Vκ, which is grouped into seven subgroups; Vλ, which is grouped into ten subgroups; and VH, which is grouped into seven subgroups.

Fully human VH sequences preferably include, but are not limited to, for example, VH sequences of:

subgroup VH1 (for example, VH1-2, VH1-3, VH1-8, VH1-18, VH1-24, VH1-45, VH1-46, VH1-58, and VH1-69);
subgroup VH2 (for example, VH2-5, VH2-26, and VH2-70);
subgroup VH3 (VH3-7, VH3-9, VH3-11, VH3-13, VH3-15, VH3-16, VH3-20, VH3-21, VH3-23, VH3-30, VH3-33, VH3-35, VH3-38, VH3-43, VH3-48, VH3-49, VH3-53, VH3-64, VH3-66, VH3-72, VH3-73, and VH3-74);
subgroup VH4 (VH4-4, VH4-28, VH4-31, VH4-34, VH4-39, VH4-59, and VH4-61);
subgroup VH5 (VH5-51);
subgroup VH6 (VH6-1); and
subgroup VH7 (VH7-4 and VH7-81).
These are also described in known documents (Matsuda et al. (J. Exp. Med. (1998) 188, 1973-1975)) and such, and thus persons skilled in the art can appropriately design antigen-binding molecules of the present invention based on the information of these sequences. It is also preferable to use other fully human frameworks or framework sub-regions.

Fully human Vk sequences preferably include, but are not limited to, for example:
A20, A30, L1, L4, L5, L8, L9, L11, L12, L14, L15, L18, L19, L22, L23, L24, O2, O4, O8, O12, O14, and O18 grouped into subgroup Vk1;
A1, A2, A3, A5, A7, A17, A18, A19, A23, O1, and O11, grouped into subgroup Vk2;
A11, A27, L2, L6, L10, L16, L20, and L25, grouped into subgroup Vk3;
B3, grouped into subgroup Vk4;
B2 (herein also referred to as Vk5-2), grouped into subgroup Vk5; and
A10, A14, and A26, grouped into subgroup Vk6 (Kawasaki et al. (Eur. J. Immunol. (2001) 31, 1017-1028); Schable and Zachau (Biol. Chem. Hoppe Seyler (1993) 374, 1001-1022); Brensing-Kuppers et al. (Gene (1997) 191, 173-181)).

Fully human VL sequences preferably include, but are not limited to, for example:
V1-2, V1-3, V1-4, V1-5, V1-7, V1-9, V1-11, V1-13, V1-16, V1-17, V1-18, V1-19, V1-20, and V1-22, grouped into subgroup VL1;
V2-1, V2-6, V2-7, V2-8, V2-11, V2-13, V2-14, V2-15, V2-17, and V2-19, grouped into subgroup VL1;
V3-2, V3-3, and V3-4, grouped into subgroup VL3;
V4-1, V4-2, V4-3, V4-4, and V4-6, grouped into subgroup VL4; and
V5-1, V5-2, V5-4, and V5-6, grouped into subgroup VL5 (Kawasaki et al. (Genome Res. (1997) 7, 250-261)).

Normally, these framework sequences are different from one another at one or more amino acid residues. These framework sequences can be used in combination with "at least one amino acid residue that alters the antigen-binding activity of an antigen-binding molecule depending on ion concentrations" of the present invention. Other examples of the fully human frameworks used in combination with "at least one amino acid residue that alters the antigen-binding activity of an antigen-binding molecule depending on ion concentrations" of the present invention include, but are not limited to, for example, KOL, NEWM, REI, EU, TUR, TEI, LAY, and POM (for example, Kabat et al. (1991) supra; Wu et al. (J. Exp. Med. (1970) 132, 211-250)).

Without being bound by a particular theory, one reason for the expectation that the use of germ line sequences precludes adverse immune responses in most individuals is believed to be as follows. As a result of the process of affinity maturation during normal immune responses, somatic mutation occurs frequently in the variable regions of immunoglobulin. Such mutations mostly occur around CDRs whose sequences are hypervariable, but also affect residues of framework regions. Such framework mutations do not exist on the germ line genes, and also they are less likely to be immunogenic in patients. On the other hand, the normal human population is exposed to most of the framework sequences expressed from the germ line genes. As a result of immunotolerance, these germ line frameworks are expected to have low or no immunogenicity in patients. To maximize the possibility of immunotolerance, variable region-encoding genes may be selected from a group of commonly occurring functional germ line genes.

Known methods such as site-directed mutagenesis (Kunkel et al. (Proc. Natl. Acad. Sci. USA (1985) 82, 488-492)) and overlap extension PCR can be appropriately employed to produce antigen-binding molecules of the present invention in which the above-described framework sequences contain amino acids that alter the antigen-binding activity of the antigen-binding molecules depending on calcium ion concentrations.

For example, a library which contains a plurality of antigen-binding molecules of the present invention whose sequences are different from one another can be constructed by combining heavy chain variable regions prepared as a randomized variable region sequence library with a light chain variable region selected as a framework sequence originally containing at least one amino acid residue that alters the antigen-binding activity of the antigen-binding molecule depending on calcium ion concentrations. As a non-limiting example, when the ion concentration is calcium ion concentration, such preferred libraries include, for example, those constructed by combining the light chain variable region sequence of SEQ ID NO: 4 (Vk5-2) and the heavy chain variable region produced as a randomized variable region sequence library.

Alternatively, a light chain variable region sequence selected as a framework region originally containing at least one amino acid residue that alters the antigen-binding activity of an antigen-binding molecule as mentioned above can be design to contain various amino acid residues other than the above amino acid residues. Herein, such residues are referred to as flexible residues. The number and position of flexible residues are not particularly limited as long as the antigen-binding activity of the antigen-binding molecule of the present invention varies depending on ion concentrations. Specifically, the CDR sequences and/or FR sequences of the heavy chain and/or light chain may contain one or more flexible residues. For example, when the ion concentration is calcium ion concentration, non-limiting examples of flexible residues to be introduced into the light chain variable region sequence of SEQ ID NO: 4 (Vk5-2) include the amino acid residues listed in Tables 1 or 2.

TABLE 1

| CDR | Kabat NUMBERING | 70% AMINO ACID OF THE TOTAL | | | |
|---|---|---|---|---|---|
| CDR1 | 28 | S: 100% | | | |
| | 29 | I: 100% | | | |
| | 30 | E: 72% | N: 14% | S: 14% | |
| | 31 | D: 100% | | | |
| | 32 | D: 100% | | | |
| | 33 | L: 100% | | | |
| | 34 | A: 70% | N: 30% | | |
| CDR2 | 50 | E: 100% | | | |
| | 51 | A: 100% | | | |
| | 52 | S: 100% | | | |
| | 53 | H: 5% | N: 25% | S: 45% | T: 25% |

TABLE 1-continued

| CDR | Kabat NUMBERING | 70% AMINO ACID OF THE TOTAL | | | |
|---|---|---|---|---|---|
| | 54 | L: 100% | | | |
| | 55 | Q: 100% | | | |
| | 56 | S: 100% | | | |
| CDR3 | 90 | Q: 100% | | | |
| | 91 | H: 25% | S: 15% | R: 15% | Y: 45% |
| | 92 | D: 80% | N: 10% | S: 10% | |
| | 93 | D: 5% | G: 10% | N: 25% | S: 50% | R: 10% |
| | 94 | S: 50% | Y: 50% | | |
| | 95 | P: 100% | | | |
| | 96 | L: 50% | Y: 50% | | |

TABLE 2

| CDR | Kabat NUMBERING | 30% AMINO ACID OF THE TOTAL | | | |
|---|---|---|---|---|---|
| CDR1 | 28 | S: 100% | | | |
| | 29 | I: 100% | | | |
| | 30 | E: 83% | S: 17% | | |
| | 31 | D: 100% | | | |
| | 32 | D: 100% | | | |
| | 33 | L: 100% | | | |
| | 34 | A: 70% | N: 30% | | |
| CDR2 | 50 | H: 100% | | | |
| | 51 | A: 100% | | | |
| | 52 | S: 100% | | | |
| | 53 | H: 5% | N: 25% | S: 45% | T: 25% |
| | 54 | L: 100% | | | |
| | 55 | Q: 100% | | | |
| | 56 | S: 100% | | | |
| CDR3 | 90 | Q: 100% | | | |
| | 91 | H: 25% | S: 15% | R: 15% | Y: 45% |
| | 92 | D: 80% | N: 10% | S: 10% | |
| | 93 | D: 5% | G: 10% | N: 25% | S: 50% | R: 10% |
| | 94 | S: 50% | Y: 50% | | |
| | 95 | P: 100% | | | |
| | 96 | L: 50% | Y: 50% | | |

Herein, flexible residues refer to amino acid residue variations present at hypervariable positions at which several different amino acids are present on the light chain and heavy chain variable regions when the amino acid sequences of known and/or native antibodies or antigen-binding domains are compared. Hypervariable positions are generally located in the CDR regions. In an embodiment, the data provided by Kabat, Sequences of Proteins of Immunological Interest (National Institute of Health Bethesda Md.) (1987 and 1991) is useful to determine hypervariable positions in known and/or native antibodies. Furthermore, databases on the Internet (http://vbase.mrc-cpe.cam.ac.uk/, http://www-.bioinf.org.uk/abs/index.html) provide the collected sequences of many human light chains and heavy chains and their locations. The information on the sequences and locations is useful to determine hypervariable positions in the present invention. According to the present invention, when a certain amino acid position has preferably about 2 to about 20 possible amino acid residue variations, preferably about 3 to about 19, preferably about 4 to about 18, preferably 5 to 17, preferably 6 to 16, preferably 7 to 15, preferably 8 to 14, preferably 9 to 13, and preferably 10 to 12 possible amino acid residue variations, the position is hypervariable. In some embodiments, a certain amino acid position may have preferably at least about 2, preferably at least about 4, preferably at least about 6, preferably at least about 8, preferably about 10, and preferably about 12 amino acid residue variations.

Alternatively, a library containing a plurality of antigen-binding molecules of the present invention whose sequences are different from one another can be constructed by combining heavy chain variable regions produced as a randomized variable region sequence library with light chain variable regions into which at least one amino acid residue that alters the antigen-binding activity of antigen-binding molecules depending on ion concentrations as mentioned above is introduced. When the ion concentration is calcium ion concentration, non-limiting examples of such libraries preferably include, for example, libraries in which heavy chain variable regions produced as a randomized variable region sequence library are combined with light chain variable region sequences in which a particular residue(s) in a germ line sequence such as SEQ ID NO: 5 (Vk1), SEQ ID NO: 6 (Vk2), SEQ ID NO: 7 (Vk3), or SEQ ID NO: 8 (Vk4) has been substituted with at least one amino acid residue that alters the antigen-binding activity of an antigen-binding molecule depending on calcium ion concentrations. Non-limiting examples of such amino acid residues include amino acid residues in light chain CDR1. Furthermore, non-limiting examples of such amino acid residues include amino acid residues in light chain CDR2. In addition, non-limiting examples of such amino acid residues also include amino acid residues in light chain CDR3.

Non-limiting examples of such amino acid residues contained in light chain CDR1 include those at positions 30, 31, and/or 32 in the CDR1 of light chain variable region as indicated by EU numbering. Furthermore, non-limiting examples of such amino acid residues contained in light chain CDR2 include an amino acid residue at position 50 in the CDR2 of light chain variable region as indicated by Kabat numbering. Moreover, non-limiting examples of such amino acid residues contained in light chain CDR3 include an amino acid residue at position 92 in the CDR3 of light chain variable region as indicated by Kabat numbering. These amino acid residues can be contained alone or in combination as long as they form a calcium-binding motif and/or as long as the antigen-binding activity of an antigen-binding molecule varies depending on calcium ion concentrations. Meanwhile, as troponin C, calmodulin, parvalbumin, and myosin light chain, which have several calcium ion-binding sites and are believed to be derived from a common origin in terms of molecular evolution, are known, the light chain CDR1, CDR2, and/or CDR3 can be designed to have their binding motifs. For example, it is possible to use cadherin domains, EF hand of calmodulin, C2 domain of Protein kinase C, Gla domain of blood coagulation protein FactorIX, C type lectins of acyaroglycoprotein receptor and mannose-binding receptor, A domains of LDL receptors, annexin, thrombospondin type 3 domain, and EGF-like domains in an appropriate manner for the above purposes.

When heavy chain variable regions produced as a randomized variable region sequence library and light chain variable regions into which at least one amino acid residue that alters the antigen-binding activity of an antigen-binding molecule depending on ion concentrations has been introduced are combined as described above, the sequences of the light chain variable regions can be designed to contain flexible residues in the same manner as described above. The number and position of such flexible residues are not particularly limited to particular embodiments as long as the antigen-binding activity of antigen-binding molecules of the present invention varies depending on ion concentrations. Specifically, the CDR sequences and/or FR sequences of heavy chain and/or light chain can contain one or more flexible residues. When the ion concentration is calcium ion concentration, non-limiting examples of flexible residues to be introduced into the sequence of light chain variable region include the amino acid residues listed in Tables 1 and 2.

The preferred heavy chain variable regions to be combined include, for example, randomized variable region libraries. Known methods are combined as appropriate to produce a randomized variable region library. In a non-limiting embodiment of the present invention, an immune library constructed based on antibody genes derived from lymphocytes of animals immunized with a specific antigen, patients with infections, persons with an elevated antibody titer in blood as a result of vaccination, cancer patients, or auto immune disease patients, may be preferably used as a randomized variable region library.

In another non-limiting embodiment of the present invention, a synthetic library produced by replacing the CDR sequences of V genes in genomic DNA or functional reshaped V genes with a set of synthetic oligonucleotides containing sequences encoding codon sets of an appropriate length can also be preferably used as a randomized variable region library. In this case, since sequence diversity is observed in the heavy chain CDR3 sequence, it is also possible to replace the CDR3 sequence only. A criterion of giving rise to diversity in amino acids in the variable region of an antigen-binding molecule is that diversity is given to amino acid residues at surface-exposed positions in the antigen-binding molecule. The surface-exposed position refers to a position that is considered to be able to be exposed on the surface and/or contacted with an antigen, based on structure, ensemble of structures, and/or modeled structure of an antigen-binding molecule. In general, such positions are CDRs. Preferably, surface-exposed positions are determined using coordinates from a three-dimensional model of an antigen-binding molecule using a computer program such as the InsightII program (Accelrys). Surface-exposed positions can be determined using algorithms known in the art (for example, Lee and Richards (J. Mol. Biol. (1971) 55, 379-400); Connolly (J. Appl. Cryst. (1983) 16, 548-558)). Determination of surface-exposed positions can be performed using software suitable for protein modeling and three-dimensional structural information obtained from an antibody. Software that can be used for these purposes preferably includes SYBYL Biopolymer Module software (Tripos Associates). Generally or preferably, when an algorithm requires a user input size parameter, the "size" of a probe which is used in the calculation is set at about 1.4 Angstrom or smaller in radius. Furthermore, methods for determining surface-exposed regions and areas using software for personal computers are described by Pacios (Comput. Chem. (1994) 18 (4), 377-386; J. Mol. Model. (1995) 1, 46-53).

In another non-limiting embodiment of the present invention, a naive library, which is constructed from antibody genes derived from lymphocytes of healthy persons and whose repertoire consists of naive sequences, which are antibody sequences with no bias, can also be particularly preferably used as a randomized variable region library (Gejima et al. (Human Antibodies (2002) 11, 121-129); Cardoso et al. (Scand. J. Immunol. (2000) 51, 337-344)). Herein, an amino acid sequence comprising a naive sequence refers to an amino acid sequence obtained from such a naive library.

In one embodiment of the present invention, an antigen-binding domain of the present invention can be obtained from a library containing a plurality of antigen-binding molecules of the present invention whose sequences are different from one another, prepared by combining light chain variable regions constructed as a randomized variable region sequence library with a heavy chain variable region selected as a framework sequence that originally contains "at least one amino acid residue that alters the antigen-binding activity of an antigen-binding molecule depending on ion concentrations". When the ion concentration is calcium ion concentration, non-limiting examples of such libraries preferably include those constructed by combining light chain variable regions constructed as a randomized variable region sequence library with the sequence of heavy chain variable region of SEQ ID NO: 9 (6RL#9-IgG1) or SEQ ID NO: 10 (6KC4-1#85-IgG1). Alternatively, such a library can be constructed by selecting appropriate light chain variable regions from those having germ line sequences, instead of light chain variable regions constructed as a randomized variable region sequence library. Such preferred libraries include, for example, those in which the sequence of heavy chain variable region of SEQ ID NO: 9 (6RL#9-IgG1) or SEQ ID NO: 10 (6KC4-1#85-IgG1) is combined with light chain variable regions having germ line sequences.

Alternatively, the sequence of an heavy chain variable region selected as a framework sequence that originally contains "at least one amino acid residue that alters the antigen-binding activity of an antigen-binding molecule" as mentioned above can be designed to contain flexible residues. The number and position of the flexible residues are not particularly limited as long as the antigen-binding activity of an antigen-binding molecule of the present invention varies depending on ion concentrations. Specifically, the CDR and/or FR sequences of heavy chain and/or light chain can contain one or more flexible residues. When the ion concentration is calcium ion concentration, non-limiting examples of flexible residues to be introduced into the sequence of heavy chain variable region of SEQ ID NO: 9 (6RL#9-IgG1) include all amino acid residues of heavy chain CDR1 and CDR2 and the amino acid residues of the heavy chain CDR3 except those at positions 95, 96, and/or 100a. Alternatively, non-limiting examples of flexible residues to be introduced into the sequence of heavy chain variable region of SEQ ID NO: 10 (6KC4-1#85-IgG1) include all amino acid residues of heavy chain CDR1 and CDR2 and the amino acid residues of the heavy chain CDR3 except those at amino acid positions 95 and/or 101.

Alternatively, a library containing a plurality of antigen-binding molecules whose sequences are different from one another can be constructed by combining light chain variable regions constructed as a randomized variable region sequence library or light chain variable regions having germ line sequences with heavy chain variable regions into which "at least one amino acid residue responsible for the ion concentration-dependent change in the antigen-binding activity of an antigen-binding molecule" has been introduced as mentioned above. When the ion concentration is calcium ion concentration, non-limiting examples of such libraries preferably include those in which light chain variable regions constructed as a randomized variable region sequence library or light chain variable regions having germ line sequences are combined with the sequence of a heavy chain variable region in which a particular residue(s) has been substituted with at least one amino acid residue that alters the antigen-binding activity of an antigen-binding molecule depending on calcium ion concentrations. Non-limiting examples of such amino acid residues include amino acid residues of the heavy chain CDR1. Further non-limiting examples of such amino acid residues include amino acid residues of the heavy chain CDR2. In addition, non-limiting examples of such amino acid residues also include amino acid residues of the heavy chain CDR3. Non-limiting examples of such amino acid residues of heavy chain CDR3 include the amino acids of positions 95, 96, 100a, and/or 101 in the CDR3 of heavy chain variable region as indicated by the Kabat numbering. Furthermore, these amino acid residues can be contained alone or in combination as long as they form a calcium-binding motif and/or the antigen-binding activity of an antigen-binding molecule varies depending on calcium ion concentrations.

When light chain variable regions constructed as a randomized variable region sequence library or light chain variable regions having germ line sequence are combined with a heavy chain variable region into which at least one amino acid residue that alter the antigen-binding activity of an antigen-binding molecule depending on ion concentrations as mentioned above has been introduced, the sequence of the heavy chain variable region can also be designed to contain flexible residues in the same manner as described above. The number and position of flexible residues are not particularly limited as long as the antigen-binding activity of an antigen-binding molecule of the present invention varies depending on ion concentrations. Specifically, the heavy chain CDR and/or FR sequences may contain one or more flexible residues. Furthermore, randomized variable region libraries can be preferably used as amino acid sequences of CDR1, CDR2, and/or CDR3 of the heavy chain variable region other than the amino acid residues that alter the antigen-binding activity of an antigen-binding molecule. When germ line sequences are used as light chain variable regions, non-limiting examples of such sequences include those of SEQ ID NO: 5 (Vk1), SEQ ID NO: 6 (Vk2), SEQ ID NO: 7 (Vk3), and SEQ ID NO: 8 (Vk4).

Any of the above-described amino acids that alter the antigen-binding activity of an antigen-binding molecule depending on calcium ion concentrations can be preferably used, as long as they form a calcium-binding motif. Specifically, such amino acids include electron-donating amino acids. Preferred examples of such electron-donating amino acids include, serine, threonine, asparagine, glutamic acid, aspartic acid, and glutamic acid.

Condition of Hydrogen Ion Concentrations

In an embodiment of the present invention, the condition of ion concentrations refers to the condition of hydrogen ion concentrations or pH condition. In the present invention, the concentration of proton, i.e., the nucleus of hydrogen atom, is treated as synonymous with hydrogen index (pH). When the activity of hydrogen ion in an aqueous solution is represented as aH+, pH is defined as −log 10aH+. When the ionic strength of the aqueous solution is low (for example, lower than $10^{-3}$), aH+ is nearly equal to the hydrogen ion strength. For example, the ionic product of water at 25° C. and 1 atmosphere is Kw=aH+aOH=$10^{-14}$, and therefore in pure water, aH+=aOH=$10^{-7}$. In this case, pH=7 is neutral; an aqueous solution whose pH is lower than 7 is acidic or whose pH is greater than 7 is alkaline.

In the present invention, when pH condition is used as the ion concentration condition, pH conditions include high hydrogen ion concentrations or low pHs, i.e., an acidic pH range, and low hydrogen ion concentrations or high pHs, i.e., a neutral pH range. "The binding activity varies depending on pH condition" means that the antigen-binding activity of an antigen-binding molecule varies due to the difference in conditions of a high hydrogen ion concentration or low pH (an acidic pH range) and a low hydrogen ion concentration or high pH (a neutral pH range). This includes, for example, the case where the antigen-binding activity of an antigen-binding molecule is higher in a neutral pH range than in an acidic pH range and the case where the antigen-binding activity of an antigen-binding molecule is higher in an acidic pH range than in a neutral pH range.

In the present specification, neutral pH range is not limited to a specific value and is preferably selected from between pH 6.7 and pH 10.0. In another embodiment, the pH can be selected from between pH 6.7 and pH 9.5. In still another embodiment, the pH can be selected from between pH 7.0 and pH 9.0. In yet another embodiment, the pH can be selected from between pH 7.0 and pH 8.0. In particular, the preferred pH includes pH 7.4, which is close to the pH of plasma (blood) in vivo.

In the present specification, an acidic pH range is not limited to a specific value and is preferably selected from between pH 4.0 and pH 6.5. In another embodiment, the pH can be selected from between pH 4.5 and pH 6.5. In still another embodiment, the pH can be selected from between pH 5.0 and pH 6.5. In yet another embodiment, the pH can be selected from between pH 5.5 and pH 6.5. In particular, the preferred pH includes pH 5.8, which is close to the pH in the early endosome in vivo.

In the present invention, "the antigen-binding activity of an antigen-binding molecule at a high hydrogen ion concentration or low pH (an acidic pH range) is lower than that at a low hydrogen ion concentration or high pH (a neutral pH range)" means that the antigen-binding activity of an antigen-binding molecule at a pH selected from between pH 4.0 and pH 6.5 is weaker than that at a pH selected from between pH 6.7 and pH 10.0; preferably means that the antigen-binding activity of an antigen-binding molecule at a pH selected from between pH 4.5 and pH 6.5 is weaker than that at a pH selected from between pH 6.7 and pH 9.5; more preferably, means that the antigen-binding activity of an antigen-binding molecule at a pH selected from between pH 5.0 and pH 6.5 is weaker than that at a pH selected from between pH 7.0 and pH 9.0; still more preferably means that the antigen-binding activity of an antigen-binding molecule at a pH selected from between pH 5.5 and pH 6.5 is weaker than that at a pH selected from between pH 7.0 and pH 8.0; particularly preferably means that the antigen-binding activity at the pH in the early endosome in vivo is weaker than the antigen-binding activity at the pH of plasma in vivo; and specifically means that the antigen-binding activity of an antigen-binding molecule at pH 5.8 is weaker than the antigen-binding activity at pH 7.4.

Whether the antigen-binding activity of an antigen-binding molecule has changed by the pH condition can be determined, for example, by the use of known measurement methods such as those described in the section "Binding Activity" above. Specifically, the binding activity is measured under different pH conditions using the measurement methods described above. For example, the antigen-binding activity of an antigen-binding molecule is compared under the conditions of acidic pH range and neutral pH range to confirm that the antigen-binding activity of the antigen-binding molecule changes to be higher under the condition of neutral pH range than that under the condition of acidic pH range.

Furthermore, in the present invention, the expression "the antigen-binding activity at a high hydrogen ion concentration or low pH, i.e., in an acidic pH range, is lower than that at a low hydrogen ion concentration or high pH, i.e., in a neutral pH range" can also be expressed as "the antigen-binding activity of an antigen-binding molecule at a low hydrogen ion concentration or high pH, i.e., in a neutral pH range, is higher than that at a high hydrogen ion concentration or low pH, i.e., in an acidic pH range". In the present invention, "the antigen-binding activity at a high hydrogen ion concentration or low pH, i.e., in an acidic pH range, is lower than that at a low hydrogen ion concentration or high pH, i.e., in a neutral pH range" may be described as "the antigen-binding activity at a high hydrogen ion concentration or low pH, i.e., in an acidic pH range, is weaker than the antigen-binding ability at a low hydrogen ion concentration or high pH, i.e., in a neutral pH range". Alternatively, "the antigen-binding activity at a high hydrogen ion concentration or low pH, i.e., in an acidic pH range, is reduced to be lower than that at a low hydrogen ion concentration or high pH, i.e., in a neutral pH range" may be described as "the antigen-binding activity at a high hydrogen ion concentration or low pH, i.e., in an acidic pH range, is reduced to be weaker than the antigen-binding ability at a low hydrogen ion concentration or high pH, i.e., in a neutral pH range".

The conditions other than hydrogen ion concentration or pH for measuring the antigen-binding activity may be suitably selected by those skilled in the art and are not particularly limited. Measurements can be carried out, for example, at 37° C. using HEPES buffer. Measurements can be carried out, for example, using BIACORE™ system (GE Healthcare). When the antigen is a soluble antigen, the antigen-binding activity of an antigen-binding molecule can be determined by assessing the binding activity to the soluble antigen by pouring the antigen as an analyte into a chip immobilized with the antigen-binding molecule. When the antigen is a membrane antigen, the binding activity to the membrane antigen can be assessed by pouring the antigen-binding molecule as an analyte into a chip immobilized with the antigen.

As long as the antigen-binding activity of an antigen-binding molecule of the present invention at a high hydrogen ion concentration or low pH, i.e., in an acidic pH range is weaker than that at a low hydrogen ion concentration or high pH, i.e., in a neutral pH range, the ratio of the antigen-binding activity between that at a high hydrogen ion concentration or low pH, i.e., an acidic pH range, and at a low hydrogen ion concentration or high pH, i.e., a neutral pH range is not particularly limited, and the value of KD (pH 5.8)/KD (pH 7.4), which is the ratio of the dissociation constant (KD) for an antigen at a high hydrogen ion concentration or low pH, i.e., in an acidic pH range to the KD at a low hydrogen ion concentration or high pH, i.e., in a neutral pH range, is preferably 2 or more; more preferably the value of KD (pH 5.8)/KD (pH 7.4) is 10 or more; and still more preferably the value of KD (pH 5.8)/KD (pH 7.4) is 40 or more. The upper limit of KD (pH 5.8)/KD (pH 7.4) value is not particularly limited, and may be any value such as 400, 1000, or 10000, as long as the molecule can be produced by the techniques of those skilled in the art.

When the antigen is a soluble antigen, the dissociation constant (KD) can be used as the value for antigen-binding activity. Meanwhile, when the antigen is a membrane antigen, the apparent dissociation constant (KD) can be used. The dissociation constant (KD) and apparent dissociation constant (KD) can be measured by methods known to those skilled in the art, and a BIACORE™ system (GE healthcare), Scatchard plot, flow cytometer, and such can be used.

Alternatively, for example, the dissociation rate constant (kd) can be suitably used as an index for indicating the ratio of the antigen-binding activity of an antigen-binding molecule of the present invention between that at a high hydrogen ion concentration or low pH, i.e., an acidic pH range and a low hydrogen ion concentration or high pH, i.e., a neutral pH range. When kd (dissociation rate constant) is used as an index for indicating the binding activity ratio instead of KD (dissociation constant), the value of kd (in an acidic pH range)/kd (in a neutral pH range), which is the ratio of kd (dissociation rate constant) for the antigen at a high hydrogen ion concentration or low pH, i.e., in an acidic pH range to kd (dissociation rate constant) at a low hydrogen ion concentration or high pH, i.e., in a neutral pH range, is preferably 2 or more, more preferably 5 or more, still more preferably 10 or more, and yet more preferably 30 or more. The upper limit of kd (in an acidic pH range)/kd (in a neutral pH range) value is not particularly limited, and may be any value such as 50, 100, or 200, as long as the molecule can be produced by the techniques of those skilled in the art.

When the antigen is a soluble antigen, the dissociation rate constant (KD) can be used as the value for antigen-binding activity. Meanwhile, when the antigen is a membrane antigen, the apparent dissociation constant (KD) can be used. The dissociation constant (KD) and apparent dissociation constant (KD) can be measured by methods known to those skilled in the art, and a BIACORE™ system (GE healthcare), Scatchard plot, flow cytometer, and such can be used. In the present invention, when the antigen-binding activity of an antigen-binding molecule is measured at different hydrogen ion concentrations, i.e., pHs, conditions other than the hydrogen ion concentration, i.e., pH, are preferably the same.

For example, an antigen-binding domain or antibody whose antigen-binding activity at a high hydrogen ion concentration or low pH, i.e., in an acidic pH range is lower than that at a low hydrogen ion concentration or high pH, i.e., in a neutral pH range, which is one embodiment provided by the present invention, can be obtained via screening of antigen-binding domains or antibodies, comprising the following steps (a) to (c):
(a) obtaining the antigen-binding activity of an antigen-binding domain or antibody in an acidic pH range;
(b) obtaining the antigen-binding activity of an antigen-binding domain or antibody in a neutral pH range; and
(c) selecting an antigen-binding domain or antibody whose antigen-binding activity in the acidic pH range is lower than that in the neutral pH range.

Alternatively, an antigen-binding domain or antibody whose antigen-binding activity at a high hydrogen ion concentration or low pH, i.e., in an acidic pH range, is lower than that at a low hydrogen ion concentration or high pH, i.e., in a neutral pH range, which is one embodiment provided by the present invention, can be obtained via screening of antigen-binding domains or antibodies, or a library thereof, comprising the following steps (a) to (c):
(a) contacting an antigen-binding domain or antibody, or a library thereof, in a neutral pH range with an antigen;
(b) placing in an acidic pH range the antigen-binding domain or antibody bound to the antigen in step (a); and
(c) isolating the antigen-binding domain or antibody dissociated in step (b).

An antigen-binding domain or antibody whose antigen-binding activity at a high hydrogen ion concentration or low pH, i.e., in an acidic pH range is lower than that at a low hydrogen ion concentration or high pH, i.e., in a neutral pH range, which is another embodiment provided by the present invention, can be obtained via screening of antigen-binding domains or antibodies, or a library thereof, comprising the following steps (a) to (d):
(a) contacting in an acidic pH range an antigen with a library of antigen-binding domains or antibodies;
(b) selecting the antigen-binding domain or antibody which does not bind to the antigen in step (a);
(c) allowing the antigen-binding domain or antibody selected in step (b) to bind with the antigen in a neutral pH range; and
(d) isolating the antigen-binding domain or antibody bound to the antigen in step (c).

An antigen-binding domain or antibody whose antigen-binding activity at a high hydrogen ion concentration or low pH, i.e., in an acidic pH range, is lower than that at a low hydrogen ion concentration or high pH, i.e., in a neutral pH range, which is even another embodiment provided by the present invention, can be obtained by a screening method comprising the following steps (a) to (c):
(a) contacting in a neutral pH range a library of antigen-binding domains or antibodies with a column immobilized with an antigen;
(b) eluting in an acidic pH range from the column the antigen-binding domain or antibody bound to the column in step (a); and
(c) isolating the antigen-binding domain or antibody eluted in step (b).

An antigen-binding domain or antibody whose antigen-binding activity at a high hydrogen ion concentration or low pH, i.e., in an acidic pH, range is lower than that at a low hydrogen ion concentration or high pH, i.e., in a neutral pH range, which is still another embodiment provided by the present invention, can be obtained by a screening method comprising the following steps (a) to (d):
(a) allowing, in an acidic pH range, a library of antigen-binding domains or antibodies to pass a column immobilized with an antigen;
(b) collecting the antigen-binding domain or antibody eluted without binding to the column in step (a);
(c) allowing the antigen-binding domain or antibody collected in step (b) to bind with the antigen in a neutral pH range; and
(d) isolating the antigen-binding domain or antibody bound to the antigen in step (c).

An antigen-binding domain or antibody whose antigen-binding activity at a high hydrogen ion concentration or low pH, i.e., in an acidic pH range, is lower than that at a low hydrogen ion concentration or high pH, i.e., in a neutral pH range, which is yet another embodiment provided by the present invention, can be obtained by a screening method comprising the following steps (a) to (d):
(a) contacting an antigen with a library of antigen-binding domains or antibodies in a neutral pH range;
(b) obtaining the antigen-binding domain or antibody bound to the antigen in step (a);
(c) placing in an acidic pH range the antigen-binding domain or antibody obtained in step (b); and
(d) isolating the antigen-binding domain or antibody whose antigen-binding activity in step (c) is weaker than the standard selected in step (b).

The above-described steps may be repeated twice or more times. Thus, the present invention provides antigen-binding domains and antibodies whose antigen-binding activity in an acidic pH range is lower than that in a neutral pH range, which are obtained by a screening method that further comprises the steps of repeating steps (a) to (c) or (a) to (d) in the above-described screening methods. The number of times that steps (a) to (c) or (a) to (d) is repeated is not particularly limited; however, the number is 10 or less in general.

In the screening methods of the present invention, the antigen-binding activity of an antigen-binding domain or antibody at a high hydrogen ion concentration or low pH, i.e., in an acidic pH range, is not particularly limited, as long as it is the antigen-binding activity at a pH of between 4.0 and 6.5, and includes the antigen-binding activity at a pH of between 4.5 and 6.6 as the preferred pH. The antigen-binding activity also includes that at a pH of between 5.0 and 6.5, and that at a pH of between 5.5 and 6.5 as another preferred pH. The antigen-binding activity also includes that at the pH in the early endosome in vivo as the more preferred pH, and specifically, that at pH 5.8. Meanwhile, the antigen-binding activity of an antigen-binding domain or antibody at a low hydrogen ion concentration or high pH, i.e., in a neutral pH range, is not particularly limited, as long as it is the antigen-binding activity at a pH of between 6.7 and 10, and includes the antigen-binding activity at a pH of between 6.7 and 9.5 as the preferred pH. The antigen-binding activity also includes that at a pH of between 7.0 and 9.5 and that at a pH of between 7.0 and 8.0 as another preferred pH. The antigen-binding activity also includes that at the pH of plasma in vivo as the more preferred pH, and specifically, that at pH 7.4.

The antigen-binding activity of an antigen-binding domain or antibody can be measured by methods known to those skilled in the art. Those skilled in the art can suitably determine conditions other than ionized calcium concentration. The antigen-binding activity of an antigen-binding domain or antibody can be assessed based on the dissociation constant (KD), apparent dissociation constant (KD), dissociation rate constant (kd), apparent dissociation rate constant (kd), and such. These can be determined by methods known to those skilled in the art, for example, using a Biacore™ system (GE healthcare), Scatchard plot, or FACS.

Herein, the step of selecting an antigen-binding domain or antibody whose antigen-binding activity at a low hydrogen ion concentration or high pH, i.e., in a neutral pH range, is higher than that at a high hydrogen ion concentration or low pH, i.e., in an acidic pH range, is synonymous with the step of selecting an antigen-binding domain or antibody whose antigen-binding activity at a high hydrogen ion concentration or low pH, i.e., in an acidic pH range, is lower than that at a low hydrogen ion concentration or high pH, i.e., in a neutral pH range.

As long as the antigen-binding activity at a low hydrogen ion concentration or high pH, i.e., in a neutral pH range, is higher than that at a high hydrogen ion concentration or low pH, i.e., in an acidic pH range, the difference between the antigen-binding activity at a low hydrogen ion concentration or high pH, i.e., a neutral pH range, and that at a high hydrogen ion concentration or low pH, i.e., an acidic pH range, is not particularly limited; however, the antigen-binding activity at a low hydrogen ion concentration or high pH, i.e., in a neutral pH range, is preferably twice or more, more preferably 10 times or more, and still more preferably 40 times or more than that at a high hydrogen ion concentration or low pH, i.e., in an acidic pH range.

The antigen binding domain or antibody of the present invention screened by the screening methods described above may be any antigen-binding domain or antibody, and the above-mentioned antigen-binding domain or antibody may be screened. For example, antigen-binding domain or antibody having the native sequence may be screened, and antigen-binding domain or antibody in which their amino acid sequences have been substituted may be screened.

The antigen-binding domain or antibody of the present invention to be screened by the above-described screening methods may be prepared in any manner. For example, conventional antibodies, conventional libraries (phage library, etc.), antibodies or libraries prepared from B cells of immunized animals or from hybridomas obtained by immunizing animals, antibodies or libraries (libraries with increased content of amino acids with a side chain pKa of 4.0-8.0 (for example, histidine and glutamic acid) or unnatural amino acids, libraries introduced with amino acids with a side chain pKa of 4.0-8.0 (for example, histidine and glutamic acid) or unnatural amino acid mutations at specific positions, etc.) obtained by introducing amino acids with a side chain pKa of 4.0-8.0 (for example, histidine and glutamic acid) or unnatural amino acid mutations into the above-described antibodies or libraries may be used.

Methods for obtaining an antigen-binding domain or antibody whose antigen-binding activity at a low hydrogen ion concentration or high pH, i.e., in a neutral pH range, is higher than that at a high hydrogen ion concentration or low pH, i.e., in an acidic pH range, from an antigen-binding domains or antibodies prepared from hybridomas obtained by immunizing animals or from B cells of immunized animals preferably include, for example, the antigen-binding molecule or antibody in which at least one of the amino acids of the antigen-binding domain or antibody is substituted with an amino acid with a side chain pKa of 4.0-8.0 (for example, histidine and glutamic acid) or an unnatural amino acid mutation, or the antigen-binding domain or antibody inserted with an amino acid with a side chain pKa of 4.0-8.0 (for example, histidine and glutamic acid) or unnatural amino acid, such as those described in WO 2009/125825. Examples of heavy and light chain amino acid positions (by Kabat numbering) that can be substituted with histidine are listed in Table 2 of WO 2009/125825. An English translation of that table is provided below.

Positions of Histidine Substitution not Significantly Affecting Binding Ability

H31, H50, H54, H56, H57, H58, H59, H60, H61, H62, H63, H64, H65, H100a, H100b, H102L24, L26, L27, L28, L30, L31, L32, L52, L53, L54, L56, L90, L92, L93, L94

The sites of introducing mutations of amino acids with a side chain pKa of 4.0-8.0 (for example, histidine and glutamic acid) or unnatural amino acids are not particularly limited, and may be any position as long as the antigen-binding activity in an acidic pH range becomes weaker than that in a neutral pH range (the value of KD (in an acidic pH range)/KD (in a neutral pH range) or kd (in an acidic pH range)/kd (in a neutral pH range) is increased) as compared to before substitution or insertion. For example, when the antigen-binding molecule is an antibody, antibody variable region and CDRs are suitable. Those skilled in the art can appropriately determine the number of amino acids to be substituted with or the number of amino acids with a side chain pKa of 4.0-8.0 (for example, histidine and glutamic acid) or unnatural amino acids to be inserted. It is possible to substitute with a single amino acid having a side chain pKa of 4.0-8.0 (for example, histidine and glutamic acid) or a single unnatural amino acid; it is possible to insert a single amino acid having a side chain pKa of 4.0-8.0 (for example, histidine and glutamic acid) or a single unnatural amino acid; it is possible to substitute with two or more amino acids having a side chain pKa of 4.0-8.0 (for example, histidine and glutamic acid) or two or more unnatural amino acids; and it is possible to insert two or more amino acids having a side chain pKa of 4.0-8.0 (for example, histidine and glutamic acid) or two or more unnatural amino acids. Alternatively, other amino acids can be deleted, added, inserted, and/or substituted concomitantly, aside from the substitution into amino acids having a side chain pKa of 4.0-8.0 (for example, histidine and glutamic acid) or unnatural amino acids, or the insertion of amino acids having a side chain pKa of 4.0-8.0 (for example, histidine and glutamic acid) or unnatural amino acids. Substitution into or insertion of amino acids with a side chain pKa of 4.0-8.0 (for example, histidine and glutamic acid) or unnatural amino acids can performed randomly by methods such as histidine scanning, in which the alanine of alanine scanning known to those skilled in the art is replaced with histidine. Antigen-binding molecules exhibiting a greater value of KD (in an acidic pH range)/KD (in a neutral pH range) or kd (in an acidic pH range)/kd (in a neutral pH range) as compared to before the mutation can be selected from antigen-binding domains or antibodies introduced with random insertions or substitution mutations of amino acids with a side chain pKa of 4.0-8.0 (for example, histidine and glutamic acid) or unnatural amino acids.

Preferred examples of antigen-binding molecules containing the mutation into amino acids with a side chain pKa of 4.0-8.0 (for example, histidine and glutamic acid) or unnatural amino acids as described above and whose antigen-binding activity in an acidic pH range is lower than that in a neutral pH range include, antigen-binding molecules whose antigen-binding activity in the neutral pH range after the mutation into amino acids with a side chain pKa of 4.0-8.0 (for example, histidine and glutamic acid) or unnatural amino acids is comparable to that before the mutation into amino acids with a side chain pKa of 4.0-8.0 (for example, histidine and glutamic acid) or unnatural amino acids. Herein, "an antigen-binding molecule after the mutation with amino acids having a side chain pKa of 4.0-8.0 (for example, histidine and glutamic acid) or unnatural amino acids has an antigen-binding activity comparable to that before the mutation with amino acids having a side chain pKa of 4.0-8.0 (for example, histidine and glutamic acid) or unnatural amino acids" means that, when taking the antigen-binding activity of an antigen-binding molecule before the mutation with amino acids having a side chain pKa of 4.0-8.0 (for example, histidine and glutamic acid) or unnatural amino acids as 100%, the antigen-binding activity of an antigen-binding molecule after the mutation with amino acids having a side chain pKa of 4.0-8.0 (for example, histidine and glutamic acid) or unnatural amino acids is at least 10% or more, preferably 50% or more, more preferably 80% or more, and still more preferably 90% or more. The antigen-binding activity after the mutation of amino acids with a side chain pKa of 4.0-8.0 (for example, histidine and glutamic acid) or unnatural amino acids at pH 7.4 may be higher than that before the mutation of amino acids with a side chain pKa of 4.0-8.0 (for example, histidine and glutamic acid) or unnatural amino acids at pH 7.4. If the antigen-binding activity of an antigen-binding molecule is decreased due to insertion of or substitution into amino acids with a side chain pKa of 4.0-8.0 (for example, histidine and glutamic acid) or unnatural amino acids, the antigen-binding activity can be made to be comparable to that before the insertion of or substitution into amino acids with a side chain pKa of 4.0-8.0 (for example, histidine and glutamic acid) or unnatural amino acids, by introducing a substitution, deletion, addition, and/or insertion of one or more amino acids of the antigen-binding molecule. The present invention also includes antigen-binding molecules whose binding activity has been adjusted to be comparable by substitution, deletion, addition, and/or insertion of one or more amino acids after substitution or insertion of amino acids with a side chain pKa of 4.0-8.0 (for example, histidine and glutamic acid) or unnatural amino acids.

Meanwhile, when an antigen-binding molecule is a substance containing an antibody constant region, preferred embodiments of antigen-binding molecules whose antigen-binding activity at an acidic pH range is lower than that in a neutral pH range include methods in which the antibody constant regions contained in the antigen-binding molecules have been modified. Specific examples of modified antibody constant regions preferably include the constant regions of SEQ ID NOs: 11, 12, 13, and 14.

Amino Acids that Alter the Antigen-binding Activity of Antigen-binding Domain Depending on the Hydrogen Ion Concentration Conditions Antigen-binding domains or antibodies of the present invention to be screened by the above-described screening methods may be prepared in any manner. For example, when ion concentration condition is hydrogen ion concentration condition or pH condition, conventional antibodies, conventional libraries (phage library, etc.), antibodies or libraries prepared from B cells of immunized animals or from hybridomas obtained by immunizing animals, antibodies or libraries (libraries with increased content of amino acids with a side chain pKa of 4.0-8.0 (for example, histidine and glutamic acid) or unnatural amino acids, libraries introduced with mutations of amino acids with a side chain pKa of 4.0-8.0 (for example, histidine and glutamic acid) or unnatural amino acids at specific positions, etc.) obtained by introducing mutations of amino acids with a side chain pKa of 4.0-8.0 (for example, histidine and glutamic acid) or unnatural amino acids into the above-described antibodies or libraries may be used.

In one embodiment of the present invention, a library containing multiple antigen-binding molecules of the present invention whose sequences are different from one another can also be constructed by combining heavy chain variable regions, produced as a randomized variable region sequence library, with light chain variable regions introduced with "at least one amino acid residue that changes the antigen-binding activity of an antigen-binding molecule depending on the hydrogen ion concentration condition".

Such amino acid residues include, but are not limited to, for example, amino acid residues contained in the light chain CDR1. The amino acid residues also include, but are not limited to, for example, amino acid residues contained in the light chain CDR2. The amino acid residues also include, but are not limited to, for example, amino acid residues contained in the light chain CDR3.

The above-described amino acid residues contained in the light chain CDR1 include, but are not limited to, for example, amino acid residues of positions 24, 27, 28, 31, 32, and/or 34 according to Kabat numbering in the CDR1 of light chain variable region. Meanwhile, the amino acid residues contained in the light chain CDR2 include, but are not limited to, for example, amino acid residues of positions 50, 51, 52, 53, 54, 55, and/or 56 according to Kabat numbering in the CDR2 of light chain variable region. Furthermore, the amino acid residues in the light chain CDR3 include, but are not limited to, for example, amino acid residues of positions 89, 90, 91, 92, 93, 94, and/or 95A according to Kabat numbering in the CDR3 of light chain variable region. Moreover, the amino acid residues can be contained alone or can be contained in combination of two or more amino acids as long as they allow the change in the antigen-binding activity of an antigen-binding molecule depending on the hydrogen ion concentration.

Even when the heavy chain variable region produced as a randomized variable region sequence library is combined with the above-described light chain variable region introduced with "at least one amino acid residue that changes the antigen-binding activity of an antigen-binding molecule depending on the hydrogen ion concentration condition", it is possible to design so that the flexible residues are contained in the sequence of the light chain variable region in the same manner as described above. The number and position of the flexible residues are not particularly limited to a specific embodiment, as long as the antigen-binding activity of an antigen-binding molecule of the present invention changes depending on the hydrogen ion concentration condition. Specifically, the CDR and/or FR sequences of heavy chain and/or light chain can contain one or more flexible residues. For example, flexible residues to be introduced into the sequences of the light chain variable regions include, but are not limited to, for example, the amino acid residues listed in Tables 3 and 4. Meanwhile, amino acid sequences of light chain variable regions other than the flexible residues and amino acid residues that change the antigen-binding activity of an antigen-binding molecule depending on the hydrogen ion concentration condition suitably include, but are not limited to, germ line sequences such as Vk1 (SEQ ID NO: 5), Vk2 (SEQ ID NO: 6), Vk3 (SEQ ID NO: 7), and Vk4 (SEQ ID NO: 8).

TABLE 3

| POSITION | AMINO ACID | | | | | | | | |
|---|---|---|---|---|---|---|---|---|---|
| CDR1 | | | | | | | | | |
| 28 | S: 100% | | | | | | | | |
| 29 | I: 100% | | | | | | | | |
| 30 | N: 25% | S: 25% | R: 25% | H: 25% | | | | | |
| 31 | S: 100% | | | | | | | | |
| 32 | H: 100% | | | | | | | | |
| 33 | L: 100% | | | | | | | | |
| 34 | A: 50% | N: 50% | | | | | | | |
| CDR2 | | | | | | | | | |
| 50 | H: 100% | | | | OR | A: 25% | D: 25% | G: 25% | K: 25% |
| 51 | A: 100% | | | | | A: 100% | | | |
| 52 | S: 100% | | | | | S: 100% | | | |
| 53 | K: 33.3% | N: 33.3% | S: 33.3% | | | H: 100% | | | |
| 54 | L: 100% | | | | | L: 100% | | | |
| 55 | Q: 100% | | | | | Q: 100% | | | |
| 56 | S: 100% | | | | | S: 100% | | | |
| CDR3 | | | | | | | | | |
| 90 | Q: 100% | | | | OR | Q: 100% | | | |
| 91 | H: 100% | | | | | S: 33.3% | R: 33.3% | Y: 33.3% | |
| 92 | G: 25% | N: 25% | S: 25% | Y: 25% | | H: 100% | | | |
| 93 | H: 33.3% | N: 33.3% | S: 33.3% | | | H: 33.3% | N: 33.3% | S: 33.3% | |
| 94 | S: 50% | Y: 50% | | | | S: 50% | Y: 50% | | |
| 95 | P: 100% | | | | | P: 100% | | | |
| 96 | L: 50% | Y: 50% | | | | L: 50% | Y: 50% | | |

(Position indicates Kabat numbering)

TABLE 4

| CDR | POSITION | AMINO ACID | | | |
|---|---|---|---|---|---|
| CDR1 | 28 | S: 100% | | | |
| | 29 | I: 100% | | | |
| | 30 | H: 30% | N: 10% | S: 50% | R: 10% |
| | 31 | N: 35% | S: 65% | | |
| | 32 | H: 40% | N: 20% | Y: 40% | |
| | 33 | L: 100% | | | |
| | 34 | A: 70% | N: 30% | | |
| CDR2 | 50 | A: 25% | D: 15% | G: 25% | H: 30% | K: 5% |
| | 51 | A: 100% | | | |

TABLE 4-continued

| CDR | POSITION | AMINO ACID | | | |
|---|---|---|---|---|---|
| | 52 | S: 100% | | | |
| | 53 | H: 30% | K: 10% | N: 15% | S: 45% |
| | 54 | L: 100% | | | |
| | 55 | Q: 100% | | | |
| | 56 | S: 100% | | | |
| CDR3 | 90 | Q: 100% | | | |
| | 91 | H: 30% | S: 15% | R: 10% | Y: 45% |
| | 92 | G: 20% | H: 30% | N: 20% | S: 15% | Y: 15% |
| | 93 | H: 30% | N: 25% | S: 45% | |
| | 94 | S: 50% | Y: 50% | | |
| | 95 | P: 100% | | | |
| | 96 | L: 50% | Y: 50% | | |

(Position indicates Kabat numbering)

Any amino acid residue may be suitably used as the above-described amino acid residues that change the antigen-binding activity of an antigen-binding molecule depending on the hydrogen ion concentration condition. Specifically, such amino acid residues include amino acids with a side chain pKa of 4.0-8.0. Such electron-releasing amino acids preferably include, for example, naturally occurring amino acids such as histidine and glutamic acid, as well as unnatural amino acids such as histidine analogs (US2009/0035836), m-NO2-Tyr (pKa 7.45), 3,5-Br2-Tyr (pKa 7.21), and 3, 5-I2-Tyr (pKa 7.38) (Bioorg. Med. Chem. (2003) 11 (17), 3761-2768). Particularly preferred amino acid residues include, for example, amino acids with a side chain pKa of 6.0-7.0. Such electron-releasing amino acid residues preferably include, for example, histidine.

Known methods such as site-directed mutagenesis (Kunkel et al. (Proc. Natl. Acad. Sci. USA (1985) 82, 488-492)) and Overlap extension PCR can be appropriately employed to modify the amino acids of antigen-binding domains. Furthermore, various known methods can also be used as an amino acid modification method for substituting amino acids by those other than natural amino acids (Annu Rev. Biophys. Biomol. Struct. (2006) 35, 225-249; Proc. Natl.

Acad. Sci. U.S.A. (2003) 100 (11), 6353-6357). For example, a cell-free translation system (Clover Direct (Protein Express)) containing tRNAs in which amber suppressor tRNA, which is complementary to UAG codon (amber codon) that is a stop codon, is linked with an unnatural amino acid may be suitably used.

The preferred heavy chain variable region that is used in combination includes, for example, randomized variable region libraries. Known methods are appropriately combined as a method for producing a randomized variable region library. In a non-limiting embodiment of the present invention, an immune library constructed based on antibody genes derived from animals immunized with specific antigens, patients with infection or persons with an elevated antibody titer in blood as a result of vaccination, cancer patients, or lymphocytes of auto immune diseases may be suitably used as a randomized variable region library.

In another non-limiting embodiment of the present invention, in the same manner as described above, a synthetic library in which the CDR sequences of V genes from genomic DNA or functional reconstructed V genes are replaced with a set of synthetic oligonucleotides containing the sequences encoding codon sets of an appropriate length can also be suitably used as a randomized variable region library. In this case, the CDR3 sequence alone may be replaced because variety in the gene sequence of heavy chain CDR3 is observed. The basis for giving rise to amino acid variations in the variable region of an antigen-binding molecule is to generate variations of amino acid residues of surface-exposed positions of the antigen-binding molecule. The surface-exposed position refers to a position where an amino acid is exposed on the surface and/or contacted with an antigen based on the conformation, structural ensemble, and/or modeled structure of an antigen-binding molecule, and in general, such positions are the CDRs. The surface-exposed positions are preferably determined using the coordinates derived from a three-dimensional model of the antigen-binding molecule using computer programs such as InsightII program (Accelrys). The surface-exposed positions can be determined using algorithms known in the art (for example, Lee and Richards (J. Mol. Biol. (1971) 55, 379-400); Connolly (J. Appl. Cryst. (1983) 16, 548-558)). The surface-exposed positions can be determined based on the information on the three dimensional structure of antibodies using software suitable for protein modeling. Software which is suitably used for this purpose includes the SYBYL biopolymer module software (Tripos Associates). When the algorithm requires the input size parameter from the user, the "size" of probe for use in computation is generally or preferably set at about 1.4 angstrom or less in radius. Furthermore, a method for determining surface-exposed region and area using PC software is described by Pacios (Comput. Chem. (1994) 18 (4), 377-386; and J. Mol. Model. (1995) 1, 46-53).

In still another non-limiting embodiment of the present invention, a naive library constructed from antibody genes derived from lymphocytes of healthy persons and consisting of naive sequences, which are unbiased repertoire of antibody sequences, can also be particularly suitably used as a randomized variable region library (Gejima et al. (Human Antibodies (2002) 11, 121-129); and Cardoso et al. (Scand. J. Immunol. (2000) 51, 337-344)).

FcRn

Unlike Fcγ receptor belonging to the immunoglobulin superfamily, human FcRn is structurally similar to polypeptides of major histocompatibility complex (MHC) class I, exhibiting 22% to 29% sequence identity to class I MHC molecules (Ghetie et al., Immunol. Today (1997) 18 (12): 592-598). FcRn is expressed as a heterodimer consisting of soluble β or light chain (β2 microglobulin) complexed with transmembrane α or heavy chain. Like MHC, FcRn α chain comprises three extracellular domains (α1, α2, and α3) and its short cytoplasmic domain anchors the protein onto the cell surface. α1 and α2 domains interact with the FcRn-binding domain of the antibody Fc region (Raghavan et al., Immunity (1994) 1: 303-315).

FcRn is expressed in maternal placenta and york sac of mammals, and is involved in mother-to-fetus IgG transfer. In addition, in neonatal small intestine of rodents, where FcRn is expressed, FcRn is involved in transfer of maternal IgG across brush border epithelium from ingested colostrum or milk. FcRn is expressed in a variety of other tissues and endothelial cell systems of various species. FcRn is also expressed in adult human endothelia, muscular blood vessels, and hepatic sinusoidal capillaries. FcRn is believed to play a role in maintaining the plasma IgG concentration by mediating recycling of IgG to serum upon binding to IgG. Typically, binding of FcRn to IgG molecules is strictly pH dependent. The optimal binding is observed in an acidic pH range below 7.0.

Human FcRn whose precursor is a polypeptide having the signal sequence of SEQ ID NO: 15 (the polypeptide with the signal sequence is shown in SEQ ID NO: 16) forms a complex with human β2-microglobulin in vivo. As shown in the Reference Examples described below, soluble human FcRn complexed with β2-microglobulin is produced by using conventional recombinant expression techniques. FcRn regions of the present invention can be assessed for their binding activity to such a soluble human FcRn complexed with β2-microglobulin. Herein, unless otherwise specified, human FcRn refers to a form capable of binding to an FcRn region of the present invention. Examples include a complex between human FcRn and human β2-microglobulin.

Fc Region

An Fc region contains the amino acid sequence derived from the heavy chain constant region of an antibody. An Fc region is a portion of the heavy chain constant region of an antibody, starting from the N terminal end of the hinge region, which corresponds to the papain cleavage site at an amino acid around position 216 according to the EU numbering system, and contains the hinge, CH2, and CH3 domains.

The binding activity of an Fc region of the present invention to FcRn, human FcRn in particular, can be measured by methods known to those skilled in the art, as described in the section "Binding Activity" above. Those skilled in the art can appropriately determine the conditions other than pH. The antigen-binding activity and human FcRn-binding activity of an antigen-binding molecule can be assessed based on the dissociation constant (KD), apparent dissociation constant (KD), dissociation rate (kd), apparent dissociation rate (kd), and such. These can be measured by methods known to those skilled in the art. For example, a BIACORE™ system (GE healthcare), Scatchard plot, or flow cytometer may be used.

When the human FcRn-binding activity of an Fc region of the present invention is measured, conditions other than the pH are not particularly limited, and can be appropriately selected by those skilled in the art. Measurements can be carried out, for example, at 37° C. using 2-(N-morpholino) ethanesulfonic acid (MES) buffer, as described in WO 2009125825. Alternatively, the human FcRn-binding activity of an Fc region of the present invention can be measured by methods known to those skilled in the art, and may be measured by using, for example, BIACORE™ system (GE Healthcare) or such. The binding activity of an Fc region of the present invention to human FcRn can be assessed by pouring, as an analyte, human FcRn, an Fc region, or an antigen-binding molecule of the present invention containing the Fc region into a chip immobilized with an Fc region, an antigen-binding molecule of the present invention containing the Fc region, or human FcRn.

A neutral pH range as the condition where the Fc region contained in an antigen-binding molecule of the present invention has the FcRn-binding activity means pH 6.7 to pH 10.0 in general. Preferably, the neutral pH range is a range indicated with arbitrary pH values between pH 7.0 and pH 8.0, and is preferably selected from pH 7.0, 7.1, 7.2, 7.3, 7.4, 7.5, 7.6, 7.7, 7.8, 7.9, and 8.0, and is particularly preferably pH 7.4 that is close to the pH of plasma (blood) in vivo. When the binding affinity between the human FcRn-binding domain and human FcRn at pH 7.4 is too low to assess, pH 7.0 may be used instead of pH 7.4. Herein, an acidic pH range as the condition where the Fc region contained in an antigen-binding molecule of the present invention has the FcRn-binding activity means pH 4.0 to pH 6.5 in general. Preferably, the acidic pH range means pH 5.5 to pH 6.5, particularly preferably pH 5.8 to pH 6.0 which is close to the pH in the early endosome in vivo. Regarding the temperature used as the measurement condition, the binding affinity between the human FcRn-binding domain and human FcRn may be assessed at any temperature between 10° C. and 50° C. Preferably, the binding affinity between the human FcRn-binding domain and human FcRn can be determined at 15° C. to 40° C. More preferably, the binding affinity between the human FcRn-binding domain and human FcRn can be determined in the same manner at an arbitrary temperature between 20° C. and 35° C., such as any one temperature of 20, 21, 22, 23, 24, 25, 26, 27, 28, 29, 30, 31, 32, 33, 34, and 35° C. In an embodiment of the present invention, the temperature includes, but is not limited to, for example, 25° C.

According to "The Journal of Immunology (2009) 182: 7663-7671", the human FcRn-binding activity of native human IgG1 is 1.7 µM (KD) in an acidic pH range (pH 6.0) whereas the activity is almost undetectable in the neutral pH range. Thus, in a preferred embodiment, antigen-binding molecules of the present invention having the human FcRn-binding activity in an acidic pH range and in a neutral pH range, including antigen-binding molecules whose human FcRn-binding activity in an acidic pH range is 20 µM (KD) or stronger and whose human FcRn-binding activity in a neutral pH range is comparable to or stronger than that of native human IgG may be screened. In a more preferred embodiment, antigen-binding molecules of the present invention including antigen-binding molecules whose human FcRn-binding activity in an acidic pH range is 20 µM (KD) or stronger and that in a neutral pH range is 40 µM (KD) or stronger may be screened. In a still more preferred embodiment, antigen-binding molecules of the present invention including antigen-binding molecules whose human FcRn-binding activity in an acidic pH range is 0.5 µM (KD) or stronger and that in a neutral pH range is 15 µM (KD) or stronger may be screened. The above-noted KD values can be determined by the method described in "The Journal of Immunology (2009) 182: 7663-7671 (antigen-binding molecules are immobilized onto a chip, and human FcRn is poured as an analyte)".

In the present invention, preferred Fc regions have the human FcRn-binding activity in an acidic pH range and in a neutral pH range. When an Fc region originally has the human FcRn-binding activity in an acidic pH range and in a neutral pH range, it can be used as it is. When an Fc region has only weak or no human FcRn-binding activity in an acidic pH range and/or in a neutral pH range, Fc regions having desired human FcRn-binding activity can be obtained by modifying amino acids of an antigen-binding molecule. Fc regions having desired human FcRn-binding activity in an acidic pH range and/or in a neutral pH range can also be suitably obtained by modifying amino acids of a human Fc region. Alternatively, Fc regions having desired human FcRn-binding activity can be obtained by modifying amino acids of an Fc region that originally has the human FcRn-binding activity in an acidic pH range and/or in a neutral pH range. Amino acid modifications of a human Fc region that results in such desired binding activity can be revealed by comparing the human FcRn-binding activity in an acidic pH range and/or in a neutral pH range before and after the amino acid modification. Those skilled in the art can appropriately modify the amino acids using known methods.

In the present invention, "modification of amino acids" or "amino acid modification" of an Fc region includes modification into an amino acid sequence which is different from that of the starting Fc region. The starting domain may be any Fc region, as long as a variant modified from the starting Fc region can bind to human FcRn in an acidic pH range (i.e., the starting Fc region does not necessarily need to have the human FcRn-binding activity in the neutral pH range). Fc regions preferred as the starting Fc region include, for example, the Fc region of IgG antibody, i.e., native Fc region.

Furthermore, an altered Fc region modified from a starting Fc region which has been already modified can also be used preferably as an altered Fc region of the present invention. The "starting Fc region" can refer to the polypeptide itself, a composition comprising the starting Fc region, or an amino acid sequence encoding the starting Fc region. Starting Fc regions can comprise a known IgG antibody Fc region produced via recombination described briefly in section "Antibodies". The origin of starting Fc regions is not limited, and they may be obtained from human or any nonhuman organisms. Such organisms preferably include mice, rats, guinea pigs, hamsters, gerbils, cats, rabbits, dogs, goats, sheep, bovines, horses, camels and organisms selected from nonhuman primates. In another embodiment, starting Fc regions can also be obtained from cynomolgus monkeys, marmosets, rhesus monkeys, chimpanzees, or humans. Starting Fc regions can be obtained preferably from human IgG1; however, they are not limited to any particular IgG subclass. This means that an Fc region of human IgG1, IgG2, IgG3, or IgG4 can be used appropriately as a starting Fc region, and herein also means that an Fc region of an arbitrary IgG class or subclass derived from any organisms described above can be preferably used as a starting Fc region. Examples of naturally-occurring IgG variants or modified forms are described in published documents (Curr. Opin. Biotechnol. (2009) 20 (6): 685-91; Curr. Opin. Immunol. (2008) 20 (4), 460-470; Protein Eng. Des. Sel. (2010) 23 (4): 195-202; WO 2009/086320; WO 2008/092117; WO 2007/041635; and WO 2006/105338); however, they are not limited to the examples.

Examples of alterations include those with one or more mutations, for example, mutations by substitution of different amino acid residues for amino acids of starting Fc regions, by insertion of one or more amino acid residues into starting Fc regions, or by deletion of one or more amino acids from starting Fc region. Preferably, the amino acid sequences of altered Fc regions comprise at least a part of the amino acid sequence of a non-native Fc region. Such variants necessarily have sequence identity or similarity less than 100% to their starting Fc region. In a preferred embodiment, the variants have amino acid sequence identity or similarity about 75% to less than 100%, more preferably about 80% to less than 100%, even more preferably about 85% to less than 100%, still more preferably about 90% to less than 100%, and yet more preferably about 95% to less than 100% to the amino acid sequence of their starting Fc region. In a non-limiting embodiment of the present invention, at least one amino acid is different between a modified Fc region of the present invention and its starting Fc region. Amino acid difference between a modified Fc region of the present invention and its starting Fc region can also be preferably specified based on amino acid differences at above-described particular amino acid positions according to EU numbering system.

Known methods such as site-directed mutagenesis (Kunkel et al. (Proc. Natl. Acad. Sci. USA (1985) 82, 488-492)) and Overlap extension PCR can be appropriately employed to modify the amino acids of Fc regions. Furthermore, various known methods can also be used as an amino acid modification method for substituting amino acids by those other than natural amino acids (Annu Rev. Biophys. Biomol. Struct. (2006) 35, 225-249; Proc. Natl. Acad. Sci. U.S.A. (2003) 100 (11), 6353-6357). For example, a cell-free translation system (Clover Direct (Protein Express)) containing tRNAs in which amber suppressor tRNA, which is complementary to UAG codon (amber codon) that is a stop codon, is linked with an unnatural amino acid may be suitably used.

Fc regions having human FcRn-binding activity in the neutral pH range, which are contained in the antigen-binding molecules of the present invention, can be obtained by any method. Specifically, Fc regions having human FcRn-binding activity in the neutral pH range can be obtained by modifying amino acids of human immunoglobulin of IgG type as a starting Fc region. The Fc regions of IgG type immunoglobulins adequate for modification include, for example, those of human IgGs (IgG1, IgG2, IgG3, and IgG4, and modified forms thereof). Amino acids of any positions may be modified into other amino acids, as long as the Fc regions have the human FcRn-binding activity in the neutral pH range or can increase the human FcRn-binding activity in the neutral range. When the antigen-binding molecule contains the Fc region of human IgG1 as the human Fc region, it is preferable that the resulting Fc region contains a modification that results in the effect of enhancing the human FcRn binding in the neutral pH range as compared to the binding activity of the starting Fc region of human IgG1. Amino acids that allow such modification include, for example, amino acids of positions 221 to 225, 227, 228, 230, 232, 233 to 241, 243 to 252, 254 to 260, 262 to 272, 274, 276, 278 to 289, 291 to 312, 315 to 320, 324, 325, 327 to 339, 341, 343, 345, 360, 362, 370, 375 to 378, 380, 382, 385 to 387, 389, 396, 414, 416, 423, 424, 426 to 438, 440, and 442 according to EU numbering. More specifically, such amino acid modifications include those listed in Table 5. Modification of these amino acids augments the human FcRn binding of the Fc region of IgG-type immunoglobulin in the neutral pH range.

From those described above, modifications that augment the human FcRn binding in the neutral pH range are appropriately selected for use in the present invention. Particularly preferred amino acids of the modified Fc regions include, for example, amino acids of positions 237, 248, 250, 252, 254, 255, 256, 257, 258, 265, 286, 289, 297, 298, 303, 305, 307, 308, 309, 311, 312, 314, 315, 317, 332, 334, 360, 376, 380, 382, 384, 385, 386, 387, 389, 424, 428, 433, 434, and 436 according to the EU numbering system. The human FcRn-binding activity in the neutral pH range of the Fc region contained in an antigen-binding molecule can be increased by substituting at least one amino acid selected from the above amino acids into a different amino acid.

Particularly preferred modifications include, for example:
Met for the amino acid of position 237;
Ile for the amino acid of position 248;
Ala, Phe, Ile, Met, Gln, Ser, Val, Trp, or Tyr for the amino acid of position 250;
Phe, Trp, or Tyr for the amino acid of position 252;
Thr for the amino acid of position 254;
Glu for the amino acid of position 255;
Asp, Asn, Glu, or Gln for the amino acid of position 256;
Ala, Gly, Ile, Leu, Met, Asn, Ser, Thr, or Val for the amino acid of position 257;
His for the amino acid of position 258:
Ala for the amino acid of position 265;
Ala or Glu for the amino acid of position 286;
His for the amino acid of position 289;
Ala for the amino acid of position 297;
Ala for the amino acid of position 303;
Ala for the amino acid of position 305;
Ala, Asp, Phe, Gly, His, Ile, Lys, Leu, Met, Asn, Pro, Gln, Arg, Ser, Val, Trp, or Tyr for the amino acid of position 307;
Ala, Phe, Ile, Leu, Met, Pro, Gln, or Thr for the amino acid of position 308;
Ala, Asp, Glu, Pro, or Arg for the amino acid of position 309;
Ala, His, or Ile for the amino acid of position 311;
Ala or His for the amino acid of position 312;
Lys or Arg for the amino acid of position 314;
Ala, Asp, or His for the amino acid of position 315;
Ala for the amino acid of position 317;
Val for the amino acid of position 332;
Leu for the amino acid of position 334;
His for the amino acid of position 360;
Ala for the amino acid of position 376;
Ala for the amino acid of position 380;
Ala for the amino acid of position 382;
Ala for the amino acid of position 384;
Asp or His for the amino acid of position 385;
Pro for the amino acid of position 386;
Glu for the amino acid of position 387;
Ala or Ser for the amino acid of position 389;
Ala for the amino acid of position 424;
Ala, Asp, Phe, Gly, His, Ile, Lys, Leu, Asn, Pro, Gln, Ser, Thr, Val, Trp, or Tyr for the amino acid of position 428;
Lys for the amino acid of position 433;
Ala, Phe, His, Ser, Trp, or Tyr for the amino acid of position 434; and
His, Ile, Leu, Phe, Thr, or Val for the amino acid of position 436 of the Fc region according to EU numbering. Meanwhile, the number of amino acids to be modified is not particularly limited and amino acid at only one site may be modified and amino acids at two or more sites may be modified. Combinations of amino acid modifications at two or more sites include, for example, those described in Table 6.

Antigen-binding Molecule

In the present invention, "an antigen-binding molecule" is used in the broadest sense to refer to a molecule containing an antigen-binding domain and an Fc region. Specifically, the antigen-binding molecules include various types of molecules as long as they exhibit the antigen-binding activity. Molecules in which an antigen-binding domain is linked to an Fc region include, for example, antibodies. Antibodies may include single monoclonal antibodies (including agonistic antibodies and antagonistic antibodies), human antibodies, humanized antibodies, chimeric antibodies, and such. Alternatively, when used as antibody fragments, they preferably include antigen-binding domains and antigen-binding fragments (for example, Fab, F(ab')2, scFv, and Fv). Scaffold molecules where three dimensional structures, such as already-known stable α/β barrel protein structure, are used as a scaffold (base) and only some portions of the structures are made into libraries to construct antigen-binding domains are also included in antigen-binding molecules of the present invention.

An antigen-binding molecule of the present invention may contain at least some portions of an Fc region that mediates the binding to FcRn and Fcγ receptor. In a non-limiting embodiment, the antigen-binding molecule includes, for example, antibodies and Fc fusion proteins. A fusion protein refers to a chimeric polypeptide comprising a polypeptide having a first amino acid sequence that is linked to a polypeptide having a second amino acid sequence that would not naturally link in nature. For example, a fusion protein may comprise the amino acid sequence of at least a portion of an Fc region (for example, a portion of an Fc region responsible for the binding to FcRn or a portion of an Fc region responsible for the binding to Fcγ receptor) and a non-immunoglobulin polypeptide containing, for example, the amino acid sequence of the ligand-binding domain of a receptor or a receptor-binding domain of a ligand. The amino acid sequences may be present in separate proteins that are transported together to a fusion protein, or generally may be present in a single protein; however, they are included in a new rearrangement in a fusion polypeptide. Fusion proteins can be produced, for example, by chemical synthesis, or by genetic recombination techniques to express a polynucleotide encoding peptide regions in a desired arrangement.

Respective domains of the present invention can be linked together via linkers or directly via polypeptide binding.

The linkers comprise arbitrary peptide linkers that can be introduced by genetic engineering, synthetic linkers, and linkers disclosed in, for example, Protein Engineering (1996) 9(3), 299-305. However, peptide linkers are preferred in the present invention. The length of the peptide linkers is not particularly limited, and can be suitably selected by those skilled in the art according to the purpose. The length is preferably five amino acids or more (without particular limitation, the upper limit is generally 30 amino acids or less, preferably 20 amino acids or less), and particularly preferably 15 amino acids.

For example, such peptide linkers preferably include:
Ser
Gly•Ser
Gly•Gly•Ser
Ser•Gly•Gly
Gly•Gly•Gly•Ser (SEQ ID NO: 17)
Ser•Gly•Gly•Gly (SEQ ID NO: 18)
Gly•Gly•Gly•Gly•Ser (SEQ ID NO: 19)
Ser•Gly•Gly•Gly•Gly (SEQ ID NO: 20)
Gly•Gly•Gly•Gly•Gly•Ser (SEQ ID NO: 21)
Ser•Gly•Gly•Gly•Gly•Gly (SEQ ID NO: 22)
Gly•Gly•Gly•Gly•Gly•Gly•Ser (SEQ ID NO: 23)
Ser•Gly•Gly•Gly•Gly•Gly•Gly (SEQ ID NO: 24)
(Gly•Gly•Gly•Gly•Ser (SEQ ID NO: 19))n
(Ser•Gly•Gly•Gly•Gly (SEQ ID NO: 20))n where n is an integer of 1 or larger. The length or sequences of peptide linkers can be selected accordingly by those skilled in the art depending on the purpose.

Synthetic linkers (chemical crosslinking agents) is routinely used to crosslink peptides, and for example:
N-hydroxy succinimide (NHS),
disuccinimidyl suberate (DSS),
bis(sulfosuccinimidyl) suberate ($BS^3$),
dithiobis(succinimidyl propionate) (DSP),
dithiobis(sulfosuccinimidyl propionate) (DTSSP),
ethylene glycol bis(succinimidyl succinate) (EGS),
ethylene glycol bis(sulfosuccinimidyl succinate) (sulfo-EGS),
disuccinimidyl tartrate (DST), disulfosuccinimidyl tartrate (sulfo-DST),
bis[2-(succinimidoxycarbonyloxy)ethyl]sulfone (BSOCOES),
and bis[2-(sulfosuccinimidoxycarbonyloxy)ethyl]sulfone (sulfo-BSOCOES). These crosslinking agents are commercially available.

When multiple linkers for linking the respective domains are used, they may all be of the same type, or may be of different types.

In addition to the linkers exemplified above, linkers with peptide tags such as His tag, HA tag, myc tag, and FLAG tag may also be suitably used. Furthermore, hydrogen bonding, disulfide bonding, covalent bonding, ionic interaction, and properties of binding with each other as a result of combination thereof may be suitably used. For example, the affinity between CH1 and CL of antibody may be used, and Fc regions originating from the above-described bispecific antibodies may also be used for hetero Fc region association. Moreover, disulfide bonds formed between domains may also be suitably used.

In order to link respective domains via peptide linkage, polynucleotides encoding the domains are linked together in frame. Known methods for linking polynucleotides in frame include techniques such as ligation of restriction fragments, fusion PCR, and overlapping PCR. Such methods can be appropriately used alone or in combination to construct antigen-binding molecules of the present invention. In the present invention, the terms "linked" and "fused", or "linkage" and "fusion" are used interchangeably. These terms mean that two or more elements or components such as polypeptides are linked together to form a single structure by any means including the above-described chemical linking means and genetic recombination techniques. Fusing in frame means, when two or more elements or components are polypeptides, linking two or more units of reading frames to form a continuous longer reading frame while maintaining the correct reading frames of the polypeptides. When two molecules of Fab are used as an antigen-binding domain, an antibody, which is an antigen-binding molecule of the present invention where the antigen-binding domain is linked in frame to an Fc region via peptide bond without linker, can be used as a preferred antigen-binding molecule of the present invention.

Fcγ Receptor

Fcγ receptor (also described as FcγR) refers to a receptor capable of binding to the Fc region of monoclonal IgG1, IgG2, IgG3, or IgG4 antibodies, and includes all members belonging to the family of proteins substantially encoded by an Fcγ receptor gene. In human, the family includes FcγRI (CD64) including isoforms FcγRIa, FcγRIb and FcγRIc; FcγRII (CD32) including isoforms FcγRIIa (including allotype H131 and R131), FcγRIIb (including FcγRIIb-1 and FcγRIIb-2), and FcγRIIc; and FcγRIII (CD16) including isoform FcγRIIIa (including allotype V158 and F158) and FcγRIIIb (including allotype FcγRIIIb-NA1 and FcγRIIIb-NA2); as well as all unidentified human FcγRs, FcγR isoforms, and allotypes thereof. However, Fcγ receptor is not limited to these examples. Without being limited thereto, FcγR includes those derived from humans, mice, rats, rabbits, and monkeys. FcγR may be derived from any organisms. Mouse FcγR includes, without being limited to, FcγRI (CD64), FcγRII (CD32), FcγRIII (CD16), and FcγRIII-2 (FcγRIV, CD16-2), as well as all unidentified mouse FcγRs, FcγR isoforms, and allotypes thereof. Such preferred Fcγ receptors include, for example, human FcγRI (CD64), FcγRIIa (CD32), FcγRIIb (CD32), FcγRIIIa (CD16), and/or FcγRIIIb (CD16). The polynucleotide sequence and amino acid sequence of FcγRI are shown in SEQ ID NOs: 25 (NM_000566.3) and 26 (NP_000557.1), respectively; the polynucleotide sequence and amino acid sequence of FcγRIIa (allotype H131) are shown in SEQ ID NOs: 27 (BC020823.1) and 28 (AAH20823.1) (allotype R131 is a sequence in which amino acid at position 166 of SEQ ID NO: 28 is substituted with Arg), respectively; the polynucleotide sequence and amino acid sequence of FcγIIB are shown in SEQ ID NOs: 29 (BC146678.1) and 30 (AAI46679.1), respectively; the polynucleotide sequence and amino acid sequence of FcγRIIIa are shown in SEQ ID NOs: 31 (BC033678.1) and 32 (AAH33678.1), respectively; and the polynucleotide sequence and amino acid sequence of FcγRIIIb are shown in SEQ ID NOs: 33 (BC128562.1) and 34 (AAI28563.1), respectively (RefSeq accession number is shown in each parentheses).

For example, as described in Reference Example 27 and such as FcγRIIIaV when allotype V158 is used, unless otherwise specified, allotype F158 is used; however, the allotype of isoform FcγRIIIa described herein should not be interpreted as being particularly limited.

Whether an Fcγreceptor has binding activity to the Fc region of a monoclonal IgG1, IgG2, IgG3, or IgG4 antibody can be assessed by ALPHA™ screen (Amplified Luminescent Proximity Homogeneous Assay), surface plasmon resonance (SPR)-based BIACORE™ method, and others (Proc. Natl. Acad. Sci. USA (2006) 103 (11), 4005-4010), in addition to the above-described FACS and ELISA formats.

Meanwhile, "Fc ligand" or "effector ligand" refers to a molecule and preferably a polypeptide that binds to an antibody Fc region, forming an Fc/Fc ligand complex. The molecule may be derived from any organisms. The binding of an Fc ligand to Fc preferably induces one or more effector functions. Such Fc ligands include, but are not limited to, Fc receptors, FcγR, FcαR, FcεR, FcRn, C1q, and C3, mannan-binding lectin, mannose receptor, *Staphylococcus* Protein A, *Staphylococcus* Protein G, and viral FcγRs. The Fc ligands also include Fc receptor homologs (FcRH) (Davis et al., (2002) Immunological Reviews 190, 123-136), which are a family of Fc receptors homologous to FcγR. The Fc ligands also include unidentified molecules that bind to Fc.

In FcγRI (CD64) including FcγRIa, FcγRIb, and FcγRIc, and FcγRIII (CD 16) including isoforms FcγRIIIa (including allotypes V158 and F158) and FcγRIIIb (including allotypes FcγRIIIb-NA1 and FcγRIIIb-NA2), a chain that binds to the Fc portion of IgG is associated with common γ chain having ITAM responsible for transduction of intracellular activation signal. Meanwhile, the cytoplasmic domain of FcγRII (CD32) including isoforms FcγRIIa (including allotypes H131 and R131) and FcγRIIc contains ITAM. These receptors are expressed on many immune cells such as macrophages, mast cells, and antigen-presenting cells. The activation signal transduced upon binding of these receptors to the Fc portion of IgG results in enhancement of the phagocytic activity of macrophages, inflammatory cytokine production, mast cell degranulation, and the enhanced function of antigen-presenting cells. Fcγ receptors having the ability to transduce the activation signal as described above are also referred to as activating Fcγ receptors.

Meanwhile, the intracytoplasmic domain of FcγRIIb (including FcγRIIb-1 and FcγRIIb-2) contains ITIM responsible for transduction of inhibitory signals. The crosslinking between FcγRIIb and B cell receptor (BCR) on B cells suppresses the activation signal from BCR, which results in suppression of antibody production via BCR. The crosslinking of FcγRIII and FcγRIIb on macrophages suppresses the phagocytic activity and inflammatory cytokine production. Fcγ receptors having the ability to transduce the inhibitory signal as described above are also referred to as inhibitory Fcγ receptor.

ALPHA screen is performed by the ALPHA technology based on the principle described below using two types of beads: donor and acceptor beads. A luminescent signal is detected only when molecules linked to the donor beads interact biologically with molecules linked to the acceptor beads and when the two beads are located in close proximity. Excited by laser beam, the photosensitizer in a donor bead converts oxygen around the bead into excited singlet oxygen. When the singlet oxygen diffuses around the donor beads and reaches the acceptor beads located in close proximity, a chemiluminescent reaction within the acceptor beads is induced. This reaction ultimately results in light emission. If molecules linked to the donor beads do not interact with molecules linked to the acceptor beads, the singlet oxygen produced by donor beads do not reach the acceptor beads and chemiluminescent reaction does not occur.

For example, a biotin-labeled antigen-binding molecule comprising Fc region is immobilized to the donor beads and glutathione S-transferase (GST)-tagged Fcγ receptor is immobilized to the acceptor beads. In the absence of an antigen-binding molecule comprising a competitive Fc region variant, Fcγ receptor interacts with a polypeptide complex comprising a wild-type Fc region, inducing a signal of 520 to 620 nm as a result. The antigen-binding molecule having a non-tagged Fc region variant competes with the antigen-binding molecule comprising a native Fc region for the interaction with Fcγ receptor. The relative binding affinity can be determined by quantifying the reduction of fluorescence as a result of competition. Methods for biotinylating the antigen-binding molecules such as antibodies using Sulfo-NHS-biotin or the like are known. Appropriate methods for adding the GST tag to an Fcγ receptor include methods that involve fusing polypeptides encoding Fcγ and GST in-frame, expressing the fused gene using cells introduced with a vector to which the gene is operablye linked, and then purifying using a glutathione column. The induced signal can be preferably analyzed, for example, by fitting to a one-site competition model based on nonlinear regression analysis using software such as GRAPHPAD PRISM (GraphPad; San Diego).

One of the substances for observing their interaction is immobilized as a ligand onto the gold thin layer of a sensor chip. When light is shed on the rear surface of the sensor chip so that total reflection occurs at the interface between the gold thin layer and glass, the intensity of reflected light is partially reduced at a certain site (SPR signal). The other substance for observing their interaction is injected as an analyte onto the surface of the sensor chip. The mass of immobilized ligand molecule increases when the analyte binds to the ligand. This alters the refraction index of solvent on the surface of the sensor chip. The change in refraction index causes a positional shift of SPR signal (conversely, the dissociation shifts the signal back to the original position). In the BIACORE™ system, the amount of shift described above (i.e., the change of mass on the sensor chip surface) is plotted on the vertical axis, and thus the change of mass over time is shown as measured data (sensorgram). Kinetic parameters (association rate constant (ka) and dissociation rate constant (kd)) are determined from the curve of sensorgram, and affinity (KD) is determined from the ratio between these two constants. Inhibition assay is preferably used in the BIACORE™ methods. Examples of such inhibition assay are described in Proc. Natl. Acad. Sci. USA (2006) 103 (11), 4005-4010.

Figure 48:
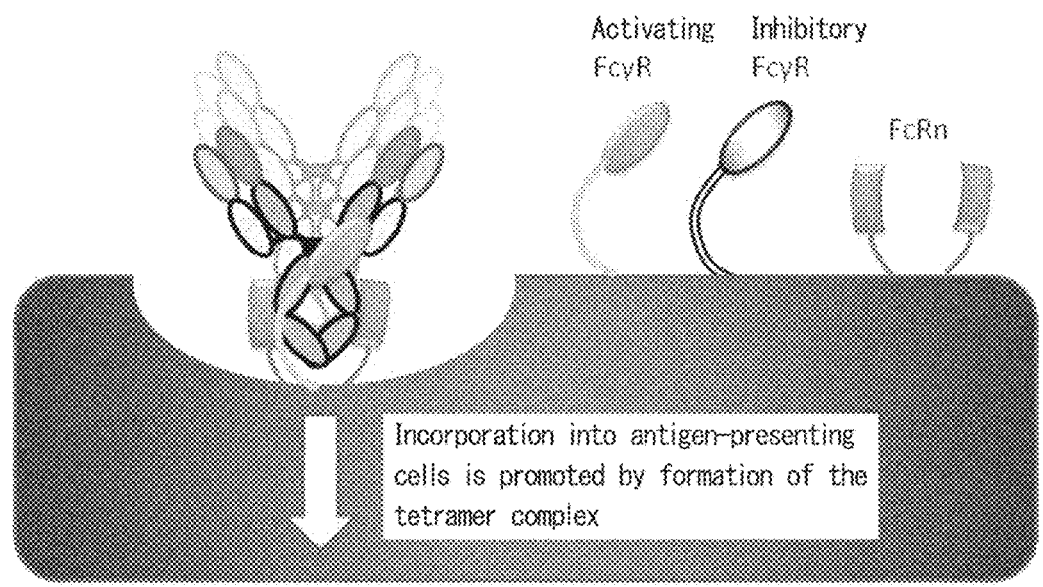
FIG. 48 is a schematic diagram showing the formation of a tetramer complex consisting of one molecule of an Fc region that has FcRn-binding activity in a neutral pH range, two molecules of FcRn, and one molecule of FcγR.

Heterocomplex Comprising the Four Elements of: Two Molecules of FcRn and One Molecule of Activating Fcγ Receptor Crystallographic studies on FcRn and IgG antibodies demonstrated that an FcRn-IgG complex is composed of one molecule of IgG for two molecules of FcRn, and the two molecules are thought to bind near the interface of the CH2 and CH3 domains located on both sides of the Fc region of IgG (Burmeister et al. (Nature (1994) 372, 336-343)). Meanwhile, as shown in Example 3 below, the antibody Fc region was demonstrated to be able to form a complex containing the four elements of: two molecules of FcRn and one molecule of activating Fcγ receptor (FIG. 48). This heterocomplex formation is a phenomenon that was revealed as a result of analyzing the properties of antigen-binding molecules containing an Fc region having an FcRn-binding activity under conditions of a neutral pH range.

Without being bound to a particular principle, it can be considered that in vivo administered antigen-binding molecules produce the effects described below on the in vivo pharmacokinetics (plasma retention) of the antigen-binding molecules and the immune response (immunogenicity) to the administered antigen-binding molecules, as a result of the formation of heterocomplexes containing the four elements of: the Fc region contained in the antigen-binding molecules, two molecules of FcRn, and one molecule of activating Fcγ receptor. As described above, in addition to the various types of activating Fcγ receptor, FcRn is expressed on immune cells, and the formation by antigen-binding molecules of such four-part complexes on immune cells suggests that affinity toward immune cells is increased, and that cytoplasmic domains are assembled, leading to amplification of the internalization signal and promotion of incorporation into immune cells. The same also applies to antigen-presenting cells, and the possibility that formation of four-part complexes on the cell membrane of antigen-presenting cells makes the antigen-binding molecules to be easily incorporated into antigen-presenting cells is suggested. In general, antigen-binding molecules incorporated into antigen-presenting cells are degraded in the lysosomes of the antigen-presenting cells and are presented to T cells. As a result, because incorporation of antigen-binding molecules into antigen-presenting cells is promoted by the formation of the above-described four-part complexes on the cell membrane of the antigen-presenting cells, plasma retention of the antigen-binding molecules may be worsened. Similarly, an immune response may be induced (aggravated).

Figure 49:
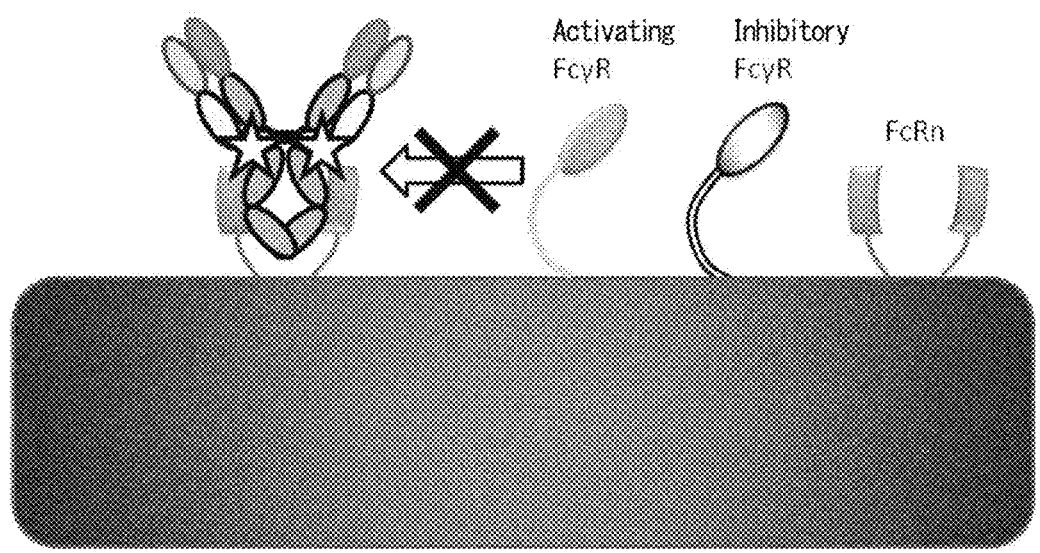
FIG. 49 is a schematic diagram showing the interaction of two FcRn molecules and one FcγR molecule with an Fc region that has FcRn-binding activity in a neutral pH range and a lower binding activity to activating FcγR than that of a native Fc region.

For this reason, it is conceivable that, when an antigen-binding molecule having an impaired ability to form such four-part complexes is administered to the body, plasma retention of the antigen-binding molecules would improve and induction of immune response in the body would be suppressed. Preferred embodiments of such antigen-binding molecules which inhibit the formation of these complexes on immune cells, including antigen-presenting cells, include the three embodiments described below. ( Embodiment 1) An Antigen-binding Molecule Containing an Fc Region having FcRn-binding Activity under Conditions of a Neutral pH Range and whose Binding Activity Toward Activating FcγR is Lower than the Binding Activity of a Native Fc Region Toward ctivating FcγR The antigen-binding molecule of Embodiment 1 forms a three-part complex by binding to two molecules of FcRn; however, it does not form any complex containing activating FcγR (FIG. 49). An Fc region whose binding activity toward activating FcγR is lower than the binding activity of a native Fc region toward activating FcγR may be prepared by modifying the amino acids of the native Fc region as described above. Whether the binding activity toward activating FcγR of the modified Fc region is lower than the binding activity toward activating FcγR of the native Fc region can be suitably tested using the methods described in the section "Binding Activity" above.

Examples of preferable activating Fcγ receptors include FcγRI (CD64) which includes FcγRIa, FcγRIb, and FcγRIc; FcγRIIa (including allotypes R131 and H131); and FcγRIII (CD16) which includes isoforms FcγRIIIa (including allotypes V158 and F158) and FcγRIIIb (including allotypes FcγRIIIb-NA1 and FcγRIIIb-NA2).

For the pH conditions to measure the binding activity of the Fc region and the Fcγ receptor contained in the antigen-binding molecule of the present invention, conditions in an acidic pH range or in a neutral pH range may be suitably used. The neutral pH range, as a condition to measure the binding activity of the Fc region and the Fcγ receptor contained in the antigen-binding molecule of the present invention, generally indicates pH 6.7 to pH 10.0. Preferably, it is a range indicated with arbitrary pH values between pH 7.0 and pH 8.0; and preferably, it is selected from pH 7.0, pH 7.1, pH 7.2, pH 7.3, pH 7.4, pH 7.5, pH 7.6, pH 7.7, pH 7.8, pH 7.9, and pH 8.0; and particularly preferably, it is pH 7.4, which is close to the pH of plasma (blood) in vivo. Herein, the acidic pH range, as a condition for having a binding activity of the Fc region and the Fcγ receptor contained in the antigen-binding molecule of the present invention, generally indicates pH 4.0 to pH 6.5. Preferably, it indicates pH 5.5 to pH 6.5, and particularly preferably, it indicates pH 5.8 to pH 6.0, which is close to the pH in the early endosome in vivo. With regard to the temperature used as measurement condition, the binding affinity between the Fc region and the human Fcγ receptor can be evaluated at any temperature between 10° C. and 50° C. Preferably, a temperature between 15° C. and 40° C. is used to determine the binding affinity between the human Fc region and the Fcγ receptor. More preferably, any temperature between 20° C. and 35° C., such as any from 20° C., 21° C., 22° C., 23° C., 24° C., 25° C., 26° C., 27° C., 28° C., 29° C., 30° C., 31° C., 32° C., 33° C., 34° C., or 35° C., can similarly be used to determine the binding affinity between the Fc region and the Fcγ receptor. A temperature of 25° C. is a non-limiting example in an embodiment of the present invention.

Herein, "the binding activity of the Fc region variant toward activating Fcγ receptor is lower than the binding activity of the native Fc region toward activating Fcγ receptor" means that the binding activity of the Fc region variant toward any of the human Fcγ receptors of FcγRI, FcγRIIa, FcγRIIIa, and/or FcγRIIIb is lower than the binding activity of the native Fc region toward these human Fcγ receptors.

For example, it means that, based on an above-described analytical method, the binding activity of the antigen-binding molecule containing an Fc region variant is 95% or less, preferably 90% or less, 85% or less, 80% or less, 75% or less, particularly preferably 70% or less, 65% or less, 60% or less, 55% or less, 50% or less, 45% or less, 40% or less, 35% or less, 30% or less, 25% or less, 20% or less, 15% or less, 10% or less, 9% or less, 8% or less, 7% or less, 6% or less, 5% or less, 4% or less, 3% or less, 2% or less, or 1% or less as compared to the binding activity of an antigen-binding molecule containing a native Fc region as a control. As native Fc region, the starting Fc region may be used, and Fc regions of wild-type antibodies of different isotypes may also be used.

Meanwhile, the binding activity of the native form toward activating FcγR is preferably a binding activity toward the Fcγ receptor for human IgG1. To reduce the binding activity toward the Fcγ receptor, other than performing the above-described modifications, the isotype may also be changed to human IgG2, human IgG3, or human IgG4. Alternatively, other than performing the above-described modifications, the binding activity toward Fcγ receptor can also be reduced by expressing the antigen-binding molecule containing the Fc region having a binding activity toward the Fcγ receptor in hosts that do not add sugar chains, such as *Escherichia coli*.

As antigen-binding molecule containing an Fc region that is used as a control, antigen-binding molecules having an Fc region of a monoclonal IgG antibody may be suitably used. The structures of such Fc regions are shown in SEQ ID NO: 1 (A is added to the N terminus of RefSeq Accession No. AAC82527.1), SEQ ID NO: 2 (A is added to the N terminus of RefSeq Accession No. AAB59393.1), SEQ ID NO: 3 (RefSeq Accession No. CAA27268.1), and SEQ ID NO: 4 (A is added to the N terminus of RefSeq Accession No. AAB59394.1). Further, when an antigen-binding molecule containing an Fc region of a particular antibody isotype is used as the test substance, the effect of the binding activity of the antigen-binding molecule containing that Fc region toward the Fcγ receptor is tested by using as a control an antigen-binding molecule having an Fc region of a monoclonal IgG antibody of that particular isotype. In this way, antigen-binding molecules containing an Fc region whose binding activity toward the Fcγ receptor was demonstrated to be high are suitably selected.

In a non-limiting embodiment of the present invention, preferred examples of Fc regions whose binding activity toward activating FcγR is lower than that of the native Fc region toward activating FcγR include Fc regions in which one or more amino acids at any of positions 234, 235, 236, 237, 238, 239, 270, 297, 298, 325, 328, and 329 as indicated by EU numbering are modified into amino acids that are different from those of the native Fc region, among the amino acids of an above-described Fc region. The modifications in the Fc region are not limited to the above example, and they may be, for example, modifications such as deglycosylation (N297A and N297Q), IgG1-L234A/L235A, IgG1-A325A/A330S/P331S, IgG1-C226S/C229S, IgG1-C226S/C229S/E233P/L234V/L235A, IgG1-L234F/L235E/P331S, IgG1-S267E/L328F, IgG2-V234A/G237A, IgG2-H268Q/V309L/A330S/A331S, IgG4-L235A/G237A/E318A, and IgG4-L236E described in Current Opinion in Biotechnology (2009) 20 (6), 685-691; modifications such as G236R/L328R, L235G/G236R, N325A/L328R, and N325LL328R described in WO 2008/092117; amino acid insertions at positions 233, 234, 235, and 237 according to EU numbering; and modifications at the positions described in WO 2000/042072.

In a non-limiting embodiment of the present invention, examples of a favorable Fc region include Fc regions having one or more of the following modifications as indicated by EU numbering in an aforementioned Fc region:
the amino acid at position 234 is any one of Ala, Arg, Asn, Asp, Gln, Glu, Gly, His, Lys, Met, Phe, Pro, Ser, Thr, or Trp;
the amino acid at position 235 is any one of Ala, Asn, Asp, Gln, Glu, Gly, His, Ile, Lys, Met, Pro, Ser, Thr, Val, or Arg;
the amino acid at position 236 is any one of Arg, Asn, Gln, His, Leu, Lys, Met, Phe, Pro, or Tyr;
the amino acid at position 237 is any one of Ala, Asn, Asp, Gln, Glu, His, Ile, Leu, Lys, Met, Pro, Ser, Thr, Val, Tyr, or Arg;
the amino acid at position 238 is any one of Ala, Asn, Gln, Glu, Gly, His, Ile, Lys, Thr, Trp, or Arg;
the amino acid at position 239 is any one of Gln, His, Lys, Phe, Pro, Trp, Tyr, or Arg;
the amino acid at position 265 is any one of Ala, Arg, Asn, Gln, Gly, His, Ile, Leu, Lys, Met, Phe, Ser, Thr, Trp, Tyr, or Val;
the amino acid at position 266 is any one of Ala, Arg, Asn, Asp, Gln, Glu, Gly, His, Lys, Phe, Pro, Ser, Thr, Trp, or Tyr;
the amino acid at position 267 is any one of Arg, His, Lys, Phe, Pro, Trp, or Tyr;
the amino acid at position 269 is any one of Ala, Arg, Asn, Gln, Gly, His, Ile, Leu, Lys, Met, Phe, Pro, Ser, Thr, Trp, Tyr, or Val;
the amino acid at position 270 is any one of Ala, Arg, Asn, Gln, Gly, His, Ile, Leu, Lys, Met, Phe, Pro, Ser, Thr, Trp, Tyr, or Val;
the amino acid at position 271 is any one of Arg, His, Phe, Ser, Thr, Trp, or Tyr;
the amino acid at position 295 is any one of Arg, Asn, Asp, Gly, His, Phe, Ser, Trp, or Tyr;
the amino acid at position 296 is any one of Arg, Gly, Lys, or Pro;
the amino acid at position 297 is any one of Ala;
the amino acid at position 298 is any one of Arg, Gly, Lys, Pro, Trp, or Tyr;
the amino acid at position 300 is any one of Arg, Lys, or Pro;
the amino acid at position 324 is any one of Lys or Pro;
the amino acid at position 325 is any one of Ala, Arg, Gly, His, Ile, Lys, Phe, Pro, Thr, Trp, Tyr, or Val;
the amino acid at position 327 is any one of Arg, Gln, His, Ile, Leu, Lys, Met, Phe, Pro, Ser, Thr, Trp, Tyr, or Val;
the amino acid at position 328 is any one of Arg, Asn, Gly, His, Lys, or Pro;
the amino acid at position 329 is any one of Asn, Asp, Gln, Glu, Gly, His, Ile, Leu, Lys, Met, Phe, Ser, Thr, Trp, Tyr, Val, or Arg;
the amino acid at position 330 is any one of Pro or Ser;
the amino acid at position 331 is any one of Arg, Gly, or Lys; or
the amino acid at position 332 is any one of Arg, Lys, or Pro.

Figure 50:
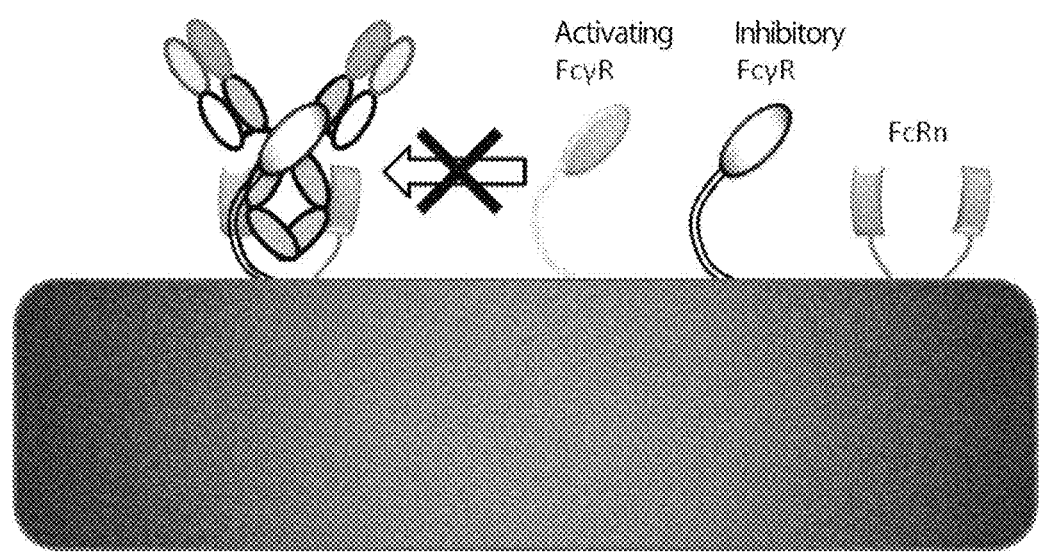
FIG. 50 is a schematic diagram showing the interaction of two FcRn molecules and one FcγR molecule with an Fc region that has FcRn-binding activity in a neutral pH range and selective binding activity to inhibitory FcγR.

(Embodiment 2) An Antigen-binding Molecule Containing an Fc Region Having FcRn-binding Activity under Conditions of a Neutral pH Range and whose Binding Activity Toward Inhibitory FcγR is Higher than the Binding Activity Toward Activating Fcγ Receptor By binding to two molecules of FcRn and one molecule of inhibitory FcγR, the antigen-binding molecule of Embodiment 2 can form a complex comprising these four elements. However, since a single antigen-binding molecule can bind only one molecule of FcγR, the antigen-binding molecule in a state bound to an inhibitory FcγR cannot bind to other activating FcγRs (FIG. 50). Furthermore, it has been reported that antigen-binding molecules that are incorporated into cells in a state bound to inhibitory FcγR are recycled onto the cell membrane and thus escape from intracellular degradation (Immunity (2005) 23, 503-514). Thus, antigen-binding molecules having selective binding activity toward inhibitory FcγR are thought not to be able to form heterocomplexes containing activating FcγR and two molecules of FcRn, which cause the immune response.

Examples of preferable activating Fcγ receptors include FcγRI (CD64) which includes FcγRIa, FcγRIb, and FcγRIc; FcγRIIa (including allotypes R131 and H131); and FcγRIII (CD16) which includes isoforms FcγRIIIa (including allotypes V158 and F158) and FcγRIIIb (including allotypes FcγRIIIb-NA1 and FcγRIIIb-NA2). Meanwhile, examples of preferred inhibitory Fcγ receptors include FcγRIIb (including FcγRIIb-1 and FcγRIIb-2).

Herein, "the binding activity toward inhibitory FcγR is higher than the binding activity toward activating Fcγ receptor" means that the binding activity of the Fc region variant toward FcγRIIb is higher than the binding activity toward any of the human Fcγ receptors FcγRI, FcγRIIa, FcγRIIIa, and/or FcγRIIIb. For example, it means that, based on an above-described analytical method, the binding activity toward FcγRIIb of the antigen-binding molecule containing an Fc region variant is 105% or more, preferably 110% or more, 120% or more, 130% or more, 140% or more, particularly preferably 150% or more, 160% or more, 170% or more, 180% or more, 190% or more, 200% or more, 250% or more, 300% or more, 350% or more, 400% or more, 450% or more, 500% or more, 750% or more, 10 times or more, 20 times or more, 30 times or more, 40 times or more, 50 times or more as compared with the binding activity toward any of the human Fcγ receptors of FcγRI, FcγRIIa, FcγRIIIa, and/or FcγRIIIb.

Most preferably, the binding activity toward FcγRIIb is higher than each of the binding activities toward FcγRIa, FcγRIIa (including allotypes R131 and H131), and FcγRIIIa (including allotypes V158 and F158). FcγRIa shows markedly high affinity toward native IgG1; thus, the binding is thought to be saturated in vivo due to the presence of a large amount of endogenous IgG1. For this reason, inhibition of complex formation may be possible even if the binding activity toward FcγRIIb is greater than the binding activities toward FcγRIIa and FcγRIIIa and lower than the binding activity toward FcγRIa.

As antigen-binding molecule containing an Fc region that is used as a control, antigen-binding molecules having an Fc region of a monoclonal IgG antibody may be suitably used. The structures of such Fc regions are shown in SEQ ID NO: 11 (A is added to the N terminus of RefSeq Accession No. AAC82527.1), SEQ ID NO: 12 (A is added to the N terminus of RefSeq Accession No. AAB59393.1), SEQ ID NO: 13 (RefSeq Accession No. CAA27268.1), and SEQ ID NO: 14 (A is added to the N terminus of RefSeq Accession No. AAB59394.1). Further, when an antigen-binding molecule containing an Fc region of a particular antibody isotype is used as the test substance, the effect of the binding activity of the antigen-binding molecule containing that Fc region toward the Fcγ receptor is tested by using as a control an antigen-binding molecule having an Fc region of a monoclonal IgG antibody of that particular isotype. In this way, antigen-binding molecules containing an Fc region whose binding activity toward the Fcγ receptor was demonstrated to be high are suitably selected.

In a non-limiting embodiment of the present invention, preferred examples of Fc regions having a selective binding activity toward inhibitory FcγR include Fc regions in which, among the amino acids of an above-described Fc region, the amino acid at 328 or 329 as indicated by EU numbering is modified into an amino acid that is different from that of the native Fc region. Furthermore, as Fc regions having selective binding activity toward inhibitory Fcγ receptor, the Fc regions or modifications described in US 2009/0136485 can be suitably selected.

In another non-limiting embodiment of the present invention, a preferred example is an Fc region having one or more of the following modifications as indicated by EU numbering in an aforementioned Fc region: the amino acid at position 238 is Asp; or the amino acid at position 328 is Glu.

In still another non-limiting embodiment of the present invention, examples of a favorable Fc region include Fc regions having one or more of the following modifications: a substitution of Pro at position 238 according to EU numbering to Asp, the amino acid at position 237 according to EU numbering is Trp, the amino acid at position 237 according to EU numbering is Phe, the amino acid at position 267 according to EU numbering is Val, the amino acid at position 267 according to EU numbering is Gln, the amino acid at position 268 according to EU numbering is Asn, the amino acid at position 271 according to EU numbering is Gly, the amino acid at position 326 according to EU numbering is Leu, the amino acid at position 326 according to EU numbering is Gln, the amino acid at position 326 according to EU numbering is Glu, the amino acid at position 326 according to EU numbering is Met, the amino acid at position 239 according to EU numbering is Asp, the amino acid at position 267 according to EU numbering is Ala, the amino acid at position 234 according to EU numbering is Trp, the amino acid at position 234 according to EU numbering is Tyr, the amino acid t position 237 according to EU numbering is Ala, the amino acid at position 237 according to EU numbering is Asp, the amino acid at position 237 according to EU numbering is Glu, the amino acid at position 237 according to EU numbering is Leu, the amino acid at position 237 according to EU numbering is Met, the amino acid at position 237 according to EU numbering is Tyr, the amino acid at position 330 according to EU numbering is Lys, the amino acid at position 330 according to EU numbering is Arg, the amino acid at position 233 according to EU numbering is Asp, the amino acid at position 268 according to EU numbering is Asp, the amino acid at position 268 according to EU numbering is Glu, the amino acid at position 326 according to EU numbering is Asp, the amino acid at position 326 according to EU numbering is Ser, the amino acid at position 326 according to EU numbering is Thr, the amino acid at position 323 according to EU numbering is Ile, the amino acid at position 323 according to EU numbering is Leu, the amino acid at position 323 according to EU numbering is Met, the amino acid at position 296 according to EU numbering is Asp, the amino acid at position 326 according to EU numbering is Ala, the amino acid at position 326 according to EU numbering is Asn, and the amino acid at position 330 according to EU numbering is Met.

Figure 51:
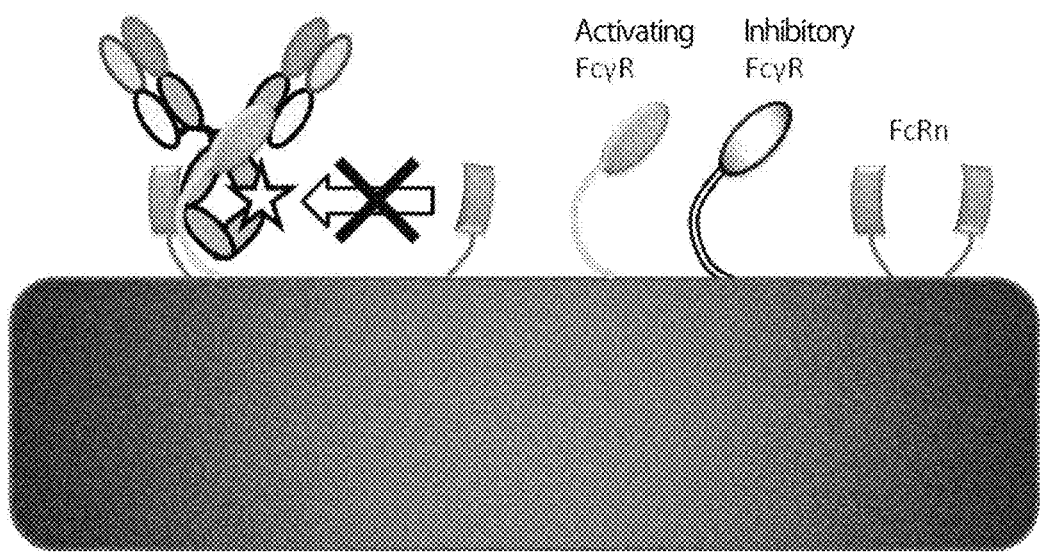
FIG. 51 is a schematic diagram showing the interaction of two FcRn molecules and one FcγR molecule with an Fc region in which only one of the two polypeptides of FcRn-binding domain has FcRn-binding activity in a neutral pH range and the other does not have FcRn-binding activity in a neutral pH range.

(Embodiment 3) An Antigen-binding Molecule Containing an Fc Region, in which One of the Two Polypeptides Forming the Fc Region has an FcRn-binding Activity under Conditions of a Neutral PH Range and the other does not have any FcRn-binding Activity under Conditions of a Neutral PH Range By binding to one molecule of FcRn and one molecule of FcγR, the antigen-binding molecule of Embodiment 3 can form a three part complex; however, it does not form any heterocomplex containing the four elements of two molecules of FcRn and one molecule of FcγR (FIG. 51). As Fc region in which one of the two polypeptides forming the Fc region has an FcRn-binding activity under conditions of a neutral pH range and the other does not have any FcRn-binding activity under conditions of a neutral pH range contained in the antigen-binding molecule of Embodiment 3, Fc regions derived from bispecific antibodies may be suitably used. Bispecific antibodies are two types of antibodies having specificities toward different antigens. Bispecific antibodies of IgG type can be secreted from hybrid hybridomas (quadromas) resulting from fusion of two types of hybridomas producing IgG antibodies (Milstein et al. (Nature (1983) 305, 537-540).

When an antigen-binding molecule of Embodiment 3 described above is produced by using recombination techniques such as those described in the above section "Antibody", one can use a method in which genes encoding the polypeptides that constitute the two types of Fc regions of interest are introduced into cells to co-express them. However, the produced Fc regions will be a mixture in which the following will exist at a molecular ratio of 2:1:1: Fc regions in which one of the two polypeptides forming the Fc region has an FcRn-binding activity under conditions of a neutral pH range and the other polypeptide does not have any FcRn-binding activity under conditions of a neutral pH range; Fc regions in which the two polypeptides forming the Fc region both have an FcRn-binding activity under conditions of a neutral pH range; and Fc regions in which the two polypeptides forming the Fc region both do not have any FcRn-binding activity under conditions of a neutral pH range. It is difficult to purify antigen-binding molecules containing the desired combination of Fc regions from the three types of IgGs.

When producing the antigen-binding molecules of Embodiment 3 using such recombination techniques, antigen-binding molecules containing a heteromeric combination of Fc regions can be preferentially secreted by adding appropriate amino acid substitutions in the CH3 domains constituting the Fc regions.

Specifically, this method is conducted by substituting an amino acid having a larger side chain (knob (which means "bulge")) for an amino acid in the CH3 domain of one of the heavy chains, and substituting an amino acid having a smaller side chain (hole (which means "void")) for an amino acid in the CH3 domain of the other heavy chain so that the knob is placed in the hole. This promotes heteromeric H chain formation and simultaneously inhibits homomeric H chain formation (WO 1996027011; Ridgway et al., Protein Engineering (1996) 9, 617-621; Merchant et al., Nature Biotechnology (1998) 16, 677-681).

Furthermore, there are also known techniques for producing a bispecific antibody by applying methods for controlling polypeptide association, or association of polypeptide-formed heteromeric multimers to the association between the two polypeptides that form an Fc region. Specifically, methods for controlling polypeptide association may be employed to produce a bispecific antibody (WO 2006/106905), in which amino acid residues forming the interface between two polypeptides that form the Fc region are altered to inhibit the association between Fc regions having the same sequence and to allow the formation of polypeptide complexes formed by two Fc regions of different sequences.

Such methods can be used for preparing the antigen-binding molecule of embodiment 3 of the present invention.

In a non-limiting embodiment of the present invention, two polypeptides constituting an Fc region derived from a bispecific antibody described above can be suitably used as the Fc region. More specifically, two polypeptides constituting an Fc region may be suitably used, in which, of the amino acid sequence of one of the polypeptides, the amino acid at position 349 as indicated by EU numbering is Cys and the amino acid at position 366 is Trp, and of the amino acid sequence of the other of the polypeptides, the amino acid at position 356 as indicated by EU numbering is Cys, the amino acid at position 366 is Ser, the amino acid at position 368 is Ala, and the amino acid at position 407 is Val.

In another non-limiting embodiment of the present invention, two polypeptides constituting an Fc region, in which, of the amino acid sequence of one of the polypeptides, the amino acid at position 409 according to EU numbering is Asp, and of the amino acid sequence of the other of the polypeptides, the amino acid at position 399 according to EU numbering is Lys, may be suitably used as the Fc region. In the above embodiment, the amino acid at position 409 may be Glu instead of Asp, and the amino acid at position 399 may be Arg instead of Lys. Moreover, in addition to the amino acid Lys at position 399, Asp may suitably be added as amino acid at position 360 or Asp may suitably be added as amino acid at position 392.

In still another non-limiting embodiment of the present invention, two polypeptides constituting an Fc region, in which, of the amino acid sequence of one of the polypeptides, the amino acid at position 370 according to EU numbering is Glu, and of the amino acid sequence of the other of the polypeptides, the amino acid at position 357 according to EU numbering is Lys, may be suitably used as the Fc region.

In yet another non-limiting embodiment of the present invention, two polypeptides constituting an Fc region, in which, of the amino acid sequence of one of the polypeptides, the amino acid at position 439 according to EU numbering is Glu, and of the amino acid sequence of the other of the polypeptides, the amino acid at position 356 according to EU numbering is Lys, may be suitably used as the Fc region.

In still yet another non-limiting embodiment of the present invention, any of the embodiments indicated below, in which the above have been combined, may be suitably used as the Fc region:

two polypeptides constituting an Fc region, in which, of the amino acid sequence of one of the polypeptides, the amino acid at position 409 according to EU numbering is Asp and the amino acid at position 370 is Glu, and of the amino acid sequence of the other of the polypeptides, the amino acid at position 399 according to EU numbering is Lys and the amino acid at position 357 is Lys (in this embodiment, the amino acid at position 370 according to EU numbering may be Asp instead of Glu, and the amino acid Asp at position 392 according to EU numbering may be used instead of the amino acid Glu at position 370 according to EU numbering);

two polypeptides constituting an Fc region, in which, of the amino acid sequence of one of the polypeptides, the amino acid at position 409 according to EU numbering is Asp and the amino acid at position 439 is Glu, and of the amino acid sequence of the other of the polypeptides, the amino acid at position 399 according to EU numbering is Lys and the amino acid at position 356 is Lys (in this embodiment, the amino acid Asp at position 360 according to EU numbering, the amino acid Asp at position 392 according to EU numbering, or the amino acid Asp at position 439 according to EU numbering may be used instead of the amino acid Glu at position 439 according to EU numbering);

two polypeptides constituting an Fc region, in which, of the amino acid sequence of one of the polypeptides, the amino acid at position 370 according to EU numbering is Glu and the amino acid at position 439 is Glu, and of the amino acid sequence of the other of the polypeptides, the amino acid at position 357 according to EU numbering is Lys and the amino acid at position 356 is Lys; and two polypeptides constituting an Fc region, in which, of the amino acid sequence of one of the polypeptides, the amino acid at position 409 according to EU numbering is Asp, the amino acid at position 370 is Glu, and the amino acid at position 439 is Glu, and of the amino acid sequence of the other of the polypeptides, the amino acid at position 399 according to EU numbering is Lys, the amino acid at position 357 is Lys, and the amino acid at position 356 is Lys (in this embodiment, the amino acid at position 370 according to EU numbering may not be substituted to Glu, and furthermore, when the amino acid at position 370 is not substituted to Glu, the amino acid at position 439 may be Asp instead of Glu, or the amino acid Asp at position 392 may be used instead of the amino acid Glu at position 439).

Further, in another non-limiting embodiment of the present invention, two polypeptides constituting an Fc region, in which, of the amino acid sequence of one of the polypeptides, the amino acid at position 356 according to EU numbering is Lys, and of the amino acid sequence of the other of the polypeptides, the amino acid at position 435 according to EU numbering is Arg and the amino acid at position 439 is Glu, may also be suitably used.

In still another non-limiting embodiment of the present invention, two polypeptides constituting an Fc region, in which, of the amino acid sequence of one of the polypeptides, the amino acid at position 356 according to EU numbering is Lys and the amino acid at position 357 is Lys, and of the amino acid sequence of the other of the polypeptides, the amino acid at position 370 according to EU numbering is Glu, the amino acid at position 435 is Arg, and the amino acid at position 439 is Glu, may also be suitably used.

These antigen-binding molecules of Embodiments 1 to 3 are expected to be able to reduce immunogenicity and improve plasma retention as compared to antigen-binding molecules capable of forming four part complexes.

Impairment of Immune Response (Reduction of Immunogenicity)

Whether the immune response against the antigen-binding molecule of the present invention has been modified can be evaluated by measuring the response reaction in an organism into which a pharmaceutical composition comprising the antigen-binding molecule as an active ingredient has been administered. Response reactions of an organism mainly include two immune responses: cellular immunity (induction of cytotoxic T cells that recognize peptide fragments of antigen-binding molecules bound to MHC class I) and humoral immunity (induction of production of antibodies that bind to antigen-binding molecules). Regarding protein pharmaceuticals in particular, the production of antibodies against the administered antigen-binding molecules is referred to as immunogenicity. There are two types of methods for assessing the immunogenicity: methods for assessing antibody production in vivo and methods for assessing the reaction of immune cells in vitro.

The in vivo immune response (immunogenicity) can be assessed by measuring the antibody titer after administration of the antigen-binding molecules to an organism. For example, antibody titers are measured after administering antigen-binding molecules A and B to mice. When the antibody titer for antigen-binding molecule A is higher than that for B, or when following administration to several mice, administration of antigen-binding molecule A gave a higher incidence of mice with elevated antibody titer, then A is judged to have higher immunogenicity than B. Antibody titers can be measured using methods for measuring molecules that specifically bind to administered molecules using ELISA, ECL, or SPR which are known to those skilled in the art (J. Pharm. Biomed. Anal. (2011) 55 (5), 878-888).

Methods for assessing in vitro the immune response of an organism against the antigen-binding molecules (immunogenicity) include methods of reacting in vitro human peripheral blood mononuclear cells isolated from donors (or fractionated cells thereof) with antigen-binding molecules and measuring the cell number or percentage of helper T cells and such that react or proliferate or the amount of cytokines produced (Clin. Immunol. (2010) 137 (1), 5-14; Drugs R D. (2008) 9 (6), 385-396). For example, upon evaluation of antigen-binding molecules A and B by such in vitro immunogenicity tests, when the response with antigen-binding molecule A was higher than that with B, or when several donors were evaluated and the reaction positivity rate with antigen-binding molecule A was higher, then A is judged to have higher immunogenicity than B.

Without being bound by a particular theory, since antigen-binding molecules having FcRn-binding activity in a neutral pH range can form hetero tetramer complexes comprising two molecules of FcRn and one molecule of FcγR on the cell membrane of antigen-presenting cells, the immune response is thought to be readily induced because of enhanced incorporation into antigen-presenting cells. There are phosphorylation sites in the intracellular domains of FcγR and FcRn. In general, phosphorylation of the intracellular domains of receptors expressed on a cell surface occurs upon assembly of the receptors and their phosphorylation causes internalization of the receptors. Assembly of the intracellular domains of FcγR does not occur even if native IgG1 forms a dimeric complex of FcγR/IgG1 on antigen-presenting cells. However, in the case an IgG molecule having a binding activity toward FcRn under conditions of a neutral pH range forms a complex containing the four elements of FcγR/two molecules of FcRn/IgG, the three intracellular domains of the FcγR and FcRn would assemble, and it is possible that as a result, internalization of the heterocomplex containing the four elements of FcγR/two molecules of FcRn/IgG is induced. The heterocomplexes containing the four elements of FcγR/two molecules of FcRn/IgG are thought to be formed on antigen-presenting cells co-expressing FcγR and FcRn, and it is possible that the amount of antibody molecules incorporated into antigen-presenting cells is thereby increased, resulting in worsened immunogenicity. It is thought that, by inhibiting the above-described complex formation on antigen-presenting cells using any one of the methods of Embodiments 1, 2, or 3 revealed in the present invention, incorporation into antigen-presenting cells may be reduced and consequently, immunogenicity may be improved.

Improvement of Pharmacokinetics

Without being bound by a particular principle, the reasons why the number of antigens a single antigen-binding molecule can bind is increased and why the dissipation of antigen concentration in the plasma is accelerated following promotion of incorporation into the cells of an organism upon administration into the organism of, for example, an antigen-binding molecule comprising an Fc region having a binding activity toward human FcRn under conditions of a neutral pH range and an antigen-binding domain whose antigen-binding activity changes depending on the conditions of ion concentrations so that the antigen-binding activity under conditions of an acidic pH range is lower than the antigen-binding activity in a neutral pH range may be explained, for example, as follows.

For example, when the antigen-binding molecule is an antibody that binds to a membrane antigen, the antibody administered into the body binds to the antigen and then is taken up via internalization into endosomes in the cells together with the antigen while the antibody is kept bound to the antigen. Then, the antibody translocates to lysosomes while the antibody is kept bound to the antigen, and the antibody is degraded by the lysosome together with the antigen. The internalization-mediated elimination from the plasma is called antigen-dependent elimination, and such elimination has been reported with numerous antibody molecules (Drug Discov Today (2006) 11(1-2): 81-88). When a single molecule of IgG antibody binds to antigens in a divalent manner, the single antibody molecule is internalized while the antibody is kept bound to the two antigen molecules, and degraded in the lysosome. Accordingly, in the case of common antibodies, one molecule of IgG antibody cannot bind to three or more molecules of antigen. For example, a single IgG antibody molecule having a neutralizing activity cannot neutralize three or more antigen molecules.

The relatively prolonged retention (slow elimination) of IgG molecules in the plasma is due to the function of human FcRn which is known as a salvage receptor of IgG molecules. When taken up into endosomes via pinocytosis, IgG molecules bind to human FcRn expressed in the endosomes under the acidic condition in the endosomes. While IgG molecules that did not bind to human FcRn transfer to lysosomes where they are degraded, IgG molecules that are bound to human FcRn translocate to the cell surface and return again in the plasma by dissociating from human FcRn under the neutral condition in the plasma.

Alternatively, when the antigen-binding molecule is an antibody that binds to a soluble antigen, the antibody administered into the body binds to the antigen and then is taken up into cells while the antibody is kept bound to the antigen. Most of the antibodies incorporated into the cells bind to FcRn in the endosomes and translocate to the cell surface. Antibodies dissociate from human FcRn under the neutral condition in the plasma and are released to the outside of the cells. However, antibodies having ordinary antigen-binding domains whose antigen-binding activity does not change depending on conditions of ion concentration such as pH are released to the outside of the cells while remaining bound to the antigens; thus, they are unable to bind again to antigens. Accordingly, similarly to antibodies that bind to membrane antigens, a single ordinary IgG antibody molecule whose antigen-binding activity does not change depending on conditions of ion concentration such as pH are unable to bind to three antigen molecules or more.

Antibodies that bind to antigens in a pH-dependent manner, which antibodies strongly bind to antigens under conditions of a neutral pH range in the plasma and dissociate from the antigens under conditions of an acidic pH range in the endosomes (antibodies that bind to antigens under conditions of a neutral pH range and dissociate under conditions of an acidic pH range), and antibodies that bind to antigens in a calcium ion concentration-dependent manner, which antibodies strongly bind to antigens under conditions of a high calcium ion concentration in the plasma and dissociate from the antigens under conditions of a low calcium ion concentration in the endosomes (antibodies that bind to antigens under conditions of a high calcium ion concentration and dissociate under conditions of a low calcium ion concentration) can dissociate from the antigens in the endosomes. Antibodies that bind to antigens in a pH-dependent manner or antibodies that bind to antigens in a calcium ion concentration-dependent manner are able to bind to antigens again after they dissociate from the antigens and are recycled to the plasma by FcRn. Thus, a single antibody molecule can repeatedly bind to several antigen molecules. Meanwhile, the antigens bound to the antigen-binding molecules dissociate from the antibodies in the endosomes and are degraded in lysosomes without being recycled to the plasma. By administering such antigen-binding molecules to organisms, incorporation of antigens into the cells is promoted and the antigen concentration in the plasma can be reduced.

Incorporation into cells of antigens against which antigen-binding molecules bind is further promoted by giving an ability to bind human FcRn under conditions of a neutral pH range (pH 7.4) to antibodies that bind to antigens in a pH-dependent manner, which antibodies strongly bind to antigens under conditions of a neutral pH range in the plasma and dissociate from the antigens under conditions of an acidic pH range in the endosomes (antibodies that bind to antigens under conditions of a neutral pH range and dissociate under conditions of an acidic pH range), and antibodies that bind to antigens in a calcium ion concentration-dependent manner, which antibodies strongly bind to antigens under conditions of a high calcium ion concentration in the plasma and dissociate from the antigens under conditions of a low calcium ion concentration in the endosomes (antibodies that bind to antigens under conditions of a high calcium ion concentration and dissociate under conditions of a low calcium ion concentration). Thus, by administering such antigen-binding molecules to organisms, antigen elimination is promoted and the antigen concentration in the plasma can be reduced. Ordinary antibodies that lack the ability of binding to antigens in a pH-dependent manner or the ability of binding to antigens in a calcium ion concentration-dependent manner, as well as antigen-antibody complexes thereof, are incorporated into cells by non-specific endocytosis, transported to the cell surface following binding with FcRn under the acidic condition in the endosomes, and recycled in the plasma following dissociation from the FcRn under the neutral condition on cell surface. For this reason, when an antibody that binds to an antigen in a sufficiently pH-dependent manner (that binds under conditions of a neutral pH range and dissociate under conditions of an acidic pH range) or an antibody that binds to an antigen in a sufficient calcium ion concentration-dependent manner (that binds under conditions of a high calcium ion concentration and dissociates under conditions of a low calcium ion concentration) binds to an antigen in the plasma and dissociates in the endosomes from the antigen it is bound to, the rate of antigen elimination will be equivalent to the rate of incorporation into cells by non-specific endocytosis of the antibody or antigen-antibody complex thereof. When the pH-dependency or the calcium ion concentration-dependency of the binding between the antibodies and the antigens is insufficient, the antigens that did not dissociate from the antibodies in the endosomes will be recycled to the plasma along with the antibodies. However, when the pH-dependency or calcium ion concentration-dependency is sufficient, the rate of incorporation into cells by non-specific endocytosis will be rate-limiting for the rate of antigen elimination. Meanwhile, since FcRn transports antibodies from the endosomes to the cell surface, a part of the FcRn is thought to also be present on the cell surface.

In general, IgG-type immunoglobulin, which is an embodiment of the antigen-binding molecule, shows almost no FcRn-binding activity in the neutral pH range. The present inventors considered that IgG-type immunoglobulin having an FcRn-binding activity in the neutral pH range can bind to FcRn on the cell surface, and will be incorporated into cells in an FcRn-dependent manner by binding to the FcRn on the cell surface. The rate of FcRn-mediated incorporation into cells is more rapid than the incorporation into cells by non-specific endocytosis. Thus, the present inventors considered that the rate of antigen elimination by the antigen-binding molecules can be further accelerated by conferring an FcRn-binding ability in the neutral pH range. Specifically, antigen-binding molecules having FcRn-binding ability in the neutral pH range would send antigens into cells more rapidly than the native IgG-type immunoglobulins, release the antigens in the endosomes, be recycled to cell surface or plasma again, once again bind to antigens there, and be incorporated again into cells via FcRn. The rate of this cycle can be accelerated by increasing the FcRn-binding ability in the neutral pH range; thus, the rate of elimination of the antigens from the plasma is accelerated. Moreover, the rate of antigen elimination from the plasma can be further accelerated by reducing the antigen-binding activity in an acidic pH range of an antigen-binding molecule as compared with the antigen-binding activity in the neutral pH range. In addition, the number of antigen molecules to which a single antigen-binding molecule can bind is thought to increase due to the increase in number of cycles that results from acceleration of the rate of this cycle. The antigen-binding molecules of the present invention comprise an antigen-binding domain and an FcRn-binding domain, and the FcRn-binding domain does not affect the antigen binding. Moreover, in light of the mechanism described above, they do not depend on the type of the antigens. Thus, by reducing the antigen-binding activity (binding ability) of an antigen-binding molecule under conditions of an acidic pH range or ion concentrations such as low calcium ion concentration as compared with the antigen-binding activity (binding ability) under conditions of a neutral pH range or ion concentrations such as high calcium ion concentration, and/or by increasing the FcRn-binding activity under the pH of the plasma, incorporation into cells of the antigens by the antigen-binding molecules can be promoted and the rate of antigen elimination can be accelerated.

Herein, "antigen incorporation into cells" by antigen-binding molecules means that the antigens are incorporated into cells by endocytosis. Furthermore, herein, "to promote incorporation into cells" indicates that the rate of incorporation into cells of the antigen-binding molecules that bound to antigens in the plasma is promoted, and/or the amount of incorporated antigens that are recycled to the plasma is reduced. In this case, the rate of incorporation into cells of an antigen-binding molecule that has a human FcRn-binding activity in the neutral pH range, or of an antigen-binding molecule that has this human FcRn-binding activity and whose antigen-binding activity in an acidic pH range is lower than that in the neutral pH range should be promoted when compared to an antigen-binding molecule that does not have a human FcRn-binding activity in the neutral pH range, or to an antigen-binding molecule whose antigen-binding activity in an acidic pH range is lower than that in the neutral pH range. In another embodiment, the rate of incorporation into cells of an antigen-binding molecule of the present invention is preferably promoted as compared to that of a native human IgG, and particular preferably it is promoted as compared to that of a native human IgG. Thus, in the present invention, whether or not incorporation by antigen-binding molecules of antigens into cells is promoted can be determined based on whether or not the rate of antigen incorporation into cells is increased. The rate of cellular incorporation of antigens can be measured, for example, by adding the antigen-binding molecules and antigens to a culture medium containing cells expressing human FcRn and measuring the reduction over time of the concentration of the antigens in the medium, or by measuring over time the amount of antigens incorporated into cells expressing human FcRn. By using methods for promoting the cellular incorporation of antigens mediated by the antigen-binding molecules of the present invention, for example, by administering the antigen-binding molecules, the rate of antigen elimination from the plasma can be promoted. Thus, whether or not incorporation by antigen-binding molecules of antigens into cells is promoted can also be assessed, for example, by measuring whether or not the rate of elimination of the antigens present in the plasma is accelerated or measuring whether or not the total antigen concentration in the plasma is reduced after administration of the antigen-binding molecules.

Herein, "native human IgG" refers to unmodified human IgG, and is not limited to a particular IgG subclass. This means that human IgG1, IgG2, IgG3, or IgG4 can be used as "native human IgG" as long as it is capable of binding to human FcRn in an acidic pH range. Preferably, the "native human IgG" may be human IgG1.

Herein, the "ability to eliminate the antigens in plasma" refers to the ability to eliminate the antigens present in the plasma from the plasma after in vivo administration of the antigen-binding molecules or in vivo secretion of the antigen-binding molecules. Thus, herein, "the ability of the antigen-binding molecules to eliminate the antigens in the plasma is increased" means that, when the antigen-binding molecules are administered, the human FcRn-binding activity of the antigen-binding molecules in the neutral pH range is increased, or that, in addition to this increase of the human FcRn-binding activity, the rate of antigen elimination from plasma is accelerated as compared to before reducing the antigen-binding activity in an acidic pH range as compared to that in the neutral pH range. Whether or not the ability of an antigen-binding molecule to eliminate the antigens in the plasma is increased can be assessed, for example, by administering soluble antigens and the antigen-binding molecule in vivo and measuring the plasma concentration of the soluble antigens after administration. If the concentration of the soluble antigens in the plasma is decreased after administration of the soluble antigens and the antigen-binding molecules after increasing the human FcRn-binding activity in the neutral pH range of the antigen-binding molecules, or, in addition to increasing this human FcRn-binding activity, reducing the antigen-binding activity in an acidic pH range as compared to that in the neutral pH range, then the ability of the antigen-binding molecules to eliminate the antigens in the plasma is judged to be increased. The soluble antigen may be an antigen that is bound to an antigen-binding molecule or an antigen that is not bound to an antigen-binding molecule, and its concentration can be determined as a "plasma concentration of the antigen bound to the antigen-binding molecules" or as a "plasma concentration of the antigen that is not bound to the antigen-binding molecules", respectively (the latter is synonymous with "free antigen concentration in plasma"). "The total antigen concentration in the plasma" means the sum of antigen-binding molecule bound antigen and non-bound antigen concentration, or the "free antigen concentration in plasma" which is the antigen-binding molecule non-bound antigen concentration. Thus, the concentration of soluble antigen can be determined as the "total antigen concentration in plasma".

Various methods for measuring "total antigen concentration in plasma" or "free antigen concentration in plasma" are well known in the art as described hereinafter. Herein, "enhancement of pharmacokinetics", "improvement of pharmacokinetics", and "superior pharmacokinetics" can be restated as "enhancement of plasma (blood) retention", "improvement of plasma (blood) retention", "superior plasma (blood) retention", and "prolonged plasma (blood) retention". These terms are synonymous.

Herein, "improvement of pharmacokinetics" means not only prolongation of the period until elimination from the plasma (for example, until the antigen-binding molecule is degraded intracellularly or the like and cannot return to the plasma) after administration of the antigen-binding molecule to humans, or non-human animals such as mice, rats, monkeys, rabbits, and dogs, but also prolongation of the plasma retention of the antigen-binding molecule in a form that allows antigen binding (for example, in an antigen-free form of the antigen-binding molecule) during the period of administration to elimination due to degradation. Human IgG having wild-type Fc region can bind to FcRn from non-human animals. For example, mouse can be preferably used to be administered in order to confirm the property of the antigen-binding molecule of the invention since human IgG having wild-type Fc region can bind to mouse FcRn stronger than to human FcRn (Int Immunol. (2001) 13(12): 1551-1559). As another example, mouse in which its native FcRn genes are disrupted and a transgene for human FcRn gene is harbored to be expressed (Methods Mol Biol. 2010; 602: 93-104) can also be preferably used to be administered in order to confirm the property of the antigen-binding molecule of the invention described hereinafter. Specifically, "improvement of pharmacokinetics" also includes prolongation of the period until elimination due to degradation of the antigen-binding molecule not bound to antigens (the antigen-free form of antigen-binding molecule). The antigen-binding molecule in plasma cannot bind to a new antigen if the antigen-binding molecule has already bound to an antigen. Thus, the longer the period that the antigen-binding molecule is not bound to an antigen, the longer the period that it can bind to a new antigen (the higher the chance of binding to another antigen). This enables reduction of the time period that an antigen is free of the antigen-binding molecule in vivo and prolongation of the period that an antigen is bound to the antigen-binding molecule. The plasma concentration of the antigen-free form of antigen-binding molecule can be increased and the period that the antigen is bound to the antigen-binding molecule can be prolonged by accelerating the antigen elimination from the plasma by administration of the antigen-binding molecule. Specifically, herein "improvement of the pharmacokinetics of antigen-binding molecule" includes the improvement of a pharmacokinetic parameter of the antigen-free form of the antigen-binding molecule (any of prolongation of the half-life in plasma, prolongation of mean retention time in plasma, and impairment of plasma clearance), prolongation of the period that the antigen is bound to the antigen-binding molecule after administration of the antigen-binding molecule, and acceleration of antigen-binding molecule-mediated antigen elimination from the plasma. The improvement of pharmacokinetics of antigen-binding molecule can be assessed by determining any one of the parameters, half-life in plasma, mean plasma retention time, and plasma clearance for the antigen-binding molecule or the antigen-free form thereof ("Pharmacokinetics: Enshuniyoru Rikai (Understanding through practice)" Nanzando). For example, the plasma concentration of the antigen-binding molecule or antigen-free form thereof is determined after administration of the antigen-binding molecule to mice, rats, monkeys, rabbits, dogs, or humans. Then, each parameter is determined. When the plasma half-life or mean plasma retention time is prolonged, the pharmacokinetics of the antigen-binding molecule can be judged to be improved. The parameters can be determined by methods known to those skilled in the art. The parameters can be appropriately assessed, for example, by noncompartmental analysis using the pharmacokinetics analysis software WinNonlin (Pharsight) according to the appended instruction manual. The plasma concentration of antigen-free antigen-binding molecule can be determined by methods known to those skilled in the art, for example, using the assay method described in Clin Pharmacol. 2008 April; 48(4): 406-417.

Herein, "improvement of pharmacokinetics" also includes prolongation of the period that an antigen is bound to an antigen-binding molecule after administration of the antigen-binding molecule. Whether the period that an antigen is bound to the antigen-binding molecule after administration of the antigen-binding molecule is prolonged can be assessed by determining the plasma concentration of free antigen. The prolongation can be judged based on the determined plasma concentration of free antigen or the time period required for an increase in the ratio of free antigen concentration to the total antigen concentration.

The plasma concentration of free antigen not bound to the antigen-binding molecule or the ratio of free antigen concentration to the total concentration can be determined by methods known to those skilled in the art, for example, by the method used in Pharm Res. 2006 January; 23 (1): 95-103. Alternatively, when an antigen exhibits a particular function in vivo, whether the antigen is bound to an antigen-binding molecule that neutralizes the antigen function (antagonistic molecule) can be assessed by testing whether the antigen function is neutralized. Whether the antigen function is neutralized can be assessed by assaying an in vivo marker that reflects the antigen function. Whether the antigen is bound to an antigen-binding molecule that activates the antigen function (agonistic molecule) can be assessed by assaying an in vivo marker that reflects the antigen function.

Determination of the plasma concentration of free antigen and ratio of the amount of free antigen in plasma to the amount of total antigen in plasma, in vivo marker assay, and such measurements are not particularly limited; however, the assays are preferably carried out after a certain period of time has passed after administration of the antigen-binding molecule. In the present invention, the period after administration of the antigen-binding molecule is not particularly limited; those skilled in the art can determine the appropriate period depending on the properties and the like of the administered antigen-binding molecule. Such periods include, for example, one day after administration of the antigen-binding molecule, three days after administration of the antigen-binding molecule, seven days after administration of the antigen-binding molecule, 14 days after administration of the antigen-binding molecule, and 28 days after administration of the antigen-binding molecule. Herein, the concept "plasma antigen concentration" comprises both "total antigen concentration in plasma" which is the sum of antigen-binding molecule bound antigen and non-bound antigen concentration or "free antigen concentration in plasma" which is antigen-binding molecule non-bound antigen concentration.

Total antigen concentration in plasma can be lowered by administration of antigen-binding molecule of the present invention by 2-fold, 5-fold, 10-fold, 20-fold, 50-fold, 100-fold, 200-fold, 500-fold, 1,000-fold, or even higher compared to the administration of a reference antigen-binding molecule comprising the wild-type IgG Fc region as a reference antigen-binding molecule or compared to when antigen-binding domain molecule of the present invention is not administered.

Molar antigen/antigen-binding molecule ratio can be calculated as shown below;
value A: Molar antigen concentration at each time point
value B: Molar antigen-binding molecule concentration at each time point
value C: Molar antigen concentration per molar antigen-binding molecule concentration (molar antigen/antigen-binding molecule ratio) at each time point $$C=A/B.$$

Smaller value C indicates higher efficiency of antigen elimination per antigen-binding molecule whereas higher value C indicates lower efficiency of antigen elimination per antigen-binding molecule.

Molar antigen/antigen-binding molecule ratio can be calculated as described above.

Molar antigen/antigen-binding molecule ratio can be lowered by administration of antigen-binding molecule of present invention by 2-fold, 5-fold, 10-fold, 20-fold, 50-fold, 100-fold, 200-fold, 500-fold, 1,000-fold, or even higher as compared to the administration of a reference antigen-binding molecule comprising the wild-type human IgG Fc region as a human FcRn-binding domain.

Herein, a wild-type human IgG1, IgG2, IgG3 or IgG4 is preferably used as the wild-type human IgG for a purpose of a reference wild-type human IgG to be compared with the antigen-binding molecules for their human FcRn binding activity or in vivo binding activity. Preferably, a reference antigen-binding molecule comprising the same antigen-binding domain as an antigen-binding molecule of the interest and wild-type human IgG Fc region as a human FcRn-binding domain can be appropriately used. More preferably, an intact human IgG1 is used for a purpose of a reference wild-type human IgG to be compared with the antigen-binding molecules for their human FcRn binding activity or in vivo activity.

Reduction of total antigen concentration in plasma or molar antigen/antibody ratio can be assessed as described in Examples 4, 5, and 12. More specifically, using human FcRn transgenic mouse line 32 or line 276 (Jackson Laboratories, Methods Mol Biol. 2010; 602: 93-104), they can be assessed by either antigen-antibody co-injection model or steady-state antigen infusion model when antigen-binding molecule do not cross-react to the mouse counterpart antigen. When an antigen-binding molecule cross-react with mouse counterpart, they can be assessed by simply injecting antigen-binding molecule to human FcRn transgenic mouse line 32 or line 276 (Jackson Laboratories). In co-injection model, mixture of antigen-binding molecule and antigen is administered to the mouse. In steady-state antigen infusion model, infusion pump containing antigen solution is implanted to the mouse to achieve constant plasma antigen concentration, and then antigen-binding molecule is injected to the mouse. Test antigen-binding molecule is administered at same dosage. Total antigen concentration in plasma, free antigen concentration in plasma and plasma antigen-binding molecule concentration is measured at appropriate time point using method known to those skilled in the art.

Total or free antigen concentration in plasma and molar antigen/antigen-binding molecule ratio can be measured at 2, 4, 7, 14, 28, 56, or 84 days after administration to evaluate the long-term effect of the present invention. In other words, a long term plasma antigen concentration is determined by measuring total or free antigen concentration in plasma and molar antigen/antigen-binding molecule ratio at 2, 4, 7, 14, 28, 56, or 84 days after administration of an antigen-binding molecule in order to evaluate the property of the antigen-binding molecule of the present invention. Whether the reduction of plasma antigen concentration or molar antigen/antigen-binding molecule ratio is achieved by antigen-binding molecule described in the present invention can be determined by the evaluation of the reduction at any one or more of the time points described above.

Total or free antigen concentration in plasma and molar antigen/antigen-binding molecule ratio can be measured at 15 min, 1, 2, 4, 8, 12, or 24 hours after administration to evaluate the short-term effect of the present invention. In other words, a short term plasma antigen concentration is determined by measuring total or free antigen concentration in plasma and molar antigen/antigen-binding molecule ratio at 15 min, 1, 2, 4, 8, 12, or 24 hours after administration of an antigen-binding molecule in order to evaluate the property of the antigen-binding molecule of the present invention.

Route of administration of an antigen-binding molecule of the present invention can be selected from intradermal, intravenous, intravitreal, subcutaneous, intraperitoneal, parenteral and intramuscular injection.

In the present invention, improvement of pharmacokinetics of antigen-binding molecule in human is preferred. When the plasma retention in human is difficult to determine, it may be predicted based on the plasma retention in mice (for example, normal mice, human antigen-expressing transgenic mice, human FcRn-expressing transgenic mice) or monkeys (for example, cynomolgus monkeys).

Herein, "the improvement of the pharmacokinetics and prolonged plasma retention of an antigen-binding molecule" means improvement of any pharmacokinetic parameter (any of prolongation of the half-life in plasma, prolongation of mean retention time in plasma, reduction of plasma clearance, and bioavailability) after in vivo administration of the antigen-binding molecule, or an increase in the concentration of the antigen-binding molecule in the plasma in an appropriate time after administration. It may be determined by measuring any parameter such as half-life in plasma, mean retention time in plasma, plasma clearance, and bioavailability of the antigen-binding molecule (Pharmacokinetics: Enshu-niyoru Rikai (Understanding through practice), (Nanzando)). For example, when an antigen-binding molecule is administered to mice (normal mice and human FcRn transgenic mice), rats, monkeys, rabbits, dogs, humans, and so on, and the concentration of the antigen-binding molecule in the plasma is determined and each of the parameters is calculated, the pharmacokinetics of the antigen-binding molecule can be judged to be improved when the plasma half-life or mean retention time in the plasma is prolonged. These parameters can be determined by methods known to those skilled in the art. For example, the parameters can be appropriately assessed by non-compartmental analysis using pharmacokinetics analysis software WinNonlin (Pharsight) according to the attached instruction manual.

Without being bound by a particular theory, since an antigen-binding molecule that has an FcRn-binding activity in the neutral pH range can form a tetramer complex comprising two molecules of FcRn and one molecule of FcγR on the cell membrane of antigen-presenting cells, incorporation into antigen-presenting cells is promoted, and thus the plasma retention is thought to be reduced and the pharmacokinetics worsened. There are phosphorylation sites in the cytoplasmic domains of FcγR and FcRn. In general, phosphorylation of the cytoplasmic domain of a cell surface-expressed receptor occurs upon assembly of the receptors, and the phosphorylation induces receptor internalization. Even if native IgG1 forms an FcγR/IgG1 dimeric complex on the antigen-presenting cells, assembly of the cytoplasmic domains of FcγR does not occur. However, when an IgG molecule having an FcRn-binding activity under conditions of a neutral pH range forms a heteromeric tetramer complex comprising FcγR/two molecules of FcRn/IgG, the three cytoplasmic domains of FcγR and FcRn would assemble, and the internalization of the heteromeric tetramer complex comprising FcγR/two molecules of FcRn/IgG may thereby be induced. Formation of the heteromeric tetramer complexes comprising FcγR/two molecules of FcRn/IgG is thought to occur on antigen-presenting cells co-expressing FcγR and FcRn, and consequently, the amount of antibody molecules incorporated into the antigen-presenting cells may be increased, and the pharmacokinetics may be worsened as a result. Thus, by inhibiting the above-described complex formation on antigen-presenting cells using any one of the methods of Embodiments 1, 2 and 3 revealed in the present invention, incorporation into antigen-presenting cells may be reduced, and as a result, the pharmacokinetics may be improved.

Method for Producing Antigen-binding Molecules whose Binding Activity Varies Depending on the Conditions of Ion Concentration In a non-limiting embodiment of the present invention, after isolating a polynucleotide encoding an antigen-binding domain whose binding activity changes depending on the condition selected as described above, the polynucleotide is inserted into an appropriate expression vector. For example, when the antigen-binding domain is an antibody variable region, once a cDNA encoding the variable region is obtained, the cDNA is digested with restriction enzymes that recognize the restriction sites inserted at the two ends of the cDNA. Preferably, the restriction enzymes recognize and digest a nucleotide sequence that appears at a low frequency in the nucleotide sequence composing the gene of the antigen-binding molecule. Furthermore, restriction enzymes that provide cohesive ends are preferably inserted to insert a single copy of a digested fragment into the vector in the correct orientation. The cDNA encoding a variable region of an antigen-binding molecule digested as described above is inserted into an appropriate expression vector to obtain an expression vector for the antigen-binding molecule of the present invention. At this time, a gene encoding an antibody constant region (C region) may be fused in frame with the gene encoding the variable region.

To produce an antigen-binding molecule of interest, a polynucleotide encoding the antigen-binding molecule is inserted in a manner operably linked to a regulatory sequence into an expression vector. Regulatory sequences include, for example, enhancers and promoters. Furthermore, an appropriate signal sequence may be linked to the N terminus so that the expressed antigen-binding molecule is secreted to the outside of the cells. As signal sequence, for example, a peptide having the amino acid sequence MGWSCIILFLVATATGVHS (SEQ ID NO: 3) is used; however, it is also possible to link other appropriate signal sequences. The expressed polypeptide is cleaved at the carboxyl terminus of the above-described sequence, and the cleaved polypeptide is secreted as a mature polypeptide to the outside of cells. Then, appropriate host cells are transformed with this expression vector so that recombinant cells expressing the polynucleotide encoding the antigen-binding molecule of interest can be obtained. The antigen-binding molecules of the present invention can be produced from the recombinant cells by following the methods described above in the section on antibodies.

In a non-limiting embodiment of the present invention, after isolating a polynucleotide encoding the above-described antigen-binding molecule whose binding activity varies depending on a selected condition, a variant of the polynucleotide is inserted into an appropriate expression vector. Such variants preferably include those prepared via humanization based on the polynucleotide sequence encoding an antigen-binding molecule of the present invention obtained by screening as a randomized variable region library a synthetic library or an immune library constructed originating from nonhuman animals. The same methods as described above for producing above-described humanized antibodies can be used as a method for producing humanized antigen-binding molecule variants.

In another embodiment, such variants preferably include those obtained by introducing an alteration that increases the antigen affinity (affinity maturation) of an antigen-binding molecule of the present invention into an isolated polynucleotide sequence for the molecule obtained by screening using a synthetic library or a naive library as a randomized variable region library. Such variants can be obtained by various known procedures for affinity maturation, including CDR mutagenesis (Yang et al. (J. Mol. Biol. (1995) 254, 392-403)), chain shuffling (Marks et al. (Bio/Technology (1992) 10, 779-783)), use of E. coli mutant strains (Low et al. (J. Mol. Biol. (1996) 250, 359-368)), DNA shuffling (Patten et al. (Curr. Opin. Biotechnol. (1997) 8, 724-733)), phage display (Thompson et al. (J. Mol. Biol. (1996) 256, 77-88)), and sexual PCR (Clameri et al. (Nature (1998) 391, 288-291)).

As described above, antigen-binding molecules that are produced by the production methods of the present invention include antigen-binding molecules having an Fc region. Various variants can be used as Fc regions. In an embodiment, variants of the present invention preferably include polynucleotides encoding antigen-binding molecules having a heavy chain in which a polynucleotide encoding an Fc region variant as described above is linked in frame to a polynucleotide encoding the above-described antigen-binding molecule whose binding activity varies depending on a selected condition.

In a non-limiting embodiment of the present invention, Fc regions preferably include, for example, Fc constant regions of antibodies such as IgG1 of SEQ ID NO: 11 (Ala is added to the N terminus of AAC82527.1), IgG2 of SEQ ID NO: 12 (Ala is added to the N terminus of AAB59393.1), IgG3 of SEQ ID NO: 13 (CAA27268.1), and IgG4 of SEQ ID NO: 14 (Ala is added to the N terminus of AAB59394.1). The plasma retention of IgG molecules is relatively long (the elimination from plasma is slow) since FcRn, particularly human FcRn, functions as a salvage receptor for IgG molecules. IgG molecules incorporated into endosomes by pinocytosis bind under the endosomal acidic condition to FcRn, particularly human FcRn, expressed in endosomes. IgG molecules that cannot bind to FcRn, particularly human FcRn, are transferred to lysosomes, and degraded there. Meanwhile, IgG molecules bound to FcRn, particularly human FcRn, are transferred to cell surface, and then return to plasma as a result of dissociation from FcRn, particularly human FcRn, under the neutral condition in plasma.

Since antibodies comprising a typical Fc region do not have a binding activity to FcRn, particularly to human FcRn, under the plasma neutral pH range condition, typical antibodies and antibody-antigen complexes are incorporated into cells by non-specific endocytosis and transferred to cell surface by binding to FcRn, particularly human FcRn, in the endosomal acidic pH range condition. FcRn, particularly human FcRn, transports antibodies from the endosome to the cell surface. Thus, some of FcRn, particularly human FcRn, is thought to be also present on the cell surface. However, antibodies are recycled to plasma, since they dissociated from FcRn, particularly human FcRn, in the neutral pH range condition on cell surface.

Fc regions having the human FcRn-binding activity in the neutral pH range, which are included in antigen-binding molecules of the present invention, can be obtained by any method. Specifically, Fc regions having human FcRn-binding activity in the neutral pH range can be obtained by altering amino acids of human IgG-type immunoglobulin as a starting Fc region. Preferred Fc regions of human IgG-type immunoglobulin for alteration include, for example, those of human IgGs (IgG1, IgG2, IgG3, and IgG4, and variants thereof). Amino acids at any positions may be altered to other amino acids as long as the resulting regions have the human FcRn-binding activity in the neutral pH range or increased human FcRn-binding activity in the neutral range. When an antigen-binding molecule comprises the Fc region of human IgG1 as human Fc region, it is preferable that the resulting region comprises an alteration that results in the effect to enhance the human FcRn binding in the neutral pH range as compared to the binding activity of the starting Fc region of human IgG1. Amino acids that allow such alterations include, for example, amino acids at positions 221 to 225, 227, 228, 230, 232, 233 to 241, 243 to 252, 254 to 260, 262 to 272, 274, 276, 278 to 289, 291 to 312, 315 to 320, 324, 325, 327 to 339, 341, 343, 345, 360, 362, 370, 375 to 378, 380, 382, 385 to 387, 389, 396, 414, 416, 423, 424, 426 to 438, 440, and 442 (indicated by EU numbering). More specifically, such amino acid alterations include those listed in Table 5. Alteration of these amino acids enhances the human FcRn binding of the Fc region of IgG-type immunoglobulin in the neutral pH range.

Among those described above, appropriate alterations that enhance the human FcRn binding in the neutral pH range are selected for use in the present invention. Particularly preferred amino acids for such Fc region variants include, for example, amino acids at positions 237, 248, 250, 252, 254, 255, 256, 257, 258, 265, 286, 289, 297, 298, 303, 305, 307, 308, 309, 311, 312, 314, 315, 317, 332, 334, 360, 376, 380, 382, 384, 385, 386, 387, 389, 424, 428, 433, 434, and 436 (indicated by EU numbering). The human FcRn-binding activity of the Fc region included in an antigen-binding molecule can be increased in the neutral pH range by substituting at least one amino acid with a different amino acid.

Particularly preferred alterations in the Fc region include, for example, substitutions of:
Met for the amino acid at position 237;
Ile for the amino acid at position 248;
Ala, Phe, Ile, Met, Gln, Ser, Val, Trp, or Tyr for the amino acid at position 250;
Phe, Trp, or Tyr for the amino acid at position 252;
Thr for the amino acid at position 254;
Glu for the amino acid at position 255;
Asp, Asn, Glu, or Gln for the amino acid at position 256;
Ala, Gly, Ile, Leu, Met, Asn, Ser, Thr, or Val for the amino acid at position 257;
His for the amino acid at position 258;
Ala for the amino acid at position 265;
Ala or Glu for the amino acid at position 286;
His for the amino acid at position 289;
Ala for the amino acid at position 297;
Ala for the amino acid at position 303;
Ala for the amino acid at position 305;
Ala, Asp, Phe, Gly, His, Ile, Lys, Leu, Met, Asn, Pro, Gln, Arg, Ser, Val, Trp, or Tyr for the amino acid at position 307;
Ala, Phe, Ile, Leu, Met, Pro, Gln, or Thr for the amino acid at position 308;
Ala, Asp, Glu, Pro, or Arg for the amino acid at position 309;
Ala, His, or Ile for the amino acid at position 311;
Ala or His for the amino acid at position 312;
Lys or Arg for the amino acid at position 314;
Ala, Asp, or His for the amino acid at position 315;
Ala for the amino acid at position 317;
Val for the amino acid at position 332;
Leu for the amino acid at position 334;
His for the amino acid at position 360;
Ala for the amino acid at position 376;
Ala for the amino acid at position 380;
Ala for the amino acid at position 382;
Ala for the amino acid at position 384;
Asp or His for the amino acid at position 385;
Pro for the amino acid at position 386;
Glu for the amino acid at position 387;
Ala or Ser for the amino acid at position 389;
Ala for the amino acid at position 424;
Ala, Asp, Phe, Gly, His, Ile, Lys, Leu, Asn, Pro, Gln, Ser, Thr, Val, Trp, or Tyr for the amino acid at position 428;
Lys for the amino acid at position 433;
Ala, Phe, His, Ser, Trp, or Tyr for the amino acid at position 434; and
His, Ile, Leu, Phe, Thr, or Val for the amino acid at position 436 in the EU numbering system.

Meanwhile, the number of altered amino acids is not particularly limited; such amino acid alterations include single amino acid alteration and alteration of amino acids at two or more sites. Combinations of amino acid alterations at two or more sites include, for example, those described in Table 6.

The present invention is not limited to a particular theory, but provides methods for producing antigen-binding molecules which comprise not only an above-described alteration but also an alteration of the Fc region so as not to form the hetero tetramer complex consisting of the Fc region included in antigen-binding molecule, two molecules of FcRn, and activating Fcγ receptor. Preferred embodiments of such antigen-binding molecules include three embodiments described below.

(Embodiment 1) Antigen-binding Molecules that Comprise an Fc Region having the FcRn-binding Activity under the Neutral PH Range Condition and whose Binding Activity to Activating FcγR is Lower than that of the Native Fc Region Antigen-binding molecules of Embodiment 1 form trimer complexes by binding to two molecules of FcRn; however, they do not form complex including activating FcγR (FIG. 49). Fc regions whose binding activity to activating FcγR is lower than that of the native Fc region can be prepared by altering the amino acids of native Fc region as described above. Whether the binding activity of an altered Fc region to activating FcγR is lower than that of the native Fc region can be appropriately tested using the methods described in the section "Binding activity" above.

Herein, the binding activity of an altered Fc region to activating Fcγ receptor is lower than that of native Fc region means that the binding activity of an altered Fc region to any human Fcγ receptors, FcγRIa, FcγRIIa, FcγRIIIa, and/or FcγRIIIb, is lower than that of the native Fc region, and, for example, means that, when compared based on an above-described analytical method, the binding activity of an antigen-binding molecule having an Fc region variant is 95% or less, preferably 90% or less, 85% or less, 80% or less, 75% or less, particularly preferably 70% or less, 65% or less, 60% or less, 55% or less, 50% or less, 45% or less, 40% or less, 35% or less, 30% or less, 25% or less, 20% or less, 15% or less, 10% or less, 9% or less, 8% or less, 7% or less, 6% or less, 5% or less, 4% or less, 3% or less, 2% or less, 1% or less as compared to the binding activity of a control antigen-binding molecule having the native Fc region. Such native Fc regions include the starting Fc region and Fc regions from wild-type antibodies of different isotypes.

Appropriate antigen-binding molecules having an Fc region as a control include those having an Fc region from a monoclonal IgG antibody. The structures of such Fc regions are shown in SEQ ID NOs: 11 (A is added to the N terminus of RefSeq accession No. AAC82527.1), 12 (A is added to the N terminus of RefSeq accession No. AAB59393.1), 13 (RefSeq accession No. CAA27268.1), and 14 (A is added to the N terminus of RefSeq accession No. AAB59394.1). Meanwhile, when an antigen-binding molecule that has the Fc region from an antibody of a certain isotype is used as a test substance, the Fcγ receptor-binding activity of the antigen-binding molecule having the Fc region can be tested by using as a control an antigen-binding molecule having the Fc region from a monoclonal IgG antibody of the same isotype. It is adequate to select antigen-binding molecule comprising an Fc region whose Fcγ receptor-binding activity has been demonstrated to be high as described above.

In a non-limiting embodiment of the present invention, preferred Fc regions whose binding activity to activating FcγR is lower than that of the native Fc region include, for example, Fc regions in which any one or more of amino acids at positions 234, 235, 236, 237, 238, 239, 270, 297, 298, 325, and 329 (indicated by EU numbering) among the amino acids of an above-described Fc region are substituted with different amino acids of the native Fc region. Such alterations of Fc region are not limited to the above-described alterations, and include, for example, alterations such as deglycosylated chains (N297A and N297Q), IgG1-L234A/L235A, IgG1-A325A/A330S/P331S, IgG1-C226S/C229S, IgG1-C226S/C229S/E233P/L234V/L235A, IgG1-L234F/L235E/P331S, IgG1-S267E/L328F, IgG2-V234A/G237A, IgG2-H268Q/V309L/A330S/A331S, IgG4-L235A/G237A/E318A, and IgG4-L236E described in Current Opinion in Biotechnology (2009) 20 (6), 685-691; alterations such as G236R/L328R, L235G/G236R, N325A/L328R, and N325LL328R described in WO 2008/092117; amino acid insertions at positions 233, 234, 235, and 237 (indicated by EU numbering); and alterations at the sites described in WO 2000/042072.

Furthermore, in a non-limiting embodiment of the present invention, preferred Fc regions include those altered to have one or more alterations of:

a substitution of Ala, Arg, Asn, Asp, Gln, Glu, Gly, His, Lys, Met, Phe, Pro, Ser, Thr, or Trp for the amino acid at position 234;

a substitution of Ala, Asn, Asp, Gln, Glu, Gly, His, Ile, Lys, Met, Pro, Ser, Thr, Val, or Arg for the amino acid at position 235;

a substitution of Arg, Asn, Gln, His, Leu, Lys, Met, Phe, Pro, or Tyr for the amino acid at position 236;

a substitution of Ala, Asn, Asp, Gln, Glu, His, Ile, Leu, Lys, Met, Pro, Ser, Thr, Val, Tyr, or Arg for the amino acid at position 237;

a substitution of Ala, Asn, Gln, Glu, Gly, His, Ile, Lys, Thr, Trp, or Arg for the amino acid at position 238;

a substitution of Gln, His, Lys, Phe, Pro, Trp, Tyr, or Arg for the amino acid at position 239;

a substitution of Ala, Arg, Asn, Gln, Gly, His, Ile, Leu, Lys, Met, Phe, Ser, Thr, Trp, Tyr, or Val for the amino acid at position 265;

a substitution of Ala, Arg, Asn, Asp, Gln, Glu, Gly, His, Lys, Phe, Pro, Ser, Thr, Trp, or Tyr for the amino acid at position 266;

a substitution of Arg, His, Lys, Phe, Pro, Trp, or Tyr for the amino acid at position 267;

a substitution of Ala, Arg, Asn, Gln, Gly, His, Ile, Leu, Lys, Met, Phe, Pro, Ser, Thr, Trp, Tyr, or Val for the amino acid at position 269;

a substitution of Ala, Arg, Asn, Gln, Gly, His, Ile, Leu, Lys, Met, Phe, Pro, Ser, Thr, Trp, Tyr, or Val for the amino acid at position 270;

a substitution of Arg, His, Phe, Ser, Thr, Trp, or Tyr for the amino acid at position 271;

a substitution of Arg, Asn, Asp, Gly, His, Phe, Ser, Trp, or Tyr for the amino acid at position 295;

a substitution of Arg, Gly, Lys, or Pro for the amino acid at position 296;

a substitution of Ala for the amino acid at position 297;

a substitution of Arg, Gly, Lys, Pro, Trp, or Tyr for the amino acid at position 298;

a substitution of Arg, Lys, or Pro for the amino acid at position 300;

a substitution of Lys or Pro for the amino acid at position 324;

a substitution of Ala, Arg, Gly, His, Ile, Lys, Phe, Pro, Thr, Trp, Tyr, or Val for the amino acid at position 325;

a substitution of Arg, Gln, His, Ile, Leu, Lys, Met, Phe, Pro, Ser, Thr, Trp, Tyr, or Val for the amino acid at position 327;

a substitution of Arg, Asn, Gly, His, Lys, or Pro for the amino acid at position 328;

a substitution of Asn, Asp, Gln, Glu, Gly, His, Ile, Leu, Lys, Met, Phe, Ser, Thr, Trp, Tyr, Val, or Arg for the amino acid at position 329;

a substitution of Pro or Ser for the amino acid at position 330;

a substitution of Arg, Gly, or Lys for the amino acid at position 331; and a substitution of Arg, Lys, or Pro for the amino acid at position 332 in the EU numbering system in the Fc region.

(Embodiment 2) Antigen-binding Molecules that Comprise an Fc Region having the FcRn-binding Activity under the Neutral pH Range Condition and whose Binding Activity to Inhibitory FcγR is Higher than the Binding Activity to Activating Fcγ Receptor Antigen-binding molecules of Embodiment 2 can form the tetramer complex by binding to two molecules of FcRn and one molecule of inhibitory FcγR. However, since one antigen-binding molecule can bind to only one molecule of FcγR, an antigen-binding molecule bound to inhibitory FcγR cannot further bind to activating FcγR (FIG. 50). Furthermore, it has been reported that antigen-binding molecules incorporated into cells in a state bound to inhibitory FcγR are recycled onto cell membrane and thus escape from intracellular degradation (Immunity (2005) 23, 503-514). Specifically, it is assumed that antigen-binding molecules having the selective binding activity to inhibitory FcγR cannot form the heteromeric complex comprising activating FcγR, which is responsible for the immune response, and two molecules of FcRn.

Herein, "the binding activity to inhibitory FcγR is higher than the binding activity to activating Fcγ receptor" means that the binding activity of an Fc region variant to FcγRIIb is higher than the binding activity to any human Fcγ receptors, FcγRI, FcγRIIa, FcγRIIIa, and/or FcγRIIIb. For example, it means that, based on an above-described analytical method, the FcγRIIb-binding activity of an antigen-binding molecule having an Fc region variant is 105% or more, preferably 110% or more, 120% or more, 130% or more, 140% or more, particularly preferably 150% or more, 160% or more, 170% or more, 180% or more, 190% or more, 200% or more, 250% or more, 300% or more, 350% or more, 400% or more, 450% or more, 500% or more, 750% or more, 10 times or more, 20 times or more, 30 times or more, 40 times or more, 50 times or more the binding activity to any human Fcγ receptors, FcγRI, FcγRIIa, FcγRIIIa, and/or FcγRIIIb.

As control antigen-binding molecules having an Fc region, those having an Fc region from a monoclonal IgG antibody can appropriately be used. The structures of such Fc regions are shown in SEQ ID NOs: 11 (A is added to the N terminus of RefSeq accession No. AAC82527.1), 12 (A is added to the N terminus of RefSeq accession No. AAB59393.1), 13 (RefSeq accession No. CAA27268.1), and 14 (A is added to the N terminus of RefSeq accession No. AAB59394.1). Meanwhile, when an antigen-binding molecule that has the Fc region from an antibody of a certain isotype is used as a test substance, the Fcγ receptor-binding activity of the antigen-binding molecule having the Fc region can be tested by using as a control an antigen-binding molecule having the Fc region of a monoclonal IgG antibody of the same isotype. As described above, an antigen-binding molecule comprising an Fc region whose binding activity to Fcγ receptor has been demonstrated to be high is appropriately selected.

In a non-limiting embodiment of the present invention, preferred Fc regions having the selective binding activity to inhibitory FcγR include, for example, Fc regions in which amino acid at position 238 or 328 (indicated by EU numbering) among the amino acids of an above-described Fc region is altered to a different amino acid of the native Fc region. Furthermore, as Fc regions having the selective binding activity to inhibitory FcγR, it is also possible to appropriately select Fc regions or alterations from those described in US 2009/0136485.

In another non-limiting embodiment of the present invention, preferred Fc regions include those in which any one or more of: amino acid at position 238 (indicated by EU numbering) is substituted with Asp and amino acid at position 328 (indicated by EU numbering) is substituted with Glu in an above-described Fc region.

In still another non-limiting embodiment of the present invention, preferred Fc regions include substitution of Asp for Pro at position 238 (indicated by EU numbering), and those in which one or more of:

a substitution of Trp for the amino acid at position 237 (indicated by EU numbering),
a substitution of Phe for the amino acid at position 237 (indicated by EU numbering),
a substitution of Val for the amino acid at position 267 (indicated by EU numbering),
a substitution of Gln for the amino acid at position 267 (indicated by EU numbering),
a substitution of Asn for the amino acid at position 268 (indicated by EU numbering),
a substitution of Gly for the amino acid at position 271 (indicated by EU numbering),
a substitution of Leu for the amino acid at position 326 (indicated by EU numbering),
a substitution of Gln for the amino acid at position 326 (indicated by EU numbering),
a substitution of Glu for the amino acid at position 326 (indicated by EU numbering),
a substitution of Met for the amino acid at position 326 (indicated by EU numbering),
a substitution of Asp for the amino acid at position 239 (indicated by EU numbering),
a substitution of Ala for the amino acid at position 267 (indicated by EU numbering),
a substitution of Trp for the amino acid at position 234 (indicated by EU numbering),
a substitution of Tyr for the amino acid at position 234 (indicated by EU numbering),
a substitution of Ala for the amino acid at position 237 (indicated by EU numbering),
a substitution of Asp for the amino acid at position 237 (indicated by EU numbering),
a substitution of Glu for the amino acid at position 237 (indicated by EU numbering),
a substitution of Leu for the amino acid at position 237 (indicated by EU numbering),
a substitution of Met for the amino acid at position 237 (indicated by EU numbering),
a substitution of Tyr for the amino acid at position 237 (indicated by EU numbering),
a substitution of Lys for the amino acid at position 330 (indicated by EU numbering),
a substitution of Arg for the amino acid at position 330 (indicated by EU numbering),
a substitution of Asp for the amino acid at position 233 (indicated by EU numbering),
a substitution of Asp for the amino acid at position 268 (indicated by EU numbering),
a substitution of Glu for the amino acid at position 268 (indicated by EU numbering),
a substitution of Asp for the amino acid at position 326 (indicated by EU numbering),
a substitution of Ser for the amino acid at position 326 (indicated by EU numbering),
a substitution of Thr for the amino acid at position 326 (indicated by EU numbering),
a substitution of Ile for the amino acid at position 323 (indicated by EU numbering),
a substitution of Leu for the amino acid at position 323 (indicated by EU numbering),
a substitution of Met for the amino acid at position 323 (indicated by EU numbering),
a substitution of Asp for the amino acid at position 296 (indicated by EU numbering), a substitution of Ala for the amino acid at position 326 (indicated by EU numbering),
a substitution of Asn for the amino acid at position 326 (indicated by EU numbering), and
a substitution of Met for the amino acid at position 330 (indicated by EU numbering).

(Embodiment 3) Antigen-binding Molecules Comprising an Fc Region in which One of the Two Polypeptides Constituting Fc Region has the FcRn-binding Activity under the Neutral pH Range Condition and the other does not have the FcRn-binding Activity under the Neutral pH Range Condition Antigen-binding molecule of Embodiment 3 can form trimer complexes by binding to one molecule of FcRn and one molecule of FcγR; however, they do not form the hetero tetramer complex comprising two molecules of FcRn and one molecule of FcγR (FIG. 51). Fc regions derived from bispecific antibodies can be appropriately used as Fc regions in which one of the two polypeptides constituting Fc region has the FcRn-binding activity under the neutral pH range condition and the other does not have the FcRn-binding activity under the neutral pH range condition, which are included in the antigen-binding molecule of Embodiment 3. A bispecific antibody refers to two types of antibodies which have specificity to different antigens. Bispecific antibodies of IgG type can be secreted from hybrid hybridomas (quadromas) resulting from fusion of two types of hybridomas producing IgG antibodies (Milstein et al. (Nature (1983) 305, 537-540).

When antigen-binding molecules of Embodiment 3 above are produced by using recombination techniques such as described in the section "Antibody", one can use a method in which the genes encoding polypeptides that constitute the two types of Fc regions of interest are introduced into cells to co-express them. However, the produced Fc region is a mixture which contains, at a molecular ratio of 2:1:1, Fc region in which one of the two polypeptides constituting the Fc region has the FcRn-binding activity under the neutral pH range condition and the other does not have the FcRn-binding activity under the neutral pH range condition, Fc region in which both polypeptides constituting the Fc region have the FcRn-binding activity under the neutral pH range condition, and Fc region in which both polypeptides constituting the Fc region do not have the FcRn-binding activity under the neutral pH range condition. It is difficult to purify antigen-binding molecules comprising a desired combination of Fc regions from the three types of IgGs.

When producing antigen-binding molecules of Embodiment 3 using recombination techniques such as described above, antigen-binding molecules comprising the hetero combination of Fc regions can be preferentially secreted by altering the CH3 domain that constitutes an Fc region using appropriate amino acid substitutions. Specifically, it is a method of enhancing hetero H chain formation and inhibiting homo H chain formation by substituting amino acid side chain in one heavy chain CH3 domain with a bulker side chain (knob (meaning "projection")) while substituting amino acid side chain in the other heavy chain CH3 domain with a smaller side chain (hole (meaning "void")) so that the "knob" is placed in the "hole" (WO 1996027011, Ridgway et al. (Protein Engineering (1996) 9, 617-621), Merchant et al. (Nat. Biotech. (1998) 16, 677-681)).

Furthermore, known techniques for producing bispecific antibodies include those in which a means for regulating polypeptide association or association to form heteromeric multimers constituted by polypeptides is applied to the association of a pair of polypeptides that constitute an Fc region. Specifically, to produce bispecific antibodies, one can use methods for regulating polypeptide association by altering amino acid residues forming interface between a pair of polypeptides that constitute an Fc region so as to form a complex of two polypeptides with different sequences constituting the Fc region, while inhibiting the association of polypeptides having an identical sequence which constitute the Fc region (WO 2006/106905). Such methods can be used to produce antigen-binding molecules of the present invention described in Embodiment 3.

In a non-limiting embodiment of the present invention, a pair of polypeptides that constitute an above-described Fc region originating from a bispecific antibody can be appropriately used as an Fc region. More specifically, a pair of polypeptides that constitute an Fc region, one of which has an amino acid sequence in which the amino acids at positions 349 and 366 (indicated by EU numbering) are Cys and Trp, respectively, and the other has an amino acid sequence in which the amino acid at position 356 (indicated by EU numbering) is Cys, the amino acid at position 366 (indicated by EU numbering) is Ser, the amino acid at position 368 is Ala, and the amino acid at position 407 (indicated by EU numbering) is Val, is preferably used as Fc regions.

In another non-limiting embodiment of the present invention, a pair of polypeptides that constitute an Fc region, one of which has an amino acid sequence in which the amino acid at position 409 (indicated by EU numbering) is Asp, and the other has an amino acid sequence in which the amino acid at position 399 (indicated by EU numbering) is Lys is preferably used as Fc regions. In the above-described embodiment, the amino acid at position 409 may be Glu instead of Asp, and the amino acid at position 399 may be Arg instead of Lys. Alternatively, it is preferable that, when the amino acid at position 399 is Lys, additionally the amino acid at position 360 may be Asp or the amino acid at position 392 may be Asp.

In still another non-limiting embodiment of the present invention, a pair of polypeptides that constitute an Fc region, one of which has an amino acid sequence in which the amino acid at position 370 (indicated by EU numbering) is Glu, and the other has an amino acid sequence in which the amino acid at position 357 (indicated by EU numbering) is Lys is preferably used as Fc regions.

In yet another non-limiting embodiment of the present invention, a pair of polypeptides that constitute an Fc region, one of which has an amino acid sequence in which the amino acid at position 439 (indicated by EU numbering) is Glu, and the other has an amino acid sequence in which the amino acid at position 356 (indicated by EU numbering) is Lys, is preferably used as Fc regions.

In still yet another non-limiting embodiment of the present invention, such preferred Fc regions include those as a combination of any of the above embodiments, such as:
a pair of polypeptides that constitute an Fc region, one of which has an amino acid sequence in which the amino acids at positions 409 and 370 (indicated by EU numbering) are Asp and Glu, respectively, and the other has an amino acid sequence in which the amino acids at positions 399 and 357 (indicated by EU numbering) are both Lys (in this embodiment, the amino acid at position 370 (indicated by EU numbering) may be Asp instead of Glu, or the amino acid at position 392 may be Asp, instead of Glu at amino acid position 370);
a pair of polypeptides that constitute an Fc region, one of which has an amino acid sequence in which the amino acids at positions 409 and 439 (indicated by EU numbering) are Asp and Glu, respectively, and the other has an amino acid sequence in which the amino acids at positions 399 and 356 (indicated by EU numbering) are both Lys (in this embodiment, instead of Glu at amino acid position 439 (indicated by EU numbering), the amino acid at position 360 may be Asp, the amino acid at position 392 may be Asp, or the amino acid at position 439 may be Asp);

a pair of polypeptides that constitute an Fc region, one of which has an amino acid sequence in which the amino acids at positions 370 and 439 (indicated by EU numbering) are both Glu, and the other has an amino acid sequence in which the amino acids at positions 357 and 356 (indicated by EU numbering) are both Lys; and a pair of polypeptides that constitute an Fc region, one of which has an amino acid sequence in which the amino acids at positions 409, 370, and 439 (indicated by EU numbering) are Asp, Glu, and Glu, respectively, and the other has an amino acid sequence in which the amino acids at positions 399, 357, and 356 (indicated by EU numbering) are all Lys (in this embodiment, the amino acid at position 370 may not be substituted with Glu, and further, when the amino acid at position 370 is not substituted with Glu, the amino acid at position 439 may be Asp instead of Glu, or the amino acid at position 439 may be Asp, instead of Glu at amino acid position 392).

In another non-limiting embodiment of the present invention, a pair of polypeptides that constitute an Fc region, one of which has an amino acid sequence in which the amino acids at position 356 (indicated by EU numbering) is Lys, and the other has an amino acid sequence in which the amino acids at positions 435 and 439 (indicated by EU numbering) are Arg and Glu, respectively, is preferably used.

These antigen-binding molecules of Embodiments 1 to 3 are expected to have reduced immunogenicity and improved plasma retention as compared to antigen-binding molecules capable of forming the tetramer complex.

Appropriate known methods such as site-directed mutagenesis (Kunkel et al. (Proc. Natl. Acad. Sci. USA (1985) 82, 488-492)) and overlap extension PCR can be applied to alter the amino acids of Fc regions. Furthermore, various known methods can also be used as an amino acid alteration method for substituting amino acids with those other than natural amino acids (Annu Rev. Biophys. Biomol. Struct. (2006) 35, 225-249; Proc. Natl. Acad. Sci. U.S.A. (2003) 100 (11), 6353-6357). For example, it is also preferable to use a cell-free translation system (Clover Direct (Protein Express)) comprising tRNAs in which an unnatural amino acid is linked to an amber suppressor tRNA, which is complementary to UAG stop codon (amber codon).

In an embodiment of variants of the present invention, polynucleotides encoding antigen-binding molecules which have a heavy chain where a polynucleotide encoding an Fc region modified to have an amino acid mutation as described above is linked in frame to a polynucleotide encoding the above-described antigen-binding molecule whose binding activity varies depending on a selected condition.

The present invention provides methods for producing antigen-binding molecules, comprising collecting the antigen-binding molecules from culture media of cells introduced with vectors in which a polynucleotide encoding an Fc region is operably linked in frame to a polynucleotide encoding an antigen-binding domain whose binding activity varies depending on ion concentration condition. Furthermore, the present invention also provides methods for producing antigen-binding molecules, comprising collecting the antigen-binding molecules from culture media of cells introduced with vectors constructed by operably linking a polynucleotide encoding an antigen-binding domain whose binding activity varies depending on ion concentration condition to a polynucleotide encoding an Fc region which is in advance operably linked to a vector.

Pharmaceutical Compositions

When a conventional neutralizing antibody against a soluble antigen is administered, the plasma retention of the antigen is expected to be prolonged by binding to the antibody. In general, antibodies have a long half-life (one week to three weeks) while the half-life of antigen is generally short (one day or less). Meanwhile, antibody-bound antigens have a significantly longer half-life in plasma as compared to when the antigens are present alone. For this reason, administration of existing neutralizing antibody results in an increased antigen concentration in plasma. Such cases have been reported with various neutralizing antibodies that target soluble antigens including, for example, IL-6 (J. Immunotoxicol. (2005) 3, 131-139), amyloid beta (mAbs (2010) 2 (5), 1-13), MCP-1 (ARTHRITIS & RHEUMATISM (2006) 54, 2387-2392), hepcidin (AAPS J. (2010) 4, 646-657), and sIL-6 receptor (Blood (2008) 112 (10), 3959-64). Administration of existing neutralizing antibodies has been reported to increase the total plasma antigen concentration to about 10 to 1,000 times (the level of increase varies depending on antigen) the base line. Herein, the total plasma antigen concentration refers to a concentration as a total amount of antigen in plasma, i.e., the sum of concentrations of antibody-bound and antibody-unbound antigens. An increase in the total plasma antigen concentration is undesirable for such antibody pharmaceuticals that target a soluble antigen. The reason is that the antibody concentration has to be higher than at least the total plasma antigen concentration to neutralize the soluble antigen. Specifically, "the total plasma antigen concentration is increased to 10 to 1,000 times" means that, in order to neutralize the antigen, the plasma antibody concentration (i.e., antibody dose) has to be 10 to 1,000 times higher as compared to when increase in the total plasma antigen concentration does not occur. Conversely, if the total plasma antigen concentration can be reduced by 10 to 1,000 times as compared to the existing neutralizing antibody, the antibody dose can also be reduced to similar extent. Thus, antibodies capable of decreasing the total plasma antigen concentration by eliminating the soluble antigen from plasma are highly useful as compared to existing neutralizing antibodies.

The present invention is not limited to a particular theory, but one can explain, for example, as follows why the number of antigens to which single antigen-binding molecules can bind is increased and why the antigen elimination from plasma is accelerated when antigen-binding molecules that have an antigen-binding domain whose antigen-binding activity varies depending on ion concentration condition so that the antigen-binding activity in an acidic pH range is lower than under the neutral pH range condition and additionally have an FcRn-binding domain such as an antibody constant region exhibiting the human FcRn-binding activity under the neutral pH range condition are administered in vivo and in vivo uptake into cells are enhanced.

For example, when an antibody that binds to a membrane antigen is administered in vivo, after binding to an antigen, the antibody is, in a state bound to the antigen, incorporated into the endosome via intracellular internalization. Then, the antibody is transferred to the lysosome while remaining bound to the antigen, and is degraded together with the antigen there. The internalization-mediated elimination from plasma is referred to as antigen-dependent elimination, and has been reported for many antibody molecules (Drug Discov Today (2006) 11(1-2), 81-88). When a single IgG antibody molecule binds to antigens in a divalent manner, the single antibody molecule is internalized while remaining bound to the two antigens, and is degraded in the lysosome. In the case of typical antibodies, thus, a single IgG antibody molecule cannot bind to three antigen molecules or more. For example, a single IgG antibody molecule having a neutralizing activity cannot neutralize three antigen molecules or more.

The plasma retention of IgG molecule is relatively long (the elimination is slow) since human FcRn, which is known as a salvage receptor for IgG molecule, functions. IgG molecules incorporated into endosomes by pinocytosis bind under the endosomal acidic condition to human FcRn expressed in endosomes. IgG molecules that cannot bind to human FcRn are transferred to lysosomes and degraded there. Meanwhile, IgG molecules bound to human FcRn are transferred to cell surface. The IgG molecules are dissociated from human FcRn under the neutral condition in plasma, and recycled back to plasma.

Alternatively, when antigen-binding molecules are antibodies that bind to a soluble antigen, the in vivo administered antibodies bind to antigens, and then the antibodies are incorporated into cells while remaining bound to the antigens. Most of antibodies incorporated into cells bind to FcRn in the endosome and then are transferred to cell surface. The antibodies are dissociated from human FcRn under the neutral condition in plasma and released to the outside of cells. However, antibodies having typical antigen-binding domains whose antigen-binding activity does not vary depending on ion concentration condition such as pH are released to the outside of cells while remaining bound to the antigens, and thus cannot bind to an antigen again. Thus, like antibodies that bind to membrane antigens, single typical IgG antibody molecule whose antigen-binding activity does not vary depending on ion concentration condition such as pH cannot bind to three antigen molecules or more.

Antibodies that bind to antigens in a pH-dependent manner, which strongly bind to antigens under the neutral pH range condition in plasma and are dissociated from antigens under the endosomal acidic pH range condition (antibodies that bind to antigens under the neutral pH range condition and are dissociated under an acidic pH range condition), and antibodies that bind to antigens in a calcium ion concentration-dependent manner, which strongly bind to antigens under a high calcium ion concentration condition in plasma and are dissociated from antigens under a low calcium ion concentration condition in the endosome (antibodies that bind to antigens under a high calcium ion concentration condition and are dissociated under a low calcium ion concentration condition) can be dissociated from antigen in the endosome. Antibodies that bind to antigens in a pH-dependent manner or in a calcium ion concentration-dependent manner, when recycled to plasma by FcRn after dissociation from antigens, can again bind to an antigen. Thus, such single antibody molecule can repeatedly bind to several antigen molecules. Meanwhile, antigens bound to antigen-binding molecules are dissociated from antibody in the endosome and degraded in the lysosome without recycling to plasma. By administering such antigen-binding molecules in vivo, antigen uptake into cells is accelerated, and it is possible to decrease plasma antigen concentration.

Uptake of antigens bound by antigen-binding molecules into cells are further promoted by conferring the human FcRn-binding activity under the neutral pH range condition (pH 7.4) to antibodies that bind to antigens in a pH-dependent manner, which strongly bind to antigens under the neutral pH range condition in plasma and are dissociated from antigens under the endosomal acidic pH range condition (antibodies that bind to antigens under the neutral pH range condition and are dissociated under an acidic pH range condition), and antibodies that bind to antigens in a calcium ion concentration-dependent manner, which strongly bind to antigens under a high calcium ion concentration condition in plasma and are dissociated from antigens under a low calcium ion concentration condition in the endosome (antibodies that bind to antigens under a high calcium ion concentration condition and are dissociated under a low calcium ion concentration condition). Specifically, by administering such antigen-binding molecules in vivo, the antigen elimination is accelerated, and it is possible to reduce plasma antigen concentration. Typical antibodies that do not have the ability to bind to antigens in a pH-dependent manner or in a calcium ion concentration-dependent manner, and antigen-antibody complexes of such antibodies are incorporated into cells by non-specific endocytosis, and transported onto cell surface by binding to FcRn under the endosomal acidic condition. They are dissociated from FcRn under the neutral condition on cell surface and recycled to plasma. Thus, when an antibody that binds to an antigen in a fully pH-dependent manner (that binds under the neutral pH range condition and is dissociated under an acidic pH range condition) or in a fully calcium ion concentration-dependent manner (that binds under a high calcium ion concentration condition and is dissociated under a low calcium ion concentration condition) binds to an antigen in plasma and is dissociated from the antigen in the endosome, the rate of antigen elimination is considered to be equal to the rate of uptake into cells of the antibody or antigen-antibody complex by non-specific endocytosis. When the pH or calcium ion concentration dependency of antigen-antibody binding is insufficient, antigens that are not dissociated from antibodies in the endosome are, along with the antibodies, recycled to plasma. On the other hand, when the pH or calcium ion concentration dependency is sufficiently strong, the rate limiting step of antigen elimination is the cellular uptake by non-specific endocytosis. Meanwhile, FcRn transports antibodies from the endosome to the cell surface, and a fraction of FcRn is expected to be also distributed on the cell surface.

In general, IgG-type immunoglobulin, which is an embodiment of antigen-binding molecules, has little FcRn-binding activity in the neutral pH range. The present inventors conceived that IgG-type immunoglobulin having the FcRn-binding activity in the neutral pH range can bind to FcRn on cell surface and is incorporated into cells in an FcRn-dependent manner by binding to FcRn on cell surface. The rate of FcRn-mediated cellular uptake is more rapid than the cellular uptake by non-specific endocytosis. Thus, the present inventors suspected that the rate of antigen elimination by antigen-binding molecules can be further increased by conferring the FcRn-binding ability in the neutral pH range to antigen-binding molecules. Specifically, antigen-binding molecules that have the FcRn-binding ability in the neutral pH range deliver antigens into cells more rapidly than native IgG-type immunoglobulin does; the molecules are dissociated from antigens in the endosome and again recycled to cell surface or plasma; and again bind to antigens there, and are incorporated into cells via FcRn. The cycling rate can be accelerated by increasing the FcRn-binding ability in the neutral pH range, resulting in the acceleration of antigen elimination from plasma. Moreover, the rate of antigen elimination from plasma can further be accelerated by lowering the antigen-binding activity of an antigen-binding molecule in an acidic pH than in the neutral pH range. In addition, the number of antigen molecules to which a single antigen-binding molecule can bind is predicted to be increased due to an increase in cycling number as a result of acceleration of the cycling rate. Antigen-binding molecules of the present invention comprise an antigen-binding domain and an FcRn-binding domain. Since the FcRn-binding domain does not affect the antigen binding, and does not depend on antigen type based on the mechanism described above, the antigen-binding molecule-mediated antigen uptake into cells can be enhanced to accelerate the rate of antigen elimination by reducing the antigen-binding activity (binding ability) of an antigen-binding molecule so as to be lower under a condition of ion concentration such as an acidic pH range or low calcium ion concentration than under a condition of ion concentration such as a neutral pH range or high calcium ion concentration and/or by increasing the FcRn-binding activity at the plasma pH. Thus, antigen-binding molecules of the present invention are expected to exhibit more excellent effects than conventional therapeutic antibodies from the viewpoint of reduction of side effects of antigens, increased antibody dose, improvement of in vivo dynamics of antibodies, etc.

FIG. 1 shows a mechanism in which soluble antigens are eliminated from plasma by administering a pH-dependent antigen-binding antibody that has increased FcRn-binding activity at neutral pH as compared to a conventional neutralizing antibody. After binding to the soluble antigen in plasma, the existing neutralizing antibody that does not have the pH-dependent antigen-binding ability is slowly incorporated into cells by non-specific interaction with the cells. The complex between the neutralizing antibody and soluble antigen incorporated into the cell is transferred to the acidic endosome and then recycled to plasma by FcRn. Meanwhile, the pH-dependent antigen-binding antibody that has the increased FcRn-binding activity under the neutral condition is, after binding to the soluble antigen in plasma, rapidly incorporated into cells expressing FcRn on their cell membrane. Then, the soluble antigen bound to the pH-dependent antigen-binding antibody is dissociated from the antibody in the acidic endosome due to the pH-dependent binding ability. The soluble antigen dissociated from the antibody is transferred to the lysosome and degraded by proteolytic activity. Meanwhile, the antibody dissociated from the soluble antigen is recycled onto cell membrane and then released to plasma again. The free antibody, recycled as described above, can again bind to other soluble antigens. By repeating such cycle: FcRn-mediated uptake into cells; dissociation and degradation of the soluble antigen; and antibody recycling, such pH-dependent antigen-binding antibodies as described above having the increased FcRn binding activity under the neutral condition can transfer a large amount of soluble antigen to the lysosome and thereby decrease the total antigen concentration in plasma.

Specifically, the present invention also relates to pharmaceutical compositions comprising antigen-binding molecules of the present invention, antigen-binding molecules produced by alteration methods of the present invention, or antigen-binding molecules produced by production methods of the present invention. Antigen-binding molecules of the present invention or antigen-binding molecules produced by production methods of the present invention are useful as pharmaceutical compositions since they, when administered, have the strong effect to reduce the plasma antigen concentration as compared to typical antigen-binding molecules, and exhibit the improved in vivo immune response, pharmacokinetics, and others in animals administered with the molecules. The pharmaceutical compositions of the present invention may comprise pharmaceutically acceptable carriers.

In the present invention, pharmaceutical compositions generally refer to agents for treating or preventing, or testing and diagnosing diseases.

The pharmaceutical compositions of the present invention can be formulated by methods known to those skilled in the art. For example, they can be used parenterally, in the form of injections of sterile solutions or suspensions including water or other pharmaceutically acceptable liquid. For example, such compositions can be formulated by mixing in the form of unit dose required in the generally approved medicine manufacturing practice, by appropriately combining with pharmacologically acceptable carriers or media, specifically with sterile water, physiological saline, vegetable oil, emulsifier, suspension, surfactant, stabilizer, flavoring agent, excipient, vehicle, preservative, binder, or such. In such formulations, the amount of active ingredient is adjusted to obtain an appropriate amount in a pre-determined range.

Sterile compositions for injection can be formulated using vehicles such as distilled water for injection, according to standard formulation practice.

Aqueous solutions for injection include, for example, physiological saline and isotonic solutions containing dextrose or other adjuvants (for example, D-sorbitol, D-mannose, D-mannitol, and sodium chloride). It is also possible to use in combination appropriate solubilizers, for example, alcohols (ethanol and such), polyalcohols (propylene glycol, polyethylene glycol, and such), non-ionic surfactants (polysorbate 80™, HCO-50, and such).

Oils include sesame oil and soybean oils. Benzyl benzoate and/or benzyl alcohol can be used in combination as solubilizers. It is also possible to combine buffers (for example, phosphate buffer and sodium acetate buffer), soothing agents (for example, procaine hydrochloride), stabilizers (for example, benzyl alcohol and phenol), and/or antioxidants. Appropriate ampules are filled with the prepared injections.

The pharmaceutical compositions of the present invention are preferably administered parenterally. For example, the compositions in the dosage form for injections, transnasal administration, transpulmonary administration, or transdermal administration are administered. For example, they can be administered systemically or locally by intravenous injection, intramuscular injection, intraperitoneal injection, subcutaneous injection, or such.

Administration methods can be appropriately selected in consideration of the patient's age and symptoms. The dose of a pharmaceutical composition containing an antigen-binding molecule can be, for example, from 0.0001 to 1,000 mg/kg for each administration. Alternatively, the dose can be, for example, from 0.001 to 100,000 mg per patient. However, the present invention is not limited by the numeric values described above. The doses and administration methods vary depending on the patient's weight, age, symptoms, and such. Those skilled in the art can set appropriate doses and administration methods in consideration of the factors described above.

Furthermore, the present invention provides kits for use in the methods of the present invention, which comprise at least an antigen-binding molecule of the present invention. In addition to the above, pharmaceutically acceptable carriers, media, instruction manuals describing the using method, and such may be packaged into the kits.

Furthermore, the present invention relates to agents for improving the pharmacokinetics of antigen-binding molecules or agents for reducing the immunogenicity of antigen-binding molecules, which comprise as an active ingredient an antigen-binding molecule of the present invention or an antigen-binding molecule produced by the production method of present invention.

The present invention also relates to methods for treating immune inflammatory diseases, which comprise the step of administering to subjects (test subjects) an antigen-binding molecule of the present invention or an antigen-binding molecule produced by the production method of present invention.

The present invention also relates to the use of antigen-binding molecules of the present invention or antigen-binding molecules produced by the production methods of present invention in producing agents for improving the pharmacokinetics of antigen-binding molecules or agents for reducing the immunogenicity of antigen-binding molecules.

In addition, the present invention relates to antigen-binding molecules of the present invention and antigen-binding molecules produced by the production methods of present invention for use in the methods of the present invention.

Amino acids contained in the amino acid sequences of the present invention may be post-translationally modified (for example, the modification of an N-terminal glutamine into a pyroglutamic acid by pyroglutamylation is well-known to those skilled in the art). Naturally, such post-translationally modified amino acids are included in the amino acid sequences in the present invention.

All prior art documents cited in the specification are incorporated herein by reference.

EXAMPLES

Herein below, the present invention will be specifically described with reference to the Examples, but it is not to be construed as being limited thereto.

Example 1

Effect of Enhancing Binding to Human FcRn under Neutral Conditions on Plasma Retention and Immunogenicity of pH-dependent Human IL-6 Receptor-binding Human Antibody It is important for an FcRn binding domain, such as the Fc region of antigen binding molecules such as antibodies that interacts with FcRn (Nat. Rev. Immunol. (2007) 7 (9), 715-25), to have binding activity to FcRn in the neutral pH range in order to eliminate soluble antigen from plasma. As indicated in Reference Example 5, research has been conducted on an FcRn binding domain mutant (amino acid substitution) that has binding activity to FcRn in the neutral pH region of the FcRn binding domain. F1 to F600 which were developed as Fc mutants were evaluated for their binding activity to FcRn in the pH neutral region, and it was confirmed that elimination of antigen from plasma is accelerated by enhancing binding activity to FcRn in the neutral pH region. In order to develop these Fc mutants as pharmaceuticals, in addition to having preferable pharmacological properties (such as acceleration of antigen elimination from the plasma by enhancing FcRn binding), it is also preferable to have superior stability and purity of antigen-binding molecules, superior plasma retention of antigen-binding molecules in the body, and low immunogenicity.

Antibody plasma retention is known to worsen as a result of binding to FcRn under neutral conditions. If an antibody ends up bound to FcRn under neutral conditions, even if the antibody returns to the cell surface by binding to FcRn under acidic conditions in endosomes, an IgG antibody is not recycled to the plasma unless the IgG antibody dissociates from FcRn in the plasma under neutral conditions, thereby conversely causing plasma retention to be impaired. For example, antibody plasma retention has been reported to worsen in the case of administering antibody to mice for which binding to mouse FcRn has been observed under neutral conditions (pH 7.4) as a result of introducing an amino acid substitution into IgG1 (Non-Patent Document 10). On the other hand, however, it has also been reported that in the case where an antibody has been administered to cynomolgus monkeys in which human FcRn-binding has been observed under neutral conditions (pH 7.4), there was no improvement in antibody plasma retention, and changes in plasma retention were not observed (Non-Patent Documents 10, 11 and 12).

In addition, FcRn has been reported to be expressed in antigen presenting cells and involved in antigen presentation. In a report describing evaluation of the immunogenicity of a protein (hereinafter referred to as MBP-Fc) obtained by fusing the Fc region of mouse IgG1 to myelin basic protein (MBP), although not an antigen-binding molecule, T cells that specifically react with MBP-Fc undergo activation and proliferation as a result of culturing in the presence of MBP-Fc. T cell activation is known to be enhanced in vitro by increasing incorporation into antigen presenting cells mediated by FcRn expressed in antigen presenting cells by adding a modification to the Fc region of MBP-Fc that causes an increase in FcRn binding. However, since plasma retention worsens as a result of adding a modification that causes an increase in FcRn binding, T cell activation has been reported to conversely diminish in vivo (Non-Patent Document 43).

In this manner, the effect of enhancing FcRn binding under neutral conditions on the plasma retention and immunogenicity of antigen-binding molecules has not been adequately investigated. In the case of developing antigen-binding molecules as pharmaceuticals, the plasma retention of these antigen-binding molecules is preferably as long as possible, and immunogenicity is preferably as low as possible.

(1-1) Production of Human IL-6 Receptor-binding Human Antibodies

Therefore, in order to evaluate the plasma retention of antigen-binding molecules that contain an FcRn binding domain having the ability to bind to human FcRn under conditions of the neutral pH region, and evaluate the immunogenicity of those antigen-binding molecules, human IL-6 receptor-binding human antibodies having binding activity to human FcRn under conditions of the neutral pH region were produced in the form of Fv4-IgG1 composed of VH3-IgG1 (SEQ ID NO: 35) and VL3-CK (SEQ ID NO: 36), Fv4-IgG1-F1 composed of VH3-IgG1-F1 (SEQ ID NO: 37) and VL3-CK, Fv4-IgG1-F157 composed of VH3-IgG1-F157 (SEQ ID NO: 38) and VL3-CK, Fv4-IgG1-F20 composed of VH3-IgG1-F20 (SEQ ID NO: 39) and VL3-CK, and Fv4-IgG1-F21 composed of VH3-IgG1-F21 (SEQ ID NO: 40) and VL3-CK according to the methods shown in Reference Example 1 and Reference Example 2.

(1-2) Kinetic Analysis of Mouse FcRn Binding

Antibodies containing VH3-IgG1 or VH3-IgG1-F1 for the heavy chain and L(WT)-CK (SEQ ID NO: 41) for the light chain were produced using the method shown in Reference Example 2, and binding activity to mouse FcRn was evaluated in the manner described below.

The binding between antibody and mouse FcRn was kinetically analyzed using a BIACORE™ T100 surface plasmon resonance system (GE Healthcare). An appropriate amount of protein L (ACTIGEN® protein (Alltech)) was immobilized onto Sensor chip CM4(GE Healthcare) by the amino coupling method, and the chip was allowed to capture an antibody of interest. Then, diluted FcRn solutions and running buffer (as a reference solution) were injected to allow mouse FcRn to interact with the antibody captured on the sensor chip. The running buffer used contains 50 mmol/l sodium phosphate, 150 mmol/l NaCl, and 0.05% (w/v) polysorbate 20 (Tween20®) (pH 7.4). FcRn was diluted using each buffer. The sensorchip was regenerated using 10 mmol/l glycine-HCl (pH 1.5). Assays were carried out exclusively at 25 degrees C. The association rate constant ka (1/Ms) and dissociation rate constant kd (1/s), both of which are kinetic parameters, were calculated based on the sensorgrams obtained in the assays, and the KD (M) of each antibody for mouse FcRn was determined from these values. Each parameter was calculated using BIACORE™ T100 Evaluation Software (GE Healthcare).

As a result, although KD(M) of IgG1 was not detected, KD(M) of the produced IgG1-F1 was 1.06E-06(M). This indicated that the binding activity of the produced IgG1-F1 to mouse FcRn is enhanced under conditions of the neutral pH region (pH 7.4).

(1-3) In Vivo PK Study Using Normal Mice

A PK study was conducted using the method shown below using normal mice having the produced pH-dependent human IL-6 receptor-binding human antibodies, Fv4-IgG1 and Fv4-IgG1-F1. The anti-human IL-6 receptor antibody was administered at 1 mg/kg in a single administration to a caudal vein or beneath the skin of the back of normal mice (C57BL/6J mouse, Charles River Japan). Blood was collected at 5 minutes, 7 hours and 1, 2, 4, 7, 14, 21 and 28 days after administration of the anti-human IL-6 receptor antibody. Plasma was obtained by immediately centrifuging the collected blood for 15 minutes at 4° C. and 15,000 rpm. The separated plasma was stored in a freezer set to −20° C. or lower until the time of measurement.

(1-4) Measurement of Plasma Anti-human IL-6 Receptor Antibody Concentration by ELISA Concentration of anti-human IL-6 receptor antibody in mouse plasma was measured by ELISA. First, Anti-Human IgG (γ-chain specific) F(ab')2 Fragment of Antibody (SIGMA) was dispensed into a Nunc-Immuno Plate, MaxiSoup (Nalge Nunc International) followed by allowing this to stand undisturbed overnight at 4° C. to produce an anti-human IgG solid phase plate. Calibration curve samples containing 0.8, 0.4, 0.2, 0.1, 0.05, 0.025 and 0.0125 µg/mL of anti-human IL-6 receptor antibody in plasma concentration, and mouse plasma measurement samples diluted by 100-fold or more, were prepared. Mixtures obtained by adding 200 µl of 20 ng/mL soluble human IL-6 receptor to 100 µl of the calibration curve samples and plasma measurement samples were then allowed to stand undisturbed for 1 hour at room temperature. Subsequently, the anti-human IgG solid phase plate in which the mixtures had been dispensed into each of the wells thereof was further allowed to stand undisturbed for 1 hour at room temperature. Subsequently, the chromogenic reaction of a reaction liquid obtained upon one hour of reaction with a biotinylated anti-human IL-6 R antibody (R&D) at room temperature and one hour of reaction with Streptavidin-PolyHRP80 (Stereospecific Detection Technologies) at room temperature was carried out using TMB One Component HRP Microwell Substrate (BioFX Laboratories) as substrate. After the reaction was stopped by adding 1N-sulfuric acid (Showa Chemical), absorbance at 450 nm of the reaction liquid of each well was measured with a microplate reader. Antibody concentrations in the mouse plasma were calculated from absorbance values of the calibration curve using the SOFTmax PRO analysis software (Molecular Devices).

Figure 2:
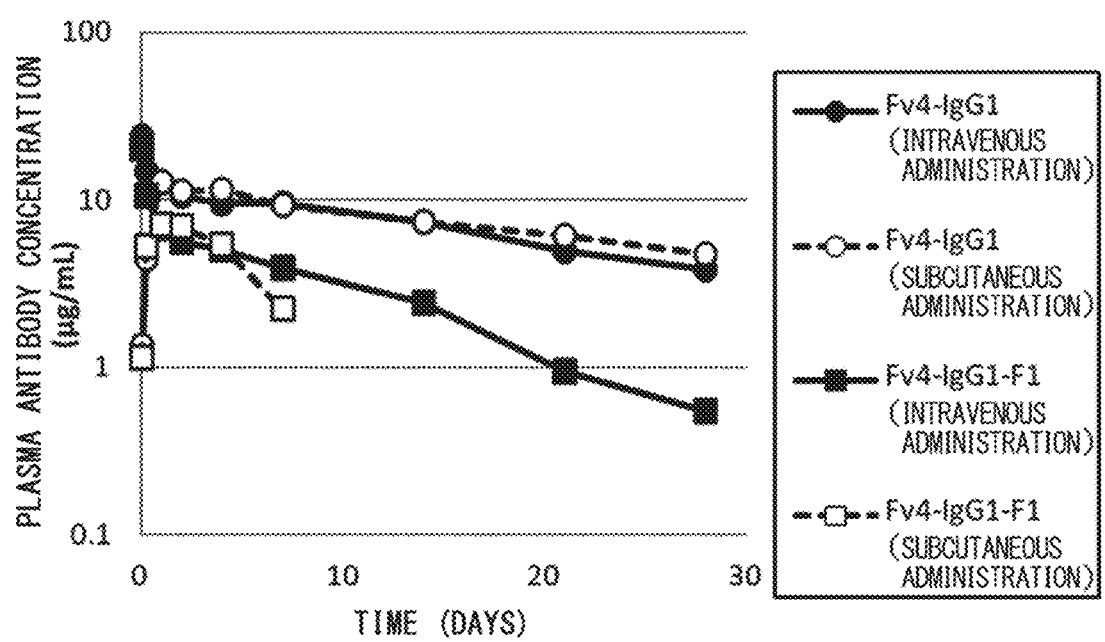
FIG. 2 is a graph showing a plasma concentration time course after intravenous or subcutaneous administration of Fv4-IgG1 or Fv4-IgG1-F1 to normal mice.
Figure 3:
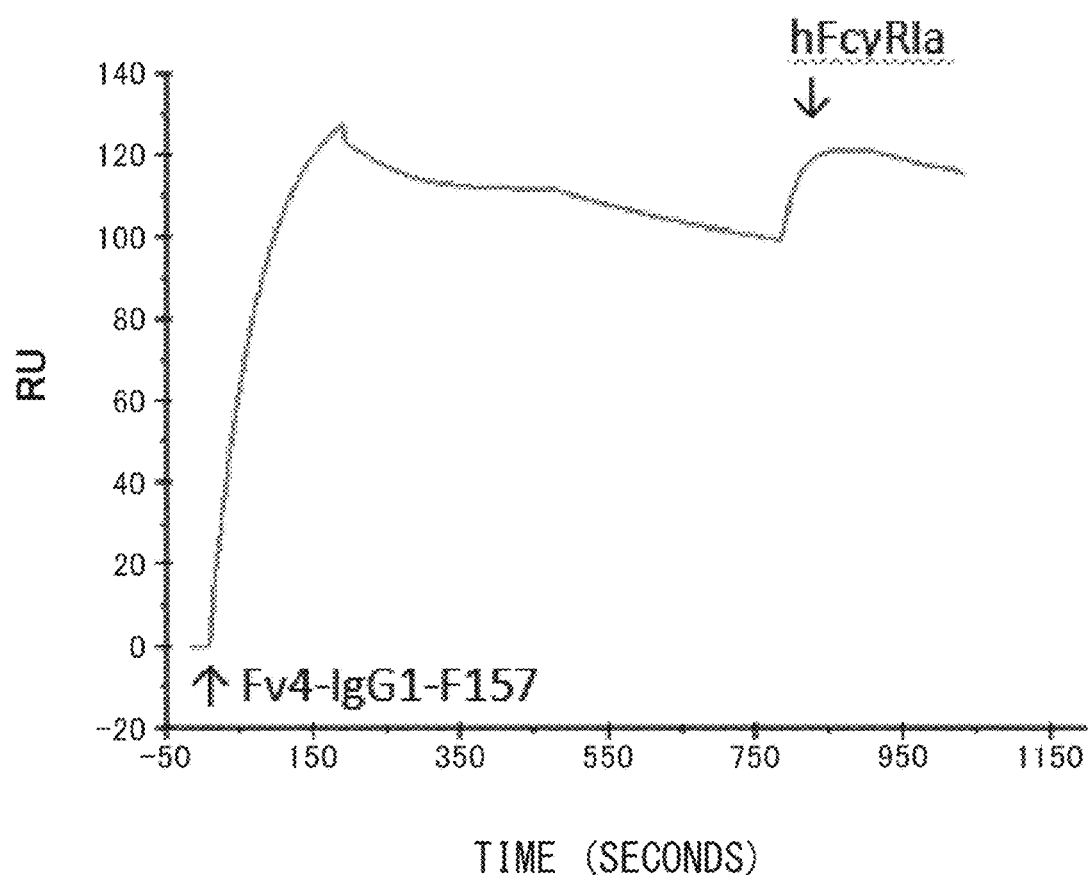
FIG. 3 is a graph demonstrating that in a human FcRn-bound state, Fv4-IgG1-F157 binds to human FcγRIa.
Figure 4:
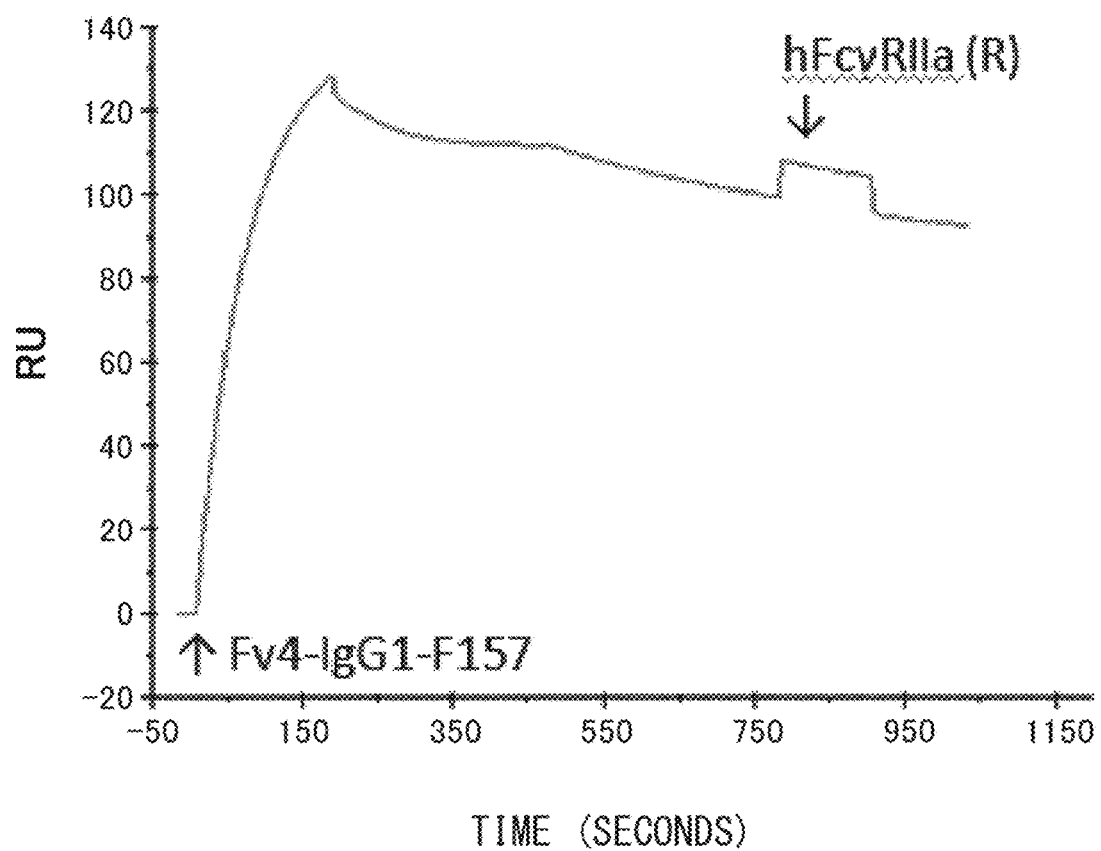
FIG. 4 is a graph demonstrating that in a human FcRn-bound state, Fv4-IgG1-F157 binds to human FcγRIIa(R).
Figure 5:
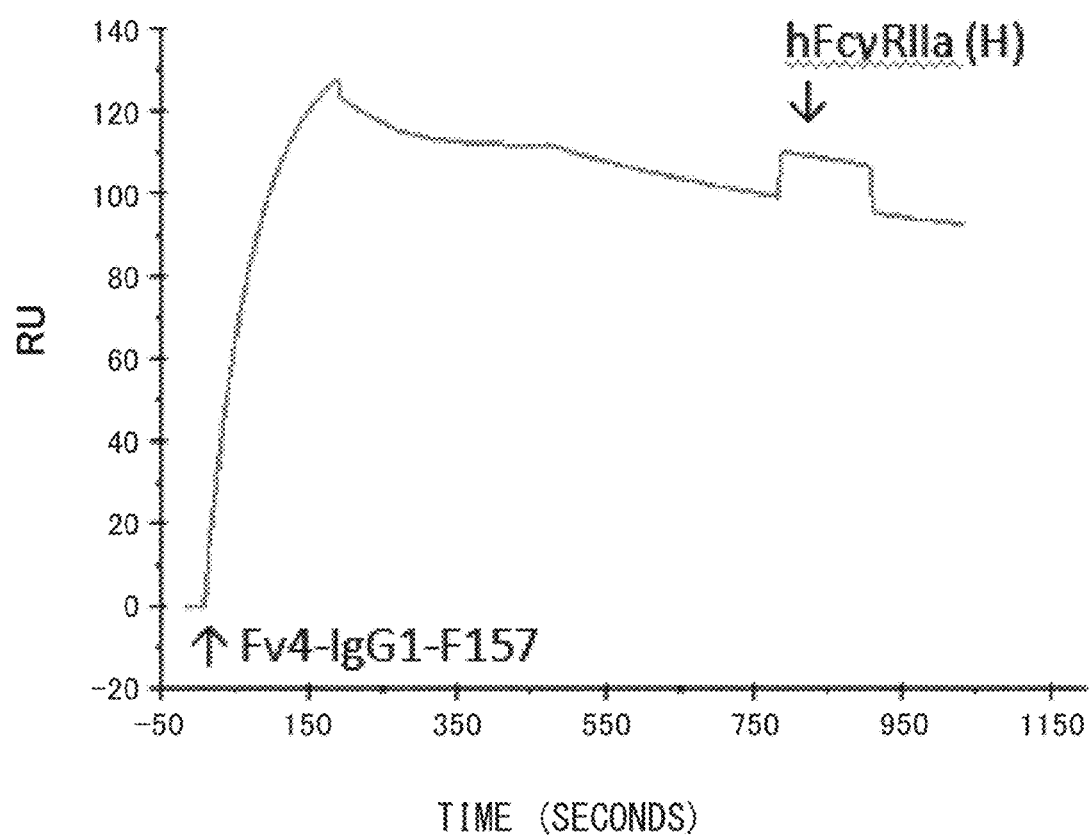
FIG. 5 is a graph demonstrating that in a human FcRn-bound state, Fv4-IgG1-F157 binds to human FcγRIIa(H).
Figure 6:
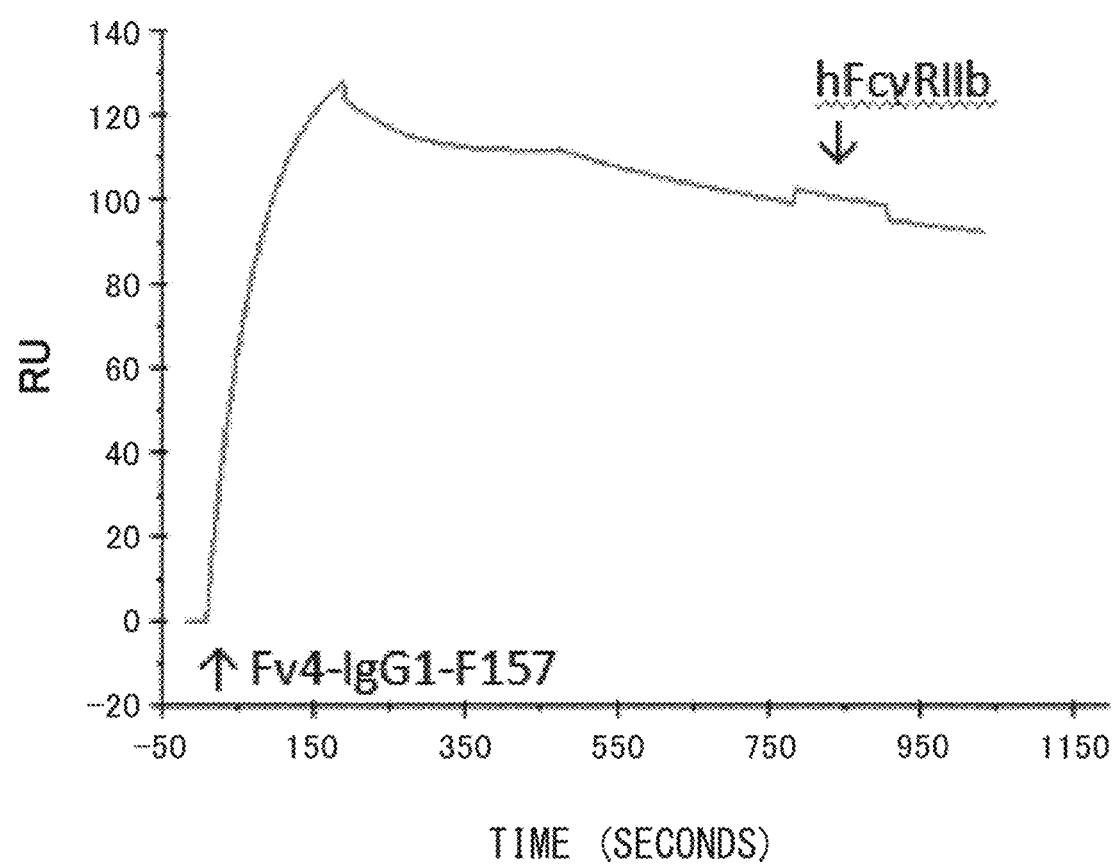
FIG. 6 is a graph demonstrating that in a human FcRn-bound state, Fv4-IgG1-F157 binds to human FcγRIIb.
Figure 7:
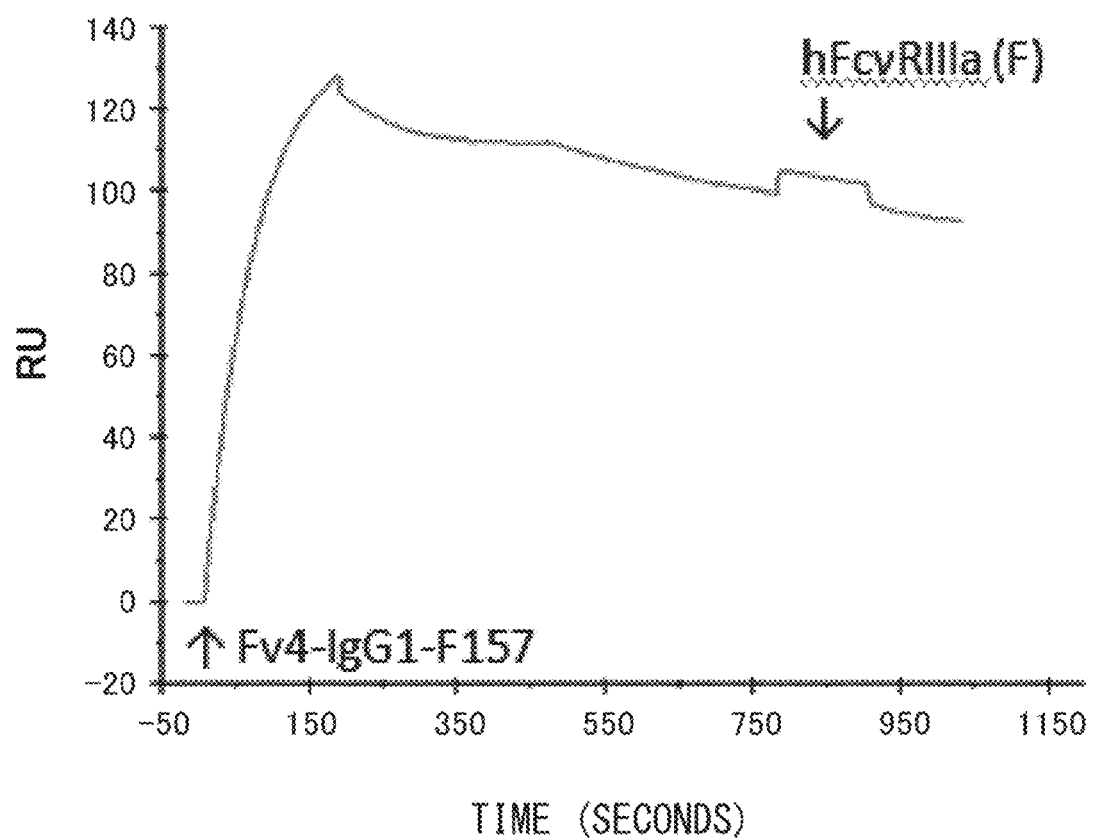
FIG. 7 is a graph demonstrating that in a human FcRn-bound state, Fv4-IgG1-F157 binds to human FcγRIIIa(F).
Figure 8:
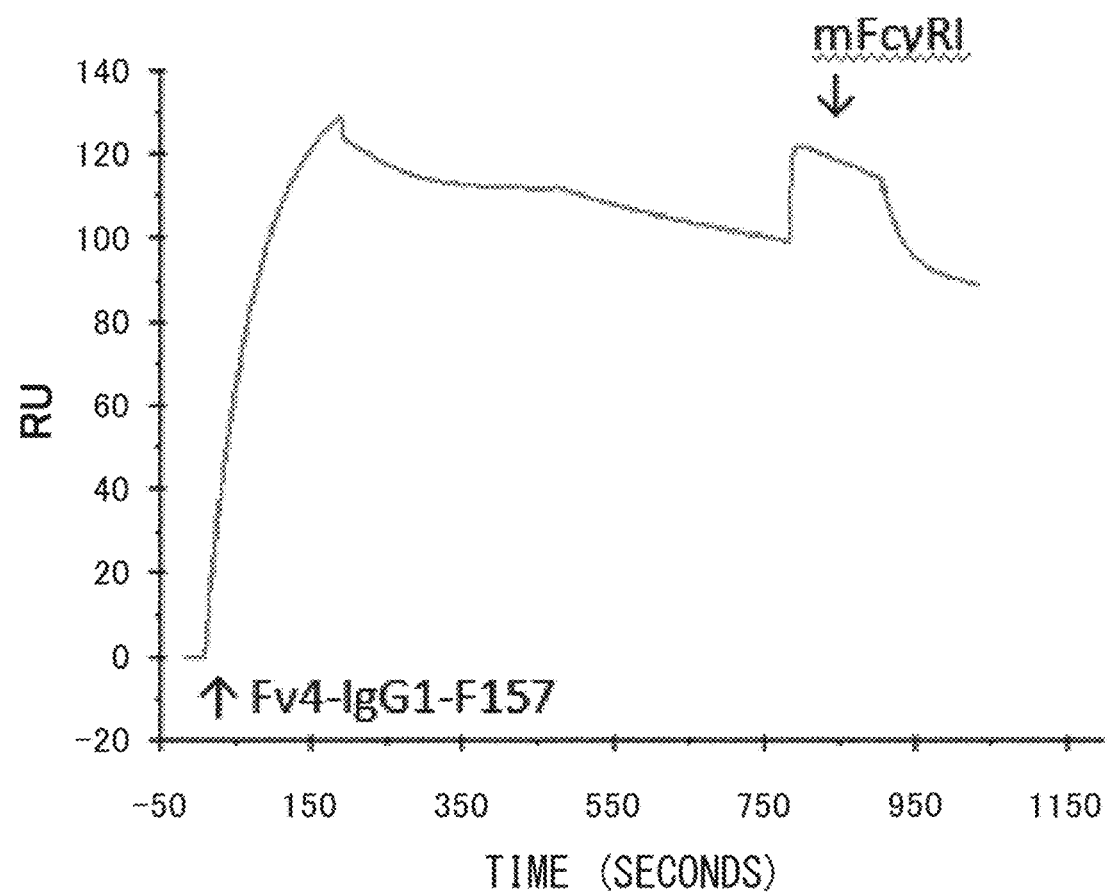
FIG. 8 is a graph demonstrating that in a human FcRn-bound state, Fv4-IgG1-F157 binds to mouse FcγRI.
Figure 9:
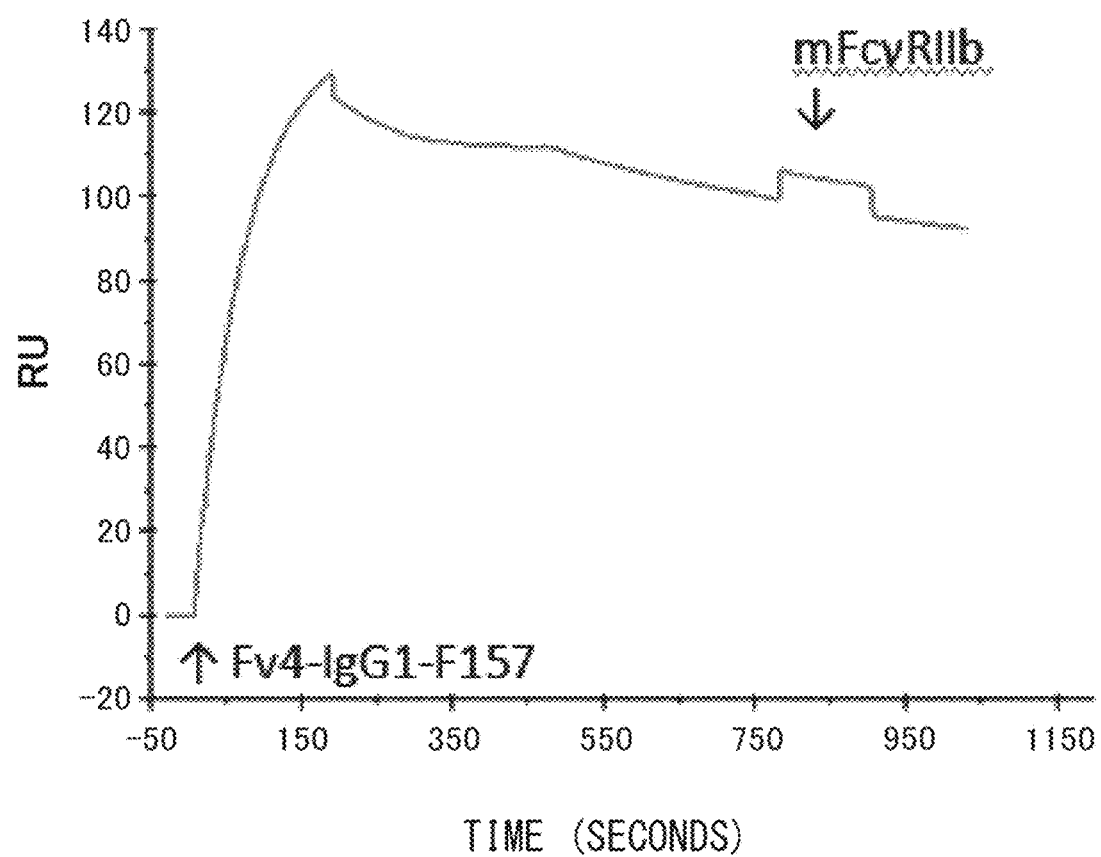
FIG. 9 is a graph demonstrating that in a human FcRn-bound state, Fv4-IgG1-F157 binds to mouse FcγRIIb.
Figure 10:
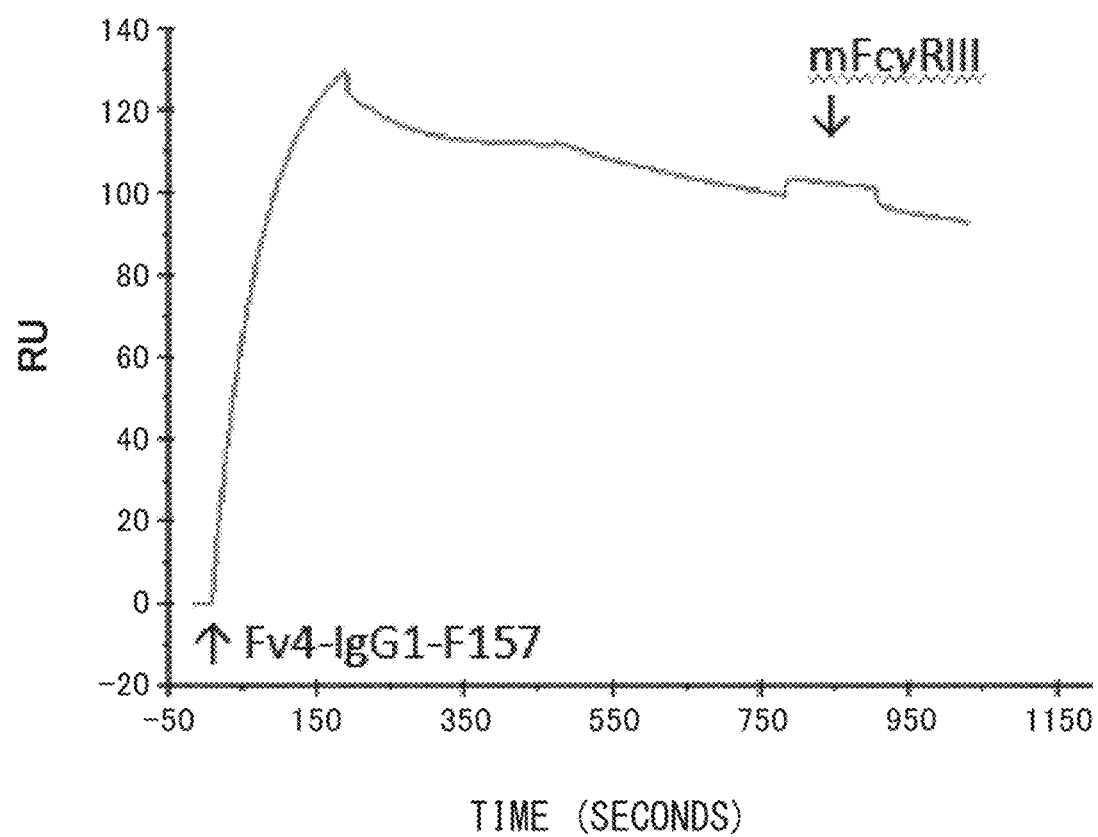
FIG. 10 is a graph demonstrating that in a human FcRn-bound state, Fv4-IgG1-F157 binds to mouse FcγRIII.
Figure 11:
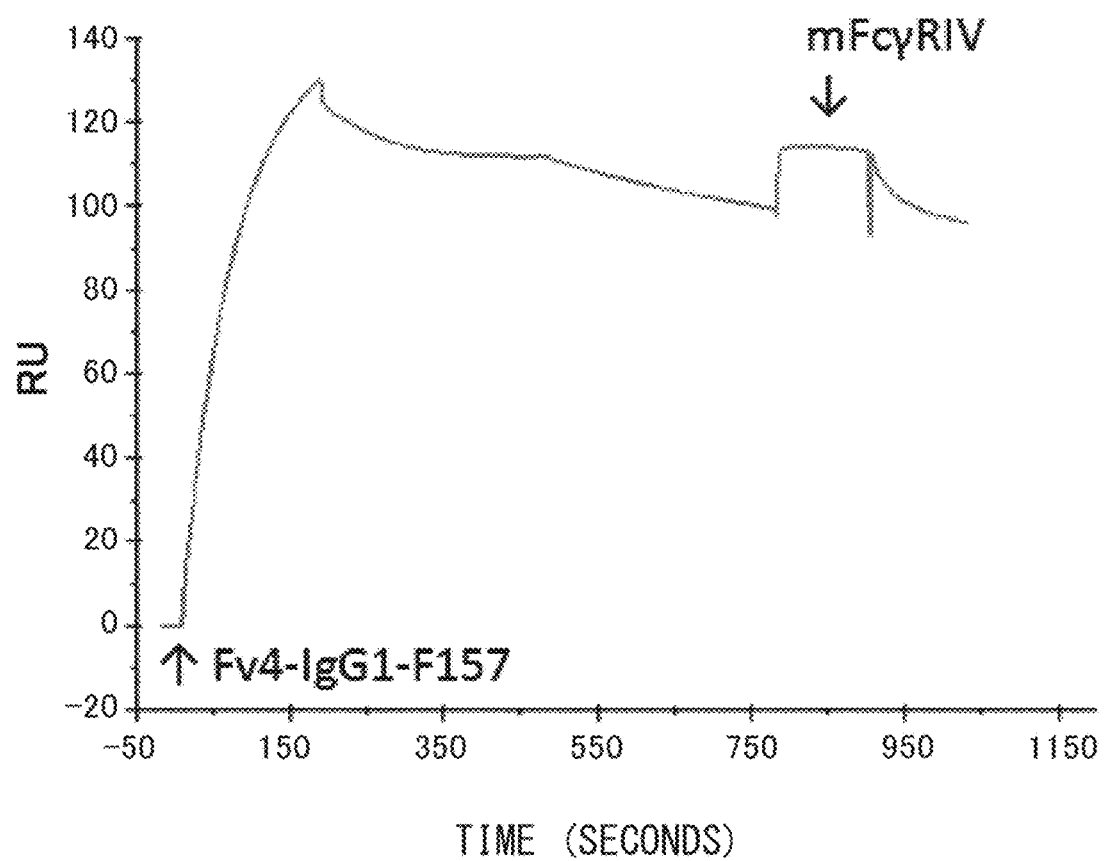
FIG. 11 is a graph demonstrating that in a human FcRn-bound state, Fv4-IgG1-F157 binds to mouse FcγRIV.

Concentrations of the pH-dependent human IL-6 receptor-binding antibodies in plasma following intravenous or subcutaneous administration of the pH-dependent human IL-6 receptor-binding human antibodies to normal mice are shown in FIG. 2. Based on the results of FIG. 2, in comparison with intravenously administered Fv4-IgG1, plasma retention was shown to worsen in intravenous administration of Fv4-IgG1-F1, for which binding to mouse FcRn under neutral conditions was enhanced. On the other hand, while subcutaneously administered Fv4-IgG1 demonstrated comparable plasma retention to that when administered intravenously, in the case of subcutaneously administered Fv4-IgG1-F1, a sudden decrease in plasma concentration that was thought to be due to the production of mouse anti-Fv4-IgG1-F1 antibody was observed 7 days after administration, and on day 14 after administration Fv4-IgG1-F1 was not detected in plasma. On the basis of this result, plasma retention and immunogenicity were confirmed to worsen as a result of enhancing the binding of antigen-binding molecules to FcRn under neutral conditions.

Example 2

Production of Human IL-6 Receptor-binding Mouse Antibody having Binding Activity to Mouse FcRn under Conditions of the Neutral pH Region Mouse antibody having binding activity to mouse FcRn under conditions of the neutral pH region was produced according to the method shown below.

(2-1) Production of Human IL-6 Receptor-binding Mouse Antibody

The amino acid sequence of a mouse antibody having the ability to bind to human IL-6R, Mouse PM-1 (Sato, K., et al., Cancer Res. (1993) 53 (4), 851-856) was used for the variable region of mouse antibody. In the following descriptions, the heavy chain variable region of Mouse PM-1 is referred to as mPM1H (SEQ ID NO: 42), while the light chain variable region is referred to as mPM1L (SEQ ID NO: 43).

In addition, naturally-occurring mouse IgG1 (SEQ ID NO: 44, hereinafter referred to as mIgG1) was used for the heavy chain constant region, while naturally-occurring mouse kappa (SEQ ID NO: 45, hereinafter referred to as mk1) was used for the light chain constant region.

An expression vector having the base sequences of heavy chain mPM1H-mIgG1 (SEQ ID NO: 46) and light chain mPM1L-mk1 (SEQ ID NO: 47) was produced according to the method of Reference Example 1. In addition, mPM1-mIgG1 which is a human IL-6R-binding mouse antibody composed of mPM1H-mIgG1 and mPM1L-mk1 was produced according to the method of Reference Example 2.

(2-2) Production of mPM1 Antibody having the Ability to Bind to Mouse FcRn under Conditions of the Neutral pH Region The produced mPM1-mIgG1 is a mouse antibody that contains a naturally-occurring mouse Fc region, and does not have binding activity to mouse FcRn under conditions of the neutral pH region. Therefore, an amino acid modification was introduced into the heavy chain constant region of mPM1-mIgG1 in order to impart binding activity to mouse FcRn under conditions of the neutral pH region.

More specifically, mPH1H-mIgG1-mF3 (SEQ ID NO: 48) was produced by adding an amino acid substitution obtained by substituting Tyr for Thr at position 252 of mPH1H-mIgG1 as indicated by EU numbering, an amino acid substitution obtained by substituting Glu for Thr at position 256 (EU numbering), an amino acid substitution obtained by substituting Lys for His at position 433 (EU numbering), and an amino acid substitution obtained by substituting Phe for Asn at position 434 (EU numbering).

Similarly, mPH1H-mIgG1-mF14 (SEQ ID NO: 49) was produced by adding an amino acid substitution obtained by substituting Tyr for Thr at position 252 (EU numbering) of mPH1H-mIgG1, an amino acid substitution obtained by substituting Glu for Thr at position 256 (EU numbering), and an amino acid substitution obtained by substituting Lys for His at position 433 (EU numbering).

Moreover, mPM1H-mIgG1-mF38 (SEQ ID NO: 50) was produced by adding an amino acid substitution obtained by substituting Tyr for Thr at position 252 (EU numbering) of mPH1H-mIgG1, an amino acid substitution obtained by substituting Glu for Thr at position 256 (EU numbering), and an amino acid substitution obtained by substituting Trp for Asn at position 434 (EU numbering).

As a mouse IgG1 antibody having the ability to bind to mouse FcRn under conditions of the neutral pH region, mPM1-mIgG1-mF3 which is composed of mPM1H-mIgG1-mF3 and mPM1L-mk1 was produced using the method of Reference Example 2.

(2-3) Confirmation of Binding Activity to Mouse FcRn with Biacore

Antibodies were produced that contained mPM1-mIgG1 or mPM1-mIgG1-mF3 for the heavy chain and L(WT)-CK (SEQ ID NO: 41) for the light chain, and the binding activity of these antibodies to mouse FcRn at pH 7.0 (dissociation constant KD) was measured. The results are shown in Table 5 below.

TABLE 5

| MUTANT NAME | mFcRn KD (M) | AMINO ACID SUBSTITUTION |
| --- | --- | --- |
| mIgG1 | NOT DETECTED | |
| mIgG1-mF3 | 1.6E-09 | T252Y/T256E/H433K/N434F |

Example 3

Binding Experiment on the Binding Of Antigen-binding Molecules having Fc Region to FcRn and FcγR In Example 1, plasma retention and immunogenicity were confirmed to worsen as a result of enhancing the binding of antigen-binding molecules to FcRn under neutral conditions. Since naturally-occurring IgG1 does not have binding activity to human FcRn in the neutral region, plasma retention and immunogenicity were thought to worsen as a result of imparting the ability to bind to FcRn under neutral conditions.

(3-1) FcRn-binding Domain and FcγR-binding Domain

A binding domain to FcRn and a binding domain to FcγR are present in the antibody Fc region. The FcRn-binding domain is present at two locations in the Fc region, and two molecules of FcRn have been previously reported to be able to simultaneously bind to the Fc region of a single antibody molecule (Nature (1994) 372 (6504), 379-383). On the other hand, although an FcγR-binding domain is also present at two locations in the Fc region, two molecules of FcγR are thought to not be able to bind simultaneously. This is because the second FcγR molecule is unable to bind due to a structural change in the Fc region that occurs from binding of the first FcγR molecule to the Fc region (J. Biol. Chem. (2001) 276 (19), 16469-16477).

As previously described, active FcγR is expressed on the cell membranes of numerous immune cells such as dendritic cells, NK cells, macrophages, neutrophils and adipocytes. Moreover, in humans FcRn has been reported to be expressed in immune cells such as antigen-presenting cells, for example, dendritic cells, macrophages and monocytes (J. Immunol. (2001) 166 (5), 3266-3276). Since normal naturally-occurring IgG1 is unable to bind to FcRn in the neutral pH region and is only able to bind to FcγR, naturally-occurring IgG1 binds to antigen-presenting cells by forming a binary complex of FcγR/IgG1. Phosphorylation sites are present in the intracellular domains of FcγR and FcRn. Typically, phosphorylation of intracellular domains of receptors expressed on cell surfaces occurs by receptor conjugation, and receptors are internalized as a result of that phosphorylation. Even if naturally-occurring IgG1 forms a binary complex of FcγR/IgG1 on antigen-presenting cells, conjugation of the intracellular domain of FcγR does not occur. However, when hypothetically an IgG molecule having binding activity to FcRn under conditions of the neutral pH region forms a complex containing four components: FcγR/two molecules of FcRn/IgG, internalization of a heterocomplex containing four components consisting of FcγR/two molecules of FcRn/IgG may be induced as a result since conjugation of three intracellular domains of FcγR and FcRn occurs. The formation of a heterocomplex containing four components consisting of FcγR/two molecules of FcRn/IgG is thought to occur on antigen-presenting cells expressing both FcγR and FcRn, and as a result thereof, plasma retention of antibody molecules incorporated into antigen-presenting cells was thought to worsen, and the possibility of immunogenicity worsening was also considered.

However, there have been no reports verifying the manner in which antigen-binding molecules containing an FcRn-binding domain, such as an Fc region having binding activity to FcRn under conditions of the neutral pH region, bind to immune cells such as antigen-presenting cells expressing FcγR and FcRn together.

Whether or not a quaternary complex of FcγR/two molecules of FcRn/IgG can be formed can be determined by whether or not an antigen-binding molecule containing an Fc region having binding activity to FcRn under conditions of the neutral pH region is able to simultaneously bind to FcγR and FcRn. Therefore, an experiment of simultaneous binding to FcRn and FcγR by an Fc region contained in an antigen-binding molecule was conducted according to the method indicated below.

(3-2) Evaluation of Simultaneous Binding to FcRn and FcγR using Biacore

An evaluation was made as to whether or not human or mouse FcRn and human or mouse FcγRs simultaneously bind to an antigen-binding molecule using the BIACORE™ T100 or T200 surface plasmon resonance system (GE Healthcare). The antigen-binding molecule being tested was captured by human or mouse FcRn immobilized on the CM4 Sensor Chip (GE Healthcare) by amine coupling. Next, diluted human or mouse FcγRs and a running buffer used as a blank were injected to allow the human or mouse FcγRs to interact with the antigen-binding molecule bound to FcRn on the sensor chip. A buffer consisting of 50 mmol/L sodium phosphate, 150 mmol/L NaCl and 0.05% (w/v) polysorbate 20 (Tween 20®) (pH 7.4) was used for the running buffer, and this buffer was also used to dilute the FcγRs. 10 mmol/L Tris-HCl (pH 9.5) was used to regenerate the sensor chip. All binding measurements were carried out at 25° C.

(3-3) Simultaneous Binding Experiment on Human IgG, Human FcRn, Human FcγR or Mouse FcγR An evaluation was made as to whether or not Fv4-IgG1-F157 produced in Example 1, which is a human antibody that has the ability to bind to human FcRn under conditions of the neutral pH region, binds to various types of human FcγR or various types of mouse FcγR while simultaneously binding to human FcRn.

The result showed that Fv4-IgG1-F157 was able to bind to human FcγRIa, FcγRIIa(R), FcγRIIa(H), FcγRIIb and FcγRIIIa(F) simultaneously with binding to human FcRn (FIGS. 3, 4, 5, 6 and 7). In addition, Fv4-IgG1-F157 was shown to be able to bind to mouse FcγRI, FcγRIIb, FcγRIII and FcγRIV simultaneously with binding to human FcRn (FIGS. 8, 9, 10 and 11).

On the basis of the above, human antibodies having binding activity to human FcRn under conditions of the neutral pH region were shown to be able to bind to various types of human FcγR and various types of mouse FcγR such as human FcγRIa, FcγRIIa(R), FcγRIIa(H), FcγRIIb and FcγRIIIa(F) as well as mouse FcγRI, FcγRIIb, FcγRIII and FcγRIV simultaneously with binding to human FcRn.

(3-4) Simultaneous Binding Experiment on Human IgG, Mouse FcRn and Mouse FcγR

An evaluation was made as to whether or not Fv4-IgG1-F20 produced in Example 1, which is a human antibody having binding activity to mouse FcRn under conditions of the neutral pH region, binds to various types of mouse FcγR simultaneously with binding to mouse FcRn.

Figure 12:
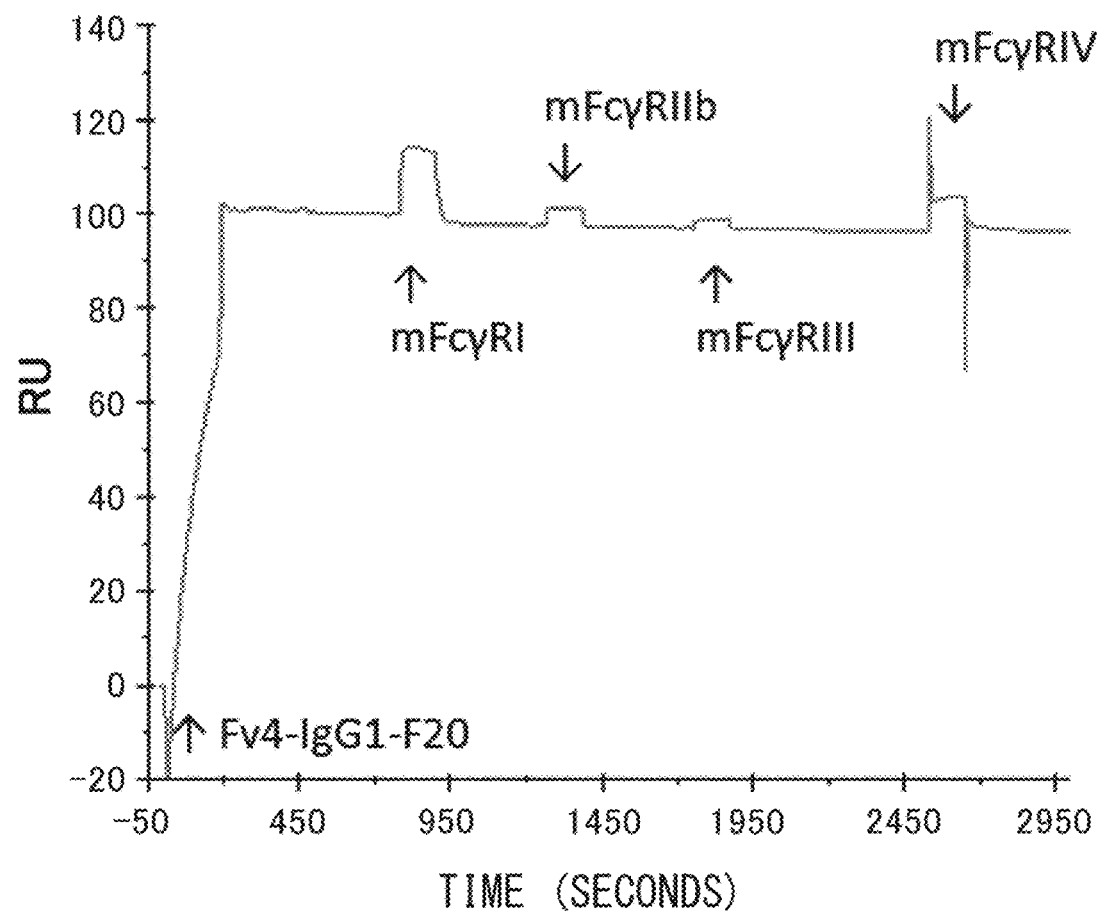
FIG. 12 is a graph demonstrating that in a mouse FcRn-bound state, Fv4-IgG1-F20 binds to mouse FcγRI, mouse FcγRIIb, mouse FcγRIII, and mouse FcγRIV.

The result showed that Fv4-IgG1-F20 was able to bind to mouse FcγRI, FcγRIIb, FcγRIII and FcγRIV simultaneously with binding to mouse FcRn (FIG. 12).

(3-5) Simultaneous Binding Experiment on Mouse IgG, Mouse FcRn and Mouse FcγR

An evaluation was made as to whether or not mPM1-mIgG1-mF3 produced in Example 2, which is a mouse antibody having binding activity to mouse FcRn under conditions of the neutral pH region, binds to various types of mouse FcγR simultaneously with binding to mouse FcRn.

Figure 13:
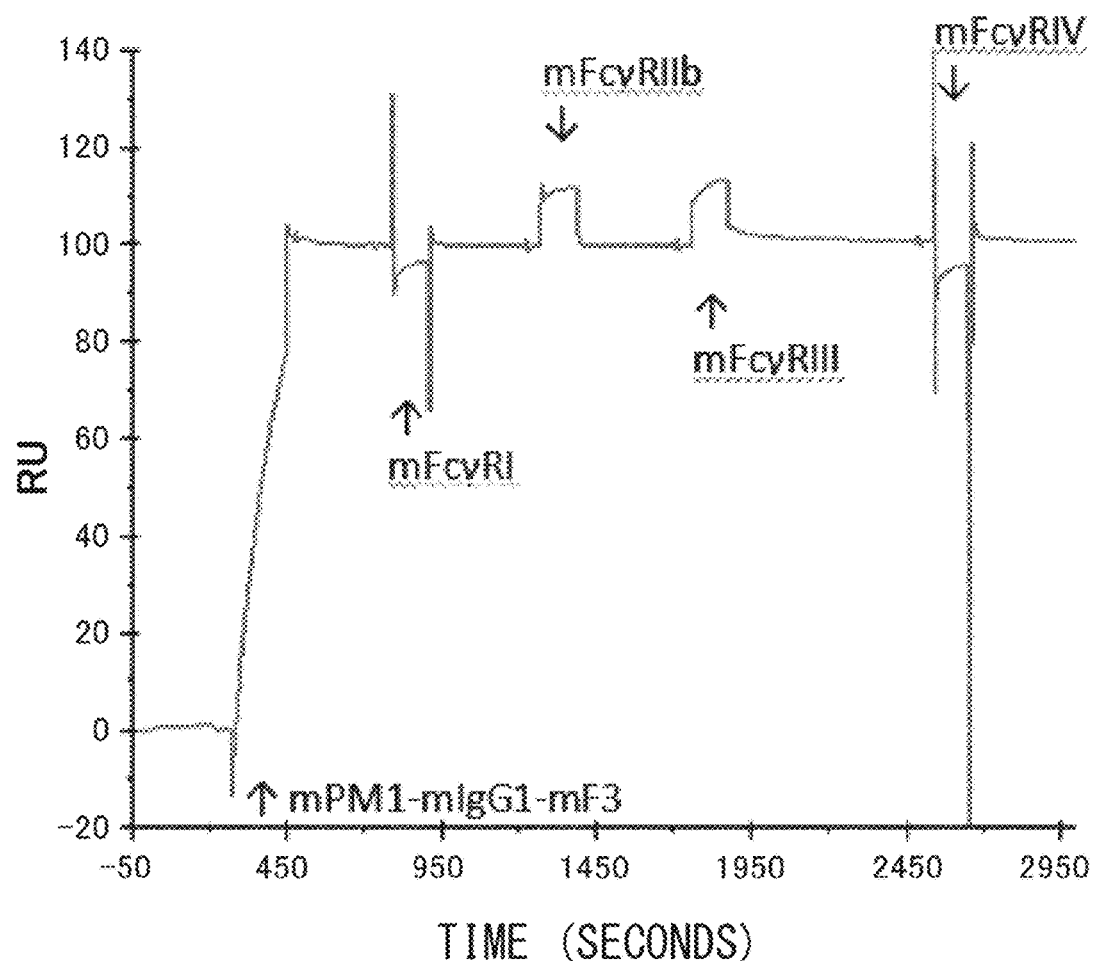
FIG. 13 is a graph demonstrating that in a mouse FcRn-bound state, mPM1-mIgG1-mF3 binds to mouse FcγRIIb and mouse FcγRIII.

The result showed that mPM1-mIgG1-mF3 was able to bind to mouse FcγRIIb and FcγRIII simultaneously with binding to mouse FcRn (FIG. 13). When judging from the report that a mouse IgG1 antibody does not have the ability to bind to mouse FcγRI and FcγRIV (J. Immunol. (2011) 187 (4), 1754-1763), the result that binding to mouse FcγRI and FcγRIV was not confirmed is considered to be a reasonable result.

On the basis of these findings, human antibodies and mouse antibodies having binding activity to mouse FcRn under conditions of the neutral pH region were shown to be able to also bind to various types of mouse FcγR simultaneously with binding to mouse FcRn.

The above finding indicates the possibility of formation of a heterocomplex comprising one molecule of Fc, two molecules of FcRn and one molecule of FcγR without any mutual interference, although an FcRn binding region and FcγR binding region are present in the Fc region of human and mouse IgG.

This property of the antibody Fc region of being able to form such a heterocomplex has not been previously reported, and was determined here for the first time. As previously described, various types of active FcγR and FcRn are expressed on antigen-presenting cells, and the formation of this type of quaternary complex on antigen-presenting cells by antigen-binding molecules is suggested to improve affinity for antigen-presenting molecules while further promoting incorporation into antigen-presenting cells by enhancing internalization signals through conjugation of the intracellular domain. In general, antigen-binding molecules incorporated into antigen presenting cells are broken down in lysosomes within the antigen-presenting cells and then presented to T cells.

Namely, antigen-binding molecules having binding activity to FcRn in the neutral pH region form a heterocomplex containing four components including one molecule of active FcγR and two molecules of FcRn, and this is thought to result in an increase in incorporation into antigen-presenting cells, thereby worsening plasma retention and further worsening immunogenicity.

Consequently, in the case of introducing a mutation into an antigen-binding molecule having binding activity to FcRn in the neutral pH region, producing an antigen-binding molecule in which the ability to form such a quaternary complex has decreased, and administering that antigen-binding molecule into the body, plasma retention of that antigen-binding molecule improves, and induction of an immune response by the body can be inhibited (namely, immunogenicity can be lowered). Examples of preferable embodiments of antigen-binding molecules incorporated into cells without forming such a complex include the three types shown below.

(Embodiment 1) Antigen-binding Molecules that have Binding Activity to FcRn under Conditions of the Neutral pH Region and whose Binding Activity to Active FcγR is Lower than Binding Activity of the Native FcγR Binding Domain.

The antigen-binding molecules of Embodiment 1 form a complex containing three components by binding to two molecules of FcRn, but do not form a complex containing active FcγR.

(Embodiment 2) Antigen-binding Molecules that have Binding Activity to FcRn under Conditions of the Neutral pH Region and have Selective Binding Activity to Inhibitory FcγR Antigen-binding molecules of Embodiment 2 are able to form a complex containing four components by binding to two molecules of FcRn and one molecule of inhibitory FcγR. However, since one antigen-binding molecule is only able to bind to one molecule of FcγR, a single antigen-binding molecule is unable to bind to another active FcγR while bound to inhibitory FcγR. Moreover, antigen-binding molecules that are incorporated into cells while still bound to inhibitory FcγR are reported to be recycled onto the cell membrane to avoid being broken down within cells (Immunity (2005) 23, 503-514). Namely, antigen-binding molecules having selective binding activity to inhibitory FcγR are thought to be unable to form a complex containing active FcγR that causes an immune response.

(Embodiment 3) Antigen-binding Molecules in which only One of Two Polypeptides Composing the FcRn-binding Domain has Binding Activity to FcRn under Conditions of the Neutral pH Region while the other does not have Binding Activity to FcRn under Conditions of the Neutral pH Region Although antigen-binding molecules of Embodiment 3 are able to form a ternary complex by binding to one molecule of FcRn and one molecule of FcγR, they do not form a heterocomplex containing four components including two molecules of FcRn and one molecule of FcγR.

The antigen-binding molecules of Embodiments 1 to 3 are expected to be able to improve plasma retention and lower immunogenicity in comparison with antigen-binding molecules that are capable of forming complexes containing four components including two molecules of FcRn and one molecule of FcγR.

Example 4

Evaluation of Plasma Retention of Human Antibodies that have Binding Activity to Human FcRn in the Neutral pH Region and whose Binding Activity to Human and Mouse FcγR is Lower than Binding Activity of a Native FcγR Binding Domain (4-1) Production of Antibody whose Binding Activity to Human FcγR is Lower than Binding Activity of a Native FcγR-binding Domain and which Binds to Human IL-6 Receptor in a pH-dependent Manner Antigen-binding molecules of Embodiment 1 among the three embodiments shown in Example 3, namely antigen-binding molecules having binding activity to FcRn under conditions of the neutral pH region and whose binding activity to active FcγR is lower than binding activity of a native FcγR binding domain, were produced in the manner described below.

Fv4-IgG1-F21 and Fv4-IgG1-F157 produced in Example 1 are antibodies that have binding activity to human FcRn under conditions of the neutral pH region and bind to human IL-6 receptor in a pH-dependent manner. Variants were produced in which binding to mouse FcγR was decreased by an amino acid substitution in which Lys was substituted for Ser at position 239 (EU numbering) in the amino acid sequences thereof. More specifically, VH3-IgG1-F140 (SEQ ID NO: 51) was produced in which Lys was substituted for Ser at position 239 (EU numbering) of the amino acid sequence of VH3-IgG1-F21. In addition, VH3-IgG1-F424 (SEQ ID NO: 52) was produced in which Lys was substituted for Ser at position 239 (EU numbering) of the amino acid sequence of VH3-IgG1-F157.

Fv4-IgG1-F140 and Fv4-IgG1-F424 containing these heavy chains and the light chain of VL3-CK were produced using the method of Reference Example 2.

(4-2) Confirmation of Binding Activity to Human FcRn and Mouse FcγR

Binding activity (dissociation constant KD) to human FcRn at pH 7.0 and binding activity to mouse FcγR at pH 7.4 of antibodies containing the produced VH3-IgG1-F21, VH3-IgG1-F140, VH3-IgG1-F157 or VH3-IgG1-F424 for the heavy chain and L(WT)-CK for the light chain were measured using the method shown below.

(4-3) Kinetic Analysis of Binding to Human FcRn

A kinetic analysis of binding between human FcRn and the aforementioned antibodies was carried out using the BIACORE™ T100 or T200 surface plasmon resonance system (GE Healthcare). The antibodies being tested were captured on the CM4 Sensor Chip (GE Healthcare) on which a suitable amount of Protein L (ACTIGEN® protein (Alltech)) was suitably immobilized by amine coupling. Next, diluted human FcRn and a running buffer used as a blank were injected to allow the human FcRn to interact with the antibody captured on the sensor chip. A buffer consisting of 50 mmol/L sodium phosphate, 150 mmol/L NaCl and 0.05% (w/v) polysorbate 20 (Tween 20®) (pH 7.0 or pH 7.4) was used for the running buffer, and each buffer was also used to dilute the human FcRn. 10 mmol/L glycine-HCl (pH 1.5) was used to regenerate the sensor chip. All measurements of binding were carried out at 25° C. The KD(M) of each antibody to human FcRn was calculated based on kinetics parameters, i.e., the association rate constant ka (1/Ms) and the dissociation rate constant kd (1/s) calculated from a sensorgram obtained by the measurement. The BIACORE™ T100 or T200 Evaluation Software (GE Healthcare) was used to calculate each parameter.

The results are shown in Table 6 below.

TABLE 6

| MUTANT NAME | KD (M) | AMINO ACID SUBSTITUTION |
|---|---|---|
| IgG1-F21 | $3.0E^{-08}$ | M252Y/V308P/N434Y |
| IgG1-F140 | $3.6E^{-08}$ | S239K/M252Y/V308P/N434Y |
| IgG1-F157 | $1.5E^{-07}$ | P257A/V308P/M428L/N434Y |
| IgG1-F424 | $9.4E^{-08}$ | S239K/P257A/V308P/M428L/N434Y |

Binding activity to mouse FcγR at pH 7.4 was measured using the method shown below.

(4-4) Evaluation of Binding Activity to Mouse FcγR

Binding activity between the antibodies and mouse FcγRI, FcγRII, FcγRIII and FcγRIV (R&D Systems, Sino Biological) (hereinafter referred to as mouse FcγRs) was evaluated using the BIACORE™ T100 or T200 surface plasmon resonance system (GE Healthcare). The antibodies being tested were captured by Protein L (ACTIGEN® protein (Alltech)) that was immobilized in suitable amounts on the CM4 Sensor Chip (GE Healthcare) by amine coupling. Next, the diluted mouse FcγRs and a running buffer used as a blank were injected to allow interaction with the antibody captured on the sensor chip. A buffer consisting of 20 mmol/L N-(2-acetamido)-2-aminoethanesulfonic acid (ACES), 150 mmol/L NaCl and 0.05% (w/v) polysorbate 20 (Tween 20®) (pH 7.4) was used for the running buffer, and this buffer was also used to dilute the mouse FcγRs. 10 mmol/L glycine-HCl (pH 1.5) was used to regenerate the sensor chip. All measurements were carried out at 25° C.

Binding activity to mouse FcγRs can be represented by the relative binding activity to mouse FcγRs. Antibody was captured by Protein L, and the amount of change in a sensorgram before and after the antibody was captured was defined as X1. Next, mouse FcγRs were allowed to interact with the antibody, and the value obtained by subtracting binding activity of mouse FcγRs represented as the amount of change in a sensorgram before and after allowing the running buffer to interact with antibody captured by Protein L (ΔA2) from the value obtained by multiplying by 1500 the value obtained by dividing the binding activity of mouse FcγRs represented as the amount of change in a sensorgram before and after that interaction (ΔA1) by the captured amount (X) of each antibody, was divided by the captured amount of each antibody (X) followed by multiplying by 1500 to obtain the binding activity of the mouse FcγRs (Y) (Equation 1).

Binding activity of mouse FcγRs $(Y) = (\Delta A1 - \Delta A2)/X \times 1500$ [Equation 1]

The results are shown in Table 7 below.

TABLE 7

| | BINDING AMOUNT (RU) | | | |
|---|---|---|---|---|
| | mFcgRI | mFcgRIIb | mFcgRIII | mFcgRIV |
| IgG1 | 304.2 | 114.1 | 390.1 | 240.3 |
| IgG1-F21 | 315.3 | 111.8 | 371.2 | 241.6 |
| IgG1-F140 | 7.4 | −1.8 | 46.6 | 107.9 |
| IgG1-F157 | 315.1 | 129.0 | 275.7 | 242.9 |
| IgG1-F424 | 4.1 | −2.5 | 4.3 | 137.7 |

According to the results of Tables 2 and 3, Fv4-IgG1-F140 and Fv4-IgG1-F424 demonstrated a decrease in binding to mouse FcγR without affecting binding activity to human FcRn in comparison with Fv4-IgG1-F21 and Fv4-IgG1-F157.

(4-5) In Vivo PK Study using Human FcRn Transgenic Mice

A PK study in administration of the produced Fv4-IgG1-F140, Fv4-IgG1-F424, Fv4-IgG1-F21 and Fv4-IgG1-F157 antibodies to human FcRn transgenic mice was carried out according to the method shown below.

Anti-human IL-6 receptor antibody was administered at 1 mg/kg in a single administration into a caudal vein of human FcRn transgenic mice (B6.mFcRn−/−.hFcRn Tg line 32+/+ mouse, Jackson Laboratories, Methods Mol. Biol. (2010) 602, 93-104). Blood was collected at 15 minutes, 7 hours and 1, 2, 3, 4, 7, 14, 21 and 28 days after administration of the anti-human IL-6 receptor antibody. Plasma was obtained by immediately centrifuging the collected blood for 15 minutes at 4° C. and 15,000 rpm. The separated plasma was stored in a freezer set to −20° C. or lower until the time of measurement.

(6-6) Measurement of Plasma Anti-Human IL-6 Receptor Antibody Concentration by ELISA Concentration of anti-human IL-6 receptor antibody in mouse plasma was measured by ELISA. First, Anti-Human IgG (γ-chain specific) F(ab')2 Fragment of Antibody (SIGMA) was dispensed into a Nunc-Immuno Plate, MaxiSoup (Nalge Nunc International) followed by allowing this to stand undisturbed overnight at 4° C. to produce an anti-human IgG solid phase plate. Calibration curve samples containing 0.8, 0.4, 0.2, 0.1, 0.05, 0.025 and 0.0125 μg/mL of anti-human IL-6 receptor antibody in plasma antibody concentration, and mouse plasma measurement samples diluted by 100-fold or more, were prepared. Mixtures obtained by adding 200 μl of 20 ng/mL soluble human IL-6 receptor to 100 μl of the calibration curve samples and plasma measurement samples were then allowed to stand undisturbed for 1 hour at room temperature. Subsequently, the anti-human IgG solid phase plate in which the mixtures had been dispensed into each of the wells thereof was further allowed to stand undisturbed for 1 hour at room temperature. Subsequently, the chromogenic reaction of a reaction liquid obtained upon reaction with a biotinylated anti-human IL-6 R antibody (R&D) for 1 hour at room temperature and further reaction with Streptavidin-PolyHRP80 (Stereospecific Detection Technologies) for 1 hour at room temperature was carried out using TMB One Component HRP Microwell Substrate (BioFX Laboratories) as substrate. After the reaction was stopped by adding 1N-Sulfuric acid (Showa Chemical), absorbance at 450 nm of the reaction liquids of each well was measured with a microplate reader. Antibody concentrations in the mouse plasma were calculated from absorbance values of the calibration curve using the SOFTmax PRO analysis software (Molecular Devices).

Figure 14:
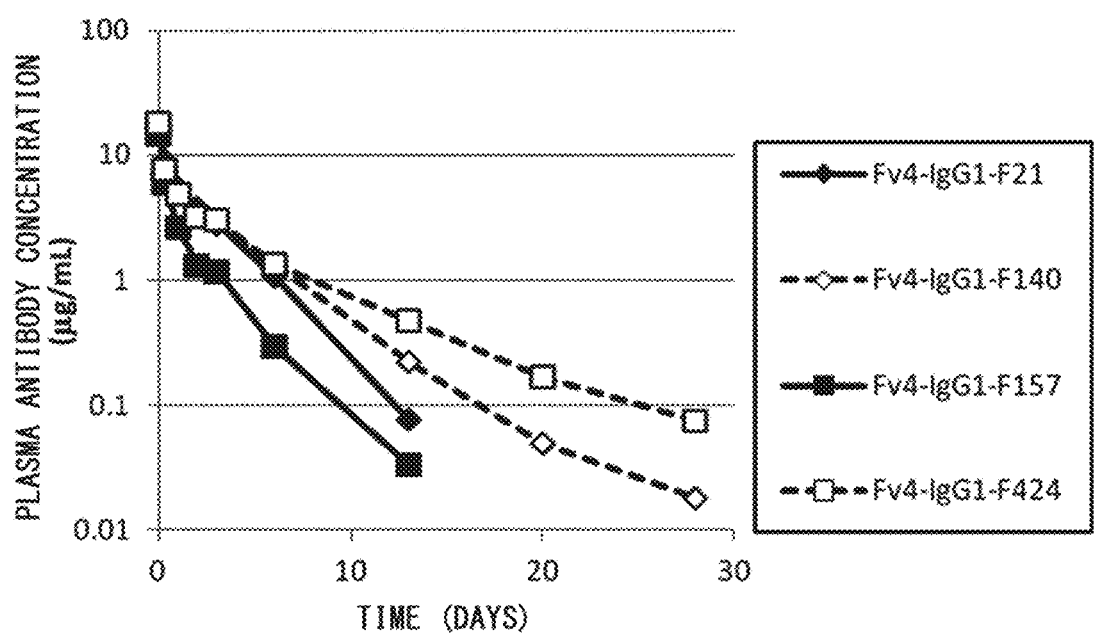
FIG. 14 is a graph showing a plasma concentration time course of Fv4-IgG1-F21, Fv4-IgG1-F140, Fv4-IgG1-F157, and Fv4-IgG1-F424 in human FcRn transgenic mice.

Concentrations of the pH-dependent human IL-6 receptor-binding antibodies in plasma following intravenous administration of the pH-dependent human IL-6 receptor-binding antibodies to human FcRn transgenic mice are shown in FIG. 14.

Based on the results of FIG. 14, Fv4-IgG1-F140 whose binding to mouse FcγR was lower in comparison with Fv4-IgG1-F21 was observed to demonstrate improvement of plasma retention in comparison with Fv4-IgG1-F21. Similarly, Fv4-IgG1-F424 whose binding to mouse FcγR was lower in comparison with Fv4-IgG1-F157 was observed to demonstrate prolongation of plasma retention in comparison with Fv4-IgG1-F157.

Based on this, an antibody that has binding activity to human FcRn under conditions of the neutral pH region, and has an FcγR-binding domain whose binding activity to FcγR is lower than that of a normal FcγR-binding domain, was shown to have higher plasma retention than an antibody having the normal FcγR-binding domain.

Although the present invention is not bound to a specific theory, the reason for having observed such improvement of plasma retention of antigen-binding molecules is thought to be that since the antigen-binding molecules have binding activity to human FcRn under conditions of the neutral pH region, and have an FcγR domain whose binding activity to FcγR is lower than that of the naturally-occurring FcγR-binding domain, the formation of the quaternary complex described in Example 3 was inhibited. In other words, Fv4-IgG1-F21 and Fv4-IgG1-F157, which form a quaternary complex on the cell membrane of antigen-presenting cells, are thought to be more easily incorporated into antigen-presenting cells. On the other hand, in Fv4-IgG1-F140 and Fv4-IgG1-F424, which are classified as Embodiment 1 indicated in Example 3 and do not form a quaternary complex on the cell membrane of antigen-presenting cells, incorporation into antigen-presenting cells is thought to be inhibited. Here, incorporation of antigen-binding molecules into cells such as vascular endothelial cells that do not express active FcγR is thought to mainly include non-specific incorporation or incorporation mediated by FcRn on the cell membrane, and is not considered to be affected by a decrease in binding activity to FcγR. In other words, the improvement of plasma retention that was observed as previously described is thought to be the result of selective inhibition of incorporation into immune cells, including antigen-presenting cells.

Example 5

Evaluation of Plasma Retention of Human Antibodies that have Binding Activity to Human FcRn in the Neutral pH Region, but do not have Binding Activity to Mouse FcγR (5-1) Production of Human Antibodies that do not have Binding Activity to Human and Mouse FcγR, and Bind to Human IL-6 Receptor in a pH-dependent Manner Antibodies were produced in the manner shown below in order to produce human antibodies that do not have binding activity to human and mouse FcγR and bind to human IL-6 receptor in a pH-dependent manner. VH3-IgG1-F760 (SEQ ID NO: 53) that does not have binding activity to human and mouse FcγR was produced by an amino acid substitution obtained by substituting Arg for Leu at position 235 (EU numbering) and an amino acid substitution obtained by substituting Lys for Ser at position 239 of the amino acid sequence of VH3-IgG1.

Similarly, VH3-IgG1-F821 (SEQ ID NO: 57), VH3-IgG1-F939 (SEQ ID NO: 58) and VH3-IgG1-F1009 (SEQ ID NO: 59) that do not have binding activity to human and mouse FcγR were produced by an amino acid substitution obtained by substituting Arg for Leu at position 235 (EU numbering) and an amino acid substitution obtained by substituting Lys for Ser at position 239 of the respective amino acid sequences of VH3-IgG1-F11 (SEQ ID NO: 54), VH3-IgG1-F890 (SEQ ID NO: 55) and VH3-IgG1-F947 (SEQ ID NO: 56).

Fv4-IgG1, Fv4-IgG1-F11, Fv4-IgG1-F890, Fv4-IgG1-F947, Fv4-IgG1-F760, Fv4-IgG1-F821, Fv4-IgG1-F939 and Fv4-IgG1-F1009 containing these antibodies for the heavy chains and VL3-CK for the light chain were produced using the method of Reference Example 2.

(5-2) Confirmation of Binding Activity to Human FcRn and Mouse FcγR

Binding activity (dissociation constant KD) to human FcRn at pH 7.0 of antibodies containing VH3-IgG1, VH3-IgG1-F11, VH3-IgG1-F890, VH3-IgG1-F947, VH3-IgG1-F760, VH3-IgG1-F821, VH3-IgG1-F939 or VH3-IgG1-F1009 for the heavy chain and L(WT)-CK for the light chain produced using the method of Reference Example 2 was measured using the method of Example 4. The measurement results are shown in Table 8 below.

TABLE 8

| MUTANT NAME | KD (M) | AMINO ACID SUBSTITUTION |
|---|---|---|
| G1d | NOT DETECTED | |
| F760 | NOT DETECTED | L235R/S239K |
| F11 | 3.1E−07 | M252Y/N434Y |
| F821 | 3.1E−07 | L235R/S239K/M252Y/N434Y |
| F890 | 1.1E−07 | M252Y/N434Y/Y436V |
| F939 | 1.5E−07 | L235R/S239K/M252Y/N434Y/Y436V |
| F947 | 1.1E−08 | T250V/M252Y/T307Q/V308P/Q311A/N434Y/Y436V |
| F1009 | 1.2E−08 | L235R/S239K/T250V/M252Y/T307Q/V308P/Q311A/N434Y/Y436V |

Binding activity to mouse FcγR at pH 7.4 of antibodies containing VH3-IgG1, VH3-IgG1-F11, VH3-IgG1-F890, VH3-IgG1-F760, VH3-IgG1-F947, VH3-IgG1-F821, VH3-IgG1-F939 or VH3-IgG1-F1009 for the heavy chain and L(WT)-CK for the light chain was measured in the same manner as the method of Example 4. The measurement results are shown in Table 9 below.

TABLE 9

| MUTANT NAME | BINDING AMOUNT(RU) | | | |
|---|---|---|---|---|
| | mFcgR I | mFcgR IIb | mFcgR III | mFcgR IV |
| G1d | 304.2 | 114.1 | 390.1 | 240.3 |
| F760 | −1.9 | −2.2 | −15.1 | 8.1 |
| F11 | 290.8 | 80.2 | 330.3 | 241.2 |
| F821 | 0.6 | −4.5 | −20.3 | −3.8 |
| F890 | 268.3 | 69.3 | 284.2 | 230.1 |
| F939 | −2.0 | −6.3 | −24.9 | −7.3 |
| F947 | 299.0 | 117.3 | 381.8 | 241.7 |
| F1009 | 0.6 | −1.5 | −12.9 | 7.2 |

According to the results of Tables 4 and 5, Fv4-IgG1-F760, Fv4-IgG1-F821, Fv4-IgG1-F939 and Fv4-IgG1-F1009 demonstrated a decrease in binding to mouse FcγR without affecting binding activity to human FcRn in comparison with Fv4-IgG1, Fv4-IgG1-F11, Fv4-IgG1-F890 and Fv4-IgG1-F947.

(5-3) In Vivo PK Study using Human FcRn Transgenic Mice

A PK study in administration of the produced Fv4-IgG1 and Fv4-IgG1-F760 antibodies to human FcRn transgenic mice was carried out according to the method shown below.

Anti-human IL-6 receptor antibody was administered at 1 mg/kg in a single administration into a caudal vein of human FcRn transgenic mice (B6.mFcRn−/−.hFcRn Tg line 32+/+ mouse, Jackson Laboratories, Methods Mol. Biol. (2010) 602, 93-104). Blood was collected at 15 minutes, 7 hours and 1, 2, 3, 4, 7, 14, 21 and 28 days after administration of the anti-human IL-6 receptor antibody. Plasma was obtained by immediately centrifuging the collected blood for 15 minutes at 4° C. and 15,000 rpm. The separated plasma was stored in a freezer set to −20° C. or lower until the time of measurement.

Figure 15:
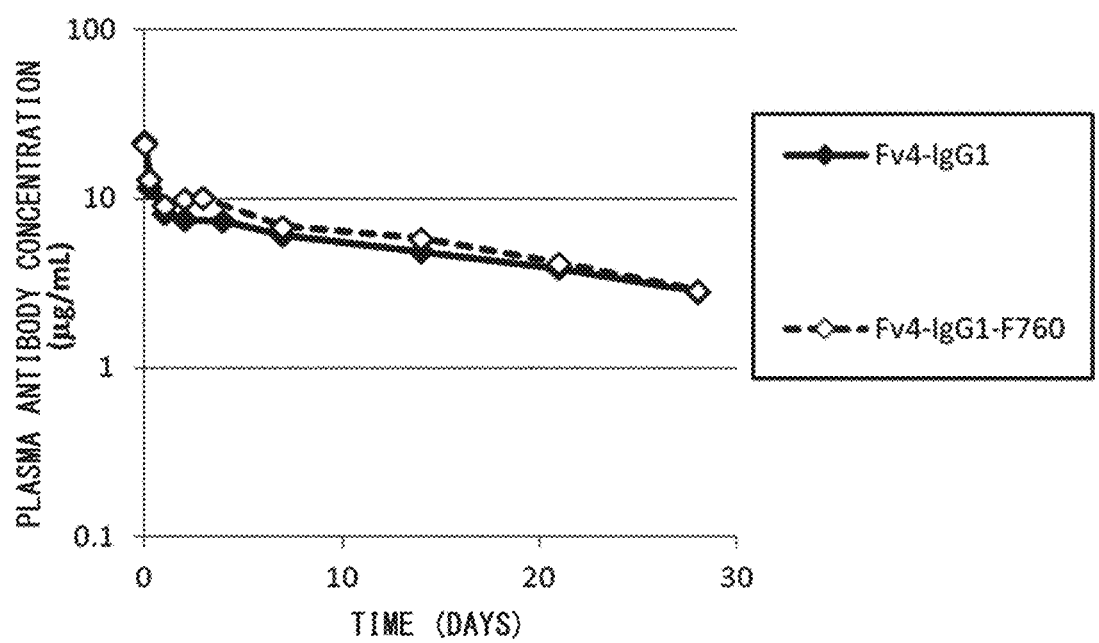
FIG. 15 is a graph showing a plasma concentration time course of Fv4-IgG1 and Fv4-IgG1-F760 in human FcRn transgenic mice.

Concentration of the anti-human IL-6 receptor antibody in the mouse plasma was measured by ELISA in the same manner as the method of Example 4. The results are shown in FIG. 15. Fv4-IgG1-F760, which lowered the binding activity of Fv4-IgG1 to mouse FcγR, demonstrated plasma retention nearly equal to that of Fv4-IgG1-F11; however, an effect of improving plasma retention by decreasing binding activity to FcγR was not observed.

(5-4) In Vivo PK Study using Human FcRn Transgenic Mice

A PK study in administration of the produced Fv4-IgG1-F11, Fv4-IgG1-F890, Fv4-IgG1-F947, Fv4-IgG1-F821, Fv4-IgG1-F939 and Fv4-IgG1-F1009 antibodies to human FcRn transgenic mice was carried out according to the method shown below.

Anti-human IL-6 receptor antibody was administered at 1 mg/kg in a single administration beneath the skin of the back of human FcRn transgenic mice (B6.mFcRn−/−.hFcRn Tg line 32+/+mouse, Jackson Laboratories, Methods Mol. Biol. (2010)602, 93-104). Blood was collected at 15 minutes, 7 hours and 1, 2, 3, 4, 7, 14, 21 and 28 days after administration of the anti-human IL-6 receptor antibody. Plasma was obtained by immediately centrifuging the collected blood for 15 minutes at 4° C. and 15,000 rpm. The separated plasma was stored in a freezer set to −20° C. or lower until the time of measurement.

Figure 16:
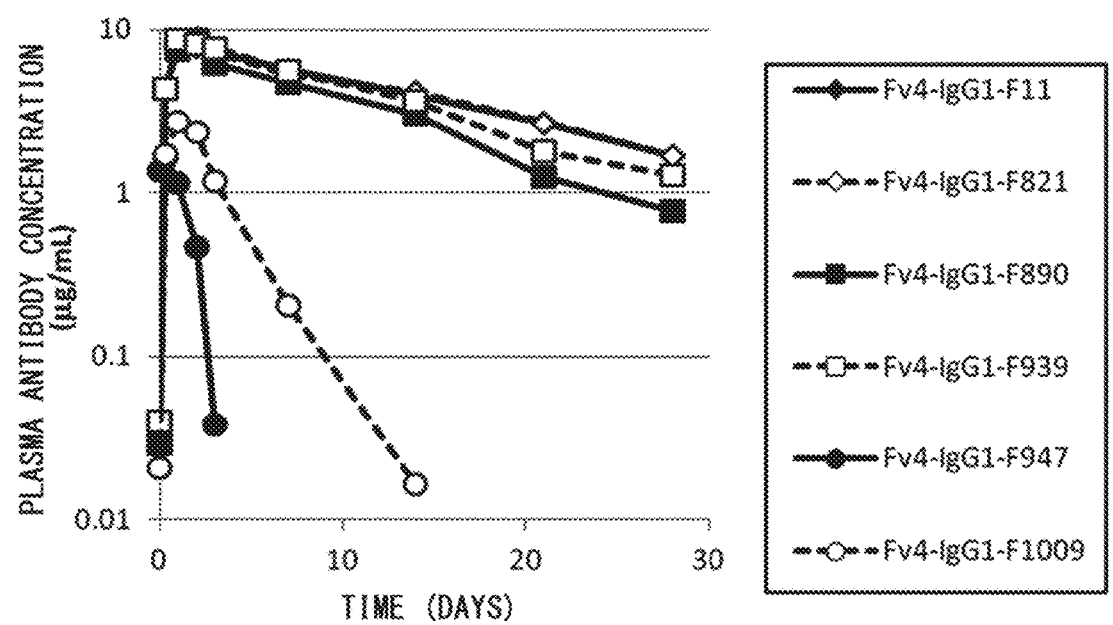
FIG. 16 is a graph showing a plasma concentration time course of Fv4-IgG1-F11, Fv4-IgG1-F890, Fv4-IgG1-F947, Fv4-IgG1-F821, Fv4-IgG1-F939, and Fv4-IgG1-F1009 in human FcRn transgenic mice.

Concentration of anti-human IL-6 receptor antibody in the mouse plasma was measured by ELISA in the same manner as the method of Example 4. The results are shown in FIG. 16. Fv4-IgG1-F821, which lowered the binding activity of Fv4-IgG1-F11 to mouse FcγR, demonstrated plasma retention nearly equal to that of Fv4-IgG1-F11. On the other hand, Fv4-IgG1-F939, which lowered the binding activity of Fv4-IgG1-F890 to mouse FcγR, was observed to demonstrate improved plasma retention in comparison with Fv4-IgG1-F890. Similarly, Fv4-IgG1-F1009, which lowered the binding activity of Fv4-IgG1-F947 to mouse FcγR, was observed to demonstrate improved plasma retention in comparison with Fv4-IgG1-F947.

On the other hand, since there were no differences observed in plasma retention for both Fv4-IgG1 and IgG1-F760, and Fv4-IgG1, which does not have FcRn binding activity in the neutral pH region, is able to form a binary complex with FcγR on immune cells but is unable to form a quaternary complex, improvement of plasma retention attributable to a decrease in binding activity to FcγR was thought to not have been observed. Namely, improvement of plasma retention can be said to only be observed as a result of decreasing the binding activity to FcγR of antigen-binding molecules having FcRn-binding activity in the neutral pH region, and inhibiting the formation of a quaternary complex. On the basis of this finding as well, the formation of a quaternary complex is thought to fulfill an important role in exacerbation of plasma retention.

(5-5) Production of Human Antibodies that do not have Binding Activity to Human and Mouse FcγR, and Bind to Human IL-6 Receptor in a pH-dependent Manner VH3-IgG1-F1326 (SEQ ID NO: 155), in which binding activity to human and mouse FcγR is decreased, was produced by an amino acid substitution obtained by substituting Ala for Leu at position 234 (EU numbering) and an amino acid substitution obtained by substituting Ala for Leu at position 235 of the amino acid sequence of VH3-IgG1-F947 (SEQ ID NO: 56).

Fv4-IgG1-F1326 containing VH3-IgG1-F1326 for the heavy chain and VL3-CK for the light chain was produced using the method of Reference Example 2.

(5-6) Confirmation of Binding Activity to Human FcRn and Mouse FcγR

Binding activity (dissociation constant KD) to human FcRn at pH 7.0 of antibody containing VH3-IgG1-F1326 for the heavy chain and L(WT)-CK for the light chain produced using the method of Reference Example 2 was measured using the method of Example 4. In addition, binding activity to mouse FcγR at pH 7.4 was measured in the same manner as the method of Example 4. The measurement results are shown in Table 10 below.

activity to mouse FcγR, affinity (KD) to human FcRn at pH 7.0 is preferably greater than 310 nM and more preferably 110 nM or less.

As a result, plasma retention was confirmed to improve by imparting the properties of Embodiment 1 to antigen-binding molecules in the same manner as Example 4. Here, the observed improvement of plasma retention is thought to have been due to selective inhibition of incorporation into immune cells, including antigen-presenting cells, and as a result thereof, it is expected to be possible to inhibit induction of an immune response.

Example 6

Evaluation of Plasma Retention of Mouse Antibodies that have Binding Activity to Mouse FcRn in the Neutral pH Region, but do not have Binding Activity to Mouse FcγR (6-1) Production of Mouse Antibodies that Bind to Human IL-6 Receptor but do not have Binding Activity to Mouse FcγR In Examples 4 and 5, antigen-binding molecules having binding activity to human FcRn under conditions of the neutral pH region, and containing an FcγR-binding domain whose binding activity to mouse FcγR is lower than the binding activity of a native FcγR binding domain, were indicated to demonstrate improved plasma retention in

TABLE 10

| | | MUTANT NAME | |
| --- | --- | --- | --- |
| | G1d | F947 | F1326 |
| AMINO ACID SUBSTITUTION | | T250V/M252Y/T307Q/V308P/ Q311A/N434Y/Y436V | L234A/L235A/T250V/M252Y/ T307Q/V308P/Q311A/N434Y/ Y436V |
| hFcRn KD (M) | ND | 1.1E−08 | 1.1E−08 |
| BINDING AMOUNT mFcgRI | 321.21 | 329.10 | 25.51 |
| mFcgRII | 138.20 | 128.72 | 19.18 |
| mFcgRIII | 761.04 | 663.66 | 532.38 |
| mFcgRIV | 271.88 | 279.04 | 85.59 |

According to the results of Table 10, Fv4-IgG1-F1326 demonstrated a decrease in binding to mouse FcγR without affecting binding activity to human FcRn in comparison with Fv4-IgG1-F947.

(5-7) In Vivo PK Study Using Human FcRn Transgenic Mice

Figure 54:
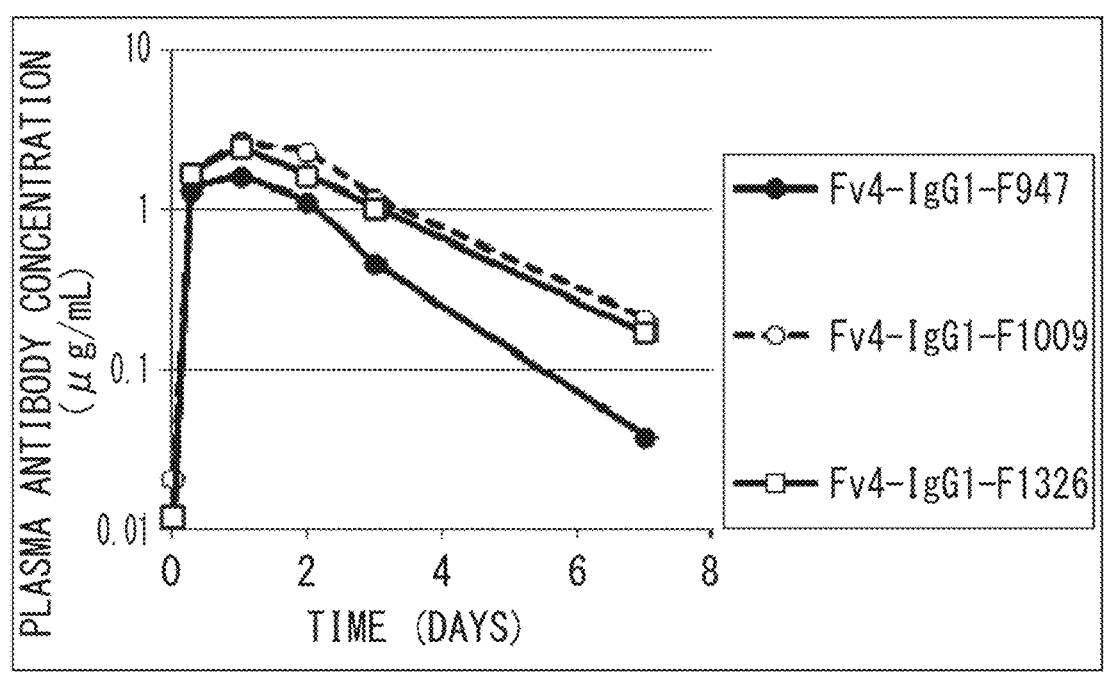
FIG. 54 is a graph showing a plasma concentration time course of Fv4-IgG1-F947 and Fv4-IgG1-F1326 in human FcRn transgenic mice administered with Fv4-IgG1-F947 or Fv4-IgG1-F1326.

A PK study in administration of the produced Fv4-IgG1-F1326 antibody to human FcRn transgenic mice was carried out in the same manner as the method of Example 5-4. Concentration of anti-human IL-6 receptor antibody in the mouse plasma was measured by ELISA in the same manner as the method of Example 4. The results are shown in FIG. 54 along with the results for Fv4-IgG1-F947 obtained in Example 5-4. Fv4-IgG1-F1326, which lowered the binding activity of Fv4-IgG1-F947 to mouse FcγR, was observed to demonstrate improvement of plasma retention in comparison with Fv4-IgG1-F947.

On the basis of the above, in the case of a human antibody having enhanced binding to human FcRn under neutral conditions, it was indicated to be possible to improve plasma retention in human FcRn transgenic mice by decreasing binding activity to mouse FcγR and inhibiting the formation of a quaternary complex. Here, in order to demonstrate the effect of improving plasma retention by decreasing binding human FcRn transgenic mice. Similarly, whether or not plasma retention in normal mice is improved was verified for antigen-binding molecules that have binding activity to mouse FcRn under conditions of the neutral pH region and contain an FcγR-binding domain whose binding activity to mouse FcγR is lower than the binding activity of a native FcγR-binding domain.

mPM1H-mIgG1-mF40 (SEQ ID NO: 60) was produced by an amino acid substitution obtained by substituting Lys for Pro at position 235 (EU numbering) and an amino acid substitution obtained by substituting Lys for Ser at position 239 in the amino acid sequence of mPM1H-mIgG1-mF38 produced in Example 2, while mPM1H-mIgG1-mF39 (SEQ ID NO: 61) was produced by an amino acid substitution obtained by substituting Lys for Pro at position 235 (EU numbering) and an amino acid substitution obtained by substituting Lys for Ser at position 239 of the amino acid sequence of mPM1H-mIgG1-mF14.

(6-2) Confirmation of Binding Activity to Mouse FcRn and Mouse FcγR

Binding activity (dissociation constant KD) to mouse FcRn at pH 7.0 was measured using the method of Example 2. The results are shown in Table 11 below.

TABLE 11

| MUTANT NAME | KD (M) | AMINO ACID SUBSTITUTION |
|---|---|---|
| mIgG1 | ND | |
| mF14 | 2.8E−08 | T252Y/T256E/H433K |
| mF38 | 4.0E−09 | T252Y/T256E/N434W |
| mF39 | 2.1E−08 | P235K/S239K/T252Y/T256E/H433K |
| mF40 | 3.2E−09 | P235K/S239K/T252Y/T256E/N434W |

Binding activity to mouse FcγR at pH 7.4 was measured using the method of Example 4. The results are shown in Table 12 below.

TABLE 12

| MUTANT NAME | BINDING AMOUNT (RU) | | | |
|---|---|---|---|---|
| | mFcgR I | mFcgR IIb | mFcgR III | mFcgR IV |
| mIgG1 | −2.0 | 202.1 | 450.0 | −3.5 |
| mF14 | −3.7 | 183.6 | 447.3 | −8.0 |
| mF38 | −2.0 | 161.1 | 403.0 | −4.1 |
| mF39 | −3.1 | −3.0 | −8.4 | −3.8 |
| mF40 | −3.0 | −5.2 | −18.7 | −8.9 |

(6-3) In Vivo PK Study Using Normal Mice

A PK study in administration of the produced mPM1-mIgG1-mF14, mPM1-mIgG1-mF38, mPM1-mIgG1-mF39 and mPM1-mIgG1-mF40 to normal mice was carried out according to the method indicated below.

Anti-human IL-6 receptor antibody was administered at 1 mg/kg in a single administration beneath the skin of the back of normal mice (C57BL/6J mouse, Charles River Japan). Blood was collected at 5 minutes, 7 hours and 1, 2, 4, 7 and 14 days after administration of the anti-human IL-6 receptor antibody. Plasma was obtained by immediately centrifuging the collected blood for 15 minutes at 4° C. and 15,000 rpm. The separated plasma was stored in a freezer set to −20° C. or lower until the time of measurement.

(6-4) Measurement of Plasma Anti-human IL-6 Receptor Mouse Antibody Concentration by ELISA Concentration of anti-human IL-6 receptor mouse antibody in mouse plasma was measured by ELISA. First, soluble human IL-6 receptor was dispensed into a Nunc-Immuno Plate, MaxiSoup (Nalge Nunc International) followed by allowing this to stand undisturbed overnight at 4° C. to produce a soluble human IL-6 receptor solid phase plate. Calibration curve samples containing of 1.25, 0.625, 0.313, 0.156, 0.078, 0.039 and 0.020 μg/mL of anti-human IL-6 receptor mouse antibody in plasma antibody concentration, and mouse plasma measurement samples diluted by 100-fold or more, were prepared. 100 μL aliquots of these calibration curve samples and plasma measurement samples were dispensed into each well of the soluble human IL-6 receptor solid phase plate followed by allowing this to stand undisturbed for 2 hours at room temperature. Subsequently, the chromogenic reaction of a reaction liquid obtained by reacting with Anti-Mouse IgG-Peroxidase Antibody (SIGMA) for 1 hour at room temperature and further reacting with Streptavidin-PolyHRP80 (Stereospecific Detection Technologies) for 1 hour at room temperature was carried out using TMB One Component HRP Microwell Substrate (BioFX Laboratories) as substrate. After the reaction was stopped by adding 1N-Sulfuric Acid (Showa Chemical), absorbance at 450 nm of the reaction liquids of each well was measured with a microplate reader. Antibody concentrations in the mouse plasma were calculated from absorbance values of the calibration curve using the SOFTmax PRO analysis software (Molecular Devices). Changes in the antibody concentration in normal mouse plasma following intravenous administration as measured with this method are shown in FIG. 17.

Figure 17:
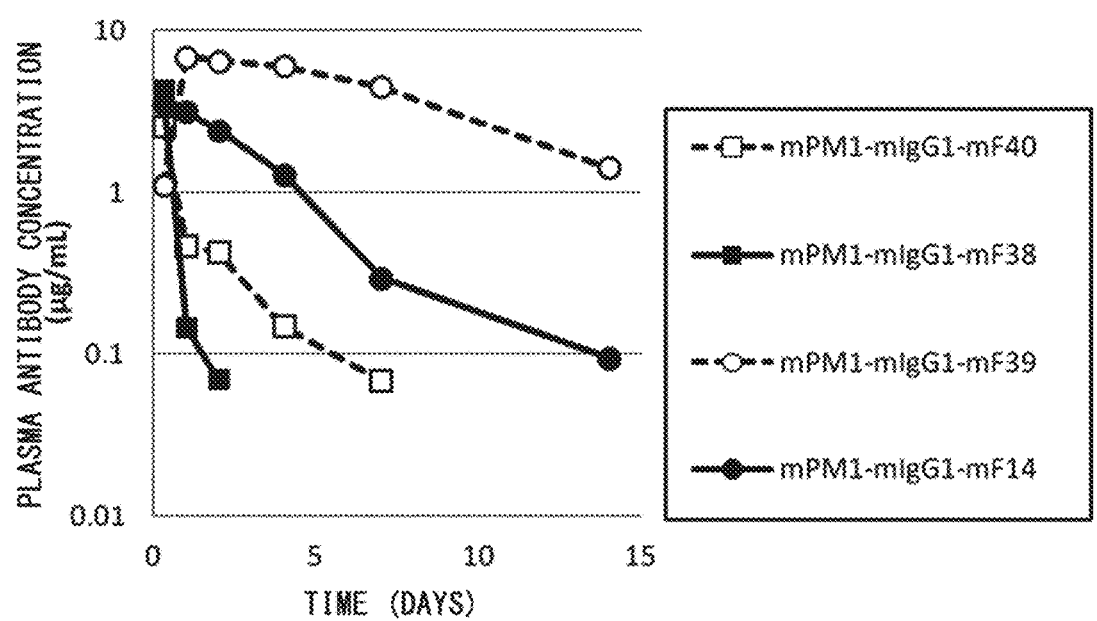
FIG. 17 is a graph showing a plasma concentration time course of mPM1-mIgG1-mF14, mPM1-mIgG1-mF38, mPM1-mIgG1-mF39, and mPM1-mIgG1-mF40 in normal mice.

Based on the results shown in FIG. 17, mPM1-mIgG1-mF40, which does not have binding activity to mouse FcγR, was observed to demonstrate improvement of plasma retention in comparison with mPM1-mIgG1-mF38. In addition, mPM1-mIgG1-mF39, which does not have binding activity to mouse FcγR, was observed to demonstrate improvement of plasma retention in comparison with mPM1-mIgG1-mF14.

On the basis of the above, an antibody having binding activity to mouse FcRn under conditions of the neutral pH region and having a FcγR-binding domain that does not have binding activity to mouse FcγR, was shown to have higher plasma retention in normal mice than an antibody having a normal FcγR-binding domain.

As a result, in the same manner as Examples 4 and 5, plasma retention was confirmed to be high for antigen-binding molecules having the properties of antigen-binding molecules of Embodiment 1. Although the present invention is not bound to a specific theory, the improvement of plasma retention observed here is thought to be the result of selective inhibition of incorporation into immune cells, including antigen-presenting cells, and as a result thereof, it is expected to be possible to inhibit induction of an immune response.

Example 7

In Vitro Evaluation of Immunogenicity of a Humanized Antibody (Anti-human IL-6 Receptor Antibody) having Binding Activity to Human FcRn in the Neutral pH Region and Containing an FcγR-binding Domain whose Binding Activity to Human FcγR is Lower than Binding Activity of a Native FcγR Binding Domain In order to evaluate immunogenicity in humans of an antigen-binding molecule of Embodiment 1, namely an antigen-binding molecule having binding activity to FcRn under conditions of the neutral pH region and containing an antigen-binding domain whose binding activity to active FcγR is lower than binding activity of a native FcγR binding domain, T cell response to the antigen-binding molecule in vitro was evaluated according to the method shown below.

(7-1) Confirmation of Binding Activity to Human FcRn

The association constants (KD) of VH3/L(WT)-IgG1, VH3/L(WT)-IgG1-F21 and VH3/L(WT)-IgG1-F140 to human FcRn under conditions of the neutral pH region (pH 7.0) measured in Example 4 are shown in Table 13 below.

TABLE 13

| MUTANT NAME | KD (M) | AMINO ACID SUBSTITUTION |
|---|---|---|
| IgG1 | NOT DETECTED | |
| IgG1-F21 | 3.0E−08 | M252Y/V308P/N434Y |
| IgG1-F140 | 3.6E−08 | S239K/M252Y/V308P/N434Y |

(7-2) Evaluation of Binding Activity to Human FcγR

The binding activities of VH3/L(WT)-IgG1, VH3/L(WT)-IgG1-F21 and VH3/L(WT)-IgG1-F140 to human FcγR at pH 7.4 were measured using the method shown below.

Binding activity between the antibodies and human FcγRIa, FcγRIIa(H), FcγRIIa(R), FcγRIIb and FcγγRIIIa(F) (hereinafter referred to as human FcγRs) was evaluated using the BIACORE™ T100 or T200 surface plasmon resonance system (GE Healthcare). The antibodies being tested were captured by Protein L (ACTIGEN® protein (Alltech)) that was immobilized in suitable amounts on the CM4 Sensor Chip (GE Healthcare) by amine coupling. Next, the diluted human FcγRs and a running buffer used as a blank were injected to allow interaction with the antibodies captured on the sensor chip. A buffer consisting of 20 mmol/L N-(2-acetamido)-2-aminoethanesulfonic acid (ACES), 150 mmol/L NaCl and 0.05% (w/v) polysorbate 20 (Tween 20®) (pH 7.4) was used for the running buffer, and this buffer was also used to dilute the human FcγRs. 10 mmol/L glycine-HCl (pH 1.5) was used to regenerate the sensor chip. All measurements were carried out at 25° C.

Binding activity to human FcγRs can be represented by the relative binding activity to human FcγRs. Antibody was captured by Protein L, and the amount of change in a sensorgram before and after the antibody was captured was defined as X1. Next, human FcγRs were allowed to interact with the antibody, and the value obtained by subtracting binding activity of human FcγRs represented as the amount of change in a sensorgram before and after allowing the running buffer to interact with antibody captured by Protein L (ΔA2) from the value obtained by multiplying by 1500 the value obtained by dividing the binding activity of human FcγRs represented as the amount of change in a sensorgram before and after that interaction (ΔA1) by the captured amount (X) of each antibody, was divided by the captured amount of each antibody (X) followed by multiplying by 1500 to obtain the binding activity of the human FcγRs (Y) (Equation 2).

Binding activity of human FcγRs $(Y)=(\Delta A1-\Delta A2)/X \times 1500$   [Equation 2]

The results are shown in Table 14 below.

TABLE 14

| | BINDING AMOUNT (RU) | | | | |
|---|---|---|---|---|---|
| | hFcgRIa | hFcgRIIa(R) | hFcgRIIa(H) | hFcgRIIb | hFcgRIIIa(F) |
| IgG1 | 399.6 | 158.9 | 158.7 | 81.4 | 143.8 |
| IgG1-F21 | 403.0 | 145.2 | 153.6 | 63.4 | 146.7 |
| IgG1-F140 | 335.1 | 7.6 | 8.8 | 2.2 | 1.8 |

According to the results of Table 14, Fv4-IgG1-F140 demonstrated a decrease in binding to each human FcγR without affecting the binding activity to human FcRn in comparison with Fv4-IgG1-F21.

(7-3) In Vitro Immunogenicity Study Using Human PBMCs

An in vitro immunogenicity study was carried out as shown below using Fv4-IgG1-F21 and Fv4-IgG1-F140 produced in Example 1.

Peripheral blood mononuclear cells (PBMCs) were isolated from blood collected from healthy volunteers. After separating the PBMCs from the blood by Ficoll (GE Healthcare) density gradient centrifugation, CD8$^+$ T cells were removed from the PBMCs magnetically using Dynabeads CD8 (Invitrogen) in accordance with the standard protocol provided. Next, CD25$^{hi}$ T cells were removed magnetically using Dynabeads CD25 (Invitrogen) in accordance with the standard protocol provided.

A proliferation assay was carried out in the manner described below. Namely, PBMCs from each donor, from which CD8$^+$ T cells and CD25$^{hi}$T cells had been removed and which had been re-suspended in AIMV medium (Invitrogen) containing 3% deactivated human serum to a concentration of $2\times10^6$/ml, were added to a flat-bottomed 24-well plate at $2\times10^6$ cells per well.

After culturing for 2 hours under conditions of 37° C. and 5% $CO_2$, the cells to which each test substance was added to final concentrations of 10, 30, 100 and 300 μg/ml were cultured for 8 days. BrdU (Bromodeoxyuridine) was added to 150 μL, of cell suspension during culturing after transferring to a round-bottomed 96-well plate on days 6, 7 and 8 of culturing, after which the cells were further cultured for 24 hours. The BrdU that had been incorporated into the nuclei of the cells cultured with BrdU were stained using the BrdU Flow Kit (BD Bioscience) in accordance with the standard protocol provided, while surface antigens (CD3, CD4 and CD19) were stained by anti-CD3, anti-CD4 and anti-CD19 antibodies (BD Bioscience). Next, the percentage of BrdU-positive CD4$^+$ T cells was detected with BD FACS Calibur or BD FACS CantII (BD). The percentage of BrdU-positive CD4$^+$ T cells at each test substance concentration of 10, 30, 100 and 300 μg/mL on days 6, 7 and 8 of culturing was calculated, followed by calculating the average values thereof.

Figure 18:
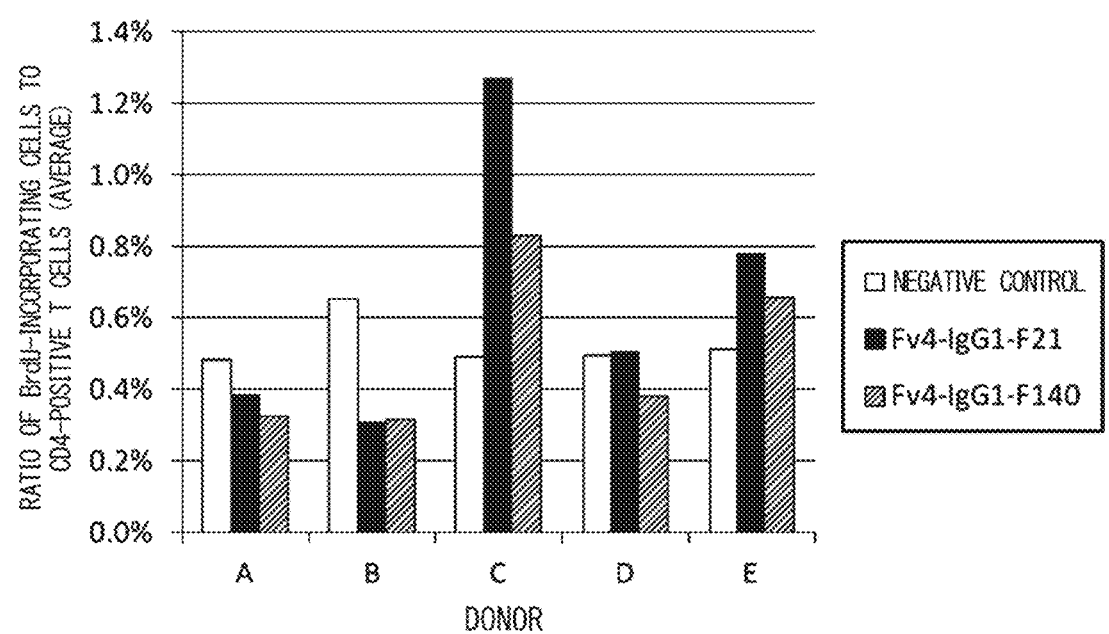
FIG. 18 is a diagram showing the result of immunogenicity assessment using Fv4-IgG1-F21 and Fv4-IgG1-F140.

The results are shown in FIG. 18. FIG. 18 indicates the proliferative responses of CD4$^+$ T cells to Fv4-IgG1-F21 and Fv4-IgG1-F140 in the PBMCs of five human donors from which CD8$^+$ T cells and CD25$^{hi}$ T cells had been removed. First, an increase in the proliferative response of CD4$^+$ T cells attributable to the addition of test substance was not observed in the PBMCs of donors A, B and D in comparison with a negative control. These donors are thought to have inherently not undergone an immune response to the test substances. On the other hand, a proliferative response of CD4$^+$ T cells attributable to the addition of test substance was observed in the PBMC of donors C and E in comparison with a negative control. One of the points to be noted here is that the proliferative response of CD4$^+$ T cells to Fv4-IgG1-F140 tended to decrease in comparison with Fv4-IgG1-F21 for both donors C and E. As previously described, Fv4-IgG1-F140 has a lower binding activity to human FcγR than Fv4-IgG1-F21, and has the properties of Embodiment 1. On the basis of the above results, it was suggested that immunogenicity can be suppressed with respect to antigen-binding molecules having binding activity to FcRn under conditions of the neutral pH region and containing an antigen-binding domain whose binding activity to human FcγR is lower than the binding activity of a native FcγR binding domain.

Example 8

In Vitro Evaluation of the Immunogenicity of a Humanized Antibody (Anti-human A33 Antibody) having Binding Activity to Human FcRn in the Neutral pH Region and Containing an Antigen-binding Domain whose Binding Activity to Human FcγR is Lower than the Binding Activity of a Native FcγR Binding Domain (8-1) Production of hA33-IgG1

Since human PBMCs inherently have a low immune response to Fv4-IgG1-F21 as indicated in Example 7, they were suggested not to be suitable for evaluating suppression of immune response to Fv4-IgG1-F140 containing an antigen-binding domain whose binding activity to FcγR is lower than the binding activity of a native FcγR binding domain. Therefore, a humanized A33 antibody (hA33-IgG1), which is a humanized IgG1 antibody to the A33 antigen, was produced in order to enhance the capability of detecting immunogenicity-lowering effects in an in vitro immunogenicity evaluation system.

In hA33-IgG1, the anti-antibody has been confirmed to be produced in 33% to 73% of subjects in a clinical study (Hwang, et al. (Methods (2005) 36, 3-10) and Walle, et al. (Expert Opin. Bio. Ther. (2007) 7(3), 405-418)). Since the high immunogenicity of hA33-IgG1 originates in the variable region sequence, for molecules in which binding activity to FcRn in the neutral pH region had been enhanced for hA33-IgG1, it would be easy to detect immunogenicity lowering effects that arise from inhibiting formation of a quaternary complex by lowering the binding activity to FcγR.

The amino acid sequences of hA33H (SEQ ID NO: 62) used for the heavy chain variable region of the humanized A33 antibody and hA33L (SEQ ID NO: 63) used for the light chain variable region were acquired from known information (British Journal of Cancer (1995) 72, 1364-1372). In addition, naturally-occurring human IgG1 (SEQ ID NO: 11, hereinafter referred to as IgG1) was used for the heavy chain constant region, and naturally-occurring human kappa (SEQ ID NO: 64, hereinafter referred to as k0) was used for the light chain constant region.

An expression vector containing the base sequences of heavy chain hA33H-IgG1 and light chain hA33L-k0 was produced according to the method of Reference Example 1. In addition, a humanized A33 antibody in the form of hA33-IgG1 containing heavy chain hA33H-IgG1 and light chain hA33L-k0 was produced in accordance with the method of Reference Example 2.

(8-2) Production of an A33-Binding Antibody having Binding Activity to Human FcRn under Conditions of the Neutral pH Region Since the produced hA33-IgG1 is a human antibody having a naturally-occurring human Fc region, it does not have binding activity to human FcRn under conditions of the neutral pH region. Therefore, an amino acid modification was introduced into the heavy chain constant region of hA33-IgG1 in order to impart the ability to bind to human FcRn under conditions of the neutral pH region.

More specifically, hA33H-IgG1-F21 (SEQ ID NO: 65) was produced by substituting Tyr for Met at position 252 (EU numbering), substituting Pro for Val at position 308 (EU numbering) and substituting Tyr for Asn at position 434 (EU numbering) in the heavy chain constant region of hA33-IgG1 in the form of hA33H-IgG1. Using the method of Reference Example 2, an A33-binding antibody having binding activity to human FcRn under conditions of the neutral pH region was produced in the form of hA33-IgG1-F21 containing hA33H-IgG1-F21 for the heavy chain and hA33L-k0 for the light chain.

(8-3) Production of an A33-binding Antibody Containing an FcγR-Binding Domain whose Binding Activity to Human FcγR under Conditions of the Neutral pH Region is Lower than the Binding Activity of a Native FcγR-binding Domain hA33-IgG1-F140 (SEQ ID NO: 66) was produced in which Lys is substituted for Ser at position 239 (EU numbering) in the amino acid sequence of hA33-IgG1-F21 in order to lower the binding activity of hA33-IgG1-F21 to human FcγR.

(8-4) Immunogenicity Evaluation of Various Types of A33-binding Antibodies by In Vitro T-cell Assay The immunogenicity of the produced hA33-IgG1-F21 and hA33-IgG1-F140 was evaluated using the same method as that of Example 7. Furthermore, the healthy volunteers serving as donors were not the same individuals as the healthy volunteers from whom the PBMCs used in Example 7 were isolated. In other words, donor A in Example 7 and donor A in this study were different healthy volunteers.

Figure 19:
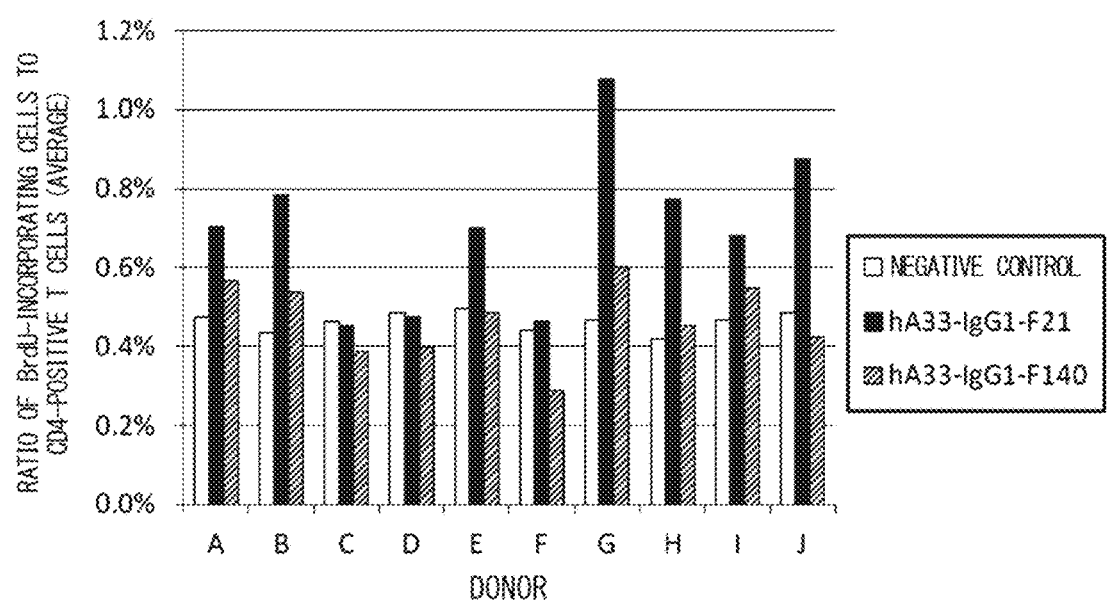
FIG. 19 is a diagram showing the result of immunogenicity assessment using hA33-IgG1-F21 and hA33-IgG1-F140.

The study results are shown in FIG. 19. In FIG. 19, a comparison is made between the results for hA33-IgG1-F21 which has binding activity to human FcRn in the neutral pH region, and hA33-IgG1-F140 which contains an FcγR-binding domain whose binding activity to human FcγR is lower than the binding activity of a native FcγR-binding domain. Since a response to hA33-IgG1-F21 was not observed in PBMCs isolated from donors C, D and F in comparison with a negative control, donors C, D and F are thought to be donors in whom an immune response to hA33-IgG1-F21 does not occur. A strong immune response to hA33-IgG1-F21 was observed in the PBMCs isolated from the other seven donors (donors A, B, E, G, H, I and J) in comparison with the negative control; and hA33-IgG1-F21 demonstrated a high level of immunogenicity in vitro as expected. On the other hand, an effect was observed in which the immune response of PBMCs isolated from all of these seven donors (donors A, B, E, G, H, I and J) to hA33-IgG1-F140 which contains an FcγR binding domain whose binding activity to human FcγR is lower than the binding activity of a native FcγR binding domain, was decreased in comparison with that to hA33-IgG1-F21. In addition, since the immune response of the PBMCs isolated from donors E and J to hA33-IgG1-F140 was also about the same as that of the negative control, it was thought that immunogenicity can be reduced in antigen-binding molecules having binding activity to human FcRn in the neutral pH region by lowering binding activity to human FcγR to a level lower than the binding activity of a native FcγR binding domain and inhibiting the formation of a quaternary complex.

Example 9

In Vitro Immunogenicity Evaluation of a Humanized Antibody (Anti-human A33 Antibody) that Hhs Binding Activity to Human FcRn under Conditions of the Neutral pH Region but does not have Binding Activity to Human FcγR (9-1) Production of an A33-binding Antibody having Strong Binding Activity to Human FcRn under Conditions of the Neutral pH Region hA33H-IgG1-F698 (SEQ ID NO: 67) was produced according to the method of Reference Example 1 by substituting Tyr for Met at position 252 (EU numbering), substituting Glu for Asn at position 286 (EU numbering), substituting Gln for Thr at position 307 (EU numbering), substituting Ala for Gln at position 311 (EU numbering), and substituting Tyr for Asn at position 434 (EU numbering) in the amino acid sequence of hA33H-IgG1. A human A33-binding antibody having strong binding activity to human FcRn under the conditions of the neutral pH region was produced in the form of hA33-IgG1-F698 containing hA33H-IgG1-F698 for the heavy chain and hA33L-k0 for the light chain.

(9-2) Production of an A33-binding Antibody Containing an Antigen-binding Domain whose Binding Activity to Human FcγR under Conditions of the Neutral pH Region is Lower than the Binding Activity of a Native FcγR-binding Domain hA33H-IgG1-F699 (SEQ ID NO: 68) was produced in which Lys was substituted for Ser at position 239 (EU numbering) of hA33H-F698 and which contains an antigen-binding domain whose binding activity to human FcγR is lower than the binding activity of a native FcγR binding domain.

Binding activity to human FcRn at pH 7.0 of VH3/L(WT)-IgG1, VH3/L(WT)-IgG1-F698 and VH3/L(WT)-IgG1-F699 was measured using the method of Example 4. Moreover, binding activity to human FcγR at pH 7.4 of VH3/L(WT)-IgG1, VH3/L(WT)-IgG1-F698 and VH3/L(WT)-IgG1-F699 was measured using the method of Example 7. The results for both are shown in Table 15 below.

TABLE 15

| MUTANT NAME | hFcRn KD (nM) | BINDING AMOUNT (RU) | | | | |
|---|---|---|---|---|---|---|
| | | hFcgRIa | hFcgRIIa(R) | hFcgRIIa(H) | hFcgRIIb | hFcgRIIIa(F) |
| IgG1 | ND | 392.1 | 154.3 | 154.8 | 75.8 | 102.3 |
| IgG1-F698 | 22 | 392.1 | 116.7 | 115.8 | 42.1 | 55.9 |
| IgG1-F699 | 23 | 163.5 | 3.2 | 3.5 | −0.3 | −2.0 |

As is shown in Table 15, VH3/L(WT)-IgG1-F699, in which Lys is substituted for Ser at position 239 (EU numbering) and which contains an antigen-binding domain whose binding activity to each type of human FcγR is lower than the binding activity of a native FcγR binding domain, demonstrated binding activity to hFcgRI even though binding to hFcgRIIa(R), hFcgRIIa(H), hFcgRIIb and hFcgRIIIa(F) was decreased.

(9-3) Immunogenicity Evaluation of Various Types of A33-binding Antibodies by in Vitro T-cell Assay Immunogenicity to the produced hA33-IgG1-F698 and hA33-IgG1-F699 was evaluated according to the same method as Example 7. Furthermore, the healthy volunteers serving as donors were not the same individuals as the healthy volunteers from whom the PBMC used in Examples 7 and 8 were isolated. In other words, donor A in Examples 7 and 8 and donor A in this study were different healthy volunteers.

Figure 20:
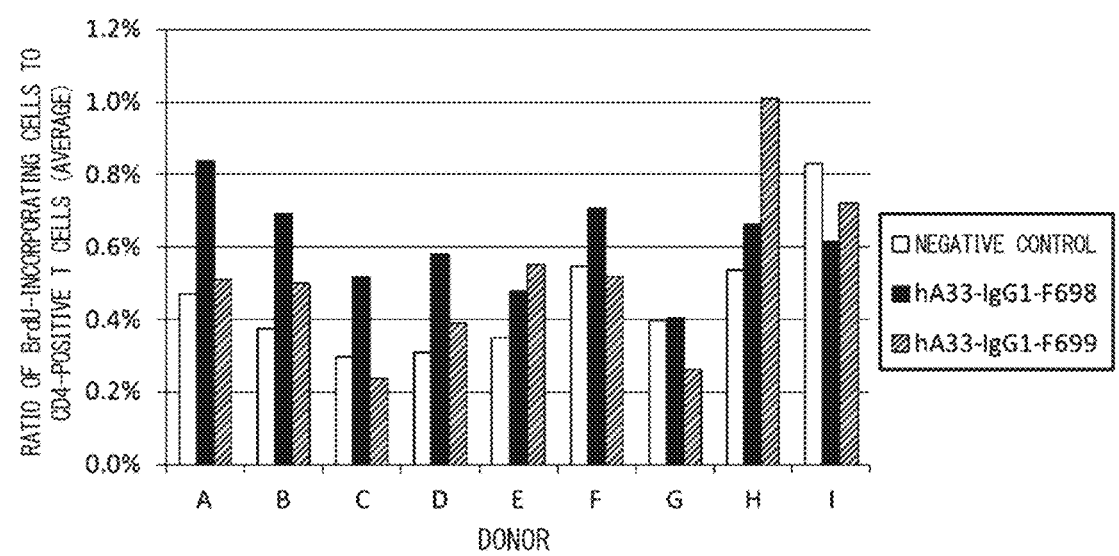
FIG. 20 is a diagram showing the result of immunogenicity assessment using hA33-IgG1-F698 and hA33-IgG1-F699.

The study results are shown in FIG. 20. In FIG. 20, a comparison is made between the results for hA33-IgG1-F698 which has strong binding activity to human FcRn under conditions of the neutral pH region, and hA33-IgG1-F699 which contains an FcγR binding domain whose binding activity to human FcγR is lower than binding activity of a naturally-occurring FcγR domain. Since a response to hA33-IgG1-F698 was not observed in PBMCs isolated from donors G and I in comparison with a negative control, donors G and I are thought to be donors in whom an immune response to hA33-IgG1-F698 does not occur. A strong immune response to hA33-IgG1-F698 was observed in the PBMCs isolated from the other seven donors (donors A, B, C, D, E, F and H) in comparison with the negative control, and a high level of immunogenicity was demonstrated in vitro in the same manner as the aforementioned hA33-IgG1-F21. On the other hand, an effect was observed in which the immune response of PBMCs isolated from five donors (donors A, B, C, D and F) to hA33-IgG1-F699 which contains an FcγR binding domain whose binding activity to human FcγR is lower than the binding activity of a native FcγR binding domain, was decreased in comparison with that to hA33-IgG1-F698. In particular, the immune response of the PBMCs isolated from donors C and F to hA33-IgG1-F699 was confirmed to be about the same as that of the negative control. The fact that the effect of reducing immunogenicity was confirmed not only for hA33-IgG1-F21 but also for hA33-IgG1-F698 which has strong binding activity to human FcRn showed that immunogenicity can be reduced in antigen-binding molecules having binding activity to human FcRn in the neutral pH region, by making the binding activity to human FcγR lower than the binding activity of a native FcγR binding domain, and inhibiting the formation of a quaternary complex.

(9-4) Production of an A33-binding Antibody not having Binding Activity to Human FcγRIa under Conditions of the Neutral pH Region As previous described in (9-3), hA33-IgG1-F699 demonstrated a decreased binding activity to various types of human FcγR by substituting Lys for Ser at position 239 (EU numbering) in hA33-IgG1-F698, and binding to hFcgRI remained although binding to hFcgRIIa(R), hFcgRIIa(H), hFcgRIIb and hFcgRIIIa(F) decreased considerably.

Therefore, in order to produce an A33-binding antibody that contains an FcγR-binding domain not having binding activity to all human FcγR including hFcgRIa, hA33H-IgG1-F763 (SEQ ID NO: 69) was produced in which Arg was substituted for Leu at position 235 (EU numbering) and Lys was substituted for Ser at position 239 (EU numbering) in hA33H-IgG1-F698 (SEQ ID NO: 67).

Association constants (KD) for human FcRn under conditions of the neutral pH region (pH 7.0) were measured for VH3/L(WT)-IgG1, VH3/L(WT)-IgG1-F698 and VH3/L(WT)-IgG1-F763 using the method of Example 4. In addition, binding activity to human FcγR was evaluated for VH3/L(WT)-IgG1, VH3/L(WT)-IgG1-F698 and VH3/L(WT)-IgG1-F763 according to the method described in Example 7. Those results are also shown in Table 16 below.

TABLE 16

| MUTANT NAME | hFcRn KD (nM) | BINDING AMOUNT (RU) | | | | |
|---|---|---|---|---|---|---|
| | | hFcgRIa | hFcgRIIa(R) | hFcgRIIa(H) | hFcgRIIb | hFcgRIIIa |
| IgG1 | ND | 392.1 | 154.3 | 154.8 | 75.8 | 102.3 |
| IgG1-F698 | 22 | 392.1 | 116.7 | 115.8 | 42.1 | 55.9 |
| IgG1-F763 | 35 | −0.4 | −1.0 | −0.8 | −1.0 | −2.9 |

As shown in Table 16, IgG1-F763, in which Arg was substituted for Leu at position 235 (EU numbering) and Lys was substituted for Ser at position 239 (EU numbering), was shown to demonstrate decreased binding activity to all human FcγR including hFcγRIa.

(9-5) Immunogenicity Evaluation of Various Types of A33-binding Antibodies by in Vitro T-cell Assay The immunogenicity of the produced hA33-IgG1-F698 and hA33-IgG1-F763 was evaluated using the same method as that of Example 7. Furthermore, in the same manner as previously described, the healthy volunteers serving as donors were not the same individuals as the healthy volunteers from whom the PBMCs used in the aforementioned examples were isolated. In other words, donor A in the aforementioned examples and donor A in this study were different healthy volunteers.

Figure 21:
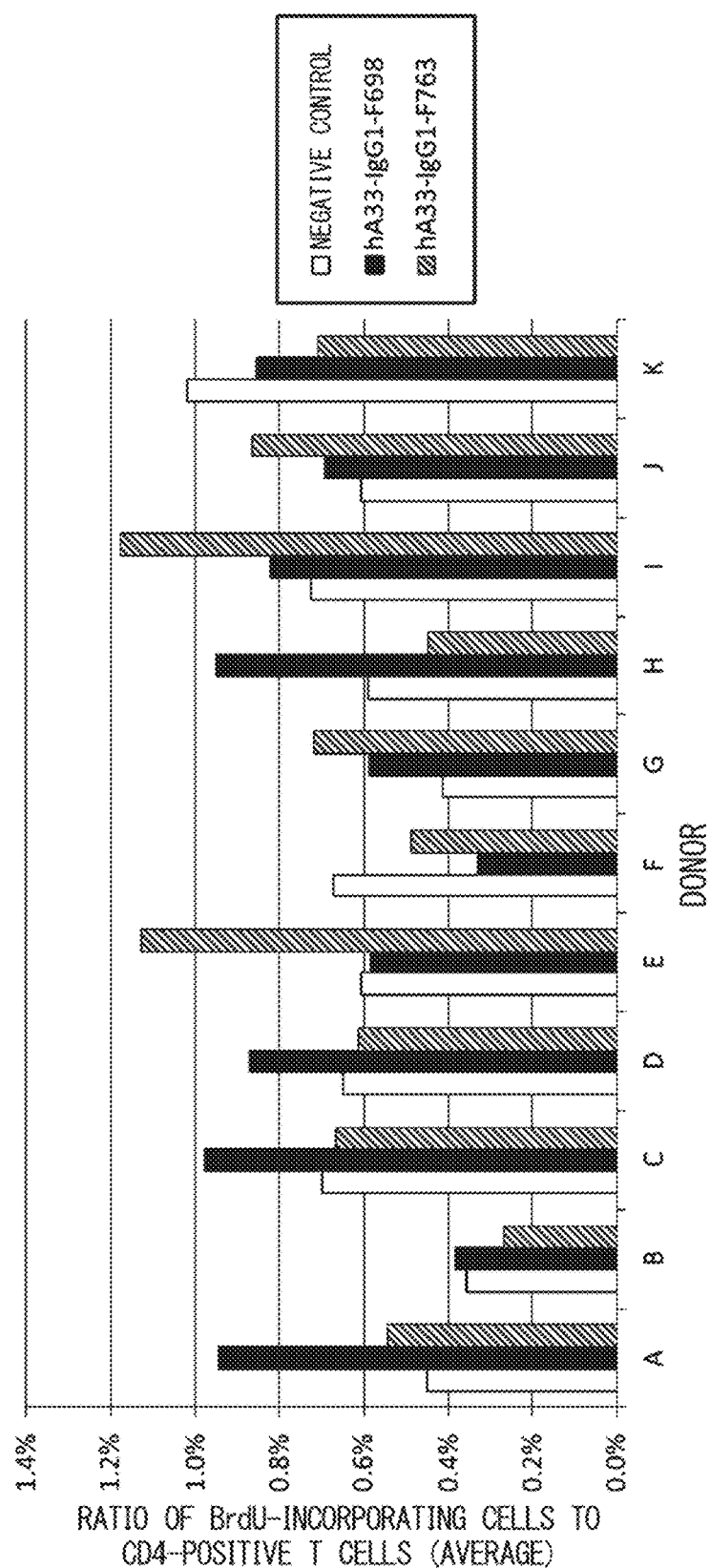
FIG. 21 is a diagram showing the result of immunogenicity assessment using hA33-IgG1-F698 and hA33-IgG1-F763.

The study results are shown in FIG. 21. In FIG. 21, a comparison is made between the results for hA33-IgG1-F698 which has strong binding activity to human FcRn under conditions of the neutral pH region, and hA33-IgG1-F763 which contains an FcγR binding domain whose binding activity to human FcγR is lower than binding activity of a native FcγR binding domain. Since a response to hA33-IgG1-F698 was not observed in PBMCs isolated from donors B, E, F and K in comparison with a negative control, donors B, E, F and K are thought to be donors in whom an immune response to hA33-IgG1-F698 does not occur. A strong immune response to hA33-IgG1-F698 was observed in the PBMCs isolated from the other seven donors (donors A, C, D, G, H, I and J) in comparison with the negative control. On the other hand, an effect was observed in which the immune response of PBMCs isolated from four donors (donors A, C, D and H) to hA33-IgG1-F763 which contains an FcγR binding domain whose binding activity to human FcγR is lower than the binding activity of a naturally-occurring FcγR domain, was decreased in comparison with that to hA33-IgG1-F698. Among these four donors, the immune response of the PBMCs isolated from donors C, D and H in particular to hA33-IgG1-F763 was about the same as that of the negative control, and among the four donors in whom the immune response of PBMCs was decreased as a result of decreasing binding to FcγR, it was in fact possible to completely inhibit the PBMC immune response in three donors. Also based on this finding, antigen-binding molecules containing an FcγR binding domain whose binding activity to human FcγR is low are considered to be extremely effective molecules having reduced immunogenicity.

Based on the results of Examples 7, 8 and 9, an immune response to antigen-binding molecules in which the formation of a quaternary complex was inhibited by decreasing binding to active FcγR (Embodiment 1) was confirmed to be inhibited in numerous donors in comparison with antigen-binding molecules that are able to form a quaternary complex on antigen-presenting cells. The above results showed that the formation of a quaternary complex on antigen-presenting cells is important for the immune response of antigen-binding molecules, and that antigen-binding molecules which do not form that quaternary complex make it possible to reduce immunogenicity in numerous donors.

Example 10

In Vivo Immunogenicity Evaluation of a Humanized Antibody that has Binding Activity to Human FcRn in the Neutral pH Region but does not have Binding Activity to Mouse FcγR It was demonstrated by the in vitro experiment in Examples 7, 8 and 9 that immunogenicity is reduced in antigen-binding molecules having binding activity to human FcRn in the neutral pH region and containing an FcγR binding domain whose binding activity to FcγR is lower than the binding activity of a native FcγR binding domain in comparison with antigen-binding molecules in which the FcγR binding activity has not been lowered. The following study was conducted to confirm whether or not this effect is also demonstrated in vivo.

(10-1) In Vivo Immunogenicity Study in Human FcRn Transgenic Mice

Antibody production to Fv4-IgG1-F11, Fv4-IgG1-F890, Fv4-IgG1-F947, Fv4-IgG1-F821, Fv4-IgG1-F939 and Fv4-IgG1-F1009 was evaluated using mouse plasma obtained in Example 5 according to the method indicated below.

(10-2) Measurement of Anti-administered Specimen Antibody in Plasma by Electrochemical Luminescence Antibody against an administered specimen antibody present in mouse plasma was measured by electrochemical luminescence. First, the administered antibody was dispensed into an Uncoated Multi-Array Plate (Meso Scale Discovery) followed by allowing this to stand undisturbed overnight at 4° C. to produce an administered antibody solid phase plate. Samples for mouse plasma measurement were prepared by diluting 50-fold followed by dispension into the solid phase plate and overnight reaction at 4° C. Subsequently, Anti-Mouse IgG (whole molecule) (Sigma) ruthenated with Sulfo-Tag NHS Ester (Meso Scale Discovery) was allowed to react for 1 hour at room temperature, and Read Buffer T (×4) (Meso Scale Discovery) was added, followed immediately by measurement with the Sector PR 400 (Meso Scale Discovery). The plasma from five animals that were not administered with the antibody was measured as a negative control sample for each measurement system, and the value (X), obtained by adding the product of multiplying the standard deviation (SD) of values measured using the plasma of those five animals by 1.645 to the mean (MEAN) of values measured using the five animals, was used as the criterion for determining a positive reaction (Equation 3). Those animals that demonstrated a reaction exceeding the positive criterion even once on any of the blood collection days were judged to have positive antibody production response to the test substance.

Positive criterion for antibody production
$$(X)=MEAN+1.645\times SD \quad \text{[Equation 3]}$$

Figure 22:
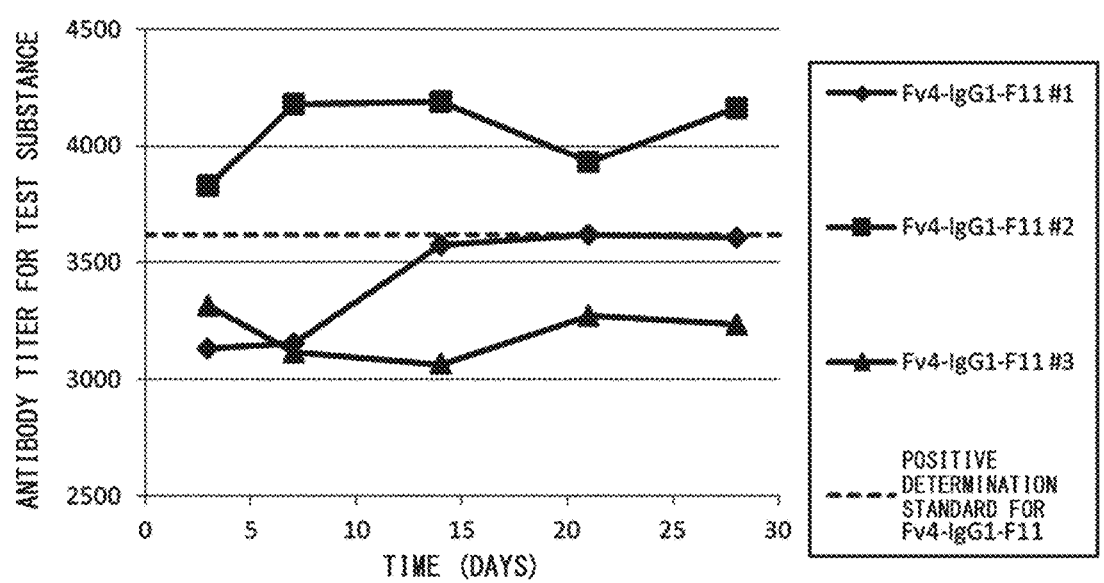
FIG. 22 is a graph showing titers of mouse antibody produced against Fv4-IgG1-F11, 3, 7, 14, 21, and 28 days after administration to human FcRn transgenic mice.
Figure 23:
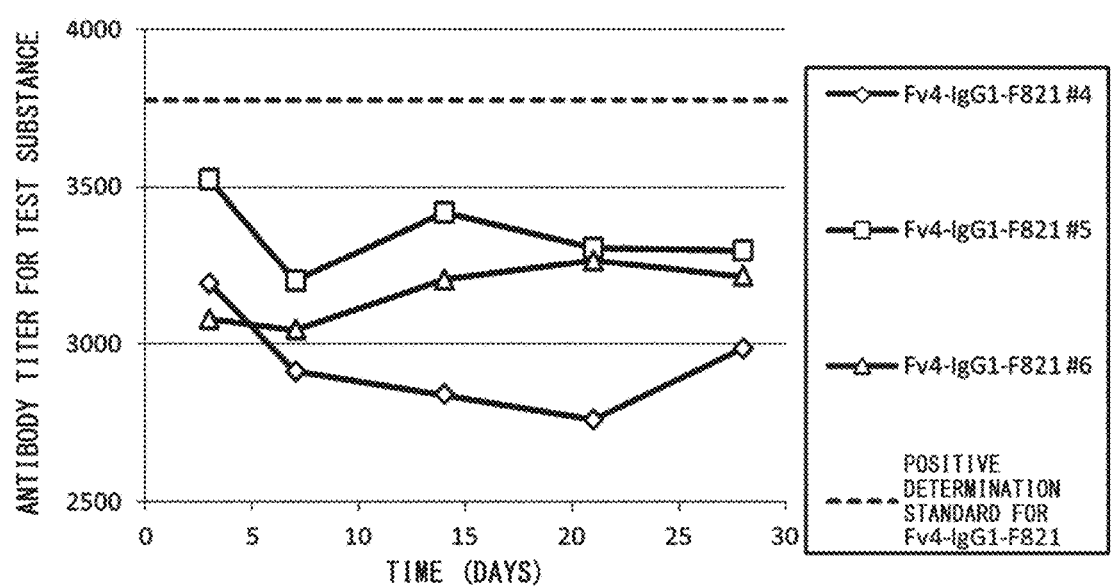
FIG. 23 is a graph showing titers of mouse antibody produced against Fv4-IgG1-F821, 3, 7, 14, 21, and 28 days after administration to human FcRn transgenic mice.
Figure 24:
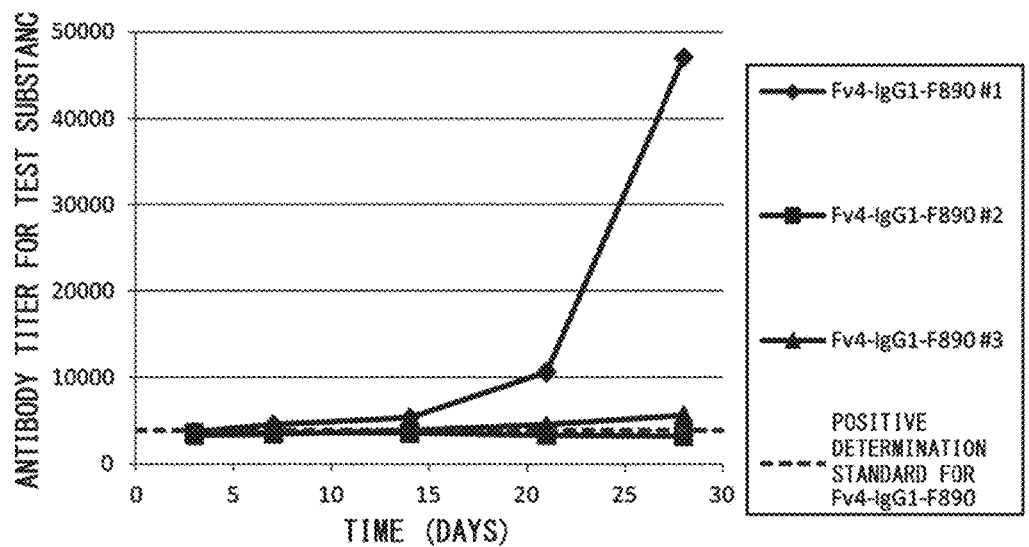
FIG. 24 is a graph showing titers of mouse antibody produced against Fv4-IgG1-F890, 3, 7, 14, 21, and 28 days after administration to human FcRn transgenic mice. B is an enlargement of A
Figure 24:
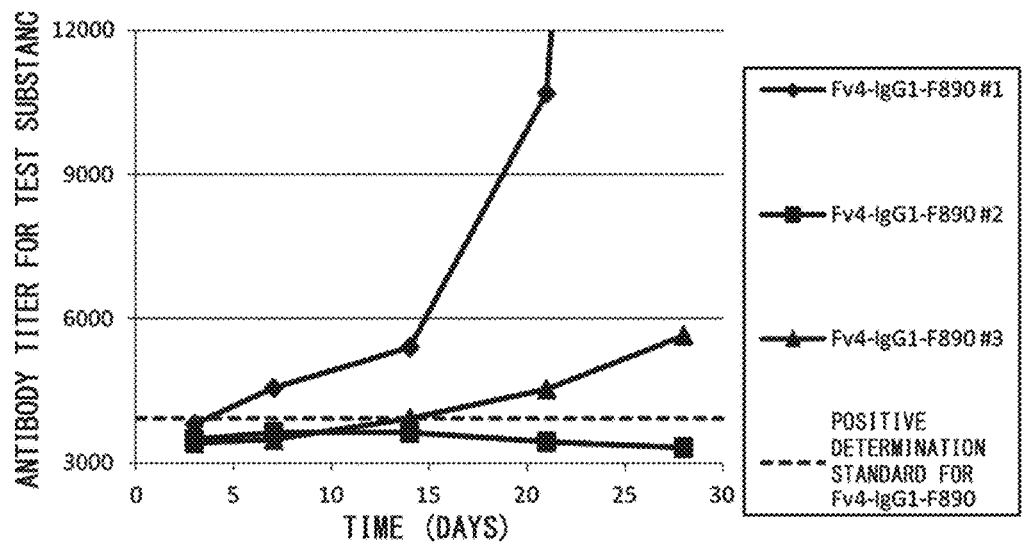

(10-3) Inhibitory Effect on in Vivo Immunogenicity by Decreasing Binding Activity to FcγR The results are shown in FIGS. 22 to 27. FIG. 22 shows the titers of mouse antibody produced in response to Fv4-IgG1-F11 at 3, 7, 14, 21 and 28 days after administration of Fv4-IgG1-F11 to human FcRn transgenic mice. Production of mouse antibody to Fv4-IgG1-F11 was shown to be positive in one of the three mice (#3) on each day blood was collected following administration (positive rate: 1/3). On the other hand, FIG. 23 shows the titers of mouse antibody produced in response to Fv4-IgG1-F821 at 3, 7, 14, 21 and 28 days after administration of Fv4-IgG1-F821 to human FcRn transgenic mice. Production of mouse antibody to Fv4-IgG1-F821 was shown to be negative in all three of the mice on each day blood was collected following administration (positive rate: 0/3).

Figure 25:
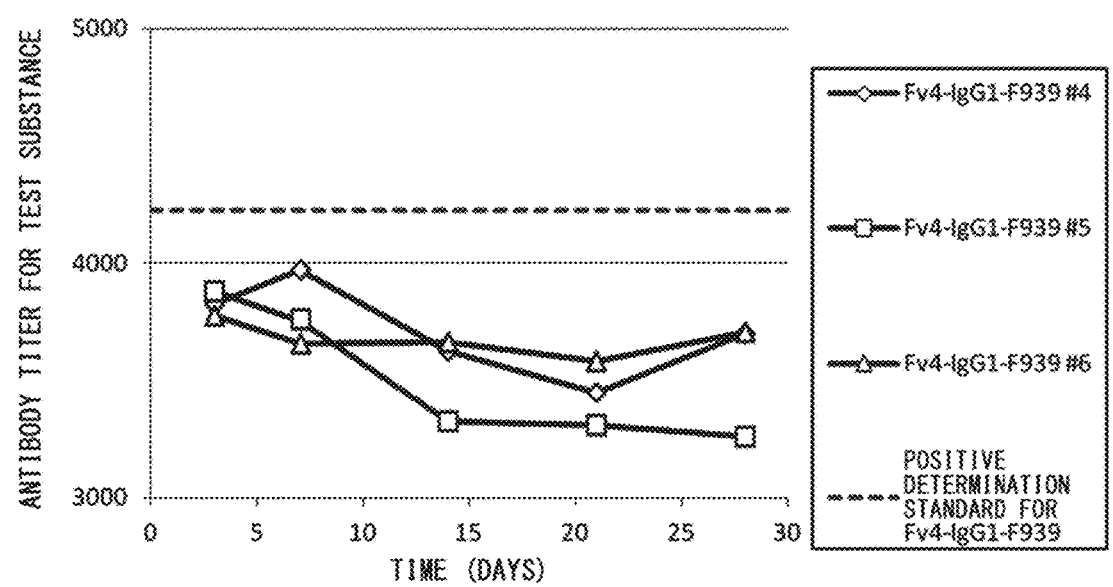
FIG. 25 is a graph showing titers of mouse antibody produced against Fv4-IgG1-F939, 3, 7, 14, 21, and 28 days after administration to human FcRn transgenic mice.

FIG. 24A and its enlarged view in the form of FIG. 24B show titers of mouse antibody produced in response to Fv4-IgG1-F890 at 3, 7, 14, 21 and 28 days after administration of Fv4-IgG1-F890 to human FcRn transgenic mice. Production of mouse antibody to Fv4-IgG1-F890 was shown to be positive in two of the three mice (#1 and #3) at 21 and 28 days after administration (positive rate: 2/3). On the other hand, FIG. 25 shows titers of mouse antibody produced in response to Fv4-IgG1-F939 at 3, 7, 14, 21 and 28 days after administration of Fv4-IgG1-F939 to human FcRn transgenic mice. Production of mouse antibody to Fv4-IgG1-F939 was shown to be negative in all three mice on each day blood was collected following administration (positive rate: 0/3).

Figure 26:
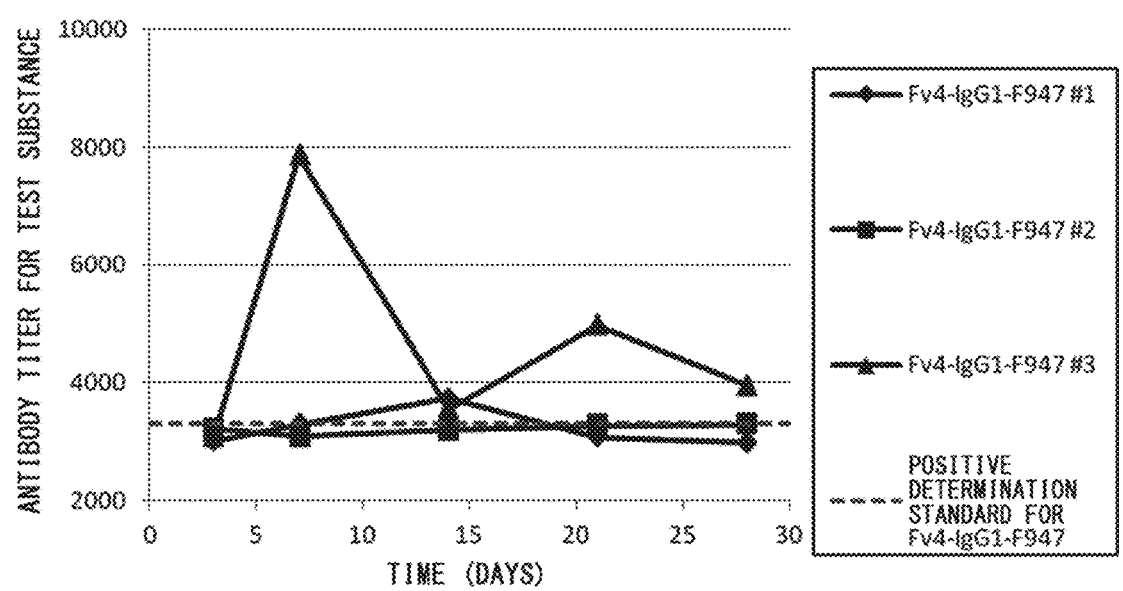
FIG. 26 is a graph showing titers of mouse antibody produced against Fv4-IgG1-F947, 3, 7, 14, 21, and 28 days after administration to human FcRn transgenic mice.
Figure 27:
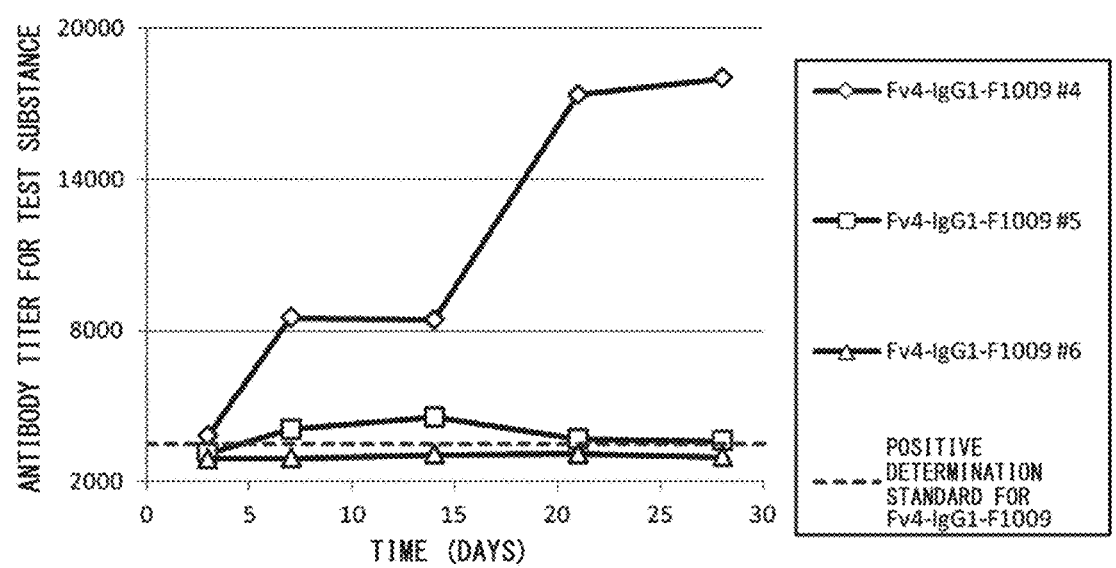
FIG. 27 is a graph showing titers of mouse antibody produced against Fv4-IgG1-F1009, 3, 7, 14, 21, and 28 days after administration to human FcRn transgenic mice.

FIG. 26 shows titers of mouse antibody produced in response to Fv4-IgG1-F947 at 3, 7, 14, 21 and 28 days after administration of Fv4-IgG1-F947 to human FcRn transgenic mice. Production of mouse antibody to Fv4-IgG1-F947 was shown to be positive in two of the three mice (#1 and #3) at 14 days after administration (positive rate: 2/3). On the other hand, FIG. 27 shows titers of mouse antibody produced in response to Fv4-IgG1-F1009 at 3, 7, 14, 21 and 28 days after administration of Fv4-IgG1-F1009 to human FcRn transgenic mice. Production of mouse antibody to Fv4-IgG1-F1009 was shown to be positive in two of the three mice (#4 and #5) starting 7 days after administration (positive rate: 2/3).

As was indicated in Example 5, Fv4-IgG1-821 has decreased binding to various types of mouse FcγR with respect to Fv4-IgG1-F11, Fv4-IgG1-F939 similarly has decreased binding to various types of mouse FcγR with respect to Fv4-IgG1-F890, and Fv4-IgG1-F1009 similarly has decreased binding to various types of mouse FcγR with respect to Fv4-IgG1-F947.

It was indicated that in vivo immunogenicity can be remarkably reduced by decreasing binding of Fv4-IgG1-F11 and Fv4-IgG1-F890 to various types of mouse FcγR. On the other hand, the effect of reducing in vivo immunogenicity was not demonstrated as a result of decreasing binding of Fv4-IgG1-F947 to various types of mouse FcγR.

Although not bound to a specific theory, the reason for observing this inhibitory effect on immunogenicity can be explained in the manner described below.

As was described in Example 3, inhibition of the formation of a quaternary complex on the cell membrane of antigen-presenting cells is thought to be possible by decreasing the binding activity to FcγR of antigen-binding molecules having binding activity to FcRn under conditions of the neutral pH region. As a result of inhibiting the formation of a quaternary complex, incorporation of antigen-binding molecules into antigen presenting cells is thought to be inhibited, and as a result thereof, induction of immunogenicity to the antigen-binding molecules is thought to be suppressed. Fv4-IgG1-F11 and Fv4-IgG1-F890 are thought to have suppressed induction of immunogenicity in this manner by decreasing binding activity to FcγR.

On the other hand, Fv4-IgG1-F947 did not demonstrate the effect of suppressing immunogenicity as a result of decreasing binding activity to FcγR. Although not bound to a specific theory, the reason for this can be discussed in the manner indicated below.

As shown in FIG. 16, elimination of Fv4-IgG1-F947 and Fv4-IgG1-F1009 from the plasma is extremely fast. Here, Fv4-IgG1-F1009 is thought to have undergone a decrease in binding activity to mouse FcγR, and the formation of a quaternary complex on antigen-presenting cells is thought to be inhibited. Consequently, Fv4-IgG1-F1009 is thought to be incorporated into cells as a result of binding only to FcRn expressed on the cell membrane of such cells as vascular endothelial cells or hematopoietic cells. Here, since FcRn is also expressed on the cell membranes of some antigen-presenting cells, Fv4-IgG1-F1009 can also be incorporated into antigen-presenting cells by binding only to FcRn. In other words, among the rapid elimination of Fv4-IgG1-F1009 from plasma, a portion may be incorporated into antigen-presenting cells.

Moreover, Fv4-IgG1-F1009 is a human antibody, and is a completely foreign protein to mice. In other words, mice are thought to have numerous T-cell populations that specifically respond to Fv4-IgG1-F1009. The mere small quantity of Fv4-IgG1-F1009 incorporated into antigen-presenting cells is presented to T cells after processing within cells, and since mice have numerous T-cell populations that specifically respond to Fv4-IgG1-F1009, an immune response to Fv4-IgG1-F1009 is thought to be easily induced. In reality, when a foreign protein in the form of human soluble IL-6 receptor is administered to mice as indicated in Reference Example 4, the human soluble IL-6 receptor is eliminated in a short period of time, and an immune response to the human soluble IL-6 receptor is induced. The fact that immunogenicity was induced even though human soluble IL-6 receptor does not have binding activity to FcγR and FcRn in the neutral pH region is thought to be due to the rapid elimination of human soluble IL-6 receptor and the large quantity being incorporated into antigen-presenting cells.

In other words, in the case when an antigen-binding molecule is a foreign protein (such as in the case of administering a human protein to mice), it is thought to be more difficult to suppress an immune response by inhibiting the formation of a quaternary complex on antigen-presenting cells in comparison with the case of the antigen-binding molecule being a homologous protein (such as in the case of administering a murine protein to mice).

In reality, in the case when the antigen-binding molecule is an antibody, since the antibody administered to humans is a humanized antibody or human antibody, an immune response occurs to homologous protein. Therefore, an evaluation was carried out in Example 11 as to whether or not inhibition of the formation of a quaternary complex leads to a reduction in immunogenicity by administering a mouse antibody to mice.

Example 11

In Vivo Immunogenicity Evaluation of Mouse Antibodies that have Binding Activity to Mouse FcRn under Conditions of the Neutral pH Region but do not have Binding Activity to Mouse FcγR (11-1) In Vivo Immunogenicity Study in Normal Mice The following study was conducted for the purpose of verifying the inhibitory effect on immunogenicity obtained by inhibiting the formation of a quaternary complex on antigen-presenting cells in the case when the antigen-binding molecule is a homologous protein (as in the case of administering a mouse antibody to mice).

Antibody production to mPM1-mIgG1-mF38, mPM1-mIgG1-mF40, mPM1-mIgG1-mF14 and mPM1-mIgG1-mF39 was evaluated using mouse plasma obtained in Example 6 according to the method indicated below.

(11-2) Measurement of Anti-administered Specimen Antibody in Plasma by Electrochemical Luminescence Antibody against an administered specimen present in mouse plasma was measured by electrochemical luminescence. First, the administered specimen was dispensed into a multi-array 96-well plate, followed by 1 hour of reaction at room temperature. After washing of the plate, 50-fold diluted mouse plasma measurement samples were prepared; and after 2 hours of reaction at room temperature and washing of the plate, the administered specimen ruthenated with Sulfo-Tag NHS Ester (Meso Scale Discovery) was dispensed, followed by overnight reaction at 4° C. After the plate was washed on the following day, Read Buffer T (×4) (Meso Scale Discovery) was dispensed, followed immediately by measurement with the Sector PR 2400 Reader (Meso Scale Discovery). The plasma from five animals that were not administered with the antibody was measured as a negative control sample for each measurement system, and the value (X) obtained by adding the product of multiplying the standard deviation (SD) of values measured using the plasma of those five animals by 1.645 to the mean (MEAN) of values measured using the plasma of the five animals, was used as the criterion for determining a positive reaction (Equation 3). Those animals that demonstrated a reaction exceeding positive criterion even once on any of the blood collection days were judged to have positive antibody production response to the test substance.

Positive evaluation criterion for antibody production
(X)=MEAN+1.645×SD　　　　　　　　　　　　　[Equation 3]

Figure 28:
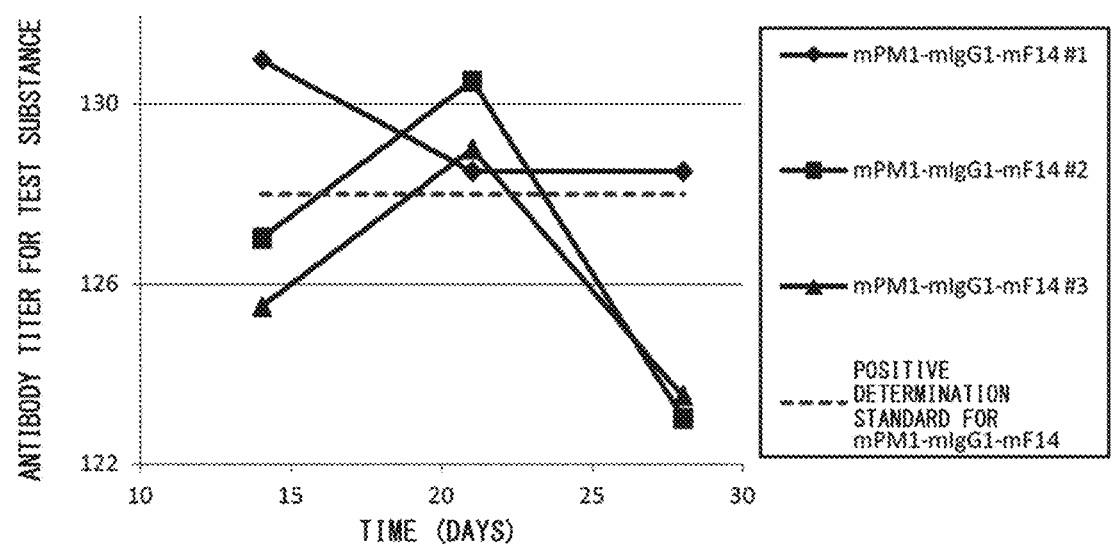
FIG. 28 is a graph showing titers of mouse antibody produced against mPM1-IgG1-mF14, 14, 21, and 28 days after administration to normal mice.
Figure 29:
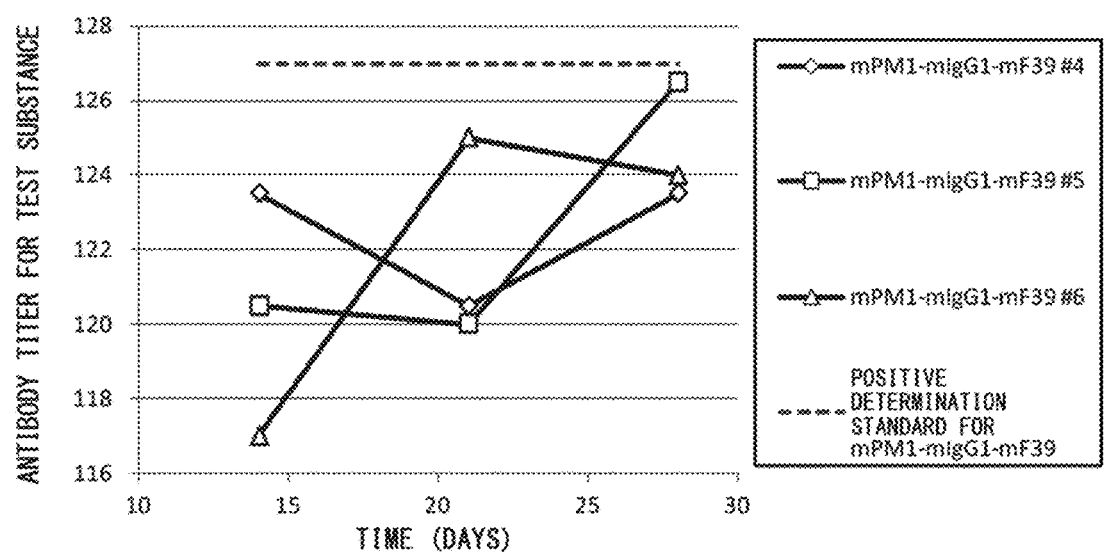
FIG. 29 is a graph showing titers of mouse antibody produced against mPM1-IgG1-mF39, 14, 21, and 28 days after administration to normal mice.

(11-3) Inhibitory Effect on in Vivo Immunogenicity by Decreasing Binding Activity to FcγR The results are shown in FIGS. 28 to 31. FIG. 28 shows the titers of mouse antibody produced in response to mPM1-mIgG1-mF14 at 14, 21 and 28 days after administration of mPM1-mIgG1-mF14 to normal mice. Production of mouse antibody to mPM1-mIgG1-mF14 was shown to be positive in all three mice at 21 days after administration (positive rate: 3/3). On the other hand, FIG. 29 shows the titers of mouse antibody produced in response to mPM1-mIgG1-mF39 at 14, 21 and 28 days after administration of mPM1-mIgG1-mF39 to normal mice. Production of mouse antibody to mPM1-mIgG1-mF39 was shown to be negative in all three of the mice on each day blood was collected following administration (positive rate: 0/3).

Figure 30:
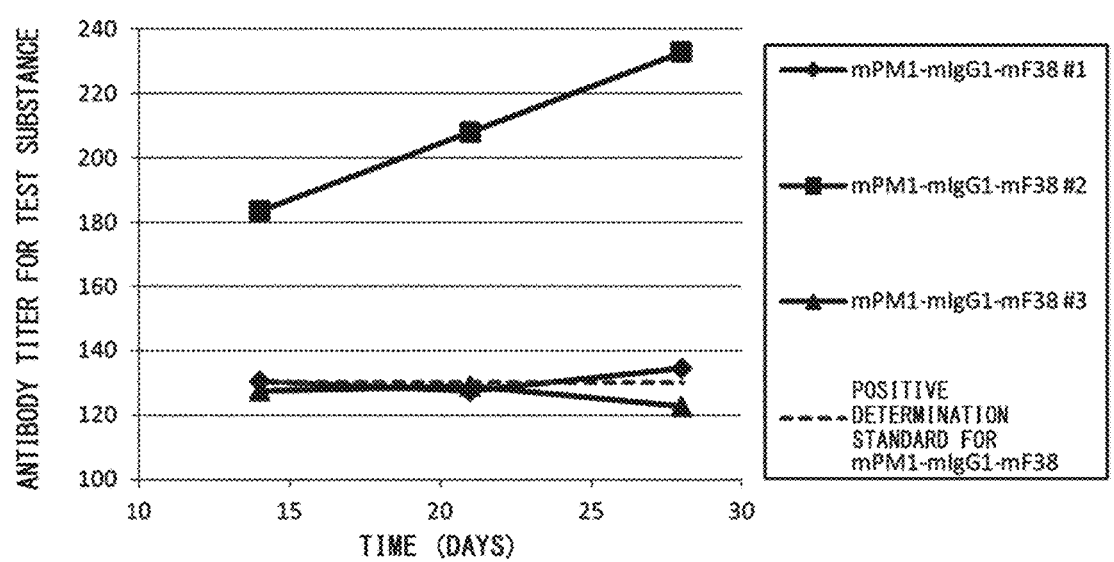
FIG. 30 is a graph showing titers of mouse antibody produced against mPM1-IgG1-mF38, 14, 21, and 28 days after administration to normal mice.
Figure 31:
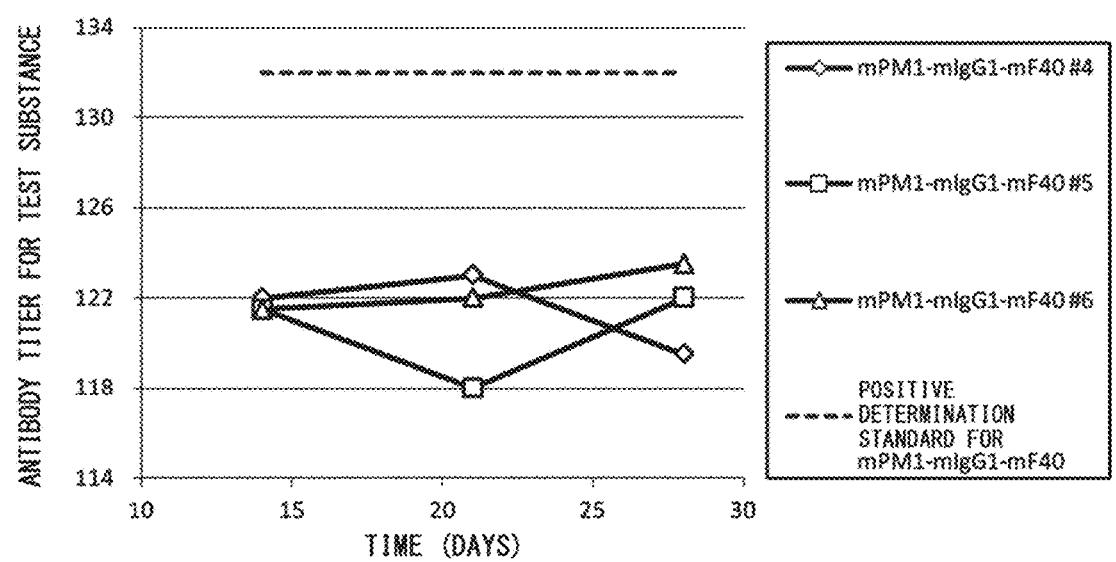
FIG. 31 is a graph showing titers of mouse antibody produced against mPM1-IgG1-mF40, 14, 21, and 28 days after administration to normal mice.

FIG. 30 shows titers of mouse antibody produced in response to mPM1-mIgG1-mF38 at 14, 21 and 28 days after administration of mPM1-mIgG1-mF38 to normal mice. Production of mouse antibody to mPM1-mIgG1-mF38 was shown to be positive in two of the three mice (#1 and #2) at 28 days after administration (positive rate: 2/3). On the other hand, FIG. 31 shows titers of mouse antibody produced in response to mPM1-mIgG1-mF40 at 14, 21 and 28 days after administration of mPM1-mIgG1-mF40 to normal mice. Production of mouse antibody to mPM1-mIgG1-mF40 was shown to be negative in all three mice on each day blood was collected following administration (positive rate: 0/3).

As was shown in Example 6, relative to mPM1-mIgG1-mF38, mPM1-mIgG1-mF40 has decreased binding to various types of mouse FcγR, and similarly relative to mPM1-mIgG1-mF14, mPM1-mIgG1-mF39 has decreased binding to various types of mouse FcγR.

These results confirmed that even if mouse antibodies mPM1-mIgG1-mF38 and mPM1-mIgG1-mF14 which are homologous proteins were administered to normal mice, antibody production was confirmed in response to the administered antibody and an immune response was confirmed. As indicated in Examples 1 and 2, this is thought to be due to promotion of the incorporation into antigen-presenting cells through formation of a quaternary complex on antigen-presenting cells by enhancing binding activity to FcRn in the neutral pH region.

It was shown that it is possible to reduce in vivo immunogenicity by inhibiting formation of a quaternary complex by decreasing binding of such antigen-binding molecules having binding activity to human FcRn in the neutral pH region to various types of mouse FcγR.

These results indicate that by decreasing binding activity to FcγR of an antigen-binding molecule having binding activity to FcRn under conditions of the neutral pH region, the immunogenicity of that antigen-binding molecule can be decreased extremely effectively both in vitro and in vivo. In other words, the immunogenicity of an antigen-binding molecule that has binding activity to FcRn under conditions of the neutral pH region and whose binding activity to active FcγR is lower than the binding activity of a native FcγR binding domain (namely, an antigen-binding molecule of Embodiment 1 described in Example 3) was indicated to be decreased remarkably in comparison with an antigen-binding molecule having binding activity roughly comparable to that of the native FcγR binding domain (namely, an antigen-binding molecule capable of forming a quaternary complex as described in Example 3).

Example 12

Production and Evaluation of Human Antibodies having Binding Activity to Human FcRn in the Neutral pH Region and whose Binding Activity to Human FcγR is Lower than Binding Activity of a Native FcγR-binding Domain (12-1) Production and Evaluation of Human IgG1 Antibodies having Binding Activity to Human FcRn in the Neutral pH Region and Whose Binding Activity to Human FcγR is Lower than Binding Activity of a Native FcγR-binding Domain In a non-limiting aspect of the present invention, although preferable examples of an Fc region whose binding activity to active FcγR is lower than binding activity to active FcγR of a naturally-occurring Fc region include Fc regions in which one or more amino acids at any of positions 234, 235, 236, 237, 238, 239, 270, 297, 298, 325 and 329 (EU numbering) among the amino acids of the aforementioned Fc region is modified to an amino acid that differs from the naturally-occurring Fc region, modification of the Fc region is not limited to that described above, but rather may also be, for example, deglycosylation (N297A, N297Q) described in Current Opinion in Biotechnology (2009) 20(6), 685-691, modifications such as IgG1-L234A/L235A, IgG1-A325A/A330S/P331S, IgG1-C226S/C229S, IgG1-C226S/C229S/E233P/L234V/L235A, IgG1-L234F/L235E/P331S, IgG1-S267E/L328F, IgG2-V234A/G237A, IgG2-H268Q/V309L/A330S/A331S, IgG4-L235A/G237A/E318A or IgG4-L236E, as well as modifications such as G236R/L328R, L235G/G236R, N325A/L328R or N325LL328R described in WO 2008/092117, insertion of amino acids at positions 233, 234, 235 and 237 (EU numbering), and modifications of the locations described in WO 2000/042072.

The Fv4-IgG1-F890 and Fv4-IgG1-F947 produced in Example 5 are antibodies that have binding activity to human FcRn under conditions of the neutral pH region and bind to human IL-6 receptor in a pH-dependent manner. Various variants have been produced in which binding to human FcγR was decreased by introducing amino acid substitutions into the amino acid sequences thereof (Table 17). More specifically, variants were produced including VH3-IgG1-F938 (SEQ ID NO: 156), in which Lys was substituted for Leu at position 235 (EU numbering) and Lys was substituted for Ser at position 239 of the amino acid sequence of VH3-IgG1-F890, VH3-IgG1-F1315 (SEQ ID NO: 157), in which Lys was substituted for Gly at position 237 (EU numbering) and Lys was substituted for Ser at position 239 of the amino acid sequence of VH3-IgG1-F890, VH3-IgG1-F1316 (SEQ ID NO: 158), in which Arg was substituted for Gly at position 237 (EU numbering) and Lys was substituted for Ser at position 239 in the amino acid sequence of VH3-IgG1-F890, VH3-IgG1-F1317 (SEQ ID NO: 159), in which Lys was substituted for Ser at position 239 (EU numbering) and Lys was substituted for Pro at position 329 in the amino acid sequence of VH3-IgG1-F890, VH3-IgG1-F1318 (SEQ ID NO: 160), in which Lys was substituted for Ser at position 239 (EU numbering) and Arg was substituted for Pro at position 329 of the amino acid sequence of VH3-IgG1-F890, VH3-IgG1-F1324 (SEQ ID NO: 161), in which Ala was substituted for Leu at position 234 (EU numbering) and Ala was substituted for Leu at position 235 of the amino acid sequence of VH3-IgG1-F890, VH3-IgG1-F1325 (SEQ ID NO: 162), in which Ala was substituted for Leu at position 234 (EU numbering), Ala was substituted for Leu at position 235 and Ala was substituted for Asn at position 297 of the amino acid sequence of VH3-IgG1-F890, VH3-IgG1-F1333 (SEQ ID NO: 163), in which Arg was substituted for Leu at position 235 (EU numbering), Arg was substituted for Gly at position 236 and Lys was substituted for Ser at position 239 of the amino acid sequence of VH3-IgG1-F890, VH3-IgG1-F1356 (SEQ ID NO: 164), in which Arg was substituted for Gly at position 236 (EU numbering) and Arg was substituted for Leu at position 328 of the amino acid sequence of VH3-IgG1-F890, VH3-IgG1-F1326 (SEQ ID NO: 155), in which Ala was substituted for Leu at position 234 (EU numbering) and Ala was substituted for Leu at position 235 of the amino acid sequence of VH3-IgG1-F947, and VH3-IgG1-F1327 (SEQ ID NO: 165), in which Ala was substituted for Leu at position 234 (EU numbering), Ala was substituted for Leu at position 235 and Ala was substituted for Asn at position 297 of the amino acid sequence of VH3-IgG1-F947.

TABLE 17

| MUTANT NAME | AMINO ACID SUBSTITUTION |
|---|---|
| G1d | |
| F890 | M252Y/N434Y/Y436V |
| F938 | L235K/S239K/M252Y/N434Y/Y436V |
| F939 | L235R/S239K/M252Y/N434Y/Y436V |
| F1315 | G237K/S239K/M252Y/N434Y/Y436V |
| F1316 | G237R/S239K/M252Y/N434Y/Y436V |
| F1317 | S239K/M252Y/P329K/N434Y/Y436V |
| F1318 | S239K/M252Y/P329R/N434Y/Y436V |
| F1324 | L234A/L235A/M252Y/N434Y/Y436V |
| F1325 | L234A/L235A/M252Y/N297A/N434Y/Y436V |
| F1333 | L235R/G236R/S239K/M252Y/N434Y/Y436V |
| F1356 | G236R/M252Y/L328R/N434Y/Y436V |
| F947 | T250V/M252Y/T307Q/V308P/Q311A/N434Y/Y436V |

TABLE 17-continued

| MUTANT NAME | AMINO ACID SUBSTITUTION |
|---|---|
| F1009 | L235R/S239K/T250V/M252Y/T307Q/V308P/Q311A/N434Y/Y436V |
| F1326 | L234A/L235A/T250V/M252Y/T307Q/V308P/Q311A/N434Y/Y436V |
| F1327 | L234A/L235A/T250V/M252Y/N297A/T307Q/V308P/Q311A/N434Y/Y436V |

(12-2) Confirmation of Binding Activity to Human FcRn and Human FcγR

Binding activity (dissociation constant KD) to human FcRn at pH 7.0 of antibodies containing each of the amino acid sequences produced in (12-1) as heavy chains and containing L(WT)-CK as light chain was measured using the method of Example 4. In addition, binding activity to human FcγR at pH 7.4 was measured using the method of Example 7. The measurement results are shown in Table 18 below.

TABLE 18

| MUTANT NAME | hFcRn KD(nM) | BINDING AMOUNT (RU) | | | | | |
|---|---|---|---|---|---|---|---|
| | | hFcgRIa | hFcgRIIa(R) | hFcgRIIa(H) | hFcgRIIb | hFcgRIIIa(F) | hFcgRIIIa(V) |
| G1d | ND | 374.86 | 166.62 | 162.97 | 88.89 | 120.92 | 233.51 |
| F890 | 107 | 363.43 | 128.07 | 116.52 | 54.14 | 63.54 | 179.55 |
| F938 | 161 | −0.49 | −0.12 | −0.05 | −0.14 | −0.34 | 1.20 |
| F939 | 153 | −2.37 | −0.80 | −0.90 | −0.20 | 0.51 | −0.75 |
| F1315 | 152 | −2.71 | −1.14 | −1.37 | 0.63 | −0.33 | −2.69 |
| F1316 | 149 | −0.12 | −0.33 | −0.34 | −0.44 | −0.26 | −0.42 |
| F1317 | 138 | −1.46 | −1.48 | −0.76 | −0.23 | −0.94 | −2.76 |
| F1318 | 143 | −0.31 | −1.59 | −1.12 | 0.26 | −1.03 | −3.63 |
| F1324 | 132 | 226.78 | 9.10 | 6.97 | 3.85 | 5.83 | 39.49 |
| F1325 | 213 | −0.47 | −1.17 | −0.62 | 1.46 | −0.54 | −2.40 |
| F1333 | 123 | −0.35 | −0.15 | −0.56 | −0.20 | −1.01 | −1.42 |
| F1356 | 158 | −0.90 | −0.23 | −0.22 | 0.63 | 4.09 | 0.09 |
| F947 | 11 | 367.87 | 147.83 | 154.42 | 70.56 | 104.52 | 221.45 |
| F1009 | 12 | 0.31 | −0.27 | −0.02 | 0.16 | −0.68 | 3.64 |
| F1326 | 11 | 264.64 | 11.74 | 11.42 | 5.46 | 9.51 | 61.62 |
| F1327 | 14 | 0.87 | −0.20 | −1.14 | 0.74 | −1.85 | −0.60 |

According to the results of Table 18, there are no particular limitations on the amino acid modifications introduced in order to decrease binding activity to various types of human FcγR in comparison with the binding activity of a native FcγR binding domain, and this can be accomplished by using various amino acid modifications.

(12-3) Production of an Anti-glypican-3 Binding Antibody

A comprehensive analysis was made of the binding to each FcγR of variants of amino acid residues thought to be the binding sites for FcγR in the Fc region of IgG1 in order to discover modifications in which binding to FcgR decreases in comparison with naturally-occurring IgG1. The variable region of an anti-glypican-3 antibody having improved plasma dynamics disclosed in WO 2009/041062 in the form of glypican-3 antibody containing the CDR of GpH7 (SEQ ID NO: 74) was used for the antibody H chain. Similarly, GpL16-k0 of the glypican-3 antibody which has improved plasma dynamics as disclosed in WO 2009/041062 (SEQ ID NO: 75) was used in common for the antibody L chain. In addition, B3, obtained by introducing a mutation of K439E into G1d, in which Gly and Lys had been deleted from the C terminus of IgG1 (SEQ ID NO: 76), was used for the antibody H chain constant region. This H chain is subsequently referred to as GpH7-B3 (SEQ ID NO: 77), while the L chain is subsequently referred to as GpL16-k0 (SEQ ID NO: 75).

(12-4) Kinetic Analysis of Binding to Various Types of FcγR

First, in order to verify the validity of comprehensive analysis using GpH7-B3/GpL16-k0 as a control, a comparison was made of binding ability to each FcgR between GpH7-B3/GpL16-k0 and GpH7-G1d/GpL16-k0 (Table 19). Binding to each human FcγR (FcγRIa, FcγRIIa(H), FcγRIIa (R), FcγRIIb and FcγRIIa(F)) of both antibodies following expression and purification according to the method of Reference Example 2 was evaluated according to the method indicated below.

Interaction between each modified antibody and Fcγ receptor prepared in the manner described above was analyzed using the BIACORE™ T100 surface plasmon resonance system (GE Healthcare), BIACORE™ T200 surface plasmon resonance system (GE Healthcare), BIACORE™ A100 surface plasmon resonance system or BIACORE™ 4000 surface plasmon resonance system. HBS-EP+ (GE Healthcare) was used for the running buffer, and measurements were carried out at 25° C. The chips used were chips in which antigen peptides, Protein A (Thermo Scientific), Protein A/G (Thermo Scientific) or Protein L (ACTIGEN® protein (Alltech or BioVision) were immobilized on the Series S Sensor Chip CM5 (GE Healthcare) or Series S Sensor Chip CM4 (GE Healthcare) by amine coupling, or chips in which preliminarily biotinylated antigen peptides were allowed to interact and then immobilized on the Series S Sensor Chip SA (certified) (GE Healthcare). The target antibodies were captured on these sensor chips, Fcγ receptor diluted with the running buffer was allowed to interact, followed by measurement of the amount of bound antibody. The amounts bound were compared between antibodies. However, since the amount of Fcγ receptor bound depends on the amount of captured antibody, the values used for comparison were first corrected by dividing the amount of Fcγ receptor bound by the captured amount of each antibody. Through reaction with 10 mM glycine-HCl at pH 1.5, the sensor chips were regenerated by washing off antibody captured on the sensor chips and used repeatedly.

Binding strength was analyzed according to the following method based on the results of analyzing the interaction with each FcγR. The value obtained by dividing the value of the amount of GpH7-B3/GpL16-k0 bound to FcγR by the value of the amount of GpH7-G1d/GpL16-k0 bound to FcγR, and multiplying that value by 100 was used as an indicator of relative binding activity to each FcγR. Based on the results shown in Table 19, since binding of GpH7-B3/GpL16-k0 to each FcgR was roughly equal to that of GpH7-G1d/GpL16-k0, it was judged that GpH7-B3/GpL16-k0 can be used as a control in subsequent studies.

TABLE 19

| VARIANT NAME | FcγRIa | FcγRIIaR | FcγRIIaH | FcγRIIb | FcγRIIIaF |
|---|---|---|---|---|---|
| GpH7-G1d/ GpL16-k0 | 100 | 100 | 100 | 100 | 100 |
| GpH7-B3/ GpL16-k0 | 109 | 94 | 92 | 88 | 88 |

(12-5) Production and Evaluation of Fc Mutants

Next, those amino acids and their surrounding amino acids thought to be involved in FcγR binding in the amino acid sequence of GpH7-B3 (from position 234 to position 239, position 265 to position 271, position 295, position 296, position 298, position 300 and position 324 to position 327 (EU numbering)) were respectively substituted with 18 types of amino acids excluding original amino acids and Cys. These Fc mutants are referred to as B3 variants. Binding of B3 variants, expressed and purified according to the method of Reference Example 2, to each FcγR (FcγRIa, FcγRIIa(H), FcγRIIa(R), FcγRIIb and FcγRIIIa(F)) was comprehensively evaluated according to the method of (12-4).

Binding strength was evaluated according to the following method based on the results of analyzing the interaction with each FcγR. The value of the amount of antibody derived from each B3 variant bound to FcγR was divided by the value of the amount of comparative antibody in which mutations were not introduced into B3 (antibody having the sequence of naturally-occurring human IgG1 at position 234 to position 239, position 265 to position 271, position 295, position 296, position 298, position 300 and position 324 to position 337, indicated by EU numbering) bound to FcγR. That value was then further multiplied by 100, and the resulting value was used as an indicator of relative binding activity to each FcγR.

Those modifications that decreased binding to all FcgR among from the analyzed variants are shown in Table 21. The 236 types of modifications shown in Table 20 are modifications that reduced binding to at least one type of FcgR in comparison with antibody prior to introduction of a modification (GpH7-B3/GpL16-k0), and are thought to be modifications having the effect of similarly reducing binding to at least one type of FcgR even when introduced into naturally-occurring IgG1.

Consequently, there are no particular limitations on the amino acid modifications introduced to decrease binding activity to each type of human FcγR in comparison with the binding activity of a native FcγR binding domain, and it was shown to be possible to achieve this by introducing the amino acid modifications shown in Table 20 into at least one location. In addition, the amino acid modifications introduced here may be at one location or a combination of multiple locations.

TABLE 20

| ALTERATION INTRODUCED INTO GpH7-B3 | FcgRIa | FcgRIIaR | FcgRIIaH | FcgRIIb | FcgRIIIaF |
|---|---|---|---|---|---|
| L234W | 94 | 64 | 63 | 90 | 36 |
| L234K | 54 | -2 | 1 | -3 | 1 |
| L234R | 50 | 0 | 2 | 0 | 4 |
| L234G | 28 | 9 | 11 | 10 | 11 |
| L234D | 31 | 51 | 18 | 77 | 51 |
| L234E | 82 | 48 | 21 | 62 | 63 |
| L234S | 63 | 20 | 21 | 19 | 22 |
| L234H | 65 | 21 | 29 | 24 | 32 |
| L234Q | 80 | 18 | 16 | 19 | 25 |
| L234T | 93 | 33 | 30 | 27 | 30 |
| L234A | 79 | 26 | 25 | 24 | 22 |
| L234P | 83 | 41 | 45 | 33 | 45 |
| L234M | 100 | 65 | 57 | 53 | 50 |
| L234N | 67 | 36 | 35 | 44 | 47 |
| L234F | 96 | 52 | 62 | 68 | 49 |
| L235K | -1 | -5 | 0 | -3 | 6 |
| L235R | 0 | -4 | 1 | -2 | 9 |
| L235G | 16 | 6 | 7 | 3 | 13 |
| L235Q | 29 | 28 | 34 | 20 | 35 |
| L235T | 8 | 28 | 47 | 26 | 48 |
| L235S | 11 | 29 | 39 | 23 | 36 |
| L235P | 3 | 38 | 33 | 32 | 47 |
| L235N | 3 | 35 | 37 | 27 | 35 |
| L235A | 66 | 50 | 48 | 37 | 49 |
| L235V | 69 | 50 | 68 | 47 | 77 |
| L235D | 1 | 87 | 60 | 88 | 60 |
| L235H | 2 | 91 | 88 | 66 | 28 |
| L235E | 15 | 72 | 52 | 64 | 56 |

TABLE 20-continued

| ALTERATION INTRODUCED INTO GpH7-B3 | FcgRIa | FcgRIIaR | FcgRIIaH | FcgRIIb | FcgRIIIaF |
|---|---|---|---|---|---|
| L235M | 93 | 72 | 72 | 63 | 42 |
| L235I | 93 | 81 | 89 | 88 | 85 |
| G236R | 6 | 0 | 3 | 0 | -1 |
| G236P | 2 | 12 | 22 | 1 | 1 |
| G236L | 18 | 20 | 23 | 4 | 1 |
| G236H | 34 | 32 | 91 | 6 | 7 |
| G236F | 81 | 23 | 68 | 15 | 24 |
| G236Y | 76 | 22 | 86 | 16 | 39 |
| G236M | 70 | 23 | 42 | 14 | 9 |
| G236Q | 45 | 38 | 80 | 19 | 8 |
| G236K | 13 | 9 | 18 | 19 | 1 |
| G236N | 42 | 54 | 81 | 75 | 8 |
| G237K | 2 | 0 | 0 | -1 | -1 |
| G237R | 3 | 0 | -1 | -1 | 0 |
| G237P | 3 | 8 | 0 | 5 | 0 |
| G237T | 27 | 13 | 2 | 7 | 2 |
| G237H | 12 | 14 | 1 | 11 | 0 |
| G237V | 8 | 55 | 10 | 12 | 2 |
| G237I | 6 | 69 | 6 | 29 | 2 |
| G237A | 45 | 85 | 9 | 49 | 4 |
| G237Q | 14 | 15 | 0 | 5 | 0 |
| G237Y | 7 | 77 | 4 | 85 | 0 |
| G237M | 14 | 56 | 1 | 36 | 0 |
| G237N | 15 | 75 | 0 | 65 | 0 |
| G237L | 7 | 58 | 1 | 51 | 0 |
| G237S | 50 | 45 | 3 | 26 | 1 |
| G237D | 26 | 74 | 0 | 95 | 0 |
| G237E | 18 | 23 | 1 | 18 | 0 |
| P238K | 8 | -2 | -1 | -2 | -1 |
| P238T | 67 | 19 | 6 | 8 | 0 |
| P238R | 1 | -1 | -1 | -2 | -1 |
| P238G | 65 | 4 | 1 | 27 | 0 |
| P238A | 95 | 38 | 15 | 26 | 5 |
| P238S | 91 | 32 | 13 | 28 | 3 |
| P238N | 64 | 5 | 1 | 27 | -1 |
| P238I | 99 | 43 | 19 | 31 | 3 |
| P238E | 95 | 21 | 2 | 97 | 1 |
| P238W | 99 | 25 | 2 | 13 | -1 |
| P238Q | 84 | 19 | 4 | 43 | -1 |
| P238H | 80 | 25 | 3 | 19 | -1 |
| S239K | 6 | 4 | 4 | 1 | 0 |
| S239Y | 69 | 11 | 5 | 12 | 6 |
| S239R | 52 | 8 | 13 | 5 | 1 |
| S239F | 77 | 20 | 11 | 12 | 3 |
| S239W | 69 | 19 | 9 | 17 | 19 |
| S239H | 64 | 38 | 19 | 24 | 6 |
| S239Q | 96 | 57 | 58 | 68 | 29 |
| S239P | 89 | 49 | 4 | 61 | -1 |
| D265Y | 5 | -1 | 0 | -2 | -1 |
| D265W | 3 | -1 | 0 | -2 | -2 |
| D265I | 2 | -1 | 0 | -2 | -1 |
| D265F | 2 | -1 | 0 | -2 | -2 |
| D265V | 3 | -1 | 0 | -1 | -1 |
| D265L | 7 | 0 | 0 | 0 | -1 |
| D265N | 3 | -1 | 0 | -2 | -1 |
| D265M | 17 | -1 | 0 | -2 | -1 |
| D265S | 20 | 0 | 2 | 1 | 2 |
| D265K | 8 | -1 | 0 | 0 | -2 |
| D265R | 5 | -1 | 0 | -1 | -1 |
| D265T | 48 | 2 | 5 | 1 | -2 |
| D265G | 11 | 1 | 1 | -1 | -1 |
| D265A | 36 | 3 | 5 | 1 | -1 |
| D265Q | 67 | 13 | 13 | 4 | -1 |
| D265H | 59 | 26 | 18 | 11 | 0 |
| V266R | 5 | -6 | -1 | -2 | -1 |
| V266P | 1 | -5 | -1 | -3 | -1 |
| V266K | 15 | 0 | -1 | -1 | -1 |
| V266D | 67 | 3 | 2 | 2 | 1 |
| V266E | 69 | -3 | 0 | 0 | -1 |
| V266Y | 75 | 18 | 2 | 15 | 0 |
| V266G | 86 | 27 | 10 | 22 | 3 |
| V266S | 79 | 26 | 5 | 18 | 3 |
| V266H | 62 | 22 | 2 | 14 | 0 |
| V266F | 80 | 91 | 8 | 88 | 2 |
| V266N | 84 | 58 | 32 | 40 | 5 |
| V266W | 78 | 37 | 0 | 26 | -1 |
| V266A | 95 | 68 | 41 | 55 | 26 |
| V266T | 89 | 66 | 18 | 52 | 12 |
| V266Q | 88 | 47 | 11 | 34 | 3 |
| S267R | 78 | -6 | -1 | 0 | 0 |
| S267K | 68 | 1 | 1 | 3 | 1 |
| S267P | 78 | 0 | 2 | 5 | 0 |
| S267Y | 96 | 10 | 2 | 14 | 1 |
| S267F | 91 | 13 | 1 | 18 | 0 |
| S267W | 97 | 26 | 2 | 29 | 2 |
| S267H | 95 | 27 | 3 | 42 | 1 |
| E269K | 71 | 4 | 22 | 1 | 11 |
| E269R | 72 | 2 | 13 | 0 | 7 |
| E269H | 95 | 12 | 24 | 8 | 12 |
| E269W | 96 | 21 | 30 | 13 | 9 |
| E269L | 98 | 20 | 40 | 12 | 10 |
| E269I | 94 | 16 | 32 | 9 | 10 |
| E269Q | 96 | 24 | 64 | 13 | 38 |
| E269Y | 97 | 21 | 43 | 13 | 14 |
| E269N | 90 | 24 | 31 | 15 | 21 |
| E269F | 99 | 19 | 41 | 13 | 10 |
| E269V | 92 | 16 | 35 | 10 | 12 |
| E269M | 98 | 23 | 50 | 15 | 20 |
| E269S | 93 | 33 | 48 | 19 | 29 |
| E269A | 93 | 20 | 51 | 13 | 28 |
| E269T | 93 | 35 | 39 | 19 | 26 |
| E269G | 94 | 38 | 46 | 25 | 27 |
| E269P | 93 | 34 | 33 | 26 | 14 |
| D270P | 64 | -3 | 0 | -1 | -1 |
| D270R | 45 | -5 | 11 | -5 | 2 |
| D270K | 45 | -4 | 16 | -5 | 5 |
| D270G | 82 | 3 | 29 | 3 | 6 |
| D270W | 74 | -2 | 38 | -2 | 7 |
| D270V | 84 | 1 | 37 | 3 | 19 |
| D270N | 68 | -1 | 34 | -2 | 13 |
| D270I | 88 | 3 | 43 | 1 | 23 |
| D270S | 73 | 0 | 49 | -1 | 17 |
| D270Y | 78 | -2 | 53 | -2 | 9 |
| D270H | 70 | 0 | 53 | -2 | 11 |
| D270Q | 82 | 2 | 78 | 0 | 49 |
| D270M | 90 | 7 | 57 | 6 | 29 |
| D270A | 87 | 3 | 66 | 5 | 23 |
| D270F | 88 | 5 | 62 | 5 | 12 |
| D270L | 90 | 6 | 61 | 3 | 33 |
| D270T | 81 | 1 | 38 | -2 | 9 |
| P271Y | 98 | 38 | 48 | 28 | 33 |
| P271W | 100 | 46 | 75 | 33 | 57 |
| P271F | 99 | 49 | 55 | 38 | 39 |
| P271H | 98 | 58 | 58 | 53 | 50 |
| P271R | 100 | 89 | 99 | 87 | 76 |
| P271S | 99 | 83 | 67 | 82 | 62 |
| P271T | 98 | 73 | 42 | 78 | 31 |
| Q295W | 81 | 26 | 38 | 16 | 10 |
| Q295G | 89 | 36 | 41 | 28 | 55 |
| Q295S | 100 | 524 | 67 | 40 | 87 |
| Q295D | 95 | 43 | 37 | 40 | 64 |
| Q295H | 97 | 45 | 78 | 29 | 52 |
| Q295F | 99 | 46 | 74 | 30 | 46 |
| Q295N | 99 | 56 | 74 | 41 | 68 |
| Q295R | 100 | 61 | 94 | 46 | 52 |
| Q295Y | 95 | 38 | 70 | 24 | 49 |
| Y296P | 45 | 10 | 8 | 7 | 8 |
| Y296K | 99 | 70 | 66 | 45 | 21 |
| Y296G | 100 | 77 | 83 | 58 | 21 |
| Y296R | 100 | 77 | 74 | 52 | 38 |
| S298P | 15 | 0 | 0 | -1 | 0 |
| S298W | 69 | 19 | 17 | 9 | 11 |
| S298R | 92 | 62 | 36 | 22 | 20 |
| S298K | 88 | 79 | 38 | 34 | 25 |
| S298Y | 100 | 33 | 35 | 23 | 71 |
| S298G | 100 | 89 | 43 | 68 | 59 |
| Y300P | 9 | -1 | 0 | -1 | -1 |
| Y300R | 91 | 38 | 34 | 25 | 12 |
| Y300K | 95 | 59 | 56 | 45 | 35 |
| S324K | 94 | 75 | 97 | 64 | 74 |
| S324P | 91 | 34 | 14 | 36 | 35 |
| N325K | 55 | 0 | 0 | -1 | -2 |

TABLE 20-continued

| ALTERATION INTRODUCED INTO GpH7-B3 | FcgRIa | FcgRIIaR | FcgRIIaH | FcgRIIb | FcgRIIIaF |
|---|---|---|---|---|---|
| N325R | 56 | 0 | 1 | 0 | −1 |
| N325P | 50 | 2 | 1 | 3 | 0 |
| N325A | 94 | 38 | 14 | 27 | 6 |
| N325H | 93 | 34 | 13 | 27 | 37 |
| N325T | 98 | 59 | 27 | 49 | 10 |
| N325W | 94 | 55 | 4 | 48 | −2 |
| N325V | 84 | 37 | 9 | 35 | 2 |
| N325I | 94 | 76 | 8 | 97 | 1 |
| N325F | 92 | 65 | 6 | 72 | −1 |
| N325Y | 92 | 42 | 9 | 39 | 5 |
| N325G | 95 | 26 | 7 | 22 | 1 |
| A327R | 51 | −11 | −2 | −3 | 1 |
| A327K | 57 | −8 | 0 | 0 | 5 |
| A327Q | 94 | 34 | 47 | 29 | 18 |
| A327M | 95 | 38 | 55 | 40 | 24 |
| A327Y | 97 | 17 | 26 | 18 | 13 |
| A327L | 98 | 31 | 16 | 34 | 13 |
| A327H | 93 | 32 | 23 | 35 | 14 |
| A327F | 95 | 17 | 37 | 22 | 16 |
| A327P | 95 | 14 | 16 | 18 | 20 |
| A327W | 100 | 34 | 21 | 34 | 17 |
| A327I | 98 | 37 | 12 | 46 | 8 |
| A327S | 88 | 59 | 51 | 62 | 42 |
| A327T | 64 | 27 | 12 | 37 | 10 |
| A327V | 97 | 46 | 17 | 43 | 18 |
| L328K | 30 | −17 | −2 | −4 | 0 |
| L328R | 26 | −13 | −1 | −3 | −1 |
| L328P | 78 | 15 | 8 | 15 | 3 |
| L328G | 92 | 66 | 52 | 62 | 8 |
| L328H | 95 | 76 | 47 | 82 | 13 |
| L328N | 98 | 25 | 34 | 78 | 22 |
| P329K | 6 | −2 | −1 | −2 | −1 |
| P329R | 9 | −2 | −1 | −3 | −2 |
| P329M | 69 | 2 | 2 | 0 | 0 |
| P329L | 68 | 2 | 2 | 1 | 0 |
| P329Q | 43 | −1 | 0 | −2 | −1 |
| P329F | 79 | 1 | 1 | 0 | 0 |
| P329I | 89 | 22 | 21 | 13 | 2 |
| P329T | 43 | −2 | 0 | −4 | −1 |
| P329V | 95 | 24 | 28 | 13 | 7 |
| P329H | 50 | −1 | 0 | −3 | −1 |
| P329N | 45 | 4 | 5 | 0 | 3 |
| P329S | 60 | 0 | 1 | −1 | 1 |
| P329G | 92 | 1 | 1 | 0 | 4 |
| P329W | 94 | 1 | 0 | 0 | 0 |
| P329Y | 76 | −1 | 0 | −3 | 0 |
| P329E | 33 | −1 | 0 | −2 | −1 |
| P329D | 23 | −1 | −1 | −2 | −1 |
| A330S | 58 | 0 | 0 | −3 | 0 |
| A330P | 87 | 42 | 25 | 39 | 56 |
| P331G | 88 | 13 | 9 | 8 | 9 |
| P331R | 95 | 64 | 59 | 55 | 38 |
| P331K | 98 | 72 | 58 | 63 | 34 |
| I332R | 95 | 28 | 70 | 23 | 61 |
| I332K | 77 | 12 | 59 | 27 | 7 |
| I332P | 100 | 34 | 26 | 41 | 14 |

(12-6) Production and Evaluation of a Human IgG2 Antibody and a Human IgG4 Antibody that have Binding Activity to Human FcRn in the Neutral pH Region and whose Binding Activity to Human FcγR is Lower than the Binding Activity of a Native FcγR-binding Domain An Fc region that has binding activity to human FcRn in the neutral pH region and whose binding activity to human FcγR is lower than the binding activity of a native FcγR binding domain was produced in the manner described below using human IgG2 or human IgG4.

Antibody containing VH3-IgG2 (SEQ ID NO: 166) for the heavy chain and L(WT)-CK (SEQ ID NO: 41) for the light chain was produced according to the method shown in Reference Example 2 for use as human IL-6 receptor-binding antibody having human IgG2 for the constant region. Similarly, antibody containing VH3-IgG4 (SEQ ID NO: 167) for the heavy chain and L(WT)-CK (SEQ ID NO: 41) for the light chain was produced according to the method shown in Reference Example 2 for use as human IL-6 receptor-binding antibody having human IgG4 for the constant region.

Amino acid substitutions were introduced into each constant region of VH3-IgG2 and VH3-IgG4 in order to impart human FcRn-binding activity under conditions of the neutral pH region. More specifically, VH3-IgG2-F890 (SEQ ID NO: 168) and VH3-IgG4-F890 (SEQ ID NO: 169) were produced by an amino acid substitution of VH3-IgG2 and VH3-IgG4 in which Tyr was substituted for Met at position 252 (EU numbering), Tyr was substituted for Asn at position 434 and Val was substituted for Tyr at position 436.

Amino acid substitutions were introduced into each constant region of VH3-IgG2-F890 and VH3-IgG4-F890 in order to lower binding to human FcγR. More specifically, VH3-IgG2-F939 (SEQ ID NO: 170) was produced by an amino acid substitution of VH3-IgG2-F890 in which Arg was substituted for Ala at position 235 (EU numbering) and Lys was substituted for Ser at position 239. In addition, VH3-IgG4-F939 (SEQ ID NO: 171) was produced by an amino acid substitution of VHE-IgG4-F890 in which Arg was substituted for Leu at position 235 (EU numbering) and Lys was substituted for Ser at position 239.

Antibody containing the produced VH3-IgG2-F890, VH3-IgG4-F890, VH3-IgG2-F939 or VH3-IgG4-F939 as heavy chain and L(WT)-CK (SEQ ID NO: 41) as light chain was produced according to the method shown in Reference Example 2.

(12-7) Evaluation of a Human IgG2 Antibody and a Human IgG4 Antibody that have Binding Activity to Human FcRn in the Neutral pH Region and Whose Binding Activity to Human FcγR is Lower than the Binding Activity of a Native FcγR-binding Domain Binding activity (dissociation constant IUD) to human FcRn at pH 7.0 of the antibody (Table 21) produced in (12-6) was measured using the method of Example 4. In addition, binding activity to human FcγR at pH 7.4 was measured using the method of Example 7. The measurement results are shown in Table 22 below.

TABLE 21

| MUTANT NAME | AMINO ACID SUBSTITUTION |
|---|---|
| IgG2 | |
| IgG2-F890 | M252Y/N434Y/Y436V |
| IgG2-F939 | A235R/S239K/M252Y/N434Y/Y436V |
| IgG4 | |
| IgG4-F890 | M252Y/N434Y/Y436V |
| IgG4-F939 | L235R/S239K/M252Y/N434Y/Y436V |

TABLE 22

| MUTANT NAME | hFcRn KD(nM) | BINDING AMOUNT(RU) | | | | | |
|---|---|---|---|---|---|---|---|
| | | hFcgRIa | hFcgRIIa(R) | hFcgRIIa(H) | hFcgRIIb | hFcgRIIIa(F) | hFcgRIIIa(V) |
| IgG2 | ND | 38.6 | 187.8 | 265.9 | 55.5 | 16.3 | 50.1 |
| IgG2-F890 | 110 | 19.7 | 120.5 | 203.7 | 31.9 | 9.3 | 28.1 |
| IgG2-F939 | 140 | 1.3 | 1.0 | 1.0 | 0.4 | 0.6 | 1.1 |
| IgG4 | ND | 379.2 | 123.5 | 71.1 | 109.9 | 10.9 | 39.6 |
| IgG4-F890 | 140 | 367.0 | 92.8 | 37.5 | 71.8 | 3.4 | 15.5 |
| IgG4-F939 | 110 | 1.2 | −0.2 | −0.7 | 0.4 | −1.7 | −0.5 |

The results of Table 22 showed that it is possible to achieve an Fc region that has binding activity to human FcRn in the neutral pH region and whose binding activity to human FcγR is lower than the binding activity of a native FcγR binding domain by using human IgG1 without particular limitation, and human IgG2 or IgG4 can also be used.

Example 13

Production and Evaluation of an Antigen-binding Molecule in which Only One of Two Polypeptides that Compose the FcRn-binding Domain has Binding Activity to FcRn under Conditions of the Neutral pH Region An antigen-binding molecule in which only one of the two polypeptides that compose the FcRn-binding domain has binding activity to FcRn under conditions of the neutral pH region, while the other does not have binding activity to FcRn under conditions of the neutral pH region as shown in Embodiment 3 in Example 3, was produced in the manner indicated below.

(13-1) Production of an Antigen-binding Molecule in which Only One of Two Polypeptides that Compose the FcRn-binding Domain has Binding Activity to FcRn Under Conditions of the Neutral pH Region while the other does not have Binding Activity to FcRn Under Conditions of the Neutral pH Region First, VH3-IgG1-F947 (SEQ ID NO: 70) was produced according to the method of Reference Example 1 as the heavy chain of an anti-human IL-6R antibody having binding activity to FcRn under conditions of the neutral pH region. In addition, VH3-IgG1-F46 (SEQ ID NO: 71) was produced by adding an amino acid substitution obtained by substituting Ala for Ile at position 253 (EU numbering) VH3-IgG1 for use as an antigen-binding molecule that does not having binding activity to FcRn in both the acidic pH region and neutral pH region.

The use of Fc regions in which one Fc region of an antibody contains substitutions in which Lys is substituted for Asp at position 356 (EU numbering) and Lys is substituted for Glu at position 357 (EU numbering), and the other Fc region contains substitutions in which Glu is substituted for Lys at position 370 (EU numbering), Arg is substituted for His at position 435 (EU numbering) and Glu is substituted for Lys at position 439 (EU numbering) is known as a method for obtaining a heterodimer of an antibody with high purity (WO 2006/106905).

VH3-IgG1-FA6a (SEQ ID NO: 72) was produced in which Lys is substituted for Asp at position 356 (EU numbering) and Lys is substituted for Glu at position 357 (EU numbering) of VH3-IgG1-F947 (hereinafter referred to as Heavy Chain A). In addition, VH3-IgG1-FB4a (SEQ ID NO: 73) was produced in which Glu is substituted for Lys at position 370 (EU numbering), Arg is substituted for His at position 435 (EU numbering) and Glu is substituted for Lys at position 439 (EU numbering) of VH3-IgG1-F46 (hereinafter referred to as Heavy Chain B) (Table 23).

TABLE 23

| MUTANT NAME | | AMINO ACID SUBSTITUTION | hFcRn KD (nM) |
|---|---|---|---|
| HEAVY CHAIN A | FA6a | T250V/M252Y/T307Q/V308P/Q311A/D356K/E357K/N434Y/Y436V | 11 |
| HEAVY CHAIN B | FB4a | I253A/K370E/H435R/K439E | ND |

Fv4-IgG1-FA6a/FB4a was produced with reference to the method of Reference Example 2 that has VH3-IgG1-FA6a and VH3-IgG1-FB4a as heavy chains, and VL3-CK for the light chain by adding equal amounts of heavy chain plasmids in the form of VH3-IgG1-FA6a and VH3-IgG1-FB4a.
(13-2) PK Study of an Antigen-binding Molecule in which Only One of Two Polypeptides that Compose the FcRn-binding Domain has Binding Activity to FcRn under Conditions of the Neutral pH Region while the other does not have Binding Activity to FcRn under Conditions of the Neutral pH Region A PK study was conducted according to the method described below in administration of Fv4-IgG1-F947 and Fv4-IgG1-FA6a/FB4a to human FcRn transgenic mice.

Anti-human IL-6 receptor antibody was administered at 1 mg/kg in a single administration beneath the skin of the back of human FcRn transgenic mice (B6.mFcRn−/−.hFcRn Tg line 32+/+mouse, Jackson Laboratories, Methods Mol. Biol. (2010)602, 93-104). Blood was collected at 15 minutes, 7 hours and 1, 2, 3, 4 and 7 days after administration of the anti-human IL-6 receptor antibody. Plasma was obtained by immediately centrifuging the collected blood for 15 minutes at 4° C. and 15,000 rpm. The separated plasma was stored in a freezer set to −20° C. or lower until the time of measurement.

Figure 32:
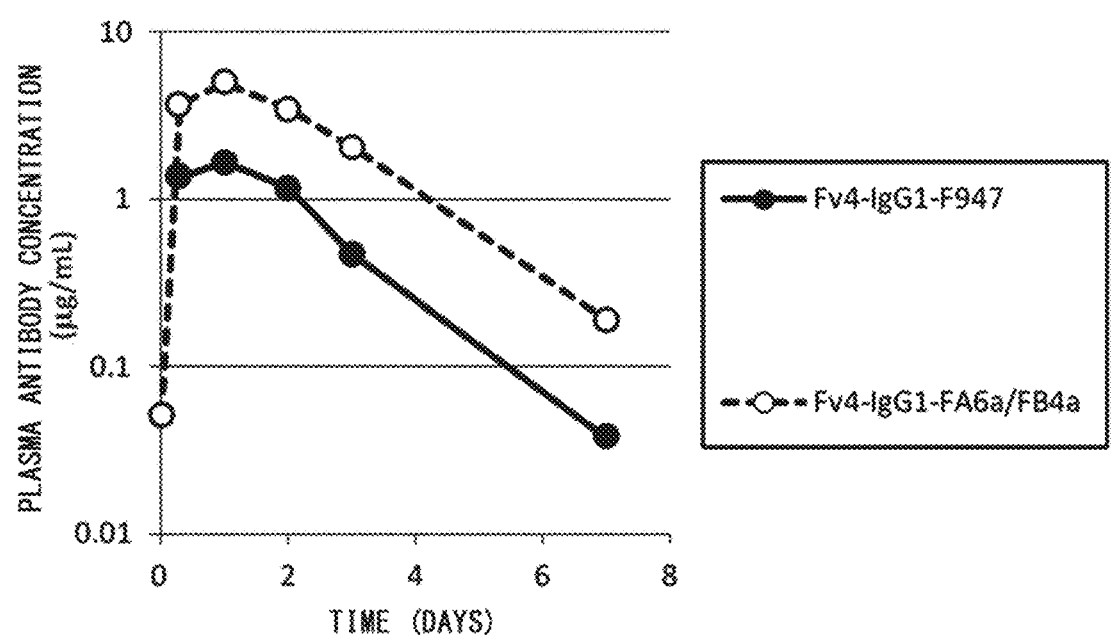
FIG. 32 is a graph showing the plasma antibody concentrations for Fv4-IgG1-F947 and Fv4-IgG1-FA6a/FB4a 15 minutes, seven hours, one, two, three, four, and seven days after administration to human FcRn transgenic mice.
Figure 33:
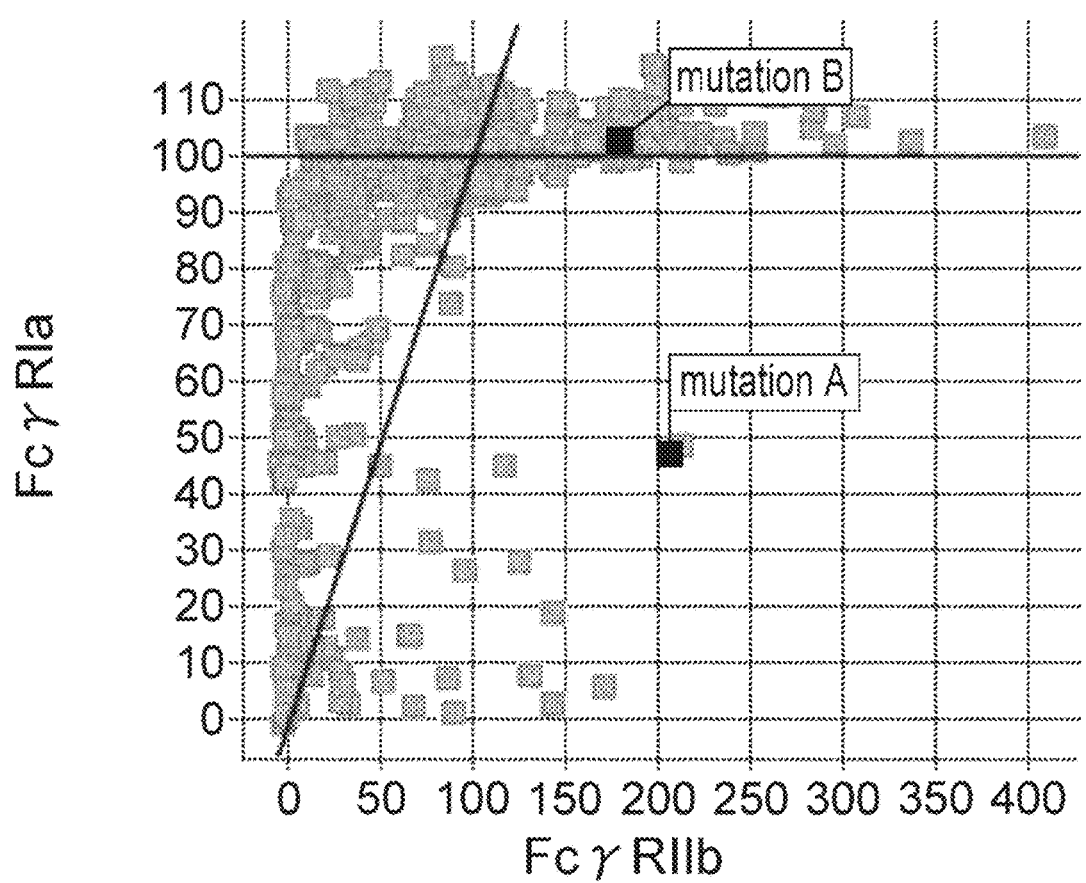
FIG. 33 is a diagram showing variance in the binding of each B3 mutant to FcγRIIb and FcγRIa.
Figure 34:
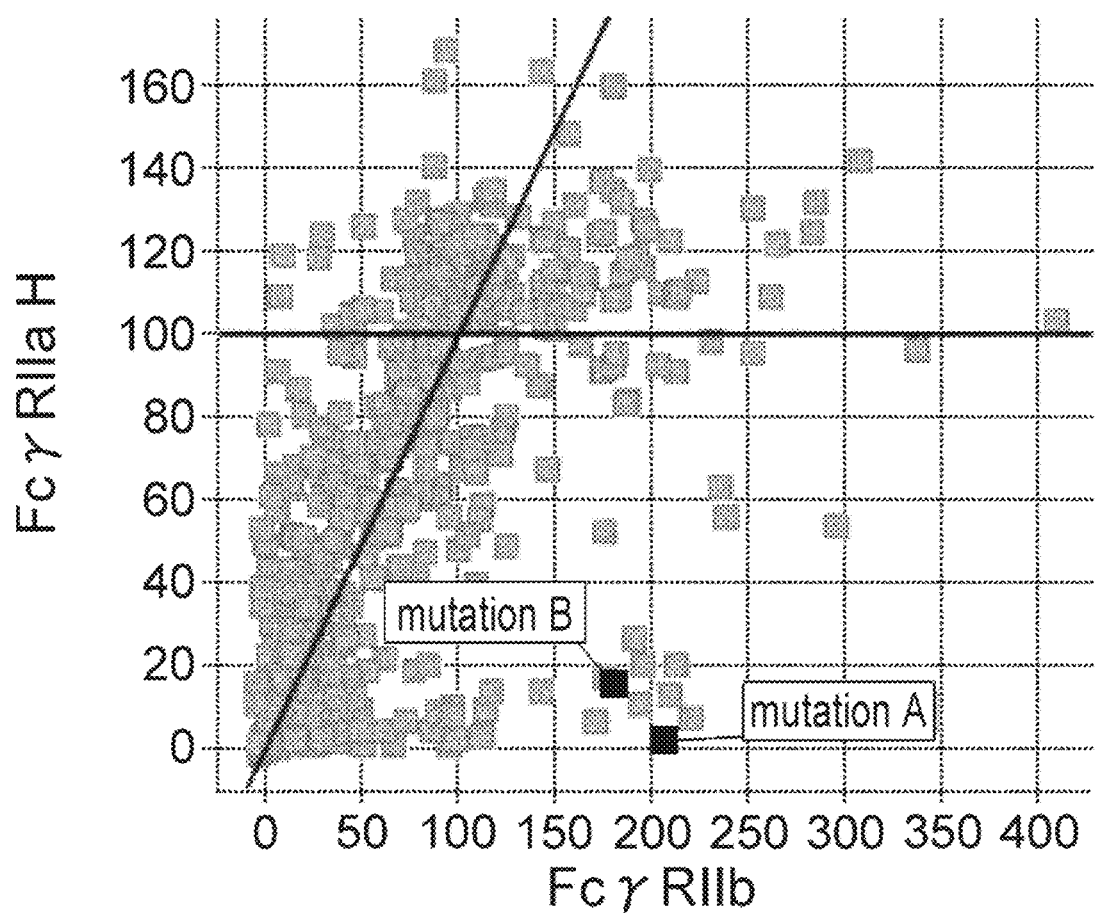
FIG. 34 is a diagram showing variance in the binding of each B3 mutant to FcγRIIb and FcγRIIa(H).
Figure 35:
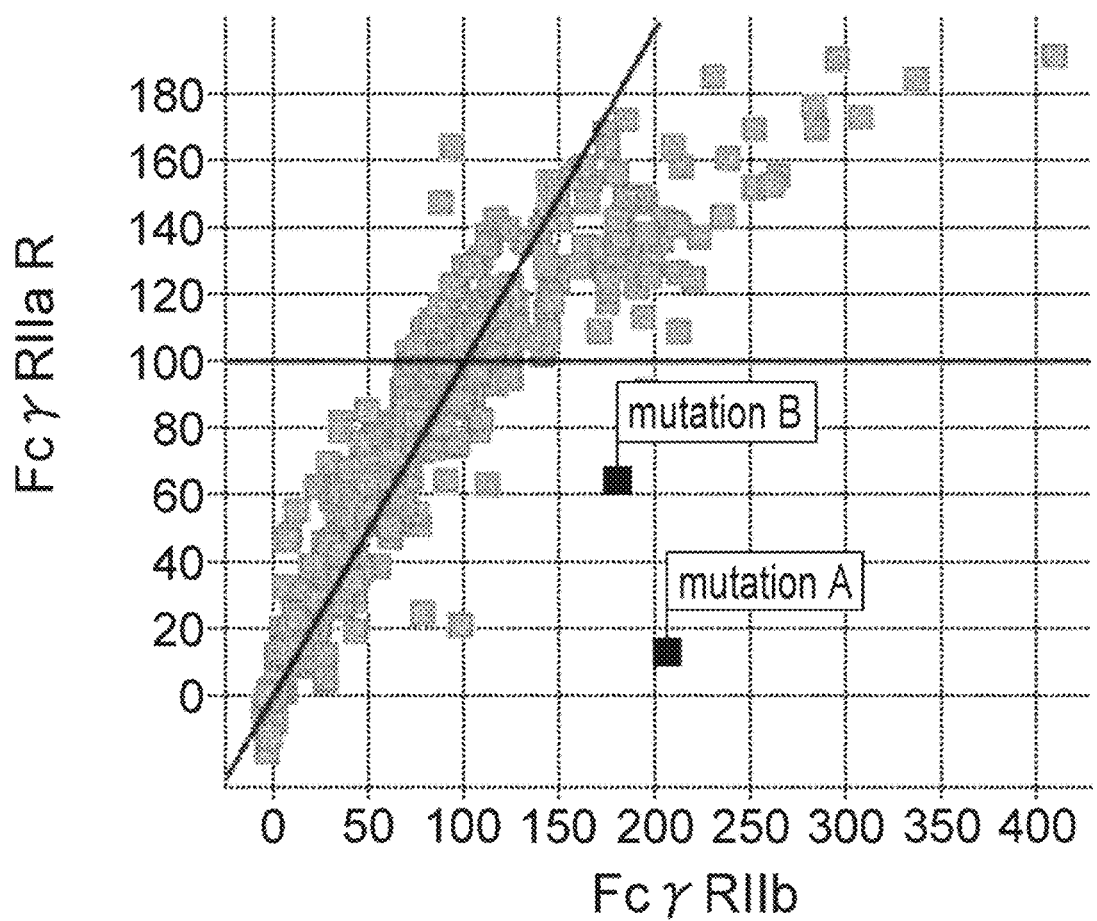
FIG. 35 is a diagram showing variance in the binding of each B3 mutant to FcγRIIb and FcγRIIa(R).
Figure 36:
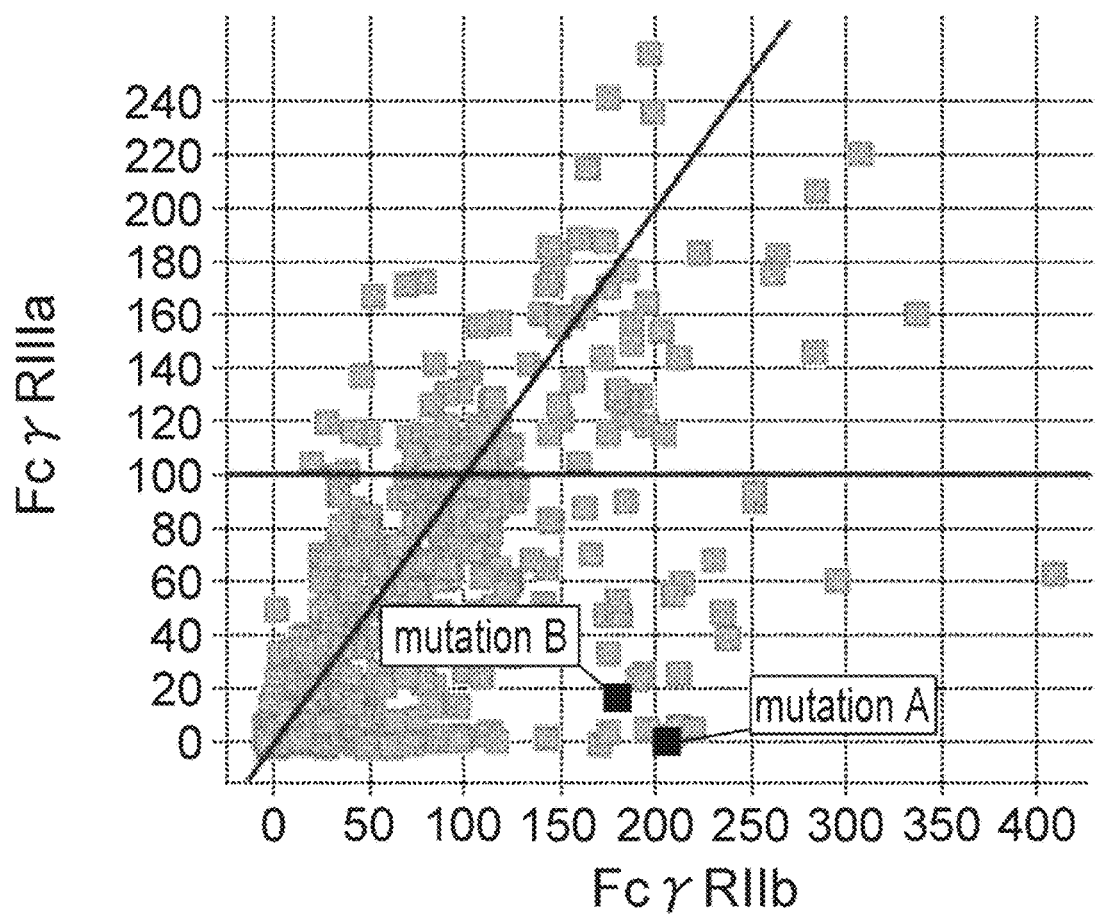
FIG. 36 is a diagram showing variance in the binding of each B3 mutant to FcγRIIb and FcγRIIIa.

Concentration of the anti-human IL-6 receptor antibody in mouse plasma was measured by ELISA in the same manner as the method of Example 4. The results are shown in FIG. 32. Fv4-IgG1-FA6a/FB4a, which is able to bind to only one molecule of human FcRn through a single binding region, was shown to demonstrate a shift of higher plasma concentration in comparison with Fv4-IgG1-F947, which is able to bind to two molecules of human FcRn through two binding regions.

As was previously described, although there are two FcRn-binding regions in the Fc region of IgG, it has been reported that molecules having an Fc from which one of the two FcRn binding regions has been deleted are eliminated from plasma more rapidly in comparison with molecules having a naturally-occurring Fc region (Scand. J. Immunol., 1994; 40:457-465). In other words, IgG having two binding regions that bind to FcRn under conditions of the acidic pH region are known to demonstrate improved plasma retention in comparison with IgG having a single FcRn binding region. These showed that IgG incorporated into cells is recycled back into plasma by binding to FcRn within endosomes, and since naturally-occurring IgG is able to bind to two molecules of FcRn by means of two FcRn binding regions, it binds to FcRn with a high binding capacity and a large amount of IgG is therefore thought to be recycled. On the other hand, IgG having only a single FcRn-binding region has a low binding capacity for FcRn within endosomes, and since it cannot be adequately recycled, it is thought to be eliminated from plasma more rapidly.

Consequently, in Fv4-IgG1-FA6a/FB4a having only a single FcRn-binding site under conditions of the neutral pH region as shown in FIG. 32, the phenomenon by which an improvement in plasma retention is observed was completely unexpected since it is the opposite of that in the case of naturally-occurring IgG.

Although the present invention is not bound to a specific theory, one possible reason for the observed transition of these high levels of plasma retention is an increase in the absorption rate of antibody from beneath the skin in subcutaneous administration of antibody to mice.

In general, antibody that has been administered subcutaneously is thought to migrate to the plasma after being absorbed through the lymphatic system (J. Pharm. Sci. (2000)89(3), 297-310). Since a large number of immune cells are present in the lymphatic system, antibody that has been administered subcutaneously is thought to migrate to the plasma after being exposed to a large number of immune cells. In general, immunogenicity is known to be enhanced when antibody pharmaceutical preparations are administered subcutaneously in comparison with their intravenous administration, and one possible cause of this is that subcutaneously administered antibodies are exposed to a large number of immune cells in the lymphatic system. In reality, as shown in Example 1, it was confirmed that when subcutaneously administered, Fv4-IgG1-F1 was rapidly eliminated from the plasma, and this suggests production of mouse antibody to Fv4-IgG1-F1. On the other hand, in the case of intravenous administration, rapid elimination of Fv4-IgG1-F1 from plasma was not confirmed, suggesting that mouse antibody to Fv4-IgG1-F1 was not produced.

Namely, during the course of absorption of a subcutaneously administered antibody, when the antibody is incorporated into immune cells present in the lymphatic system, it causes a decrease in bioavailability and at the same time becomes a cause of immunogenicity.

However, in the case of subcutaneous administration of the antigen-binding molecule shown as an example of Embodiment 3 in Example 3 in which only one of two polypeptides that compose the FcRn-binding domain has binding activity to FcRn under conditions of the neutral pH region while the other polypeptide does not have binding activity to FcRn under conditions of the neutral pH region, even if exposed to immune cells present in the lymphatic system during the course of absorption, a quaternary complex is not thought to be formed on the cell membrane of immune cells. Consequently, an increase in bioavailability occurs due to inhibition of incorporation into immune cells present in the lymphatic system, and as a result, it is considered possible that an increase in plasma concentration might have occurred.

Methods for causing an increase in plasma concentration or decrease in immunogenicity by increasing the bioavailability of a subcutaneously administered antibody are not limited to antigen-binding molecules shown as Embodiment 3 of Example 3. Rather, any antigen-binding molecule may be used provided it is an antigen-binding molecule that does not form a quaternary complex on the cell membrane of immune cells. That is, when administered subcutaneously, any of the antigen-binding molecules of Embodiments 1, 2 and 3 is thought to be able to improve plasma retention and at the same time increase bioavailability, and further cause a decrease in immunogenicity, in comparison with antigen-binding molecules capable of forming a quaternary complex.

A portion of antigen-binding molecules that remain in plasma are thought to always migrate to the lymphatic system. In addition, immune cells are also present in blood. Consequently, although adaptation of the present invention is by no means limited to a specific administration route, an example expected to demonstrate effects particularly easily is thought to be an administration route that is mediated by the lymphatic system during the course of absorption of an antigen-binding molecule, and one of these examples is subcutaneous administration.

Example 14

Production of Antibody having Binding Activity to Human FcRn under Conditions of the Neutral pH Region and Selective Binding Activity to Inhibitory FcγR In addition, the antigen-binding molecule of Embodiment 2 shown in Example 3 can be produced by using a modification that brings about enhancement of selective binding activity to inhibitory FcγRIIb for an antigen-binding molecule having enhanced binding to FcRn under neutral conditions. In other words, an antigen-binding molecule that has binding activity to FcRn under neutral conditions and into which a modification is introduced to bring about enhancement of selective binding activity to inhibitory FcγRIIb is able to form a quaternary complex mediated by two molecules of FcRn and one molecule of FcγR. However, since selective binding to inhibitory FcγR is brought about by the effect of that modification, binding activity to active FcγR is reduced. It is thought that a quaternary complex containing inhibitory FcγR is preferentially formed on antigen-presenting cells as a result. As previously described, it is thought that immunogenicity is caused by the formation of a quaternary complex containing active FcγR, and immune response can be inhibited as a result of forming a quaternary complex containing inhibitory FcγR in this manner.

Therefore, the following study was conducted in order to discover amino acid mutations that bring about enhancement of selective binding activity to inhibitory FcγRIIb.
(14-1) Comprehensive Analysis of FcγR Binding of Fc Variant A comprehensive analysis was conducted on binding activity to each FcγR of a plurality of IgG1 antibody variants into which were introduced a mutation that reduces Fc-mediated binding to active FcγR, in particular either of the polymorphisms of the H type and R type of FcγRIIa, in comparison to naturally-occurring IgG1 and enhances binding to FcγRIIb.

The variable region of an anti-glypican-3 antibody having improved plasma dynamics disclosed in WO 2009/041062 in the form of a glypican-3 antibody containing the CDR of GpH7 (SEQ ID NO: 74) was used for the antibody H chain. Similarly, GpL16-k0 of the glypican-3 antibody having improved plasma dynamics disclosed in WO 2009/041062 (SEQ ID NO: 75) was used in common for the antibody L chain in combination with the different H chain. In addition, B3, obtained by introducing a mutation of K439E into G1d, in which Gly and Lys had been deleted from the C terminus of IgG1 (SEQ ID NO: 76), was used for the antibody H chain constant region. This H chain is subsequently referred to as GpH7-B3 (SEQ ID NO: 77), while the L chain is subsequently referred to as GpL16-k0 (SEQ ID NO: 75).

Those amino acids and their surrounding amino acids thought to be involved in FcγR binding in the amino acid sequence of GpH7-B3 (from position 234 to position 239, position 265 to position 271, position 295, position 296, position 298, position 300 and position 324 to position 337 (EU numbering)) were respectively substituted with 18 types of amino acids excluding former amino acids and Cys. These Fc variants are referred to as B3 variants. The binding activity of B3 variants expressed and purified according to the method of Reference Example 2 to each FcγR (FcγRIa, FcγRIIa(H), FcγRIIa(R), FcγRIIb and FcγRIIIa) was comprehensively evaluated in compliance with the method described in Example 9.

Diagrams were prepared for each FcγR in accordance with the method described below. Namely, the value of the amount of antibody derived from each B3 variant bound to each FcγR was divided by the value of the amount of control antibody which has no mutations introduced into B3 (antibody having the sequence of naturally-occurring human IgG1 at position 234 to position 239, position 265 to position 271, position 295, position 296, position 298, position 300 and position 324 to position 337 (EU numbering)). That value was then further multiplied by 100, and the resulting value was expressed as the value of binding to each FcγR. Binding of each variant to FcγRIIb was represented on the horizontal axis, and values of each active FcγR in the form of FcγRIa, FcγRIIa(H), FcγRIIa(R) and FcγRIIIa were respectively represented on the vertical axis (FIGS. 33, 34, 35 and 36).

As a result, as indicated by the labels of FIGS. 33 to 36, among all of the modifications, mutation A (modification obtained by substituting Asp for Pro at position 238 (EU numbering)) and mutation B (modification obtained by substituting Glu for Leu at position 328 (EU numbering)) demonstrated remarkably enhanced binding to FcγRIIb in comparison with naturally-occurring IgG1, and were found to demonstrate an effect of remarkably suppressing binding to both types of FcγRIIa.

(14-2) SPR Analysis of FcγRIIb Selective Binding Variants

A more detailed analysis was conducted of binding to each FcγR of the variant obtained by substituting Asp for Pro at position 238 (EU numbering) discovered in (14-1).

For the H chain of IgG1, the variable region of IL6R-H disclosed in WO 2009/125825 (SEQ ID NO: 78) which is the variable region of an antibody against human interleukin-6 receptor is used as antibody H chain variable region, and IL6R-G1d (SEQ ID NO: 79) containing a G1d constant region from which Gly and Lys of the C terminal of human IgG1 had been removed is used as antibody H chain constant region. IL6R-G1d_v1 (SEQ ID NO: 80) was produced in which Asp was substituted for Pro at position 238 (EU numbering) of IL6R-G1d. Next, IL6R-G1d_v2 (SEQ ID NO: 81) was produced in which Glu was substituted for Leu at position 328 (EU numbering) of IL6R-G1d. For the sake of comparison, IL6R-G1d_v3 (SEQ ID NO: 82) which is an IL6R-G1d variant was produced, into which a known mutation (Mol. Immunol. (2008)45, 3926-3933) was introduced by substituting Glu for Ser at position 267 (EU numbering) and substituting Phe for Leu at position 328 (EU numbering). IL6R-L (SEQ ID NO: 83) which is the L chain of tocilizumab was used in common for the antibody L chain in combination with these heavy chains. Antibodies were expressed and purified in accordance with the method of Reference Example 2. Antibodies containing as antibody H chain IL6R-G1d, IL6R-G1d_v1, IL6R-G1d_v2 and IL6R-G1d_v3 are hereinafter respectively referred to as IgG1, IgG1-v1, IgG1-v2 and IgG1-v3.

Next, interaction between these antibodies and FcγR was analyzed kinetically using the BIACORE™ T100 (GE Healthcare). The interaction was measured at a temperature of 25° C. using HBS-EP+ (GE Healthcare) for the running buffer. The Series S Sensor Chip CM5 (GE Healthcare) was used after immobilizing Protein A by amine coupling. Binding of each FcγR to antibody was measured by allowing each FcγR diluted with running buffer to act on the chip on which a target antibody had been captured. Antibody captured on the chip was washed by allowing 10 mM glycine-HCl (pH 1.5) to react following measurement. The chip regenerated in this manner was used repeatedly. The dissociation constant KD (mol/L) was calculated from the association rate constant ka (L/mol/s) and dissociation rate constant kd (1/s) as calculated by global-fitting the measurement results with a 1:1 Langmuir binding model using the BIACORE™ Evaluation Software.

Since binding of IgG1-v1 and IgG1-v2 to FcγRIIa(H) or FcγRIIIa was extremely weak, KD could not be calculated by global-fitting the measurement results with the aforementioned 1:1 Langmuir binding model using the BIACORE™ Evaluation Software. KD could be calculated for interaction of IgG1-v1 and IgG1-v2 with FcγRIIa(H) or FcγRIIIa by using the following 1:1 binding model described in the BIACORE™ T100 Software Handbook BR1006-48, Edition AE.

Behavior of the interacting molecules in the BIACORE™ system using the 1:1 binding model can be represented by Equation 4 below.

$$Req = C \times Rmax/(KD+C) + RI \qquad \text{[Equation 4]}$$

The meaning of each parameter in the aforementioned Equation 4 is as follows:
Req (RU): Steady state binding level
C (M): Analyte concentration
C: Concentration
Rmax (RU): Analyte surface binding capacity
RI (RU): Bulk refractive index contribution in sample
KD (M): Equilibrium dissociation constant
KD can be expressed in the manner of Equation 5 below by transforming Equation 4.

$$KD = C \times Rmax/(Req-RI) - C \qquad \text{[Equation 5]}$$

KD can be calculated by substituting the values of Rmax, RI and C into this equation. Under the measurement conditions used here, values substituted into the equation were RI=0 and C=2 μmol/L. The value obtained by dividing the value of Rmax obtained when global-fitting the results of analyzing the interaction of IgG1 with each FcγR using the 1:1 Langmuir binding model by the amount of IgG1 captured and multiplying by the captured amounts of IgG1-v1 and IgG1-v2 was used for Rmax.

Under the measurement conditions used here, binding of IgG1-v1 and IgG1-v2 to FcγRIIa(H) was about 2.5 RU and 10 RU, respectively, and binding of IgG1-v1 and IgG1-v2 to FcγRIIIa was about 2.5 RU and 5 RU, respectively. The captured amounts of IgG1-v1 and IgG1-v2 antibodies on the sensor chip during analysis of the interaction of IgG1 with FcγRIIa(H) were 469.2 RU and 444.2 RU, and the captured amounts of IgG1-v1 and IgG1-v2 antibodies on the sensor chip during analysis of the interaction of IgG1 with FcγRIIIa were 470.8 RU and 447.1 RU. In addition, the values of Rmax obtained by global fitting the results of analyzing the interaction of IgG1 with FcγRIIa(H) and FcγRIIIa using the 1:1 Langmuir binding model were 69.8 RU and 63.8 RU, respectively, and the amounts of antibody captured on the sensor chip were 452 RU and 454.5 RU, respectively. The values of Rmax of IgG1-v1 and IgG1-v2 to FcγRIIa(H) were calculated to be 72.5 RU and 68.6 RU, respectively, while the values of Rmax of IgG1-v1 and IgG1-v2 to FcγRIIIa were calculated to be 66.0 RU and 62.7 RU, respectively, using these values. Values of KD for IgG1-v1 and IgG1-v2 to FcγRIIa(H) and FcγRIIIa were calculated by substituting these values into Equation 5.

$$KD = C \times R\mathrm{max}/(\mathrm{Req}-RI)-C \quad \text{[Equation 5]}$$

KD values of IgG1, IgG1-v1, IgG1-v2 and IgG1-v3 to each FcγR (KD values of each antibody to each FcγR) are shown in Table 24, while relative KD values of IgG1-v1, IgG1-v2 and IgG1-v3, obtained by dividing the KD values of IgG1 to each FcγR by the KD values of IgG1-v1, IgG1-v2 and IgG1-v3 to each FcγR (relative KD values of each antibody to each FcγR) are shown in Table 25.

TABLE 24

|  | IgG1 | IgG1-v1 | IgG1-v2 | IgG1-v3 |
| --- | --- | --- | --- | --- |
| Fcγ RIa | 3.4E−10 | 7.3E−09 | 4.6E−10 | 1.9E−10 |
| Fcγ RIIa (R) | 1.2E−06 | 1.2E−05 | 2.9E−06 | 2.3E−09 |
| Fcγ RIIa (H) | 7.7E−07 | 5.6E−05* | 1.2E−05* | 1.5E−06 |
| Fcγ RIIb | 5.3E−06 | 1.1E−06 | 2.3E−06 | 1.3E−08 |
| Fcγ RIIIa | 3.1E−06 | 5.1E−05* | 2.3E−05* | 8.8E−06 |

In Table 24 above, asterisks indicate KD values that were calculated using Equation 5 when binding of FcγR to IgG was not adequately observed.

$$KD = C \times R\mathrm{max}/(\mathrm{Req}-RI)-C \quad \text{[Equation 5]}$$

TABLE 25

|  | IgG1-v1 | IgG1-v2 | IgG1-v3 |
| --- | --- | --- | --- |
| Fcγ RIa | 0.047 | 0.74 | 1.8 |
| Fcγ RIIa (R) | 0.10 | 0.41 | 522 |
| Fcγ RIIa (H) | 0.014 | 0.064 | 0.51 |
| Fcγ RIIb | 4.8 | 2.3 | 408 |
| Fcγ RIIIa | 0.061 | 0.14 | 0.35 |

As shown in Table 25, affinity of IgG1-v1 for FcγRIa decreased to 0.047 times in comparison with IgG1, affinity for FcγRIIa(R) decreased to 0.10 times, affinity for FcγRIIa (H) decreased to 0.014 times, and affinity for FcγRIIIa decreased to 0.061 times. On the other hand, affinity for FcγRIIb improved 4.8 times.

In addition, as shown also in Table 25, affinity of IgG1-v2 for FcγRIa decreased to 0.74 times in comparison with IgG1, affinity for FcγRIIa(R) decreased to 0.41 times, affinity for FcγRIIa(H) decreased to 0.064 times, and affinity for FcγRIIIa decreased to 0.14 times. On the other hand, affinity for FcγRIIb improved 2.3 times.

Namely, based on these results, IgG1-v1, in which Asp was substituted for Pro at position 238 (EU numbering), and IgG1-v2, in which Glu was substituted for Leu at position 328 (EU numbering) demonstrated decreased binding to all active forms of FcγR including both polymorphisms of FcγRIIa; and binding to FcγRIIb which is inhibitory FcγR was clearly increased. So far, alterations having such properties have not been reported, and they are very rare as shown in FIGS. 33 to 36. Alterations produced by substituting Pro at position 238 (EU numbering) with Asp or substituting Leu at position 328 (EU numbering) with Glu are very useful for the development of therapeutic agents for immunological inflammatory diseases and such.

Furthermore, as shown in Table 25, IgG1-v3 certainly shows a 408-fold enhanced binding to FcγRIIb, while the binding to FcγRIIa (H) is decreased to 0.51 fold, and the binding to FcγRIIa (R) is enhanced to 522 fold. Accordingly, since IgG1-v1 and IgG1-v2 suppress their binding to both FcγRIIa (R) and FcγRIIa (H), and enhance their binding to FcγRIIb, they are considered to be variants that bind with a greater FcγRIIb selectivity compared with IgG1-v3. Specifically, alterations produced by substituting Pro at position 238 (EU numbering) with Asp or substituting Leu at position 328 (EU numbering) with Glu are very useful for the development of therapeutic agents for immunological inflammatory diseases and such.

(14-3) Effects of Combining Modification of Selective Binding to FcγRIIb and other Fc Region Amino Acid Substitutions In (14-2), a variant obtained by substituting Asp for Pro at position 238 (EU numbering) in the amino acid sequence of naturally-occurring human IgG1, or a variant obtained by substituting Glu for Leu at position 328 (EU numbering), were found to demonstrate decreased Fc-mediated binding to FcγRIa, FcγRIIIa and either of the polymorphisms of FcγRIIa, as well as improved binding to FcγRIIb. Therefore, Fc variants were created to have further reduced binding to any of FcγRI, FcγRIIa(H), FcγRIIa(R) and FcγRIIIa, and further improved binding to FcγRIIb as a result of introducing additional amino acid substitutions into the variant obtained by substituting Asp for Pro at position 238 (EU numbering) or the variant obtained by substituting Glu for Leu at position 328 (EU numbering).

(14-4) Production of Antibodies having Binding Activity to Human FcRn under Conditions of the Neutral pH Region and whose Binding Activity to Human FcγRIIb has been Selectively Enhanced Antibodies were produced according to the method shown below in order to selectively enhance binding activity to human FcγRIIb for VH3-IgG1 and VH3-IgG1-F11. VH3-IgG1-F648 (SEQ ID NO: 84) was produced by introducing an amino acid substitution obtained by substituting Asp for Pro at position 238 (EU numbering) into VH3-IgG1 according to the method of Reference Example 1. Similarly, VH3-IgG1-F652 (SEQ ID NO: 85) was produced by introducing an amino acid substitution obtained by substituting Asp for Pro at position 238 (EU numbering) into VH3-IgG1-F11 according to the method of Reference Example 1.

(14-5) Evaluation of Antibodies having Binding Activity to Human FcRn under Conditions of the Neutral pH Region and whose Binding Activity to Human FcγRIIb has been Selectively Enhanced Antibodies containing VH3-IgG1, VH3-IgG1-F648, VH3-IgG1-F11 or VH3-IgG1-F652 for the heavy chain and L(WT)-CK for the light chain were produced according to the method of Reference Example 2.

Interaction of these antibodies with FcγRIIa(R) and FcγRIIb was analyzed using the BIACORE™ T100 surface plasmon resonance system (GE Healthcare). Measurements were carried out at 25° C. using a buffer consisting of 20 mM N-(2-acetamido)-2-aminoethanesulfonic acid (ACES), 150 mM NaCl and 0.05% polysorbate 20 (Tween 20®) (pH 7.4) for the running buffer. The Series S Sensor Chip CM4 (GE Healthcare) was used after immobilizing Protein L by amine coupling. Interaction of each FcγR with antibody was measured by allowing each FcγR diluted with running buffer to act on the chip on which a target antibody had been captured. Antibody captured on the chip was washed by reacting with 10 mM glycine-HCl (pH 1.5) following measurement, and the chip regenerated in this manner was used repeatedly.

Measurement results were analyzed using the BIACORE™ Evaluation Software. Antibody was captured by Protein L, and the amount of change in a sensorgram before and after the antibody was captured was defined as X1. Next, human FcγRs were allowed to interact with the antibody, and the value obtained by subtracting binding activity of human FcγRs represented as the amount of change in a sensorgram before and after allowing the running buffer to interact with antibody captured by Protein L ($\Delta A2$) from the value obtained by multiplying by 1500 the value obtained by dividing the binding activity of human FcγRs represented as the amount of change in a sensorgram before and after that interaction ($\Delta A1$) by the captured amount (X) of each antibody, was divided by the captured amount of each antibody (X) followed by multiplying by 1500 to obtain the binding activity of the human FcγRs (Y) (Equation 1).

Binding activity of mouse FcγRs $(Y)=(\Delta A1-\Delta A2)/X \times 1500$ [Equation 1]

The results are shown in Table 26 below. The effect of selectively enhancing binding activity to human FcγRIIb by introducing a mutation obtained by substituting Asp for Pro at position 238 (EU numbering) was confirmed to be equally observed even in the case of introducing into an antibody having binding activity to human FcRn under conditions of the neutral pH region.

TABLE 26

| | BINDING AMOUNT(RU) | |
|---|---|---|
| | hFcgRIIa(R) | hFcgRIIb |
| IgG1 | 117.1 | 34.5 |
| IgG1-F648 | 12.2 | 75.5 |
| IgG1-F11 | 95.4 | 22.7 |
| IgG1-F652 | 9.1 | 64.0 |

The IgG1-F652 obtained here is an antibody that has binding activity to FcRn under conditions of the neutral pH region and which brings about enhancement of selective binding activity to inhibitory FcγRIIb. Namely, this antibody corresponds to an antigen-binding molecule of Embodiment 2 shown in Example 3. In other words, IgG1-F652 is able to form a quaternary complex mediated by two molecules of FcRn and one molecule of FcγR; however, since it brings about enhancement of selective binding activity to inhibitory FcγR, binding activity to active FcγR decreases. As a result, a quaternary complex containing inhibitory FcγR is thought to be preferentially formed on antigen-presenting cells. As previously described, it is thought that immunogenicity is caused by the formation of a quaternary complex containing active FcγR, and that immune response is inhibited as a result of forming a quaternary complex containing inhibitory FcγR in this manner.

Reference Example 1

Construction of Expression Vectors of Amino Acid-substituted Igg Antibodies

Mutants were prepared using the QuikChange Site-Directed Mutagenesis Kit (Stratagene) by the method described in the appended instruction manual. Plasmid fragments containing the mutants were inserted into animal cell expression vectors to construct desired H-chain and L-chain expression vectors. The nucleotide sequences of the resulting expression vectors were determined by the methods known to those skilled in the art.

Reference Example 2

Expression and Purification of Igg Antibodies

Antibodies were expressed using the following method. Human embryonic kidney cancer-derived HEK293H cell line (Invitrogen) was suspended in DMEM (Invitrogen) supplemented with 10% Fetal Bovine Serum (Invitrogen). The cells were plated at 10 ml per dish in dishes for adherent cells (10 cm in diameter; CORNING) at a cell density of 5 to 6×10$^5$ cells/ml and cultured in a $CO_2$ incubator (37° C., 5% $CO_2$) for one whole day and night. Then, the medium was removed by aspiration, and 6.9 ml of CHO-S-SFM-II medium (Invitrogen) was added. The prepared plasmid was introduced into the cells by the lipofection method. The resulting culture supernatants were collected, centrifuged (approximately 2,000×g, 5 min, room temperature) to remove cells, and sterilized by filtering through 0.22-μm filter MILLEX (registered trademark)-GV (Millipore) to obtain the supernatants. Antibodies were purified from the obtained culture supernatants by a method known to those skilled in the art using rProtein A Sepharose™ Fast Flow (Amersham Biosciences). To determine the concentration of the purified antibody, absorbance was measured at 280 nm using a spectrophotometer. Antibody concentrations were calculated from the determined values using an absorbance coefficient calculated by the method described in Protein Science (1995) 4: 2411-2423.

Reference Example 3

Preparation of Soluble Human IL-6 Receptor (hsIL-6R)

Recombinant human IL-6 receptor of human IL-6 receptor which is an antigen was prepared in the manner described below. A CHO line that constantly expresses soluble human IL-6 receptor composed of an amino acid sequence consisting of the 1st to 357th amino acid from the N terminus as reported in J. Immunol. (1994) 152, 4958-4968 (hereinafter referred to as hsIL-6R) was constructed using a method known among persons with ordinary skill in the art. Soluble human IL-6 receptor was expressed by culturing this CHO line. Soluble human IL-6 receptor was purified from culture supernatant of the resulting CHO line by the two steps of Blue Sepharose 6 FF column chromatography and gel filtration column chromatography. The fraction that eluted as the main peak in the final step was used as the final purified product.

Reference Example 4

PK Study on Soluble Human IL-6 Receptor and Human Antibodies in normal mice

To examine the plasma retention and immunogenicity of soluble human IL-6 receptor and human antibodies in a normal mouse, the following test was conducted.

(4-1) Examination of Plasma Retention and Immunogenicity of Soluble Human IL-6 Receptor in Normal Mice To examine the plasma retention and immunogenicity of soluble human IL-6 receptor in a normal mouse, the following test was conducted.

A single dose (50 µg/kg) of soluble human IL-6 receptor (prepared in Reference example 3) was administered into the caudal vein of a normal mouse (C57BL/6J mouse, Charles River Japan). Blood samples were collected at 15 minutes, 7 hours and 1, 2, 3, 4, 7, 14, and 21 days after the administration of soluble human IL-6 receptor. The blood samples were immediately centrifuged for 15 minutes at 4° C. and 15,000 rpm to separate plasma. The separated plasma was stored in a freezer set to −20° C. or lower until the time of measurement. The plasma concentration of soluble human IL-6 receptor and the antibody titer of soluble mouse anti-human IL-6 receptor antibody were determined as described below.

The plasma concentration of soluble human IL-6 receptor in a mouse was determined by an electrochemiluminescence method. A soluble human IL-6 receptor calibration curve sample, prepared at 2,000, 1,000, 500, 250, 125, 62.5, or 31.25 pg/mL, and a mouse plasma measurement sample, diluted by 50-fold or above, were mixed with a monoclonal anti-human IL-6R antibody (R&D) ruthenated with SULFO-TAG NHS Ester (Meso Scale Discovery), a biotinylated anti-human IL-6 R antibody (R&D), and tocilizumab, followed by overnight reaction at 37° C. Tocilizumab was prepared at a final concentration of 333 µg/mL. Subsequently, the reaction liquid was dispensed into an MA400 PR Streptavidin Plate (Meso Scale Discovery). In addition, after washing the reaction liquid that was allowed to react for 1 hour at room temperature, Read Buffer T (×4) (Meso Scale Discovery) was dispensed. Subsequently, the reaction liquid was immediately subjected to measurement using a SECTOR PR 400 reader (Meso Scale Discovery). The concentration of soluble human IL-6 receptor was calculated from the response of the calibration curve using the SOFTmax PRO analysis software (Molecular Devices).

The titer of mouse anti-human IL-6 receptor antibody in mouse plasma was determined by an electrochemiluminescence method. First, human IL-6 receptor was dispensed into an MA100 PR Uncoated Plate (Meso Scale Discovery). The plate was allowed to stand undisturbed overnight at 4° C. to prepare a human IL-6 receptor-solid phase plate. The human IL-6 receptor-solid phase plate, with a 50-fold diluted mouse plasma measurement sample dispensed, was allowed to stand undisturbed overnight at 4° C. Subsequently, said plate that was allowed to react with the anti-mouse IgG (whole molecule) (Sigma-Aldrich) ruthenated with SULFO-TAG NHS Ester (Meso Scale Discovery), for 1 hour at room temperature was washed. Read Buffer T (×4) (Meso Scale Discovery) was dispensed into said plate, immediately followed by measurement using a SECTOR PR 400 reader (Meso Scale Discovery).

Figure 37:
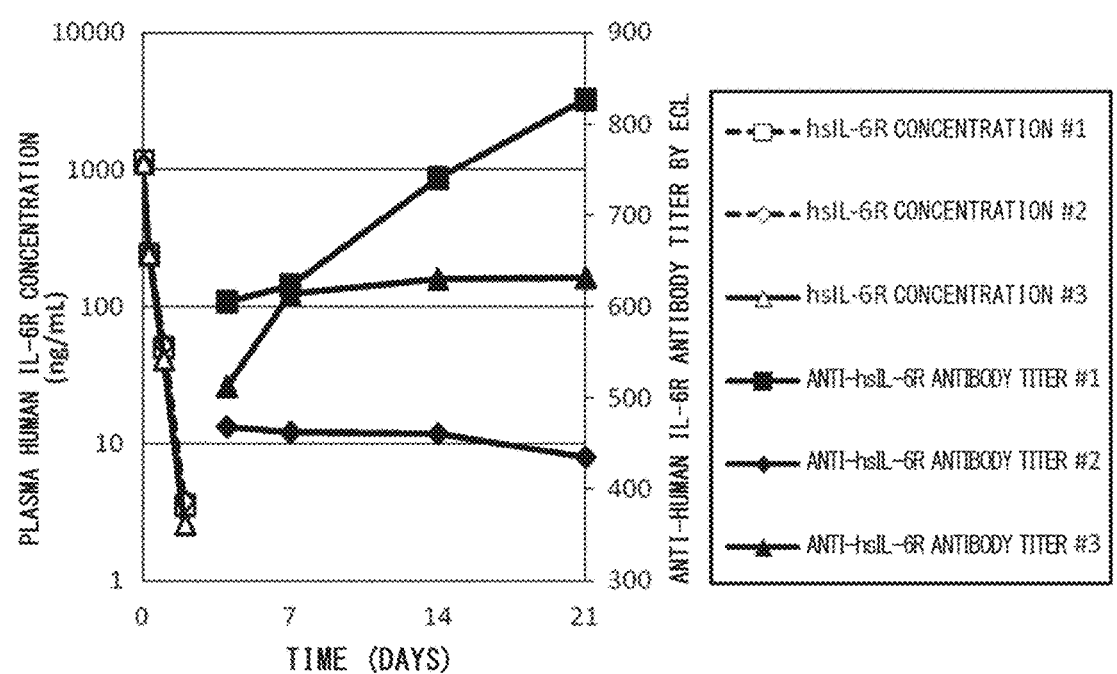
FIG. 37 is a graph showing the plasma kinetics of a soluble human IL-6 receptor in normal mice and the antibody titer of mouse antibody against the soluble human IL-6 receptor in mouse plasma.

Results are shown in FIG. 37. The results demonstrate that soluble human IL-6 receptor in the mouse plasma rapidly disappeared. Of three mice that received soluble human IL-6 receptor, two mice (Nos. 1 and 3) showed an increased antibody titer of soluble mouse anti-human IL-6 receptor antibody in plasma. It is suggested that these two mice developed an immune response to soluble human IL-6 receptor, resulting in the production of mouse antibodies.

(4-2) Immunogenicity Evaluation of Soluble Human IL-6 Receptor in Steady-state Model To examine the effects of mouse antibody production against soluble human IL-6 receptor on the plasma concentration of soluble human IL-6 receptor, the following test was conducted.

The following study model was constructed as a model for maintaining plasma concentration of soluble human IL-6 receptor in the steady state (about 20 ng/mL). An infusion pump (MODEL2004, alzet MINI-OSMOTIC PUMP), filled with soluble human IL-6 receptor, was subcutaneously implanted into the back of a normal mouse (C57BL/6J mouse, Charles River Japan) to create an animal model with plasma concentration of soluble human IL-6 receptor maintained in the steady state.

The study was conducted in two groups (n=4 per group). To the group of mice that mimic immune tolerance, a single dose (20 mg/kg) of monoclonal anti-mouse CD4 antibody (R&D) was administered into the caudal vein to inhibit the production of mouse antibodies against soluble human IL-6 receptor. Subsequently, the antibody was similarly administered once in 10 days (hereinafter referred to as anti-mouse CD4 antibody administration group). The other group was used as a control group, i.e., anti-mouse CD4 antibody non-administration group that received no monoclonal anti-mouse CD4 antibody. Subsequently, an infusion pump filled with 92.8 µg/mL soluble human IL-6 receptor was subcutaneously implanted into the back of a mouse. After the implantation of an infusion pump, blood samples were collected over time, immediately followed by centrifugation for 15 minutes at 4° C. and 15,000 rpm to obtain plasma. The separated plasma was stored in a freezer set to −20° C. or lower until the time of measurement. The plasma concentration of soluble human IL-6 receptor (hsIL-6R) was determined in the same manner as in Reference example 4-1.

Figure 38:
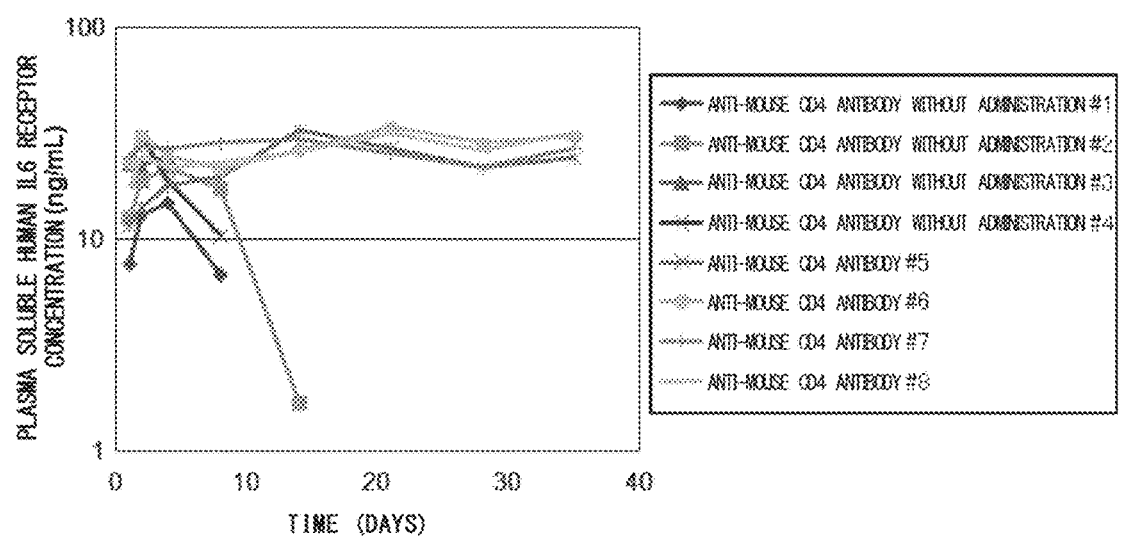
FIG. 38 is a graph showing the plasma kinetics of a soluble human IL-6 receptor in normal mice administered with an anti-mouse CD4 antibody and the antibody titer of mouse antibody against the soluble human IL-6 receptor in mouse plasma.

Changes in the plasma concentration of soluble human IL-6 receptor in an individual normal mouse, determined as described above, are shown in FIG. 38.

As a result, on day 14 after the infusion pump was subcutaneously implanted into the back of a mouse, it is observed that the plasma concentrations of soluble human IL-6 receptor were reduced in all the mice of anti-mouse CD4 antibody non-administration group. On the other hand, it was not observed that the plasma concentrations of soluble human IL-6 receptor were reduced in all of the mice that received anti-mouse CD4 antibody to inhibit the production of mouse antibodies against soluble human IL-6 receptor.

The results of (4-1) and (4-2) indicate the following three points:

(1) Soluble human IL-6 receptor, after administered to a mouse, rapidly disappears from the plasma;

(2) soluble human IL-6 receptor is a foreign protein for mice, which is immunogenic when administered to a mouse, inducing the production of mouse antibodies against soluble human IL-6 receptor; and (3) if production of mouse antibodies against soluble human IL-6 receptor occurs, the disappearance of soluble human IL-6 receptor is further accelerated, even in a model with the plasma concentration of soluble human IL-6 receptor maintained at a certain level, reduction of plasma concentration occurs.

(4-3) Examination of the Plasma Retention and Immunogenicity of Human Antibody in a Normal Mouse To examine the plasma retention and immunogenicity of human antibody in a normal mouse, the following test was conducted.

A single dose (1 mg/kg) of anti-human IL-6 receptor antibody, Fv4-IgG1, was administered into the caudal vein of a normal mouse (C57BL/6J mouse, Charles River Japan). Blood samples were collected at 15 minutes, 7 hours and 1, 2, 3, 4, 7, 14, and 21 days after the administration of anti-human IL-6 receptor antibody. The blood samples obtained were immediately centrifuged at 15,000 rpm for 15 minutes at 4° C. to separate plasma. The separated plasma was stored in a freezer set to −20° C. or lower until the time of measurement.

The plasma concentration of anti-human IL-6 receptor antibody in a mouse was determined by ELISA. First, Anti-Human IgG (γ-chain specific) F(ab')2 Fragment of Antibody (SIGMA) was dispensed into a Nunc-Immuno Plate, MaxiSoup (Nalge Nunc International), and was allowed to stand undisturbed overnight at 4° C. to prepare an anti-human IgG-solid phase plate. Calibration curve samples containing anti-human IL-6 receptor antibody at a plasma concentration of 0.8, 0.4, 0.2, 0.1, 0.05, 0.025, or 0.0125 µg/mL, and mouse plasma measurement samples diluted by 100-fold or above were prepared. A mixture of 100 µL of the calibration curve sample and the plasma measurement sample and 200 µL of 20 ng/mL soluble human IL-6 receptor was allowed to stand undisturbed for 1 hour at room temperature. Subsequently, the anti-human IgG-solid phase plate in which the mixture had been dispensed into each of the wells thereof was further allowed to stand undisturbed for 1 hour at room temperature. Subsequently, the plate was allowed to react with Biotinylated Anti-human IL-6 R Antibody (R&D) for 1 hour at room temperature. The chromogenic reaction of the reaction liquid obtained by reacting with Streptavidin-PolyHRP80 (Stereospecific Detection Technologies) for 1 hour at room temperature was conducted using TMB One Component HRP Microwell Substrate (BioFX Laboratories) as a substrate. After the reaction was stopped by adding 1N-Sulfuric acid (Showa Chemical), absorbance at 450 nm of the reaction liquid in each well was measured using a microplate reader. The plasma concentration of antibody in a mouse was calculated from the absorbance of the calibration curve using the SOFTmax PRO analysis software (Molecular Devices).

Figure 39:
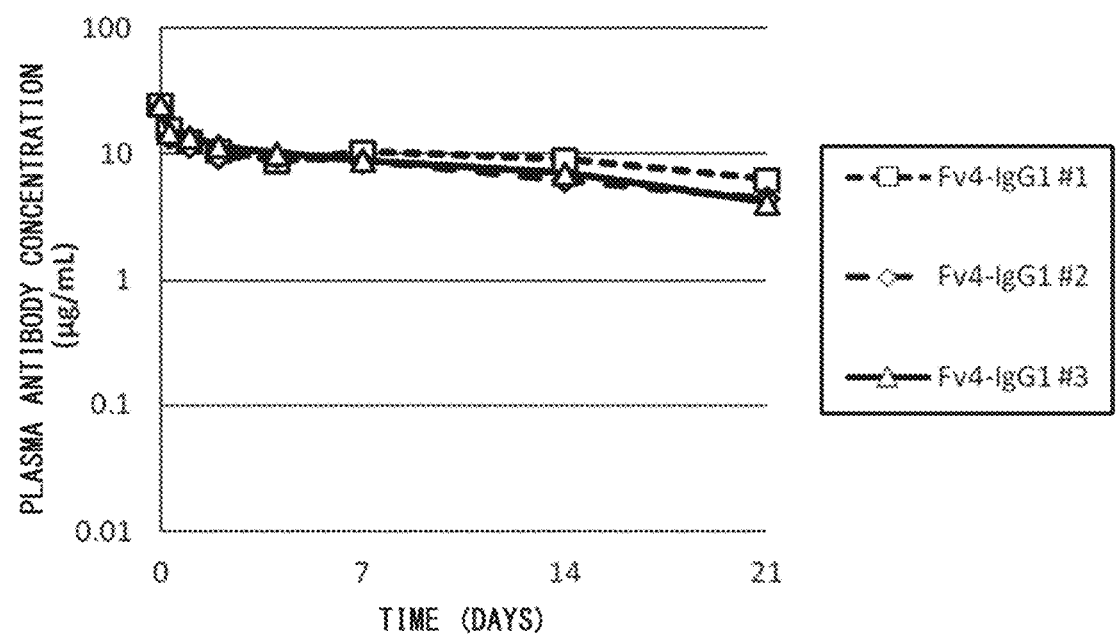
FIG. 39 is a graph showing the plasma kinetics of an anti-IL-6 receptor antibody in normal mice.

Results are shown in FIG. 39. The plasma retention of human antibody when a single dose of human antibody was administered to a mouse was significantly higher than that of soluble human IL-6 receptor when a single dose of soluble human IL-6 receptor was administered (FIG. 37), and the high plasma concentration was demonstrated to be maintained even on day 21 after the administration. This is probably because human antibodies that are incorporated into cells bind to mouse FcRn within the endosome to be recycled into the plasma. On the other hand, soluble human IL-6 receptor that is incorporated into cells is thought to rapidly disappear from the plasma, because it has no pathway to be recycled from the endosome.

Furthermore, the reduced plasma concentration, seen in the steady-state model of soluble human IL-6 receptor (FIG. 38), was not observed in any of three mice that received human antibody. In other words, it was suggested that unlike human IL-6 receptor, no mouse antibody was produced against human antibody.

The results of (4-1), (4-2), and (4-3) can suggest the following. First, both human soluble IL-6 receptor and human antibody are foreign proteins in mice. Thus, mice are thought to have a large T cell population that specifically responds to them.

When human soluble IL-6 receptor, i.e., a foreign protein, was administered to a mouse, it disappeared from the plasma in a short time and immune response to the human soluble IL-6 receptor was confirmed. Here, the rapid disappearance of human soluble IL-6 receptor from the plasma suggests that many human soluble IL-6 receptors are incorporated into antigen-presenting cells in a short time and subjected to processing within the cells, and then activate T cells that specifically respond to human soluble IL-6 receptor. It is thought that immune response to human soluble IL-6 receptor (i.e., production of mouse antibody against human soluble IL-6 receptor) occurs as a result.

On the other hand, when a human antibody, i.e., a foreign protein, was administered to a mouse, its plasma retention was significantly longer than that of human soluble IL-6 receptor and immune response to the human antibody did not occur. The longer plasma retention indicates the presence of only a small amount of human antibodies that are incorporated into antigen-presenting cells and subjected to processing. Thus, it is thought that even if the mouse has a T cell population that specifically responds to the human antibody, the T cells are not activated through antigen presentation, and as a result, immune response to the human antibody (i.e., production of mouse antibody against the human antibody) does not occur.

Reference Example 5

Preparation and Evaluation of Various Antibody Fc Variants With Increased Binding Affinity to Human FcRn at Neutral pH (5-1) Preparation and Binding Activity Evaluation of Various Antibody Fc Variants with Increased Binding Affinity to Human FcRn at Neutral pH To increase the binding affinity to human FcRn at a neutral pH range, various mutations were introduced into VH3-IgG1 (SEQ ID NO: 35) for evaluation. Variants (IgG1-F1 to IgG1-F1052) containing the created heavy and light chains L (WT)-CK (SEQ ID NO: 41) were expressed and purified according to the method described in Reference Example 2.

The binding of antibody to human FcRn was analyzed according to the method described in Example 4. In other words, the binding activities of human FcRn variants under neutral conditions (pH 7.0), determined using a BIA-CORE™ system, are shown in Tables 27-1 to 27-32.

TABLE 27-1

| VARIANT | KD (M) | AMINO ACID ALTERATION POSITION |
|---|---|---|
| F1 | 8.10E−07 | N434W |
| F2 | 3.20E−06 | M252Y/S254T/T256E |
| F3 | 2.50E−06 | N434Y |
| F4 | 5.80E−06 | N434S |
| F5 | 6.80E−06 | N434A |
| F7 | 5.60E−06 | M252Y |
| F8 | 4.20E−06 | M252W |
| F9 | 1.40E−07 | M252Y/S254T/T256E/N434Y |
| F10 | 6.90E−08 | M252Y/S254T/T256E/N434W |
| F11 | 3.10E−07 | M252Y/N434Y |
| F12 | 1.70E−07 | M252Y/N434W |
| F13 | 3.20E−07 | M252W/N434Y |
| F14 | 1.80E−07 | M252W/N434W |
| F19 | 4.60E−07 | P257L/N434Y |

TABLE 27-1-continued

| VARIANT | KD (M) | AMINO ACID ALTERATION POSITION |
|---|---|---|
| F20 | 4.60E−07 | V308F/N434Y |
| F21 | 3.00E−08 | M252Y/V308P/N434Y |
| F22 | 2.00E−06 | M428L/N434S |
| F25 | 9.20E−09 | M252Y/S254T/T256E/V308P/N434W |
| F26 | 1.00E−06 | I332V |
| F27 | 7.40E−07 | G237M |
| F29 | 1.40E−06 | I332V/N434Y |
| F31 | 2.80E−06 | G237M/V308F |
| F32 | 8.00E−07 | S254T/N434W |
| F33 | 2.30E−06 | S254T/N434Y |
| F34 | 2.80E−07 | T256E/N434W |
| F35 | 8.40E−07 | T256E/N434Y |
| F36 | 3.60E−07 | S254T/T256E/N434W |
| F37 | 1.10E−06 | S254T/T256E/N434Y |
| F38 | 1.00E−07 | M252Y/S254T/N434W |
| F39 | 3.00E−07 | M252Y/S254T/N434Y |
| F40 | 8.20E−08 | M252Y/T256E/N434W |
| F41 | 1.50E−07 | M252Y/T256E/N434Y |

Table 27-2 is a continuation of Table 27-1.

TABLE 27-2

| F42 | 1.00E−06 | M252Y/S254T/T256E/N434A |
|---|---|---|
| F43 | 1.70E−06 | M252Y/N434A |
| F44 | 1.10E−06 | M252W/N434A |
| F47 | 2.40E−07 | M252Y/T256Q/N434W |
| F48 | 3.20E−07 | M252Y/T256Q/N434Y |
| F49 | 5.10E−07 | M252F/T256D/N434W |
| F50 | 1.20E−06 | M252F/T256D/N434Y |
| F51 | 8.10E−06 | N434F/Y436H |
| F52 | 3.10E−06 | H433K/N434F/Y436H |
| F53 | 1.00E−06 | I332V/N434W |
| F54 | 8.40E−08 | V308P/N434W |
| F56 | 9.40E−07 | I332V/M428L/N434Y |
| F57 | 1.10E−05 | G385D/Q386P/N389S |
| F58 | 7.70E−07 | G385D/Q386P/N389S/N434W |
| F59 | 2.40E−06 | G385D/Q386P/N389S/N434Y |
| F60 | 1.10E−05 | G385H |
| F61 | 9.70E−07 | G385H/N434W |
| F62 | 1.90E−06 | G385H/N434Y |
| F63 | 2.50E−06 | N434F |
| F64 | 5.30E−06 | N434H |
| F65 | 2.90E−07 | M252Y/S254T/T256E/N434F |
| F66 | 4.30E−07 | M252Y/S254T/T256E/N434H |
| F67 | 6.30E−07 | M252Y/N434F |
| F68 | 9.30E−07 | M252Y/N434H |
| F69 | 5.10E−07 | M428L/N434W |
| F70 | 1.50E−07 | M428L/N434Y |
| F71 | 8.30E−08 | M252Y/S254T/T256E/M428L/N434W |
| F72 | 2.00E−07 | M252Y/S254T/T256E/M428L/N434Y |
| F73 | 1.70E−07 | M252Y/M428L/N434W |
| F74 | 4.60E−07 | M252Y/M428L/N434Y |
| F75 | 1.40E−06 | M252Y/M428L/N434A |
| F76 | 1.00E−06 | M252Y/S254T/T256E/M428L/N434A |
| F77 | 9.90E−07 | T256E/M428L/N434Y |
| F78 | 7.80E−07 | S254T/M428L/N434W |

Table 27-3 is a continuation of Table 27-2.

TABLE 27-3

| F79 | 5.90E−06 | S254T/T256E/N434A |
|---|---|---|
| F80 | 2.70E−06 | M252Y/T256Q/N434A |
| F81 | 1.60E−06 | M252Y/T256E/N434A |
| F82 | 1.10E−06 | T256Q/N434W |
| F83 | 2.60E−06 | T256Q/N434Y |
| F84 | 2.80E−07 | M252W/T256Q/N434W |
| F85 | 5.50E−07 | M252W/T256Q/N434Y |
| F86 | 1.50E−06 | S254T/T256Q/N434W |
| F87 | 4.30E−06 | S254T/T256Q/N434Y |
| F88 | 1.90E−07 | M252Y/S254T/T256Q/N434W |
| F89 | 3.60E−07 | M252Y/S254T/T256Q/N434Y |
| F90 | 1.90E−08 | M252Y/T256E/V308P/N434W |
| F91 | 4.80E−08 | M252Y/V308P/M428L/N434Y |

TABLE 27-3-continued

| F92 | 1.10E−08 | M252Y/S254T/T256E/V308P/M428L/N434W |
|---|---|---|
| F93 | 7.40E−07 | M252W/M428L/N434W |
| F94 | 3.70E−07 | P257L/M428L/N434Y |
| F95 | 2.60E−07 | M252Y/S254T/T256E/M428L/N434F |
| F99 | 6.20E−08 | M252Y/T256E/N434H |
| F101 | 1.10E−07 | M252W/T256Q/P257L/N434Y |
| F103 | 4.40E−08 | P238A/M252Y/V308P/N434Y |
| F104 | 3.70E−08 | N252Y/D265A/V308P/N434Y |
| F105 | 7.50E−08 | M252Y/T307A/V308P/N434Y |
| F106 | 3.70E−08 | M252Y/V303A/V308P/N434Y |
| F107 | 3.40E−08 | M252Y/V308P/D376A/N434Y |
| F108 | 4.10E−08 | M252Y/V305A/V308P/N434Y |
| F109 | 3.20E−08 | M252Y/V308P/Q311A/N434Y |
| F111 | 3.20E−08 | M252Y/V308P/K317A/N434Y |
| F112 | 6.40E−08 | M252Y/V308P/E380A/N434Y |
| F113 | 3.20E−08 | M252Y/V308P/E382A/N434Y |
| F114 | 3.80E−08 | M252Y/V308P/S424A/N434Y |
| F115 | 6.60E−06 | T307A/N434A |
| F116 | 8.70E−06 | E380A/N434A |
| F118 | 1.40E−05 | M428L |
| F119 | 5.40E−06 | T250Q/M428L |

Table 27-4 is a continuation of Table 27-3.

TABLE 27-4

| F120 | 6.30E−08 | P257L/V308P/M428L/N434Y |
|---|---|---|
| F121 | 1.50E−08 | M252Y/T256E/V308P/M428L/N434W |
| F122 | 1.20E−07 | M252Y/T256E/M428L/N434W |
| F123 | 3.00E−08 | M252Y/T256E/V308P/N434Y |
| F124 | 2.90E−07 | M252Y/T256E/M428L/N434Y |
| F125 | 2.40E−08 | M252Y/S254T/T256E/V308P/M428L/N434Y |
| F128 | 1.70E−07 | P257L/M428L/N434W |
| F129 | 2.20E−07 | P257A/M428L/N434Y |
| F131 | 3.00E−06 | P257G/M428L/N434Y |
| F132 | 2.10E−07 | P257I/M428L/N434Y |
| F133 | 4.10E−07 | P257M/M428L/N434Y |
| F134 | 2.70E−07 | P257N/M428L/N434Y |
| F135 | 7.50E−07 | P257S/M428L/N434Y |
| F136 | 3.80E−07 | P257T/M428L/N434Y |
| F137 | 4.60E−07 | P257V/M428L/N434Y |
| F139 | 1.50E−08 | M252W/V308P/N434W |
| F140 | 3.60E−08 | S239K/M252Y/V308P/N434Y |
| F141 | 3.50E−08 | M252Y/S298G/V308P/N434Y |
| F142 | 3.70E−08 | M252Y/D270F/V308P/N434Y |
| F143 | 2.00E−07 | M252Y/V308A/N434Y |
| F145 | 5.30E−08 | M252Y/V308F/N434Y |
| F147 | 2.40E−07 | M252Y/V308I/N434Y |
| F149 | 1.90E−07 | M252Y/V308L/N434Y |
| F150 | 2.00E−07 | M252Y/V308M/N434Y |
| F152 | 2.70E−07 | M252Y/V308Q/N434Y |
| F154 | 1.80E−07 | M252Y/V308T/N434Y |
| F157 | 1.50E−07 | P257A/V308P/M428L/N434Y |
| F158 | 5.90E−08 | P257T/V308P/M428L/N434Y |
| F159 | 4.40E−08 | P257V/V308P/M428L/N434Y |
| F160 | 8.50E−07 | M252W/M428I/N434Y |
| F162 | 1.60E−07 | M252W/M428Y/N434Y |
| F163 | 4.20E−07 | M252W/M428F/N434Y |
| F164 | 3.70E−07 | P238A/M252W/N434Y |
| F165 | 2.90E−07 | M252W/D265A/N434Y |

Table 27-5 is a continuation of Table 27-4.

TABLE 27-5

| F166 | 1.50E−07 | M252W/T307Q/N434Y |
|---|---|---|
| F167 | 2.90E−07 | M252W/V303A/N434Y |
| F168 | 3.20E−07 | M252W/D376A/N434Y |
| F169 | 2.90E−07 | M252W/V305A/N434Y |
| F170 | 1.70E−07 | M252W/Q311A/N434Y |
| F171 | 1.90E−07 | M252W/D312A/N434Y |
| F172 | 2.20E−07 | M252W/K317A/N434Y |
| F173 | 7.70E−07 | M252W/E380A/N434Y |
| F174 | 3.40E−07 | M252W/E382A/N434Y |
| F175 | 2.70E−07 | M252W/S424A/N434Y |
| F176 | 2.90E−07 | S239K/M252W/N434Y |
| F177 | 2.80E−07 | M252W/S298G/N434Y |

TABLE 27-5-continued

| | | |
|---|---|---|
| F178 | 2.70E-07 | M252W/D270F/N434Y |
| F179 | 3.10E-07 | M252W/N325G/N434Y |
| F182 | 6.60E-08 | P257A/M428L/N434W |
| F183 | 2.20E-07 | P257T/M428L/N434W |
| F184 | 2.70E-07 | P257V/M428L/N434W |
| F185 | 2.60E-07 | M252W/I332V/N434Y |
| F188 | 3.00E-06 | P257I/Q311I |
| F189 | 1.90E-07 | M252Y/T307A/N434Y |
| F190 | 1.10E-07 | M252Y/T307Q/N434Y |
| F191 | 1.60E-07 | P257L/T307A/M428L/N434Y |
| F192 | 1.10E-07 | P257A/T307A/M428L/N434Y |
| F193 | 8.50E-08 | P257T/T307A/M428L/N434Y |
| F194 | 1.20E-07 | P257V/T307A/M428L/N434Y |
| F195 | 5.60E-08 | P257L/T307Q/M428L/N434Y |
| F196 | 3.50E-08 | P257A/T307Q/M428L/N434Y |
| F197 | 3.30E-08 | P257T/T307Q/M428L/N434Y |
| F198 | 4.80E-08 | P257V/T307Q/M428L/N434Y |
| F201 | 2.10E-07 | M252Y/T307D/N434Y |
| F203 | 2.40E-07 | M252Y/T307F/N434Y |
| F204 | 2.10E-07 | M252Y/T307G/N434Y |
| F205 | 2.00E-07 | M252Y/T307H/N434Y |
| F206 | 2.30E-07 | M252Y/T307I/N434Y |

Table 27-6 is a continuation of Table 27-5.

TABLE 27-6

| | | |
|---|---|---|
| F207 | 9.40E-07 | M252Y/T307K/N434Y |
| F208 | 3.90E-07 | M252Y/T307L/N434Y |
| F209 | 1.30E-07 | M252Y/T307M/N434Y |
| F210 | 2.90E-07 | M252Y/T307N/N434Y |
| F211 | 2.40E-07 | M252Y/T307P/N434Y |
| F212 | 6.80E-07 | M252Y/T307R/N434Y |
| F213 | 2.30E-07 | M252Y/T307S/N434Y |
| F214 | 1.70E-07 | M252Y/T307V/N434Y |
| F215 | 9.60E-08 | M252Y/T307W/N434Y |
| F216 | 2.30E-07 | M252Y/T307Y/N434Y |
| F217 | 2.30E-07 | M252Y/K334L/N434Y |
| F218 | 2.60E-07 | M252Y/G385H/N434Y |
| F219 | 2.50E-07 | M252Y/T289H/N434Y |
| F220 | 2.50E-07 | M252Y/Q311H/N434Y |
| F221 | 3.10E-07 | M252Y/D312H/N434Y |
| F222 | 3.40E-07 | M252Y/N315H/N434Y |
| F223 | 2.70E-07 | M252Y/K360H/N434Y |
| F225 | 1.50E-06 | M252Y/L314R/N434Y |
| F226 | 5.40E-07 | M252Y/L314K/N434Y |
| F227 | 1.20E-07 | M252Y/N286E/N434Y |
| F228 | 2.30E-07 | M252Y/L309E/N434Y |
| F229 | 5.10E-07 | M252Y/R255E/N434Y |
| F230 | 2.50E-07 | M252Y/P387E/N434Y |
| F236 | 8.90E-07 | K248I/M428L/N434Y |
| F237 | 2.30E-07 | M252Y/M428A/N434Y |
| F238 | 7.40E-07 | M252Y/M428D/N434Y |
| F240 | 7.20E-07 | M252Y/M428F/N434Y |
| F241 | 1.50E-06 | M252Y/M428G/N434Y |
| F242 | 8.50E-07 | M252Y/M428H/N434Y |
| F243 | 1.80E-07 | M252Y/M428I/N434Y |
| F244 | 1.30E-06 | M252Y/M428K/N434Y |
| F245 | 4.70E-07 | M252Y/M428N/N434Y |
| F246 | 1.10E-06 | M252Y/M428P/N434Y |
| F247 | 4.40E-07 | M252Y/M428Q/N434Y |

Table 27-7 is a continuation of Table 27-6.

TABLE 27-7

| | | |
|---|---|---|
| F249 | 6.40E-07 | M252Y/M428S/N434Y |
| F250 | 2.90E-07 | M252Y/M428T/N434Y |
| F251 | 1.90E-07 | M252Y/M428V/N434Y |
| F252 | 1.00E-06 | M252Y/M428W/N434Y |
| F253 | 7.10E-07 | M252Y/M428Y/N434Y |
| F254 | 7.50E-08 | M252W/T307Q/M428Y/N434Y |
| F255 | 1.10E-07 | M252W/Q311A/M428Y/N434Y |
| F256 | 5.40E-08 | M252W/T307Q/Q311A/M428Y/N434Y |
| F257 | 5.00E-07 | M252Y/T307A/M428Y/N434Y |
| F258 | 3.20E-07 | M252Y/T307Q/M428Y/N434Y |
| F259 | 2.80E-07 | M252Y/D270F/N434Y |

TABLE 27-7-continued

| | | |
|---|---|---|
| F260 | 1.30E-07 | M252Y/T307A/Q311A/N434Y |
| F261 | 8.40E-08 | M252Y/T307Q/Q311A/N434Y |
| F262 | 1.90E-07 | M252Y/T307A/Q311H/N434Y |
| F263 | 1.10E-07 | M252Y/T307Q/Q311H/N434Y |
| F264 | 2.80E-07 | M252Y/E382A/N434Y |
| F265 | 6.80E-07 | M252Y/E382A/M428Y/N434Y |
| F266 | 4.70E-07 | M252Y/T307A/E382A/M428Y/N434Y |
| F267 | 3.20E-07 | M252Y/T307Q/E382A/M428Y/N434Y |
| F268 | 6.30E-07 | P238A/M252Y/M428F/N434Y |
| F269 | 5.20E-07 | M252Y/V305A/M428F/N434Y |
| F270 | 6.60E-07 | M252Y/N325G/M428F/N434Y |
| F271 | 6.90E-07 | M252Y/D376A/M428F/N434Y |
| F272 | 6.80E-07 | M252Y/E380A/M428F/N434Y |
| F273 | 6.50E-07 | M252Y/E382A/M428F/N434Y |
| F274 | 7.60E-07 | M252Y/E380A/E382A/M428F/N434Y |
| F275 | 4.20E-08 | S239K/M252Y/V308P/E382A/N434Y |
| F276 | 4.10E-08 | M252Y/D270F/V308P/E382A/N434Y |
| F277 | 1.30E-07 | S239K/M252Y/V308P/M428Y/N434Y |
| F278 | 3.00E-08 | M252Y/T307Q/V308P/E382A/N434Y |
| F279 | 6.10E-08 | M252Y/V308P/Q311H/E382A/N434Y |
| F280 | 4.10E-08 | S239K/M252Y/D270F/V308P/N434Y |
| F281 | 9.20E-08 | M252Y/V308P/E382A/M428F/N434Y |
| F282 | 2.90E-08 | M252Y/V308P/E382A/M428L/N434Y |

Table 27-8 is a continuation of Table 27-7.

TABLE 27-8

| | | |
|---|---|---|
| F283 | 1.00E-07 | M252Y/V308P/E382A/M428Y/N434Y |
| F284 | 1.00E-07 | M252Y/V308P/M428Y/N434Y |
| F285 | 9.90E-08 | M252Y/V308P/M428F/N434Y |
| F286 | 1.20E-07 | S239K/M252Y/V308P/E382A/M428Y/N434Y |
| F287 | 1.00E-07 | M252Y/V308P/E380A/E382A/M428F/N434Y |
| F288 | 1.90E-07 | M252Y/T256E/E382A/N434Y |
| F289 | 4.80E-07 | M252Y/T256E/M428Y/N434Y |
| F290 | 4.60E-07 | M252Y/T256E/E382A/M428Y/N434Y |
| F292 | 2.30E-08 | S239K/M252Y/V308P/E382A/M428I/N434Y |
| F293 | 5.30E-08 | M252Y/V308P/E380A/E382A/M428I/N434Y |
| F294 | 1.10E-07 | S239K/M252Y/V308P/M428F/N434Y |
| F295 | 6.80E-07 | S239K/M252Y/E380A/E382A/M428F/N434Y |
| F296 | 4.90E-07 | M252Y/Q311A/M428Y/N434Y |
| F297 | 5.10E-07 | M252Y/D312A/M428Y/N434Y |
| F298 | 4.80E-07 | M252Y/Q311A/D312A/M428Y/N434Y |
| F299 | 9.40E-08 | S239K/M252Y/V308P/Q311A/M428Y/N434Y |
| F300 | 8.30E-08 | S239K/M252Y/V308P/D312A/M428Y/N434Y |
| F301 | 7.20E-08 | S239K/M252Y/V308P/Q311A/D312A/M428Y/N434Y |
| F302 | 1.90E-07 | M252Y/T256E/T307P/N434Y |
| F303 | 6.70E-08 | M252Y/T307P/M428Y/N434Y |
| F304 | 1.60E-08 | M252W/V308P/M428Y/N434Y |
| F305 | 2.70E-08 | M252Y/T256E/V308P/E382A/N434Y |
| F306 | 3.60E-08 | M252W/V308P/E382A/N434Y |
| F307 | 3.60E-08 | S239K/M252W/V308P/E382A/N434Y |
| F308 | 1.90E-08 | S239K/M252W/V308P/E382A/M428Y/N434Y |
| F310 | 9.40E-08 | S239K/M252W/V308P/E382A/M428I/N434Y |
| F311 | 2.80E-08 | S239K/M252W/V308P/M428F/N434Y |
| F312 | 4.50E-07 | S239K/M252W/E380A/E382A/M428F/N434Y |
| F313 | 6.50E-07 | S239K/M252Y/T307P/M428Y/N434Y |
| F314 | 3.20E-07 | M252Y/T256E/Q311A/D312A/M428Y/N434Y |
| F315 | 6.80E-07 | S239K/M252Y/M428Y/N434Y |
| F316 | 7.00E-08 | S239K/M252Y/D270F/M428Y/N434Y |
| F317 | 1.10E-07 | S239K/M252Y/D270F/V308P/M428Y/N434Y |
| F318 | 1.80E-08 | S239K/M252Y/V308P/M428I/N434Y |

Table 27-9 is a continuation of Table 27-8.

TABLE 27-9

| | | |
|---|---|---|
| F320 | 2.00E-08 | S239K/M252Y/V308P/N325G/E382A/M428I/N434Y |
| F321 | 3.20E-08 | S239K/M252Y/D270F/V308P/N325G/N434Y |
| F322 | 9.20E-08 | S239K/M252Y/D270F/T307P/V308P/N434Y |
| F323 | 2.70E-08 | S239K/M252Y/T256E/D270F/V308P/N434Y |
| F324 | 2.80E-08 | S239K/M252Y/D270F/T307Q/V308P/N434Y |
| F325 | 2.10E-08 | S239K/M252Y/D270F/T307Q/V308P/Q311A/N434Y |
| F326 | 7.50E-08 | S239K/M252Y/D270F/T307Q/Q311A/N434Y |
| F327 | 6.50E-08 | S239K/M252Y/T256E/D270F/T307Q/Q311A/N434Y |
| F328 | 1.90E-08 | S239K/M252Y/D270F/V308P/M428I/N434Y |
| F329 | 1.20E-08 | S239K/M252Y/D270F/N286E/V308P/N434Y |

TABLE 27-9-continued

| | | |
|---|---|---|
| F330 | 3.60E−08 | S239K/M252Y/D270F/V308P/L309E/N434Y |
| F331 | 3.00E−08 | S239K/M252Y/D270F/V308P/P387E/N434Y |
| F333 | 7.40E−08 | S239K/M252Y/D270F/T307Q/L309E/Q311A/N434Y |
| F334 | 1.90E−08 | S239K/M252Y/D270F/V308P/N325G/M428I/N434Y |
| F335 | 1.50E−08 | S239K/M252Y/T256E/D270F/V308P/M428I/N434Y |
| F336 | 1.40E−08 | S239K/M252Y/D270F/T307Q/V308P/Q311A/M428I/N434Y |
| F337 | 5.60E−08 | S239K/M252Y/D270F/T307Q/Q311A/M428I/N434Y |
| F338 | 7.70E−09 | S239K/M252Y/D270F/N286E/V308P/M428I/N434Y |
| F339 | 1.90E−08 | S239K/M252Y/D270F/V308P/L309E/M428I/N434Y |
| F343 | 3.20E−08 | S239K/M252Y/D270F/V308P/M428L/N434Y |
| F344 | 3.00E−08 | S239K/M252Y/V308P/M428L/N434Y |
| F349 | 1.50E−07 | S239K/M252Y/V308P/L309P/M428L/N434Y |
| F350 | 1.70E−07 | S239K/M252Y/V308P/L309R/M428L/N434Y |
| F352 | 6.00E−07 | S239K/M252Y/L309P/M428L/N434Y |
| F353 | 1.10E−06 | S239K/M252Y/L309R/M428L/N434Y |
| F354 | 2.80E−08 | S239K/M252Y/T307Q/V308P/M428L/N434Y |
| F356 | 3.40E−08 | S239K/M252Y/D270F/V308P/L309E/P387E/N434Y |
| F357 | 1.60E−08 | S239K/M252Y/T256E/D270F/V308P/N325G/M428I/N434Y |
| F358 | 1.00E−07 | S239K/M252Y/T307Q/N434Y |
| F359 | 4.20E−07 | P257V/T307Q/M428I/N434Y |
| F360 | 1.30E−06 | P257V/T307Q/M428V/N434Y |
| F362 | 5.40E−08 | P257V/T307Q/N325G/M428L/N434Y |
| F363 | 4.10E−08 | P257V/T307Q/Q311A/M428L/N434Y |
| F364 | 3.50E−08 | P257V/T307Q/Q311A/N325G/M428L/N434Y |

Table 27-10 is a continuation of Table 27-9.

TABLE 27-10

| | | |
|---|---|---|
| F365 | 5.10E−08 | P257V/V305A/T307Q/M428L/N434Y |
| F367 | 1.50E−08 | S239K/M252Y/E258H/D270F/T307Q/V308P/Q311A/N434Y |
| F368 | 2.00E−08 | S239K/M252Y/D270F/V308P/N325G/E382A/M428I/N434Y |
| F369 | 7.50E−08 | M252Y/P257V/T307Q/M428I/N434Y |
| F372 | 1.30E−08 | S239K/M252W/V308P/M428Y/N434Y |
| F373 | 1.10E−08 | S239K/M252W/V308P/Q311A/M428Y/N434Y |
| F374 | 1.20E−08 | S239K/M252W/T256E/V308P/M428Y/N434Y |
| F375 | 5.50E−09 | S239K/M252W/N286E/V308P/M428Y/N434Y |
| F376 | 9.60E−08 | S239K/M252Y/T256E/D270F/N286E/V308P/N434Y |
| F377 | 1.30E−07 | S239K/M252Y/T307P/M428Y/N434Y |
| F379 | 9.00E−09 | S239K/M252W/T256E/V308P/Q311A/M428Y/N434Y |
| F380 | 5.60E−09 | S239K/M252W/T256E/N286E/V308P/M428Y/N434Y |
| F381 | 1.10E−07 | P257V/T307A/Q311A/M428L/N434Y |
| F382 | 8.70E−08 | P257V/V305A/T307A/M428L/N434Y |
| F386 | 3.20E−08 | M252Y/V308P/L309E/N434Y |
| F387 | 1.50E−07 | M252Y/V308P/L309D/N434Y |
| F388 | 7.00E−08 | M252Y/V308P/L309A/N434Y |
| F389 | 1.70E−08 | M252W/V308P/L309E/M428Y/N434Y |
| F390 | 6.80E−08 | M252W/V308P/L309D/M428Y/N434Y |
| F391 | 3.60E−08 | M252W/V308P/L309A/M428Y/N434Y |
| F392 | 6.90E−09 | S239K/M252Y/N286E/V308P/M428I/N434Y |
| F393 | 1.20E−08 | S239K/M252Y/N286E/V308P/N434Y |
| F394 | 5.30E−08 | S239K/M252Y/T307Q/Q311A/M428I/N434Y |
| F395 | 2.40E−08 | S239K/M252Y/T256E/V308P/N434Y |
| F396 | 2.00E−08 | S239K/M252Y/D270F/N286E/T307Q/Q311A/M428I/N434Y |
| F397 | 4.50E−08 | S239K/M252Y/D270F/T307Q/Q311A/P387E/M428I/N434Y |
| F398 | 4.40E−09 | S239K/M252Y/D270F/N286E/T307Q/V308P/Q311A/M428I/N434Y |
| F399 | 6.50E−09 | S239K/M252Y/D270F/N286E/T307Q/V308P/M428I/N434Y |
| F400 | 6.10E−09 | S239K/M252Y/D270F/N286E/V308P/Q311A/M428I/N434Y |
| F401 | 6.90E−09 | S239K/M252Y/D270F/N286E/V308P/P387E/M428I/N434Y |
| F402 | 2.30E−08 | P257V/T307Q/M428L/N434W |
| F403 | 5.10E−08 | P257V/T307A/M428L/N434W |
| F404 | 9.40E−08 | P257A/T307Q/L309P/M428L/N434Y |
| F405 | 1.70E−07 | P257V/T307Q/L309P/M428L/N434Y |

Table 27-11 is a continuation of Table 27-10.

TABLE 27-11

| | | |
|---|---|---|
| F406 | 1.50E−07 | P257A/T307Q/L309R/M428L/N434Y |
| F407 | 1.60E−07 | P257V/T307Q/L309R/M428L/N434Y |
| F408 | 2.50E−07 | P257V/N286E/M428L/N434Y |
| F409 | 2.00E−07 | P257V/P387E/M428L/N434Y |
| F410 | 2.20E−07 | P257V/T307H/M428L/N434Y |
| F411 | 1.30E−07 | P257V/T307N/M428L/N434Y |
| F412 | 8.80E−08 | P257V/T307G/M428L/N434Y |
| F413 | 1.20E−07 | P257V/T307P/M428L/N434Y |
| F414 | 1.10E−07 | P257V/T307S/M428L/N434Y |
| F415 | 5.60E−08 | P257V/N286E/T307A/M428L/N434Y |
| F416 | 9.40E−08 | P257V/T307A/P387E/M428L/N434Y |
| F418 | 6.20E−07 | S239K/M252Y/T307P/N325G/M428Y/N434Y |
| F419 | 1.60E−07 | M252Y/T307A/Q311H/K360H/N434Y |
| F420 | 1.50E−07 | M252Y/T307A/Q311H/P387E/N434Y |
| F421 | 1.30E−07 | M252Y/T307A/Q311H/M428A/N434Y |
| F422 | 1.80E−07 | M252Y/T307A/Q311H/E382A/N434Y |
| F423 | 8.40E−08 | M252Y/T307W/Q311H/N434Y |
| F424 | 9.40E−08 | S239K/P257A/V308P/M428L/N434Y |
| F425 | 8.00E−08 | P257A/V308P/L309E/M428L/N434Y |
| F426 | 8.40E−08 | P257V/T307Q/N434Y |
| F427 | 1.10E−07 | M252Y/P257V/T307Q/M428V/N434Y |
| F428 | 8.00E−08 | M252Y/P257V/T307Q/M428L/N434Y |
| F429 | 3.70E−08 | M252Y/P257V/T307Q/N434Y |
| F430 | 8.10E−08 | M252Y/P257V/T307Q/M428Y/N434Y |
| F431 | 6.50E−08 | M252Y/P257V/T307Q/M428F/N434Y |
| F432 | 9.20E−07 | P257V/T307Q/Q311A/N325G/M428V/N434Y |
| F433 | 6.00E−08 | P257V/T307Q/Q311A/N325G/N434Y |
| F434 | 2.00E−08 | P257V/T307Q/Q311A/N325G/M428Y/N434Y |
| F435 | 2.50E−08 | P257V/T307Q/Q311A/N325G/M428F/N434Y |
| F436 | 2.50E−07 | P257A/T307Q/M428V/N434Y |
| F437 | 5.70E−08 | P257A/T307Q/N434Y |
| F438 | 3.60E−08 | P257A/T307Q/M428Y/N434Y |
| F439 | 4.00E−08 | P257A/T307Q/M428F/N434Y |
| F440 | 1.50E−08 | P257V/N286E/T307Q/Q311A/N325G/M428L/N434Y |

Table 27-12 is a continuation of Table 27-11.

TABLE 27-12

| | | |
|---|---|---|
| F441 | 1.80E−07 | P257A/Q311A/M428L/N434Y |
| F442 | 2.00E−07 | P257A/Q311H/M428L/N434Y |
| F443 | 5.50E−08 | P257A/T307Q/Q311A/M428L/N434Y |
| F444 | 1.40E−07 | P257A/T307A/Q311A/M428L/N434Y |
| F445 | 6.20E−08 | P257A/T307Q/Q311H/M428L/N434Y |
| F446 | 1.10E−07 | P257A/T307A/Q311H/M428L/N434Y |
| F447 | 1.40E−08 | P257A/N286E/T307Q/M428L/N434Y |
| F448 | 5.30E−08 | P257A/N286E/T307A/M428L/N434Y |
| F449 | 5.70E−07 | S239K/M252Y/D270F/T307P/N325G/M428Y/N434Y |
| F450 | 5.20E−07 | S239K/M252Y/T307P/L309E/N325G/M428Y/N434Y |
| F451 | 1.00E−07 | P257S/T307A/M428L/N434Y |
| F452 | 1.40E−07 | P257M/T307A/M428L/N434Y |
| F453 | 7.80E−08 | P257N/T307A/M428L/N434Y |
| F454 | 9.60E−08 | P257I/T307A/M428L/N434Y |
| F455 | 2.70E−08 | P257V/T307Q/M428Y/N434Y |
| F456 | 3.40E−08 | P257V/T307Q/M428F/N434Y |
| F457 | 4.00E−08 | S239K/P257V/V308P/M428L/N434Y |
| F458 | 1.50E−08 | P257V/T307Q/V308P/N325G/M428L/N434Y |
| F459 | 1.30E−08 | P257V/T307Q/V308P/Q311A/N325G/M428L/N434Y |
| F460 | 4.70E−08 | P257V/T307A/V308P/N325G/M428L/N434Y |
| F462 | 8.50E−08 | P257A/V308P/N325G/M428L/N434Y |
| F463 | 1.30E−07 | P257A/T307A/V308P/M428L/N434Y |
| F464 | 5.50E−08 | P257A/T307Q/V308P/M428L/N434Y |
| F465 | 2.10E−08 | P257V/N286E/T307Q/N325G/M428L/N434Y |
| F466 | 3.50E−08 | T256E/P257V/N434Y |
| F467 | 5.70E−07 | T256E/P257T/N434Y |
| F468 | 5.70E−08 | S239K/P257T/V308P/M428L/N434Y |
| F469 | 5.60E−08 | P257T/V308P/N325G/M428L/N434Y |
| F470 | 5.40E−08 | T256E/P257T/V308P/N325G/M428L/N434Y |
| F471 | 6.60E−08 | P257T/V308P/N325G/E382A/M428L/N434Y |
| F472 | 5.40E−08 | P257T/V308P/N325G/P387E/M428L/N434Y |
| F473 | 4.50E−08 | P257T/V308P/L309P/N325G/M428L/N434Y |
| F474 | 3.50E−07 | P257T/V308P/L309R/N325G/M428L/N434Y |
| F475 | 4.30E−08 | T256E/P257V/T307Q/M428L/N434Y |

Table 27-13 is a continuation of Table 27-12.

TABLE 27-13

| | | |
|---|---|---|
| F476 | 5.50E−08 | P257V/T307Q/E382A/M428L/N434Y |
| F477 | 4.30E−08 | P257V/T307Q/P387E/M428L/N434Y |
| F480 | 3.90E−08 | P257L/V308P/N434Y |
| F481 | 5.60E−08 | P257T/T307Q/N434Y |
| F482 | 7.00E−08 | P257V/T307Q/N325G/N434Y |
| F483 | 5.70E−08 | P257V/T307Q/Q311A/N434Y |
| F484 | 6.20E−08 | P257V/V305A/T307Q/N434Y |
| F485 | 9.70E−08 | P257V/N286E/T307A/N434Y |
| F486 | 3.40E−07 | P257V/T307Q/L309R/Q311H/M428L/N434Y |
| F488 | 3.50E−08 | P257V/V308P/N325G/M428L/N434Y |
| F490 | 7.50E−08 | S239K/P257V/V308P/Q311H/M428L/N434Y |
| F492 | 9.80E−08 | P257V/V305A/T307A/N325G/M428L/N434Y |
| F493 | 4.90E−07 | S239K/D270F/T307P/N325G/M428Y/N434Y |
| F497 | 3.10E−06 | P257T/T307A/M428V/N434Y |
| F498 | 1.30E−06 | P257A/M428V/N434Y |
| F499 | 5.20E−07 | P257A/T307A/M428V/N434Y |
| F500 | 4.30E−08 | P257S/T307Q/M428L/N434Y |
| F506 | 1.90E−07 | P257V/N297A/T307Q/M428L/N434Y |
| F507 | 5.10E−08 | P257V/N286A/T307Q/M428L/N434Y |
| F508 | 1.10E−08 | P257V/T307Q/N315A/M428L/N434Y |
| F509 | 5.80E−08 | P257V/T307Q/N384A/M428L/N434Y |
| F510 | 5.30E−08 | P257V/T307Q/N389A/M428L/N434Y |
| F511 | 4.20E−07 | P257V/N434Y |
| F512 | 5.80E−08 | P257T/N434Y |
| F517 | 3.10E−07 | P257V/N286E/N434Y |
| F518 | 4.20E−07 | P257T/N286E/N434Y |
| F519 | 2.60E−08 | P257V/N286E/T307Q/N434Y |
| F521 | 1.10E−08 | P257V/N286E/T307Q/M428Y/N434Y |
| F523 | 2.60E−08 | P257V/V305A/T307Q/M428Y/N434Y |
| F526 | 1.90E−07 | P257T/T307Q/M428Y/N434Y |
| F527 | 9.40E−09 | P257T/T307Q/V308P/N325G/M428Y/N434Y |
| F529 | 2.50E−08 | P257T/T307Q/M428F/N434Y |
| F533 | 1.20E−08 | P257A/N286E/T307Q/M428F/N434Y |
| F534 | 1.20E−08 | P257A/N286E/T307Q/M428Y/N434Y |

Table 27-14 is a continuation of Table 27-13.

TABLE 27-14

| | | |
|---|---|---|
| F535 | 3.90E−08 | T250A/P257V/T307Q/M428L/N434Y |
| F538 | 9.90E−08 | T250F/P257V/T307Q/M428L/N434Y |
| F541 | 6.00E−08 | T250I/P257V/T307Q/M428L/N434Y |
| F544 | 3.10E−08 | T250M/P257V/T307Q/M428L/N434Y |
| F549 | 5.40E−08 | T250S/P257V/T307Q/M428L/N434Y |
| F550 | 5.90E−08 | T250V/P257V/T307Q/M428L/N434Y |
| F551 | 1.20E−07 | T250W/P257V/T307Q/M428L/N434Y |
| F552 | 1.10E−07 | T250Y/P257V/T307Q/M428L/N434Y |
| F553 | 1.70E−07 | M252Y/Q311A/N434Y |
| F554 | 2.80E−08 | S239K/M252Y/S254T/V308P/N434Y |
| F556 | 1.50E−06 | M252Y/T307Q/Q311A |
| F559 | 8.00E−08 | M252Y/S254T/N286E/N434Y |
| F560 | 2.80E−08 | M252Y/S254T/V308P/N434Y |
| F561 | 1.40E−07 | M252Y/S254T/T307A/N434Y |
| F562 | 8.30E−08 | M252Y/S254T/T307Q/N434Y |
| F563 | 1.30E−07 | M252Y/S254T/Q311A/N434Y |
| F564 | 1.90E−07 | M252Y/S254T/Q311H/N434Y |
| F565 | 9.20E−08 | M252Y/S254T/T307A/Q311A/N434Y |
| F566 | 6.10E−08 | M252Y/S254T/T307Q/Q311A/N434Y |
| F567 | 2.20E−07 | M252Y/S254T/M428I/N434Y |
| F568 | 1.10E−07 | M252Y/T256E/T307A/Q311H/N434Y |
| F569 | 2.00E−07 | M252Y/T256Q/T307A/Q311H/N434Y |
| F570 | 1.30E−07 | M252Y/S254T/T307A/Q311H/N434Y |
| F571 | 8.10E−08 | M252Y/N286E/T307A/Q311H/N434Y |
| F572 | 1.00E−07 | M252Y/T307A/Q311H/M428I/N434Y |
| F576 | 1.60E−06 | M252Y/T256E/T307Q/Q311H |
| F577 | 1.30E−06 | M252Y/N286E/T307A/Q311A |
| F578 | 5.70E−07 | M252Y/N286E/T307Q/Q311A |
| F580 | 8.60E−07 | M252Y/N286E/T307Q/Q311A |
| F581 | 7.20E−08 | M252Y/T256E/N286E/N434Y |
| F582 | 7.50E−07 | S239K/M252Y/V308P |
| F583 | 7.80E−07 | S239K/M252Y/V308P/E382A |
| F584 | 6.30E−07 | S239K/M252Y/T256E/V308P |
| F585 | 2.90E−07 | S239K/M252Y/N286E/V308P |

Table 27-15 is a continuation of Table 27-14.

TABLE 27-15

| | | |
|---|---|---|
| F586 | 1.40E−07 | S239K/M252Y/N286E/V308P/M428I |
| F587 | 1.90E−07 | M252Y/N286E/M428I/N434Y |
| F592 | 2.00E−07 | M252Y/S254T/E382A/N434Y |
| F593 | 3.10E−08 | S239K/M252Y/S254T/V308P/M428I/N434Y |
| F594 | 1.60E−08 | S239K/N252Y/T256E/V308P/M428I/N434Y |
| F595 | 1.80E−08 | S239K/M252Y/M428I/N434Y |
| F596 | 4.00E−07 | M252Y/D312A/E382A/M428Y/N434Y |
| F597 | 2.20E−07 | M252Y/E382A/P387E/N434Y |
| F598 | 1.40E−07 | M252Y/D312A/P387E/N434Y |
| F599 | 5.20E−07 | M252Y/P387E/M428Y/N434Y |
| F600 | 2.80E−07 | M252Y/T256Q/E382A/N434Y |
| F601 | 9.60E−09 | M252Y/N286E/V308P/N434Y |
| F608 | | G236A/S239D/I332E |
| F611 | 2.80E−07 | M252Y/V305T/T307P/V308I/L309A/N434Y |
| F612 | 3.60E−07 | M252Y/T307P/V308I/L309A/N434Y |
| F613 | | S239D/A330L/I332E |
| F616 | | S239D/K326D/L328Y |
| F617 | 7.40E−07 | S239K/N434W |
| F618 | 6.40E−07 | S239K/V308F/N434Y |
| F619 | 3.10E−07 | S239K/M252Y/N434Y |
| F620 | 2.10E−07 | S239K/M252Y/S254T/N434Y |
| F621 | 1.50E−07 | S239K/M252Y/T307A/Q311H/N434Y |
| F622 | 3.50E−07 | S239K/M252Y/T256Q/N434Y |
| F623 | 1.80E−07 | S239K/M252W/N434W |
| F624 | 1.40E−08 | S239K/P257A/N286E/T307Q/M428L/N434Y |
| F625 | 7.60E−08 | S239K/P257A/T307Q/M428L/N434Y |
| F626 | 1.30E−06 | V308P |
| F629 | 3.90E−08 | M252Y/V279L/V308P/N434Y |
| F630 | 3.70E−08 | S239K/M252Y/V279L/V308P/N434Y |
| F633 | 2.40E−08 | M252Y/V282D/V308P/N434Y |
| F634 | 3.20E−08 | S239K/M252Y/V282D/V308P/N434Y |
| F635 | 4.50E−08 | M252Y/V284K/V308P/N434Y |
| F636 | 4.80E−08 | S239K/M252Y/V284K/V308P/N434Y |
| F637 | 1.50E−07 | M252Y/K288S/V308P/N434Y |

Table 27-16 is a continuation of Table 27-15.

TABLE 27-16

| | | |
|---|---|---|
| F638 | 1.40E−07 | S239K/M252Y/K288S/V308P/N434Y |
| F639 | 2.70E−08 | M252Y/V308P/G385R/N434Y |
| F640 | 3.60E−08 | S239K/M252Y/V308P/G385R/N434Y |
| F641 | 3.00E−08 | M252Y/V308P/Q386K/N434Y |
| F642 | 3.00E−08 | S239K/M252Y/V308P/Q386K/N434Y |
| F643 | 3.20E−08 | L235G/G236R/S239K/M252Y/V308P/N434Y |
| F644 | 3.00E−08 | G236R/S239K/M252Y/V308P/N434Y |
| F645 | 3.30E−08 | S239K/M252Y/V308P/L328R/N434Y |
| F646 | 3.80E−08 | S239K/M252Y/N297A/V308P/N434Y |
| F647 | 2.90E−08 | P238D/M252Y/V308P/N434Y |
| F648 | | P238D |
| F649 | 1.20E−07 | S239K/M252Y/N286E/N434Y |
| F650 | 1.70E−07 | S239K/M252Y/T256E/N434Y |
| F651 | 1.80E−07 | S239K/M252Y/Q311A/N434Y |
| F652 | 2.40E−07 | P238D/M252Y/N434Y |
| F654 | 3.20E−08 | L235K/S239K/M252Y/V308P/N434Y |
| F655 | 3.40E−08 | L235R/S239K/M252Y/V308P/N434Y |
| F656 | 3.30E−08 | G237K/S239K/M252Y/V308P/N434Y |
| F657 | 3.20E−08 | G237R/S239K/M252Y/V308P/N434Y |
| F658 | 3.20E−08 | P238K/S239K/M252Y/V308P/N434Y |
| F659 | 3.00E−08 | P238R/S239K/M252Y/V308P/N434Y |
| F660 | 3.10E−08 | S239K/M252Y/V308P/P329K/N434Y |
| F661 | 3.40E−08 | S239K/M252Y/V308P/P329R/N434Y |
| F663 | 6.40E−09 | S239K/M252Y/N286E/T307Q/V308P/Q311A/N434Y |
| F664 | 3.90E−08 | M252Y/N286A/V308P/N434Y |
| F665 | 2.00E−08 | M252Y/N286D/V308P/N434Y |
| F666 | 2.10E−08 | M252Y/N286F/V308P/N434Y |
| F667 | 3.00E−08 | M252Y/N286G/V308P/N434Y |
| F668 | 4.00E−08 | M252Y/N286H/V308P/N434Y |
| F669 | 3.50E−08 | M252Y/N286I/V308P/N434Y |
| F670 | 2.10E−07 | M252Y/N286K/V308P/N434Y |
| F671 | 2.20E−08 | M252Y/N286L/V308P/N434Y |
| F672 | 2.40E−08 | M252Y/N286M/V308P/N434Y |
| F673 | 2.30E−08 | M252Y/N286P/V308P/N434Y |

Table 27-17 is a continuation of Table 27-16.

TABLE 27-17

| | | |
|---|---|---|
| F674 | 3.20E−08 | M252Y/N286Q/V308P/N434Y |
| F675 | 5.10E−08 | M252Y/N286R/V308P/N434Y |
| F676 | 3.20E−08 | M252Y/N286S/V308P/N434Y |
| F677 | 4.70E−08 | M252Y/N286T/V308P/N434Y |
| F678 | 3.30E−08 | M252Y/N286V/V308P/N434Y |
| F679 | 1.70E−08 | M252Y/N286W/V308P/N434Y |
| F680 | 1.50E−08 | M252Y/N286Y/V308P/N434Y |
| F681 | 4.90E−08 | M252Y/K288A/V308P/N434Y |
| F682 | 8.20E−08 | M252Y/K288D/V308P/N434Y |
| F683 | 5.00E−08 | M252Y/K288E/V308P/N434Y |
| F684 | 5.10E−08 | M252Y/K288F/V308P/N434Y |
| F685 | 5.30E−08 | M252Y/K288G/V308P/N434Y |
| F686 | 4.60E−08 | M252Y/K288H/V308P/N434Y |
| F687 | 4.90E−08 | M252Y/K288I/V308P/N434Y |
| F688 | 2.80E−08 | M252Y/K288L/V308P/N434Y |
| F689 | 4.10E−08 | M252Y/K288M/V308P/N434Y |
| F690 | 1.00E−07 | M252Y/K288N/V308P/N434Y |
| F691 | 3.20E−08 | M252Y/K288P/V308P/N434Y |
| F692 | 3.90E−08 | M252Y/K288Q/V308P/N434Y |
| F693 | 3.60E−08 | M252Y/K288R/V308P/N434Y |
| F694 | 4.70E−08 | M252Y/K288V/V308P/N434Y |
| F695 | 4.00E−08 | M252Y/K288W/V308P/N434Y |
| F696 | 4.40E−08 | M252Y/K288Y/V308P/N434Y |
| F697 | 3.10E−08 | S239K/M252Y/V308P/N325G/N434Y |
| F698 | 2.20E−08 | M252Y/N286E/T307Q/Q311A/N434Y |
| F699 | 2.30E−08 | S239K/M252Y/N286E/T307Q/Q311A/N434Y |
| F700 | 5.20E−08 | M252Y/V308P/L328E/N434Y |
| F705 | 7.10E−09 | M252Y/N286E/V308P/M428I/N434Y |
| F706 | 1.80E−08 | M252Y/N286E/T307Q/Q311A/M428I/N434Y |
| F707 | 5.90E−09 | M252Y/N286E/T307Q/V308P/Q311A/N434Y |
| F708 | 4.10E−09 | M252Y/N286E/T307Q/V308P/Q311A/M428I/N434Y |
| F709 | 2.00E−08 | S239K/M252Y/N286E/T307Q/Q311A/M428I/N434Y |
| F710 | 1.50E−08 | P238D/M252Y/N286E/T307Q/Q311A/M428I/N434Y |
| F711 | 6.50E−08 | S239K/M252Y/T307Q/Q311A/N434Y |

Table 27-18 is a continuation of Table 27-17.

TABLE 27-18

| | | |
|---|---|---|
| F712 | 6.00E−08 | P238D/M252Y/T307Q/Q311A/N434Y |
| F713 | 2.00E−08 | P238D/M252Y/N286E/T307Q/Q311A/N434Y |
| F714 | 2.30E−07 | P238D/M252Y/N325S/N434Y |
| F715 | 2.30E−07 | P238D/M252Y/N325M/N434Y |
| F716 | 2.70E−07 | P238D/M252Y/N325L/N434Y |
| F717 | 2.60E−07 | P238D/M252Y/N325I/N434Y |
| F718 | 2.80E−07 | P238D/M252Y/Q295M/N434Y |
| F719 | 7.40E−08 | P238D/M252Y/N325G/N434Y |
| F720 | 2.40E−08 | M252Y/T307Q/V308P/Q311A/N434Y |
| F721 | 1.50E−08 | M252Y/T307Q/V308P/Q311A/M428I/N434Y |
| F722 | 2.70E−07 | P238D/M252Y/A327G/N434Y |
| F723 | 2.80E−07 | P238D/M252Y/L328D/N434Y |
| F724 | 2.50E−07 | P238D/M252Y/L328E/N434Y |
| F725 | 4.20E−08 | L235K/G237R/S239K/M252Y/V308P/N434Y |
| F726 | 3.70E−08 | L235K/P238K/S239K/M252Y/V308P/N434Y |
| F729 | 9.20E−08 | T307A/Q311A/N434Y |
| F730 | 6.00E−07 | T307Q/Q311A/N434Y |
| F731 | 8.50E−07 | T307A/Q311H/N434Y |
| F732 | 6.80E−07 | T307Q/Q311H/N434Y |
| F733 | 3.20E−07 | M252Y/L328E/N434Y |
| F734 | 3.10E−07 | G236D/M252Y/L328E/N434Y |
| F736 | 3.10E−07 | M252Y/S267M/L328E/N434Y |
| F737 | 3.10E−07 | M252Y/S267L/L328E/N434Y |
| F738 | 3.50E−07 | P238D/M252Y/T307P/N434Y |
| F739 | 2.20E−07 | M252Y/T307P/Q311A/N434Y |
| F740 | 2.90E−07 | M252Y/T307P/Q311H/N434Y |
| F741 | 3.10E−07 | P238D/T250A/M252Y/N434Y |
| F744 | 9.90E−07 | P238D/T250F/M252Y/N434Y |
| F745 | 6.60E−07 | P238D/T250G/M252Y/N434Y |
| F746 | 6.00E−07 | P238D/T250H/M252Y/N434Y |
| F747 | 2.80E−07 | P238D/T250I/M252Y/N434Y |
| F749 | 5.10E−07 | P238D/T250L/M252Y/N434Y |
| F750 | 3.00E−07 | P238D/T250M/M252Y/N434Y |
| F751 | 5.30E−07 | P238D/T250N/M252Y/N434Y |

Table 27-19 is a continuation of Table 27-18.

TABLE 27-19

| | | |
|---|---|---|
| F753 | 1.80E−07 | P238D/T250Q/M252Y/N434Y |
| F755 | 3.50E−07 | P238D/T250S/M252Y/N434Y |
| F756 | 3.70E−07 | P238D/T250V/M252Y/N434Y |
| F757 | 1.20E−06 | P238D/T250W/M252Y/N434Y |
| F758 | 1.40E−06 | P238D/T250Y/M252Y/N434Y |
| F759 | | L235K/S239K |
| F760 | | L235R/S239K |
| F761 | 1.10E−06 | P238D/N434Y |
| F762 | 3.60E−08 | L235K/S239K/M252Y/N286E/T307Q/Q311A/N434Y |
| F763 | 3.50E−08 | L235R/S239K/M252Y/N286E/T307Q/Q311A/N434Y |
| F764 | 6.30E−07 | P238D/T307Q/Q311A/N434Y |
| F765 | 8.50E−08 | P238D/M252Y/T307Q/L309E/Q311A/N434Y |
| F766 | 6.00E−07 | T307A/L309E/Q311A/N434Y |
| F767 | 4.30E−07 | T307Q/L309E/Q311A/N434Y |
| F768 | 6.40E−07 | T307A/L309E/Q311H/N434Y |
| F769 | 4.60E−07 | T307Q/L309E/Q311H/N434Y |
| F770 | 3.00E−07 | M252Y/T256A/N434Y |
| F771 | 4.00E−07 | M252Y/E272A/N434Y |
| F772 | 3.80E−07 | M252Y/K274A/N434Y |
| F773 | 3.90E−07 | M252Y/V282A/N434Y |
| F774 | 4.00E−07 | M252Y/N286A/N434Y |
| F775 | 6.20E−07 | M252Y/K338A/N434Y |
| F776 | 3.90E−07 | M252Y/K340A/N434Y |
| F777 | 3.90E−07 | M252Y/E345A/N434Y |
| F779 | 3.90E−07 | M252Y/N361A/N434Y |
| F780 | 3.90E−07 | M252Y/Q362A/N434Y |
| F781 | 3.70E−07 | M252Y/S375A/N434Y |
| F782 | 3.50E−07 | M252Y/Y391A/N434Y |
| F783 | 4.00E−07 | M252Y/D413A/N434Y |
| F784 | 5.00E−07 | M252Y/L309A/N434Y |
| F785 | 7.40E−07 | M252Y/L309H/N434Y |
| F786 | 2.80E−08 | M252Y/S254T/N286E/T307Q/Q311A/N434Y |
| F787 | 8.80E−08 | M252Y/S254T/T307Q/L309E/Q311A/N434Y |
| F788 | 4.10E−07 | M252Y/N315A/N434Y |

Table 27-20 is a continuation of Table 27-19.

TABLE 27-20

| | | |
|---|---|---|
| F789 | 1.50E−07 | M252Y/N315D/N434Y |
| F790 | 2.70E−07 | M252Y/N315E/N434Y |
| F791 | 4.40E−07 | M252Y/N315F/N434Y |
| F792 | 4.40E−07 | M252Y/N315G/N434Y |
| F793 | 3.30E−07 | M252Y/N315I/N434Y |
| F791 | 4.10E−07 | M252Y/N315K/N434Y |
| F795 | 3.10E−07 | M252Y/N315L/N434Y |
| F796 | 3.40E−07 | M252Y/N315M/N434Y |
| F798 | 3.50E−07 | M252Y/N315Q/N434Y |
| F799 | 4.10E−07 | M252Y/N315R/N434Y |
| F800 | 3.80E−07 | M252Y/N315S/N434Y |
| F801 | 4.40E−07 | M252Y/N315T/N434Y |
| F802 | 3.30E−07 | M252Y/N315V/N434Y |
| F803 | 3.60E−07 | M252Y/N315W/N434Y |
| F804 | 4.00E−07 | M252Y/N315Y/N434Y |
| F805 | 3.00E−07 | M252Y/N325A/N434Y |
| F806 | 3.10E−07 | M252Y/N384A/N434Y |
| F807 | 3.20E−07 | M252Y/N389A/N434Y |
| F808 | 3.20E−07 | M252Y/N389A/N390A/N434Y |
| F809 | 2.20E−07 | M252Y/S254T/T256S/N434Y |
| F810 | 2.20E−07 | M252Y/A378V/N434Y |
| F811 | 4.90E−07 | M252Y/E380S/N434Y |
| F812 | 2.70E−07 | M252Y/E382V/N434Y |
| F813 | 2.80E−07 | M252Y/S424E/M434Y |
| F814 | 1.20E−07 | M252Y/N434Y/Y436I |
| F815 | 5.50E−07 | M252Y/N434Y/T437R |
| F816 | 3.60E−07 | P238D/T250V/M252Y/T307P/N434Y |
| F817 | 9.80E−08 | P238D/T250V/M252Y/T307Q/Q311A/N434Y |
| F819 | 1.40E−07 | P238D/M252Y/N286E/N434Y |
| F820 | 3.40E−07 | L235K/S239K/M252Y/N434Y |
| F821 | 3.10E−07 | L235R/S239K/M252Y/N434Y |
| F822 | 1.10E−06 | P238D/T250Y/M252Y/W313Y/N434Y |
| F823 | 1.10E−06 | P238D/T250Y/M252Y/W313F/N434Y |
| F828 | 2.50E−06 | P238D/T250V/M252Y/I253V/N434Y |

Table 27-21 is a continuation of Table 27-20.

TABLE 27-21

| | | |
|---|---|---|
| F831 | 1.60E−06 | P238D/T250V/M252Y/R255A/N434Y |
| F832 | 2.60E−06 | P238D/T250V/M252Y/R255D/N434Y |
| F833 | 8.00E−07 | P238D/T250V/M252Y/R255E/N434Y |
| F834 | 8.10E−07 | P238D/T250V/M252Y/R255F/N434Y |
| F836 | 5.00E−07 | P238D/T250V/M252Y/R255H/N434Y |
| F837 | 5.60E−07 | P238D/T250V/M252Y/R255I/N434Y |
| F838 | 4.30E−07 | P238D/T250V/M252Y/R255K/N434Y |
| F839 | 3.40E−07 | P238D/T250V/M252Y/R255L/N434Y |
| F840 | 4.20E−07 | P238D/T250V/M252Y/R255M/N434Y |
| F841 | 1.10E−06 | P238D/T250V/M252Y/R255N/N434Y |
| F843 | 6.60E−07 | P238D/T250V/M252Y/R255Q/N434Y |
| F844 | 1.30E−06 | P238D/T250V/M252Y/R255S/N434Y |
| F847 | 3.40E−07 | P238D/T250V/M252Y/R255W/N434Y |
| F848 | 8.30E−07 | P238D/T250V/M252Y/R255Y/N434Y |
| F849 | 3.30E−07 | M252Y/D280A/N434Y |
| F850 | 2.90E−07 | M252Y/D280E/N434Y |
| F852 | 3.30E−07 | M252Y/D280G/N434Y |
| F853 | 3.20E−07 | M252Y/D280H/N434Y |
| F855 | 3.20E−07 | M252Y/D280K/N434Y |
| F858 | 3.20E−07 | M252Y/D280N/N434Y |
| F860 | 3.30E−07 | M252Y/D280Q/N434Y |
| F861 | 3.20E−07 | M252Y/D280R/N434Y |
| F862 | 3.00E−07 | M252Y/D280S/N434Y |
| F863 | 2.70E−07 | M252Y/D280T/N434Y |
| F867 | 2.80E−07 | M252Y/N384A/N389A/N434Y |
| F868 | 2.00E−08 | G236A/S239D/M252Y/N286E/T307Q/Q311A/N434Y |
| F869 | | G236A/S239D |
| F870 | 7.30E−08 | L235K/S239K/M252Y/T307Q/Q311A/N434Y |
| F871 | 7.10E−08 | L235R/S239K/M252Y/T307Q/Q311A/N434Y |
| F872 | 1.30E−07 | L235K/S239K/M252Y/N286E/N434Y |
| F873 | 1.20E−07 | L235R/S239K/M252Y/N286E/N434Y |
| F875 | 4.80E−07 | M252Y/N434Y/Y436A |
| F877 | 8.30E−07 | M252Y/N434Y/Y436E |
| F878 | 1.90E−07 | M252Y/N434Y/Y436F |

Table 27-22 is a continuation of Table 27-21.

TABLE 27-22

| | | |
|---|---|---|
| F879 | 9.20E−07 | M252Y/N434Y/Y436G |
| F880 | 3.90E−07 | M252Y/N434Y/Y436H |
| F881 | 3.10E−07 | M252Y/N434Y/Y436K |
| F882 | 1.30E−07 | M252Y/N434Y/Y436L |
| F883 | 2.10E−07 | M252Y/N434Y/Y436M |
| F884 | 4.00E−07 | M252Y/N434Y/Y436N |
| F888 | 4.80E−07 | M252Y/N434Y/Y436S |
| F889 | 2.20E−07 | M252Y/N434Y/Y436T |
| F890 | 1.10E−07 | M252Y/N434Y/Y436V |
| F891 | 1.70E−07 | M252Y/N434Y/Y436W |
| F892 | 7.10E−08 | M252Y/S254T/N434Y/Y436I |
| F893 | 9.80E−08 | L235K/S239K/M252Y/N434Y/Y436I |
| F894 | 9.20E−08 | L235R/S239K/M252Y/N434Y/Y436I |
| F895 | 2.10E−08 | L235K/S239K/M252Y/N286E/T307Q/Q311A/N315E/N434Y |
| F896 | 2.00E−08 | L235R/S239K/M252Y/N286E/T307Q/Q311A/N315E/N434Y |
| F897 | 9.70E−08 | M252Y/N315D/N384A/N389A/N434Y |
| F898 | 1.70E−07 | M252Y/N315E/N384A/N389A/N434Y |
| F899 | 1.10E−07 | M252Y/N315D/G316A/N434Y |
| F900 | 1.70E−07 | M252Y/N315D/G316D/N434Y |
| F901 | 1.30E−07 | M252Y/N315D/G316E/N434Y |
| F902 | 2.20E−07 | M252Y/N315D/G316F/N434Y |
| F903 | 2.30E−07 | M252Y/N315D/G316H/N434Y |
| F904 | 1.00E−07 | M252Y/N315D/G316I/N434Y |
| F905 | 1.30E−07 | M252Y/N315D/G316K/N434Y |
| F906 | 1.50E−07 | M252Y/N315D/G316L/N434Y |
| F907 | 1.30E−07 | M252Y/N315D/G316M/N434Y |
| F908 | 1.50E−07 | M252Y/N315D/G316N/N434Y |
| F909 | 1.30E−07 | M252Y/N315D/G316P/N434Y |
| F910 | 1.40E−07 | M252Y/N315D/G316Q/N434Y |
| F911 | 1.30E−07 | M252Y/N315D/G316R/N434Y |
| F912 | 1.20E−07 | M252Y/N315D/G316S/N434Y |
| F913 | 1.10E−07 | M252Y/N315D/G316T/N434Y |
| F914 | 1.50E−07 | M252Y/N315D/G316V/N434Y |
| F915 | 2.30E−07 | M252Y/N315D/G316W/N434Y |

Table 27-23 is a continuation of Table 27-22.

TABLE 27-23

| | | |
|---|---|---|
| F917 | 2.50E−07 | M252Y/N286S/N434Y |
| F918 | 2.80E−07 | M252Y/D280E/N384A/N389A/N434Y |
| F919 | 3.30E−07 | M252Y/D280G/N384A/N389A/N434Y |
| F920 | 2.50E−07 | M252Y/N286S/N384A/N389A/N434Y |
| F921 | 1.20E−07 | M252Y/N286E/N384A/N389A/N434Y |
| F922 | 5.90E−08 | L235K/S239K/M252Y/N286E/N434Y/Y436I |
| F923 | 6.00E−08 | L235R/S239K/M252Y/N286E/N434Y/Y436I |
| F924 | 3.40E−08 | L235K/S239K/M252Y/T307Q/Q311A/N434K/Y436I |
| F925 | 3.20E−08 | L235R/S239K/M252Y/T307Q/Q311A/N434Y/Y436I |
| F926 | 1.10E−07 | L235K/S239K/M252Y/S254T/N434Y/Y436I |
| F927 | 1.00E−07 | L235R/S239K/M252Y/S254T/N434Y/Y436I |
| F928 | 2.90E−08 | M252Y/T307Q/Q311A/N434Y/Y436I |
| F929 | 2.90E−08 | M252Y/S254T/T307Q/Q311A/N434Y/Y436I |
| F930 | 1.40E−07 | P238D/T250V/M252Y/N286E/N434Y |
| F931 | 1.20E−07 | P238D/T250V/M252Y/N434Y/Y436I |
| F932 | 3.20E−07 | T250V/M252Y/N434Y |
| F933 | 3.00E−07 | L234R/P238D/T250V/M252Y/N434Y |
| F934 | 3.10E−07 | G236K/P238D/T250V/M252Y/N434Y |
| F935 | 3.20E−07 | G237K/P238D/T250V/M252Y/N434Y |
| F936 | 3.20E−07 | G237R/P238D/T250V/M252Y/N434Y |
| F937 | 3.10E−07 | P238D/S239K/T250V/M252Y/N434Y |
| F938 | 1.60E−07 | L235K/S239K/M252Y/N434Y/Y436V |
| F939 | 1.50E−07 | L235R/S239K/M252Y/N434Y/Y436V |
| F940 | 1.50E−07 | P238D/T250V/M252Y/N434Y/Y436V |
| F941 | 1.20E−08 | M252Y/N286E/T307Q/Q311A/N434Y/Y436V |
| F942 | 4.20E−08 | L235K/S239K/M252Y/T307Q/Q311A/N434Y/Y436V |
| F943 | 4.00E−08 | L235R/S239K/M252Y/T307Q/Q311A/N434Y/Y436V |
| F944 | 1.70E−07 | T250V/M252Y/N434Y/Y436V |
| F945 | 1.70E−08 | T250V/M252Y/V308P/N434Y/Y436V |
| F946 | 4.30E−08 | M252Y/T307Q/Q311A/N434Y/Y436V |
| F947 | 1.10E−08 | T250V/M252Y/T307Q/V308P/Q311A/N434Y/Y436V |
| F954 | 5.30E−07 | M252Y/N434Y/H435K/Y436V |
| F957 | 7.70E−07 | M252Y/N434Y/H435N/Y436V |
| F960 | 8.00E−07 | M252Y/N434Y/H435R/Y436V |

Table 27-24 is a continuation of Table 27-23.

TABLE 27-24

| | | |
|---|---|---|
| F966 | 3.10E−07 | M252Y/S254A/N434Y |
| F970 | 2.50E−06 | M252Y/S254G/N434Y |
| F971 | 2.60E−06 | M252Y/S254H/N434Y |
| F972 | 2.60E−06 | M252Y/S254I/N434Y |
| F978 | 1.30E−06 | M252Y/S254Q/N434Y |
| F980 | 1.80E−07 | M252Y/S254V/N434Y |
| F987 | 4.00E−08 | P238D/T250V/M252Y/T307Q/Q311A/N434Y/Y436V |
| F988 | 6.90E−08 | P238D/T250V/M252Y/N286E/N434Y/Y436V |
| F989 | 1.40E−08 | L235R/S239K/M252Y/V308P/N434Y/Y436V |
| F990 | 9.40E−09 | L235R/S239K/M252Y/T307Q/V308P/Q311A/N434Y/Y436V |
| F991 | 1.30E−08 | L235R/S239K/M252Y/N286E/T307Q/Q311A/N434Y/Y436V |
| F992 | 5.10E−08 | L235R/S239K/M252Y/T307Q/Q311A/M428I/N434Y/Y436V |
| F993 | 3.80E−08 | M252Y/T307Q/Q311A/N434Y/Y436V |
| F994 | 2.80E−07 | M252Y/N325G/N434Y |
| F995 | 2.90E−07 | L235R/P238D/S239K/M252Y/N434Y |
| F996 | 1.30E−07 | L235R/P238D/S239K/M252Y/N434Y/Y436V |
| F997 | 3.80E−07 | K248I/T250V/M252Y/N434Y/Y436V |
| F998 | 8.50E−07 | K248Y/T250V/M252Y/N434Y/Y436V |
| F999 | 2.10E−07 | T250V/M252Y/E258H/N434Y/Y436V |
| F1005 | | N325G |
| F1008 | 1.70E−07 | L235R/S239K/T250V/M252Y/N434Y/Y436V |
| F1009 | 1.20E−08 | L235R/S239K/T250V/M252Y/T307Q/V308P/Q311A/N434Y/Y436V |
| F1010 | 1.90E−07 | L235R/S239K/M252Y/T307A/Q311H/N434Y |
| F1011 | 4.50E−08 | T250V/M252Y/V308P/N434Y |
| F1012 | 4.70E−08 | L235R/S239K/T250V/M252Y/V308P/N434Y |
| F1013 | 3.00E−08 | T250V/M252Y/T307Q/V308P/Q311A/N434Y |
| F1014 | 3.20E−08 | L235R/S239K/T250V/M252Y/T307Q/V308P/Q311A/N434Y |
| F1015 | 2.20E−08 | L235R/S239K/M252Y/T307Q/V308P/Q311A/N434Y |
| F1016 | 3.80E−09 | T250V/M252Y/N286E/T307Q/V308P/Q311A/N434Y/Y436V |
| F1017 | 4.20E−09 | L235R/S239K/T250V/M252Y/N286E/T307Q/V308P/Q311A/N431Y/Y436V |
| F1018 | 3.20E−09 | L235R/S239K/M252Y/N286E/T307Q/V308P/Q311A/N434Y/Y436V |
| F1019 | 3.40E−07 | P238D/T250V/M252Y/N325G/N434Y |
| F1020 | 8.50E−08 | P238D/T250V/M252Y/T307Q/Q311A/N325G/N434Y |

Table 27-25 is a continuation of Table 27-24.

TABLE 27-25

| | | |
|---|---|---|
| F1021 | 3.30E−07 | P238D/T250V/M252Y/N325A/N434Y |
| F1022 | | K326D/L328Y |
| F1023 | 4.40E−08 | S239D/T250V/M252Y/T307Q/Q311A/N434Y/Y436V |
| F1024 | 4.00E−08 | T250V/M252Y/T307Q/Q311A/K326D/L328Y/N434Y/Y436V |
| F1025 | 3.60E−08 | S239D/T250V/M252Y/T307Q/Q311A/K326D/L328Y/N434Y/Y436V |
| F1026 | 8.40E−08 | M252Y/T307A/Q311H/N434Y/Y436V |
| F1027 | 8.60E−08 | L235R/S239K/M252Y/T307A/Q311H/N434Y/Y436V |
| F1028 | 4.60E−08 | G236A/S239D/T250V/M252Y/T307Q/Q311A/N434Y/Y436V |
| F1029 | 5.10E−08 | T250V/M252Y/T307Q/Q311A/I332E/N434Y/Y436V |
| F1030 | | I332E |
| F1031 | 5.30E−08 | G236A/S239D/T250V/M252Y/T307Q/Q311A/I332E/N434Y/Y436V |
| F1032 | 4.30E−08 | P238D/T250V/M252Y/T307Q/Q311A/N325G/N434Y/Y436V |
| F1033 | 1.00E−06 | P238D/N434W |
| F1034 | 1.50E−08 | L235K/S239K/M252Y/V308P/N434Y/Y436V |
| F1035 | 1.00E−08 | L235K/S239K/M252Y/T307Q/V308P/Q311A/N434Y/Y436V |
| F1036 | 1.40E−08 | L235K/S239K/M252Y/N286E/T307Q/Q311A/N434Y/Y436V |

TABLE 27-25-continued

| | | |
|---|---|---|
| F1037 | 6.10E−08 | L235K/S239K/M252Y/T307Q/Q311A/M428I/N434Y/Y436V |
| F1038 | 2.80E−07 | L235K/P238D/S239K/M252Y/N434Y |
| F1039 | 1.30E−07 | L235K/P238D/S239K/M252Y/N434Y/Y436V |
| F1040 | 2.00E−07 | L235K/S239K/T250V/M252Y/N434Y/Y436V |
| F1041 | 1.40E−08 | L235K/S239K/T250V/M252Y/T307Q/V308P/Q311A/N434Y/Y436V |
| F1042 | 2.00E−07 | L235K/S239K/M252Y/T307A/Q311H/N434Y |
| F1043 | 5.20E−08 | L235K/S239K/T250V/M252Y/V308P/N434Y |
| F1044 | 3.50E−08 | L235K/S239K/T250V/M252Y/T307Q/V308P/Q311A/N434Y |
| F1045 | 2.50E−08 | L235K/S239K/M252Y/T307Q/V308P/Q311A/N434Y |
| F1046 | 4.50E−09 | L235K/S239K/T250V/M252Y/N286E/T307Q/V308P/Q311A/N434Y/Y436V |
| F1047 | 3.40E−09 | L235K/S239K/M252Y/N286E/T307Q/V308P/Q311A/N434Y/Y436V |
| F1048 | 9.90E−08 | L235K/S239K/M252Y/T307A/Q311H/N434Y/Y436V |
| F1050 | 3.50E−09 | T250V/M252Y/N286E/T307Q/V308P/Q311A/M428I/N434Y/Y436V |
| F1051 | 3.90E−09 | L235K/S239K/T250V/M252Y/N286E/T307Q/V308P/Q311A/M428I/N434Y/Y436V |
| F1052 | 3.20E−09 | L235R/S239K/M252Y/N286E/T307Q/V308P/Q311A/M428I/N434Y/Y436V |

Table 27-26 is a continuation of Table 27-25.

TABLE 27-26

| | | |
|---|---|---|
| F1053 | 4.23E−08 | L235R/S239K/T250V/M252Y/T307Q/Q311A/N434Y/Y436V |
| F1058 | 1.31E−07 | M252Y/Q386E/N434Y/Y436V |
| F1059 | 1.39E−07 | M252Y/Q386R/N434Y/Y436V |
| F1060 | 1.43E−07 | M252Y/Q386S/N434Y/Y436V |
| F1061 | 1.19E−07 | M252Y/P387E/N434Y/Y436V |
| F1062 | 1.2E−07 | M252Y/P387R/N434Y/Y436V |
| F1063 | 1.43E−07 | M252Y/P387S/N434Y/Y436V |
| F1064 | 1.32E−07 | M252Y/V422E/N434Y/Y436V |
| F1065 | 1.38E−07 | M252Y/V422R/N434Y/Y436V |
| F1066 | 1.45E−07 | M252Y/V422S/N434Y/Y436V |
| F1067 | 1.26E−07 | M252Y/S424E/N434Y/Y436V |
| F1068 | 1.69E−07 | M252Y/S424R/N434Y/Y436V |
| F1069 | 1.39E−07 | M252Y/N434Y/Y436V/Q438E |
| F1070 | 1.73E−07 | M252Y/N434Y/Y436V/Q438R |
| F1071 | 1.24E−07 | M252Y/N434Y/Y436V/Q438S |
| F1072 | 1.35E−07 | M252Y/N434Y/Y436V/S440E |
| F1073 | 1.34E−07 | M252Y/N434Y/Y436V/S440R |
| F1074 | 1.32E−07 | S239D/M252Y/N434Y/Y436V |
| F1075 | 1.4E−07 | M252Y/K326D/L328Y/N434Y/Y436V |
| F1076 | 1.27E−07 | S239D/M252Y/K326D/L328Y/N434Y/Y436V |
| F1077 | 2.03E−06 | K248N/M252Y/N434Y |
| F1078 | 4.7E−07 | M252Y/E380N/E382S/N434Y |
| F1079 | 3.44E−07 | M252Y/E382N/N384S/N434Y |
| F1080 | 3.19E−07 | M252Y/S424N/N434Y |
| F1081 | 6.2E−07 | M252Y/N434Y/Y436N/Q438T |
| F1082 | 2.76E−07 | M252Y/N434Y/Q438N |
| F1083 | 3.45E−07 | M252Y/N434Y/S440N |
| F1094 | 2.6E−07 | M252Y/N434Y/S442N |
| F1095 | 2.86E−07 | M252Y/S383N/G385S/N434Y |
| F1096 | 2.72E−07 | M252Y/Q386T/N434Y |
| F1097 | 2.82E−07 | M252Y/G385N/P387S/N434Y |
| F1098 | 2.58E−07 | S239D/M252Y/N434Y |
| F1099 | 2.57E−07 | M252Y/K326D/L328Y/N434Y |
| F1100 | 2.41E−07 | S239D/M252Y/K326D/L328Y/N434Y |
| F1101 | 6.59E−08 | S239D/M252Y/T307Q/Q311A/N434Y |
| F1102 | 6.46E−08 | M252Y/T307Q/Q311A/K326D/L328Y/N434Y |
| F1103 | 6.11E−08 | S239D/M252Y/T307Q/Q311A/K326D/L328Y/N434Y |
| F1104 | 1.77E−07 | M252Y/V422E/S424R/N434Y/Y436V |
| F1105 | 1.54E−07 | M252Y/V422S/S424R/N434Y/Y436V |
| F1106 | 1.42E−07 | M252Y/N434Y/Y436V/Q438R/S440E |
| F1107 | 1.23E−07 | M252Y/V422D/N434Y/Y436V |

Table 27-27 is a continuation of Table 27-26.

TABLE 27-27

| | | |
|---|---|---|
| F1108 | 1.26E−07 | M252Y/V422K/N434Y/Y436V |
| F1109 | 1.27E−07 | M252Y/V422T/N434Y/Y436V |
| F1110 | 1.33E−07 | M252Y/V422Q/N434Y/Y436V |
| F1111 | 1.65E−07 | M252Y/S424K/N434Y/Y436V |
| F1112 | 1.23E−07 | M252Y/N434Y/Y436V/Q438K |
| F1113 | 1.18E−07 | M252Y/N434Y/Y436V/S440D |
| F1114 | 1.31E−07 | M252Y/N434Y/Y436V/S440Q |
| F1115 | 1.35E−07 | M252Y/S424N/N434Y/Y436V |
| F1116 | 7.44E−08 | M252Y/T307Q/Q311A/S424N/N434Y |
| F1117 | 4.87E−08 | T250V/M252Y/T307Q/Q311A/S424N/N434Y/Y436V |
| F1118 | 1.32E−08 | T250V/M252Y/T307Q/V308P/Q311A/S424N/N434Y/Y436V |
| F1119 | 1.03E−08 | T250V/M252Y/T307Q/V308P/Q311A/V422E/N434Y/Y436V |
| F1120 | 1.04E−08 | T250V/M252Y/T307Q/V308P/Q311A/S424R/N434Y/Y436V |
| F1121 | 1.04E−08 | T250V/M252Y/T307Q/V308P/Q311A/V422E/S424R/N434Y/Y436V |
| F1122 | 1.37E−08 | T250V/M252Y/T307Q/V308P/Q311A/N434Y/Y436V/Q438R |
| F1123 | 9.55E−09 | T250V/M252Y/T307Q/V308P/Q311A/N434Y/Y436V/S440E |
| F1124 | 1.22E−08 | T250V/M252Y/T307Q/V308P/Q311A/N434Y/Y436V/Q438R/S440E |
| F1125 | 5.18E−08 | M252V/T307Q/N434Y/Y436V |
| F1126 | 8.95E−08 | M252Y/T307A/N434Y/Y436V |
| F1127 | 7.94E−08 | M252Y/Q311A/N434Y/Y436V |
| F1128 | 1.17E−07 | M252Y/Q311H/N434Y/Y436V |
| F1129 | 4.48E−08 | M252Y/T307Q/Q311H/N434Y/Y436V |
| F1130 | 5.54E−08 | M252Y/T307A/Q311A/N434Y/Y436V |
| F1131 | 1.29E−07 | L235R/S239K/M252Y/V422E/N434Y/Y436V |
| F1132 | 1.4E−07 | L235R/S239K/M252Y/V422S/N434Y/Y436V |
| F1133 | 1.58E−07 | L235R/S239K/M252Y/S424R/N434Y/Y436V |
| F1134 | 1.66E−07 | L235R/S239K/M252Y/N434Y/Y436V/Q438R |
| F1135 | 1.26E−07 | L235R/S239K/M252Y/N434Y/Y436V/S440E |
| F1136 | 1.63E−07 | L235R/S239K/M252Y/V422E/S424R/N434Y/Y436V |
| F1137 | 1.58E−07 | L235R/S239K/M252Y/V422S/S424R/N434Y/Y436V |
| F1138 | 1.65E−07 | L235R/S239K/M252Y/N434Y/Y436V/Q438R/S440E |
| F1139 | 1.52E−07 | L235R/S239K/M252Y/S424N/N434Y/Y436V |
| F1140 | 1.62E−07 | M252Y/V422E/S424R/N434Y/Y436V/Q438R/S440E |
| F1141 | 1.77E−07 | M252Y/V422S/S424R/N434Y/Y436V/Q438R/S440E |
| F1142 | 1.87E−07 | L235R/S239K/M252Y/V422E/S424R/N434Y/Y436V/Q438R/S440E |
| F1143 | 1.98E−07 | L235R/S239K/M252Y/V422S/S424R/N434Y/Y436V/Q438R/S440E |
| F1144 | 1.44E−08 | L235R/S239K/T250V/M252Y/T307Q/V308P/Q311A/N434Y/Y436V/Q438R/S440E |
| F1145 | 5.23E−08 | T250V/M252Y/T307Q/N434Y/Y436V/Q438R/S440E |
| F1146 | 6.24E−08 | L235R/S239K/T250V/M252Y/T307Q/Q311A/N434Y/Y436V/Q438R/S440E |
| F1147 | 7.19E−08 | M252Y/T307Q/Q311A/N434Y/Q438R/S440E |

Table 27-28 is a continuation of Table 27-27.

TABLE 27-28

| | | |
|---|---|---|
| F1148 | 7.63E−08 | L235R/S239K/M252Y/T307Q/Q311A/N434Y/Q438R/S440E |
| F1151 | 2.51E−07 | L235R/S239K/M252Y/S424N/N434Y |
| F1152 | 7.38E−08 | L235R/S239K/M252Y/T307Q/Q311A/S424N/N434Y |
| F1153 | 4.85E−08 | L235R/S239K/T250V/M252Y/T307Q/Q311A/S424N/N434Y/Y436V |
| F1154 | 1.34E−08 | L235R/S239K/T250V/M252Y/T307Q/V308P/Q311A/S424N/N434Y/Y436V |
| F1157 | 2.09E−07 | M252Y/N434Y/Q438R/S440E |
| F1158 | 2.44E−07 | L235R/S239K/M252Y/N434Y/Q438R/S440E |
| F1159 | 4.79E−07 | S424N/N434W |
| F1160 | 2.88E−07 | V308F/S424N/N434Y |
| F1161 | 1.07E−06 | I332V/S424N/N434Y |
| F1162 | 3.43E−07 | P238D/T250Y/M252Y/N434Y/Y436V |
| F1163 | 1.54E−07 | P238D/T250Y/M252Y/T307Q/Q311A/N434Y |
| F1164 | 6.96E−08 | P238D/T250Y/M252Y/T307Q/Q311A/N434Y/Y436V |
| F1165 | 1.63E−08 | P238D/T250Y/M252Y/T307Q/V308P/Q311A/N434Y/Y436V |
| F1174 | 4.9E−07 | P257I/N434H |
| F1176 | 1.98E−06 | V308F |
| F1178 | 8.72E−07 | V259I/V308F/M428L |
| F1183 | 1.28E−06 | E380A/M428L/N434S |
| F1184 | 1E−06 | T307A/M428L/N434S |
| F1185 | 9.17E−07 | T307A/E380A/M428L/N434S |
| F1188 | 1.72E−06 | T307A/E380A/N434H |
| F1189 | 1.57E−07 | M252Y/H433D/N434Y/Y436V/Q438R/S440E |
| F1190 | 2.4E−07 | M252Y/H433E/N434Y/Y436V/Q438R/S440E |
| F1191 | 2.11E−07 | M252Y/N434Y/Y436V/T437A/Q438R/S440E |
| F1192 | 1.27E−07 | M252Y/N434Y/Y436V/T437G/Q438R/S440E |
| F1194 | 1.55E−07 | M252Y/N434Y/Y436V/Q438R/K439D/S440E |
| F1195 | 1.76E−07 | M252Y/N434Y/Y436V/Q438R/S440E/L441A |
| F1196 | 1.51E−07 | M252Y/N434Y/Y436V/Q438R/S440E/L441E |
| F1197 | 9.46E−08 | M252Y/S254T/N434Y/Y436V/Q438R/S440E |
| F1198 | 7.83E−08 | M252Y/T256E/N434Y/Y436V/Q438R/S440E |
| F1199 | 6.25E−08 | M252Y/S254T/T256E/N434Y/Y436V/Q438R/S440E |
| F1200 | 1.26E−07 | T250V/M252Y/S254T/N434Y/Y436V/Q438R/S440E |
| F1201 | 1.07E−07 | T250V/M252Y/T256E/N434Y/Y436V/Q438R/S440E |
| F1202 | 8.81E−08 | T250V/M252Y/S254T/T256E/N434Y/Y436V/Q438R/S440E |
| F1203 | 1.52E−07 | M252Y/T256Q/N434Y/Y436V/Q438R/S440E |
| F1204 | 1.18E−07 | M252Y/S254T/T256Q/N434Y/Y436V/Q438R/S440E |
| F1205 | 1.98E−07 | T250V/M252Y/T256Q/N434Y/Y436V/Q438R/S440E |
| F1206 | 1.69E−07 | T250V/M252Y/S254T/T256Q/N434Y/Y436V/Q438R/S440E |
| F1207 | 1.11E−06 | I332E/M428L/N434S |
| F1208 | 5.71E−07 | L251A/M252Y/N434Y/Y436V |
| F1211 | 1.23E−06 | L251H/M252Y/N434Y/Y436V |

Table 27-29 is a continuation of Table 27-28.

TABLE 27-29

| | | |
|---|---|---|
| F1213 | 6.33E−07 | L251N/M252Y/N434Y/Y436V |
| F1216 | 1.16E−06 | L251S/M252Y/N434Y/Y436V |
| F1217 | 1.14E−06 | L251T/M252Y/N434Y/Y436V |
| F1218 | 2.51E−07 | L251V/M252Y/N434Y/Y436V |
| F1229 | 2.81E−06 | M252Y/I253V/N434Y/Y436V |
| F1230 | 1.12E−07 | M252Y/N434Y/Y436V/Q438R/S440D |
| F1231 | 9.73E−08 | M252Y/N434Y/Y436V/Q438K/S440E |
| F1232 | 9.79E−08 | M252Y/N434Y/Y436V/Q438K/S440D |
| F1243 | 1.25E−07 | L235R/S239K/M252Y/S254T/N434Y/Y436V/Q438R/S440E |
| F1244 | 1.02E−07 | L235R/S239K/M252Y/T256E/N434Y/Y436V/Q438R/S440E |
| F1245 | 8.2E−08 | L235R/S239K/M252Y/S254T/T256E/N434Y/Y436V/Q438R/S440E |
| F1246 | 1.73E−07 | L235R/S239K/T250V/M252Y/S254T/N434Y/Y436V/Q438R/S440E |
| F1247 | 1.45E−07 | L235R/S239K/T250V/M252Y/T256E/N434Y/Y436V/Q438R/S440E |

TABLE 27-29-continued

| | | |
|---|---|---|
| F1248 | 1.2E−07 | L235R/S239K/T250V/M252Y/S254T/T256E/N434Y/Y436V/Q438R/S440E |
| F1249 | 2.06E−07 | L235R/S239K/M252Y/T256Q/N434Y/Y436V/Q438R/S440E |
| F1250 | 1.66E−07 | L235R/S239K/M252Y/S254T/T256Q/N434Y/Y436V/Q438R/S440E |
| F1251 | 2.77E−07 | L235R/S239K/T250V/M252Y/T256Q/N434Y/Y436V/Q438R/S440E |
| F1252 | 2.33E−07 | L235R/S239K/T250V/M252Y/S254T/T256Q/N434Y/Y436V/Q438R/S440E |
| F1253 | 1.12E−07 | L235R/S239K/M252Y/T307A/N434Y/Y436V/Q438R/S440E |
| F1254 | 6.42E−08 | L235R/S239K/M252Y/T307Q/N434Y/Y436V/Q438R/S440E |
| F1255 | 1.11E−07 | L235R/S239K/M252Y/Q311A/N434Y/Y436V/Q438R/S440E |
| F1256 | 1.56E−07 | L235R/S239K/M252Y/Q311H/N434Y/Y436V/Q438R/S440E |
| F1257 | 7.81E−08 | L235R/S239K/M252Y/T307A/Q311A/N434Y/Y436V/Q438R/S440E |
| F1258 | 1.05E−07 | L235R/S239K/M252Y/T307A/Q311H/N434Y/Y436V/Q438R/S440E |
| F1259 | 4.46E−08 | L235R/S239K/M252Y/T307Q/Q311A/N434Y/Y436V/Q438R/S440E |
| F1260 | 6.53E−08 | L235R/S239K/M252Y/T307Q/Q311H/N434Y/Y436V/Q438R/S440E |
| F1261 | 1.35E−07 | L235R/S239K/M252Y/N434Y/Y436V/Q438R/S440D |
| F1262 | 1.26E−07 | L235R/S239K/M252Y/N434Y/Y436V/Q438K/S440E |
| F1263 | 1.24E−07 | L235R/S239K/M252Y/N434Y/Y436V/Q438K/S440D |
| F1264 | 1.27E−07 | L235R/S239K/M252Y/T256A/N434Y/Y436V/Q438R/S440E |
| F1265 | 1.57E−07 | L235R/S239K/M252Y/T256G/N434Y/Y436V/Q438R/S440E |
| F1266 | 9.99E−08 | L235R/S239K/M252Y/T256N/N434Y/Y436V/Q438R/S440E |
| F1267 | 1.5E−07 | L235R/S239K/M252Y/S254A/N434Y/Y436V/Q438R/S440E |
| F1268 | 2E−07 | L235R/S239K/M252Y/H433D/N434Y/Y436V/Q438R/S440E |
| F1269 | 1.69E−07 | L235R/S239K/M252Y/H433D/N434Y/Y436V/Q438K/S440D |
| F1270 | 1.18E−07 | L235R/S239K/M252Y/S254A/N434Y/Y436V/Q438K/S440D |
| F1271 | 2.05E−07 | L235R/S239K/M252Y/S254A/H433D/N434Y/Y436V/Q438R/S440E |
| F1272 | 1.71E−07 | L235R/S239K/M252Y/S254A/H433D/N434Y/Y436V/Q438K/S440D |
| F1273 | 1.53E−07 | L235R/S239K/M252Y/T256Q/N434Y/Y436V/Q438K/S440D |
| F1274 | 2.48E−07 | L235R/S239K/M252Y/T256Q/H433D/N434Y/Y436V/Q438R/S440E |
| F1275 | 2.09E−07 | L235R/S239K/M252Y/T256Q/H433D/N434Y/Y436V/Q438K/S440D |

Table 27-30 is a continuation of Table 27-29.

TABLE 27-30

| | | |
|---|---|---|
| F1276 | 1.02E−07 | L235R/S239K/M252Y/T256A/N434Y/Y436V/Q438K/S440D |
| F1277 | 1.69E−07 | L235R/S239K/M252Y/T256A/H433D/N434Y/Y436V/Q438R/S440E |
| F1278 | 1.4E−07 | L235R/S239K/M252Y/T256A/H433D/N434Y/Y436V/Q438K/S440D |
| F1279 | 1.23E−07 | L235R/S239K/M252Y/T256G/N434Y/Y436V/Q438K/S440D |
| F1280 | 2.09E−07 | L235R/S239K/M252Y/T256G/H433D/N434Y/Y436V/Q438R/S440E |
| F1281 | 1.74E−07 | L235R/S239K/M252Y/T256G/H433D/N434Y/Y436V/Q438K/S440D |
| F1282 | 7.69E−08 | L235R/S239K/M252Y/T256N/N434Y/Y436V/Q438K/S440D |
| F1283 | 1.34E−07 | L235R/S239K/M252Y/T256N/H433D/N434Y/Y436V/Q438R/S440E |
| F1284 | 1.12E−07 | L235R/S239K/M252Y/T256N/H433D/N434Y/Y436V/Q438K/S440D |
| F1285 | 9.36E−08 | L235R/S239K/M252Y/S254T/N434Y/Y436V/Q438K/S440D |
| F1286 | 1.57E−07 | L235R/S239K/M252Y/S254T/H433D/N434Y/Y436V/Q438R/S440E |
| F1287 | 1.5E−07 | L235R/S239K/M252Y/S254T/H433D/N434Y/Y436V/Q438K/S440D |
| F1288 | 7.95E−08 | L235R/S239K/M252Y/T256E/N434Y/Y436V/Q438K/S440D |
| F1289 | 1.33E−07 | L235R/S239K/M252Y/T256E/H433D/N434Y/Y436V/Q438R/S440E |
| F1290 | 1.11E−07 | L235R/S239K/M252Y/T256E/H433D/N434Y/Y436V/Q438K/S440D |
| F1291 | 1.51E−07 | L235R/S239K/M252Y/H433D/N434Y/Y436V |
| F1292 | 4.24E−07 | L235R/S239K/H433D/N434W/Y436V/Q438R/S440E |
| F1293 | 1.61E−07 | L235R/S239K/M252Y/T256E/N434Y/Q438R/S440E |
| F1294 | 2E−07 | L235R/S239K/M252Y/T256E/N434Y/Y436T/Q438R/S440E |
| F1295 | 9.84E−08 | L235R/S239K/M252Y/T256E/N434Y/Y436F/Q438R/S440E |
| F1296 | 2.27E−07 | L235R/S239K/M252Y/T256E/H433D/N434Y/Q438R/S440E |
| F1297 | 2.5E−07 | L235R/S239K/M252Y/T256E/H433D/N434Y/Y436T/Q438R/S440E |
| F1298 | 1.47E−07 | L235R/S239K/M252Y/T256E/H433D/N434Y/Y436F/Q438R/S440E |
| F1299 | 1.5E−07 | L235R/S239K/M252Y/T256E/N434Y/Q438K/S440D |
| F1300 | 1.63E−07 | L235R/S239K/M252Y/T256E/N434Y/Y436T/Q438K/S440D |
| F1301 | 8.3E−08 | L235R/S239K/M252Y/T256E/N434Y/Y436F/Q438K/S440D |
| F1302 | 2.15E−07 | L235R/S239K/M252Y/T256E/H433D/N434Y/Q438K/S440D |
| F1303 | 2.1E−07 | L235R/S239K/M252Y/T256E/H433D/N434Y/Y436T/Q438K/S440D |
| F1304 | 1.24E−07 | L235R/S239K/M252Y/T256E/H433D/N434Y/Y436F/Q438K/S440D |
| F1305 | 2.05E−07 | L235R/S239K/M252Y/H433D/N434Y/Y436V/Q438R/S440D |
| F1306 | 1.92E−07 | L235R/S239K/M252Y/H433D/N434Y/Y436V/Q438K/S440E |
| F1307 | 1.44E−07 | L235R/S239K/M252Y/V422A/S424A/N434Y/Y436V |
| F1308 | 2.06E−07 | L235R/S239K/M252Y/V422L/S424L/N434Y/Y436V |
| F1309 | 1.26E−07 | L235R/S239K/M252Y/N434Y/Y436V/Q438A/S440A |
| F1310 | 2.28E−07 | L235R/S239K/M252Y/N434Y/Y436V/Q438L/S440L |
| F1311 | 1.69E−07 | L235R/S239K/M252Y/V422A/S424A/H433D/N434Y/Y436V |
| F1312 | 1.79E−07 | L235R/S239K/M252Y/V422L/S424L/H433D/N434Y/Y436V |
| F1313 | 1.77E−07 | L235R/S239K/M252Y/H433D/N434Y/Y436V/Q438A/S440A |
| F1314 | 2.27E−07 | L235R/S239K/M252Y/H433D/N434Y/Y436V/Q438L/S440L |
| F1315 | 1.52E−07 | G237K/S239K/M252Y/N434Y/Y436V |
| F1316 | 1.49E−07 | G237R/S239K/M252Y/N434Y/Y436V |

Table 27-31 is a continuation of Table 27-30.

TABLE 27-31

| | | |
|---|---|---|
| F1317 | 1.38E−07 | S239K/M252Y/P329K/N434Y/Y436V |
| F1318 | 1.43E−07 | S239K/M252Y/P329R/N434Y/Y436V |
| F1319 | 2.67E−07 | M252Y/L328Y/N434Y |
| F1320 | 1.22E−07 | L235R/S239K/M252Y/S254T/N434Y/Y436V/Q438R/S440D |
| F1321 | 1.03E−07 | L235R/S239K/M252Y/S254T/N434Y/Y436V/Q438K/S440E |
| F1322 | 1.6E−07 | L235R/S239K/M252Y/S254T/H433D/N434Y/Y436V/Q438R/S440D |
| F1323 | 1.49E−07 | L235R/S239K/M252Y/S254T/H433D/N434Y/Y436V/Q438K/S440E |
| F1324 | 1.32E−07 | L234A/L235A/M252Y/N434Y/Y436V |
| F1325 | 2.13E−07 | L234A/L235A/M252Y/N297A/N434Y/Y436V |
| F1326 | 1.09E−08 | L234A/L235A/T250V/M252Y/T307Q/V308P/Q311A/N434Y/Y436V |
| F1327 | 1.41E−08 | L234A/L235A/T250V/M252Y/N297A/T307Q/V308P/Q311A/N434Y/Y436V |
| F1328 | 1.52E−07 | L235R/G236R/S239K/M252Y/N434Y/Y436V/Q438R/S440E |
| F1329 | 1.29E−07 | L235R/G236R/S239K/M252Y/S254T/N434Y/Y436V/Q438R/S440E |
| F1330 | 1.03E−07 | L235R/G236R/S239K/M252Y/T256E/N434Y/Y436V/Q438R/S440E |
| F1331 | 7.75E−08 | L235R/G236R/S239K/M252Y/S254T/T256E/N434Y/Y436V/Q438R/S440E |
| F1333 | 1.23E−07 | L235R/G236R/S239K/M252Y/N434Y/Y436V |
| F1334 | 1.04E−07 | L235R/G236R/S239K/M252Y/N434Y/Y436V/Q438K/S440D |
| F1335 | 8.78E−08 | L235R/G236R/S239K/M252Y/S254T/N434Y/Y436V/Q438K/S440D |
| F1336 | 7.18E−08 | L235R/G236R/S239K/M252Y/T256E/N434Y/Y436V/Q438K/S440D |
| F1337 | 7.41E−08 | L235R/S239K/M252Y/T256E/N434Y/Y436V/Q438K/S440E |
| F1338 | 1.04E−07 | L235R/S239K/M252Y/T256E/H433D/N434Y/Y436V/Q438K/S440E |
| F1339 | 2.51E−07 | L235R/S239K/M252Y/S254T/T256E/H433D/N434Y/Y436T/Q438K/S440E |
| F1340 | 5.58E−08 | L235R/S239K/M252Y/S254T/T256E/N434Y/Y436V/Q438K/S440E |
| F1341 | 3.22E−07 | L235R/S239K/M252Y/S254T/N434Y/Y436T/Q438K/S440E |
| F1342 | 2.51E−07 | L235R/S239K/M252Y/T256E/N434Y/Y436T/Q438K/S440E |
| F1343 | 2.01E−07 | L235R/S239K/M252Y/S254T/T256E/N434Y/Y436T/Q438K/S440E |
| F1344 | 3.96E−07 | L235R/S239K/M252Y/N434Y/Y436T/Q438K/S440E |
| F1345 | 1.05E−07 | L235R/G236R/S239K/M252Y/N434Y/Y436V/Q438K/S440E |
| F1346 | 8.59E−08 | L235R/G236R/S239K/M252Y/S254T/N434Y/Y436V/Q438K/S440E |
| F1347 | 7.14E−08 | L235R/G236R/S239K/M252Y/T256E/N434Y/Y436V/Q438K/S440E |
| F1348 | 5.52E−08 | L235R/G236R/S239K/M252Y/S254T/T256E/N434Y/Y436V/Q438K/S440E |
| F1349 | 3.36E−07 | L235R/S239K/M252Y/N434Y/Y436T/Q438R/S440E |
| F1350 | 1.18E−07 | L235R/S239K/M252Y/N434Y/Y436F/Q438K/S440E |
| F1351 | 1.62E−07 | L235R/S239K/M252Y/N434Y/Y436F/Q438R/S440E |
| F1352 | 3.93E−07 | L235R/S239K/M252Y/H433D/N434Y/Y436T/Q438K/S440E |
| F1353 | 4.33E−07 | L235R/S239K/M252Y/H433D/N434Y/Y436T/Q438R/S440E |
| F1354 | 2.29E−07 | L235R/S239K/M252Y/H433D/N434Y/Y436F/Q438K/S440E |
| F1355 | 2.47E−07 | L235R/S239K/M252Y/H433D/N434Y/Y436F/Q438R/S440E |
| F1356 | 1.58E−07 | G236R/M252Y/L328R/N434Y/Y436V |
| F1357 | 2.81E−07 | L235R/S239K/M252Y/S254T/N434Y/Y436T/Q438K/S440E |
| F1358 | 9.07E−08 | L235R/S239K/M252Y/S254T/N434Y/Y436F/Q438K/S440E |

Table 27-32 is a continuation of Table 27-31.

TABLE 27-32

| | | |
|---|---|---|
| F1359 | 1.28E−07 | L235R/S239K/M252Y/S254T/N434Y/Y436F/Q438R/S440E |
| F1360 | 3.12E−07 | L235R/S239K/M252Y/S254T/H433D/N434Y/Y436T/Q438K/S440E |
| F1361 | 3.52E−07 | L235R/S239K/M252Y/S254T/H433D/N434Y/Y436T/Q438R/S440E |
| F1362 | 1.41E−07 | L235R/S239K/M252Y/S254T/H433D/N434Y/Y436F/Q438K/S440E |
| F1363 | 1.9E−07 | L235R/S239K/M252Y/S254T/H433D/N434Y/Y436F/Q438R/S440E |
| F1364 | 7.49E−08 | L235R/S239K/M252Y/T256E/N434Y/Y436F/Q438K/S440E |
| F1365 | 3.14E−07 | L235R/S239K/M252Y/T256E/H433D/N434Y/Y436T/Q438K/S440E |
| F1366 | 1.17E−07 | L235R/S239K/M252Y/T256E/H433D/N434Y/Y436F/Q438K/S440E |
| F1367 | 1.79E−07 | L235R/S239K/M252Y/S254T/T256E/N434Y/Y436T/Q438R/S440E |
| F1368 | 5.49E−08 | L235R/S239K/M252Y/S254T/T256E/N434Y/Y436F/Q438K/S440E |
| F1369 | 7.6E−08 | L235R/S239K/M252Y/S254T/T256E/N434Y/Y436F/Q438R/S440E |
| F1370 | 9.14E−08 | L235R/S239K/M252Y/S254T/T256E/H433D/N434Y/Y436V/Q438K/S440E |
| F1371 | 1.09E−07 | L235R/S239K/M252Y/S254T/T256E/H433D/N434Y/Y436V/Q438R/S440E |
| F1372 | 2.28E−07 | L235R/S239K/M252Y/S254T/T256E/H433D/N434Y/Y436T/Q438R/S440E |
| F1373 | 8.67E−08 | L235R/S239R/M252Y/S254T/T256E/H433D/N434Y/Y436F/Q438K/S440E |
| F1374 | 1.2E−07 | L235R/S239K/M252Y/S254T/T256E/H433D/N434Y/Y436F/Q438R/S440E |
| F1375 | 1.03E−07 | L235R/S239K/M252Y/S254T/N434Y/Y436V |
| F1376 | 9.09E−08 | L235R/S239K/M252Y/S254T/T256E/N434Y/Y436V |
| F1377 | 8.27E−08 | L235R/S239K/M252Y/T256E/N434Y/Y436V |
| F1378 | 3.61E−07 | L235R/S239K/M252Y/N434Y/Y436T |
| F1379 | 2.85E−07 | L235R/S239K/M252Y/N434Y/Y436F |

(5-2) In Vivo Test of pH-dependent Human IL-6 Receptor-binding Antibodies with Enhanced Human FcRn Binding under the pH Neutral Condition pH-dependent human IL-6 receptor-binding antibodies having human FcRn binding ability under a neutral condition were produced using the heavy chains prepared as described in Example 5-1 to have human FcRn binding ability under a neutral condition. The antibodies were assessed for their in vivo antigen elimination effect. Specifically, the antibodies listed below were expressed and purified by methods known to those skilled in the art as described in Reference Example 2:

Fv4-IgG1 comprising VH3-IgG1 (SEQ ID NO: 35) and VL3-CK (SEQ ID NO: 36);
Fv4-IgG1-v2 comprising VH3-IgG1-v2 (SEQ ID NO: 37) and VL3-CK (SEQ ID NO: 36);
Fv4-IgG1-F14 comprising VH3-IgG1-F14 (SEQ ID NO: 86) and VL3-CK (SEQ ID NO: 36);
Fv4-IgG1-F20 comprising VH3-IgG1-F20 (SEQ ID NO: 39) and VL3-CK (SEQ ID NO: 36);
Fv4-IgG1-F21 comprising VH3-IgG1-F21 (SEQ ID NO: 40) and VL3-CK (SEQ ID NO: 36);
Fv4-IgG1-F25 comprising VH3-IgG1-F25 (SEQ ID NO: 87) and VL3-CK (SEQ ID NO: 36);
Fv4-IgG1-F29 comprising VH3-IgG1-F29 (SEQ ID NO: 88) and VL3-CK (SEQ ID NO: 36);
Fv4-IgG1-F35 comprising VH3-IgG1-F35 (SEQ ID NO: 89) and VL3-CK (SEQ ID NO: 36);
Fv4-IgG1-F48 comprising VH3-IgG1-F48 (SEQ ID NO: 90) and VL3-CK (SEQ ID NO: 36);
Fv4-IgG1-F93 comprising VH3-IgG1-F93 (SEQ ID NO: 91) and VL3-CK (SEQ ID NO: 36); and
Fv4-IgG1-F94 comprising VH3-IgG1-F94 (SEQ ID NO: 92) and VL3-CK (SEQ ID NO: 36).

The prepared pH-dependent human IL-6 receptor-binding antibodies were tested in vivo by the method described below using human FcRn transgenic mice (B6.mFcRn−/−.hFcRn Tg line 276+/+mouse, Jackson Laboratories; Methods Mol Biol. (2010) 602: 93-104). To a human FcRn transgenic mouse (B6.mFcRn−/−.hFcRn Tg line 276+/+ mouse, Jackson Laboratories, Methods Mol Biol. 2010; 602: 93-104) and normal mouse (C57BL/6J mouse, Charles River Japan), hsIL-6R (soluble human IL-6 receptor prepared in Reference Example 3) was administered alone, or soluble human IL-6 receptor and anti-human IL-6 receptor antibody were administered simultaneously to examine the pharmacokinetics of the soluble human IL-6 receptor and anti-human IL-6 receptor antibody in vivo. A single dose (10 mL/kg) of soluble human IL-6 receptor solution (5 μg/mL) or a mixture of soluble human IL-6 receptor and anti-human IL-6 receptor antibody (5 μg/mL and 0.1 mg/mL, respectively) was administered into the caudal vein. At this time, the anti-human IL-6 receptor antibody against soluble human IL-6 receptor existed in a sufficient or excessive amount. Thus, it is thought that most of the soluble human IL-6 receptors bound to the antibody. Blood samples were collected at 15 minutes, 7 hours and 1, 2, 3, 4, 7, 14, 21, and 28 days after the administration. The blood samples obtained were immediately centrifuged for 15 minutes at 4° C. and 15,000 rpm to separate plasma. The separated plasma was stored in a freezer set to −20° C. or lower until the time of measurement.

(5-3) Determination of Plasma Concentration of Soluble Human IL-6 Receptor by an Electrochemiluminescence Method A soluble human IL-6 receptor calibration curve sample prepared at 2,000, 1,000, 500, 250, 125, 62.5, or 31.25 pg/mL, and a mouse plasma measurement sample diluted by 50-fold or above, were mixed with a monoclonal anti-human IL-6R antibody (R&D) ruthenated with SULFO-TAG NHS Ester (Meso Scale Discovery), a biotinylated anti-human IL-6 R antibody (R&D), and tocilizumab, followed by overnight reaction at 37° C. Tocilizumab was prepared at a final concentration of 333 μg/mL. Subsequently, the reaction liquid was dispensed into an MA400 PR Streptavidin Plate (Meso Scale Discovery). In addition, after washing the reaction liquid that was allowed to react for 1 hour at room temperature, Read Buffer T (×4) (Meso Scale Discovery) was dispensed. Subsequently, the reaction liquid was immediately subjected to measurement using a SECTOR PR 400 reader (Meso Scale Discovery). The concentration of soluble human IL-6 receptor was calculated from the response of the calibration curve using the SOFTmax PRO analysis software (Molecular Devices).

Figure 40:
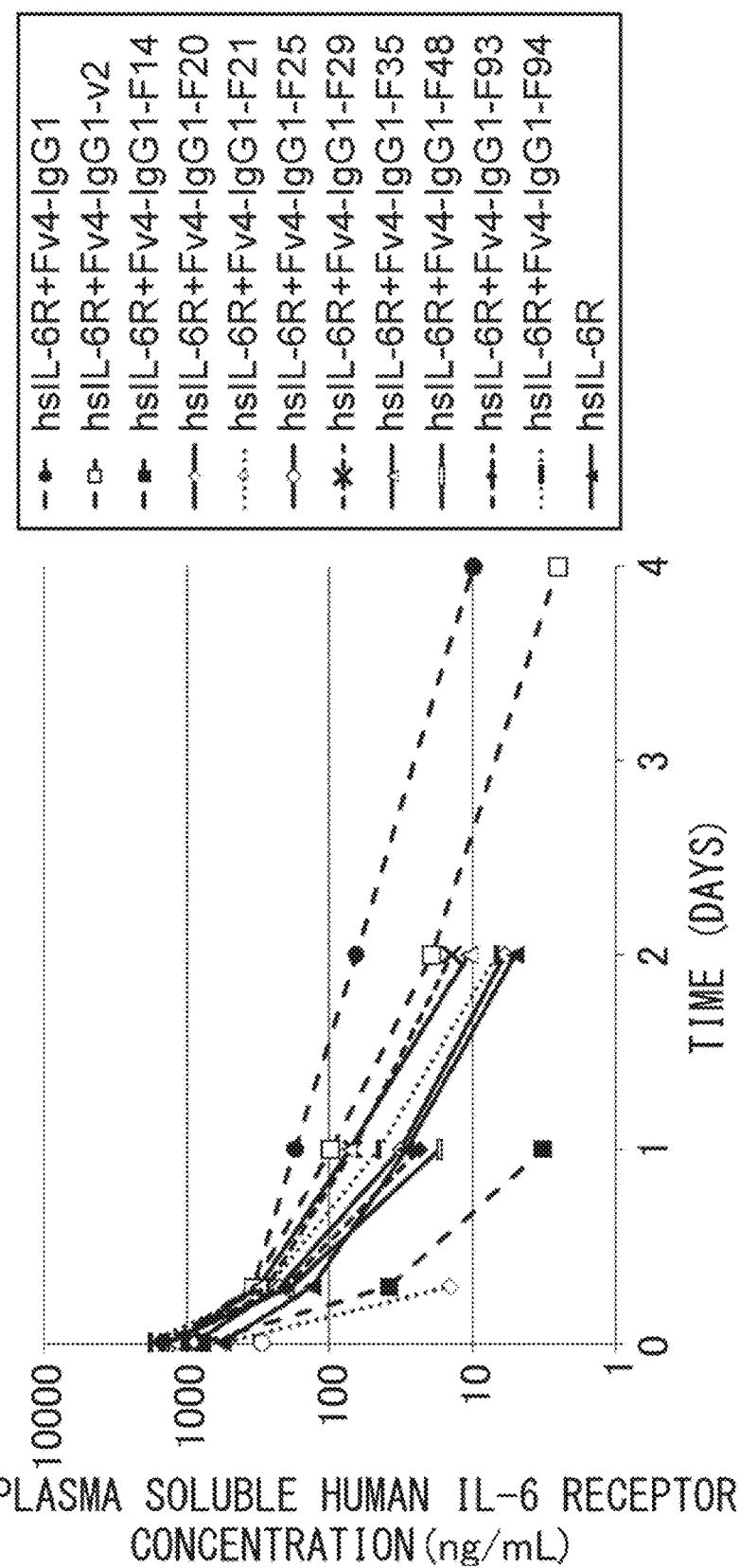
FIG. 40 is a graph showing a time course of soluble human IL-6 receptor concentration after co-administration of a soluble human IL-6 receptor and an anti-IL-6 receptor antibody to human FcRn transgenic mice.

A time course of plasma concentration of soluble human IL-6 receptor after intravenous administration to human FcRn transgenic mice is shown in FIG. 40. The test result showed that the plasma concentration of soluble human IL-6 receptor remained low over time in the presence of any of the pH-dependent human IL-6 receptor-binding antibodies with augmented human FcRn binding under neutral condition, as compared to in the presence of Fv4-IgG1 which has almost no human FcRn binding ability under neutral condition. Among others, antibodies that produced the remarkable effect include, for example, Fv4-IgG1-F14. The plasma concentration of soluble human IL-6 receptor simultaneously administered with Fv4-IgG1-F14 was demonstrated to be reduced by about 54 times one day after administration as compared to that of soluble human IL-6 receptor simultaneously administered with Fv4-IgG1. Furthermore, the plasma concentration of soluble human IL-6 receptor simultaneously administered with Fv4-IgG1-F21 was demonstrated to be reduced by about 24 times seven hours after administration as compared to that of soluble human IL-6 receptor simultaneously administered with Fv4-IgG1. In addition, the plasma concentration of soluble human IL-6 receptor simultaneously administered with Fv4-IgG1-F25 seven hours after administration was below the detection limit (1.56 ng/ml). Thus, Fv4-IgG1-F25 was expected to enable a remarkable reduction of 200 or more times in the concentration of soluble human IL-6 receptor relative to the concentration of soluble human IL-6 receptor simultaneously administered with Fv4-IgG1.

The findings described above demonstrate that augmentation of the human FcRn binding of pH-dependent antigen-binding antibodies under a neutral condition is highly effective for enhancing the antigen elimination effect. Meanwhile, the type of amino acid alteration to augment human FcRn binding under neutral condition, which is introduced to enhance the antigen elimination effect, is not particularly limited; and such alterations include those shown in Table 16. The antigen elimination effect can be predicted to be enhanced in vivo by any introduced alteration.

Reference Example 6

Acquisition of Antibodies that Bind to IL-6 Receptor in Ca-dependent Manner from a Human Antibody Library Using Phage Display Technology (6-1) Preparation of a Phage Display Library for Naive Human Antibodies A phage display library for human antibodies, consisting of multiple phages presenting the Fab domains of mutually different human antibody sequences, was constructed according to a method known to those skilled in the art using a poly A RNA prepared from human PBMC, and commercial human poly A RNA as a template.

(6-2) Acquisition of Antibody Fragments that Bind to Antigen in Ca-dependent Manner from the Library by Bead Panning The constructed phage display library for naive human antibodies was subjected to initial selection through concentration of only antibody fragments having an antigen (IL-6 receptor)-binding ability or concentration of antibody fragments using a Ca concentration-dependent antigen (IL-6 receptor)-binding ability as an indicator. Concentration of antibody fragments using a Ca concentration-dependent antigen (IL-6 receptor)-binding ability as an indicator were conducted through elution of the phage library phages bound to IL-6 receptor in the presence of Ca ions with EDTA that chelates the Ca ions Biotinylated IL-6 receptor was used as an antigen.

Phages were produced from *Escherichia coli* carrying the constructed phage display phagemid. A phage library solution was obtained by diluting with TBS a phage population precipitated by adding 2.5 M NaCl/10% PEG to the *E. coli* culture solution in which the phages were produced. Subsequently, BSA and $CaCl_2$ were added to the phage library solution at a final concentration of 4% BSA and 1.2 mM of calcium ion concentration. A common panning method using an antigen immobilized on magnetic beads was referred to as a panning method (J. Immunol. Methods. (2008) 332 (1-2), 2-9; J. Immunol. Methods. (2001) 247 (1-2), 191-203; Biotechnol. Prog. (2002) 18(2) 212-20; Mol. Cell Proteomics (2003) 2 (2), 61-9). NeutrAvidin coated beads (Sera-Mag SpeedBeads NeutrAvidin-coated) or Streptavidin coated beads (Dynabeads M-280 Streptavidin) were used as magnetic beads.

Specifically, 250 pmol of the biotin-labeled antigen was added to the prepared phage library solution to allow the contact of said phage library solution with the antigen for 60 minutes at room temperature. Magnetic beads, blocked with BSA, were added to be bound to antigen-phage complexes for 15 minutes at room temperature. The beads were washed once with 1 mL of 1.2 mM $CaCl_2$/TBS (TBS containing 1.2 mM $CaCl_2$). Subsequently, a phage solution was recovered by a general elution method to concentrate an antibody fragment having an IL-6 receptor-binding ability, or by elution from beads suspended in 2 mM EDTA/TBS (TBS containing 2 mM EDTA) to concentrate an antibody fragment using an IL-6 receptor-binding ability in a Ca concentration-dependent manner as an indicator. The recovered phage solution was added to 10 mL of the *E. coli* strain TG1 in a logarithmic growth phase (OD600 of 0.4-0.7). The *E. coli* was cultured with gentle stirring at 37° C. for 1 hour to allow the phages to infect the *E. coli*. The infected *E. coli* was inoculated into a 225 mm×225 mm plate. Subsequently, the phages were recovered from the culture medium of the *E. coli* after inoculation to prepare a phage library solution.

In the second and subsequent panning, the phages were concentrated using the Ca-dependent binding ability as an indicator. Specifically, 40 pmol of the biotin-labeled antigen was added to the prepared phage library solution to allow the contact of the phage library with the antigen for 60 minutes at room temperature. Magnetic beads, blocked with BSA, were added to be bound to antigen-phage complexes for 15 minutes at room temperature. The beads were washed with 1 mL of 1.2 mM $CaCl_2$/TBST and 1.2 mM $CaCl_2$/TBS. Subsequently, the beads, to which 0.1 mL of 2 mM EDTA/TBS was added, were suspended at room temperature. Immediately after that, the beads were separated using a magnetic stand to collect a phage solution. The recovered phage solution was added to 10 mL of the *E. coli* strain TG1 in a logarithmic growth phase (OD600 of 0.4-0.7). The *E. coli* was cultured with gentle stirring at 37° C. for 1 hour to allow the phages to infect the *E. coli*. The infected *E. coli* was inoculated into a 225 mm×225 mm plate. Subsequently, the phages were recovered from the culture medium of the *E. coli* after inoculation to collect a phage library solution. The panning using the Ca-dependent binding ability as an indicator was repeated several times.

(6-3) Examination by Phage ELISA

A phage-containing culture supernatant was collected according to a routine method (Methods Mol. Biol. (2002) 178, 133-145) from a single colony of *E. coli*, obtained as described above.

A culture supernatant containing phages, to which BSA and $CaCl_2$ were added at a final concentration of 4% BSA and 1.2 mM of calcium ion concentration was subjected to ELISA as described below. A StreptaWell 96 microtiter plate (Roche) was coated overnight with 100 μL of PBS containing the biotin-labeled antigen. Each well of said plate was washed with PBST to remove the antigen, and then the wells were blocked with 250 μL of 4% BSA-TBS for 1 hour or longer. Said plate with the prepared culture supernatant added to each well, from which the 4% BSA-TBS was removed, was allowed to stand undisturbed at 37° C. for 1 hour, allowing the binding of phage-presenting antibody to the antigen present in each well. To each well washed with 1.2 mM $CaCl_2$/TBST, 1.2 mM $CaCl_2$/TBS or 1 mM EDTA/TBS was added. The plate was allowed to stand undisturbed for 30 minutes at 37° C. for incubation. After washing with 1.2 mM $CaCl_2$/TBST, an HRP-conjugated anti-M13 antibody (Amersham Pharmacia Biotech) diluted with TBS at a final concentration of 4% BSA and 1.2 mM of ionized calcium concentration was added to each well, and the plate was incubated for 1 hour. After washing with 1.2 mM $CaCl_2$/TBST, the chromogenic reaction of the solution in each well with a TMB single solution (ZYMED) added was stopped by adding sulfuric acid. Subsequently, said color was measured by measuring absorbance at 450 nm.

As a result of the above phage ELISA, the base sequence of a gene amplified with specific primers and an antibody fragment identified as having a Ca-dependent antigen-binding ability as a template was analyzed.

(6-4) Antibody Expression and Purification

As a result of the above phage ELISA, a clone identified as having a Ca-dependent antigen-binding ability was introduced into an expression plasmid for animal cells. Antibodies were expressed as described below. FreeStyle 293-F strain (Invitrogen) derived from human fetal kidney cells was suspended in FreeStyle 293 Expression Medium (Invitrogen), followed by inoculation of 3 mL into each well of a 6-well plate at a cell density of 1.33×10⁶ cell/mL. The prepared plasmid was introduced into the cells by lipofection. The cells were cultured for 4 days in a $CO_2$ incubator (37° C., 8% $CO_2$, 90 rpm). Antibodies were purified from the culture supernatant obtained above by a method known in the art using rProtein A Sepharose (trade mark) Fast Flow (Amersham Biosciences). Absorbance of the purified antibody solution was measured at 280 nm using a spectrophotometer. Antibody concentration was calculated from the measurements obtained using an extinction coefficient calculated by the PACE method (Protein Science (1995) 4, 2411-2423).

Reference Example 7

Examination of Ca-dependent Binding Ability of the Obtained Antibodies to Human IL-6 Receptor To examine whether or not the binding activities of antibodies 6RL#9-IgG1 [heavy chain (a constant region sequence derived from IgG1 linked to SEQ ID NO: 9) and light chain (SEQ ID NO: 93)] and FH4-IgG1 [heavy chain (SEQ ID NO: 94) and light chain (SEQ ID NO: 95)], obtained in Reference Example 6, to human IL-6 receptor are Ca-dependent, the kinetic analysis of the antigen-antibody reactions of these antibodies with human IL-6 receptor was conducted using BIACORE™ T100 surface plasmon resonance system (GE Healthcare). H54/L28-IgG1 [heavy chain variable region (SEQ ID NO: 96) and light chain variable region (SEQ ID NO: 97)], described in WO2009/125825, was used as a control antibody that has no Ca-dependent binding activity to human IL-6 receptor. The kinetic analysis of the antigen-antibody reactions was conducted in solutions with 2 mM and 3 μM calcium ion concentrations, set as high and low calcium ion concentration conditions, respectively. The antibody of interest was captured on Sensor chip CM4 (GE Healthcare) on which an appropriate amount of protein A (Invitrogen) was immobilized by an amine coupling method. Two buffers [10 mM N-(2-acetamido)-2-aminoethanesulfonic acid (ACES), 150 mM NaCl, 0.05% (w/v) polysorbate 20(Tween 20®), and 2 mM $CaCl_2$ (pH 7.4) or 10 mM ACES, 150 mM NaCl, 0.05% (w/v) polysorbate 20 (Tween 20®), and 3 μmol $CaCl_2$ (pH 7.4)] were used as running buffers. These buffers were used for diluting human IL-6 receptor. All the measurements were conducted at 37° C.

In the kinetic analysis of antigen-antibody reaction using H54L28-IgG1 antibody, the H54L28-IgG1 antibody captured on the sensor chip was allowed to interact with IL-6 receptor by injecting a diluent of IL-6 receptor and running buffer (blank) at a flow rate of 20 μL/min for 3 minutes. Subsequently, after the dissociation of IL-6 receptor was observed using running buffer at a flow rate of 20 μL/min for 10 minutes, the sensor chip was regenerated by injecting 10 mM glycine-HCl (pH 1.5) at a flow rate 30 μL/min for 30 seconds. Kinetics parameters, binding constant (ka) (1/Ms) and dissociation rate constant (kd) (1/s), were calculated from the sensorgrams obtained in the measurement. These values were used to calculate the dissociation constant (KD) (M) of the H54L28-IgG1 antibody for human IL-6 receptor. Each parameter was calculated using the BIACORE™ T100 Evaluation Software (GE Healthcare).

In the kinetic analysis of antigen-antibody reaction using FH4-IgG1 and 6RL#9-IgG1 antibodies, the FH4-IgG1 or 6RL#9-IgG1 antibody captured on the sensor chip was allowed to interact with IL-6 receptor by injecting a diluent of IL-6 receptor and running buffer (blank) at a flow rate of 5μL/min for 15 minutes. Subsequently, the sensor chip was regenerated by injecting 10 mM glycine-HCl (pH 1.5) at a flow rate 30 μL/min for 30 seconds. Dissociation constants (1(D) (M) were calculated from the sensorgrams obtained in the measurement, using a steady-state affinity model. Each parameter was calculated using the BIACORE™ T100 Evaluation Software (GE Healthcare). The dissociation constants (KD) between each antibody and IL-6 receptor in the presence of 2 mM $CaCl_2$, determined by the above method, are shown in Table 28.

TABLE 28

| | ANTIBODY | | |
|---|---|---|---|
| | H54/L28-IgG1 | FH4-IgG1 | 6RL#9-IgG1 |
| kD(M) | 1.9E−9 | 5.9E−7 | 2.6E−7 |

The KD value of the H54/L28-IgG1 antibody under the condition of 3 μM Ca concentration can be calculated in the same manner as in the presence of 2 mM Ca concentration. Under the condition of 3 μM Ca concentration, FH4-IgG1 and 6RL#9-IgG1 antibodies were barely observed to be bound to IL-6 receptor, thus the calculation of KD values by the method described above is difficult. However, the KD values of these antibodies under the condition of 3 μM Ca concentration can be estimated using Formula 5 (Biacore T100 Software Handbook, BR-1006-48, AE 01/2007) described in Example 13.

The approximate results of dissociation constant KD values for the antibodies and IL-6 receptor at a Ca concentration of 3 μmol, estimated using Formula 3 described in Example 13, are shown in Table 29. In Table 29, the $R_{eq}$, $R_{max}$, RI, and C values are estimated based on the assay result.

TABLE 29

| | ANTIBODY | | |
|---|---|---|---|
| | H54/L28-IgG1 | FH4-IgG1 | 6RL#9-IgG1 |
| Req(RU) | | 5 | 10 |
| Rmax(RU) | | 39 | 72 |
| RI(RU) | | 0 | 0 |
| C(M) | | 5E−06 | 5E−06 |
| KD(M) | 2.2E−9 | 3.4E−05 | 3.1E−05 |

Based on the findings described above, it was predicted that the $K_D$ between IL-6 receptor and FH4-IgG1 antibody or 6RL#9-IgG1 antibody was increased by about 60 or 120 times (the affinity was reduced by 60 or 120 times or more) when the concentration of $CaCl_2$ in the buffer was decreased from 2 mM to 3 μM. Table 30 summarizes the $K_D$ values at $CaCl_2$ concentrations of 2 mM and 3 μM and the Ca dependency for the three types of antibodies H54/L28-IgG1, FH4-IgG1, and 6RL#9-IgG1.

TABLE 30

| | ANTIBODY | | |
|---|---|---|---|
| | H54/L28-IgG1 | FH4-IgG1 | 6RL#9-IgG1 |
| KD (M) (2 mM $CaCl_2$) | 1.9E−9 | 5.9E−7 | 2.6E−7 |
| KD (M) (3 μM $CaCl_2$) | 2.2E−9 | 3.4E−5 OR MORE | 3.1E−5 OR MORE |
| Ca DEPENDENCY | ABOUT THE SAME | ABOUT 60 TIMES OR MORE | ABOUT 120 TIMES OR MORE |

No difference in the binding of the H54/L28-IgG1 antibody to IL-6 receptor due to the difference in Ca concentration was observed. On the other hand, the binding of FH4-IgG1 and 6RL#9-IgG1 antibodies to IL-6 receptor was observed to be significantly attenuated under the condition of the low Ca concentration (Table 30).

Reference Example 8

Examination of Calcium Ion Binding to the Antibody Obtained

Subsequently, the intermediate temperature of thermal denaturation (Tm value) was measured by differential scanning calorimetry (DSC) as an indicator for examining calcium ion binding to the antibody (MicroCal VP-Capillary DSC, MicroCal). The intermediate temperature of thermal denaturation (Tm value) is an indicator of stability. The intermediate temperature of thermal denaturation (Tm value) becomes higher when a protein is stabilized through calcium ion binding, as compared with no calcium ion binding (J. Biol. Chem. (2008) 283, 37, 25140-25149). The binding activity of calcium ion to antibody was examined by examining changes in the Tm value of the antibody depending on the changes in the calcium ion concentration of the antibody solution. The purified antibody was subjected to dialysis (EasySEP, TOMY) using an external solution of 20 mM Tris-HCl, 150 mM NaCl, and 2 mM $CaCl_2$ (pH 7.4), or 20 mM Tris-HCl, 150 mM NaCl, and 3 μM $CaCl_2$ (pH 7.4). DSC measurement was conducted at a heating rate of 240° C./hr from 20 to 115° C. using an antibody solution prepared at about 0.1 mg/mL with the dialysate as a test substance. The intermediate temperatures of thermal denaturation (Tm values) of the Fab domains of each antibody, calculated based on the denaturation curve obtained by DSC, are shown in Table 31.

TABLE 31

| ANTIBODY | CALCIUM ION CONCENTRATION | | ΔTm (° C.) |
| --- | --- | --- | --- |
| | 3 μM | 2 mM | 2 mM − 3 μM |
| H54/L28-IgG1 | 92.87 | 92.87 | 0.00 |
| FH4-IgG1 | 74.71 | 78.97 | 4.26 |
| 6RL#9-IgG1 | 77.77 | 78.98 | 1.21 |

From the results shown in Table 31, it is indicated that the Tm values of the Fab of the FH4-IgG1 and 6RL#9-IgG1 antibodies, which show a calcium-dependent binding ability, varied with changes in the calcium ion concentration, while the Tm values of the Fab of the H54/L28-IgG1 antibody which shows no calcium-dependent binding ability do not vary with changes in the calcium ion concentration. The variation in the Tm values of the Fab of the FH4-IgG1 and 6RL#9-IgG1 antibodies demonstrates that calcium ions bound to these antibodies to stabilize the Fab portions. The above results show that calcium ions bound to the FH4-IgG1 and 6RL#9-IgG1 antibodies, while no calcium ion bound to the H54/L28-IgG1 antibody.

Reference Example 9

Identification of Calcium Ion-binding Site in Antibody 6Rl#9 by X-Ray Crystallography (9-1) X-ray Crystallography As described in Reference Example 8, the measurements of thermal denaturation temperature Tm suggested that antibody 6RL#9 binds to calcium ion. However, it was unpredictable which portion of antibody 6RL#9 binds to calcium ion. Then, by using the technique of X-ray crystallography, residues of antibody 6RL#9 that interact with calcium ion were identified.

(9-2) Expression and Purification of Antibody 6RL#9

Antibody 6RL#9 was expressed and purified for X-ray crystallography. Specifically, animal expression plasmids constructed to be capable of expressing the heavy chain (constant region sequence derived from IgG1 was linked to SEQ ID NO: 9) and light chain (SEQ ID NO: 93) of antibody 6RL#9 were introduced transiently into animal cells. The constructed plasmids were introduced by the lipofection method into cells of human fetal kidney cell-derived FreeStyle 293-F (Invitrogen) suspended in 800 ml of the FreeStyle 293 Expression Medium (Invitrogen) (final cell density: $1 \times 10^6$ cells/mL). The plasmid-introduced cells were cultured in a $CO_2$ incubator (37° C., 8% $CO_2$, 90 rpm) for five days. From the culture supernatant obtained as described above, antibodies were purified by a method known to those skilled in the art using the rProtein A Sepharose™ Fast Flow (Amersham Biosciences). Absorbance at 280 nm of purified antibody solutions was measured using a spectrophotometer. Antibody concentrations were calculated from the measured values using an extinction coefficient calculated by the PACE method (Protein Science (1995) 4, 2411-2423).

(9-3) Purification of Antibody 6RL#9 Fab Fragment

Antibody 6RL#9 was concentrated to 21 mg/ml using an ultrafilter with a molecular weight cutoff of 10,000 MWCO. A 5 mg/mL antibody sample (2.5 mL) was prepared by diluting the antibody solution using 4 mM L-cysteine/5 mM EDTA/20 mM sodium phosphate buffer (pH 6.5). 0.125 mg of papain (Roche Applied Science) was added to the sample. After stirring, the sample was incubated at 35° C. for two hours. After incubation, a tablet of Protease Inhibitor Cocktail Mini, EDTA-free (Roche Applied Science) was dissolved in 10 ml of 25 mM MES buffer (pH 6) and added to the sample. The sample was incubated on ice to stop the papain proteolytic reaction. Then, the sample was loaded onto a 1-ml cation-exchange column HiTrap SP HP (GE Healthcare) equilibrated with 25 mM MES buffer (pH 6), downstream of which a 1-ml HiTrap MabSelect Sure Protein A column (GE Healthcare) was connected in tandem. A purified fraction of the Fab fragment of antibody 6RL#9 was obtained by performing elution with a linear NaCl concentration gradient up to 300 mM in the above-described buffer. Then, the resulting purified fraction was concentrated to about 0.8 ml using a 5000 MWCO ultrafilter. The concentrate was loaded onto a gel filtration column Superdex 200 10/300 GL (GE Healthcare) equilibrated with 100 mM HEPES buffer (pH 8) containing 50 mM NaCl. The purified Fab fragment of antibody 6RL#9 for crystallization was eluted from the column using the same buffer. All the column treatments described above were carried out at a low temperature of 6 to 7.5° C.

(9-4) Crystallization of the Antibody 6RL#9 Fab Fragment in the Presence of Ca

Seed crystals of the 6RL#9 Fab fragment were prepared in advance under general conditions. Then, the purified Fab fragment of antibody 6RL#9 in 5 mM $CaCl_2$ was concentrated to 12 mg/ml with a 5000 MWCO ultrafilter. Next, the sample concentrated as described above was crystallized by the hanging drop vapor diffusion method using 100 mM HEPES buffer (pH 7.5) containing 20% to 29% PEG4000 as a reservoir solution. The above-described seed crystals were crushed in 100 mM HEPES buffer (pH 7.5) containing 29% PEG4000 and 5 mM $CaCl_2$, and serially diluted to 100 to 10,000 folds. Then, 0.2 μL of diluted solutions were combined with a mixture of 0.8 μl of the reservoir solution and 0.8 μl of the concentrated sample to prepare crystallization drops on a glass cover slide. The crystal drops were allowed to stand at 20° C. for two to three days to prepare thin plate-like crystals. X-ray diffraction data were collected using the crystals.

(9-5) Crystallization of the Antibody 6RL#9 Fab Fragment in the Absence of Ca

The purified Fab fragment of antibody 6RL#9 was concentrated to 15 mg/ml using a 5000 MWCO ultrafilter. Then, the sample concentrated as described above was crystallized by the hanging drop vapor diffusion method using 100 mM HEPES buffer (pH 7.5) containing 18% to 25% PEG4000 as a reservoir solution. Crystals of the antibody 6RL#9 Fab fragment obtained in the presence of Ca were crushed in 100 mM HEPES buffer (pH 7.5) containing 25% PEG4000, and serially diluted to 100 to 10,000 folds. Then, 0.2 μL of diluted solutions were combined with a mixture of 0.8 μl of the reservoir solution and 0.8 μl of the concentrated sample to prepare crystallization drops on a glass cover slide. The crystal drops were allowed to stand at 20° C. for two to three days to prepare thin plate-like crystals. X-ray diffraction data were collected using the crystals.

(9-6) X-ray Crystallographic Measurement of Fab Fragment Crystal from Antibody 6RL#9 in the Presence of Ca Crystals of the Fab fragment of antibody 6RL#9 prepared in the presence of Ca were soaked in 100 mM HEPES buffer (pH 7.5) solution containing 35% PEG4000 and 5 mM $CaCl_2$. By removing the exterior solution from the surface of a single crystal with a micro-nylon-loop pin, the single crystal was frozen in liquid nitrogen. X-ray diffraction data of the frozen crystal was collected from beam line BL-17A of the Photon Factory in the High Energy Accelerator Research Organization. The frozen crystal was maintained in the frozen state during the measurement by constantly placing it in a stream of nitrogen gas at −178° C. A total of 180 diffraction images were collected using the CCD detector Quantum315r (ADSC) attached to the beam line while rotating the crystal in 1° intervals. Lattice constant determination, diffraction spot indexing, and diffraction data analysis were performed using programs Xia2 (CCP4 Software Suite), XDS Package (Walfgang Kabsch), and Scala (CCP4 Software Suite). Finally, diffraction intensity data up to 2.2 angstrom resolution was obtained. The crystal belongs to space group P212121 with lattice constant a=45.47 angstrom, b=79.86 angstrom, c=116.25 angstrom, $\alpha$=90°, $\beta$=90°, and $\gamma$=90°.

(9-7) X-ray Crystallographic Measurement of the Fab Fragment Crystal from Antibody 6RL#9 in the Absence of Ca Crystals of the Fab fragment of antibody 6RL#9 prepared in the absence of Ca were soaked in 100 mM HEPES buffer (pH 7.5) solution containing 35% PEG4000. By removing the exterior solution from the surface of a single crystal with a micro-nylon-loop pin, the single crystal was frozen in liquid nitrogen. X-ray diffraction data of the frozen crystal was collected from beam line BL-5A of the Photon Factory in the High Energy Accelerator Research Organization. The frozen crystal was maintained in the frozen state during the measurement by constantly placing it in a stream of nitrogen gas at −178° C. A total of 180 diffraction images were collected using the CCD detector Quantum210r (ADSC) attached to the beam line while rotating the crystal in 1° intervals. Lattice constant determination, diffraction spot indexing, and diffraction data analysis were performed using programs Xia2 (CCP4 Software Suite), XDS Package (Walfgang Kabsch), and Scala (CCP4 Software Suite). Finally, diffraction intensity data up to 2.3 angstrom resolution was obtained. The crystal belongs to space group P212121 with lattice constant a=45.40 angstrom, b=79.63 angstrom, c=116.07 angstrom, $\alpha$=90°, $\beta$=90°, $\gamma$=90°, and thus is structurally identical to the crystal prepared in the presence of Ca.

(9-8) X-ray Crystallographic Measurement of the Fab Fragment Crystal from Antibody 6RL#9 in the Presence of Ca The crystal structure of the antibody 6RL#9 Fab fragment in the presence of Ca was determined by a molecular replacement method using the Phaser program (CCP4 Software Suite). The number of molecules in an asymmetrical unit was estimated to be one from the size of crystal lattice and molecular weight of the antibody 6RL#9 Fab fragment. Based on the primary sequence homology, a portion of amino acid positions 112 to 220 from A chain and a portion of amino acid positions 116 to 218 from B chain in the conformational coordinate of PDB code 1ZA6 were used as model molecules for analyzing the CL and CH1 regions. Then, a portion of amino acid positions 1 to 115 from B chain in the conformational coordinate of PDB code 1 ZA6 was used as a model molecule for analyzing the VH region. Finally, a portion of amino acid positions 3 to 147 of the light chain in the conformational coordinate of PDB code 2A9M was used as a model molecule for analyzing the VL region. Based on this order, an initial structure model for the antibody 6RL#9 Fab fragment was obtained by determining from translation and rotation functions the positions and orientations of the model molecules for analysis in the crystal lattice. The crystallographic reliability factor R for the reflection data at 25 to 3.0 angstrom resolution was 46.9% and Free R was 48.6% after rigid body refinement where the VH, VL, CH1, and CL domains were each allowed to deviate from the initial structure model. Then, model refinement was achieved by repeating structural refinement using program Refmac5 (CCP4 Software Suite) followed by model revision performed using program Coot (Paul Emsley) with reference to the Fo-Fc and 2Fo-F electron density maps where the coefficients Fo-Fc and 2Fo-Fc were calculated using experimentally determined structural factor Fo, structural factor Fc calculated based on the model, and the phases. The final refinement was carried out using program Refmac5 (CCP4 Software Suite) based on the Fo-Fc and 2Fo-F electron density maps by adding water molecule and Ca ion into the model. With 21,020 reflection data at 25 to 2.2 angstrom resolution, eventually the crystallographic reliability factor R became 20.0% and free R became 27.9% for the model consisting of 3440 atoms.

(9-9) Measurement of X-ray Diffraction Data of the Fab Fragment Crystal from Antibody 6RL#9 in the Absence of Ca The crystal structure of the antibody 6RL#9 Fab fragment in the absence of Ca was determined based on the structure of the crystal prepared in the presence of Ca. Water and Ca ion molecules were omitted from the conformational coordinate of the crystal of the antibody 6RL#9 Fab fragment prepared in the presence of Ca. The crystallographic reliability factor R for the data of reflection at 25 to 3.0 angstrom resolution was 30.3% and Free R was 31.7% after the rigid body refinement where the VH, VL, CH1, and CL domains were each allowed to deviate. Then, model refinement was achieved by repeating structural refinement using program Refmac5 (CCP4 Software Suite) followed by model revision performed using program Coot (Paul Emsley) with reference to the Fo-Fc and 2Fo-Fc electron density maps where the coefficients Fo-Fc and 2Fo-Fc were calculated using experimentally determined structural factor Fo, structural factor Fc calculated based on the model, and the phases. The final refinement was carried out using program Refmac5 (CCP4 Software Suite) based on the Fo-Fc and 2Fo-F electron density maps by adding water molecule and Ca ion into the model. With 18,357 reflection data at 25 to 2.3 angstrom resolution, eventually the crystallographic reliability factor R became 20.9% and free R became 27.7% for the model consisting of 3351 atoms.

Figure 41:
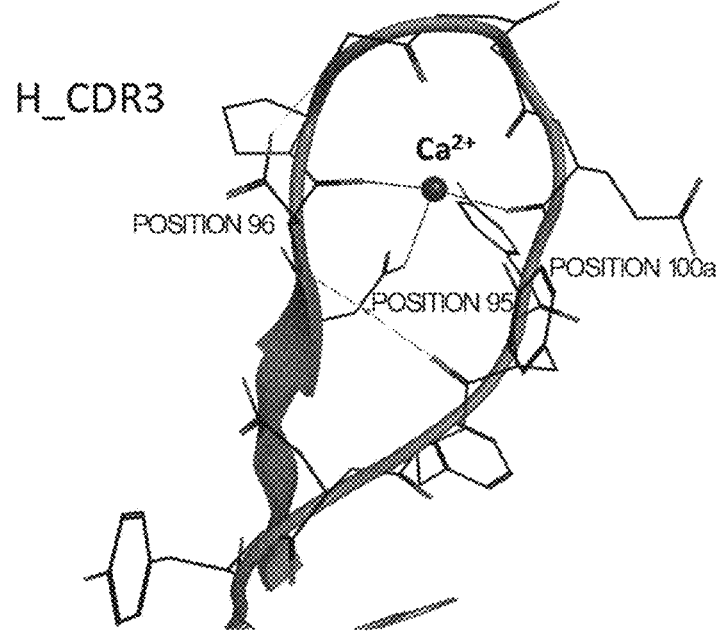
FIG. 41 is a diagram showing the structure of the Fab fragment heavy-chain CDR3 of antibody 6RL#9 determined by X-ray crystallography.
Figure 41:
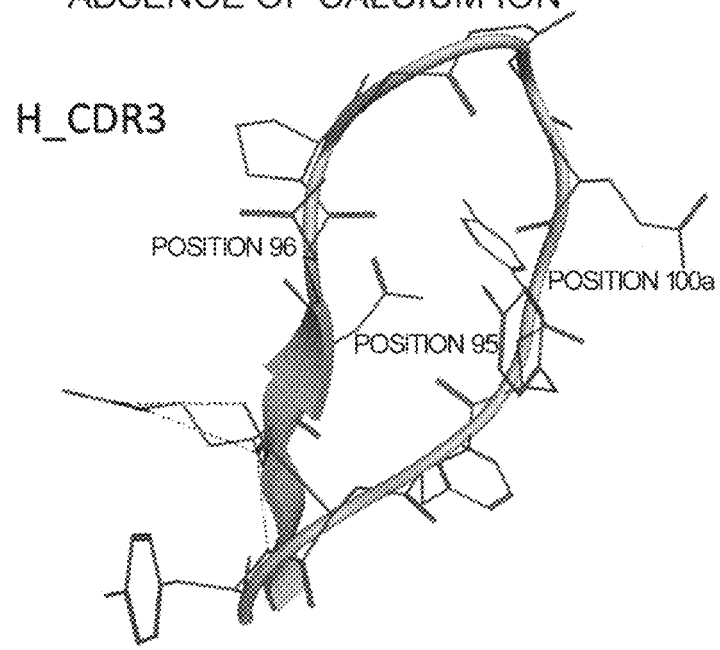

(9-10) Comparison of X-ray Crystallographic Diffraction Data of the Fab Fragments of Antibody 6RL#9 between in the Presence and Absence of Ca When the crystallographic structures of the Fab fragments of antibody 6RL#9 are compared between in the presence and absence of Ca, significant changes are seen in the heavy chain CDR3. The structure of the heavy chain CDR3 of the antibody 6RL#9 Fab fragment determined by X-ray crystallography is shown in FIG. 41. Specifically, a calcium ion resided at the center of the heavy chain CDR3 loop region of the antibody 6RL#9 Fab fragment prepared in the presence of Ca. The calcium ion was assumed to interact with positions 95, 96, and 100a (Kabat's numbering) of the heavy chain CDR3. It was believed that the heavy chain CDR3 loop which is important for the antigen binding was stabilized by calcium binding in the presence of Ca, and became an optimum structure for antigen binding. There is no report demonstrating that calcium binds to the antibody heavy chain CDR3. Thus, the calcium-bound structure of the antibody heavy chain CDR3 is a novel structure.

The calcium-binding motif present in the heavy chain CDR3, revealed in the structure of the Fab fragment of the 6RL#9 antibody, may also become a new design element for the Ca library. For example, a library containing the heavy chain CDR3 of the 6RL#9 antibody and flexible residues in other CDRs including the light chain is thought to be possible.

Reference Example 10

Preparation of Antibodies that Bind to IL-6 In A Ca-dependent Manner from a Human Antibody Library Using Phage Display Techniques (10-1) Construction of a Phage Display Library of Naïve Human Antibodies A human antibody phage display library containing multiple phages that display various human antibody Fab domain sequences was constructed by a method known to those skilled in the art using, as a template, polyA RNA prepared from human PBMC, commercially available human polyA RNA, and such.

(10-2) Preparation of Antibody Fragments that Bind to the Antigen in a Ca-dependent Manner from Library by Bead Panning Primary selection from the constructed phage display library of naïve human antibodies was carried out by enriching antibody fragments that have antigen (IL-6)-binding activity. The antigen used was biotin-labeled IL-6.

Phages were produced from $E.$ $coli$ carrying the constructed phagemid for phage display. To precipitate the phages produced by $E.$ $coli$, 2.5 M NaCl/10% PEG was added to the $E.$ $coli$ culture medium. The phage fraction was diluted with TBS to prepare a phage library solution. Then, BSA and $CaCl_2$ were added the phage library solution at final concentrations of 4% and 1.2 mM calcium ion concentration, respectively. The panning method used was a conventional panning method using antigen-immobilized magnetic beads (J. Immunol. Methods. (2008) 332(1-2): 2-9; J. Immunol. Methods. (2001) 247(1-2): 191-203; Biotechnol. Prog. (2002) 18(2): 212-20; Mol. Cell Proteomics (2003) 2(2): 61-9). The magnetic beads used were NeutrAvidin-coated beads (Sera-Mag SpeedBeads NeutrAvidin-coated) and Streptavidin-coated beads (Dynabeads M-280 Streptavidin).

Specifically, 250 pmol of the biotin-labeled antigen was added to the prepared phage library solution. Thus, the solution was contacted with the antigen at room temperature for 60 minutes. Magnetic beads blocked with BSA were added, and the antigen-phage complex was allowed to bind to the magnetic beads at room temperature for 15 minutes. The beads were washed three times with 1.2 mM $CaCl_2$/TBST (TBST containing 1.2 mM $CaCl_2$), and then twice with 1 ml of 1.2 mM $CaCl_2$/TBS (TBS containing 1.2 mM $CaCl_2$). Thereafter, 0.5 ml of 1 mg/ml trypsin was added to the beads. After 15 minutes of dispersion at room temperature, the beads were immediately separated using a magnetic stand to collect a phage suspension. The prepared phage suspension was added to 10 ml of $E.$ $coli$ of stain TG1 at the logarithmic growth phase (OD600=0.4 to 0.5). The $E.$ $coli$ was incubated with gentle stirring at 37° C. for one hour to infect the phages. The infected $E.$ $coli$ was seeded in a plate (225 mm×225 mm). Then, phages were collected from the culture medium of the seeded $E.$ $coli$ to prepare a phage library solution.

In the second round and subsequent panning, phages were enriched using the Ca-dependent binding activity as an indicator. Specifically, 40 pmol of the biotin-labeled antigen was added to the prepared phage library solution. Thus, the phage library was contacted with the antigen at room temperature for 60 minutes. Magnetic beads blocked with BSA were added, and the antigen-phage complex was allowed to bind to the magnetic beads at room temperature for 15 minutes. The beads were washed with 1 ml of 1.2 mM $CaCl_2$/TBST and 1.2 mM $CaCl_2$/TBS. Next, 0.1 ml of 2 mM EDTA/TBS was added to the beads. After dispersion at room temperature, the beads were immediately separated using a magnetic stand to collect a phage suspension. The pIII protein (helper phage-derived protein pIII) was cleaved from phages that did not display Fab by adding 5 μl of 100 mg/ml trypsin to the collected phage suspension to eliminate the ability of phages displaying no Fab to infect $E.$ $coli$. Phages collected from the trypsinized liquid phage stock was added to 10 ml of $E.$ $coli$ cells of the TG1 strain at the logarithmic growth phase (OD600=0.4 to 0.7). The $E.$ $coli$ was incubated while gently stirring at 37° C. for one hour to infect phage. The infected $E.$ $coli$ was seeded in a plate (225 mm×225 mm). Then, phages were collected from the culture medium of the seeded $E.$ $coli$ to prepare a liquid stock of phage library. Panning was performed three times using the Ca-dependent binding activity as an indicator.

(10-3) Assessment by Phage ELISA

Culture supernatants containing phages were collected from single colonies of $E.$ $coli$ obtained by the method described above according to a conventional method (Methods Mol. Biol. (2002) 178, 133-145). BSA and $CaCl_2$ were added at final concentrations of 4% and 1.2 mM calcium ion concentration, respectively, to the phage-containing culture supernatants.

The supernatants were subjected to ELISA by the following procedure. A StreptaWell 96-well microtiter plate (Roche) was coated overnight with 100 μl of PBS containing the biotin-labeled antigen. The antigen was removed by washing each well of the plate with PBST. Then, the wells were blocked with 250 μl of 4% BSA-TBS for one hour or more. After removal of 4% BSA-TBS, the prepared culture supernatants were added to the each well. The plate was incubated at 37° C. for one hour so that the antibody-displaying phages were allowed to bind to the antigen on each well. After each well was washed with 1.2 mM $CaCl_2$/TBST, 1.2 mM $CaCl_2$/TBS or 1 mM EDTA/TBS was added. The plate was left for incubation at 37° C. for 30 minutes. After washing with 1.2 mM $CaCl_2$/TBST, an HRP-conjugated anti-M13 antibody (Amersham Pharmacia Biotech) diluted with TBS containing BSA and calcium ion at final concentrations of 4% and 1.2 mM calcium ion concentration was added to each well, and the plate was incubated for one hour. After washing with 1.2 mM $CaCl_2$/TBST, the TMB single solution (ZYMED) was added to each well. The chromogenic reaction in the solution of each well was stopped by adding sulfuric acid. Then, the developed color was assessed by measuring absorbance at 450 nm.

From the 96 clones isolated, antibody 6KC4-1#85 having Ca-dependent IL-6-binding activity was obtained by phage ELISA. Using antibody fragments that were predicted to have a Ca-dependent antigen-binding activity based on the result of the phage ELISA described above as a template, genes were amplified with specific primers and their sequences were analyzed. The heavy-chain and light-chain variable region sequences of antibody 6KC4-1#85 are shown in SEQ ID NOs: 10 and 98, respectively. The polynucleotide encoding the heavy-chain variable region of antibody 6KC4-1#85 (SEQ ID NO: 10) was linked to a polynucleotide encoding an IgG1-derived sequence by PCR method. The resulting DNA fragment was inserted into an animal cell expression vector to construct an expression vector for the heavy chain of SEQ ID NO: 99. A polynucleotide encoding the light-chain variable region of antibody 6KC4-1#85 (SEQ ID NO: 98) was linked to a polynucleotide encoding the constant region of the natural Kappa chain (SEQ ID NO: 100) by PCR. A DNA fragment encoding the linked sequence shown in SEQ ID NO: 101 was inserted into an animal cell expression vector. Sequences of the constructed variants were confirmed by a method known to those skilled in the art. Sequences of the constructed variants were confirmed by a method known to those skilled in the art.

(10-4) Expression and Purification of Antibodies

Clone 6KC4-1#85 that was predicted to have a Ca-dependent antigen-binding activity based on the result of phage ELISA was inserted into animal cell expression plasmids. Antibody expression was carried out by the following method. Cells of human fetal kidney cell-derived FreeStyle 293-F (Invitrogen) were suspended in the FreeStyle 293 Expression Medium (Invitrogen), and plated at a cell density of $1.33 \times 10^6$ cells/ml (3 ml) into each well of a 6-well plate. The prepared plasmids were introduced into cells by a lipofection method. The cells were cultured for four days in a $CO_2$ incubator (37° C., 8% $CO_2$, 90 rpm). From the culture supernatants, antibodies were purified using the rProtein A Sepharose™ Fast Flow (Amersham Biosciences) by a method known to those skilled in the art. Absorbance at 280 nm of the purified antibody solutions was measured using a spectrophotometer. Antibody concentrations were calculated from the determined values using an extinction coefficient calculated by the PACE method (Protein Science (1995) 4: 2411-2423).

Reference Example 11

Assessment of Antibody 6Kc4-1#85 for Calcium Ion Binding (11-1) Assessment of Antibody 6KC4-1#85 for Calcium Ion Binding Calcium-dependent antigen-binding antibody 6KC4-1#85 which was isolated from a human antibody library was assessed for its calcium binding. Whether the measured Tm value varies depending on the ionized calcium concentration condition was assessed by the method described in Reference Example 6.

Tm values for the Fab domain of antibody 6KC4-1#85 are shown in Table 32. As shown in Table 32, the Tm value of the 6KC4-1#85 antibody Fab domain varied depending on the calcium ion concentration. This demonstrates that antibody 6KC4-1#85 binds to calcium.

TABLE 32

| ANTIBODY | CALCIUM ION CONCENTRATION | | ΔTm (° C.) |
| --- | --- | --- | --- |
|  | 3 μM | 2 mM | 2 mM − 3 μM |
| 6KC4-1#85 | 71.49 | 75.39 | 3.9 |

(11-2) Identification of Calcium Ion-Binding Site in Antibody 6KC4-1#85

As demonstrated in (11-1) of Reference Example 11, antibody 6KC4-1#85 binds to calcium ion. However, 6KC4-1#85 does not have a calcium-binding motif such as the hVk5-2 sequence which was revealed from assessment to have a calcium-binding motif. Thus, to identify residues responsible for the calcium ion binding of antibody 6KC4-1#85, altered heavy chains (6_H1-11 (SEQ ID NO: 102), 6_H1-12 (SEQ ID NO: 103), 6_H1-13 (SEQ ID NO: 104), 6_H1-14 (SEQ ID NO: 105), 6_H1-15 (SEQ ID NO: 106)) or altered light chains (6_L1-5 (SEQ ID NO: 107) and 6_L1-6 (SEQ ID NO: 108)) were constructed by substituting an Asp (D) residue in the CDR of antibody 6KC4-1#85 with an Ala (A) residue which does not participate in the binding or chelation of calcium ion. By the method described in Reference Example 6, altered antibodies were purified from the culture supernatants of animal cells introduced with expression vectors carrying the altered antibody genes. The purified altered antibodies were assessed for their calcium binding by the method described in Reference Example 6. The measurement result is shown in Table 33. As shown in Table 33, substitution of an Ala residue for the residue at position 95 or 101 (Kabat's numbering) in the heavy chain CDR3 of antibody 6KC4-1#85 resulted in loss of the calcium-binding activity of antibody 6KC4-1#85. This suggests that these residues are responsible for calcium binding. The calcium-binding motif present around the base of the loop of the heavy chain CDR3 of the 6KC4-1#85 antibody, as revealed from the calcium-binding properties of the modified 6KC4-1#85 antibody, may also become a new design element for the Ca library as described in Reference Example 9. In other words, besides a library with a calcium-binding motif introduced into the light chain variable region provided as a specific example in Reference Example 20 and etc., a library containing the calcium-binding motif present in, for example, the heavy chain CDR3 of the 6KC4-1#85 antibody and containing flexible residues in other amino acid residues is possible.

TABLE 33

| HEAVY CHAIN | LIGHT CHAIN | ALTERED RESIDUE | CALCIUM ION CONCENTRATION | | ΔTm (° C.) 2 mM − 3 μM |
| --- | --- | --- | --- | --- | --- |
|  |  |  | 3 μM | 2 mM |  |
| 6KC4-1#85 | 6KC4-1#85 | WILD-TYPE | 71.49 | 75.39 | 3.9 |
| 6H1-11 | 6KC4-1#85 | H CHAIN POSITION 61 (Kabat NUMBERING) | 71.73 | 75.56 | 3.83 |

TABLE 33-continued

| HEAVY CHAIN | LIGHT CHAIN | ALTERED RESIDUE | CALCIUM ION CONCENTRATION | | ΔTm (° C.) 2 mM − 3 μM |
|---|---|---|---|---|---|
| | | | 3 μM | 2 mM | |
| 6H1-12 | 6KC4-1#85 | H CHAIN POSITION 95 (Kabat NUMBERING) | 72.9 | 73.43 | 0.53 |
| 6H1-13 | 6KC4-1#85 | H CHAIN POSITION 100a (Kabat NUMBERING) | 70.94 | 76.25 | 5.31 |
| 6H1-14 | 6KC4-1#85 | H CHAIN POSITION 100g (Kabat NUMBERING) | 73.95 | 75.14 | 1.19 |
| 6H1-15 | 6KC4-1#85 | H CHAIN POSITION 101 (Kabat NUMBERING) | 65.37 | 66.25 | 0.87 |
| 6KC4-1#85 | 6L1-5 | L CHAIN POSITION 50 (Kabat NUMBERING) | 71.92 | 76.08 | 4.16 |
| 6KC4-1#85 | 6L1-6 | L CHAIN POSITION 92 (Kabat NUMBERING) | 72.13 | 78.74 | 6.61 |

Reference Example 12

Examination of Effects of Ca-dependent Binding Antibody on Plasma Retention of Antigen Using Normal Mice (12-1) In Vivo Test Using Normal Mice To a normal mouse (C57BL/6J mouse, Charles River Japan), hsIL-6R (soluble human IL-6 receptor prepared in Reference Example 3) alone was administered, or soluble human IL-6 receptor and anti-human IL-6 receptor antibody were administered simultaneously to examine the kinetics of the soluble human IL-6 receptor and anti-human IL-6 receptor antibody in vivo. A single dose (10 mL/kg) of the soluble human IL-6 receptor solution (5 μg/mL) or a mixture of soluble human IL-6 receptor and anti-human IL-6 receptor antibody was administered into the caudal vein. The above H54/L28-IgG1, 6RL#9-IgG1, and FH4-IgG1 were used as anti-human IL-6 receptor antibodies.

The soluble human IL-6 receptor concentration in all the mixtures is 5 μg/mL. The concentrations of anti-human IL-6 receptor antibody vary with the antibodies: 0.1 mg/mL for H54/L28-IgG1 and 10 mg/mL for 6RL#9-IgG1 and FH4-IgG1. At this time, it was thought that most of the soluble human IL-6 receptors bind to the antibody because the anti-human IL-6 receptor antibody against soluble human IL-6 receptor exists in a sufficient or excessive amount. Blood samples were collected at 15 minutes, 7 hours and 1, 2, 4, 7, 14, 21, and 28 days after the administration. The blood samples obtained were immediately centrifuged for 15 minutes at 4° C. and 12,000 rpm to separate plasma. The separated plasma was stored in a freezer set to −20° C. or lower until the time of measurement.

Figure 42:
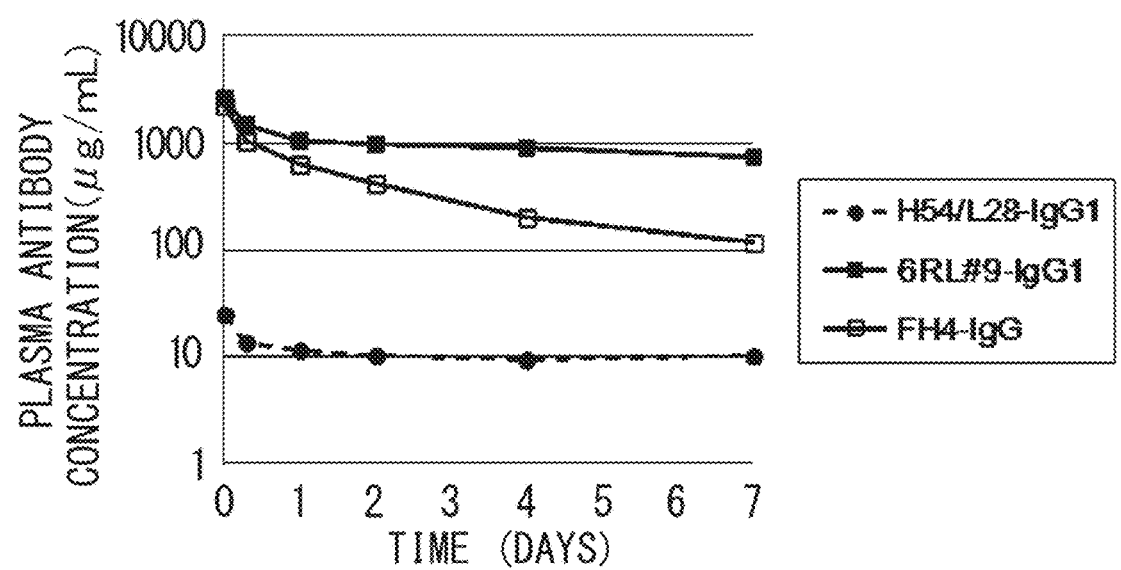
FIG. 42 is a graph showing a plasma antibody concentration time course for H54/L28-IgG1, 6RL#9-IgG1, and FH4-IgG1 in normal mice.

(12-2) Determination of Plasma Anti-human IL-6 Receptor Antibody Concentration in Normal Mice by ELISA The plasma concentration of anti-human IL-6 receptor antibody in a mouse was determined by ELISA. First, Anti-Human IgG (γ-chain specific) F(ab')2 Fragment of Antibody (SIGMA) was dispensed into a Nunc-Immuno Plate, MaxiSoup (Nalge Nunc International), and was allowed to stand undisturbed overnight at 4° C. to prepare an anti-human IgG-solid phase plate. Calibration curve samples at a plasma concentration of 0.64, 0.32, 0.16, 0.08, 0.04, 0.02, or 0.01 μg/mL, and mouse plasma measurement samples diluted by 100-fold or above were each dispensed into the anti-human IgG-solid phase plate, followed by incubation for 1 hour at 25° C. Subsequently, the plate was allowed to react with a biotinylated anti-human IL-6 R antibody (R&D) for 1 hour at 25° C., followed by reaction with Streptavidin-PolyHRP80 (Stereospecific Detection Technologies) for 0.5 hours at 25° C. The chromogenic reaction was conducted using TMB One Component HRP Microwell Substrate (BioFX Laboratories) as a substrate. After the chromogenic reaction was stopped by adding 1N-sulfuric acid (Showa Chemical), absorbance at 450 nm of the color solution was measured using a microplate reader. The plasma concentration in the mouse was calculated from the absorbance of the calibration curve using the SOFTmax PRO analysis software (Molecular Devices). Changes in the plasma concentrations of antibodies, H54/L28-IgG1, 6RL#9-IgG1, and FH4-IgG1, in the normal mice after intravenous administration, measured as described above, are shown in FIG. 42.

Figure 43:
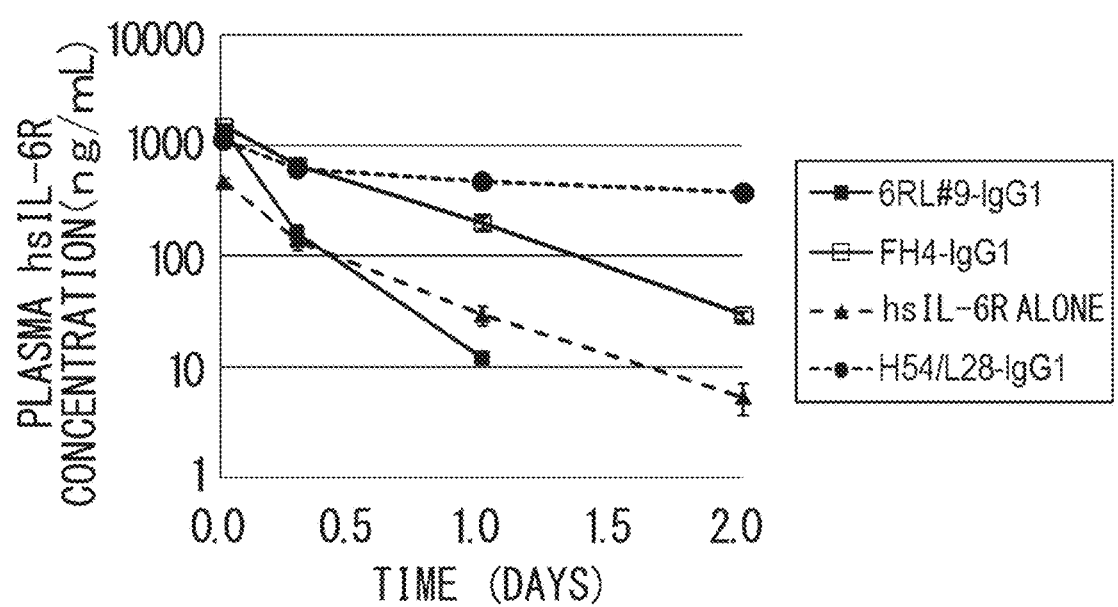
FIG. 43 is a graph showing a time course of plasma soluble human IL-6 receptor concentration in normal mice administered with H54/L28-IgG1, 6RL#9-IgG1, or FH4-IgG1.

(12-3) Determination of Plasma Soluble Human IL-6 Receptor Concentration by an Electrochemiluminescence Method The plasma concentration of soluble human IL-6 receptor in a mouse was determined by an electrochemiluminescence method. A soluble human IL-6 receptor calibration curve sample prepared at 2,000, 1,000, 500, 250, 125, 62.5, or 31.25 pg/mL, and a mouse plasma measurement sample diluted by 50-fold or above, were mixed with a monoclonal anti-human IL-6R antibody (R&D) ruthenated with SULFO-TAG NHS Ester (Meso Scale Discovery), a biotinylated anti-human IL-6 R antibody (R&D), and tocilizumab (heavy chain SEQ ID NO: 109, light chain SEQ ID NO: 83), followed by overnight reaction at 4° C. At that time, the assay buffer contained 10 mM EDTA to reduce the free Ca concentration in the sample and dissociate almost all the soluble human IL-6 receptors in the sample from 6RL#9-IgG1 or FH4-IgG1 to be bound to the added tocilizumab. Subsequently, said reaction liquid was dispensed into an MA400 PR Streptavidin Plate (Meso Scale Discovery). In addition, after washing each well of the plate that was allowed to react for 1 hour at 25° C., Read Buffer T (×4) (Meso Scale Discovery) was dispensed into each well. Immediately, the reaction liquid was subjected to measurement using a SECTOR PR 400 reader (Meso Scale Discovery). The concentration of soluble human IL-6 receptor was calculated from the response of the calibration curve using the SOFTmax PRO analysis software (Molecular Devices). Changes in the plasma concentration of soluble human IL-6 receptor in the normal mouse after intravenous administration, determined as described above, are shown in FIG. 43.

As a result, the disappearance of soluble human IL-6 receptor was very rapid when soluble human IL-6 receptor was administered alone, while the disappearance of soluble human IL-6 receptor was significantly delayed when soluble human IL-6 receptor was administered simultaneously with H54/L28-IgG1, a conventional antibody having no Ca-dependent binding ability to soluble human IL-6 receptor. In contrast, the disappearance of soluble human IL-6 receptor was significantly accelerated when soluble human IL-6 receptor was administered simultaneously with 6RL#9-IgG1 or FH4-IgG1 having 100-fold or higher Ca-dependent binding ability to soluble human IL-6 receptor. The plasma concentrations of soluble human IL-6 receptor one day after soluble human IL-6 receptor was administered simultaneously with 6RL#9-IgG1 and FH4-IgG1 were reduced 39-fold and 2-fold, respectively, as compared with simultaneous administration with H54/L28-IgG1. Thus, the calcium-dependent binding antibodies were confirmed to be able to accelerate antigen disappearance from the plasma.

Reference Example 13

Trials to Improve the Antigen Elimination-accelerating Effect of Antibody with Ca-dependent Antigen-binding (Preparation Of Antibodies)

(13-1) Regarding the Binding of IgG Antibody to FcRn

IgG antibodies have longer plasma retention time as a result of FcRn binding. The binding between IgG and FcRn is observed only under an acidic condition (pH 6.0). By contrast, the binding is almost undetectable under a neutral condition (pH 7.4). An IgG antibody is taken up into cells in a nonspecific manner. The antibody returns to the cell surface by binding to endosomal FcRn under the endosomal acidic condition, and then dissociates from FcRn under the plasma neutral condition. When the FcRn binding under the acidic condition is lost by introducing mutations into the IgG Fc region, the antibody retention time in plasma is markedly impaired because the antibody no longer recycles to the plasma from the endosome.

A reported method for improving the plasma retention of an IgG antibody is to enhance the FcRn binding under acidic conditions. Amino acid mutations are introduced into its Fc region of an IgG antibody to improve its FcRn binding under acidic conditions. This increases the efficiency of recycling of IgG antibody to the plasma from the endosome, resulting in improvement of the plasma retention of IgG antibody. When introducing amino acid substitution, it is considered important not to increase the binding to FcRn under neutral conditions. IgG antibodies that bind to FcRn under neutral conditions can return onto the cell surface through binding to FcRn under the acidic condition of the endosome, but IgG antibodies do not dissociate from the FcRn in plasma under neutral conditions and are not recycled to the plasma, and thus plasma retention of IgG antibodies was thought to be inversely impaired.

For example, as described by Dall' Acqua et al. (J. Immunol. (2002) 169 (9), 5171-5180), the plasma retention of IgG1 antibody that was allowed to bind to mouse FcRn under a neutral condition (pH 7.4) was exacerbated as a result of introducing an amino acid substitution into a mouse. In addition, as described by Yeung et al. (J. Immunol. (2009) 182 (12), 7663-7671), Datta-Mannan et al. (J. Biol. Chem. (2007) 282 (3), 1709-1717), and Dall' Acqua et al. (J. Immunol. (2002) 169 (9), 5171-5180), IgG1 antibody variants whose binding to human FcRn under an acidic condition (pH 6.0) is improved by introducing an amino acid substitution is also observed to bind to human FcRn under a neutral condition (pH 7.4). Reportedly, the plasma retention of said antibody administered to a cynomolgus monkey was not improved, showing no change in the plasma retention. Thus, in antibody engineering technology for improving antibody functions, efforts have been made to improve the plasma retention of antibody by increasing its binding to human FcRn under acidic conditions without increasing its binding to human FcRn under a neutral condition (pH 7.4). In other words, no report has been published on the advantages of IgG1 antibodies whose binding to human FcRn under a neutral condition (pH 7.4) is increased by introducing amino acid substitutions into the Fc region.

Antibodies that bind to an antigen in a Ca-dependent manner are extremely useful, because they have an effect of accelerating the disappearance of soluble antigen and the repeated binding of a single antibody molecule to soluble antigen. A method of enhancing binding to FcRn under a neutral condition (pH 7.4) was examined as a method to further improve the accelerating effect on antigen disappearance.

(13-2) Preparation of Ca-dependent Human IL-6 Receptor-binding Antibodies having FcRn-binding Ability under Neutral Conditions An amino acid mutation was introduced into the Fc regions of FH4-IgG1 and 6RL#9-IgG1 having a calcium-dependent antigen-binding ability and H54/L28-IgG1 having no calcium-dependent antigen-binding ability (used as a control) to prepare variants having an FcRn-binding ability under a neutral condition (pH 7.4). The amino acid mutation was introduced by a method known in the art using PCR. Specifically, FH4-N434W (heavy chain SEQ ID NO: 110, light chain SEQ ID NO: 95), 6RL#9-N434W (heavy chain SEQ ID NO: 111, light chain SEQ ID NO: 93), and H54/L28-N434W (heavy chain SEQ ID NO: 112, light chain SEQ ID NO: 97) with Asn (an amino acid at position 434 represented by the EU numbering) substituted by Trp in the heavy chain constant region of IgG1 were prepared. An animal cell expression vector into which a polynucleotide encoding a variant with the amino acid substitution was inserted was prepared using the QuikChange Site-Directed Mutagenesis Kit (Stratagene) by the method described in the accompanying instructions. Antibody expression and purification, and concentration measurement were conducted according to the method described in Reference Example 6.

Reference Example 14

Examination of the Effect of Accelerating Disappearance of Ca-dependent Binding Antibodies Using Normal Mice (14-1) In Vivo Test Using Normal Mice To a normal mouse (C57BL/6J mouse, Charles River Japan), hsIL-6R (soluble human IL-6 receptor prepared in Reference Example 3) alone was administered, or soluble human IL-6 receptor and anti-human IL-6 receptor antibody were administered simultaneously to examine the kinetics of the soluble human IL-6 receptor and anti-human IL-6 receptor antibody in vivo. A single dose (10 mL/kg) of soluble human IL-6 receptor solution (5 µg/mL) or a mixture of soluble human IL-6 receptor and anti-human IL-6 receptor antibody was administered into the caudal vein. The above H54/L28-N434W, 6RL#9-N434W, and FH4-N434W were used as anti-human IL-6 receptor antibodies.

The concentration of soluble human IL-6 receptor in all the mixtures is 5 μg/mL. The concentrations of anti-human IL-6 receptor antibody vary with the antibodies: prepared at 0.042 mg/mL for H54/L28-N434W, 0.55 mg/mL for 6RL#9-N434W, and 1 mg/mL for FH4-N434W. At this time, it was thought that most of the soluble human IL-6 receptors bind to the antibody because the anti-human IL-6 receptor antibody against soluble human IL-6 receptor exists in a sufficient or excessive amount. Blood samples were collected at 15 minutes, 7 hours and 1, 2, 4, 7, 14, 21, and 28 days after the administration. The blood samples were immediately centrifuged for 15 minutes at 4° C. and 12,000 rpm to separate plasma. The separated plasma was stored in a freezer set to −20° C. or lower until the time of measurement.

Figure 44:
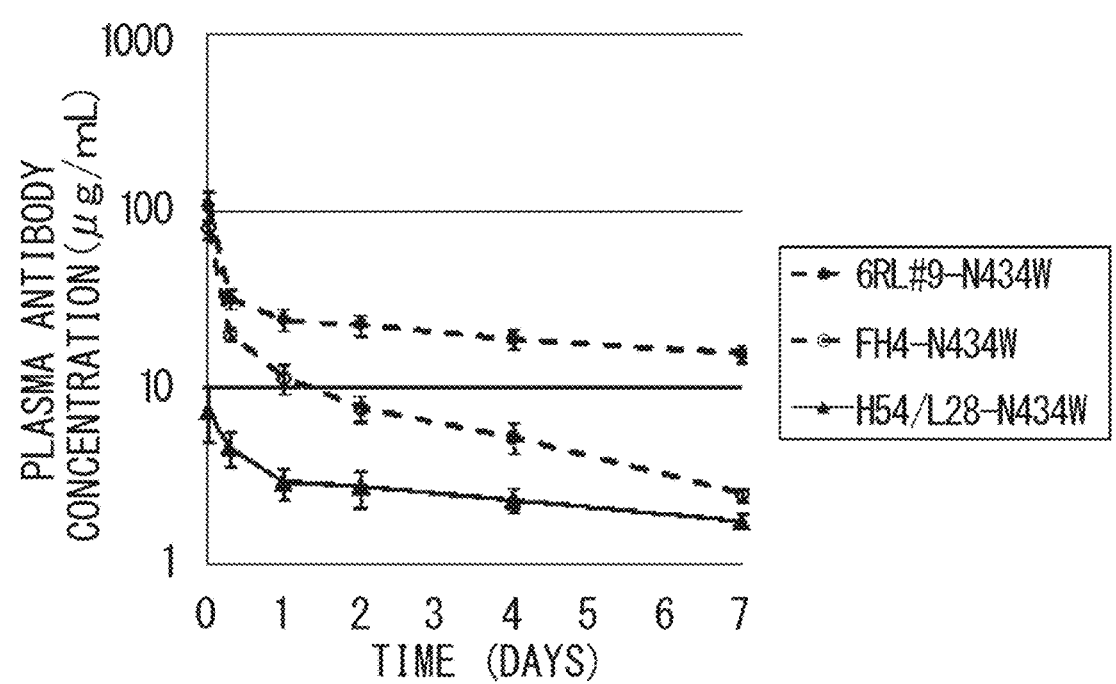
FIG. 44 is a graph showing a time course of the plasma antibody concentrations of H54/L28-N434W, 6RL#9-N434W, and FH4-N434W in normal mice.

(14-2) Determination of Plasma Anti-human IL-6 Receptor Antibody Concentration in Normal Mice by ELISA The plasma concentration of anti-human IL-6 receptor antibody in a mouse was determined by ELISA as described in Reference Example 12. Changes in the plasma concentrations of antibodies, H54/L28-N434W, 6RL#9-N434W, and FH4-N434W, in the normal mice after intravenous administration measured as described above are shown in FIG. 44.

Figure 45:
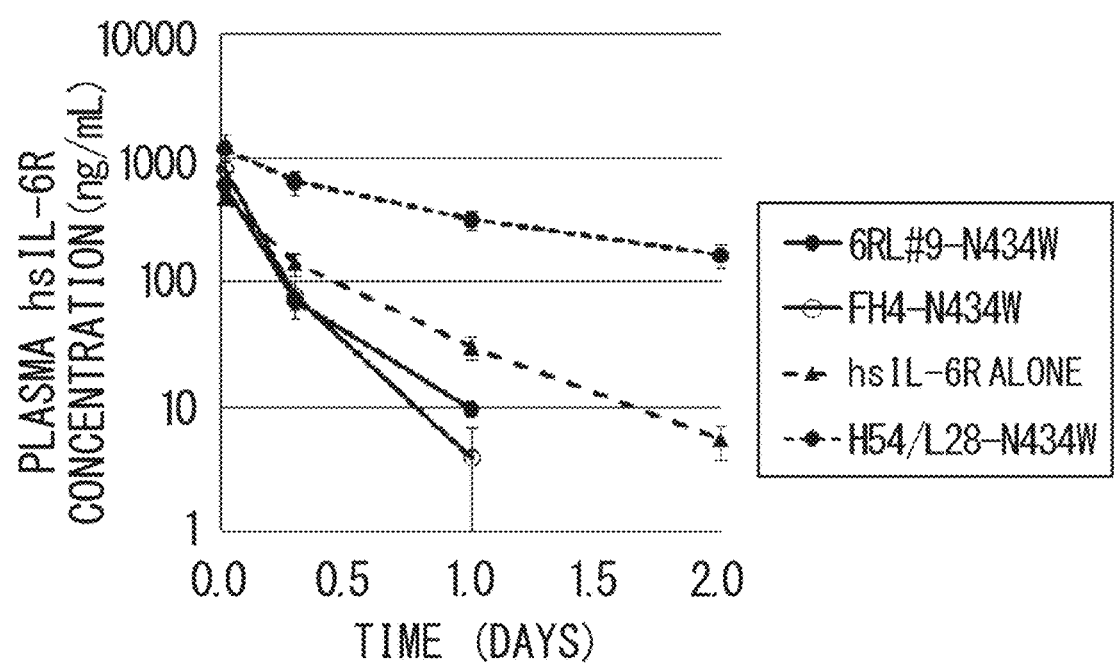
FIG. 45 is a graph showing a time course of plasma soluble human IL-6 receptor concentration in normal mice administered with H54/L28-N434W, 6RL#9-N434W, or FH4-N434W.

(14-3) Determination of Plasma Soluble Human IL-6 Receptor Concentration by an Electrochemiluminescence Method The plasma concentration of soluble human IL-6 receptor in a mouse was determined by an electrochemiluminescence method. A soluble human IL-6 receptor calibration curve sample prepared at 2,000, 1,000, 500, 250, 125, 62.5, or 31.25 pg/mL, and a mouse plasma measurement sample diluted by 50-fold or above, were mixed with a monoclonal anti-human IL-6R antibody (R&D) ruthenated with SULFO-TAG NHS Ester (Meso Scale Discovery) and a biotinylated anti-human IL-6 R antibody (R&D), followed by overnight reaction at 4° C. At that time, the assay buffer contained 10 mM EDTA to reduce the free Ca concentration in the sample and dissociate almost all soluble human IL-6 receptors in the sample from 6RL#9-N434W or FH4-N434W to exist in a free state. Subsequently, said reaction liquid was dispensed into an MA400 PR Streptavidin Plate (Meso Scale Discovery). In addition, after washing each well of the plate that was allowed to react for 1 hour at 25° C., Read Buffer T (×4) (Meso Scale Discovery) was dispensed into each well. Immediately, the reaction liquid was subjected to measurement using a SECTOR PR 400 reader (Meso Scale Discovery). The concentration of soluble human IL-6 receptor was calculated from the response of the calibration curve using the SOFTmax PRO analysis software (Molecular Devices). Changes in the plasma concentration of soluble human IL-6 receptor in the normal mouse after intravenous administration determined as described above are shown in FIG. 45.

As a result, in comparison with the administration of soluble human IL-6 receptor alone, simultaneous administration of soluble human IL-6 receptor with the H54/L28-N434W antibody which has FcRn-binding activity at pH 7.4 and does not have Ca-dependent binding activity to soluble human IL-6 receptor had a significantly delayed disappearance of soluble human IL-6 receptor. In contrast, the disappearance of soluble human IL-6 receptor was accelerated when soluble human IL-6 receptor was administered simultaneously with the 6RL#9-N434W or FH4-N434W antibody which has 100-fold or higher Ca-dependent binding ability to soluble human IL-6 receptor and FcRn-binding activity at pH 7.4, as compared with the administration of soluble human IL-6 receptor alone. The plasma concentrations of soluble human IL-6 receptor one day after soluble human IL-6 receptor was administered simultaneously with the 6RL#9-N434W or FH4-N434W antibody were reduced 3-fold and 8-fold, respectively, as compared with the administration of soluble human IL-6 receptor alone. As a result, it was confirmed that the disappearance of antigen from plasma could be further accelerated by imparting FcRn-binding activity at pH 7.4 to an antibody that binds to antigen in a calcium-dependent manner.

The 6RL#9-IgG1 or FH4-IgG1 antibody having 100-fold or higher Ca-dependent binding activity to soluble human IL-6 receptor was confirmed to increase the disappearance of soluble human IL-6 receptor, as compared with the H54/L28-IgG1 antibody having no Ca-dependent binding activity to soluble human IL-6 receptor. The 6RL#9-N434W or FH4-N434W antibody which has 100-fold or higher Ca-dependent binding activity to soluble human IL-6 receptor and FcRn-binding activity at pH 7.4 was confirmed to more strongly accelerate the disappearance of soluble human IL-6 receptor, as compared with the administration of soluble human IL-6 receptor alone. These data suggest that an antibody that binds to an antigen in a Ca-dependent manner dissociates from antigen in the endosome, similarly to an antibody that binds to antigen in a pH-dependent manner.

Reference Example 15

Exploration of Human Germline Sequences that Bind to Calcium Ion (15-1) Antibody that Binds to Antigen in a Calcium-dependent Manner Antibodies that bind to an antigen in a Ca-dependent manner (Ca-dependent antigen-binding antibodies) are those whose interactions with antigen change with calcium concentration. A Ca-dependent antigen-binding antibody is thought to bind to an antigen through calcium ion. Thus, amino acids that form an epitope on the antigen side are negatively charged amino acids that can chelate calcium ions or amino acids that can be a hydrogen-bond acceptor. These properties of amino acids that form an epitope allows targeting of an epitope other than binding molecules, which are generated by introducing histidines and bind to an antigen in a pH-dependent manner. The use of antigen-binding molecules having calcium- and pH-dependent antigen-binding properties is thought to allow the formation of antigen-binding molecules that can individually target various epitopes having broad properties. Thus, if a population of molecules containing a calcium-binding motif (Ca library) is constructed, from which antigen-binding molecules are obtained, Ca-dependent antigen-binding antibodies are thought to be effectively obtained.

(15-2) Acquisition of Human Germline Sequences

An example of the population of molecules containing a calcium-binding motif is an example in which said molecules are antibodies. In other words, an antibody library containing a calcium-binding motif may be a Ca library.

Calcium ion-binding antibodies containing human germline sequences have not been reported. Thus, the germline sequences of antibodies having human germline sequences were cloned using as a template cDNA prepared from Human Fetal Spleen Poly RNA (Clontech) to assess whether antibodies having human germline sequences bind to calcium ion. Cloned DNA fragments were inserted into animal cell expression vectors. The nucleotide sequences of the constructed expression vectors were determined by a method known to those skilled in the art. The SEQ IDs are shown in Table 34. By PCR, polynucleotides encoding SEQ ID NO: 5 (Vk1), SEQ ID NO: 6 (Vk2), SEQ ID NO: 7 (Vk3), SEQ ID NO: 8 (Vk4), and SEQ ID NO: 4 (Vk5) were linked to a polynucleotide encoding the natural Kappa chain constant region (SEQ ID NO: 100). The linked DNA fragments were inserted into animal cell expression vectors. Furthermore, polynucleotides encoding SEQ ID NO: 113 (Vk1), SEQ ID NO: 114 (Vk2), SEQ ID NO: 115 (Vk3), SEQ ID NO: 116 (Vk4), and SEQ ID NO: 117 (Vk5) were linked by PCR to a polynucleotide encoding a polypeptide (SEQ ID NO: 11) having a deletion of two amino acids at the C terminus of IgG1. The resulting DNA fragments were inserted into animal cell expression vectors. The sequences of the constructed variants were confirmed by a method known to those skilled in the art.

TABLE 34

| LIGHT CHAIN GERMLINE SEQUENCE | HEAVY CHAIN (VARIABLE REGION) SEQ ID NO | LIGHT CHAIN VARIABLE REGION SEQ ID NO |
|---|---|---|
| Vk1 | 113 | 5 |
| Vk2 | 114 | 6 |
| Vk3 | 115 | 7 |
| Vk4 | 116 | 8 |
| Vk5 | 117 | 4 |

(15-3) Expression and Purification of Antibodies

The constructed animal cell expression vectors inserted with the DNA fragments having the five types of human germ-line sequences were introduced into animal cells. Antibody expression was carried out by the following method. Cells of human fetal kidney cell-derived FreeStyle 293-F (Invitrogen) were suspended in the FreeStyle 293 Expression Medium (Invitrogen), and plated at a cell density of $1.33 \times 10^6$ cells/ml (3 ml) into each well of a 6-well plate. The prepared plasmids were introduced into cells by a lipofection method. The cells were cultured for four days in a $CO_2$ incubator (37° C., 8% $CO_2$, 90 rpm). From the culture supernatants prepared as described above, antibodies were purified using the rProtein A Sepharose™ Fast Flow (Amersham Biosciences) by a method known to those skilled in the art. Absorbance at 280 nm of the purified antibody solutions was measured using a spectrophotometer. Antibody concentrations were calculated from the determined values using an extinction coefficient calculated by the PACE method (Protein Science (1995) 4: 2411-2423).

(15-4) Assessment of Antibodies Having Human Germ-line Sequences for their Calcium Ion-binding Activity The purified antibodies were assessed for their calcium ion-binding activity. The intermediate temperature of thermal denaturation (Tm value) was measured by differential scanning calorimetry (DSC) as an indicator for examining calcium ion binding to the antibody (MicroCal VP-Capillary DSC, MicroCal). The intermediate temperature of thermal denaturation (Tm value) is an indicator of stability. It becomes higher when a protein is stabilized through calcium ion binding, as compared with the case where no calcium ion is bound (J. Biol. Chem. (2008) 283, 37, 25140-25149). The binding activity of calcium ion to antibody was evaluated by examining changes in the Tm value of the antibody depending on the changes in the calcium ion concentration in the antibody solution. The purified antibody was subjected to dialysis (EasySEP, TOMY) using an external solution of 20 mM Tris-HCl, 150 mM NaCl, and 2 mM $CaCl_2$ (pH 7.4) or 20 mM Tris-HCl, 150 mM NaCl, and 3 µM $CaCl_2$ (pH 7.4). DSC measurement was conducted at a heating rate of 240° C./hr from 20 to 115° C. using as a test substance an antibody solution prepared at about 0.1 mg/mL with the dialysate. The intermediate temperatures of thermal denaturation (Tm values) of the Fab domains of each antibody, calculated from the denaturation curve obtained by DSC, are shown in Table 35.

TABLE 35

| LIGHT CHAIN GERMLINE SEQUENCE | CALCIUM ION CONCENTRATION | | ΔTm (° C.) |
|---|---|---|---|
| | 3 µM | 2 mM | 2 mM − 3 µM |
| Vk1 | 80.32 | 80.78 | 0.46 |
| Vk2 | 80.67 | 80.61 | −0.06 |
| Vk3 | 81.64 | 81.36 | −0.28 |
| Vk4 | 70.74 | 70.74 | 0 |
| Vk5 | 71.52 | 74.17 | 2.65 |

The result showed that the Tm values of the Fab domains of antibodies having the Vk1, Vk2, Vk3, or Vk4 sequence did not vary depending on the calcium ion concentration in the Fab domain-containing solutions. Meanwhile, the Tm value for the antibody Fab domain having the Vk5 sequence varied depending on the calcium ion concentration in the Fab domain-containing solution. This demonstrates that the Vk5 sequence binds to calcium ion.

Reference Example 16

Assessment of the Human Vk5 (Hvk5) Sequence (16-1) hVk5 Sequence

The only hVk5 sequence registered in Kabat's database is hVk5-2 sequence. Hereinafter, hVk5 and hVk5-2 are used synonymously. WO2010/136598 discloses that the abundance ratio of the hVk5-2 sequence in the germline sequence is 0.4%. Other reports have been also made in which the abundance ratio of the hVk5-2 sequence in the germline sequence is 0-0.06% (J. Mol. Biol. (2000) 296, 57-86; Proc. Natl. Acad. Sci. (2009) 106, 48, 20216-20221). As described above, since the hVk5-2 sequence is a sequence of low appearance frequency in the germline sequence, it was thought to be inefficient to obtain a calcium-binding antibody from an antibody library consisting of human germline sequences or B cells obtained by immunizing a mouse expressing human antibodies. Thus, it was considered possible to design a Ca library containing a human hVk5-2 sequence. However, realization of the possibility is unknown because no report has been published on the physical properties of the hVk5-2 sequence.

(16-2) Construction, Expression, and Purification of a Non-glycosylated Form of the hVk5-2 Sequence The hVk5-2 sequence has a sequence for N glycosylation at position 20 amino acid (Kabat's numbering). Sugar chains attached to proteins exhibit heterogeneity. Thus, it is desirable to lose the glycosylation from the viewpoint of substance homogeneity. In this context, variant hVk5-2_L65 (SEQ ID NO: 118) in which the Asn (N) residue at position 20 (Kabat's numbering) is substituted with Thr (T) was constructed. Amino acid substitution was carried out by a method known to those skilled in the art using the QuikChange Site-Directed Mutagenesis Kit (Stratagene). A DNA encoding the variant hVk5-2_L65 was inserted into an animal expression vector. The animal expression vector inserted with the constructed DNA encoding variant hVk5-2_L65, in combination with an animal expression vector having an insert to express CIM_H (SEQ ID NO: 117) as a heavy chain, was introduced into animal cells by the method described in Reference Example 6. The antibody comprising hVk5-2_L65 and CIM_H, which was expressed in animal cells introduced with the vectors, was purified by the method described in Reference Example 6.

Figure 46:
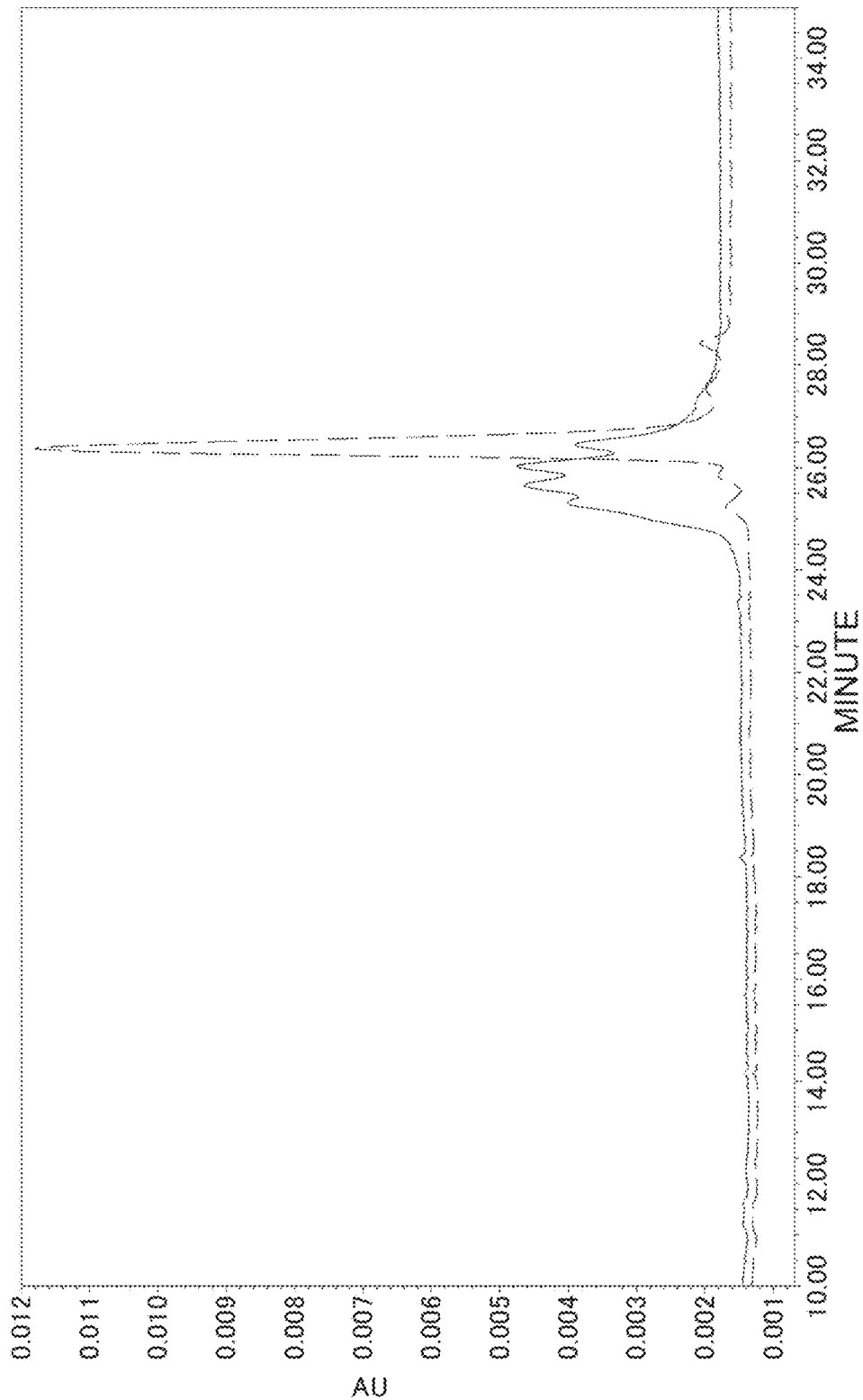
FIG. 46 is an ion-exchange chromatogram for an antibody comprising a human Vk5-2 sequence and an antibody comprising an h Vk5-2_L65 sequence which has a modified glycosylation sequence of the human Vk5-2 sequence. The solid line represents a chromatogram for the antibody comprising the human Vk5-2 sequence (heavy chain: CIM_H, SEQ ID NO: 108; and light chain: hVk5-2, SEQ ID NO: 4). The broken line represents a chromatogram for the antibody comprising the hVk5-2_L65 sequence (heavy chain: CIM_H (SEQ ID NO: 108); and light chain: hVk5-2_L65 (SEQ ID NO: 107)).

(16-3) Assessment of the Antibody having the Non-glycosylated hVk5-2 Sequence for Physical Properties The isolated antibody having the modified sequence hVk5-2_L65 was analyzed by ion-exchange chromatography to test whether it is less heterogeneous than the antibody having the original sequence hVk5-2 before modification. The procedure of ion-exchange chromatography is shown in Table 36. The analysis result showed that hVk5-2_L65 modified at the glycosylation site was less heterogeneous than the original sequence hVk5-2, as shown in FIG. 46.

TABLE 36

| | CONDITION |
|---|---|
| COLUMN | TOSOH TSKgel DEAE-NPR |
| MOBILE PHASE | A; 10 mM Tris-HCl, 3 µM CaCl$_2$(pH 8.0) B; 10 mM Tris-HCl, 500 mM NaCl, 3 µM CaCl$_2$ (pH 8.0) |
| GRADIENT SCHEDULE | % B = 0-(5 min)-0-2%/1 min |
| COLUMN TEMPERATURE | 40° C. |
| DETECTION | 280 nm |
| INJECTION VOLUME | 100 µL (5 µg) |

Next, whether the less-heterogeneous hVk5-2_L65 sequence-comprising antibody binds to calcium ion was assessed by the method described in Reference Example 15. The result showed that the Tm value for the Fab domain of the antibody having hVk5-2_L65 with altered glycosylation site also varied depending on the calcium ion concentration in the antibody solutions, as shown in Table 37. Specifically, it was demonstrated that the Fab domain of the antibody having hVk5-2_L65 with altered glycosylation site binds to calcium ion.

TABLE 37

| LIGHT CHAIN | GLYCO-SYLATED SEQUENCE | CALCIUM ION CONCENTRATION | | ΔTm (° C.) 2 mM – 3 µM |
|---|---|---|---|---|
| | | 3 µM | 2 mM | |
| hVk5-2 | YES | 71.52 | 74.17 | 2.65 |
| hVk5-2_L65 | NO | 71.51 | 73.66 | 2.15 |

Reference Example 17

Assessment of the Calcium Ion-binding Activity of Antibody Molecules having Cdr Sequence of the Hvk5-2 Sequence (17-1) Construction, Expression, and Purification of Modified Antibodies Having a CDR Sequence from the hVk5-2 Sequence The hVk5-2_L65 sequence is a sequence with altered amino acids at a glycosylation site in the framework of human Vk5-2 sequence. As described in Reference Example 16, it was demonstrated that calcium ion bound even after alteration of the glycosylation site. Meanwhile, from the viewpoint of immunogenicity, it is generally desirable that the framework sequence is a germ-line sequence. Thus, the present inventors assessed whether an antibody framework sequence could be substituted with the framework sequence of a non-glycosylated germline sequence while maintaining the calcium ion-binding activity of the antibody.

Polynucleotides encoding chemically synthesized sequences which comprise an altered framework sequence of the hVk5-2 sequence, hVk1, hVk2, hVk3, or hVk4 (CaVk1 (SEQ ID NO: 119), CaVk2 (SEQ ID NO: 120), CaVk3 (SEQ ID NO: 121), or CaVk4 (SEQ ID NO: 122), respectively) were linked by PCR to a polynucleotide encoding the constant region (SEQ ID NO: 100) of the natural Kappa chain. The linked DNA fragments were inserted into animal cell expression vectors. Sequences of the constructed variants were confirmed by a method known to those skilled in the art. Each plasmid constructed as described above was introduced into animal cells in combination with a plasmid inserted with a polynucleotide encoding heavy chain CIM_H (SEQ ID NO: 117) by the method described in Reference Example 6. The expressed antibody molecules of interest were purified from culture media of the animal cells introduced with the plasmids.

(17-2) Assessment of Altered Antibodies having the CDR Sequence of the hVk5-2 Sequence for their Calcium Ion-binding Activity Whether calcium ion binds to altered antibodies having the CDR sequence of the hVk5-2 sequence and the framework sequences of germline sequences other than hVk5-2 (hVk1, hVk2, hVk3, and hVk4) was assessed by the method described in Example 6. The assessment result is shown in Table 38. The Tm value of the Fab domain of each altered antibody was revealed to vary depending on the calcium ion concentration in the antibody solutions. This demonstrates that antibodies having a framework sequence other than the framework sequences of the hVk5-2 sequence also bind to calcium ion.

TABLE 38

| GERMLINE (LIGHT CHAIN FRAMEWORK SEQUENCE) | CALCIUM ION CONCENTRATION | | ΔTm (° C.) |
|---|---|---|---|
| | 3 µM | 2 mM | 2 mM – 3 µM |
| hVk1 | 77.51 | 79.79 | 2.28 |
| hVk2 | 78.46 | 80.37 | 1.91 |
| hVk3 | 77.27 | 79.54 | 2.27 |
| hVk4 | 80.35 | 81.38 | 1.03 |
| hVk5-2 | 71.52 | 74.17 | 2.65 |

The thermal denaturation temperature (Tm value), as an indicator of thermal stability, of the Fab domain of each antibody altered to have the CDR sequence of the hVk5-2 sequence and the framework sequence of a germ-line sequence other than the hVk5-2 sequence (hVk1, hVk2, hVk3, or hVk4) was demonstrated to be greater than that of the Fab domain of the original antibody having the hVk5-2 sequence. This result shows that antibodies having the CDR sequence of the hVk5-2 sequence and the framework sequence of hVk1, hVk2, hVk3, or hVk4 not only have calcium ion-binding activity but also are excellent molecules from the viewpoint of thermal stability.

Reference Example 18

Identification of the Calcium Ion-binding Site in Human Germline Hvk5-2 Sequence (18-1) Design of Mutation Site in the CDR Sequence of the hVk5-2 Sequence As described in Reference Example 17, antibodies having the light chain resulting from introduction of the CDR domain of the hVk5-2 sequence into the framework sequence of a different germline sequence were also demonstrated to bind to calcium ion. This result suggests that in hVk5-2 a calcium ion-binding site is localized within its CDR. Amino acids that bind to calcium ion, i.e., chelate calcium ion, include negatively charged amino acids and amino acids that can be a hydrogen bond acceptor. Thus, it was tested whether antibodies having a mutant hVk5-2 sequence with a substitution of an Ala (A) residue for an Asp (D) or Glu (E) residue in the CDR sequence of the hVk5-2 sequence bind to calcium ion.

(18-2) Construction of Variant hVk5-2 Sequences with Ala Substitution, and Expression and Purification of Antibodies Antibody molecules were prepared to comprise a light chain with substitution of an Ala residue for Asp and/or Glu residue in the CDR sequence of the hVk5-2 sequence. As described in Reference Example 16, non-glycosylated variant hVk5-2_L65 exhibited calcium ion binding and was assumed to be equivalent to the hVk5-2 sequence in terms of calcium ion binding. In this Example, amino acid substitutions were introduced into hVk5-2_L65 as a template sequence. Constructed variants are shown in Table 39. Amino acid substitutions were carried out by methods known to those skilled in the art such as using the QuikChange Site-Directed Mutagenesis Kit (Stratagene), PCR, or the In fusion Advantage PCR Cloning Kit (TAKARA) to construct expression vectors for altered light chains having an amino acid substitution.

TABLE 39

| LIGHT CHAIN VARIANT NAME | ALTERED POSITION (Kabat NUMBERING) | SEQ ID NO |
|---|---|---|
| hVk5-2_L65 | WILD TYPE | 118 |
| hVk5-2_L66 | 30 | 123 |
| hVk5-2_L67 | 31 | 124 |
| hVk5-2_L68 | 32 | 125 |
| hVk5-2_L69 | 50 | 126 |
| hVk5-2_L70 | 30, 32 | 127 |
| hVk5-2_L71 | 30, 50 | 128 |
| hVk5-2_L72 | 30, 32, 50 | 129 |
| hVk5-2_L73 | 92 | 130 |

Nucleotide sequences of the constructed expression vectors were confirmed by a method known to those skilled in the art. The expression vectors constructed for the altered light chains were transiently introduced, in combination with an expression vector for the heavy chain CIM_H (SEQ ID NO: 117), into cells of the human fetal kidney cell-derived HEK293H line (Invitrogen) or FreeStyle293 (Invitrogen) to express antibodies. From the obtained culture supernatants, antibodies were purified using the rProtein A Sepharose™ Fast Flow (GE Healthcare) by a method known to those skilled in the art. Absorbance at 280 nm of the purified antibody solutions was measured using a spectrophotometer. Antibody concentrations were calculated from the determined values using an extinction coefficient calculated by the PACE method (Protein Science (1995) 4: 2411-2423).

(18-3) Assessment of the Calcium Ion-binding Activity of Antibodies having an Ala Substitution in the hVk5-2 Sequence Whether the obtained purified antibodies bind to calcium ion was tested by the method described in Reference Example 15. The result is shown in Table 40. Some antibodies having substitution of an Asp or Glu residue in the CDR sequence of the hVk5-2 sequence with an Ala residue which cannot be involved in calcium ion binding or chelation were revealed to have an Fab domain whose Tm did not vary by the calcium ion concentration in the antibody solutions. The substitution sites at which Ala substitution did not alter the Tm (positions 32 and 92 (Kabat's numbering)) were demonstrated to be greatly important for the calcium ion-antibody binding.

TABLE 40

| LIGHT CHAIN VARIANT NAME | ALTERED POSITION (Kabat's NUMBERING) | CALCIUM ION CONCENTRATION | | $\Delta$Tm (° C.) 2 mM − |
|---|---|---|---|---|
| | | 0 µM | 2 mM | 0 µM |
| hVk5-2_L65 | WILDTYPE | 71.71 | 73.69 | 1.98 |
| hVk5-2_L66 | 30 | 71.65 | 72.83 | 1.18 |
| hVk5-2_L67 | 31 | 71.52 | 73.30 | 1.78 |
| hVk5-2_L68 | 32 | 73.25 | 74.03 | 0.78 |
| hVk5-2_L69 | 50 | 72.00 | 73.97 | 1.97 |
| hVk5-2_L70 | 30, 32 | 73.42 | 73.60 | 0.18 |
| hVk5-2_L71 | 30, 50 | 71.84 | 72.57 | 0.73 |
| hVk5-2_L72 | 30, 32, 50 | 75.04 | 75,17 | 0.13 |
| hVk5-2_L73 | 92 | 75.23 | 75.04 | −0.19 |

Reference Example 19

Assessment of the Calcium Ion-binding Activity of Antibodies having Hvk1 Sequence with Calcium Ion-binding Motif (19-1) Construction of an hVk1 Sequence with Calcium Ion-binding Motif, and Expression and Purification of Antibodies The result described in Reference Example 18 on the calcium-binding activity of the Ala substitute demonstrates that Asp or Glu residues in the CDR sequence of the hVk5-2 sequence were important for calcium binding. Thus, the present inventors assessed whether an antibody can bind to calcium ion when the residues at positions 30, 31, 32, 50, and 92 (Kabat's numbering) alone were introduced into a different germline variable region sequence. Specifically, variant LfVk1_Ca (SEQ ID NO: 131) was constructed by substituting the residues at positions 30, 31, 32, 50, and 92 (Kabat's numbering) in the hVk5-2 sequence for the residues at positions 30, 31, 32, 50, and 92 (Kabat's numbering) in the hVk1 sequence (a human germline sequence). Specifically, it was tested whether antibodies having an hVk1 sequence introduced with only 5 residues from the hVk5-2 sequence can bind to calcium. The variants were produced by the same method as described in Reference Example 17. The resulting light chain variant LfVk1_Ca and LfVk1 having the light-chain hVk1 sequence (SEQ ID NO: 132) were co-expressed with the heavy chain CIM_H (SEQ ID NO: 117). Antibodies were expressed and purified by the same method as described in Reference Example 18.

(19-2) Assessment of the Calcium Ion-binding Activity of Antibodies having a Human hVk1 Sequence with Calcium Ion-binding Motif Whether the purified antibody prepared as described above binds to calcium ion was assessed by the method described in Reference Example 15. The result is shown in Table 41. The Tm value of the Fab domain of the antibody having LfVk1 with an hVk1 sequence did not vary depending on the calcium concentration in the antibody solutions. Meanwhile, Tm of the antibody having the LfVk1_Ca sequence was shifted by 1° C. or more upon change in the calcium concentration in the antibody solutions. Thus, it was shown that the antibody having LfVk1_Ca binds to calcium. The result described above demonstrates that the entire CDR sequence of hVk5-2 is not required, while the residues introduced for construction of the LfVk1_Ca sequence alone are sufficient for calcium ion binding.

TABLE 41

| LIGHT CHAIN VARIANT | CALCIUM ION CONCENTRATION | | ΔTm (° C.) |
| --- | --- | --- | --- |
| | 3 μM | 2 mM | 2 mM − 3 μM |
| LfVk1 | 83.18 | 83.81 | 0.63 |
| LfVk1_Ca | 79.83 | 82.24 | 2.41 |

Reference Example 20

Design of a Population of Antibody Molecules (Ca Library) with a Calcium Ion-binding Motif Introduced into the Variable Region to Effectively Obtain Binding Antibodies that Bind to Antigen in a Ca Concentration-dependent Manner Preferred calcium-binding motifs include, for example, the hVk5-2 sequence and the CDR sequence, as well as residues at positions 30, 31, 32, 50, and 92 (Kabat numbering). Other calcium binding motifs include the EF-hand motif possessed by calcium-binding proteins (e.g., calmodulin) and C-type lectin (e.g., ASGPR).

The Ca library consists of heavy and light chain variable regions. A human antibody sequence was used for the heavy chain variable region, and a calcium-binding motif was introduced into the light chain variable region. The hVk1 sequence was selected as a template sequence of the light chain variable region for introducing a calcium-binding motif. An antibody containing an LfVk1_Ca sequence obtained by introducing the CDR sequence of hVk5-2 (one of calcium-binding motifs) into the hVk1 sequence was shown to bind to calcium ions, as shown in Reference Example 19. Multiple amino acids were allowed to appear in the template sequence to diversify antigen-binding molecules that constitute the library. Positions exposed on the surface of a variable region which is likely to interact with the antigen were selected as those where multiple amino acids are allowed to appear. Specifically, positions 30, 31, 32, 34, 50, 53, 91, 92, 93, 94, and 96 (Kabat numbering) were selected as flexible residues.

The type and appearance frequency of amino acid residues that were subsequently allowed to appear were determined. The appearance frequency of amino acids in the flexible residues of the hVk1 and hVk3 sequences registered in the Kabat database (KABAT, E. A. ET AL.: 'Sequences of proteins of immunological interest', vol. 91, 1991, NIH PUBLICATION) was analyzed. Based on the analysis results, the type of amino acids that were allowed to appear in the Ca library were selected from those with higher appearance frequency at each position. At this time, amino acids whose appearance frequency was determined to be low based on the analysis results were also selected to avoid the bias of amino acid properties. The appearance frequency of the selected amino acids was determined in reference to the analysis results of the Kabat database.

A Ca library containing a calcium-binding motif with emphasis on the sequence diversity as to contain multiple amino acids at each residue other than the motif were designed as a Ca library in consideration of the amino acids and appearance frequency set as described above. The detailed designs of the Ca library are shown in Tables 1 and 2 (with the positions in each table representing the EU numbering). In addition, if position 92 represented by the Kabat numbering is Asn (N) for the appearance frequencies of amino acids as described in Tables 1 and 2, position 94 may be Leu (L) instead of Ser (S).

Reference Example 21

Ca Library Preparation

Figure 52:
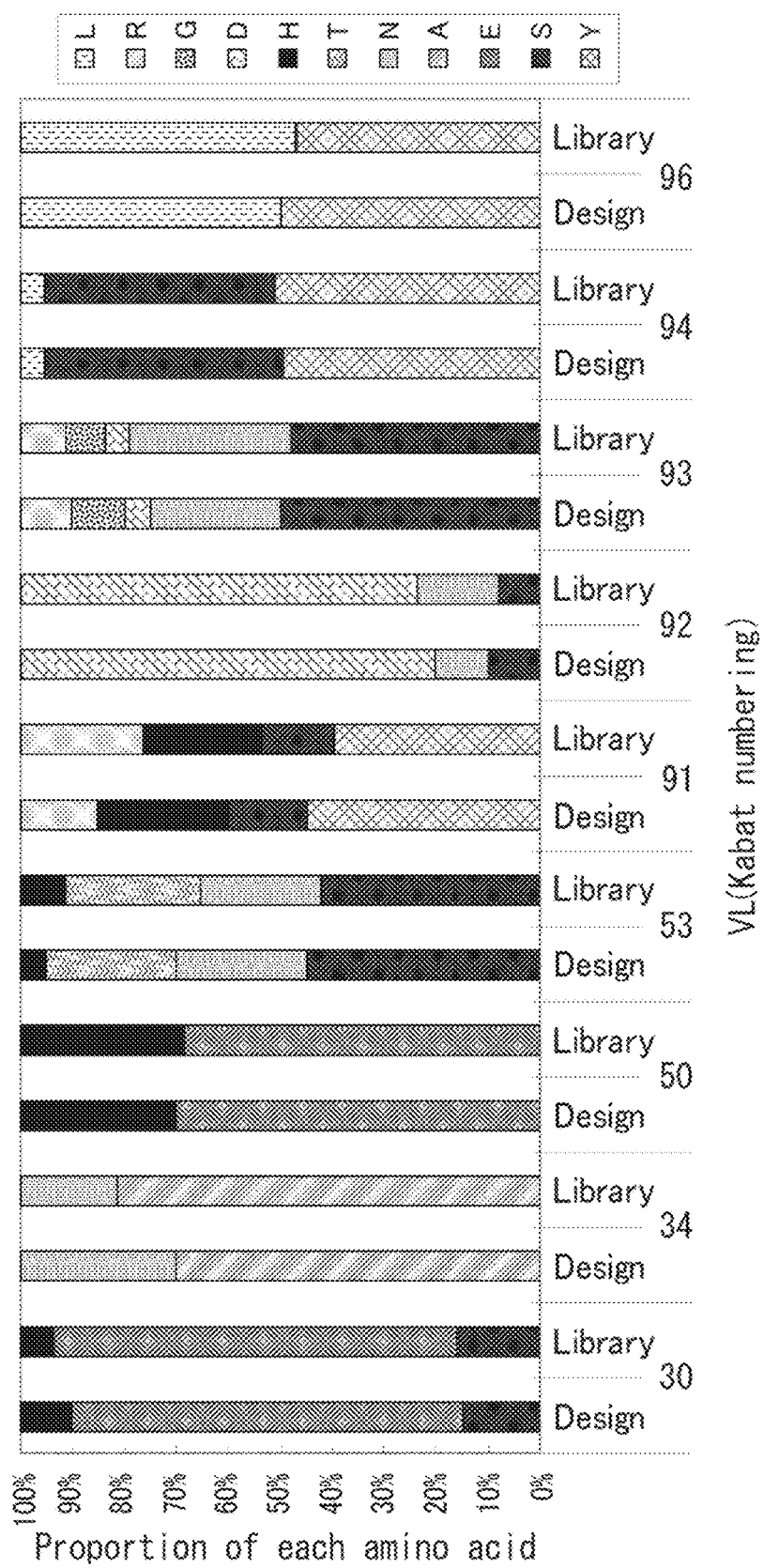
FIG. 52 is a graph showing the relationship of a designed amino acid distribution (indicated as Design) to the amino acid distribution (indicated as Library) for the sequence information on 290 clones isolated from E. coli introduced with a gene library of antibodies that bind to antigens in a Ca-dependent manner. The horizontal axis indicates amino acid positions in the Kabat numbering system. The vertical axis indicates % amino acid distribution.

A gene library of antibody heavy-chain variable regions was amplified by PCR using a poly A RNA prepared from human PBMC, and commercial human poly A RNA, etc. as a template. As described in Reference Example 20, for the light chain variable regions of antibody, light chain variable regions that increase appearance frequency of antibodies which maintain a calcium-binding motif and can bind to an antigen in a calcium concentration-dependent manner were designed. In addition, for amino acid residues among the flexible residues other than those with a calcium-binding motif introduced, a library of antibody light chain variable regions with evenly distributed amino acids of high appearance frequency in natural human antibodies was designed with reference to the information of amino acid appearance frequency in natural human antibodies (KABAT, E. A. ET AL.: 'Sequences of proteins of immunological interest', vol. 91, 1991, NIH PUBLICATION). A combination of the gene libraries of antibody heavy-chain and light-chain variable regions generated as described above, was inserted into a phagemid vector to construct a human antibody phage display library that presents Fab domains consisting of human antibody sequences (Methods Mol Biol. (2002) 178, 87-100). For construction of the library, a linker portion connecting the phagemid Fab to the phage pIII protein, and the sequences of a phage display library with a trypsin cleavage sequence inserted between the N2 and CT domains of the helper phage pIII protein gene were used. The sequences of the antibody gene portions isolated from $E.$ $coli$, into which the antibody gene library was introduced, were identified to obtain sequence information for 290 clones. The designed amino acid distribution and the amino acid distribution in the identified sequences are shown in FIG. 52. A library containing various sequences corresponding to the designed amino acid distribution was constructed.

Reference Example 22

Examination of the Calcium Ion-binding Activity of Molecules Contained in the Ca Library (22-1) Calcium Ion-binding Activity of Molecules Contained in the Ca Library As described in Reference Example 14, the hVk5-2 sequence that was demonstrated to bind to calcium ions is a sequence of low appearance frequency in the germline sequence. Thus, it was thought to be inefficient to obtain a calcium-binding antibody from an antibody library consisting of human germline sequences or from B cells obtained by immunizing a mouse expressing human antibodies. As a result, a Ca library was constructed in Reference Example 21. The presence or absence of a clone showing calcium binding to the constructed Ca library was examined.

(22-2) Expression and Purification of Antibodies

Clones included in Ca library were inserted into animal cell expression plasmids. Antibodies were expressed by the following method. Cells of human fetal kidney cell-derived FreeStyle 293-F (Invitrogen) were suspended in FreeStyle 293 Expression Medium (Invitrogen), and plated at a cell density of $1.33 \times 10^6$ cells/ml (3 ml) into each well of a 6-well plate. The prepared plasmids were introduced into cells by a lipofection method. The cells were cultured for four days in a $CO_2$ incubator (37° C., 8% $CO_2$, 90 rpm). From the culture supernatants prepared as described above, antibodies were purified using the rProtein A Sepharose™ Fast Flow (Amersham Biosciences) by a method known to those skilled in the art. Absorbance at 280 nm of purified antibody solutions was measured using a spectrophotometer. Antibody concentrations were calculated from the determined values using an extinction coefficient calculated by the PACE method (Protein Science (1995) 4: 2411-2423).

(22-3) Evaluation of Calcium Ion Binding of the Obtained Antibodies

Whether or not the purified antibody obtained as described above binds to calcium ions was determined by the method described in Reference Example 6. The results are shown in Table 42. The Tm value of the Fab domains of multiple antibodies contained in the Ca library varied with the calcium ion concentration, showing the presence of calcium ion-binding molecules.

TABLE 42

| ANTIBODY | SEQ ID NO | | CALCIUM ION CONCENTRATION | | ΔTm (° C.) 2 mM – 3 μM |
|---|---|---|---|---|---|
| | HEAVY CHAIN | LIGHT CHAIN | 3 μM | 2 mM | |
| Ca_B01 | 133 | 144 | 70.88 | 71.45 | 0.57 |
| Ca_E01 | 134 | 145 | 84.31 | 84.95 | 0.64 |
| Ca_H01 | 135 | 146 | 77.87 | 79.49 | 1.62 |
| Ca_D02 | 136 | 147 | 78.94 | 81.1 | 2.16 |
| Ca_E02 | 137 | 148 | 81.41 | 83.18 | 1.77 |
| Ca_H02 | 138 | 149 | 72.84 | 75.13 | 2.29 |
| Ca_D03 | 139 | 150 | 87.39 | 86.78 | −0.61 |
| Ca_C01 | 140 | 151 | 74.74 | 74.92 | 0.18 |
| Ca_G01 | 141 | 152 | 65.21 | 65.87 | 0.66 |
| Ca_A03 | 142 | 153 | 80.64 | 81.89 | 1.25 |
| Ca_B03 | 143 | 154 | 93.02 | 93.75 | 0.73 |

Reference Example 23

Design of pH-dependent Binding Antibody Library (23-1) Method for Acquiring pH-dependent Binding Antibodies WO2009/125825 discloses a pH-dependent antigen-binding antibody whose properties are changed in neutral and acidic pH regions by introducing a histidine into an antigen-binding molecule. The disclosed pH-dependent binding antibody is obtained by modification to substitute a part of the amino acid sequence of the antigen-binding molecule of interest with a histidine. To obtain a pH-dependent binding antibody more efficiently without preliminarily obtaining the antigen-binding molecule of interest to be modified, one method may be obtaining an antigen-binding molecule that binds to a desired antigen from a population of antigen-binding molecules (referred to as His library) with a histidine introduced into the variable region (more preferably, a region potentially involved in antigen binding). It may be possible to efficiently obtain an antigen-binding molecule having desired properties from a His library, because histidine appears more frequently in antigen-binding molecules from His library than those from conventional antibody libraries.

(23-2) Design of a Population of Antibody Molecules (His Library) with Histidine Residue Introduced into their Variable Region to Effectively Acquire Binding Antibodies that Bind to Antigen in a pH-dependent Manner First, positions for introducing a histidine were selected in a His library. WO2009/125825 discloses generation of pH-dependent antigen-binding antibodies by substituting amino acid residues in the sequences of IL-6 receptor, IL-6, and IL-31 receptor antibodies with a histidine. In addition, anti-egg white lysozyme (FEBS Letter 11483, 309, 1, 85-88) and anti-hepcidin (WO2009/139822) antibodies having a pH-dependent antigen-binding ability were generated by substituting the amino acid sequence of the antigen-binding molecule with histidines. Positions where histidines were introduced in the IL-6 receptor antibody, IL-6 antibody, IL-31 receptor antibody, egg white lysozyme antibody, and hepcidin antibody are shown in Table 43. Positions shown in Table 43 may be listed as candidate positions that can control the antigen-antibody binding. In addition, besides the position shown in Table 43, positions that are likely to have contact with antigen were also considered to be suitable for introduction of histidines.

TABLE 43

| ANTIBODY | CHAIN | POSITION (Kabat) | | | | | | | | |
|---|---|---|---|---|---|---|---|---|---|---|
| IL-6 RECEPTOR ANTIBODY | H | 27 | 31 | 32 | 35 | 50 | 58 | 62 | 100B | 102 |
| | L | 28 | 31 | 32 | 53 | 56 | 92 | | | |
| IL-6 ANTIBODY | H | 32 | 59 | 61 | 99 | | | | | |
| | L | 53 | 54 | 90 | 94 | | | | | |
| IL-31 RECEPTOR ANTIBODY | H | 33 | | | | | | | | |
| | L | | | | | | | | | |
| EGG-WHILE LYSOZYME ANTIBODY | H | 33 | 98 | | | | | | | |
| | L | 54 | | | | | | | | |
| HEPCIDIN ANTIBODY | H | 52 | 57 | 99 | 107 | | | | | |
| | L | 27 | 89 | | | | | | | |

In the His library consisting of heavy-chain and light-chain variable regions, a human antibody sequence was used for the heavy chain variable region, and histidines were introduced into the light chain variable region. The positions listed above and positions that may be involved in antigen binding, i.e., positions 30, 32, 50, 53, 91, 92, and 93 (Kabat numbering, Kabat E A et al. 1991. Sequence of Proteins of Immunological Interest. NIH) in the light chain were selected as positions for introducing histidines in the His library. In addition, the Vk1 sequence was selected as a template sequence of the light chain variable region for introducing histidines. Multiple amino acids were allowed to appear in the template sequence to diversify antigen-binding molecules that constitute the library. Positions exposed on the surface of a variable region that is likely to interact with the antigen were selected as those where multiple amino acids are allowed to appear. Specifically, positions 30, 31, 32, 34, 50, 53, 91, 92, 93, 94, and 96 of the light chain (Kabat numbering, Kabat E A et al. 1991. Sequence of Proteins of Immunological Interest. NIH) were selected as flexible residues.

The type and appearance frequency of amino acid residues that were subsequently allowed to appear were determined. The appearance frequency of amino acids in the flexible residues in the hVk1 and hVk3 sequences registered in the Kabat database (KABAT, E. A. ET AL.: 'Sequences of proteins of immunological interest', vol. 91, 1991, NIH PUBLICATION) was analyzed. Based on the analysis results, the type of amino acids that were allowed to appear in the His library were selected from those with higher appearance frequency at each position. At this time, amino acids whose appearance frequency was determined to be low based on the analysis results were also selected to avoid the bias of amino acid properties. The appearance frequency of the selected amino acids was determined in reference to the analysis results of the Kabat database.

As His libraries, His library 1 which is fixed to necessarily incorporate a single histidine into each CDR, and His library 2 which is more emphasized on sequence diversity than the His library 1 were designed by taking the amino acids and appearance frequency set as described above into consideration. The detailed designs of His libraries 1 and 2 are shown in Tables 3 and 4 (with the positions in each table representing the Kabat numbering). Ser (S) at position 94 can be excluded if position 92 represented by the Kabat numbering is Asn (N) for the appearance frequency of amino acids as described in Tables 3 and 4.

Reference Example 24

Preparation of a Phage Display Library for Human Antibodies (His Library 1) to Obtain an Antibody that Binds to Antigen in a pH-dependent Manner.

Figure 53:
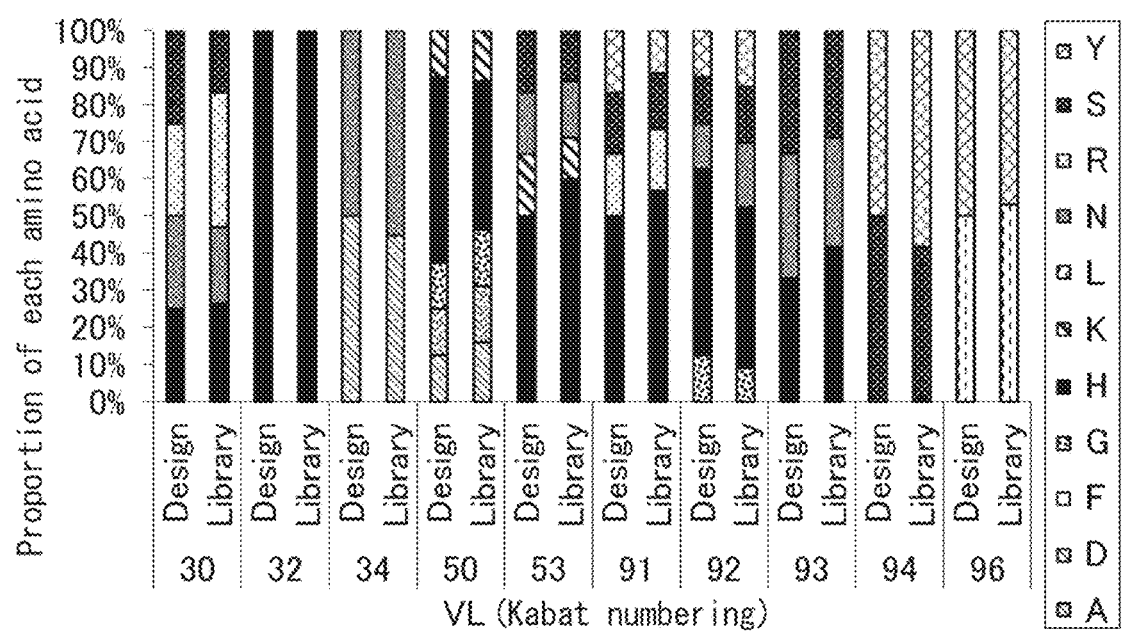
FIG. 53 is a graph showing the relationship of a designed amino acid distribution (indicated as Design) to the amino acid distribution (indicated as Library) for the sequence information on 132 clones isolated from E. coli introduced with a gene library of antibodies that bind to antigens in a pH-dependent manner. The horizontal axis indicates amino acid positions in the Kabat numbering system. The vertical axis indicates % amino acid distribution.

A gene library of antibody heavy-chain variable regions was amplified by PCR using a poly A RNA prepared from human PBMC, and commercial human poly A RNA as a template. A gene library of antibody light-chain variable regions designed as His library 1 as described in Example 1 was amplified using PCR. A combination of the gene libraries of antibody heavy-chain and light-chain variable regions generated as described above was inserted into a phagemid vector to construct a human antibody phage display library which presents Fab domains consisting of human antibody sequences. For the construction method, Methods Mol Biol. (2002) 178, 87-100 was used as a reference. For the construction of the library, a linker region connecting the phagemid Fab to the phage pIII protein, and the sequences of a phage display library with a trypsin cleavage sequence inserted between the N2 and CT domains of the helper phage pIII protein gene were used. Sequences of the antibody gene portions isolated from $E.$ $coli$ into which the antibody gene library was introduced were identified, and sequence information was obtained for 132 clones. The designed amino acid distribution and the amino acid distribution of the identified sequences are shown in FIG. 53. A library containing various sequences corresponding to the designed amino acid distribution was constructed.

Reference Example 25

Preparation of a Human Antibody Phage Display Library (His Library 2) to Obtain Antibodies that Bind to Antigen in a pH-dependent Manner A gene library of antibody heavy-chain variable regions was amplified by PCR using a poly A RNA prepared from human PBMC, and commercial human poly A RNA as a template. As described in Reference Example 23, of the light chain portions of the antibody variable regions, those with increased appearance frequency of histidine residues having a high potential to be an antigen contact region, are designed to increase the appearance frequency of antibodies having a pH-dependent antigen-binding ability. In addition, for amino acid residues other than those with histidines introduced among the flexible residues, a library of antibody light-chain variable regions with evenly distributed amino acids of high appearance frequency identified using the information of amino acid appearance frequency in natural human antibodies is designed. A gene library of antibody light-chain variable regions designed as described above was synthesized. A library can be commercially synthesized on a consignment basis. A combination of the gene libraries of antibody heavy-chain and light-chain variable regions generated as described above was inserted into a phagemid vector to construct a human antibody phage display library which presents Fab domains consisting of human antibody sequences by a known method (Methods Mol Biol. (2002) 178, 87-100). An antibody gene portion isolated from $E.$ $coli$ with an antibody gene library introduced was sequenced as described in Reference Example 24.

Reference Example 26

Effects of Combining Modification of Selective Binding to FcγRIIb with other Fc Region Amino Acid Substitutions An attempt was made to further enhance the selectivity for FcγRIIb by modifying the variant with Pro at position 238 (EU numbering) substituted by Asp which has improved selectivity for FcγRIIb as found in Example 14.

First, with regard to IL6R-G1d-v1 (SEQ ID NO: 80) which is obtained by introducing the modification of substituting Pro at position 238 (EU numbering) of IL6R-G1d with Asp, the variant IL6R-G1d-v4 (SEQ ID NO: 172) in which Leu at position 328 (EU numbering) was substituted by Glu to enhance the selectivity for FcγRIIb as described in Example 14 was prepared. IL6R-G1d-v4 expressed in combination with IL6R-L (SEQ ID NO: 83), which was used as the L chain, was prepared as described in Reference Example 2. An antibody having an amino acid sequence derived from IL6R-G1d-v4 as antibody H chain obtained here is described as IgG1-v4. Binding activities to FcγRIIb of IgG1, IgG1-v1, IgG1-v2, and IgG1-v4, examined as described in Example 14, are shown in Table 44. Modifications in the table represent those introduced into IL6R-G1d.

TABLE 44

| VARIANT | ALTERATION | KD FOR FcγRIIb (mol/L) | RELATIVE KD FOR FcγRIIb (KD FOR IgG1/KD FOR EACH VARIANT) |
|---|---|---|---|
| IgG1 (IL6R-G1d) | — | 5.30E−06 | 1 |
| IgG1-v1 | P238D | 1.10E−06 | 4.8 |
| IgG1-v2 | L328E | 2.30E−06 | 2.3 |
| IgG1-v4 | P238D/L328E | 1.10E−05 | 0.47 |

From the results of Table 44, since L328E improves the FcγRIIb-binding activity by 2.3 fold compared with IgG1, combining it with P238D which similarly improves the FcγRIIb-binding activity by 4.8 fold compared with IgG1 was anticipated to further increase the degree of improvement of FcγRIIb-binding activity; however, in reality, the FcγRIIb-binding activity of the variant containing a combination of these alterations was decreased to 0.47 fold compared with that of IgG1. This result is an effect that could not have been predicted from the respective alterations.

Similarly, into IL6R-G1d-v1 (SEQ ID NO: 80) produced by introducing into IL6R-G1d the alteration produced by substituting Pro at position 238 (indicated by EU numbering) with Asp, the substitutions of Ser at position 267 (indicated by EU numbering) with Glu and of Leu at position 328 (indicated by EU numbering) with Phe as described in Example 14 which improve FcγRIIb-binding activity were introduced, and the IL6R-G1d-v5 variant (SEQ ID NO: 173) was prepared according to the method of Reference Example 2. The obtained antibody having the amino acid sequence derived from IL6R-G1d-v5 as the antibody H chain has been called IgG1-v5. The FcγRIIb-binding activities of IgG1, IgG1-v1, IgG1-v3, and IgG1-v5 as evaluated according to the method of Example 14, are shown in Table 45.

S267E/L328F which is the modification with an enhancing effect on FcγRIIb in Example 14 was introduced into the P238D variant. Changes in the FcγRIIb-binding activities before and after introducing this alteration are shown in Table 45.

TABLE 45

| VARIANT | ALTERATION | KD FOR FcγRIIb (mol/L) | RELATIVE KD FOR FcγRIIb (KD FOR IgG1/KD FOR EACH VARIANT) |
|---|---|---|---|
| IgG1 (IL6R-G1d) | — | 5.30E−06 | 1 |
| IgG1-v1 | P238D | 1.10E−06 | 4.8 |
| IgG1-v3 | S267E/L328F | 1.30E−08 | 408 |
| IgG1-v5 | P238D/S267E/L328F | 4.50E−07 | 12 |

From the results of Table 45, since S267E/L328F improves the FcγRIIb-binding activity by 408 fold compared with IgG1, combining it with P238D which similarly improves the FcγRIIb-binding activity by 4.8 fold as compared with IgG1 was anticipated to further increase the degree of improvement of FcγRIIb-binding activity; however, in reality, in a similar manner to the former example, the FcγRIIb-binding activity of the variant containing a combination of these alterations was improved only 12 fold or so as compared with that of IgG1. This result is also an effect that could not have been predicted from the effects of the respective alterations.

These results showed that while the substitution of Pro at position 238 (indicated by EU numbering) with Asp alone improves FcγRIIb-binding activity, the effect is not exhibited when it is combined with other alterations that improve the FcγRIIb-binding activity. A reason for this may be that the structure of the interface for the interaction between Fc and FcγR is changed by introducing the substitution of Pro at position 238 (indicated by EU numbering) with Asp and the effects of alterations observed in the naturally-occurring antibody are no longer reflected in the results. Accordingly, it was considered to be extremely difficult to create an Fc with excellent selectivity for FcγRIIb using an Fc comprising substitution of Pro at position 238 (indicated by EU numbering) with Asp as a template, since the information on effects of alterations obtained with naturally-occurring antibodies could not be applied.

Reference Example 27

Comprehensive Analysis of FcγRIIb Binding of Variants Introduced with an Alteration at the Hinge Portion in Addition to the P238D Alteration As shown in Reference Example 26, in an Fc produced by substituting Pro at position 238 (indicated by EU numbering) with Asp in a naturally-occurring human IgG1, an anticipated combinatorial effect could not be obtained even by combining it with another alteration predicted to further increase FcγRIIb binding from the analysis of naturally-occurring antibodies. Therefore, in order to find variants that further enhance FcγRIIb binding, modifications were comprehensively introduced into the altered Fc produced by substituting Pro at position 238 (indicated by EU numbering) with Asp. IL6R-F11 (SEQ ID NO: 174) was produced by introducing an alteration of substituting Met at position 252 (indicated by EU numbering) with Tyr and an alteration of substituting Asn at position 434 (indicated by EU numbering) with Tyr in IL6R-G1d (SEQ ID NO: 79) which was used as the antibody H chain. Furthermore, IL6R-F652 (SEQ ID NO: 175) was prepared by introducing an alteration of substituting Pro at position 238 (indicated by EU numbering) with Asp into IL6R-F11. Expression plasmids containing an antibody H chain sequence were prepared for each of the antibody H chain sequences produced by substituting the region near the residue at position 238 (indicated by EU numbering) (positions 234 to 237, and 239 (indicated by EU numbering)) in IL6R-F652 each with 18 amino acids excluding the original amino acids and Cys. IL6R-L (SEQ ID NO: 83) was utilized as a common antibody L chain for all of the antibodies. These variants were expressed and purified by the method of Reference Example 2. These Fc variants are called PD variants. Interactions of each PD variant with FcγRIIa type R and FcγRIIb were comprehensively evaluated by the method of Example 14.

Figure 55:
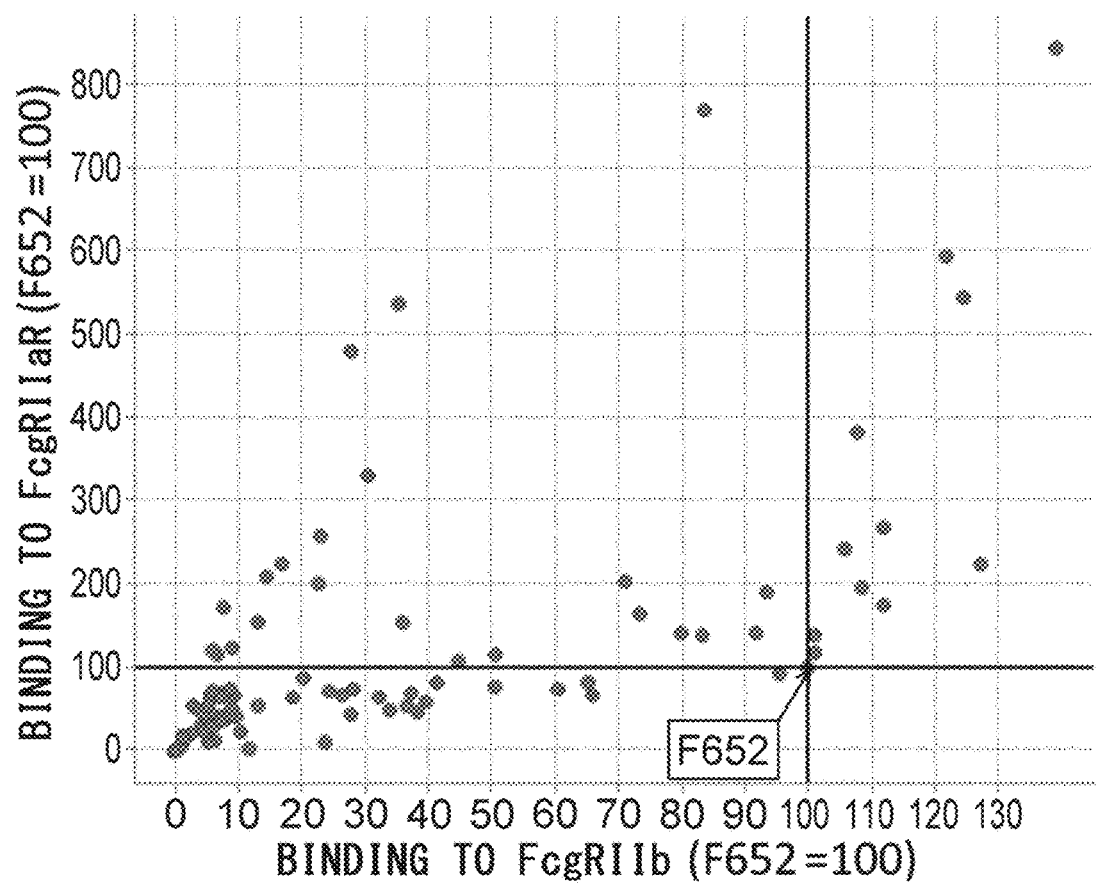
FIG. 55 shows a graph in which the horizontal axis shows the relative value of FcγRIIb-binding activity of each PD variant, and the vertical axis shows the relative value of FcγRIIa type R-binding activity of each PD variant. The value for the amount of binding of each PD variant to each FcγR was divided by the value for the amount of binding of IL6R-F652, which is a control antibody prior to introduction of the alteration (altered Fc with substitution of Pro at position 238 (indicated by EU numbering) with Asp), to each FcγR; and then the obtained value was multiplied by 100, and used as the relative binding activity value for each PD variant to each FcγR. The F652 plot in the figure shows the value for IL6R-F652.

A figure that shows the results of analyzing the interaction with the respective FcγRs was produced according to the following method. The value obtained by dividing the value for the amount of binding of each PD variant to each FcγR by the value for the amount of FcγR binding of the pre-altered antibody which is used as the control (IL6R-F652/IL6R-L, which has an alteration of substituting Pro at position 238 (indicated by EU numbering) with Asp and then multiplying the result by 100, was shown as the relative binding activity value of each PD variant to each FcγR. The horizontal axis shows relative values of the FcγRIIb-binding activity of each PD variant, and the vertical axis shows relative values of the FcγRIIa type R-binding activity values of each PD variant (FIG. 55).

As a result, it was found that the FcγRIIb binding of eleven types of alterations were enhanced compared with the antibody before introducing alterations, and they have the effects of maintaining or enhancing FcγRIIa type R-binding. The activities of these eleven variants to bind FcγRIIb and FcγRIIa R are summarized in Table 46. In the table, SEQ ID NO refers to the SEQ ID NO of the H chain of the evaluated variant, and alteration refers to the alteration introduced into IL6R-F11 (SEQ ID NO: 174).

TABLE 46

| SEQ ID NO | VARIANT NAME | ALTERATION | RELATIVE BINDING ACTIVITY FOR Fcγ RIIb | RELATIVE BINDING ACTIVITY FOR Fcγ RIIaR |
|---|---|---|---|---|
| 175 | IL6R-F652/IL6R-L | P238D | 100 | 100 |
| 176 | IL6R-PD042/IL6R-L | P238D/L234W | 106 | 240 |
| 177 | IL6R-PD043/IL6R-L | P238D/L234Y | 112 | 175 |
| 178 | IL6R-PD079/IL6R-L | P238D/G237A | 101 | 138 |
| 179 | IL6R-PD080/IL6R-L | P238D/G237D | 127 | 222 |
| 180 | IL6R-PD081/IL6R-L | P238D/G237E | 101 | 117 |
| 181 | IL6R-PD082/IL6R-L | P238D/G237F | 108 | 380 |
| 182 | IL6R-PD086/IL6R-L | P238D/G237L | 112 | 268 |
| 183 | IL6R-PD087/IL6R-L | P238D/G237M | 109 | 196 |
| 184 | IL6R-PD094/IL6R-L | P238D/G237W | 122 | 593 |
| 185 | IL6R-PD095/IL6R-L | P238D/G237Y | 124 | 543 |
| 186 | IL6R-PD097/IL6R-L | P238D/S239D | 139 | 844 |

Figure 56:
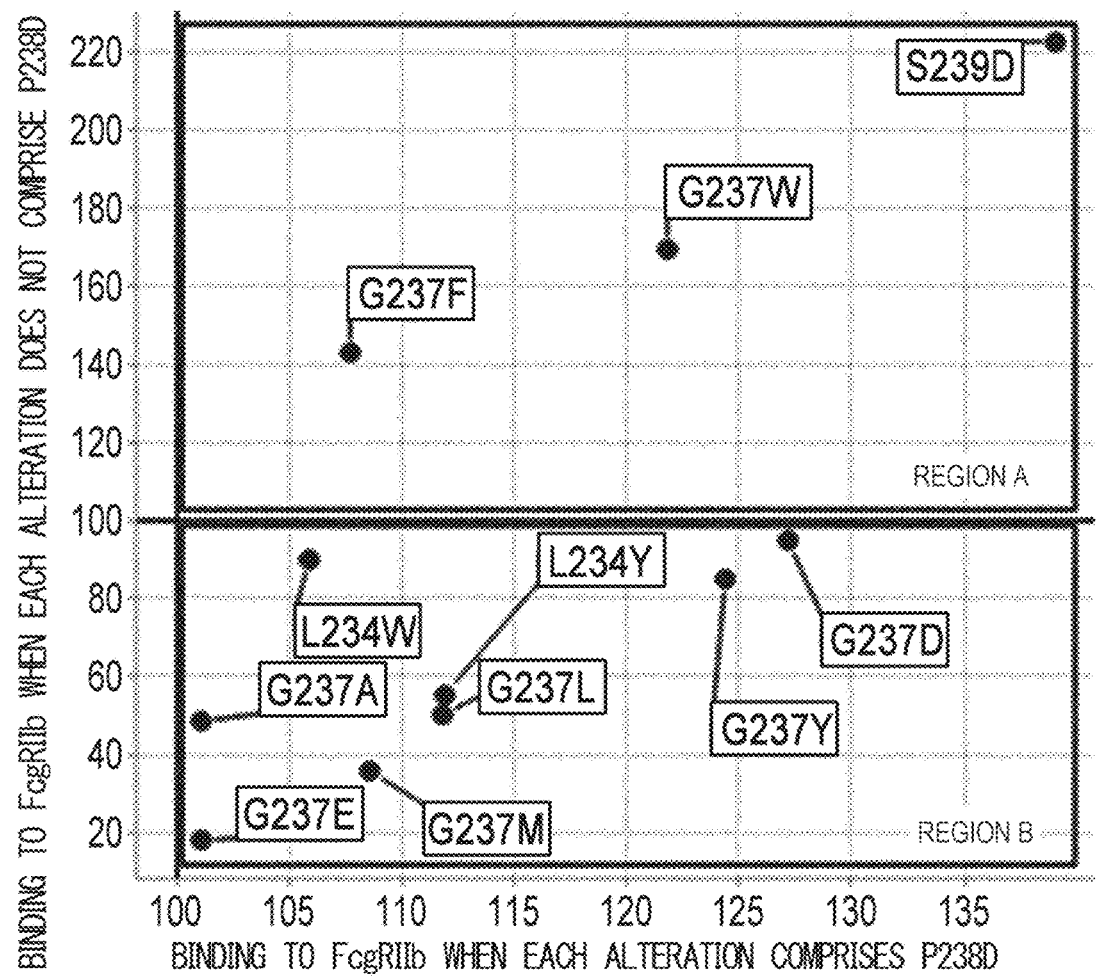
FIG. 56 shows a graph in which the vertical axis shows the relative value of FcγRIIb-binding activity of variants produced by introducing each alteration into GpH7-B3 which does not have the P238D alteration, and the horizontal axis shows the relative value of FcγRIIb-binding activity of variants produced by introducing each alteration into IL6R-F652 which has the P238D alteration. The value for the amount of FcγRIIb binding of each variant was divided by the value for the amount of FcγRIIb binding of the pre-altered antibody; and then the obtained value was multiplied by 100, and used as the value of relative binding activity. Here, region A contains alterations that exhibit the effect of enhancing FcγRIIb binding in both cases where an alteration is introduced into GpH7-B3 which does not have P238D and where an alteration is introduced into IL6R-F652 which has P238D. Region B contains alterations that exhibit the effect of enhancing FcγRIIb binding when introduced into GpH7-B3 which does not have P238D, but do not exhibit the effect of enhancing FcγRIIb binding when introduced into IL6R-F652 which has P238D.

FIG. 56 shows relative values for the FcγRIIb-binding activity obtained by additionally introducing the above eleven alterations into a variant carrying the P238D alteration, and relative values for the FcγRIIb-binding activity of a variant obtained by introducing the alterations into an Fc that does not contain the P238D. These eleven alterations enhanced the amount of FcγRIIb binding compared with before introduction when they were further introduced into the P238D variant. On the contrary, the effect of lowering FcγRIIb binding was observed for eight of those alterations except G237F, G237W, and S239D, when they were introduced into the variant that does not contain P238D (GpH7-B3/GpL16-k0) used in Example 14. Reference Example 26 and these results showed that, based on the effects of introducing alterations into a naturally-occurring IgG1, it is difficult to predict the effects of combining and introducing the same alterations into the variant containing the P238D alteration. In other words, it would not have been possible to discover these eight alterations identified this time without this investigation that introduces the same alterations are combined and introduced into the variant containing the P238D alteration.

The results of measuring KD values of the variants indicated in Table 46 for FcγRIa, FcγRIIaR, FcγRIIaH, FcγRIIb, and FcγRIIIaV by the method of Example 14 are summarized in Table 47. In the table, SEQ ID NO refers to the SEQ ID NO of the H chain of the evaluated variant, and alteration refers to the alteration introduced into IL6R-F11 (SEQ ID NO: 174). The template used for producing IL6R-F11 , IL6R-G1d/IL6R-L, is indicated with an asterisk (*). Furthermore, KD(IIaR)/KD(IIb) and KD(IIaH)/KD(IIb) in the table respectively show the value obtained by dividing the KD value of each variant for FcγRIIaR by the KD value of each variant for FcγRIIb, and the value obtained by dividing the KD value of each variant for FcγRIIaH by the KD value of each variant for FcγRIIb. KD(IIb) of the parent polypeptide/KD(IIb) of the altered polypeptide refers to a value obtained by dividing the KD value of the parent polypeptide for FcγRIIb by the KD value of each variant for FcγRIIb. In addition, Table 47 shows KD values for the stronger of the FcγRIIaR- and FcγRIIaH-binding activities of each variant/KD values for the stronger of the FcγRIIaR- and FcγRIIaH-binding activities of the parent polypeptide. Here, parent polypeptide refers to a variant which has IL6R-F11 (SEQ ID NO: 27) as the H chain. It was determined that due to weak binding of FcγR to IgG, it was sometimes impossible to accurately analyze by kinetic analysis, and thus the bolded and italicized text in Table 47 shows values calculated by using Equation 5 of Example 14.

$$KD = C \times R\text{max}/(\text{Req}-RI) - C \quad \text{[Equation 5]}$$

Table 47 shows that all variants improved their affinity for FcγRIIb in comparison with IL6R-F11 , and the range of improvement was 1.9 fold to 5.0 fold. The ratio of KD value of each variant for FcγRIIaR/KD value of each variant for FcγRIIb, and the ratio of KD value of each variant for FcγRIIaH/KD value of each variant for FcγRII b represent an FcγRIIb-binding activity relative to the FcγRIIaR-binding activity and FcγRIIaH-binding activity, respectively. That is, these values show the degree of binding selectivity of each variant for FcγRIIb, and a larger value indicates a higher binding selectivity for FcγRIIb. For the parent polypeptide IL6R-F11 /IL6R-L, the ratio of KD value for FcγRIIaR/KD value for FcγRIIb and the ratio of KD value for FcγRIIaH/KD value for FcγRIIb are both 0.7, and accordingly all variants in Table 47 showed improvement of binding selectivity for FcγRIIb in comparison with the parent polypeptide. When the KD value for the stronger of the FcγRIIaR- and FcγRIIaH-binding activities of a variant/KD value for the stronger of the FcγRIIaR- and FcγRIIaH-binding activities of the parent polypeptide is 1 or more, this means that the stronger of the FcγRIIaR- and FcγRIIaH-binding activities of a variant has equivalent or reduced binding compared with the binding by the stronger of the FcγRIIaR- and FcγRIIaH-binding activities of the parent polypeptide. Since this value was 0.7 to 5.0 for the variants obtained this time, one may say that binding by the stronger of the FcγRIIaR- and FcγRIIaH-binding activities of the variants obtained this time was nearly the same or decreased in comparison with the parent polypeptide. These results showed that compared with the parent polypeptide, the variants obtained this time have maintained or decreased binding activities to FcγRIIa type R and type H, and improved selectivity for FcγRIIb. Furthermore, compared with IL6R-F11 , all variants had lower affinity to FcγRIa and FcγRIIIaV.

TABLE 47

| | KD (mol/L) | | | | | KD (IIaR)/ KD (IIb) | KD (IIaH)/ KD (IIb) | KD(IIb) OF PARENT POLYPEPTIDE/ KD (IIb) ALTERED POLYPEPTIDE | KD VALUE FOR THE STRONGER OF THE BINDING ACTIVITIES OF A VARIANT TO FcγRIIaR AND FcγRIIaH/ KD VALUE FOR THE STRONGER OF THE BINDING ACTIVITIES OF THE PARENT POLYPEPTIDE TO FcγRIIaR AND FcγRIIaH |
|---|---|---|---|---|---|---|---|---|---|
| Alteration | FcγRIa | FcγRIIaR | FcγRIIaH | FcγRIIB | FcγRIIIaV | | | | |
| * | 3.2E−10 | 1.0E−06 | 6.7E−07 | 2.6E−06 | 3.5E−07 | 0.4 | 0.3 | 2.6 | 0.1 |
| | 9.0E−10 | 5.0E−06 | 5.0E−06 | 6.8E−06 | *1.5E−06* | 0.7 | 0.7 | 1.0 | 1.0 |
| L234W/P238D | 6.3E−08 | 1.61−05 | *1.9E−05* | 2.0E−06 | *3.7E−05* | 8.1 | 9.5 | 3.4 | 3.2 |
| L234Y/P238D | 7.5E−08 | 2,6E−05 | *2.3E−05* | 1.6E−06 | *4.5E−05* | 15.9 | 14.4 | 4.2 | 4.6 |
| G237A/P238D | 1.4E−07 | 3.2E−05 | *2.1E−05* | 3.0E−06 | 3.7E−05 | 10.5 | 7.0 | 2.3 | 4.2 |
| G237D/P238D | 1.4E−07 | 2.1E−05 | *2.5E−05* | 2.0E−06 | *4.3E−05* | 10.7 | 12.8 | 3.5 | 4.2 |
| G237E/P238D | 3.4E−07 | 3.8E−05 | *2.5E−05* | 3.6E−06 | *4.1E−05* | 10.6 | 7.0 | 1.9 | 5.0 |
| G237F/P238D | 5.2E−08 | 1.4E−05 | *1.6E−05* | 3.4E−06 | 4.3E−05 | 4.1 | 4.7 | 2.0 | 2.8 |
| G237L/P238D | 1.2E−07 | 1.8E−05 | *1.8E−05* | 2.6E−06 | 4.1E−05 | 6.9 | 7.1 | 2.7 | 3.5 |
| G237M/P238D | 5.2E−08 | 2.2E−05 | *2.0E−05* | 2.9E−06 | 3.7E−05 | 7.7 | 7.0 | 2.4 | 4.0 |
| G237W/P238D | 3.6E−08 | 7.2E−06 | *1.2E−06* | 2.3E−06 | *3.8E−05* | 3.1 | 5.2 | 2.9 | 1.4 |
| G237Y/P238D | 9.3E−08 | 7.9E−06 | *1.5E−05* | 2.3E−06 | *4.2E−05* | 3.4 | 6.4 | 2.9 | 1.6 |
| P238D/S239D | 4.9E−09 | 3.5E−06 | *1.9E−05* | 1.4E−06 | *1.7E−05* | 2.6 | 14.0 | 5.0 | 0.7 |

Reference Example 28

X-ray Crystallographic Analysis of a Complex Formed between an Fc Containing P238D and an Extracellular Region of FcγRIIb As indicated earlier in Reference Example 27, even though an alteration that is predicted from the analysis of naturally-occurring IgG1 antibodies to improve FcγRIIb-binding activity or selectivity for FcγRIIb is introduced into an Fc containing P238D, the FcγRIIb-binding activity was found to decrease, and the reason for this may be that the structure at the interacting interface between Fc and FcγRIIb is changed due to introduction of P238D. Therefore, to pursue the reason for this phenomena, the three-dimensional structure of the complex formed between an IgG1 Fc containing the P238D mutation (hereinafter, Fc(P238D)) and the extracellular region of FcγRIIb was elucidated by X-ray crystallographic analysis, and this was compared to the three-dimensional structure of the complex formed between the Fc of a naturally-occurring IgG1 (hereinafter, Fc(WT)) and the extracellular region of FcγRIIb, and the binding modes were compared. Multiple reports have been made on the three-dimensional structure of a complex formed between an Fc and an FcγR extracellular region; and the three-dimensional structures of the Fc(WT)/FcγRIIIb extracellular region complex (Nature, 2000, 400: 267-273; J. Biol. Chem. 2011, 276: 16469-16477), the Fc(WT)/FcγRIIIa extracellular region complex (Proc. Natl. Acad. Sci. USA, 2011, 108: 12669-126674), and the Fc(WT)/FcγRIIa extracellular region complex (J. Immunol. 2011, 187: 3208-3217) have been analyzed. While the three-dimensional structure of the Fc(WT)/FcγRIIb extracellular region complex has not been analyzed, the three-dimensional structure of a complex formed with Fc(WT) is known for FcγRIIa, and the extracellular regions of FcγRIIa and FcγRIIb match 93% in amino acid sequence and have very high homology. Thus, the three-dimensional structure of the Fc(WT)/FcγRIIb extracellular region complex was predicted by modeling using the crystal structure of the Fc(WT)/FcγRIIa extracellular region complex.

Figure 57:
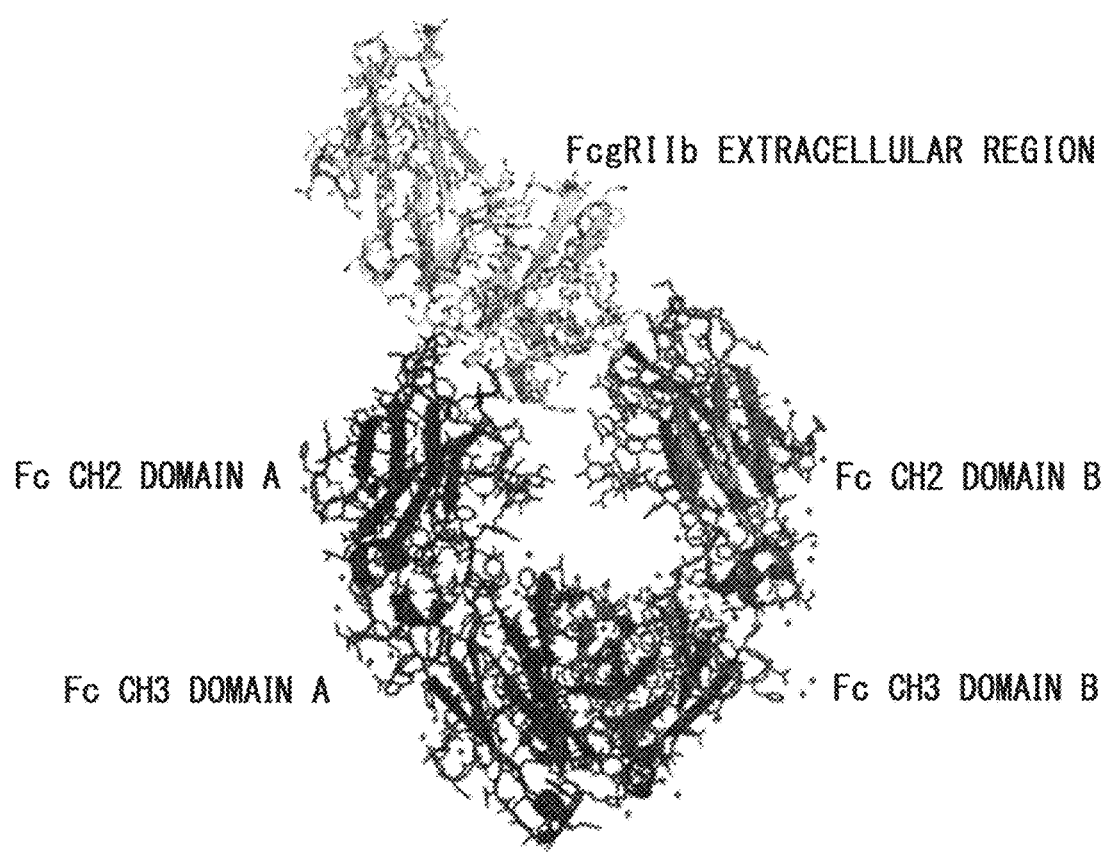
FIG. 57 shows a crystal structure of the Fc(P238D)/FcγRIIb extracellular region complex.

The three-dimensional structure of the Fc(P238D)/FcγRIIb extracellular region complex was determined by X-ray crystallographic analysis at 2.6 Å resolution. The structure obtained as a result of this analysis is shown in FIG. 57. The FcγRIIb extracellular region is bound between two Fc CH2 domains, and this was similar to the three-dimensional structures of complexes formed between Fc(WT) and the respective extracellular region of FcγRIIIa, FcγRIIIb, or FcγRIIa analyzed so far.

Figure 58:
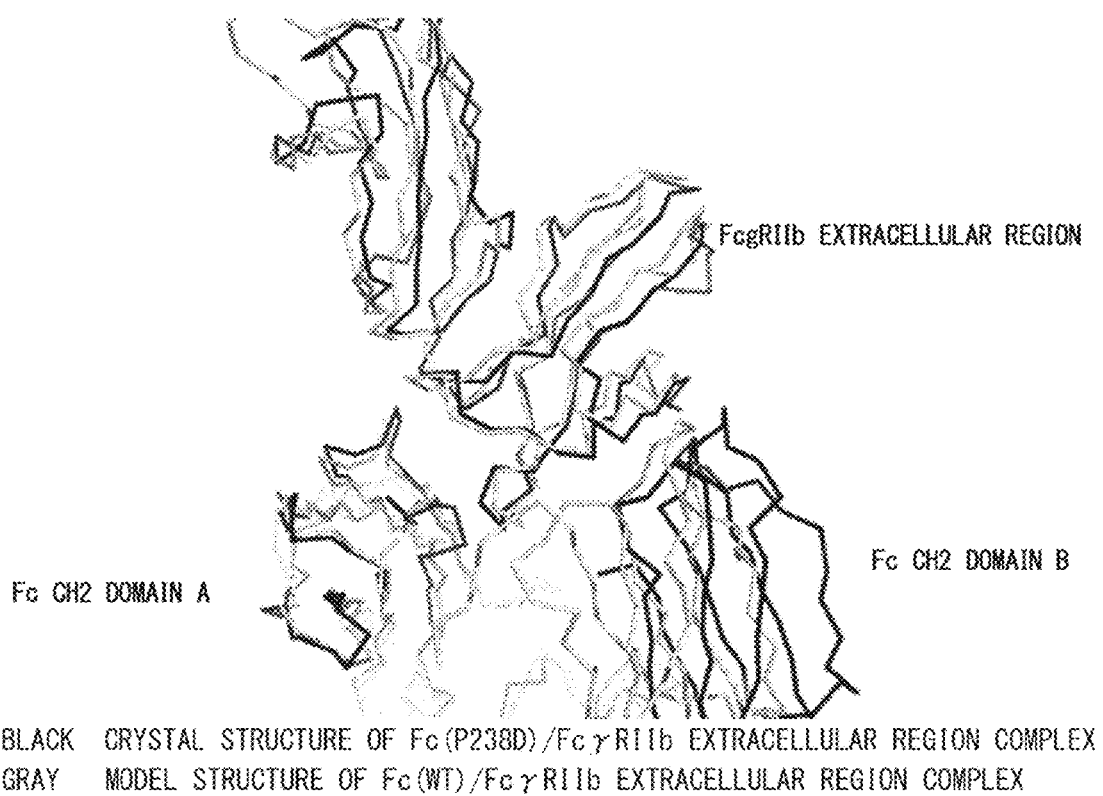
FIG. 58 shows an image of superimposing the crystal structure of the Fc(P238D)/FcγRIIb extracellular region complex and the model structure of the Fc(WT)/FcγRIIb extracellular region complex, with respect to the FcγRIIb extracellular region and the Fc CH2 domain A by the least squares fitting based on the Cα atom pair distances.

Next, for detailed comparison, the crystal structure of the Fc(P238D)/FcγRIIb extracellular region complex and the model structure of the Fc(WT)/FcγRIIb extracellular region complex were superimposed by the least squares fitting based on the Cα atom pair distances with respect to the FcγRIIb extracellular region and the Fc CH2 domain A (FIG. 58). In that case, the degree of overlap between Fc CH2 domains B was not satisfactory, and conformational differences were found in this portion. Furthermore, using the crystal structure of the Fc(P238D)/FcγRIIb extracellular region complex and the model structure of the Fc(WT)/FcγRIIb extracellular region complex, pairs of atoms that have a distance of 3.7 Å or less between the extracted FcγRIIb extracellular region and Fc CH2 domain B were extracted and compared in order to compare the interatomic interaction between FcγRIIb and Fc (WT) CH2 domain B with the interatomic interaction between FcγRIIb and Fc(P238D). As shown in Table 48, the interatomic interactions between Fc CH2 domain B and FcγRIIb in Fc(P238D) and Fc(WT) did not match.

TABLE 48

| FcγRIIb ATOM | | | Fc(P646D) CH2 DOMAIN B INTERACTION PARTNER (DISTANCE BETWEEN ATOMS, Å) | | | | Fc(WT) CH2 DOMAIN B INTERACTION PARTNER (DISTANCE BETWEEN ATOMS, Å) | | | |
|---|---|---|---|---|---|---|---|---|---|---|
| Val | 116 | CG2 | | | | | Asp | 265 | OD2 | (3.47) |
| | | | | | | | Gly | 237 | O | (3.65) |

TABLE 48-continued

| FcγRIIb ATOM | | | Fc(P646D) CH2 DOMAIN B INTERACTION PARTNER (DISTANCE BETWEEN ATOMS, Å) | | | | Fc(WT) CH2 DOMAIN B INTERACTION PARTNER (DISTANCE BETWEEN ATOMS, Å) | | | |
|---|---|---|---|---|---|---|---|---|---|---|
| Ser | 126 | OG | Ser | 298 | N | (3.31) | | | | |
| | | | Ser | 298 | CB | (3.32) | | | | |
| | | | Tyr | 296 | O | (3.05) | | | | |
| Lys | 128 | CA | Ser | 298 | OG | (3.50) | | | | |
| Phe | 129 | CB | Ser | 298 | O | (3.36) | | | | |
| Phe | 129 | CD2 | | | | | Asn | 297 | CB | (3.50) |
| | | | | | | | Asn | 297 | CG | (3.43) |
| Lys | 128 | C | Ser | 298 | OG | (3.47) | | | | |
| Phe | 129 | N | Ser | 298 | OG | (3.30) | | | | |
| Phe | 129 | O | Ser | 267 | OG | (3.54) | | | | |
| Arg | 131 | CB | | | | | Val | 266 | O | (3.02) |
| Arg | 131 | CG | | | | | Val | 266 | O | (3.22) |
| Arg | 131 | CD | | | | | Val | 266 | CG1 | (3.45) |
| | | | | | | | Val | 266 | C | (3.55) |
| | | | | | | | Val | 266 | O | (3.10) |
| Arg | 131 | NE | Ala | 327 | O | (3.60) | Val | 266 | C | (3.66) |
| | | | | | | | Val | 266 | O | (3.01) |
| | | | | | | | Val | 266 | N | (3.49) |
| Arg | 131 | CZ | Asp | 270 | CG | (3.64) | Val | 266 | N | (3.13) |
| | | | Asp | 270 | OD2 | (3.22) | | | | |
| | | | Asp | 270 | OD1 | (3.27) | | | | |
| | | | Ala | 327 | CB | (3.63) | | | | |
| Arg | 131 | NH1 | Asp | 270 | CG | (3.19) | Val | 266 | CG1 | (3.47) |
| | | | Asp | 270 | OD2 | (2.83) | Val | 266 | N | (3.43) |
| | | | Asp | 270 | OD1 | (2.99) | Thr | 299 | OG1 | (3.66) |
| | | | Ser | 267 | CB | (3.56) | Ser | 298 | O | (3.11) |
| Arg | 131 | NH2 | Asp | 270 | CG | (3.20) | Asp | 265 | CA | (3.16) |
| | | | Asp | 270 | OD2 | (2.80) | Val | 266 | N | (3.37) |
| | | | Asp | 270 | OD1 | (2.87) | | | | |
| | | | Ala | 327 | CB | (3.66) | | | | |
| Tyr | 157 | CE1 | | | | | Leu | 234 | CB | (3.64) |
| | | | | | | | Leu | 234 | CD1 | (3.61) |
| Tyr | 157 | OH | | | | | Gly | 236 | O | (3.62) |
| | | | | | | | Leu | 234 | CA | (3.48) |
| | | | | | | | Leu | 234 | CG | (3.45) |

Figure 59:
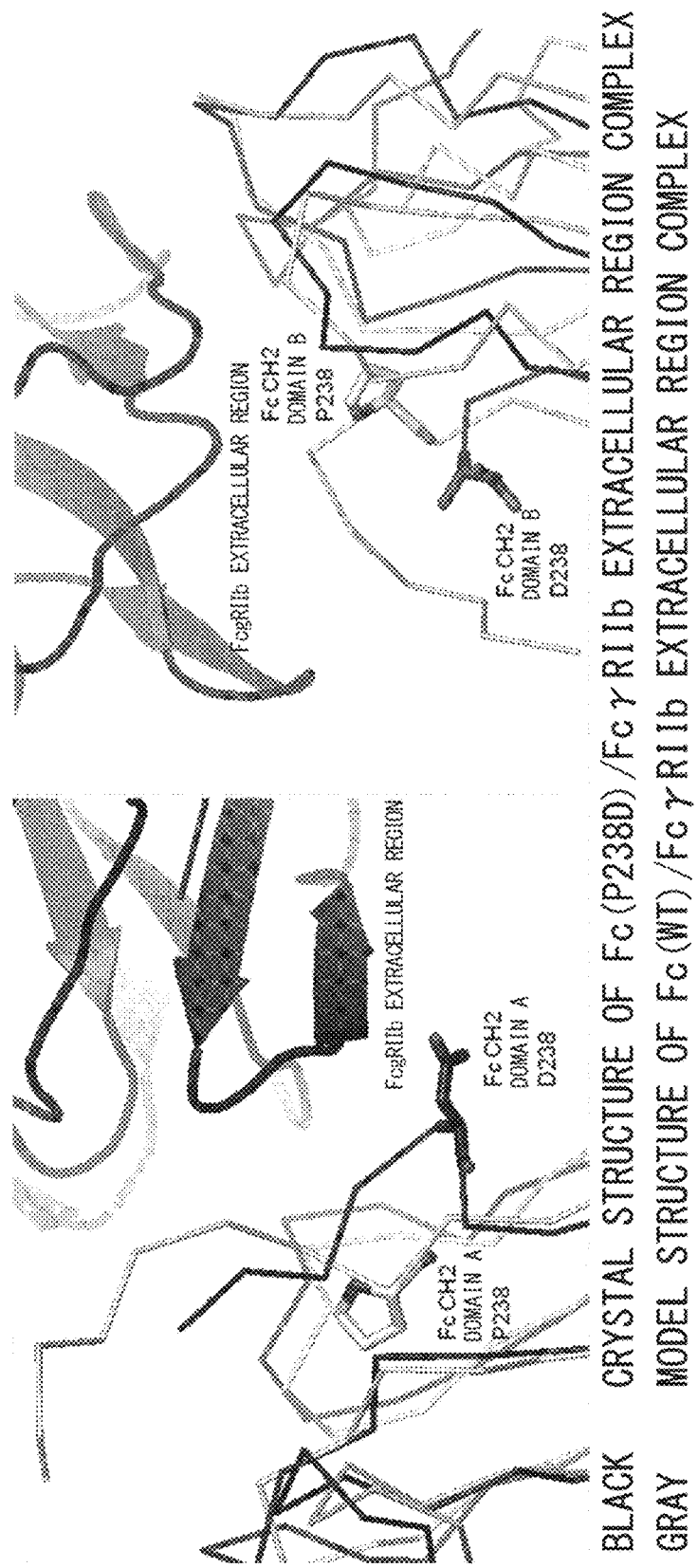
FIG. 59 shows comparison of the detailed structure around P238D after superimposing the crystal structure of the Fc(P238D)/FcγRIIb extracellular region complex and the model structure of the Fc(WT)/FcγRIIb extracellular region complex with respect to the only Fc CH2 domain A or the only Fc CH2 domain B by the least squares fitting based on the Cα atom pair distances.

Furthermore, the detailed structures around P238D were compared by superposing the X-ray crystal structure of Fc (P238D)/FcγRIIb extracellular domain complex on the model structure of the Fc (WT)/FcγRIIb extracellular domain complex using the least squares method based on the Cα atomic distance between Fc CH2 domains A and B alone. As the position of the amino acid residue at position 238 (EU numbering), i.e., a mutagenesis position of Fc (P238D), is altered from Fc (WT), the loop structure around the amino acid residue at position 238 following the hinge region is found to be different between Fc (P238D) and Fc (WT) (FIG. 59). Pro at position 238 (EU numbering) is originally located inside Fc (WT), forming a hydrophobic core with residues around position 238. However, if Pro at position 238 (EU numbering) is altered to highly hydrophilic and charged Asp, the presence of the altered Asp residue in a hydrophobic core is energetically disadvantageous in terms of desolvation. Therefore, in Fc(P238D), to cancel this energetically disadvantageous situation, the amino acid residue at position 238 (indicated by EU numbering) changes its orientation to face the solvent side, and this may have caused this change in the loop structure near the amino acid residue at position 238. Furthermore, since this loop is not far from the hinge region crosslinked by an S-S bond, its structural change will not be limited to a local change, and will affect the relative positioning of the FcCH2 domain A and domain B. As a result, the interatomic interactions between FcγRIIb and Fc CH2 domain B have been changed. Therefore, predicted effects could not be observed when alterations that improve selectivity and binding activity towards FcγRIIb in a naturally-occurring IgG were combined with an Fc containing the P238D alteration.

Figure 60:
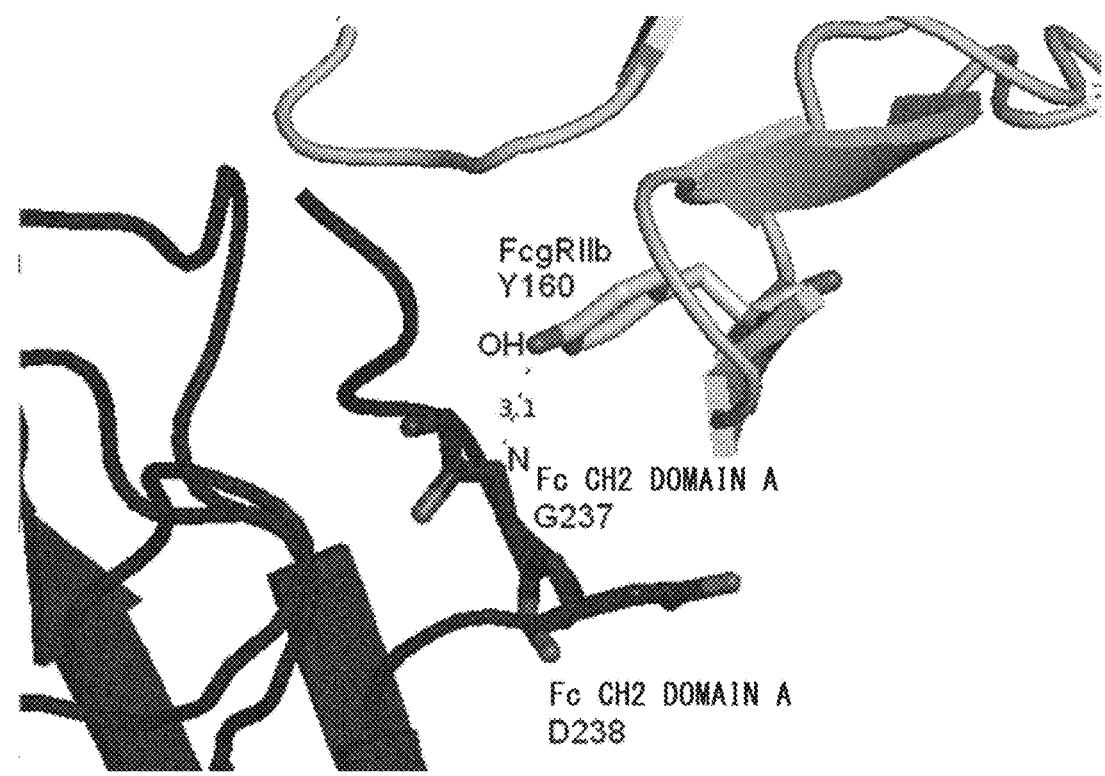
FIG. 60 shows that a hydrogen bond can be found between the main chain of Gly at position 237 (indicated by EU numbering) in Fc CH2 domain A, and Tyr at position 160 in FcγRIIb in the crystal structure of the Fc(P238D)/FcγRIIb extracellular region complex.
Figure 61:
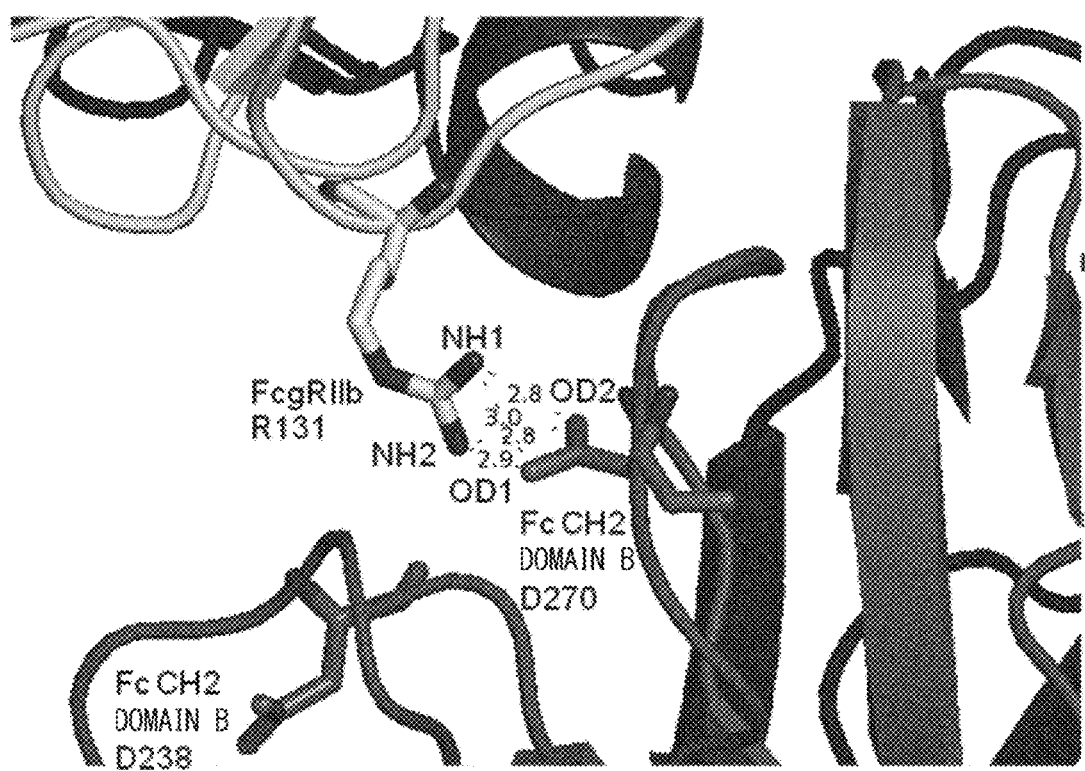
FIG. 61 shows that an electrostatic interaction can be found between Asp at position 270 (indicated by EU numbering) in Fc CH2 domain B, and Arg at position 131 in FcγRIIb in the crystal structure of the Fc(P238D)/FcγRIIb extracellular region complex.

Furthermore, as a result of structural changes due to introduction of P238D in Fc CH2 domain A, a hydrogen bond has been found between the main chain of Gly at position 237 (indicated by EU numbering), which is adjacent to P238D mutated, and Tyr at position 160 in FcγRIIb (FIG. 60). The residue in FcγRIIa that corresponds to this Tyr 160 is Phe; and when the binding is to FcγRIIa, this hydrogen bond is not formed. Considering that the amino acid at position 160 is one of the few differences between FcγRIIa and FcγRIIb at the interface of interaction with Fc, the presence of this hydrogen bond which is specific to FcγRIIb is presumed to have led to improvement of FcγRIIb-binding activity and decrease of FcγRIIa-binding activity in Fc(P238D), and improvement of its selectivity. Furthermore, in Fc CH2 domain B, an electrostatic interaction is observed between Asp at position 270 (indicated by EU numbering) and Arg at position 131 in FcγRIIb (FIG. 61). In FcγRIIa type H, which is one of the allotypes of FcγRIIa, the residue corresponding to Arg at position 131 of FcγRIIb is His, and therefore cannot form this electrostatic interaction. This can explain why the Fc(P238D)-binding activity is lowered in FcγRIIa type H compared with FcγRIIa type R. Observations based on such results of X-ray crystallographic analysis showed that the change of the loop structure beside P238D due to P238D introduction and the accompanying change in the relative domain positioning causes formation of new interactions which is not found in the binding of the naturally-occurring IgG and FcγR, and this could lead to a selective binding profile of P238D variants for FcγRIIb.

[Expression and Purification of Fc(P238D)]

An Fc containing the P238D alteration was prepared as follows. First, Cys at position 220 (indicated by EU numbering) of hIL6R-IgG1-v1 (SEQ ID NO: 80) was substituted with Ser. Then, genetic sequence of Fc(P238D) from Glu at position 236 (indicated by EU numbering) to its C terminal was cloned by PCR. Using this cloned genetic sequence, production of expression vectors, and expression and purification of Fc(P238D) were carried out according to the method of Reference Examples 1 and 2. Cys at position 220 (indicated by EU numbering) forms a disulfide bond with Cys of the L chain in general IgG1. The L chain is not co-expressed when Fc alone is prepared, and therefore, the Cys residue was substituted with Ser to avoid formation of unnecessary disulfide bonds.

[Expression and Purification of the FcγRIIb Extracellular Region]

The FcγRIIb extracellular region was prepared according to the method of Example 14.

[Purification of the Fc(P238D)/FcγRIIb Extracellular Region Complex]

To 2 mg of the FcγRIIb extracellular region sample obtained for use in crystallization, 0.29 mg of Endo F1 (Protein Science 1996, 5: 2617-2622) expressed and purified from *Escherichia coli* as a glutathione S-transferase fusion protein was added. This was allowed to react at room temperature for three days in 0.1 M Bis-Tris buffer at pH 6.5, and the N-linked oligosaccharide was cleaved, except for N-acetylglucosamine directly bound to Asn of the FcγRIIb extracellular region. Next, the FcγRIIb extracellular domain sample subjected to carbohydrate cleavage treatment, which was concentrated by ultrafiltration with 5000 MWCO, was purified by gel filtration chromatography (Superdex200 10/300) using a column equilibrated in 20 mM HEPS at pH 7.5 containing 0.05 M NaCl. Furthermore, to the obtained carbohydrate-cleaved FcγRIIb extracellular region fraction, Fc(P238D) was added so that the molar ratio of the FcγRIIb extracellular region would be present in slight excess. The mixture concentrated by ultrafiltration with 10,000 MWCO was subjected to purification by gel filtration chromatography (Superdex200 10/300) using a column equilibrated in 20 mM HEPS at pH 7.5 containing 0.05 M NaCl. Thus, a sample of the Fc(P238D)/FcγRIIb extracellular region complex was obtained.

[Crystallization of the Fc(P238D)/FcγRIIb Extracellular Region Complex]

Using the sample of the Fc(P238D)/FcγRIIb extracellular region complex which was concentrated to approximately 10 mg/mL by ultrafiltration with 10,000 MWCO, crystallization of the complex was carried out by the sitting drop vapor diffusion method. Hydra II Plus One (MATRIX) was used for crystallization; and for a reservoir solution containing 100 mM Bis-Tris pH 6.5, 17% PEG3350, 0.2 M ammonium acetate, and 2.7% (w/v) D-Galactose, a crystallization drop was produced by mixing at a ratio of reservoir solution: crystallization sample=0.2 μL: 0.2 μL. The crystallization drop after sealing was allowed to remain at 20° C., and thus thin plate-like crystals were obtained.

[Measurement of X-ray Diffraction Data from an Fc(P238D)/FcγRIIb Extracellular Region Complex Crystal]

One of the obtained single crystals of the Fc(P238D)/FcγRIIb extracellular region complex was soaked into a solution of 100 mM Bis-Tris pH 6.5, 20% PEG3350, ammonium acetate, 2.7% (w/v) D-Galactose, 22.5% (v/v) ethylene glycol. The single crystal was fished out of the solution using a pin with attached tiny nylon loop, and frozen in liquid nitrogen. The X-ray diffraction data of the crystal was measured at synchrotron radiation facility Photon Factory BL-1A in High Energy Accelerator Research Organization. During the measurement, the crystal was constantly placed in a nitrogen stream at −178° C. to maintain in a frozen state, and a total of 225 X ray diffraction images were collected using Quantum 270 CCD detector (ADSC) attached to a beam line with rotating the crystal 0.8° at a time. Determination of cell parameters, indexing of diffraction spots, and diffraction data processing from the obtained diffraction images were performed using the Xia2 program (CCP4 Software Suite), XDS Package (Wolfgang Kabsch) and Scala (CCP4 Software Suite); and finally, diffraction intensity data of the crystal up to 2.46 Å resolution was obtained. The crystal belongs to the space group $P2_1$, and has the following cell parameters; a=48.85 Å, b=76.01 Å, c=115.09 Å, α=90°, β=100.70°, γ=90°.

[X Ray Crystallographic Analysis of the Fc(P238D)/FcγRIIb Extracellular Region Complex]

Crystal structure of the Fc(P238D)/FcγRIIb extracellular region complex was determined by the molecular replacement method using the program Phaser (CCP4 Software Suite). From the size of the obtained crystal lattice and the molecular weight of the Fc(P238D)/FcγRIIb extracellular region complex, the number of complexes in the asymmetric unit was predicted to be one. From the structural coordinates of PDB code: 3SGJ which is the crystal structure of the Fc(WT)/FcγRIIIa extracellular region complex, the amino acid residue portions of the A chain positions 239-340 and the B chain positions 239-340 were taken out as separate coordinates, and they were set respectively as models for searching the Fc CH2 domains. The amino acid residue portions of the A chain positions 341-444 and the B chain positions 341-443 were taken out as a single set of coordinates from the same structural coordinates of PDB code: 3SGJ; and this was set as a model for searching the Fc CH3 domains. Finally, from the structural coordinates of PDB code: 2FCB which is a crystal structure of the FcγRIIb extracellular region, the amino acid residue portions of the A chain positions 6-178 was taken out and set as a model for searching the FcγRIIb extracellular region. The orientation and position of each search model in the crystal lattice were determined in the order of Fc CH3 domain, FcγRIIb extracellular region, and Fc CH2 domain, based on the rotation function and translation function to obtain the initial model for the crystal structure of the Fc(P238D)/FcγRIIb extracellular region complex. When rigid body refinement which moves the two Fc CH2 domains, the two Fc CH3 domains, and the FcγRIIb extracellular region was performed on the obtained initial model, the crystallographic reliability factor, R value became 40.4%, and the Free R value became 41.9% to diffraction intensity data from 25 Å to 3.0 Å at this point. Furthermore, structural refinement using the program Refmac5 (CCP4 Software Suite), and revision of the model to observe the electron density maps whose coefficient have 2Fo-Fc or Fo-Fc, which are calculated based on the experimentally determined structural factor Fo, the calculated structural factor Fc and the calculated phase using the model, was carried out by the Coot program (Paul Emsley). Model refinement was carried out by repeating these steps. Finally, as a result of incorporation of water molecules into the model based on the electron density maps which use 2Fo-Fc or Fo-Fc as the coefficient, and the following refinement, the crystallographic reliability factor, R values and the Free R value of the model containing 4846 non-hydrogen atoms became 23.7% and 27.6% to 24291 diffraction intensity data from 25 Å to 2.6 Å resolution, respectively.

[Production of a Model Structure of the Fc(WT)/FcγRIIb Extracellular Region Complex]

Based on the structural coordinates of PDB code: 3RY6 which is a crystal structure of the Fc(WT)/FcγRIIa extracellular region complex, the Build Mutants function of the Discovery Studio 3.1 program (Accelrys) was used to introduce mutations to match the amino acid sequence of FcγRIIb into FcγRIIa in this structural coordinates. In that case, the Optimization Level was set to High, Cut Radius was set to 4.5, five models were generated, and the one with the best energy score from among them was set as the model structure for the Fc(WT)/FcγRIIb extracellular region complex.

Reference Example 29

Analysis of FcγR Binding of Fc Variants whose Alteration Sites Were Determined Based on Crystal Structures.

Based on the results of X-ray crystallographic analysis on the complex formed between Fc(P238D) and the FcγRIIb extracellular region obtained in Reference Example 28, variants were constructed by comprehensively introducing alterations into sites on the altered Fc having substitution of Pro at position 238 (indicated by EU numbering) with Asp that were predicted to affect interaction with FcγRIIb (residues of positions 233, 240, 241, 263, 265, 266, 267, 268, 271, 273, 295, 296, 298, 300, 323, 325, 326, 327, 328, 330, 332, and 334 (indicated by EU numbering)), and whether combinations of alterations that further enhance FcγRIIb binding in addition to the P238D alteration can be obtained, was examined.

IL6R-B3 (SEQ ID NO: 187) was produced by introducing into IL6R-G1d (SEQ ID NO: 79) produced in Example 14, the alteration produced by substituting Lys at position 439 (indicated by EU numbering) with Glu. Next, IL6R-BF648 was produced by introducing into IL6R-B3, the alteration produced by substituting Pro at position 238 (indicated by EU numbering) with Asp. IL6R-L (SEQ ID NO: 83) was utilized as the common antibody L chain. These antibody variants expressed were purified according to the method of Reference Example 2. The binding of these antibody variants to each of the FcγRs (FcγRIa, FcγRIIa type H, FcγRIIa type R, FcγRIIb, and FcγRIIIa type V) was comprehensively evaluated by the method of Example 14.

A figure was produced according to the following method to show the results of analyzing the interactions with the respective FcγRs. The value for the amount of binding of each variant to each FcγR was divided by the value for the amount of binding of the pre-altered control antibody (IL6R-BF648/IL6R-L, alteration by substituting Pro at position 238 (indicated by EU numbering) with Asp) to each FcγR, and the obtained was then multiplied by 100 and shown as the relative binding activity value of each variant to each FcγR. The horizontal axis shows the relative binding activity value of each variant to FcγRIIb, and the vertical axis shows the relative binding activity value of each variant to FcγRIIa type R (FIG. 62).

Figure 62:
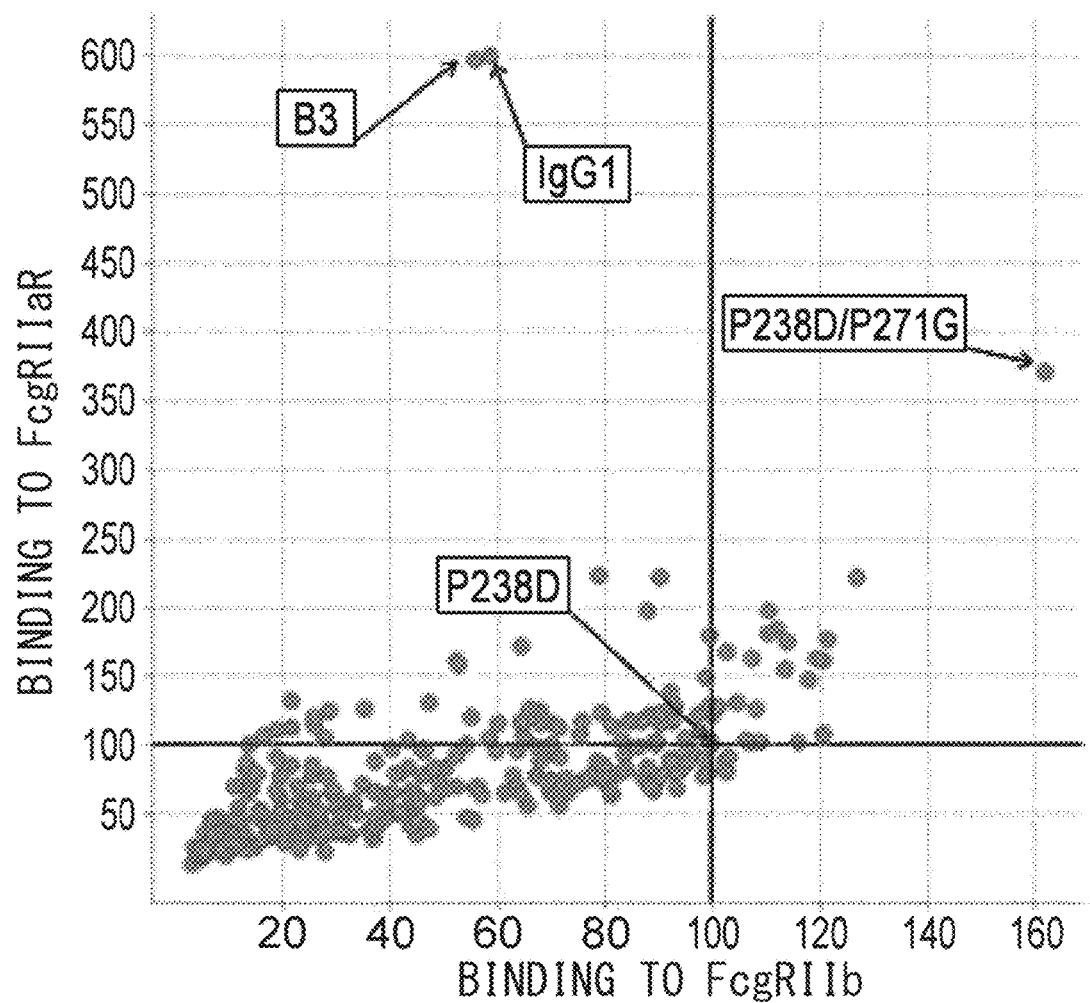
FIG. 62 shows a graph in which the horizontal axis shows the relative value of FcγRIIb-binding activity of each 2B variant, and the vertical axis shows the relative value of FcγRIIa type R-binding activity of each 2B variant. The value for the amount of binding of each 2B variant to each FcγR was divided by the value for the amount of binding of a control antibody prior to alteration (altered Fc with substitution of Pro at position 238 (indicated by EU numbering) with Asp) to each FcγR; and then the obtained value was multiplied by 100, and used as the value of relative binding activity of each 2B variant towards each FcγR.

As shown in FIG. 62, the results show that of all the alterations, 24 types of alterations were found to maintain or enhance FcγRIIb binding in comparison with the pre-altered antibody. The binding of these variants to each of the FcγRs are shown in Table 49. In the table, alteration refers to the alteration introduced into IL6R-B3 (SEQ ID NO: 187). The template used for producing IL6R-B3, IL6R-G1d/IL6R-L, is indicated with an asterisk (*).

TABLE 49

| VARIANT NAME | ALTERATION | RELATIVE BINDING | | | | |
| --- | --- | --- | --- | --- | --- | --- |
| | | FcγRIa | FcγRIIaR | FcγRIIaH | FcγRIIb | FcγRIIIa |
| IL6R-G1d/IL6R-L | * | 140 | 650 | 1670 | 62 | 3348 |
| IL6R-B3/IL6R-L | | 145 | 625 | 1601 | 58 | 3264 |
| IL6R-BF648/IL6R-L | P238D | 100 | 100 | 100 | 100 | 100 |
| IL6R-2B002/IL6R-L | P238D/E233D | 118 | 103 | 147 | 116 | 147 |
| IL6R-BP100/IL6R-L | P238D/S267A | 121 | 197 | 128 | 110 | 138 |
| IL6R-BP102/IL6R-L | P238D/S267Q | 104 | 165 | 66 | 106 | 86 |
| IL6R-BP103/IL6R-L | P238D/S267V | 56 | 163 | 69 | 107 | 77 |
| IL6R-BP106/IL6R-L | P238D/H268D | 127 | 150 | 110 | 116 | 127 |
| IL6R-BP107/IL6R-L | P238D/H268E | 123 | 147 | 114 | 118 | 129 |
| IL6R-BP110/IL6R-L | P238D/H268N | 105 | 128 | 127 | 101 | 127 |
| IL6R-BP112/IL6R-L | P238D/P271G | 119 | 340 | 113 | 157 | 102 |
| IL6R-2B128/IL6R-L | P238D/Y296D | 95 | 87 | 37 | 103 | 96 |
| IL6R-2B169/IL6R-L | P238D/V323I | 73 | 92 | 83 | 104 | 94 |
| IL6R-2B171/IL6R-L | P238D/V323L | 116 | 117 | 115 | 113 | 122 |
| IL6R-2B172/IL6R-L | P238D/V323M | 140 | 244 | 179 | 132 | 144 |
| IL6R-BP136/IL6R-L | P238D/K326A | 117 | 159 | 103 | 119 | 102 |
| IL6R-BP117/IL6R-L | P238D/K326D | 124 | 166 | 96 | 118 | 105 |
| IL6R-BP120/IL6R-L | P238D/K326E | 125 | 175 | 92 | 114 | 103 |

TABLE 49-continued

| VARIANT NAME | ALTERATION | RELATIVE BINDING | | | | |
| --- | --- | --- | --- | --- | --- | --- |
| | | FcγRIa | FcγRIIaR | FcγRIIaH | FcγRIIb | FcγRIIIa |
| IL6R-BP126/IL6R-L | P238D/K326L | 113 | 167 | 132 | 103 | 146 |
| IL6R-BP119/IL6R-L | P238D/K326M | 117 | 181 | 133 | 110 | 145 |
| IL6R-BP142/IL6R-L | P238D/K326N | 98 | 103 | 97 | 106 | 102 |
| IL6R-BP121/IL6R-L | P238D/K326Q | 118 | 155 | 135 | 113 | 157 |
| IL6R-BP118/IL6R-L | P238D/K326S | 101 | 132 | 128 | 104 | 144 |
| IL6R-BP116/IL6R-L | P238D/K326T | 110 | 126 | 110 | 108 | 114 |
| IL6R-BP911/IL6R-L | P238D/A330K | 52 | 101 | 108 | 119 | 120 |
| IL6R-BP078/IL6R-L | P238D/A330M | 106 | 101 | 89 | 105 | 91 |
| IL6R-BP912/IL6R-L | P238D/A330R | 60 | 81 | 93 | 103 | 97 |

The results of measuring KD values of the variants shown in Table 49 for FcγRIa, FcγRIIaR, FcγRIIaH, FcγRIIb, and FcγRIIIa type V by the method of Example 14 are summarized in Table 50. In the table, alteration refers to the alteration introduced into IL6R-B3(SEQ ID NO: 187). The template used for producing IL6R-B3, IL6R-G1d/IL6R-L, is indicated with an asterisk (*). Furthermore, KD(IIaR)/KD (IIb) and KD(IIaH)/KD(IIb) in the table respectively represent the value obtained by dividing the KD value of each variant for FcγRIIaR by the KD value of each variant for FcγRIIb, and the value obtained by dividing the KD value of each variant for FcγRIIaH by the KD value of each variant for FcγRIIb. KD(IIb) of the parent polypeptide/KD(IIb) of the altered polypeptide refers to the value obtained by dividing the KD value of the parent polypeptide for FcγRIIb by the KD value of each variant for FcγRIIb. In addition, the KD value for the stronger of the FcγRIIaR- and FcγRIIaH-binding activities of each variant/KD value for the stronger of the FcγRIIaR- and FcγRIIaH-binding activities of the parent polypeptide are shown in Table 50. Here, parent polypeptide refers to the variant which has IL6R-B3 (SEQ ID NO: 187) as the H chain. It was determined that due to weak binding of FcγR to IgG, it was sometimes impossible to accurately analyze by kinetic analysis, and thus the bolded and italicized text in Table 50 shows values calculated by using Equation 5 of Example 14.

$$KD = C \times R\text{max}/(Req-RI) - C \quad \text{[Equation 5]}$$

Table 50 shows that in comparison with IL6R-B3, all variants showed improvement of affinity for FcγRIIb, and the range of improvement was 2.1 fold to 9.7 fold. The ratio of KD value of each variant for FcγRIIaR/KD value of each variant for FcγRIIb, and the ratio of KD value of each variant for FcγRIIaH/KD value of each variant for FcγRIIb represent an FcγRIIb-binding activity relative to the FcγRIIaR-binding activity and FcγRIIaH-binding activity, respectively. That is, these values show the degree of binding selectivity of each variant for FcγRIIb, and a greater value indicates a higher binding selectivity for FcγRIIb. Since the ratio of KD value for FcγRIIaR/KD value for FcγRIIb, and the ratio of KD value for FcγRIIaH/KD value for FcγRIIb in the parent polypeptide IL6R-B3/IL6R-L were 0.3 and 0.2, respectively, all variants in Table 50 showed improvement of binding selectivity for FcγRIIb in comparison with the parent polypeptide. When the KD value for the stronger of the FcγRIIaR- and FcγRIIaH-binding activities of a variant/KD value for the stronger of the FcγRIIaR- and FcγRIIaH-binding activities of the parent polypeptide is 1 or more, this means that the stronger of the FcγRIIaR- and FcγRIIaH-binding activities of a variant has equivalent or decreased binding compared with the binding by the stronger of the FcγRIIaR- and FcγRIIaH-binding activities of the parent polypeptide. Since this value was 4.6 to 34.0 for the variants obtained this time, one may say that in comparison with the parent polypeptide, the variants obtained this time had reduced binding by the stronger of the FcγRIIaR- and FcγRIIaH-binding activities. These results showed that compared with the parent polypeptide, the variants obtained this time have maintained or decreased FcγRIIa type R- and type H-binding activities, enhanced FcγRIIb-binding activity, and improved selectivity for FcγRIIb. Furthermore, compared with IL6R-B3, all variants had lower affinity to FcγRIa and FcγRIIIaV.

TABLE 50

| Variant Name | Alteration | KD (mol/L) | | | | | KD (IIaR)/ KD (IIb) | KD (IIaH)/ KD (IIb) | KD (IIb) OF PARENT POLY-PEPTIDE/ KD (IIb) AL-TERED POLY-PEP-TIDE | KD VALUE FOR THE STRONGER OF THE BINDING ACTIVITIES OF A VARIANT TO FcγRIIaR AND FcγRIIaH/ KD VALUE FOR THE STRONGER OF THE BINDING ACTIVITIES OF THE PARENT POLYPEPTIDE TO FcγRIIaR AND FcγRIIaH |
|---|---|---|---|---|---|---|---|---|---|---|
| | | FcγRIa | FcγRIIaR | FcγRIIaH | FcγRIIB | FcγRIIIaV | | | | |
| IL6R-G1d/IL6R-L | * | 3.2E−10 | 1.0E−06 | 6.7E−07 | 2.6E−06 | 3.5E−07 | 0.4 | 0.3 | 1.2 | 0.9 |
| IL6R-B3/IL6R-L | | 4.2E−10 | 1.1E−06 | 7.7E−07 | 3.1E−06 | 3.3E−07 | 0.3 | 0.2 | 1.0 | 1.0 |
| IL6R-BF648/IL6R-L | P238D | 1.1E−08 | 1.5E−05 | *4.0E−05* | 1.2E−06 | *7.1E−05* | 13.0 | 33.9 | 2.5 | 19.9 |
| IL6R-2B002/IL6R-L | P238D/E233D | 6.4E−09 | 1.9E−05 | *8.6E−05* | 9.3E−07 | *5.3E−05* | 20.4 | 92.3 | 3.3 | 24.7 |
| IL6R-BP100/IL6R-L | P238D/S267A | 1.1E−09 | 7.2E−06 | *4.6E−05* | 1.1E−05 | *5.9E−05* | 7.3 | 42.6 | 2.9 | 10.2 |
| IL6R-BP102/IL6R-L | P238D/S267Q | 8.2E−09 | 8.4E−06 | *6.1E−05* | 9.0E−07 | *8.2E−05* | 9.4 | 67.6 | 3.4 | 11.0 |
| IL6R-BP103/IL6R-L | P238D/S267V | 3.5E−08 | 1.1E−05 | *8.8E−05* | 1.2E−05 | *1.1E−05* | 9.0 | 71.5 | 2.5 | 14.4 |
| IL6R-BP106/IL6R-L | P238D/H268D | 4.0E−09 | 1.1E−05 | *3.6E−05* | 9.3E−07 | *5.5E−05* | 11.6 | 38.7 | 3.3 | 14.0 |
| IL6R-BP107/IL6R-L | P238D/H268E | 1.5E−09 | 1.2E−05 | *5.2E−05* | 9.3E−07 | *6.3E−05* | 12.7 | 56.1 | 3.3 | 15.3 |
| IL6R-BP110/IL6R-L | P238D/H268N | 7.3E−09 | 1.7E−05 | *4.7E−05* | 1.5E−05 | *6.4E−05* | 11.7 | 31.5 | 2.1 | 22.6 |
| IL6R-BP112/IL6R-L | P238D/P271G | 6.5E−09 | 3.5E−06 | *3.5E−05* | 3.2E−07 | *6.9E−05* | 11.0 | 109.4 | 9.7 | 4.6 |
| IL6R-2B128/IL6R-L | P238D/Y296D | 1.3E−08 | 2.6E−05 | *3.4E−05* | 1.4E−06 | *7.2E−05* | 17.7 | 23.6 | 2.1 | 33.1 |
| IL6R-2B169/IL6R-L | P238D/V323L | 1.5E−08 | 1.9E−05 | *4.8E−05* | 1.2E−06 | *7.5E−05* | 15.8 | 40.7 | 2.6 | 24.3 |
| IL6R-2B171/IL6R-L | P238D/V323L | 9.1E−09 | 1.6E−05 | *3.4E−05* | 1.1E−05 | *5.7E−05* | 15.0 | 31.8 | 2.9 | 20.8 |
| IL6R-2B172/IL6R-L | P238D/V323M | 3.0E−09 | 6.1E−06 | *2.1E−05* | 7.7E−07 | *4.8E−05* | 8.0 | 27.3 | 4.0 | 8.0 |
| IL6R-BP136/IL6R-L | P238D/K326A | 6.6E−09 | 9.1E−06 | *3.8E−05* | 8.0E−07 | *6.9E−05* | 11.4 | 47.6 | 3.9 | 11.8 |
| IL6R-BP117/IL6R-L | P238D/K326D | 4.1E−09 | 9.2E−06 | *4.1E−05* | 8.0E−07 | *6.7E−05* | 11.6 | 51.4 | 3.9 | 12.0 |
| IL6R-BP120/IL6R-L | P238D/K326E | 6.6E−09 | 9.6E−06 | *6.5E−05* | 1.0E−06 | *7.9E−05* | 9.3 | 63.1 | 3.0 | 12.5 |
| IL6R-BP126/IL6R-L | P238D/K326L | 7.4E−09 | 1.1E−05 | *4.5E−05* | 1.4E−36 | *5.6E−05* | 7.8 | 31.7 | 2.2 | 14.4 |
| IL6R-BP119/IL6R-L | P238D/K326M | 7.0E−09 | 9.9E−06 | 4.5E−05 | 1.1E−06 | 5.6E−05 | 8.7 | 39.5 | 2.7 | 12.8 |
| IL6R-BP142/IL6R-L | P238D/K326N | 5.3E−09 | 1.8E−05 | *9.3E−05* | 1.2E−06 | *1.1E−04* | 15.5 | 79.5 | 2.6 | 23.5 |
| IL6R-BP121/IL6R-L | P238D/K326Q | 1.1E−08 | 1.36E−05 | *4.4E−05* | 1.1E−05 | *5.2E−05* | 11.7 | 40.4 | 2.8 | 16.6 |
| IL6R-BP118/IL6R-L | P238D/K326S | 1.2E−08 | 1.56E−05 | *4.6E−05* | 1.2E−05 | *5.6E−05* | 13.2 | 40.0 | 2.7 | 19.7 |
| IL6R-BP116/IL6R-L | P238D/K326T | 2.6E−09 | 1.5E−05 | *5.4E−05* | 1.1E−05 | *7.2E−05* | 13.3 | 48.2 | 2.8 | 19.4 |
| IL6R-BP911/IL6R-L | P238D/A330K | 4.9E−08 | 1.66E−05 | *3.7E−05* | 8.9E−07 | *5.8E−05* | 18.5 | 41.7 | 3.5 | 21.3 |
| IL6R-BP078/IL6R-L | P238D/A330M | 8.2E−09 | 1.5E−05 | 4.5E−05 | 1.1E−06 | *7.8E−05* | 13.4 | 31.3 | 2.8 | 19.0 |
| IL6R-BP912/IL6R-L | P238D/A330R | 3.8E−08 | 2.6E−05 | *3.8E−05* | 1.5E−05 | 156-CS | 17.8 | 25.9 | 2.1 | 34.0 |

Figure 63:
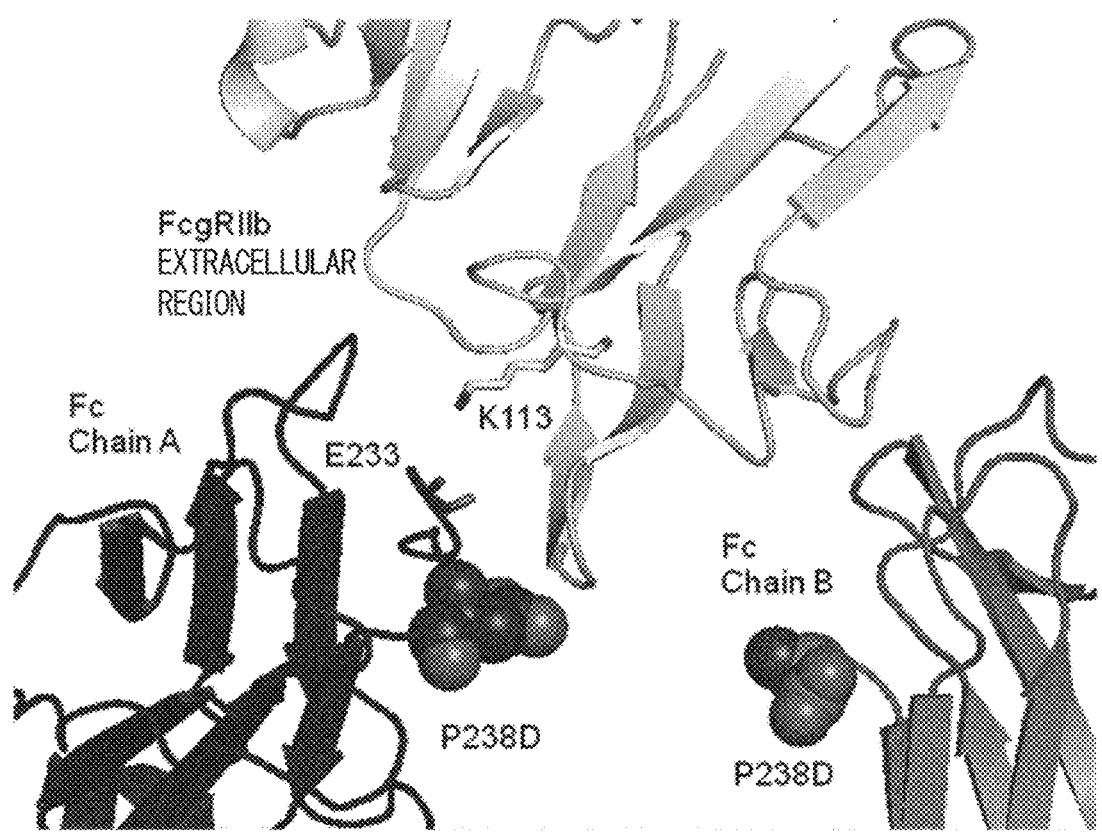
FIG. 63 shows Glu at position 233 (indicated by EU numbering) in Fc Chain A and the surrounding residues in the extracellular region of FcγRIIb in the crystal structure of the Fc(P238D)/FcγRIIb extracellular region complex.

With regard to the promising variants among the obtained combination variants, the factors leading to their effects were studied using the crystal structure. FIG. 63 shows the crystal structure of the Fc(P238D)/FcγRIIb extracellular region complex. In this figure, the H chain positioned on the left side is Fc Chain A, and the H chain positioned on the right side is Fc Chain B. Here, one can see that the site at position 233 (indicated by EU numbering) in Fc Chain A is located near Lys at position 113 of FcγRIIb. However, in this crystal structure, the E233 side chain is in a condition of considerably high mobility, and its electron density is not well observed. Therefore, the alteration produced by substituting Glu at position 233 (indicated by EU numbering) with Asp leads to decrease in the degree of freedom of the side chain since the side chain becomes one carbon shorter. As a result, the entropy loss when forming an interaction with Lys at position 113 of FcγRIIb may be decreased, and consequently this is speculated to contribute to improvement of binding free energy.

Figure 64:
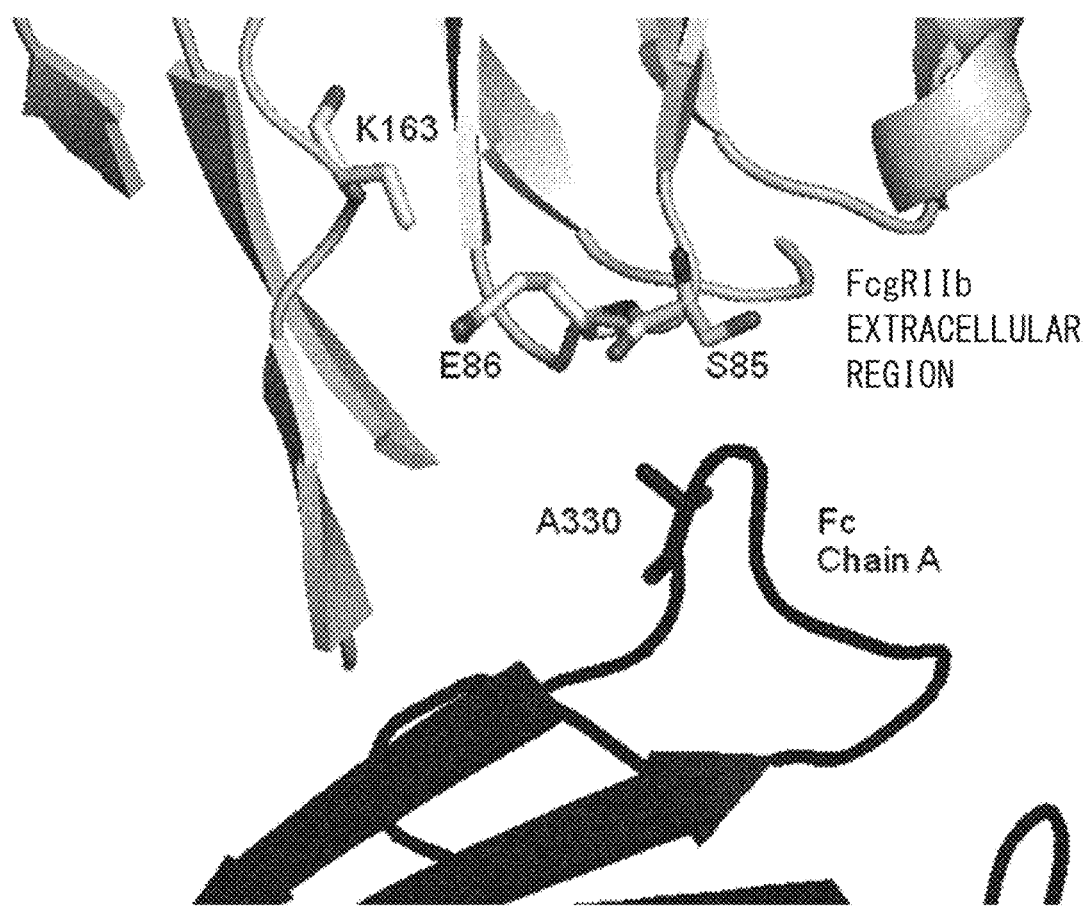
FIG. 64 shows Ala at position 330 (indicated by EU numbering) in Fc Chain A and the surrounding residues in the extracellular region of FcγRIIb in the crystal structure of the Fc(P238D)/FcγRIIb extracellular region complex.

Similarly, FIG. 64 shows the environment near the site at position 330 (indicated by EU numbering) in the structure of the Fc(P238D)/FcγRIIb extracellular region complex. This figure shows that the environment around the site at position 330 (indicated by EU numbering) of Fc Chain A of Fc (P238D) is a hydrophilic environment composed of Ser at position 85, Glu at position 86, Lys at position 163, and such of FcγRIIb. Therefore, the alteration produced by substituting Ala at position 330 (indicated by EU numbering) with Lys or Arg is speculated to contribute to strengthening the interaction with Ser at position 85 or Glu at position 86 in FcγRIIb.

Figure 65:
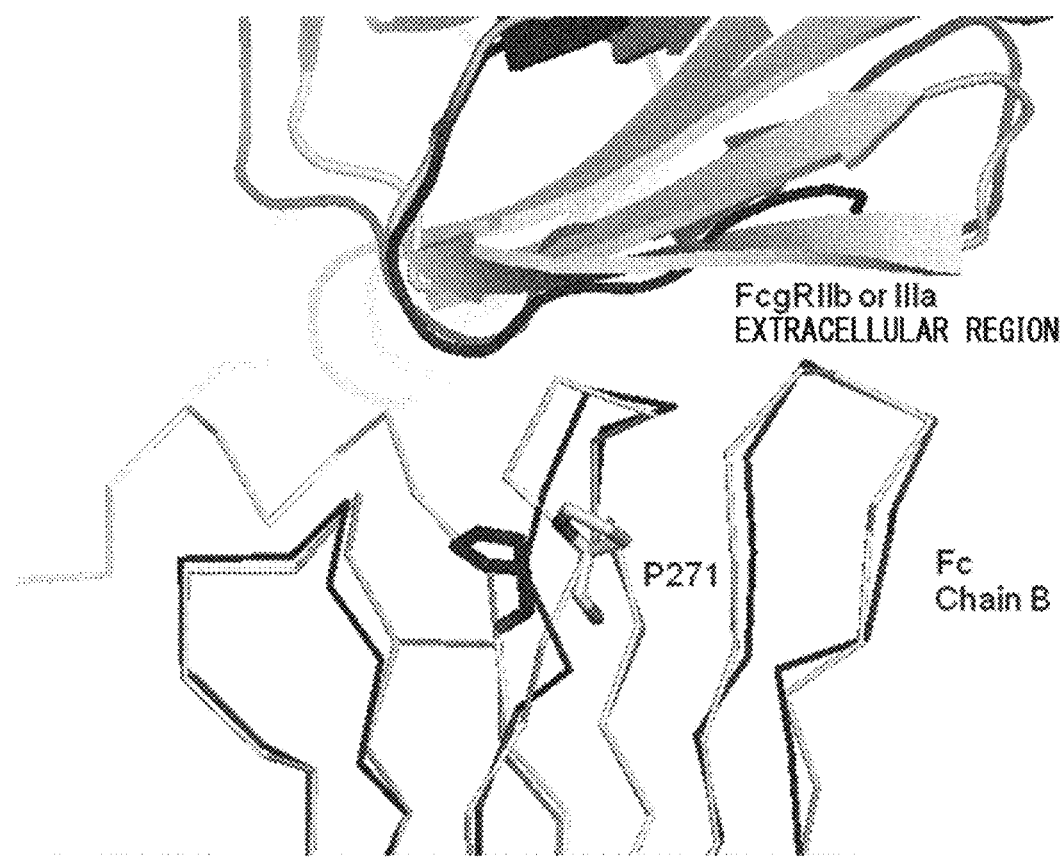
FIG. 65 shows the structures of Pro at position 271 (EU numbering) of Fc Chain B after superimposing the crystal structures of the Fc(P238D)/FcγRIIb extracellular region complex and the Fc(WT)/FcγRIIIa extracellular region complex by the least squares fitting based on the Cα atom pair distances with respect to Fc Chain B.

FIG. 65 depicts the structures of Pro at position 271 (indicated by EU numbering) of Fc Chain B after superimposing the crystal structures of the Fc(P238D)/FcγRIIb extracellular region complex and the Fc(WT)/FcγRIIIa extracellular region complex by the least squares fitting based on the Cα atom pair distances with respect to Fc Chain B. These two structures match well, but have different three-dimensional structures of Pro at position 271 (indicated by EU numbering). When the weak electron density around this area in the crystal structure of the Fc(P238D)/FcγRIIb extracellular region complex is also taken into consideration, it is suggested that there is possibility that Pro at position 271 (indicated by EU numbering) in Fc(P238D)/FcγRIIb causes a large strain on the structure, thus disturbing the loop structure to attain an optimal structure. Therefore, the alteration produced by substituting Pro at position 271 (indicated by EU numbering) with Gly gives flexibility to this loop structure, and is speculated to contribute to enhancement of binding by reducing the energetic barrier when allowing an optimum structure to form during interaction with FcγRIIb.

Example 30

Examination of the Combinatorial Effect of Alterations that Enhance FcγRIIb Binding when Combined with P238D.

Of the alterations obtained in Reference Examples 27 and 29, those that enhanced FcγRIIb binding or maintained FcγRIIb binding and showed effects of suppressing binding to other FcγRs were combined with each other, and its effect was examined.

Particularly good alterations selected from Tables 46 and 49 were introduced into the antibody H chain IL6R-BF648 in a similar manner to the method of Reference Example 29. IL6R-L was utilized as the common antibody L chain, the expressed antibodies were purified according to the method of Example 12. The binding to each of the FcγRs (FcγRIa, FcγRIIa H type, FcγRIIa R type, FcγRIIb, and FcγRIIIa V type) was comprehensively evaluated by the method of Example 14.

According to the following method, relative binding activities were calculated for the results of analyzing interactions with the respective FcγRs. The value for the amount of binding of each variant to each FcγR was divided by the value for the amount of binding of the pre-altered control antibody (IL6R-BF648/IL6R-L with substitution of Pro at position 238 (indicated by EU numbering) with Asp to each FcγR, and multiplied by 100; and then the value was shown as the relative binding activity value of each variant to each FcγR (Table 51).

In the table, alteration refers to the alteration introduced into IL6R-B3 (SEQ ID NO: 187). The template used for producing IL6R-B3, IL6R-G1d/IL6R-L, is indicated with an asterisk (*).

TABLE 51

| VARIANT | | RELATIVE BINDING ACTIVITY | | | | |
|---|---|---|---|---|---|---|
| NAME | ALTERATION | FcgRIa | FcgRIIaR | FcgRIIaH | FcgRIIb | FcgRIIIaV |
| IL6R-G1d/IL6R-L | * | 140 | 650 | 1670 | 62 | 3348 |
| IL6R-B3/IL5R-L | | 145 | 625 | 1601 | 58 | 3264 |
| IL6R-BF648/IL6R-L | P238D | 100 | 100 | 100 | 100 | 100 |
| IL6R-2B253/IL6R-L | E233D/P238D/V323M | 155 | 288 | 207 | 156 | 126 |
| IL6R-2B261/IL6R-L | E233D/P238D/Y296D | 100 | 94 | 91 | 115 | 87 |
| IL6R-BP082/IL6R-L | E233D/P238D/A330K | 74 | 126 | 106 | 136 | 87 |
| IL6R-BP083/IL6R-L | E238D/Y296D/A330K | 50 | 87 | 91 | 122 | 107 |
| IL6R-BP084/IL6R-L | P238D/V323M/A330K | 109 | 203 | 162 | 141 | 106 |
| IL6R-BP085/IL6R-L | G237D/P238D/A330K | 19 | 279 | 158 | 152 | 104 |
| IL6R-BP086/IL6R-L | P238D/K326A/A330K | 72 | 155 | 116 | 137 | 123 |
| IL6R-BP087/IL6R-L | L234Y/P238D/A330K | 33 | 163 | 179 | 137 | 158 |
| IL6R-BP088/IL6R-L | G237D/P238D/K326A/A330K | 25 | 377 | 166 | 161 | 122 |
| IL6R-BP089/IL6R-L | L234Y/P238D/K326A/A330K | 43 | 222 | 186 | 147 | 136 |
| IL6R-BP129/IL6R-L | E233D/P238D/Y296D/A330K | 68 | 111 | 98 | 138 | 95 |
| IL6R-BP130/IL6R-L | E233D/P238D/V323M/A330K | 104 | 272 | 224 | 160 | 115 |
| IL6R-BP131/IL6R-L | E233D/G237D/P238D/A330K | 33 | 364 | 253 | 160 | 118 |
| IL6R-BP132/IL6R-L | E233D/P238D/K326A/A330K | 91 | 191 | 130 | 150 | 120 |
| IL6R-BP133/IL6R-L | E233D/L234Y/P238D/A330K | 41 | 174 | 151 | 137 | 114 |
| IL6R-BP143/IL6R-L | L234Y/P238D/K326A | 86 | 238 | 143 | 133 | 114 |
| IL6R-BP144/IL6R-L | G237D/P238D/K326A | 64 | 204 | 108 | 121 | 128 |
| IL6R-BP145/IL6R-L | L234Y/G237D/P238D | 41 | 350 | 224 | 152 | 153 |
| IL6R-BP146/IL6R-L | L234Y/G237D/P238D/K326A | 50 | 445 | 203 | 156 | 180 |
| IL6R-BP147/IL6R-L | L234Y/G237D/P238D/K326A/A330K | 24 | 650 | 582 | 177 | 209 |
| IL6R-BP148/IL6R-L | E233D/L234Y/G237D/P238D/K326A/A330K | 33 | 603 | 462 | 176 | 227 |
| IL6R-BP149/IL6R-L | E233D/L234Y/G237D/P238D/Y296D/K326A/A330K | 29 | 539 | 401 | 173 | 186 |
| IL6R-BP150/IL6R-L | L234Y/G237D/P238D/K326A/A330R | 30 | 757 | 770 | 183 | 204 |
| IL6R-BP151/IL6R-L | E233D/L234Y/G237D/P238D/K326A/A330R | 39 | 705 | 621 | 180 | 221 |
| IL6R-BP152/IL6R-L | E233D/L234Y/G237D/P238D/Y296D/K326A/A330R | 34 | 638 | 548 | 178 | 146 |
| IL6R-BP176/IL6R-L | E233D/P238D/K326D/A330K | 102 | 201 | 128 | 147 | 131 |
| IL6R-BP177/IL6R-L | E233D/L234Y/G237D/P238D/P271G/K326D/A330K | 57 | 691 | 409 | 177 | 186 |
| IL6R-BP178/IL6R-L | E233D/G237D/P238D/P271G/A330K | 51 | 653 | 259 | 179 | 110 |
| IL6R-BP179/IL6R-L | G237D/P238D/P271G/K326A/A330K | 39 | 570 | 226 | 177 | 125 |
| IL6R-BP180/IL6R-L | G237D/P238D/P271G/A330K | 29 | 602 | 203 | 179 | 100 |
| IL6R-BP181/IL6R-L | E233D/P238D/P271G/K326A/A330K | 108 | 362 | 150 | 170 | 122 |
| IL6R-BP182/IL6R-L | E233D/P238D/P271G/Y296D/A330K | 95 | 413 | 139 | 173 | 120 |
| IL6R-BP183/IL6R-L | E233D/L234Y/P238D/P271G/K326A/A330K | 83 | 423 | 191 | 164 | 113 |
| IL6R-BP184/IL6R-L | E233D/P238D/P271G/A330K | 96 | 436 | 131 | 171 | 106 |
| IL6R-BP185/IL6R-L | E233D/L234Y/G237D/P238D/P271G/K326A/A330K | 47 | 670 | 446 | 179 | 191 |
| IL6R-BP186/IL6R-L | E233D/L234Y/G237D/P238D/P271G/Y296D/K326A/A330K | 43 | 614 | 368 | 175 | 143 |
| IL6R-BP187/IL6R-L | L234Y/P238D/P271G/K326A/A330K | 68 | 387 | 205 | 157 | 124 |
| IL6R-BP188/IL6R-L | E233D/G237D/P238D/H268D/P271G/A330K | 74 | 636 | 234 | 179 | 121 |
| IL6R-BP189/IL6R-L | G237D/P238D/H268D/P271G/K326A/A330K | 56 | 557 | 183 | 177 | 141 |
| IL6R-BP190/IL6R-L | G237D/P238D/H268D/P271G/A330K | 50 | 615 | 224 | 181 | 155 |
| IL6R-BP191/IL6R-L | E233D/P238D/H268D/P271G/K326A/A330K | 125 | 382 | 145 | 170 | 142 |
| IL6R-BP192/IL6R-L | E233D/P238D/H268D/P271G/Y296D/A330K | 109 | 406 | 122 | 172 | 118 |
| IL6R-BP193/IL6R-L | E233D/P238D/H268D/P271G/A330K | 113 | 449 | 154 | 173 | 135 |
| IL6R-BP194/IL6R-L | E233D/L234Y/G237D/P238D/H268D/P271G/K326A/A330K | 69 | 672 | 395 | 178 | 249 |
| IL6R-BP195/IL6R-L | E233D/L234Y/G237D/P238D/H268D/P271G/Y296D/K326A/A330K | 68 | 651 | 344 | 181 | 221 |
| IL6R-BP196/IL6R-L | L234Y/P238D/H268D/P271G/K326A/A330K | 89 | 402 | 195 | 157 | 137 |
| IL6R-BP197/IL6R-L | E233D/L234Y/G237D/P238D/H268D/P271G/Y296D/K326A/A330K | 71 | 642 | 294 | 179 | 206 |
| IL6R-BP198/IL6R-L | E233D/L234Y/P238D/H268D/P271G/K326A/A330K | 104 | 449 | 188 | 164 | 157 |
| IL6R-BP199/IL6R-L | E233D/P238D/K326A/A330R | 112 | 172 | 116 | 144 | 103 |
| IL6R-BP200/IL6R-L | E233D/L234Y/G237D/P238D/P271G/K326A/A330R | 60 | 754 | 517 | 188 | 164 |
| IL6R-BP201/IL6R-L | E233D/G237D/P238D/P271G/A330R | 57 | 696 | 359 | 186 | 121 |

TABLE 51-continued

| VARIANT | | RELATIVE BINDING ACTIVITY | | | | |
|---|---|---|---|---|---|---|
| NAME | ALTERATION | FcgRIa | FcgRIIaR | FcgRIIaH | FcgRIIb | FcgRIIIaV |
| IL6R-BP202/IL6R-L | G237D/P238D/P271G/K326A/A330R | 43 | 615 | 285 | 185 | 108 |
| IL6R-BP203/IL6R-L | G237D/P238D/P271G/A330R | 35 | 637 | 255 | 185 | 88 |
| IL6R-BP204/IL6R-L | E233D/P238D/P271G/K326A/A330R | 110 | 301 | 137 | 165 | 121 |
| IL6R-BP205/IL6R-L | E233D/P238D/P271G/Y296D/A330R | 97 | 335 | 108 | 167 | 93 |
| IL6R-BP206/IL6R-L | E233D/P238D/P271G/A330R | 101 | 362 | 123 | 168 | 92 |
| IL6R-BP207/IL6R-L | E233D/P238D/A330R | 74 | 103 | 103 | 124 | 97 |
| IL6R-BP208/IL6R-L | E233D/G237D/P238D/H268D/P271G/A330R | 81 | 690 | 310 | 188 | 118 |
| IL6R-BP209/IL6R-L | G237D/P238D/H268D/P271G/K326A/A330R | 68 | 625 | 267 | 186 | 153 |
| IL6R-BP210/IL6R-L | G237D/P238D/H268D/P271G/A330R | 57 | 661 | 279 | 187 | 135 |
| IL6R-BP211/IL6R-L | E233D/P238D/H268D/P271G/K326A/A330R | 128 | 312 | 111 | 165 | 87 |
| IL6R-BP212/IL6R-L | E233D/P238D/H268D/P271G/Y296D/A330R | 117 | 363 | 135 | 173 | 122 |
| IL6R-BP213/IL6R-L | E233D/P238D/H268D/P271G/A330R | 118 | 382 | 123 | 169 | 100 |
| IL6R-BP214/IL6R-L | E233D/L234Y/G237D/P238D/Y296D/K326A/A330K | 36 | 498 | 285 | 174 | 165 |

The results of measuring KD values of the variants shown in Table 51 for FcγRIa, FcγRIIaR, FcγRIIaH, FcγRIIb, and FcγRIIIa type V by the method of Example 14 are summarized in Tables 51-2 and 52-2. In the table, alteration refers to the alteration introduced into IL6R-B3(SEQ ID NO: 187). The template used for producing IL6R-B3, IL6R-G1d/IL6R-L, is indicated with an asterisk (*). Furthermore, KD(IIaR)/KD(IIb) and KD(IIaH)/KD(IIb) in the table respectively represent the value obtained by dividing the KD value of each variant for FcγRIIaR by the KD value of each variant for FcγRIIb, and the value obtained by dividing the KD value of each variant for FcγRIIaH by the KD value of each variant for FcγRIIb. KD(IIb) of the parent polypeptide/KD (IIb) of the altered polypeptide refers to the value obtained by dividing the KD value of the parent polypeptide for FcγRIIb by the KD value of each variant for FcγRIIb. In addition, the KD value for the stronger of the FcγRIIaR- and FcγRIIaH-binding activities of each variant/KD value for the stronger of the FcγRIIaR- and FcγRIIaH-binding activities of the parent polypeptide are shown in Tables 51-2 and 52-2. Here, parent polypeptide refers to the variant which has IL6R-B3 (SEQ ID NO: 187) as the H chain. It was determined that due to weak binding of FcγR to IgG, it was sometimes impossible to accurately analyze by kinetic analysis, and thus the bolded and italicized text in Tables 51-2 and 52-2 shows values calculated by using Equation 5 of Example 14.

$$KD = C \times Rmax/(Req-RI) - C \quad \text{[Equation 5]}$$

Tables 51-2 and 52-2 show that in comparison with IL6R-B3, all variants showed improvement of affinity for FcγRIIb, and the range of improvement was 3.0 fold to 99.0 fold. The ratio of KD value of each variant for FcγRIIaR/KD value of each variant for FcγRIIb, and the ratio of KD value of each variant for FcγRIIaH/KD value of each variant for FcγRIIb represent an FcγRIIb-binding activity relative to the FcγRIIaR-binding activity and FcγRIIaH-binding activity, respectively. That is, those values show the degree of binding selectivity of each variant for FcγRIIb, and a greater value indicates a higher binding selectivity for FcγRIIb. Since the ratio of KD value for FcγRIIaR/KD value for FcγRIIb, and the ratio of KD value for FcγRIIaH/KD value for FcγRIIb of the parent polypeptide IL6R-B3/IL6R-L were 0.3 and 0.2, respectively, all variants in Tables 51-2 and 52-2 showed improvement of binding selectivity for FcγRIIb in comparison with the parent polypeptide. When the KD value for the stronger of the FcγRIIaR- and FcγRIIaH-binding activities of a variant/KD value for the stronger of the FcγRIIaR- and FcγRIIaH-binding activities of the parent polypeptide is 1 or more, this means that the stronger of the FcγRIIaR- and FcγRIIaH-binding activities of a variant has equivalent or decreased binding compared with the binding by the stronger of the FcγRIIaR-and FcγRIIaH-binding activities of the parent polypeptide. Since this value was 0.7 to 29.9 for the variants obtained this time, one may say that binding by the stronger of the FcγRIIaR- and FcγRIIaH-binding activities of the variants obtained this time was nearly equivalent or decreased compared with that of the parent polypeptide. These results showed that compared with the parent polypeptide, the variants obtained this time have maintained or decreased FcγRIIa type R- and type H-binding activities, enhanced FcγRIIb-binding activity, and improved selectivity for FcγRIIb. Furthermore, compared with IL6R-B3, all variants had lower affinity for FcγRIa and FcγRIIIaV.

TABLE 52-1

| VARIANT NAME | ALTERATION | KD (mol/L) FcγRIa | FcγRIIaR | FcγRIIaH | FcγRIIb | FcγRIIIaV | KD (IIaR)/ KD (IIb) | KD (IIaH)/ KD (IIb) | KD(IIb) OF THE PARENT POLYPEPTIDE/ KD(IIb) OF THE ALTERED POLYPEPTIDE | KD VALUE FOR THE STRONGER OF THE FcγRIIaR- AND FcγRIIaH-BINDING ACTIVITIES OF THE VARIANT/KD VALUE FOR THE STRONGER OF THE FcγRIIaR- AND FcγRIIaH-BINDING ACTIVITIES OF THE PARENT POLYPEPTIDE |
|---|---|---|---|---|---|---|---|---|---|---|
| IL6R-G14/IL6R-L | | 3.2E−10 | 1.0E−06 | 6.7E−07 | 2.6E−06 | 3.5E−07 | 0.4 | 0.3 | 1.2 | 0.9 |
| IL6R-B3/IL6R-L | | 4.2E−10 | 1.1E−06 | 7.7E−07 | 3.1E−06 | 3.3E−07 | 0.3 | 0.2 | 1.0 | 1.0 |
| IL6R-BP648/IL6R-L | P238D | 1.1E−08 | 1.5E−06 | *4.0E−05* | 1.2E−06 | *7.1E−05* | 13.0 | 33.9 | 2.5 | 19.9 |
| IL6R-2B253/IL6R-L | P233D/P238D/V323M | 1.4E−09 | 5.0E−06 | *1.3E−05* | 4.5E−07 | *5.0E−05* | 11.5 | 30.1 | 7.2 | 6.5 |
| IL6R-2B261/IL6R-L | P233D/P238D/Y296D | 9.0E−09 | 2.2E−06 | *3.3E−05* | 1.0E−06 | *7.3E−05* | 21.8 | 32.4 | 3.0 | 26.8 |
| IL6R-BP082/IL6R-L | P233D/P238D/A330K | 1.0E−09 | 1.2E−06 | *3.7E−05* | 5.4E−07 | *8.1E−05* | 22.8 | 69.0 | 5.8 | 15.8 |
| IL6R-BP083/IL6R-L | P238D/Y296D/A330K | 3.6E−09 | 2.3E−06 | *4.4E−05* | 7.9E−07 | *6.6E−05* | 29.0 | 55.5 | 3.9 | 29.9 |
| IL6R-BP084/IL6R-L | P238D/V323M/A330K | 7.0E−09 | 7.2E−06 | *2.4E−05* | 5.0E−07 | *6.7E−05* | 14.3 | 47.6 | 6.1 | 9.4 |
| IL6R-BP085/IL6R-L | P237D/P238D/A330K | 2.9E−07 | 4.2E−06 | *2.4E−05* | 3.2E−07 | *6.8E−05* | 13.1 | 74.5 | 9.6 | 5.5 |
| IL6R-BP086/IL6R-L | P238D/K326A/A330K | 2.7E−08 | 9.7E−06 | *3.4E−05* | 5.7E−07 | *5.7E−05* | 17.1 | 89.9 | 5.4 | 12.6 |
| IL6R-BP087/IL6R-L | L234Y/P238D/A330K | 3.0E−08 | 9.7E−06 | *2.1E−05* | 6.1E−07 | *4.4E−05* | 16.0 | 34.7 | 5.1 | 12.6 |
| IL6R-BP088/IL6R-L | G237D/P238D/K326A/A330K | 3.0E−07 | 2.9E−06 | *2.3E−05* | 2.2E−07 | *5.7E−05* | 13.3 | 106.5 | 14.3 | 3.7 |
| IL6R-BP089/IL6R-L | L234Y/P238D/K326A/A330K | 6.3E−08 | 6.4E−06 | *2.0E−05* | 3.9E−07 | *5.1E−05* | 16.6 | 51.9 | 8.0 | 8.3 |
| IL6R-BP129/IL6R-L | E233D/P238D/Y296D/A330K | 2.5E−08 | 1.5E−06 | *4.0E−05* | 5.2E−07 | *7.5E−05* | 29.3 | 77.5 | 8.0 | 19.6 |
| IL6R-BP130/IL6R-L | E233D/P238D/V323M/A330K | 1.9E−09 | 5.3E−06 | *2.6E−05* | 3.0E−07 | *7.1E−05* | 17.5 | 85.5 | 10.2 | 6.9 |
| IL6R-BP131/IL6R-L | E233D/G237D/F238D/A330K | 1.2E−07 | 3.1E−06 | *1.4E−05* | 2.5E−07 | *5.9E−05* | 12.5 | 56.9 | 12.6 | 4.0 |
| IL6R-BP132/IL6R-L | E233D/P238D/K326A/A330K | 1.5E−09 | 8.0E−06 | *3.0E−05* | 2.7E−07 | *5.8E−05* | 21.5 | 81.1 | 8.4 | 10.3 |
| IL6R-BP133/IL6R-L | E233D/L234Y/P238D/A330K | 1.3E−07 | 6.6E−06 | *2.6E−05* | 5.6E−07 | *6.2E−05* | 15.5 | 46.8 | 5.6 | 11.2 |
| IL6R-BP143/IL6R-L | L234Y/P238D/K236A | 1.6E−06 | 5.7E−06 | *2.7E−05* | 5.7E−07 | *6.2E−05* | 10.0 | 47.1 | 5.4 | 7.5 |
| IL6R-BP144/IL6R-L | G237D/P238D/K326A | 3.7E−06 | 2.9E−06 | *3.6E−05* | 7.9E−07 | *5.5E−05* | 8.7 | 45.8 | 3.9 | 8.9 |
| IL6R-BP145/IL6R-L | L234Y/G237D/P238D | 1.2E−07 | 3.4E−06 | *1.7E−05* | 3.4E−07 | *4.5E−05* | 9.9 | 49.9 | 9.1 | 4.4 |
| IL6R-BP146/IL6R-L | L234Y/G237D/P238D/K326A | 7.4E−08 | 2.1E−06 | *1.8E−05* | 2.3E−07 | *3.8E−05* | 9.3 | 80.0 | 13.7 | 2.7 |
| IL6R-BP147/IL6R-L | L234Y/G237D/P238D/K326A/A330K | 1.4E−07 | 8.9E−07 | *5.1E−06* | 6.6E−08 | *3.3E−05* | 13.6 | 77.7 | 47.1 | 1.2 |
| IL6R-BP148/IL6R-L | E233D/L234Y/G237D/P238D/K326A/A330K | 8.9E−08 | 1.1E−06 | *7.0E−06* | 7.5E−08 | *3.0E−05* | 14.5 | 93.8 | 41.4 | 1.4 |
| IL6R-BP149/IL6R-L | E233D/L234Y/G237D/P238D/Y296D/K326A/ A330K | 1.2E−07 | 1.4E−06 | *8.4E−06* | 9.3E−08 | *3.7E−05* | 15.0 | 89.9 | 33.1 | 1.8 |
| IL6R-BP150/IL6R-L | L234Y/G237D/P238D/K326A/A330K | 3.2E−07 | 5.5E−07 | *3.4E−06* | 3.1E−08 | *3.4E−05* | 17.7 | 109.0 | 99.0 | 0.7 |
| IL6R-BP151/IL6R-L | E233D/L234Y/G237D/P238D/K326A/A330K | 8.4E−08 | 6.7E−07 | *4.7E−06* | 4.0E−08 | *3.1E−05* | 16.9 | 117.8 | 77.4 | 0.9 |
| IL6R-BP152/IL6R-L | E233D/L234Y/G237D/P238D/Y296D/K326A/ A330K | 7.3E−08 | 8.1E−07 | *5.6E−06* | 4.1E−08 | *4.8E−05* | 19.5 | 135.9 | 75.0 | 1.0 |
| IL6R-BP176/IL6R-L | E233D/P238D/K326D/A330K | 7.3E−09 | 6.9E−06 | *3.0E−05* | 3.6E−07 | *5.4E−05* | 19.1 | 83.1 | 8.6 | 8.9 |
| IL6R-BP177/IL6R-L | E233D/L234Y/G237D/P238D/P271G/K326D/ A330K | 3.3E−08 | 7.1E−07 | *8.2E−05* | 5.2E−08 | *3.7E−05* | 13.8 | 159.2 | 50.0 | 0.9 |
| IL6R-BP178/IL6R-L | E233D/G237D/P238D/P271G/A330K | 4.3E−08 | 9.3E−07 | *1.4E−05* | 5.1E−08 | *6.4E−05* | 18.1 | 272.4 | 50.1 | 1.2 |
| IL6R-BP179/IL6R-L | G237D/P238D/P271G/K326A/A330K | 6.4E−08 | 1.4E−06 | *1.6E−05* | 6.4E−08 | *5.6E−05* | 16.7 | 190.9 | 36.9 | 1.8 |
| IL6R-BP180/IL6R-L | G237D/P238D/P271G/A330K | 9.6E−08 | 1.2E−06 | *1.8E−05* | 6.2E−08 | *7.0E−05* | 18.6 | 290.8 | 49.9 | 1.5 |
| IL6R-BP181/IL6R-L | E233D/P238D/P271G/K326A/A330K | 7.5E−09 | 3.2E−06 | *2.6E−05* | 1.6E−07 | *5.7E−05* | 20.3 | 162.5 | 19.3 | 4.2 |
| IL6R-BP182/IL6R-L | E233D/P238D/P271G/Y296D/A330K | 1.0E−08 | 2.6E−06 | *2.8E−05* | 1.1E−07 | *5.8E−05* | 23.5 | 256.9 | 28.3 | 3.3 |

Table 52-2 is a continuation table of Table 52-1.

TABLE 52-2

| | | | | | | | | | | |
|---|---|---|---|---|---|---|---|---|---|---|
| IL6R-BP183/IL6R-L | L233D/L234Y/P238D/P271G/K326A/A330K | 1.7E−08 | 2.6E−06 | *1.5E−05* | 2.4E−07 | *5.6E−05* | 10.7 | 62.5 | 12.9 | 3.3 |
| IL6R-BP184/IL6R-L | L233D/P238D/P271G/A330K | 1.1E−08 | 2.3E−06 | *3.0E−05* | 1.3E−07 | *6.6E−05* | 18.2 | 238.1 | 24.5 | 3.0 |
| IL6R-BP185/IL6R-L | L233D/L234Y/G237/P238D/P271G/K326A/A330K | 6.3E−08 | 8.8E−07 | *7.3E−06* | 6.9E−08 | *3.6E−05* | 12.6 | 105.2 | 44.5 | 1.1 |
| IL6R-BP186/IL6R-L | L233D/L234Y/G237D/P238D/P271G/Y296D/K326A/A330K | 4.5E−08 | 9.6E−07 | *9.3E−06* | 6.1E−08 | *4.9E−05* | 15.8 | 152.5 | 50.7 | 1.3 |
| IL6R-BP187/IL6R-L | L234Y/P238D/P271G/K326A/A330K | 2.5E−08 | 2.8E−06 | *1.8E−05* | 2.9E−07 | *5.6E−05* | 9.7 | 62.3 | 10.7 | 3.6 |
| IL6R-BP188/IL6R-L | L233D/G237D/P238D/H268D/P271G/A330K | 2.1E−08 | 1.0E−06 | *1.6E−05* | 4.6E−08 | *5.8E−05* | 21.9 | 350.1 | 67.6 | 1.3 |
| IL6R-BP189/IL6R-L | G237D/P238D/H265D/P271G/K326A/A330K | 4.2E−08 | 1.4E−06 | *2.1E−05* | 7.4E−08 | *4.9E−05* | 18.5 | 283.8 | 41.8 | 1.8 |
| IL6R-BP190/IL6R-L | G237D/P238D/H265D/P271G/A330K | 6.3E−08 | 1.1E−06 | *1.7E−05* | 5.8E−08 | *4.5E−05* | 19.3 | 292.5 | 53.2 | 1.5 |
| IL6R-BP191/IL6R-L | E233D/P238D/H268D/P271G/K326A/A330K | 4.0E−09 | 3.0E−06 | *2.7E−05* | 1.5E−07 | *4.9E−05* | 20.3 | 184.9 | 21.2 | 3.8 |
| IL6R-BP192/IL6R-L | E233D/P238D/H268D/P271G/Y296D/A330K | 6.6E−09 | 2.6E−06 | *3.2E−05* | 1.1E−07 | *5.9E−05* | 23.1 | 283.2 | 27.3 | 3.4 |
| IL6R-BP193/IL6R-L | E233D/P238D/H268D/P271G/A330K | 6.3E−09 | 2.2E−06 | *2.5E−05* | 1.2E−07 | *5.2E−05* | 18.3 | 206.6 | 25.5 | 2.9 |
| IL6R-BP194/IL6R-L | L233D/L234Y/G237D/P238D/H268D/P271G/K326A/A330K | 2.4E−08 | 8.2E−07 | *8.5E−06* | 5.2E−08 | *2.7E−05* | 15.8 | 163.5 | 59.4 | 1.1 |
| IL6R-BP195/IL6R-L | L233D/L234Y/G237D/P238D/H268D/P271G/Y296D/K326A/A330K | 2.3E−08 | 9.1E−07 | *1.0E−05* | 5.0E−08 | *3.1E−05* | 18.2 | 200.8 | 62.0 | 1.2 |
| IL6R-BP196/IL6R-L | L234Y/P238D/H268D/P271G/K326A/A330K | 1.4E−08 | 3.0E−06 | *1.9E−05* | 2.2E−07 | *5.1E−05* | 13.4 | 85.2 | 13.9 | 3.9 |
| IL6R-BP197/IL6R-L | L233D/L234Y/G237D/P238D/H268D/P271G/Y296D/K326D/A330K | 1.9E−08 | 9.8E−07 | *1.2E−05* | 5.8E−08 | *3.3E−05* | 17.1 | 208.7 | 53.7 | 1.3 |
| IL6R-BP198/IL6R-L | E233D/L234Y/P238D/H268D/P271G/K326A/A330K | 1.1E−08 | 2.2E−06 | *2.0E−05* | 2.0E−07 | *4.4E−05* | 11.0 | 101.5 | 15.7 | 2.8 |
| IL6R-BP199/IL6R-L | E233D/P238D/K326D/A330K | 6.4E−09 | 8.6E−06 | *2.6E−05* | 4.9E−07 | *6.1E−05* | 17.5 | 53.0 | 6.3 | 11.1 |
| IL6R-BP200/IL6R-L | E233D/L234Y/G237D/P238D/P271G/K326D/A330K | 3.3E−08 | 6.3E−07 | *4.2E−06* | 3.4E−08 | *3.8E−05* | 18.6 | 123.9 | 91.2 | 0.8 |
| IL6R-BP201/IL6R-L | E233D/G237D/P238D/P271G/A330K | 5.1E−08 | 8.4E−07 | *6.9E−06* | 4.0E−08 | *5.2E−05* | 21.0 | 172.1 | 77.1 | 1.1 |
| IL6R-BP202/IL6R-L | G237D/P238D/P271G/K326A/A330K | 9.5E−08 | 1.2E−06 | *9.2E−06* | 6.4E−08 | *5.9E−05* | 19.2 | 144.0 | 48.4 | 1.6 |
| IL6R-BP203/IL6R-L | G237D/P238D/P271G/A330K | 1.8E−07 | 9.9E−07 | *1.1E−05* | 4.9E−08 | *7.2E−05* | 20.5 | 226.8 | 63.7 | 1.3 |
| IL6R-BP204/IL6R-L | E233D/P238D/P271G/K326A/A330K | 7.6E−09 | 4.5E−06 | *2.1E−05* | 2.5E−07 | *5.2E−05* | 17.6 | 82.7 | 12.2 | 5.8 |
| IL6R-BP205/IL6R-L | E233D/P238D/P271G/Y296D/A330K | 7.7E−09 | 3.5E−06 | *2.8E−05* | 1.6E−07 | *6.8E−05* | 21.8 | 176.1 | 19.4 | 4.5 |
| IL6R-BP206/IL6R-L | E233D/P238D/P271G/A330K | 8.2E−09 | 3.1E−06 | *2.4E−05* | 2.0E−07 | *6.9E−05* | 16.1 | 123.1 | 15.8 | 4.1 |
| IL6R-BP207/IL6R-L | E233D/P238D/A330K | 2.2E−08 | 1.9E−05 | *2.9E−05* | 6.4E−07 | *6.5E−05* | 23.0 | 34.5 | 3.7 | 25.1 |
| IL6R-BP208/IL6R-L | E233D/G237D/P238D/H268D/P271G/A330K | 1.9E−08 | 8.5E−07 | *8.3E−06* | 3.2E−08 | *5.3E−05* | 26.3 | 256.2 | 95.4 | 1.1 |
| IL6R-BP209/IL6R-L | G237D/P238D/H268D/P271G/K326A/A330K | 3.9E−08 | 1.2E−06 | *1.0E−05* | 5.1E−06 | *4.1E−05* | 22.7 | 195.3 | 60.4 | 1.5 |
| IL6R-BP210/IL6R-L | G237D/P238D/H268D/P271G/A330K | 6.5E−08 | 1.0E−06 | *9.5E−06* | 3.9E−05 | *4.6E−05* | 25.4 | 241.1 | 78.4 | 1.3 |
| IL6R-BP211/IL6R-L | E233D/P238D/H268D/P271G/K326A/A330K | 4.2E−09 | 4.1E−06 | *2.7E−05* | 2.2E−07 | *7.3E−05* | 18.5 | 120.5 | 13.8 | 5.4 |
| IL6R-BP212/IL6R-L | E233D/P238D/H268D/P271G/Y296D/A330K | 5.2E−09 | 3.5E−06 | *2.2E−05* | 1.7E−07 | *5.2E−05* | 21.1 | 133.3 | 18.7 | 4.5 |
| IL6R-BP213/IL6R-L | E233D/P238D/H268D/P271G/A330K | 4.1E−09 | 3.1E−06 | *2.4E−05* | 1.6E−07 | *6.3E−05* | 17.7 | 135.4 | 17.6 | 4.0 |
| IL6R-BP214/IL6R-L | E233D/L234Y/G237D/P238D/Y296D/K326D/A330K | 5.9E−08 | 1.7E−06 | *9.2E−06* | 1.2E−07 | *3.8E−05* | 14.5 | 78.0 | 26.2 | 2.2 |

INDUSTRIAL APPLICABILITY

The present invention provides methods for improving the pharmacokinetics of antigen-binding molecules and methods for reducing the immunogenicity of antigen-binding molecules. The present invention enables antibody therapy without causing unfavorable effects in vivo as compared to conventional antibodies.

The invention claimed is:

1. A method for reducing immunogenicity of an antibody, the method comprising:
identifying a first antibody comprising (a) an Fc region with a human FcRn-binding activity at pH 7.0 that is stronger than the human FcRn-binding activity at pH 7.0 of a native human IgG1 Fc region, and (b) an antigen-binding domain whose antigen-binding activity varies with pH as described in (i) below, or with calcium ion concentration as described in (ii) below:
  (i) the antigen-binding activity is lower at pH 5.8 than at pH 7.4, wherein the ratio of the KD value for antigen-binding activity at pH 5.8 to the KD value for antigen-binding activity at pH 7.4 (KD (pH 5.8)/KD (pH 7.4)) is 2 or more when the KD (pH 5.8) and KD (pH 7.4) values are determined using a surface plasmon resonance technique in which the antibody is immobilized, the antigen serves as analyte, and the following conditions are used: 10 mM 2-(N-morpholino)ethanesulfonic acid (MES) pH 5.8 or pH 7.4, 150 mM NaCl, 0.05% polysorbate 20, at 37° C.;
  (ii) the antigen-binding activity is lower at a calcium ion concentration of 3 μM than at a calcium ion concentration of 2 mM, wherein the ratio of the KD value for antigen-binding activity at a calcium ion concentration of 3 μM to the KD value for antigen-binding activity at a calcium ion concentration of 2 mM (KD (3 μM)/ KD (2 mM)) is 2 or more when the KD (3 μM) and KD (2 mM) values are determined using a surface plasmon resonance technique in which the antibody is immobilized, the antigen serves as analyte, and the following conditions are used: 10 mM N-(2-acetamido)-2-aminoethanesulfonic acid (ACES) pH 7.4, 150 mM NaCl, 0.05% polysorbate 20, and either 2 mM CaCl$_2$ or 3 μM CaCl$_2$, at 37° C.;
producing a second antibody whose ability to form a heterocomplex with two molecules of the human FcRn and one molecule of an activating Fcγ receptor at pH 7.4 is reduced compared to the ability of the first antibody to form such a heterocomplex at pH 7.4, and whose ability to bind to the activating Fcγ receptor is decreased compared to the ability of the native human IgG1 Fc region to bind to the activating Fcγ receptor, the second antibody being identical to the first antibody except for one or more amino acids in the Fc region, wherein the activating Fcγ receptor is human FcγRIa, human FcγRIIa(R), human FcγRIIa(H), human FcγRIIIa(V), or human FcγRIIIa(F), and wherein at least one of the following positions in the Fc region of the second antibody is occupied by one of the amino acid residues listed for that position (by EU numbering):
Ala, Arg, Asn, Asp, Gln, Glu, Gly, His, Lys, Met, Phe, Pro, Ser, Thr, or Trp at position 234;
Ala, Asn, Asp, Gln, Glu, Gly, His, Ile, Lys, Met, Pro, Ser, Thr, Val, or Arg at position 235;
Arg, Asn, Gln, His, Leu, Lys, Met, Phe, Pro, or Tyr at position 236;
Ala, Asn, Asp, Gln, Glu, His, Ile, Leu, Lys, Met, Pro, Ser, Thr, Val, Tyr, or Arg at position 237;
Ala, Asn, Gln, Glu, Gly, His, Ile, Lys, Thr, Trp, or Arg at position 238;
Gln, His, Lys, Phe, Pro, Trp, Tyr, or Arg at position 239;
Ala, Arg, Asn, Gln, Gly, His, Ile, Leu, Lys, Met, Phe, Ser, Thr, Trp, Tyr, or Val at position 265;
Ala, Arg, Asn, Asp, Gln, Glu, Gly, His, Lys, Phe, Pro, Ser, Thr, Trp, or Tyr at position 266;
Arg, His, Lys, Phe, Pro, Trp, or Tyr at position 267;
Ala, Arg, Asn, Gln, Gly, His, Ile, Leu, Lys, Met, Phe, Pro, Ser, Thr, Trp, Tyr, or Val at position 269;
Ala, Arg, Asn, Gln, Gly, His, Ile, Leu, Lys, Met, Phe, Pro, Ser, Thr, Trp, Tyr, or Val at position 270;
Arg, His, Phe, Ser, Thr, Trp, or Tyr at position 271;
Arg, Asn, Asp, Gly, His, Phe, Ser, Trp, or Tyr at position 295;
Arg, Gly, Lys, or Pro at position 296;
Ala at position 297;
Arg, Gly, Lys, Pro, Trp, or Tyr at position 298;
Arg, Lys, or Pro at position 300;
Lys or Pro at position 324;
Ala, Arg, Gly, His, Ile, Lys, Phe, Pro, Thr, Trp, Tyr, or Val at position 325;
Arg, Gln, His, Ile, Leu, Lys, Met, Phe, Pro, Ser, Thr, Trp, Tyr, or Val at position 327;
Arg, Asn, Gly, His, Lys, or Pro at position 328;
Asn, Asp, Gln, Glu, Gly, His, Ile, Leu, Lys, Met, Phe, Ser, Thr, Trp, Tyr, Val, or Arg at position 329;
Pro or Ser at position 330;
Arg, Gly, or Lys at position 331;
Arg, Lys, or Pro at position 332; and
conducting an assay to confirm that the second antibody has decreased immunogenicity compared to the first antibody.

2. A method for reducing immunogenicity of an antibody, the method comprising:
identifying a first antibody comprising (a) an Fc region with a human FcRn-binding activity at pH 7.0 that is stronger than the human FcRn-binding activity at pH 7.0 of a native human IgG1 Fc region, and (b) an antigen-binding domain whose antigen-binding activity varies with pH as described in (i) below, or with calcium ion concentration as described in (ii) below:

(i) the antigen-binding activity is lower at pH 5.8 than at pH 7.4, wherein the ratio of the KD value for antigen-binding activity at pH 5.8 to the KD value for antigen-binding activity at pH 7.4 (KD (pH 5.8)/ KD (pH 7.4)) is 2 or more when the KD values for KD (pH 5.8) and KD (pH 7.4) are determined using a surface plasmon resonance technique in which the antibody is immobilized, the antigen serves as analyte, and the following conditions are used: 10 mM 2-(N-morpholino)ethanesulfonic acid (MES) at pH 5.8 or pH 7.4, 150 mM NaCl, 0.05% polysorbate 20, at 37° C.;

(ii) the antigen-binding activity is lower at a calcium ion concentration of 3 μM than at a calcium ion concentration of 2 mM, wherein the ratio of the KD value for antigen-binding activity at a calcium ion concentration of 3 μM to the KD value for antigen-binding activity at a calcium ion concentration of 2 mM (KD (3 μM) / KD (2 mM)) is 2 or more when the KD values for KD (3 μM) and KD (2 mM) are determined using a surface plasmon resonance technique in which the antibody is immobilized, the antigen serves as analyte, and the following conditions are used: 10 mM N-(2-acetamido)-2-aminoethanesulfonic acid (ACES) at pH 7.4, 150 mM NaCl, 0.05% polysorbate 20, and either 2mM $CaCl_2$ or 3 μM $CaCl_2$, at 37° C.;

producing a second antibody whose ability to form a heterocomplex with two molecules of the human FcRn and one molecule of an activating Fcγ receptor at pH 7.4 is reduced compared to the ability of the first antibody to form such a heterocomplex at pH 7.4, the second antibody being identical to the first antibody except at one or more positions in the Fc region, including (a) position 238 (EU numbering), which in the second antibody is Asp and in the first antibody is not Asp, or (b) position 328 (EU numbering), which in the second antibody is Glu and in the first antibody is not Glu, wherein the second antibody binds more strongly to human FcγRIIb than to the activating Fcγ receptor, wherein the activating Fcγ receptor is human FcγRIa, human FcγRIIa (R), human FcγRIIa(H), human FcγRIIIa(V), or human FcγRIIIa(F); and conducting an assay to confirm that the second antibody has decreased immunogenicity compared to the first antibody.

3. A method for reducing immunogenicity of an antibody, the method comprising:

identifying a first antibody comprising (a) a first Fc region that binds to a human FcRn at pH 7.0 more strongly than a native human IgG1 Fc region binds to the human FcRn at pH 7.0, and that is able to form a heterocomplex with two molecules of the human FcRn and one molecule of an activating Fcγ receptor at pH 7.4, and (b) an antigen-binding domain whose antigen-binding activity varies with pH as described in (i) below, or with calcium ion concentration as described in (ii) below:

(i) the antigen-binding activity is lower at pH 5.8 than at pH 7.4, wherein the ratio of the KD value for antigen-binding activity at pH 5.8 to the KD value for antigen-binding activity at pH 7.4 (KD (pH 5.8)/ KD (pH 7.4)) is 2 or more when the KD (pH 5.8) and KD (pH 7.4) values are determined using a surface plasmon resonance technique in which the antibody is immobilized, the antigen serves as analyte, and the following conditions are used: 10 mM 2-(N-morpholino)ethanesulfonic acid (MES) pH 5.8 or pH 7.4, 150 mM NaCl, 0.05% polysorbate 20, at 37° C.;

(ii) the antigen-binding activity is lower at a calcium ion concentration of 3μM than at a calcium ion concentration of 2 mM, wherein the ratio of the KD value for antigen-binding activity at a calcium ion concentration of 3 μM to the KD value for antigen-binding activity at a calcium ion concentration of 2 mM (KD (3 μM)/ KD (2 mM)) is 2 or more when the KD (3 μM) and KD (2 mM) values are determined using a surface plasmon resonance technique in which the antibody is immobilized, the antigen serves as analyte, and the following conditions are used: 10 mM N-(2-acetamido)-2-aminoethanesulfonic acid (ACES) pH 7.4, 150 mM NaCl, 0.05% polysorbate 20, and either 2mM $CaCl_2$ or 3 μM $CaCl_2$, at 37° C.;

producing a second antibody comprising (A) a second Fc region comprising two Fc polypeptides with different amino acid sequences, wherein one of the two Fc polypeptides has detectable human FcRn-binding activity at pH 7.4 and the other Fc polypeptide does not, and wherein the ability of the second Fc region to form a heterocomplex with two molecules of the human FcRn and one molecule of the activating Fcγ receptor at pH 7.4 is reduced compared to the ability of the first antibody to form such a heterocomplex at pH 7.4, and (B) an antigen-binding domain identical to the antigen-binding domain of the first antibody; and conducting an assay to confirm that the second antibody has decreased immunogenicity compared to the first antibody, wherein the activating Fcγ receptor is human FcγRIa, human FcγRIIa(R), human FcγRIIa(H), human FcγRIIIa(V), or human FcγRIIIa(F).

4. The method of claim 1, wherein the Fc region of the second antibody differs from the Fc region of the first antibody by amino acid substitution at one or more positions, including at least one of the following positions: 235, 237, 238, 239, 270, 298, 325, 329 (by EU numbering).

5. The method of claim 2, wherein the Fc region of the second antibody differs from the Fc region of the first antibody by amino acid substitution at one or more positions including position 238 or 328 of a heavy chain (by EU numbering).

6. The method of claim 2, wherein the Fc region of the second antibody differs from the Fc region of the first antibody by substitution at one or more positions, including position 238 (EU numbering), which is Asp in the second antibody, and at least one additional position selected from the list below, wherein the substitution at any of the listed positions is a substitution with an amino acid residue listed for that position below (by EU numbering):

Asp at position 233;
Trp or Tyr at position 234;
Ala, Asp, Glu, Leu, Met, Phe, Trp, or Tyr at position 237;
Asp at position 239;
Ala, Gln, or Val at position 267;
Asn, Asp, or Glu at position 268;
Gly at position 271;

Ala, Asn, Asp, Gln, Glu, Leu, Met, Ser, or Thr at position 326;
Arg, Lys, or Met at position 330;
Ile, Leu, or Met at position 323; and
Asp at position 296.

7. The method of claim 1, wherein the Fc region of the first antibody and the Fc region of the second antibody differ from the native IgG1 Fc region by amino acid substitution at one or more positions, including at least one of the following positions (by EU numbering): 237, 248, 250, 252, 254, 255, 256, 257, 258, 265, 286, 289, 297, 298, 303, 305, 307, 308, 309, 311, 312, 314, 315, 317, 332, 334, 360, 376, 380, 382, 384, 385, 386, 387, 389, 424, 428, 433, 434, 436.

8. The method of claim 1, wherein at least one of the following positions (by EU numbering) in the Fc region of the second antibody is occupied by one of the amino acid residues listed for that position:
Met at position 237;
Ile at position 248;
Ala, Phe, Ile, Met, Gln, Ser, Val, Trp, or Tyr at position 250;
Phe, Trp, or Tyr at position 252;
Thr at position 254;
Glu at position 255;
Asn, Asp, Glu, or Gln at position 256;
Ala, Gly, Ile, Leu, Met, Asn, Ser, Thr, or Val at position 257;
His at position 258;
Ala at position 265;
Ala or Glu at position 286;
His at position 289;
Ala at position 297;
Gly at position 298;
Ala at position 303;
Ala at position 305;
Ala, Asp, Phe, Gly, His, Ile, Lys, Leu, Met, Asn, Pro, Gln, Arg, Ser, Val, Trp, or Tyr at position 307;
Ala, Phe, Ile, Leu, Met, Pro, Gln, or Thr at position 308;
Ala, Asp, Glu, Pro, or Arg at position 309;
Ala, His, or Ile at position 311;
Ala or His at position 312;
Lys or Arg at position 314;
Ala, Asp, or His at position 315;
Ala at position 317;
Val at position 332;
Leu at position 334;
His at position 360;
Ala at position 376;
Ala at position 380;
Ala at position 382;
Ala at position 384;
Asp or His at position 385;
Pro at position 386;
Glu at position 387;
Ala or Ser at position 389;
Ala at position 424;
Ala, Asp, Phe, Gly, His, Ile, Lys, Leu, Asn, Pro, Gln, Ser, Thr, Val, Trp, or Tyr at position 428;
Lys at position 433;
Ala, Phe, His, Ser, Trp, or Tyr at position 434;
His, Ile, Leu, Phe, Thr, or Val at position 436.

9. The method of claim 3, wherein the two Fc polypeptides differ from each other at one or more positions including at least one of the following positions: 237, 248, 250, 252, 254, 255, 256, 257, 258, 265, 286, 289, 297, 298, 303, 305, 307, 308, 309, 311, 312, 314, 315, 317, 332, 334, 360, 376, 380, 382, 384, 385, 386, 387, 389, 424, 428, 433, 434, 436 (by EU numbering).

10. The method of claim 3, wherein the second antibody's Fc polypeptide that has detectable FcRn-binding activity at pH 7.4 differs from the native human IgG1 Fc region by amino acid substitution at one or more positions, including at least one of the following positions: 237, 248, 250, 252, 254, 255, 256, 257, 258, 265, 286, 289, 297, 298, 303, 305, 307, 308, 309, 311, 312, 314, 315, 317, 332, 334, 360, 376, 380, 382, 384, 385, 386, 387, 389, 424, 428, 433, 434, 436 (by EU numbering).

11. The method of claim 3, wherein at least one of the following positions in the second antibody's Fc polypeptide that has detectable FcRn-binding activity at pH 7.4 is occupied by one of the amino acid residues listed for that position below (by EU numbering):
Met at position 237;
Ile at position 248;
Ala, Phe, Ile, Met, Gln, Ser, Val, Trp, or Tyr at position 250;
Phe, Trp, or Tyr at position 252;
Thr at position 254;
Glu at position 255;
Asn, Asp, Glu, or Gln at position 256;
Ala, Gly, Ile, Leu, Met, Asn, Ser, Thr, or Val at position 257;
His at position 258;
Ala at position 265;
Ala or Glu at position 286;
His at position 289;
Ala at position 297;
Gly at position 298;
Ala at position 303;
Ala at position 305;
Ala, Asp, Phe, Gly, His, Ile, Lys, Leu, Met, Asn, Pro, Gln, Arg, Ser, Val, Trp, or Tyr position 307;
Ala, Phe, Ile, Leu, Met, Pro, Gln, or Thr at position 308;
Ala, Asp, Glu, Pro, or Arg at position 309;
Ala, His, or Ile at position 311;
Ala or His at position 312;
Lys or Arg at position 314;
Ala, Asp, or His at position 315;
Ala at position 317;
Val at position 332;
Leu at position 334;
His at position 360;
Ala at position 376;
Ala at position 380;
Ala at position 382;
Ala at position 384;
Asp or His at position 385;
Pro at position 386;
Glu at position 387;
Ala or Ser at position 389;
Ala at position 424;
Ala, Asp, Phe, Gly, His, Ile, Lys, Leu, Asn, Pro, Gln, Ser, Thr, Val, Trp, or Tyr at position 428;
Lys at position 433;
Ala, Phe, His, Ser, Trp, or Tyr at position 434;
His, Ile, Leu, Phe, Thr, or Val at position 436.

12. The method of claim 1, comprising assaying, at a pH that is in the range from pH 6.7 to pH 10.0, the second antibody's ability to form the heterocomplex with two molecules of FcRn and one molecule of an activating FcγR.

13. The method of claim 2, comprising assaying the second antibody's binding to the human FcγRIIb and to the activating Fcγ receptor, thereby determining that the second antibody's ability to bind to the human FcγRIIb is greater than its ability to bind to the activating Fcγ receptor.

14. The method of claim 1, comprising assaying the second antibody's ability to bind to the activating Fcγ receptor and thereby determining that the second antibody's ability to bind to the activating Fcγ receptor is decreased compared to the first antibody's ability to bind to the activating Fcγ receptor.

15. The method of claim 1, wherein the antigen-binding activity of the antigen-binding domain varies with pH as described in (i), and the antigen-binding domain comprises a histidine residue at each of one or more positions selected from the group consisting of H chain variable region positions 27, 31, 32, 33, 35, 50, 58, 59, 61, 62, 99, 100b and 102, and L chain variable region positions 24, 27, 28, 31, 32, 50, 52, 53, 54, 55, 56, 89, 90, 91, 92, 93, and 94 (by Kabat numbering).

16. The method of claim 2, wherein the antigen-binding activity of the antigen-binding domain varies with pH as described in (i), and the antigen-binding domain comprises a histidine residue at each of one or more positions selected from the group consisting of H chain variable region positions 27, 31, 32, 33, 35, 50, 58, 59, 61, 62, 99, 100b and 102, and L chain variable region positions 24, 27, 28, 31, 32, 50, 52, 53, 54, 55, 56, 89, 90, 91, 92, 93, and 94 (by Kabat numbering).

17. The method of claim 3, wherein the antigen-binding activity of the antigen-binding domain varies with pH as described in (i), and the antigen-binding domain comprises a histidine residue at each of one or more positions selected from the group consisting of H chain variable region positions 27, 31, 32, 33, 35, 50, 58, 59, 61, 62, 99, 100b and 102, and L chain variable region positions 24, 27, 28, 31, 32, 50, 52, 53, 54, 55, 56, 89, 90, 91, 92, 93, and 94 (by Kabat numbering).

18. The method of claim 1, wherein the antigen-binding activity of the antigen-binding domain varies with calcium ion concentration as described in (ii), and at least one position of the antigen-binding domain selected from the following list of H and L chain positions is occupied by an amino acid residue having metal-chelating activity: H chain variable region positions 95, 96, 100a and 101, and L chain variable region positions 30, 31, 32, 50, and 92 (by Kabat numbering).

19. The method of claim 2, wherein the antigen-binding activity of the antigen-binding domain varies with calcium ion concentration as described in (ii), and at least one position of the antigen-binding domain selected from the following list of H and L chain positions is occupied by an amino acid residue having metal-chelating activity: H chain variable region positions 95, 96, 100a and 101, and L chain variable region positions 30, 31, 32, 50, and 92 (by Kabat numbering).

20. The method of claim 3, wherein the antigen-binding activity of the antigen-binding domain varies with calcium ion concentration as described in (ii), and at least one position of the antigen-binding domain selected from the following list of H and L chain positions is occupied by an amino acid residue having metal-chelating activity: H chain variable region positions 95, 96, 100a and 101, and L chain variable region positions 30, 31, 32, 50, and 92 (by Kabat numbering).

21. The method of claim 1, wherein the one or more amino acids include the amino acid at position 235 (EU numbering), which is Arg in the second antibody.

22. The method of claim 1, wherein the Fc region of the first antibody and the Fc region of the second antibody differ from the native human IgG1 Fc region by amino acid substitution at one or more positions, including at least one of the following positions: 248, 289, 314, 315, 360, 384, 386, 387, 389, 424 (by EU numbering).

23. The method of claim 2, wherein the Fc region of the first antibody and the Fc region of the second antibody differ from the native human IgG1 Fc region by amino acid substitution at one or more positions, including at least one of the following positions: 248, 289, 314, 315, 360, 384, 386, 387, 389, 424 (by EU numbering).

24. The method of claim 3, wherein the two Fc polypeptides of the second Fc region differ from each other at one or more amino acid positions, including at least one of the following positions: 248, 289, 314, 315, 360, 384, 386, 387, 389, 424 (by EU numbering).

25. The method of claim 3, wherein the second antibody's Fc polypeptide that has detectable human FcRn-binding activity at pH 7.4 differs from the native human IgG1 Fc region by amino acid substitution at one or more of the following positions: 248, 289, 314, 315, 360, 384, 386, 387, 389, 424 (by EU numbering).

26. The method of claim 1, further comprising assaying the second antibody's ability to form a heterocomplex with two molecules of the human FcRn and one molecule of the activating Fcγ receptor at pH 7.4, and thereby determining that the second antibody's ability to form such a heterocomplex is reduced compared to the ability of the first antibody to form such a heterocomplex at pH 7.4.

27. The method of claim 2, further comprising assaying the second antibody's ability to form a heterocomplex with two molecules of the human FcRn and one molecule of the activating Fcγ receptor at pH 7.4, and thereby determining that the second antibody's ability to form such a heterocomplex is reduced compared to the ability of the first antibody to form such a hetero complex at pH 7.4.

28. The method of claim 3, further comprising assaying the second antibody's ability to form a heterocomplex with two molecules of the human FcRn and one molecule of the activating Fcγ receptor at pH 7.4, and thereby determining that the second antibody's ability to form such a heterocomplex is reduced compared to the ability of the first antibody to form such a heterocomplex at pH 7.4.

29. The method of claim 2, wherein the Fc region of the first antibody and the Fc region of the second antibody differ from the native human IgG1 Fc region by amino acid substitution at one or more positions, including at least one of the following positions (by EU numbering): 237, 248, 250, 252, 254, 255, 256, 257, 258, 265, 286, 289, 297, 298, 303, 305, 307, 308, 309, 311, 312, 314, 315, 317, 332, 334, 360, 376, 380, 382, 384, 385, 386, 387, 389, 424, 428, 433, 434, 436.

30. The method of claim 2, wherein at least one of the following positions (by EU numbering) in the Fc region of the second antibody is occupied by one of the amino acid residues listed for that position:
Met at position 237;
Ile at position 248;
Ala, Phe, Ile, Met, Gln, Ser, Val, Trp, or Tyr at position 250;
Phe, Trp, or Tyr at position 252;
Thr at position 254;
Glu at position 255;
Asn, Asp, Glu, or Gln at position 256;
Ala, Gly, Ile, Leu, Met, Asn, Ser, Thr, or Val at position 257;

His at position 258;
Ala at position 265;
Ala or Glu at position 286;
His at position 289;
Ala at position 297;
Gly at position 298;
Ala at position 303;
Ala at position 305;
Ala, Asp, Phe, Gly, His, Ile, Lys, Leu, Met, Asn, Pro, Gln, Arg, Ser, Val, Trp, or Tyr at position 307;
Ala, Phe, Ile, Leu, Met, Pro, Gln, or Thr at position 308;
Ala, Asp, Glu, Pro, or Arg at position 309;
Ala, His, or Ile at position 311;
Ala or His at position 312;
Lys or Arg at position 314;
Ala, Asp, or His at position 315;
Ala at position 317;
Val at position 332;
Leu at position 334;
His at position 360;
Ala at position 376;
Ala at position 380;
Ala at position 382;
Ala at position 384;
Asp or His at position 385;
Pro at position 386;
Glu at position 387;
Ala or Ser at position 389;
Ala at position 424;
Ala, Asp, Phe, Gly, His, Ile, Lys, Leu, Asn, Pro, Gln, Ser, Thr, Val, Trp, or Tyr at position 428;
Lys at position 433;
Ala, Phe, His, Ser, Trp, or Tyr at position 434;
His, Ile, Leu, Phe, Thr, or Val at position 436.

31. The method of claim 2, comprising assaying the second antibody's ability to form the heterocomplex with two molecules of the human FcRn and one molecule of the activating Fcγ R at a pH that is in the range from pH 6.7 to pH 10.0.

32. The method of claim 3, comprising assaying the second antibody's ability to form the heterocomplex with two molecules of the human FcRn and one molecule of the activating Fcγ R at a pH that is in the range from pH 6.7 to pH 10.0.

33. The method of claim 2, wherein the heavy chain of the second antibody comprises either (1) Asp at position 238 (by EU numbering), or (2) Glu at position 328 (by EU numbering), but does not comprise both (1) and (2).

* * * * *